US011479599B2

(12) United States Patent
Corti et al.

(10) Patent No.: US 11,479,599 B2
(45) Date of Patent: *Oct. 25, 2022

(54) ANTIBODIES AGAINST SARS-COV-2 AND METHODS OF USING THE SAME

(71) Applicant: VIR BIOTECHNOLOGY, INC., San Francisco, CA (US)

(72) Inventors: Davide Corti, Bellinzona (CH); Katja Fink, Bellinzona (CH); Martina Beltramello, Bellinzona (CH); Elisabetta Cameroni, Bellinzona (CH); Dora Pinto, Bellinzona (CH); Gyorgy Snell, San Francisco, CA (US); Florian A. Lempp, San Francisco, CA (US); Amalio Telenti, San Francisco, CA (US)

(73) Assignee: Vir Biotechnology, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/384,665

(22) Filed: Jul. 23, 2021

(65) Prior Publication Data
US 2021/0371504 A1 Dec. 2, 2021

Related U.S. Application Data

(63) Continuation of application No. 17/853,340, filed on Feb. 25, 2021, now Pat. No. 11,168,128.

(60) Provisional application No. 63/052,810, filed on Jul. 16, 2020, provisional application No. 63/050,331, filed on Jul. 10, 2020, provisional application No. 63/043,653, filed on Jun. 24, 2020, provisional application No. 63/039,813, filed on Jun. 16, 2020, provisional application No. 63/025,133, filed on May 14, 2020, provisional application No. 63/023,788, filed on May 12, 2020, provisional application No. 63/014,024, filed on Apr. 22, 2020, provisional application No. 63/011,971, filed on Apr. 17, 2020, provisional application No. 63/010,589, filed on Apr. 15, 2020, provisional application No. 63/005,206, filed on Apr. 3, 2020, provisional application No. 63/003,214, filed on Mar. 31, 2020, provisional application No. 63/001,204, filed on Mar. 27, 2020, provisional application No. 62/994,235, filed on Mar. 24, 2020, provisional application No. 62/992,082, filed on Mar. 19, 2020, provisional application No. 62/990,369, filed on Mar. 16, 2020, provisional application No. 62/989,522, filed on Mar. 13, 2020, provisional application No. 62/987,298, filed on Mar. 9, 2020, provisional application No. 62/982,661, filed on Feb. 27, 2020, provisional application No. 62/981,984, filed on Feb. 26, 2020.

(51) Int. Cl.
C07K 16/10 (2006.01)

(52) U.S. Cl.
CPC ........ C07K 16/10 (2013.01); C07K 2317/522 (2013.01); C07K 2317/526 (2013.01); C07K 2317/565 (2013.01); C07K 2317/76 (2013.01)

(58) Field of Classification Search
None
See application file for complete search history.

(56) References Cited

U.S. PATENT DOCUMENTS

| | | |
|---|---|---|
| 7,396,914 B2 | 7/2008 | Ambrosino et al. |
| 7,696,330 B2 | 4/2010 | Meulen et al. |
| 7,750,123 B2 | 7/2010 | Marasco et al. |
| 7,879,329 B2 | 2/2011 | Lantto et al. |
| 8,092,994 B2 | 1/2012 | Yuen et al. |
| 8,106,170 B2 | 1/2012 | Ter Meulen et al. |
| 8,858,942 B2 | 10/2014 | Cartlidge et al. |
| 9,499,620 B2 | 11/2016 | Hsu et al. |
| 9,803,209 B2 | 10/2017 | Joergensen et al. |
| 10,081,670 B2 | 9/2018 | Kyratsous et al. |
| 10,101,333 B2 | 10/2018 | Smider et al. |
| 10,358,497 B2 | 7/2019 | Nioi et al. |
| 10,400,039 B2 | 9/2019 | Queva et al. |
| 10,406,222 B2 | 9/2019 | Kyratsous et al. |
| 10,501,526 B2 | 12/2019 | Kyratsous et al. |
| 10,787,501 B1 | 9/2020 | Babb et al. |
| 2004/0110933 A1 | 6/2004 | Rondon et al. |

(Continued)

FOREIGN PATENT DOCUMENTS

| CN | 112062859 A | 12/2020 |
|---|---|---|
| EP | 1597280 A2 | 11/2005 |

(Continued)

OTHER PUBLICATIONS

Andreano et al., "SARS-CoV-2 escape in vitro from a highly neutralizing COVID-19 convalescent plasma," bioRxiv preprint doi: https://doi.org/10.1101/2020.12.28.424451, Dec. 28, 2020. (36 pages).

Arvin et al., "A perspective on potential antibody-dependent enhancement of SARS-CoV-2," Nature 584:353-363, Jul. 13, 2020.

Ayteo et al., "Therapeutic potential of SARS-CoV-2-specific monoclonal antibody CR3022," Cell Host & Microbe, Jun. 1, 2020. (15 pages).

(Continued)

Primary Examiner — Adam Weidner
(74) Attorney, Agent, or Firm — Seed IP Law Group LLP

(57) ABSTRACT

The instant disclosure provides antibodies and antigen-binding fragments thereof that can bind to a SARS-CoV-2 antigen and, in certain embodiments, are capable of neutralizing a SARS-CoV-2 infection. Also provided are polynucleotides that encode an antibody or antigen-binding fragment, vectors and host cells that comprise a polynucleotide, pharmaceutical compositions, and methods of using the presently disclosed antibodies, antigen-binding fragments, polynucleotides, vectors, host cells, and compositions to treat or diagnose a SARS-CoV-2 infection.

30 Claims, 120 Drawing Sheets

Specification includes a Sequence Listing.

(56) References Cited

U.S. PATENT DOCUMENTS

| | | |
|---|---|---|
| 2016/0272994 A1 | 9/2016 | Abad et al. |
| 2019/0119391 A1 | 4/2019 | Youd et al. |
| 2019/0352413 A1 | 11/2019 | De Abreu Carvalho et al. |
| 2020/0024319 A1 | 1/2020 | Butz et al. |

FOREIGN PATENT DOCUMENTS

| | | |
|---|---|---|
| EP | 1 644 414 B1 | 1/2015 |
| JP | 10-2012-0054465 A | 5/2012 |
| JP | 6486268 B2 | 3/2019 |
| JP | 2019/528083 A | 10/2019 |
| JP | 2020/502507 A | 1/2020 |
| WO | 2004/089983 A2 | 10/2004 |
| WO | 2005/012360 A2 | 2/2005 |
| WO | 2008/060331 A3 | 5/2008 |
| WO | 2009/128963 A2 | 10/2009 |
| WO | 2011/056997 A1 | 5/2011 |
| WO | 2011/079257 A2 | 6/2011 |
| WO | 2013/131987 A1 | 9/2013 |
| WO | 2016/016412 A1 | 2/2016 |
| WO | 2016/073879 A2 | 5/2016 |
| WO | 2016/073906 A2 | 5/2016 |
| WO | 2016/138160 A1 | 9/2016 |
| WO | 2016/182957 A1 | 11/2016 |
| WO | 2017/153433 A1 | 9/2017 |
| WO | 2018/102746 A1 | 6/2018 |
| WO | 2019/005897 A1 | 1/2019 |
| WO | 2019/028555 A1 | 2/2019 |
| WO | 2019/039891 A1 | 2/2019 |
| WO | 2019/122884 A1 | 6/2019 |
| WO | 2021/045836 A1 | 3/2021 |
| WO | 2021/203053 A1 | 10/2021 |
| WO | 2021/211775 A1 | 10/2021 |
| WO | 2021/226560 A1 | 11/2021 |
| WO | 2021/247925 A1 | 12/2021 |
| WO | 2021/252878 A1 | 12/2021 |

OTHER PUBLICATIONS

Barnes et al., "SARS-CoV-2 neutralizing antibody structures inform therapeutic strategies," *Nature* 588:682-687, Oct. 12, 2020. (22 pages).

Baum et al., "Antibody cocktail to SARS-CoV-2 spike protein prevents rapid mutational escape seen with individual antibodies," *Science* 369:1014-1018, Jun. 15, 2020. (5 pages).

Case et al., "Neutralizing Antibody and Soluble ACE2 Inhibition of a Replication-Competent VSV-SARS-CoV-2 and a Clinical Isolate of SARS-CoV-2," *Cell Host & Microbe* 28, 475-485, Sep. 9, 2020. (22 pages).

Chen and Diamond et al., "SARS-CoV-2 variants show resistance to neutralization by many monoclonal and serum-derived polyclonal antibodies," Research Square preprint doi: https://doi.org/10.21203/rs.3.rs-228079/v1, Feb. 10, 2021. (17 pages).

Chen et al., "Enhancement and destruction of antibody function by somatic mutation: unequal occurrence is controlled by V gene combinatorial associations," *The EMBO Journal* 14(12):2784-2794, 1995.

Chen et al., "Human monoclonal antibodies block the binding of SARS-CoV-2 spike protein to angiotensin converting enzyme 2 receptor," *Cellular & Molecular Immunology* 17:641-649, Apr. 20, 2020.

Chen et al., "Human monoclonal antibodies block the binding of SARS-CoV-2 spike protein to angiotensin converting enzyme 2 receptor," medRxivpreprint doi: https://doi.org/10.1101/2020.04.06.20055475, Apr. 11, 2020. (20 pages).

Chen et al., "Resistance of SARS-CoV-2 variants to neutralization by monoclonal and serum-derived polyclonal antibodies," *Nature Medicine*, Mar. 4, 2021. (25 pages).

Chen et al., "SARS-CoV-2 Neutralizing Antibody LY-CoV555 in Outpatients with Covid-19," *The New England Journal of Medicine*, Oct. 28, 2020. (9 pages).

Chi et al., "Humanized Single Domain Antibodies Neutralize SARS-CoV-2 by Targeting Spike Receptor Binding Domain," bioRxiv preprint doi: https://doi.org/10.1101/2020.04.14.042010, Apr. 15, 2020. (24 pages).

Chi et al., "Humanized single domain antibodies neutralize SARS-CoV-2 by targeting the spike receptor binding domain," *Nature Communications* 77:4528, Sep. 10, 2020. (7 pages).

Collier et al., "SARS-CoV-2 B.1.1.7 sensitivity to mRNA vaccine-elicited, convalescent and monoclonal antibodies," medRxiv preprint doi: https://doi.org/10.1101/2021.01.19.21249840, Feb. 15, 2021. (46 pages).

Davies et al., "Estimated transmissibility and severity of novel SARS-CoV-2 Variant of Concern 202012/01 in England," medRxiv preprint doi: https://doi.org/10.1101/2020.12.24.20248822, Dec. 26, 2020. (35 page).

Dong et al., "Genetic and structural basis for recognition of SARS-CoV-2 spike protein by a two-antibody cocktail," bioRxiv preprint doi: https://doi.ord/10.1101/2021.01.27.428529, Mar. 1, 2021. (56 pages).

Eguia et al., "A human coronavirus evolves antigenically to escape antibody immunity," bioRxiv preprint doi: https://doi.org/10.1101/2020.12.17.423313, Dec. 18, 2020. (28 pages).

Greaney et al., "Complete mapping of mutations to the SARS-CoV-2 spike receptor-binding domain that escape antibody recognition," bioRxivpreprint doi: https://doi.org/10.1101/2020.09.10.292078, Sep. 10, 2020. (34 pages).

Greaney et al., "Comprehensive mapping of mutations to the SARS-CoV-2 receptor-binding domain that affect recognition of polyclonal human serum antibodies," bioRxiv preprint doi: https://doi.org/10.110172020.12.31.425021, Jan. 4, 2021 (35 pages).

Ho, "Perspectives on the development of neutralizing antibodies against SARS-CoV-2," *Antibody Therapeutics* 3(2):109-114, May 20, 2020.

Hodcrof et al., "Emergence and spread of a SARS-CoV-2 variant through Europe in the summer of 2020," medRxiv preprint doi: https://doi.org/10.1101/2020.10.25.20219063, Nov. 27, 2020. (20 pages).

Huang, "Immunological strategies against spike protein: Neutralizing antibodies and vaccine development for COVID-19," *Clinical and Translational Medicine* 10:e184, Oct. 1, 2020. (6 pages).

Huo et al., "Neutralization of SARS-CoV-2 by Destruction of the Prefusion Spike," *Cell Host & Microbe* 28:445-454, Sep. 9, 2020. (17 pages).

International Search Report and Written Opinion, dated Jun. 4, 2021, for International Application No. PCT/US2021/019531. (17 pages).

Jones et al., "LY-CoV555, a rapidly isolated potent neutralizing antibody, provides protection in a non-human primate model of SARS-CoV-2 infection," bioRxiv preprint doi: https://doi.org/10.1101/2020.09.30.318972, Oct. 9, 2020. (81 pages).

Joyce et al., "A Cryptic Site of Vulnerability on the Receptor Binding Domain of the SARS-CoV-2 Spike Glycoprotein," bioRxiv preprint doi: https://doi.org/10.1101/2020.03.15.992883, Mar. 17, 2020. (32 pages).

Ju et al., "Human neutralizing antibodies elicited by SARS-CoV-2 infection," *Nature* 584, May 26, 2020. (22 pages).

Ju et al., "Potent human neutralizing antibodies elicited by SARS-CoV-2 infection," bioRxiv preprint doi: https://doi.org/10.1101/2020.03.21.990770, Mar. 26, 2020. (42 pages).

Koenig et al., "Mutational landscape of antibody variable domains reveals a switch modulating the interdomain conformational dynamics and antigen binding," *PNAS*:E486-E495, Jan. 5, 2017.

Kupferschmidt, "New coronavirus variants could cause more reinfections, require updated vaccines," *Science*, Jan. 15, 2021. (6 pages).

Kussie et al., "A Single Engineered Amino Acid Substitution Changes Antibody Fine Specificity," *Journal of Immunology* 152(1):146-152, 1994.

Lempp et al., "Membrane lectins enhance SARS-CoV-2 infection and influence the neutralizing activity of different classes of antibodies," bioRxiv preprint doi: https://doi.org/10.1101/2021.04.03.438258a, Apr. 4, 2021. (38 pages).

(56) References Cited

OTHER PUBLICATIONS

Li et al., "Generation of antibodies against COVID-19 virus for development of diagnostic tools," medRxiv preprint doi: https://doi.org/10.1101/2020.02.20.20025999, Feb. 27, 2020. (14 pages).

Liu et al., "A combination of cross-neutralizing antibodies synergizes to prevent SARS-CoV-2 and SARS-CoV pseudovirus infection," bioRxiv preprint doi: https://doi.org/10.1101/2021.02.11.430866, Feb. 12, 2021. (57 pages).

Liu et al., "Potent neutralizing antibodies against multiple epitopes on SARS-CoV-2 spike," *Nature* 584:450-456, Jul. 22, 2020. (26 pages).

Luan et al., "Molecular Mechanism of the N501Y Mutation for Enhanced Binding between SARS-CoV-2's Spike Protein and Human ACE2 Receptor," bioRxiv preprint doi: https://doi.org/10.1101/2021.01.04.425316, Jan. 5, 2021. (18 pages).

Ma et al., "CAR-NK Cells Effectively Target the D614 and G614 SARS-CoV-2-infected Cells," bioRxiv preprint doi: https://doi.org/10.1101/2021.01.14.426742, Jan. 15, 2021. (55 pages).

McCallum et al., "Closing coronavirus spike glycoproteins by structure-guided design," bioRxiv preprint doi: https://doi.org/10.1101/2020.06.03.129817, Jun. 3, 2020. (20 pages).

McCallum et al., "SARS-CoV-2 immune evasion by variant B.1.427/B.1.429," bioRxiv preprint doi: https://doi.org/10.1101/2021.03.31.437925, Apr. 1, 2021. (30 pages).

McCallum et al., "Structure-guided covalent stabilization of coronavirus spike glycoprotein trimers in the closed conformation," *Nature Structural & Molecular Biology* 27:942-949, Aug. 4, 2020. (16 pages).

Miao et al., "A novel biparatopic antibody-ACE2 fusion that blocks SARS-CoV-2 infection: implications for therapy," bioRxiv preprint doi: https://doi.org/10.1101/2020.06.14.147868, Jun. 15, 2020. (13 pages).

Miao et al., "A novel biparatopic hybrid antibody-ACE2 fusion that blocks SARS-CoV-2 infection: implications for therapy," *mAbs* 12(1):e1804241, Aug. 17, 2020. (7 pages).

Park et al., "Spike protein binding prediction with neutralizing antibodies of SARS-CoV-2" bioRxiv preprint doi: https://doi.org/10.1101/2020.02.22.951178, Feb. 27, 2020. (22 pages).

Pater et al., "Emergence and Evolution of a Prevalent New SARS-CoV-2 Variant in the United States," bioRxiv preprint doi: https://doi.org/10.1101/2021.01.11.426287, Jan. 19, 2021. (21 pages).

Piccoli et al., "Mapping Neutralizing and Immunodominant Sites on the SARS-CoV-2 Spike Receptor-Binding Domain by Structure-Guided High-Resolution Serology," *Cell* 183:1024-1042, Sep. 16, 2020. (w/ supplemental information) (47 pages).

Pinto et al., "Cross-neutralization of SARS-CoV-2 by a human monoclonal SARS-CoV antibody," *Nature* 583:290-295, May 18, 2020. (41 pages).

Pinto et al., "Structural and functional analysis of a potent sarbecovirus neutralizing antibody," bioRxiv. Preprint, doi: 10.1101/2020.04.07.023903: 10.1101/2020.04.07.023903, Apr. 9, 2020. (28 pages).

Rappazzo et al., "An Engineered Antibody with Broad Protective Efficacy in Murine Models of SARS and COVID-19," bioRxiv preprint doi: https://doi.org/10.1101/2020.11.17.385500, Nov. 17, 2020. (59 pages).

Renn et al., "Fruitful Neutralizing Antibody Pipeline Brings Hope to Defeat SARS-Cov-2" *Trends in Pharmacological Sciences* 41(11):815-829, Jul. 31, 2020.

Shen et al., "SARS-CoV-2 variant B.1.1.7 is susceptible to neutralizing antibodies elicited by ancestral Spike vaccines," bioRxiv preprint doi: https://doi.org/10.1101/2021.01.27.428516, Jan. 29, 2021. (33 pages).

Starr et al., "Antibodies to the SARS-CoV-2 receptor-binding domain that maximize breadth and resistance to viral escape," bioRxiv preprint doi: https://doi.org/10.1101/2021.04.06.438709, Apr. 8, 2021. (36 pages).

Starr et al., "Prospective mapping of viral mutations that escape antibodies used to treat COVID-19," bioRxiv preprint doi: https://doi.org/10.1101/2020.11.30.405472, Dec. 1, 2020. (27 pages).

Sun et al., "Potent neutralization of SARS-CoV-2 by human antibody heavy-chain variable domains isolated from a large library with a new stable scaffold," *mAbs* 12(1):1-6, Jun. 16, 2020.

Tai et al., "Characterization of the receptor-binding domain (RBD) of 2019 novel coronavirus: implication for development of RBD protein as a viral attachment inhibitor and vaccine," *Cellular & Molecular Immunology* 17:613-620, Mar. 19, 2020.

Ter Meulen et al., "Human Monoclonal Antibody Combination against SARS Coronavirus: Synergy and Coverage of Escape Mutants," *PLoS Medicine* 3(7)e237:1071-1079, Jul. 4, 2006.

Ter Meulen et al., "Human Monoclonal Antibody Combination against SARS Coronavirus: Synergy and Coverage of Escape Mutants," *PLoS Medicine* 3(7):e237, Jul. 4, 2006. (9 pages).

Thomson et al., "Circulating SARS-CoV-2 spike N439K variants maintain fitness while evading antibody-mediated immunity," *Cell* 184(5):1171-1187.e20, Jan. 28, 2021. (67 pages).

Thomson et al., "The circulating SARS-CoV-2 spike variant N439K maintains fitness while evading antibody-mediated immunity," bioRxiv preprint doi: https://doi.org/10.1101/2020.11.04.355842. Nov. 5, 2020. (49 pages).

Tian et al., "Potent binding of 2019 novel coronavirus spike protein by a SARS coronavirus-specific human monoclonal antibody," *Emerging Microbes & Infections* 9:382-385, Feb. 17, 2020.

Tortorici et al., "Ultrapotent human antibodies protect against SARS-CoV-2 challenge via multiple mechanisms," *Science* 370:950-957, Sep. 24, 2020. (8 pages).

Tu et al., "Distinct Patterns of Emergence of SARS-CoV-2 Spike Variants including N501Y in Clinical Samples in Columbus Ohio," bioRxiv preprint doi: https://doi.org/10.1101/2021.01.12.426407. Jan. 26, 2021. (25 pages).

Voloch et al.," Genomic characterization of a novel SARS-CoV-2 lineage from Rio de Janeiro, Brazil," medRxiv preprint doi: https://doi.org/10.1101/2020.12.23.20248598, Dec. 26, 2020. (31 pages).

Walls et al., "Structure, Function, and Antigenicity of the SARS-CoV-2 Spike Glycoprotein," *Cell* 180:281-292, Apr. 10, 2020. (20 pages).

Walls et al., "Unexpected Receptor Functional Mimicry Elucidates Activation of Coronavirus Fusion," *Cell* 176:1026-1039, Feb. 21, 2019. (31 pages).

Wang et al., "A human monoclonal antibody blocking SARS-CoV-2 infection," bioRxiv preprint doi: https://doi.org/10.1101/2020.03.11.987958, Mar. 12, 2020. (24 pages).

Wang et al., "A human monoclonal antibody blocking SARS-CoV-2 infection," *Nature Communications* 11:2251, May 4, 2020. (6 pages).

Wang et al., "Antibody Resistance of SARS-CoV-2 Variants B.1.351 and B.l.1.7," bioRxiv preprint doi: https://doi.org/10.1101/2021.01.25.428137, Feb. 12, 2021. (24 pages).

Wang et al., "mRNA vaccine-elicited antibodies to SARS-CoV-2 and circulating variants," *Nature*, Feb. 10, 2021. (23 pages).

Wang et al., "Subunit Vaccines Against Emerging Pathogenic Human Coronaviruses," *Frontiers in Microbiology* 11(298):1-19, Feb. 28, 2020.

Wec et al., "Broad neutralization of SARS-related viruses by human monoclonal antibodies," *Science* 369:731-736, Aug. 7, 2020. (7 pages).

Weisblum et al., "Escape from neutralizing antibodies by SARS-CoV-2 spike protein variants," *eLife* 9:e61312, Oct. 28, 2020. (31 pages).

Wu et al., "Fully human single-domain antibodies against SARS-CoV-2," bioRxiv preprint doi: https://doi.org/10.1101/2020.03.30.015990, Mar. 31, 2020. (30 pages).

Wu et al., "Identification of Human Single-Domain Antibodies against SARS-CoV-2," *Cell Host & Microbe* 27:891-898, Jun. 10, 2020. (23 pages).

Yuan et al., "Isolation of and Characterization of Neutralizing Antibodies to Covid-19 from a Large Human Naïve scFv Phage Display Library," bioRxiv preprint doi: https://doi.org/10.1101/2020.05.19.104281, May 19, 2020. (15 pages).

Yuan et al., "Structural and functional ramifications of antigenic drift in recent SARS-CoV-2 variants," bioRxiv preprint doi: https://doi.org/10.1101/2021.02.16.430500, Feb. 17, 2021. (50 pages).

(56) References Cited

OTHER PUBLICATIONS

Yuan et al.," A highly conserved cryptic epitope in the receptor binding domains of SARS-CoV-2 and SARS-CoV," *Science* 368(6491):630-633, Apr. 3, 2020. (5 pages).

Zeng et al., "Blocking antibodies against SARS-CoV-2 RBD isolated from a phage display antibody library using a competitive biopanning strategy," bioRxiv preprint doi: https://doi.org/10.1101/2020.04.19.049643, Apr. 20, 2020. (8 pages).

Zeng et al., "Isolation of a human monoclonal antibody specific for the receptor binding domain of SARS-CoV-2 using a competitive phage biopanning strategy," *Antibody Therapeutics* 3(2):95-100, Apr. 30, 2020.

Zeng et al., "Isolation of a human monoclonal antibody specific for the receptor binding domain of SARS-CoV-2 using a competitive phage biopanning strategy," Published by Oxford University Press on behalf of *Antibody Therapeutics*, Apr. 22, 2020 (apparent). (12 pages).

Zhang et al., "The D614G mutation in the SARS-CoV-2 spike protein reduces S1 shedding and increases infectivity," bioRxiv preprint doi: https://doi.org/10.1101/2020.06.12.148726, Jun. 12, 2020. (25 pages).

Zheng et al., "Monoclonal antibodies for the S2 subunit of spike of SARS-CoV cross-react with the newly-emerged SARS-CoV-2," bioRxiv preprint doi: https://doi.org/10.1101/2020.03.06.980037, Mar. 7, 2020. (20 pages).

Zheng et al., "Monoclonal antibodies for the S2 subunit of spike of SARS-CoV cross-react with the newly-emerged SARS-CoV-2," *Euro Surveill.* 25(28):19-28, Jul. 16, 2020. (10 pages).

Zhou et al., "A pneumonia outbreak associated with a new coronavirus of probable bat origin," *Nature* 579:270-273, Mar. 12, 2020. (20 pages).

Jette et al., "Broad cross-reactivity across sarbecoviruses exhibited by a subset of COVID-19 donor-derived neutralizing antibodies," *Cell Reports* 36:109760, Sep. 28, 2021, (24 pages).

Li et al., "The impact of receptor-binding domain natural mutations on antibody recognition of SARS-CoV-2," *Signal Transduction and Targeted Therapy* 6:132, 2021. (3 pages).

Lv et al., "Structural basis for neutralization of SARS-CoV-2 and SARS-CoV by a potent therapeutic antibody," *Science* 369:1505-1509, Sep. 18, 2020. (6 pages).

| | EC50 |
|---|---|
| S303 | 1.056 |
| S304 | 11.38 |
| S306 | 20.83 |
| S309 | 1.439 |
| S310 | 254.3 |
| S315 | 7.589 |
| S110 | 0.7819 |
| S124 | 0.9518 |
| S230 | 0.8861 |
| S109 | 2.899 |

FIG. 12B

Hu conv SARS CoV 1 control serum

- SDS Lysate
- TX100 Lysate

ELISA OD (Inf-Unf) vs Pos Ab diln (512, 1024, 2048, 4096, 8192, 16384)

| Static dose (of EC50) | Passage | FFU/mL | % CPE at 72 hours p.i. |
|---|---|---|---|
| No Ab | 1 | 6.44E+05 | 85-90 |
| 10x | 1 | – | 0 |
| 20x | 1 | – | 0 |
| 50x | 1 | – | 0 |
| 100x | 1 | – | 0 |
| No Ab | 2 | 4.70E+05 | 80 |
| 10x | 2 | – | 0 |
| 20x | 2 | – | 0 |
| 50x | 2 | – | 0 |
| 100x | 2 | – | 0 |
| No Ab | 3 | 9.60E+05 | 80 |
| 10x | 3 | – | 0 |
| 20x | 3 | – | 0 |
| 50x | 3 | – | 0 |
| 100x | 3 | – | 0 |
| No Ab | 4 | 1.00E+05 | 80 |
| 10x | 4 | – | 0 |
| 20x | 4 | – | 0 |
| 50x | 4 | – | 0 |
| 100x | 4 | – | 0 |
| No Ab | 10 | 1.53E+06 | 70-90 |
| 10x | 10 | – | 0 |
| 20x | 10 | – | 0 |
| 50x | 10 | – | 0 |
| 100x | 10 | – | 0 |

*FIG. 44C*

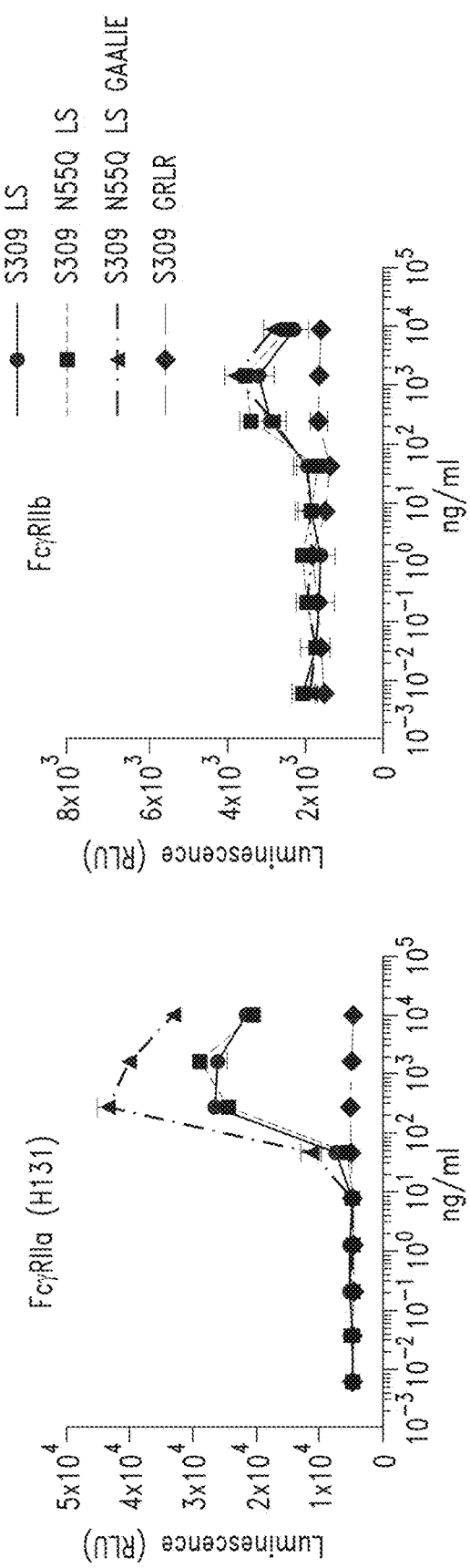
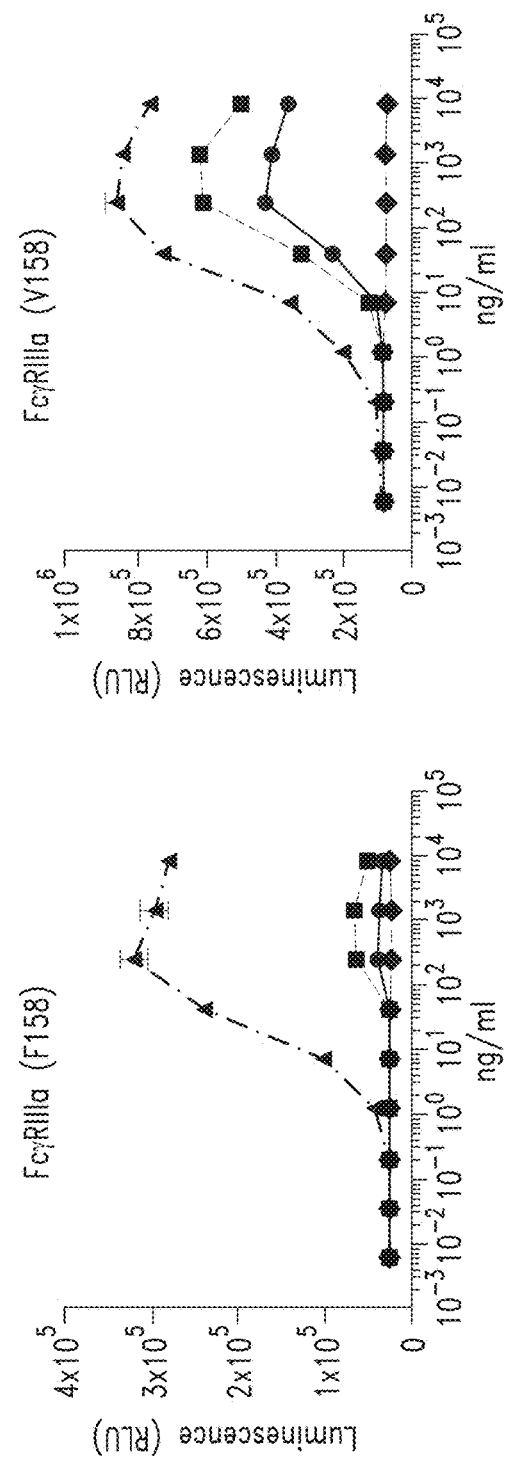
FIG. 55A, FIG. 55B, FIG. 55C, FIG. 55D

ANTIBODIES AGAINST SARS-COV-2 AND METHODS OF USING THE SAME

CROSS-REFERENCES TO RELATED APPLICATIONS

This application is a continuation application of U.S. patent application Ser. No. 17/185,340, filed Feb. 25, 2021; which claims the benefit of U.S. Provisional Application No. 62/981,984, filed Feb. 26, 2020; and claims the benefit of U.S. Provisional Application No. 62/982,661, filed Feb. 27, 2020; and claims the benefit of U.S. Provisional Application No. 62/987,298, filed Mar. 9, 2020; and claims the benefit of U.S. Provisional Application No. 62/989,522, filed Mar. 13, 2020; and claims the benefit of U.S. Provisional Application No. 62/990,369, filed Mar. 16, 2020; and claims the benefit of U.S. Provisional Application No. 62/992,082, filed Mar. 19, 2020; and claims the benefit of U.S. Provisional Application No. 62/994,235, filed Mar. 24, 2020; and claims the benefit of U.S. Provisional Application No. 63/001,204, filed Mar. 27, 2020; and claims the benefit of U.S. Provisional Application No. 63/003,214, filed Mar. 31, 2020; and claims the benefit of U.S. Provisional Application No. 63/005,206, filed Apr. 3, 2020; and claims the benefit of U.S. Provisional Application No. 63/010,589, filed Apr. 15, 2020; and claims the benefit of U.S. Provisional Application No. 63/011,971, filed Apr. 17, 2020; and claims the benefit of U.S. Provisional Application No. 63/014,024, filed Apr. 22, 2020; and claims the benefit of U.S. Provisional Application No. 63/023,788, filed May 12, 2020; and claims the benefit of U.S. Provisional Application No. 63/025,133, filed May 14, 2020; and claims the benefit of U.S. Provisional Application No. 63/039,813, filed Jun. 16, 2020; and claims the benefit of U.S. Provisional Application No. 63/043,653, filed Jun. 24, 2020; and claims the benefit of U.S. Provisional Application No. 63/050,331, filed Jul. 10, 2020; and claims the benefit of U.S. Provisional Application No. 63/052,810, filed Jul. 16, 2020; which applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 930585_402C1_SEQUENCE_LISTING.txt. The text file is 328 KB, was created on Jul. 22, 2021, and is being submitted electronically via EFS-Web.

BACKGROUND

A novel betacoronavirus emerged in Wuhan, China, in late 2019. As of Feb. 19, 2021, approximately 110 million cases of infection by this virus (termed, among other names, SARS-CoV-2 and originally identified as Wuhan coronavirus), were confirmed worldwide, and had resulted in approximately 2.45 million deaths. Modalities for preventing or treating SARS-CoV-2 infection, and diagnostic tools for diagnosing a SARS-CoV-2 infection, are needed.

BRIEF DESCRIPTION OF THE DRAWINGS

FIG. 3A shows neutralization by donor plasma from SARS-CoV-1 survivors. FIGS. 3B-3D and 3I show neutralization by supernatant from B cells expressing certain antibodies of the present disclosure. FIGS. 3E-3H show neutralization by certain recombinant IgG1 antibodies.

FIGS. 12A and 12B show concentration-dependent binding measured by flow cytometry for certain antibodies, as described in Example 9. FIG. 12A shows binding to SARS-CoV-2. FIG. 12B shows binding to SARS-CoV-1.

FIG. 17A shows antibody-dependent cytotoxicity using primary NK effector cells and SARS-CoV-2-expressing ExpiCHO cells as target cells. Bar graph at right shows ADCC for the indicated antibody(ies), calculated as area under the curve (AUC). FIG. 17B shows antibody-dependent cellular phagocytosis using PBMCs as phagocytic cells and PKF67-labelled SARS-CoV-2-expressing ExpiCHO as target cells. Line graphs show mean fluorescence intensity (MFI) of PBMCs after incubation with target cells and antibodies, determined for one representative donor with high affinity FcγRIIIa (symbols show means±SD of duplicates).

FIG. 19A shows SARS-CoV-1 RBD binding to ACE2. FIG. 19B shows SARS-CoV-2 RBD binding to ACE2.

FIG. 21A-21C show reactivity of S304 (VH SEQ ID NO.:79; VL SEQ ID NO.:83), S306 (VH SEQ ID NO.:87; VL SEQ ID NO.:91), S309 (VH SEQ ID NO.:105; VL SEQ ID NO.:168), and S310 (VH SEQ ID NO.:155; VL SEQ ID NO.:159) antibodies against SARS-CoV-2, as described in Example 15. FIG. 21A shows reactivity of S304, S306, S309, and S310 antibodies against TX100 extracted lysate of SARS-CoV-2 infected Vero E6 cells. FIG. 21B shows reactivity of the same antibodies against SDS extracted lysate of SARS-CoV-2 infected Vero E6 cells. FIG. 21C shows reactivity of human SARS-CoV-1 convalescent serum against TX100 extracted or SDS extracted lysate of SARS-CoV-2 infected Vero E6 cells. FIGS. 21A and 21B also show data for comparator antibody LCA57, which is specific for spike protein of MERS-CoV (Corti et al. *PNAS* 112(33):10473-10478 (2015).

FIG. 22A shows neutralization of SARS-CoV-2 infection by S304 S304 (VH SEQ ID NO.:79; VL SEQ ID NO.:83). FIG. 22B shows neutralization of SARS-CoV-2 infection by S309 (VH SEQ ID NO.:105; VL SEQ ID NO.:168. FIG. 22C shows neutralization of SARS-CoV-2 infection by the combination of S304 and S309. FIG. 22D shows control neutralization of SARS-CoV-2 infection by comparator antibody LCA57, which is specific for spike protein of MERS-CoV (Corti et al. *PNAS* 112(33):10473-10478 (2015)).

FIG. 24A shows antibody-dependent cell-mediated cytotoxicity (ADCC) using primary NK effector cells and SARS-CoV-2-expressing ExpiCHO cells as target cells. The graph shows the % killing of target cells after incubation with antibody or combination of antibodies shown in the legend. FIG. 24B shows ADCC for the indicated antibody(ies), calculated as area under the curve (AUC). Left panel: AUC determined using cells with VV FcγRIIIa genotype; right panel: AUC determined for cells with FF or FV FcγRIIIa genotype.

FIG. 25A shows antibody-dependent cellular phagocytosis (ADCP) using PBMCs as phagocytic cells and PKF67-labelled SARS-CoV-2-expressing ExpiCHO cells as target cells. The graph shows mean fluorescence intensity (MFI) of PBMCs after incubation with target cells and antibodies, determined for one representative donor with high affinity FcγRIIIa (symbols show means±SD of duplicates). FIG. 25B shows ADCP for the indicated antibody(ies), calculated as area under the curve (AUC).

In FIG. 27, S309 N55Q is labeled as "12," S309 W50F is labeled as "13," S309 W105F is labeled as "14," and S309 W50E-G56A-W105F is labeled as "15." Antibody binding to SARS-CoV-2 Spike protein expressed on Expi-CHO cells was detected with a fluorescently labeled secondary antibody. Data from two experiments are shown.

FIG. 28 shows neutralization of infection by antibody S309 (referred to in the figure as "Variant-11 (wt)") and four S309 variant antibodies against SARS-CoV-2 pseudotyped viruses, as described in Example 19. In FIG. 28, S309 N55Q is labeled as "Variant-12," S309 W50F is labeled as "Variant-13," S309 W105F is labeled as "Variant-14," and S309 W50E-G56A-W105F is labeled as "Variant-15." Pseudotyped viruses are VSV pseudotyped with SARS-CoV-2 Spike protein.

FIG. 29 shows a summary of results from binding and pseudovirus neutralization assays for antibody S309 ("S309-WT") and four engineered variants of S309 ("N55Q"; "W50F"; "W105F"; "W50F/G56A/W105F"). The dashed horizontal line shows change of function of engineered variant versus S309-WT baseline. Differently hatched bars show binding to glycosylated RBD as measured by SPR, binding to deglycosylated RBD as measured by SPR, binding to antigen-expressing cells, as measured by FACS, and neutralization as measured using SARS-CoV-2 pseudoviruses.

FIG. 30A shows binding kinetics of S309 wild type antibody (2 replicate experiments). FIG. 30B shows binding kinetics of S309 N55Q (bottom), as compared to S309 wild type antibody (top). FIG. 30C shows binding kinetics of S309 W50F (bottom) as compared to S309 wild type antibody (top).

FIG. 30D shows binding kinetics of S309 W105F (bottom) as compared to S309 wild type antibody (top). FIG. 30E shows binding of S309 W50F/G56A/W105F (bottom) as compared to S309 wild type antibody (top). FIG. 30F shows binding of S309 W50F/G56A/W105F using 10 minute injection period (top panel) or 3 minute injection period (bottom panel).

FIG. 33A shows binding to ExpiCHO cells transfected with SARS-CoV-2 S protein. FIG. 33B shows binding to ExpiCHO cells transfected with SARS-CoV-1 S protein. Mean fluorescence intensity was measured by flow cytometry for each antibody. Antibody concentrations tested are indicated in the x-axis.

FIG. 35A shows Spike protein variants occurring with a frequency of n>1 as spheres mapped onto the closed (left) and open (right) form of the full trimeric Spike ectodomain. The RBD and other Spike protein domains are shown as indicated. 40 mutations (out of 2229 total) are shown. Only residue 367 (n=8) is highlighted in the RBD, and residues 476 (n=7) and 483 (n=17) are not. FIG. 35B shows the prevalence of variants in Spike glycoprotein by amino acid. Each dot is a distinct variant. The locations of Domain A and RBD are shown. Variants passing a frequency threshold of 0.1% are as indicated.

FIG. 39A shows binding of recombinant antibody S300 (VH: SEQ ID NO.:1; VL: SEQ ID NO.:5). FIG. 39B shows binding of recombinant antibody S307. Symbols show the values of a single measurement. Left panel of each figure shows data presented as % positive cells and right panel shows data presented as mean fluorescent intensity (MFI).

FIG. 42A shows binding to ExpiCHO cells transfected with SARS-CoV-2 S protein. FIG. 42B shows binding to ExpiCHO cells transfected with SARS-CoV-1 S protein. Mean fluorescence intensity was measured by flow cytometry for each antibody. Antibody concentrations tested are indicated in the x axis.

FIGS. 44A-44C show resistance selection of SARS-CoV-2, as described in Example 23. FIG. 44A is a flow chart showing a method for resistance selection. FIG. 44B is a timeline showing the procedure used for each passage of the resistance selection process. FIG. 44C shows the results of selecting for SARS-CoV-2 resistant to antibody S309 N55Q MLNS GAALIE, comprising a VH according to SEQ ID NO.:113 and a VL according to SEQ ID NO.:168, with G236A, A330L, I332E, M428L and N434S mutations in the Fc (EU numbering).

FIG. 48A shows photographs of representative wells, in which cell nuclei were stained blue and SARS-CoV-2 nucleocapsid were stained red, which shows up more brightly in the photographs. Each red spot in each image represents an individual infected cell. The neutralization of infection by antibody S309 can be observed as a decrease in the number of bright spots, indicating infected cells, as the concentration of S309 was increased. Antibody concentrations are shown across the top, and viral concentrations in MOI (multiplicity of infection) units are shown on the left. FIG. 48B shows quantified data from the IFA assay. Calculated IC50 values for each MOI are shown in the boxes below the graph.

Figure 50A:
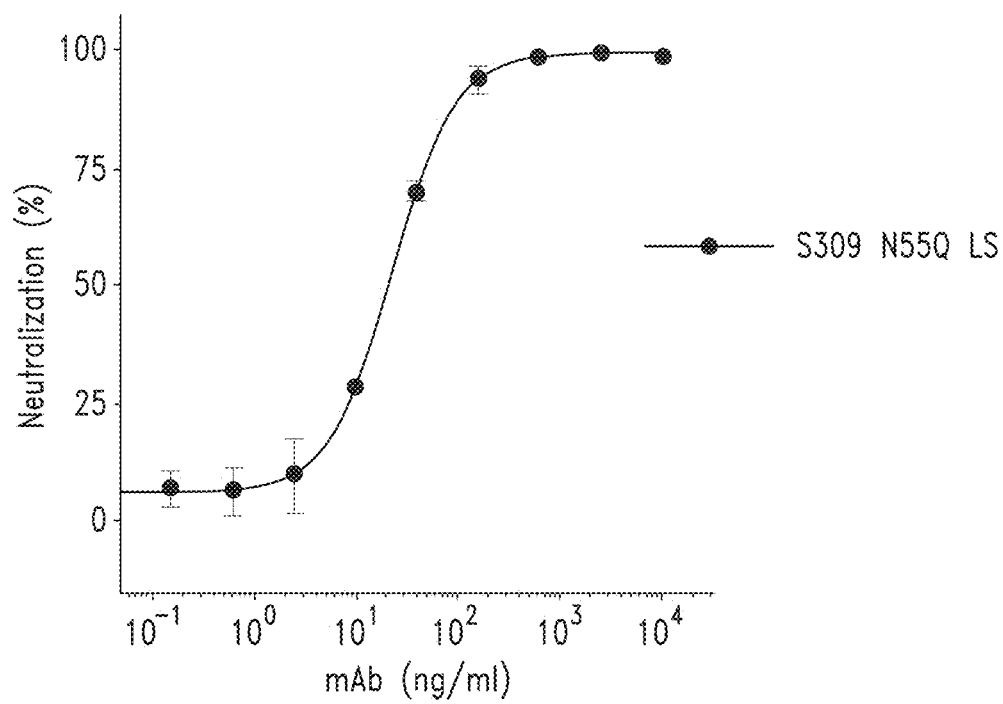
Figure 50B:
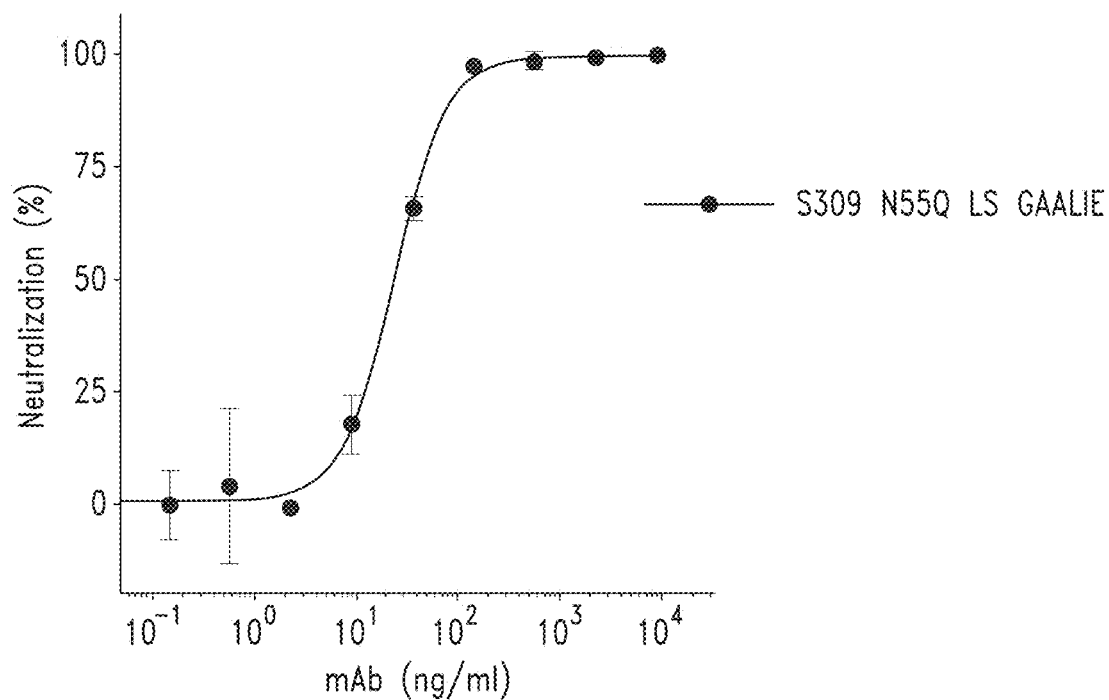

FIGS. 50A and 50B show neutralization of infection by SARS-CoV-2 pseudotyped viruses using antibodies S309 N55Q LS (also referred to herein as S309 N55Q MLNS, comprising M428L/N434S Fc mutations (EU numbering)) (FIG. 50A) and S309 N55Q LS GAALIE (also referred to herein as S309 N55Q MLNS GAALIE, comprising G236A, A330L, I332E, M428L, and N434S Fc mutations (EU numbering)) (FIG. 50B). See Example 27. Pseudotyped viruses are VSV pseudotyped with SARS-CoV-2 Spike protein. Data represent the means of duplicates, +/−standard deviation. Each graph shown is representative of four independent experiments.

Figure 51A:
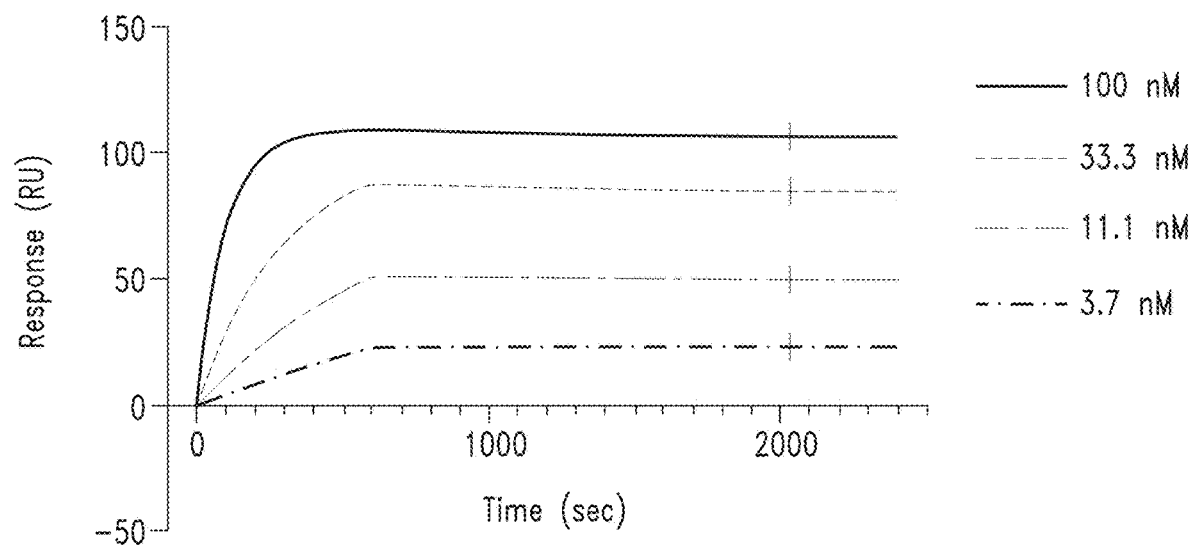
Figure 51B:
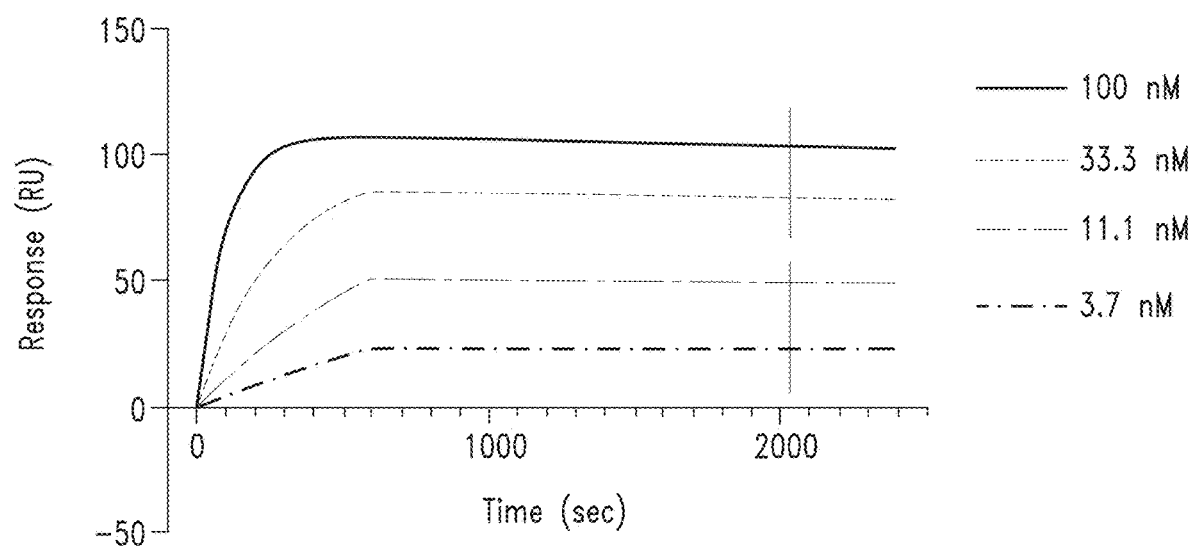

FIGS. 51A and 51B show binding of antibodies S309 N55Q MLNS (FIG. 51A) and S309 N55Q MLNS GAALIE (FIG. 51B) to SARS-CoV-2 RBD, as measured by surface plasmon resonance (SPR). See Example 28. Values are from two independent experiments.

Figure 52A:
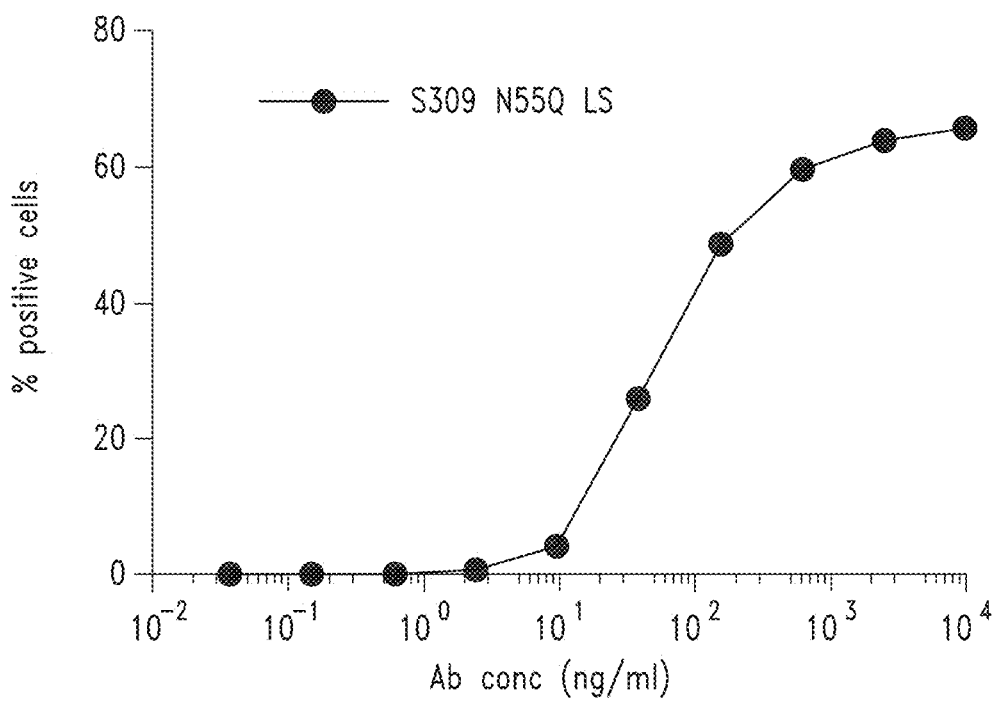
Figure 52B:
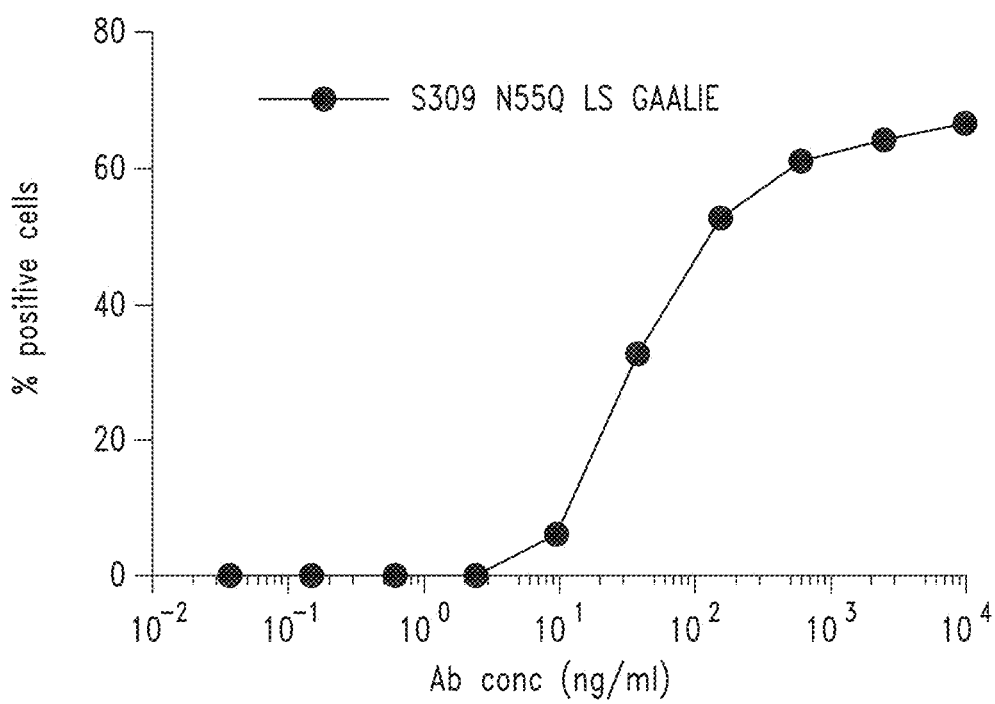

FIGS. 52A and 52B show binding of antibodies S309 N55Q LS (also referred to herein as S309 N55Q MLNS, comprising M428L/N434S Fc mutations (EU numbering)) (FIG. 52A) and S309 N55Q LS GAALIE (also referred to herein as S309 N55Q MLNS GAALIE, comprising G236A, A330L, I332E, M428L, and N434S Fc mutations (EU numbering)) (FIG. 52B) to cell surface-expressed SARS-CoV-2 Spike protein, as measured by flow cytometry. See Example 29. Data are expressed as the percentage of cells identified as positive for antibody binding. Results shown are from one experiment and representative of three independent individual experiments performed.

Figure 53:
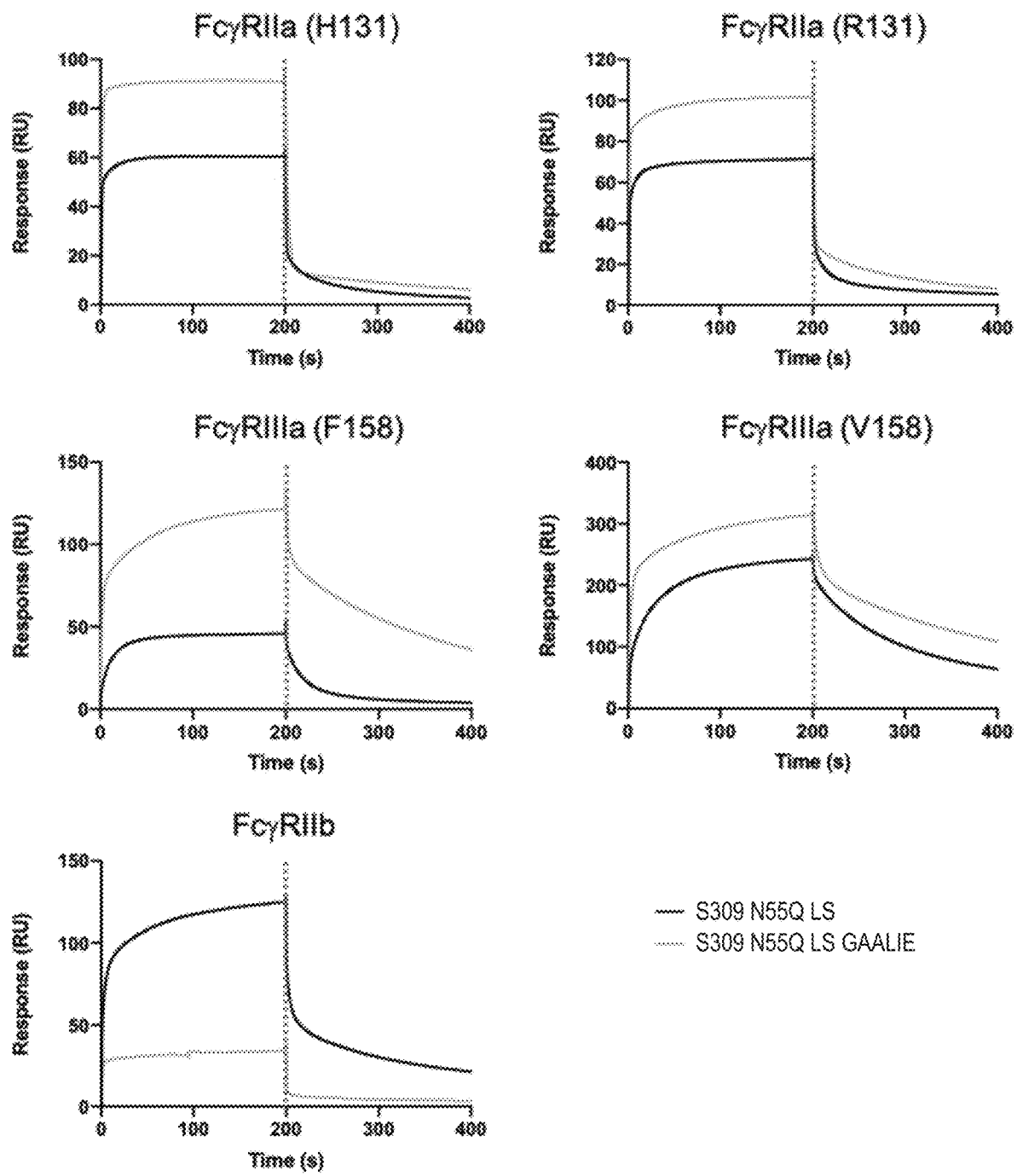

FIG. 53 shows binding of antibodies S309 N55Q MLNS and S309 N55Q MLNS GAALIE to human FcγRIIa (both low affinity R131 and high affinity H131 alleles), FcγRIIIa (both low affinity F158 and high affinity V158 alleles), and FCγRIIb, using SPR. See Example 30. Biotinylated purified FcγRs were captured on the sensor chip surface prior to injection of the antibody. Association and dissociation profiles (separated by the vertical dotted line in each graph) were measured in real time as change in the SPR signal.

Figure 54:
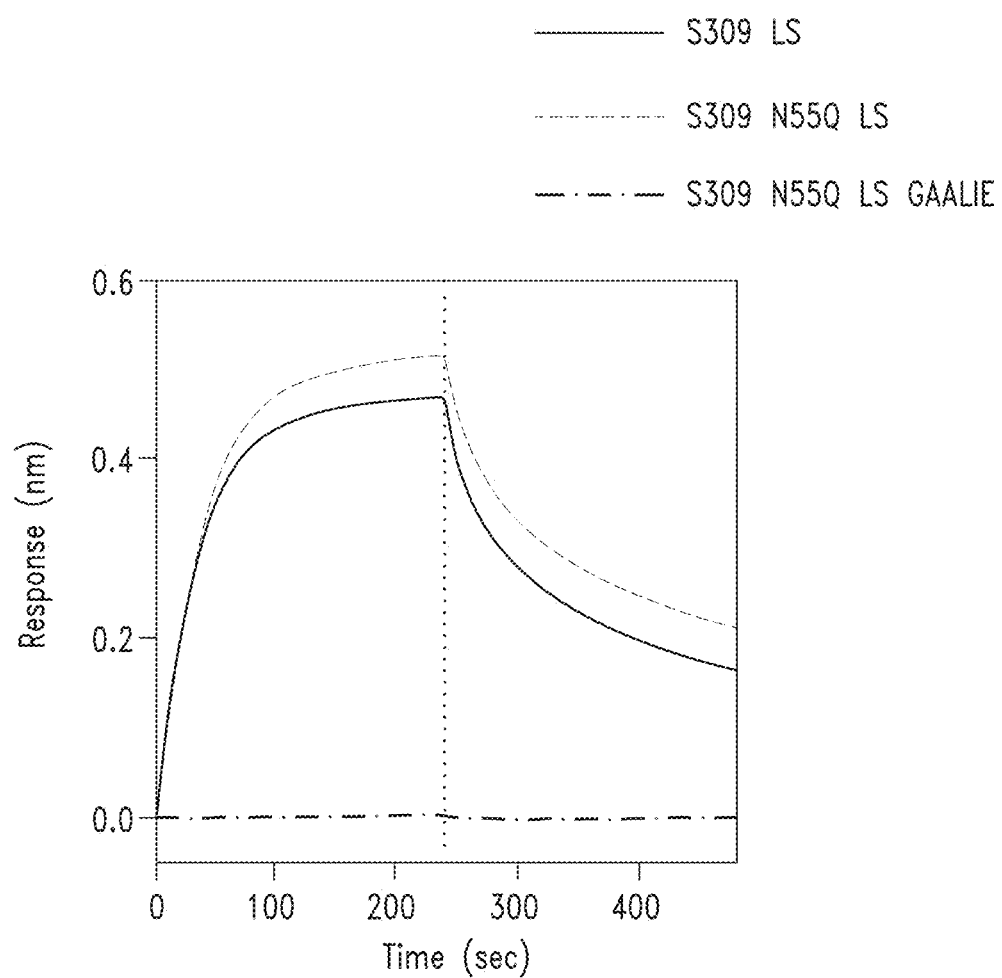

FIG. 54 shows binding of antibodies S309 (VH: SEQ ID NO.:105; VL: SEQ ID NO.:168) LS (also referred to herein as S309 MLNS, comprising M428L/N434S Fc mutations), S309 N55Q (VH: SEQ ID NO.:113; VL: SEQ ID NO.:168) LS (also referred to herein as S309 N55Q MLNS, comprising M428L and N434S Fc mutations (EU numbering)), and S309 N55Q LS GAALIE (also referred to herein as S309 N55Q MLNS GAALIE, comprising G236A, A330L, I332E, M428L, and N434S Fc mutations (EU numbering)) to complement component C1q, as measured by BLI on an Octet instrument. See Example 31. Association and dissociation profiles (separated by the vertical dotted line on the graph) were measured in real time as change in the interference pattern.

FIGS. 55A-55D show in vitro activation of human FcγRs by antibodies S309 (VH: SEQ ID NO.:105; VL: SEQ ID NO.:168) LS (also referred to herein as S309 MLNS, comprising M428L/N434S Fc mutations), S309 N55Q (VH: SEQ ID NO.:113; VL: SEQ ID NO.:168) LS (also referred to herein as S309 N55Q MLNS, comprising M428L/N434S Fc mutations) (EU numbering)), and S309 N55Q LS GAALIE (also referred to herein as S309 N55Q MLNS GAALIE, comprising G236A, A330L, I332E, M428L, and N434S Fc mutations (EU numbering)), along with negative control antibody S309 GRLR. See Example 32. CHO cells stably transfected with the SARS-CoV-2 Spike protein served as antibody targets. Serial dilutions of antibody were incubated with target cells at room temperature for 15 minutes. Jurkat effector cells expressing the indicated FcγR and engineered with a NFAT-mediated luciferase reporter were resuspended in assay buffer and then added to assay plates. After incubation at 37° C. for 18 hours, Bio-Glo™ Luciferase Assay Reagent (Promega) was added and luminescence was quantified using a liminometer (Bio-Tek). Graphs show activation of human FcγRIIa (top left), FcγRIIb (top right), FcγRIIIa low affinity F158 allele (bottom left) and FCγRIIb high affinity V158 allele (bottom right). Data shown are means+/−standard deviation of duplicates.

Figures 56A, 56B:
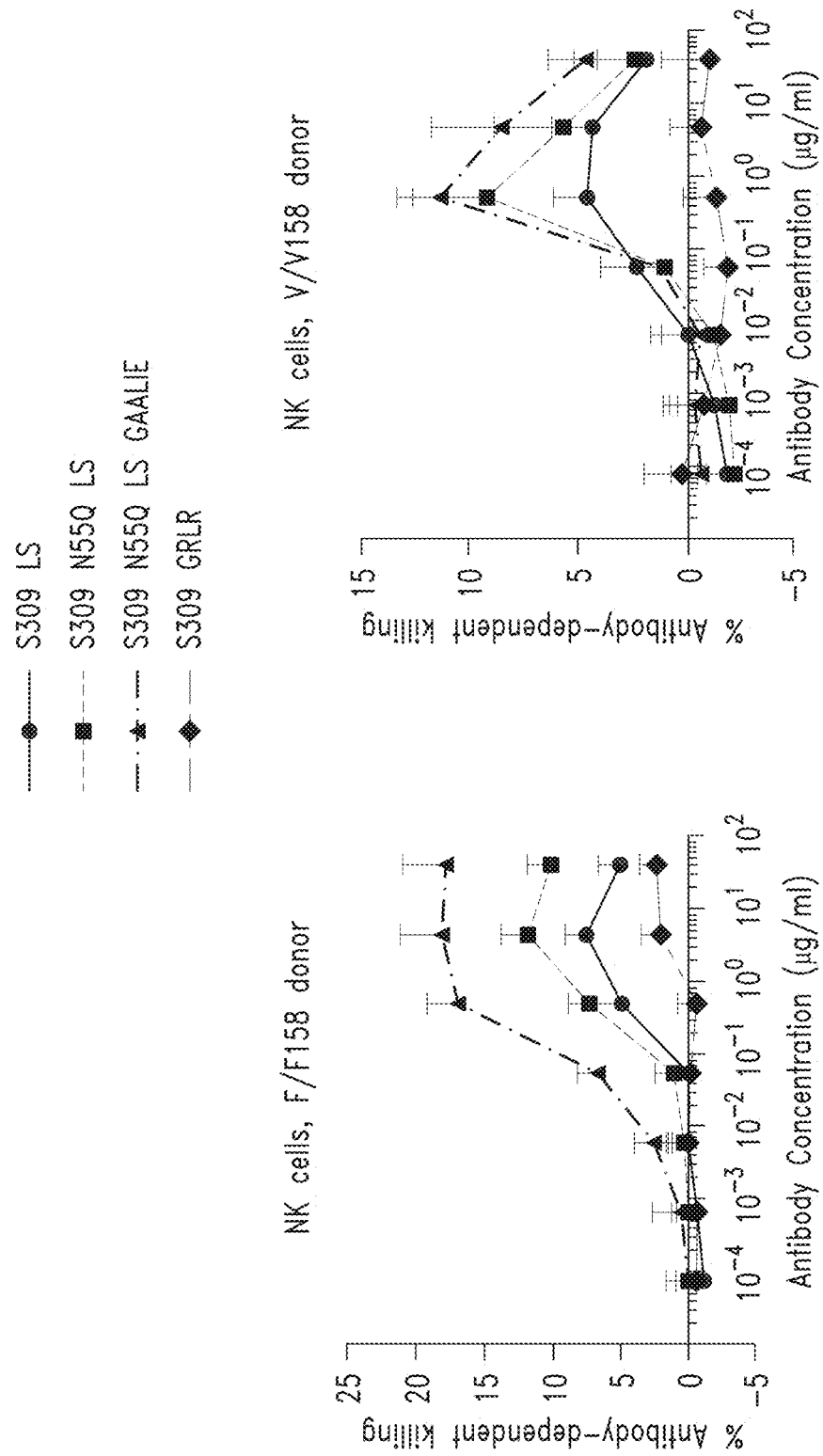

FIGS. 56A and 56B show in vitro NK cell mediated killing (ADCC) of cells expressing SARS-CoV-2 Spike protein in the presence of antibodies S309 (VH: SEQ ID NO.:105; VL: SEQ ID NO.:168) LS (also referred to herein as S309 MLNS, comprising M428L/N434S Fc mutations), S309 N55Q (VH: SEQ ID NO.:105; VL: SEQ ID NO.:168) LS (also referred to herein as S309 N55Q MLNS, comprising M428L/N434S Fc mutations (EU numbering)), or S309 N55Q LS GAALIE (also referred to herein as S309 N55Q MLNS GAALIE, comprising G236A, A330L, I332E, M428L, and N434S Fc mutations (EU numbering)), or control antibody S309 GRLR. See Example 33. Serial dilutions of antibody (serially diluted 10-fold in AIM-V Medium from 40,000 ng/ml to 0.075 ng/ml) were incubated with CHO-CoV-2 Spike cells for 10 minutes before mixing with NK cells for 4 hours. NK cells were freshly isolated from two donors previously genotyped for homozygous expression of low-affinity (F/F158; FIG. 56A) or high-affinity (V/V158; FIG. 56B). ADCC was measured using LDH release assay. Data shown are means+/−standard deviation of quadruplicates.

Figure 57:
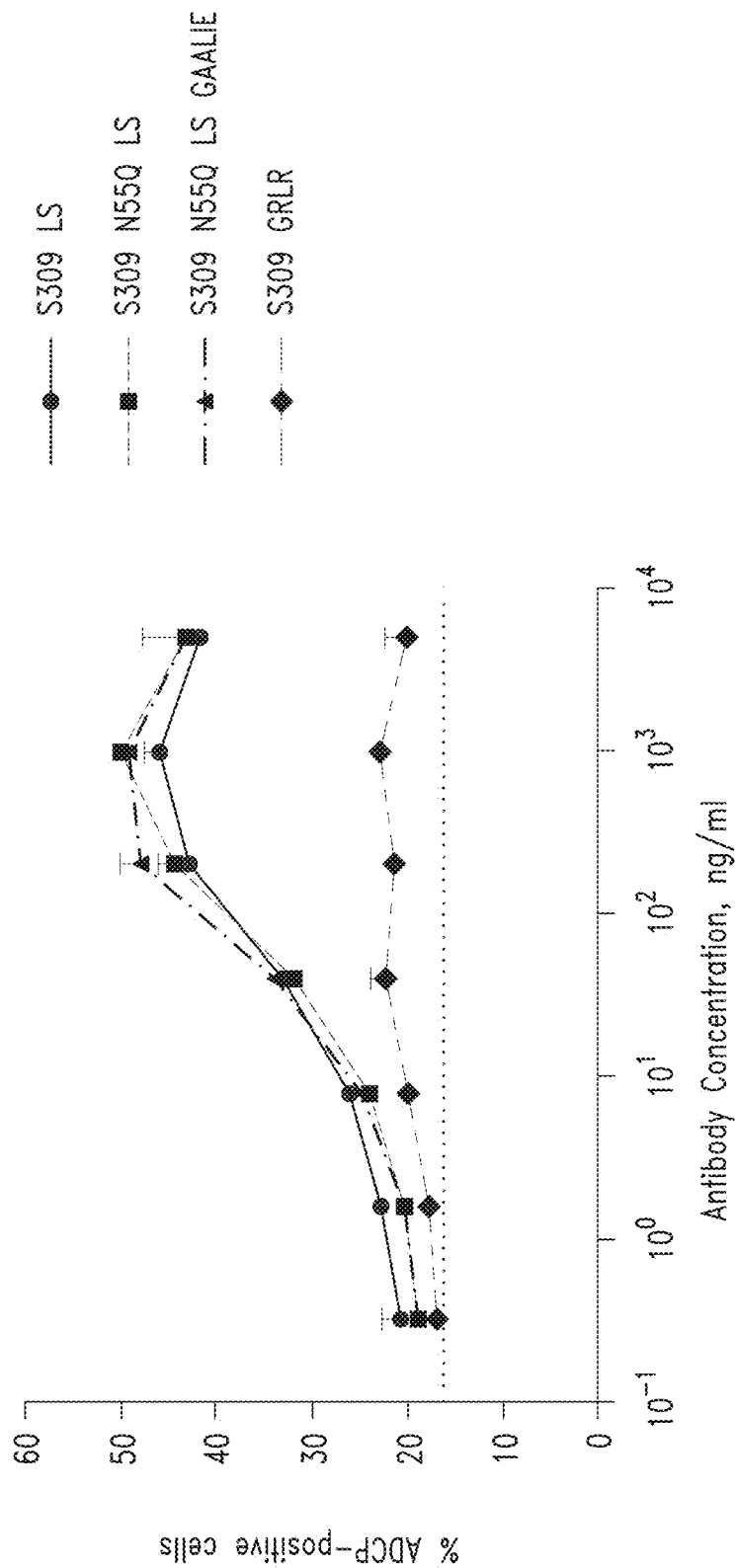

FIG. 57 shows in vitro monocyte-mediated phagocytosis (ADCP) of cells expressing SARS-CoV-2 Spike protein in the presence of antibodies S309 (VH: SEQ ID NO.:105; VL: SEQ ID NO.:168) LS (also referred to herein as S309 MLNS, comprising M428L/N434S Fc mutations), S309 N55Q (VH: SEQ ID NO.:113; VL: SEQ ID NO.:168) LS (also referred to herein as S309 N55Q MLNS, comprising M428L and N434S Fc mutations (EU numbering)), or S309 N55Q LS GAALIE (also referred to herein as S309 N55Q MLNS GAALIE, comprising G236A, A330L, I332E, M428L, and N434S Fc mutations (EU numbering)), or control antibody S309 GRLR. See Example 33. Antibodies were incubated with PKH67-labeled CHO-CoV-2-Spike cells for 10 minutes before mixing with freshly isolated, cell trace violet labeled PBMCs. ADCP activity was measured after overnight incubation by flow cytometry as percentage of CD14+ monocytes that were double positive for PKH67 and cell trace violet. Data shown are means+/−standard deviation of duplicates.

Figure 58A:
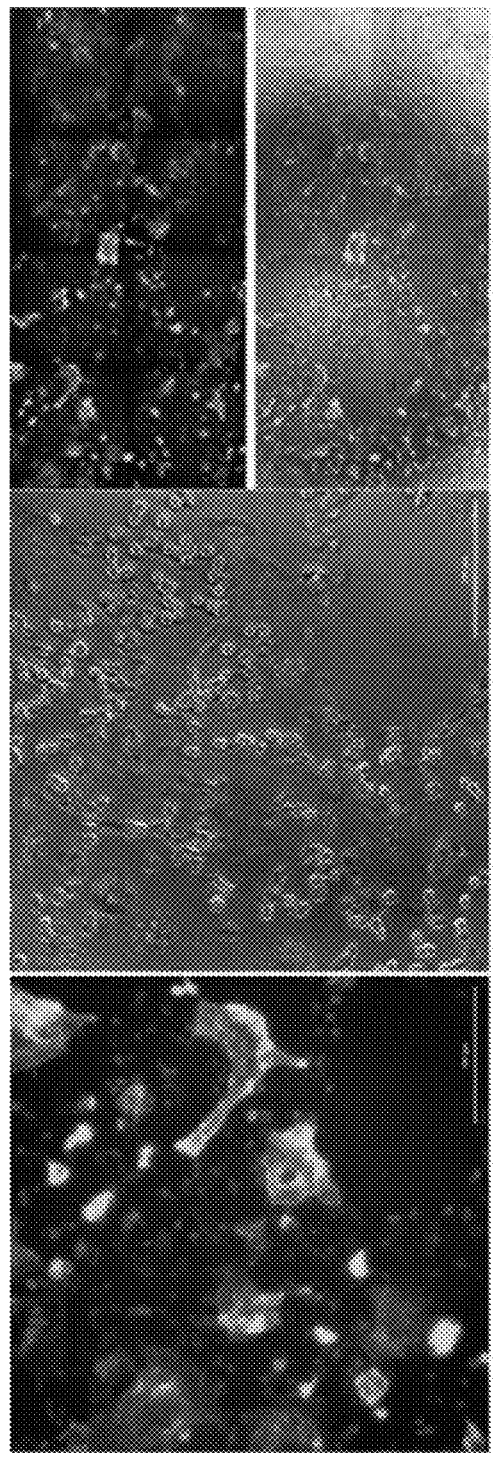
Figure 58A:
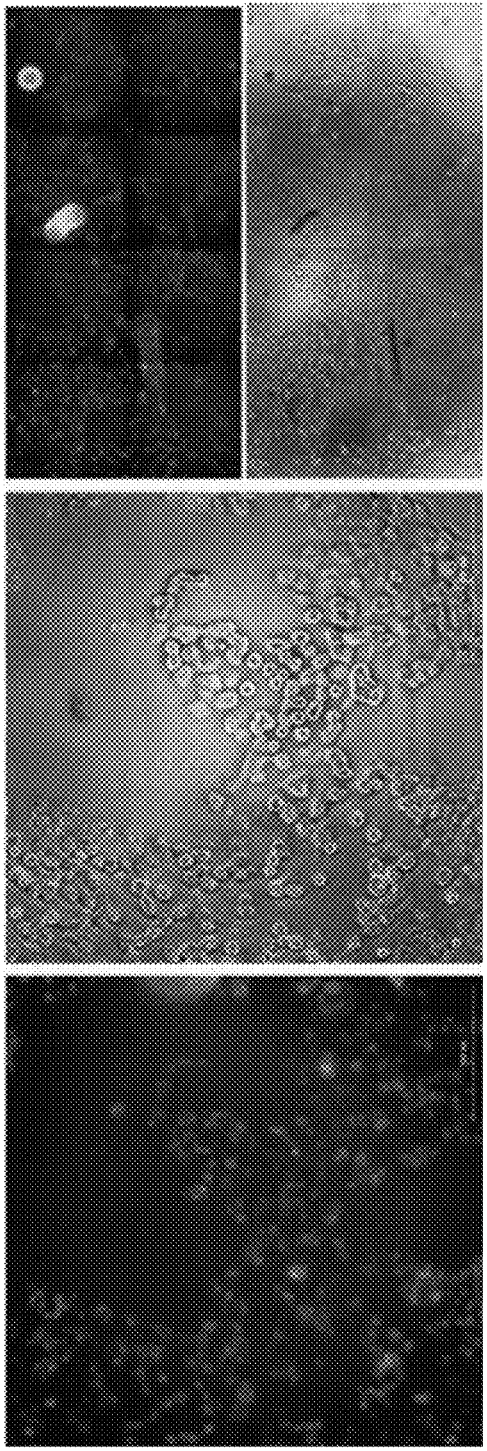
Figure 58B:
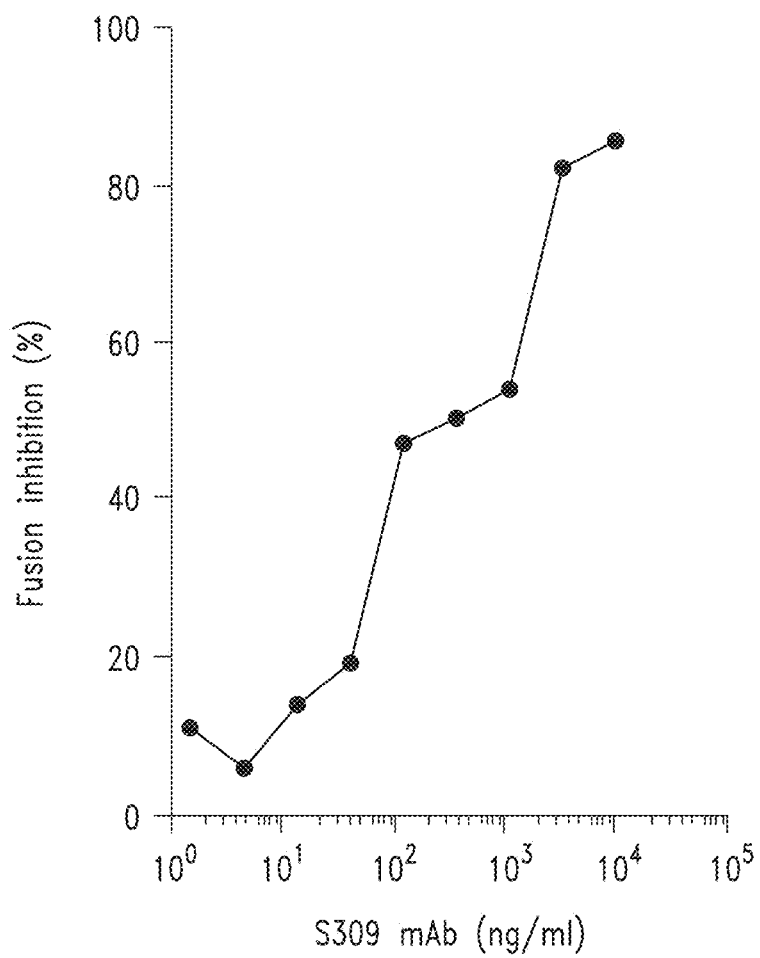

FIGS. 58A and 58B show that antibody S309 (VH: SEQ ID NO.:105; VL: SEQ ID NO.:168) inhibits SARS-CoV-2 Spike protein-mediated cell-cell fusion. See Example 34. FIG. 58A shows micrographs of cells engineered to overexpress SARS-CoV-2 Spike protein in the presence (bottom panel) or absence (upper panel) of S309. FIG. 58B shows quantified data from the fusion inhibition assay at various concentrations of antibody.

Figure 59:
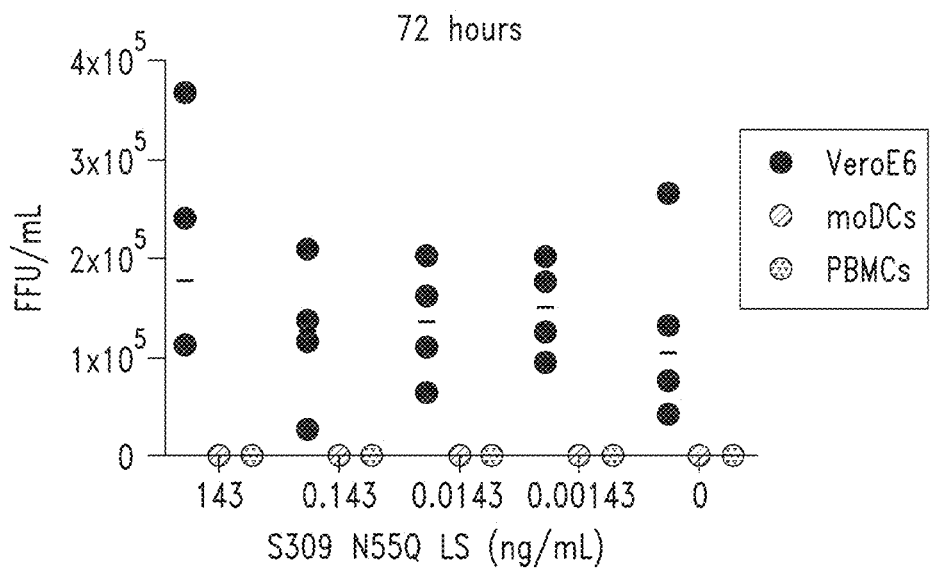
Figure 59:
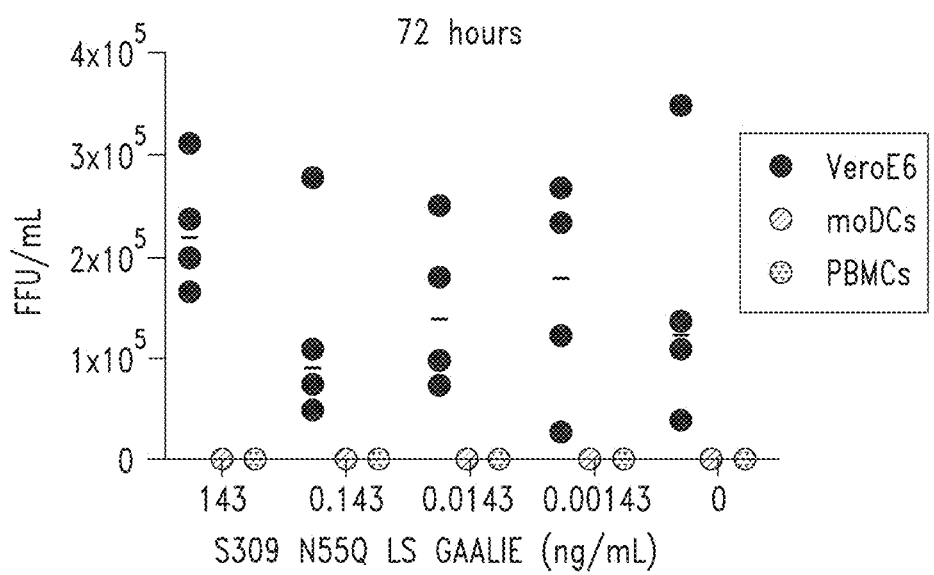

FIG. 59 provides data from a focus-forming units (FFU) assay showing that S309 N55Q variant antibodies do not cause antibody-mediated enhancement of SARS-CoV-2 replication in human donor-derived PBMCs or dendritic cells. See Example 35.

Figure 60:
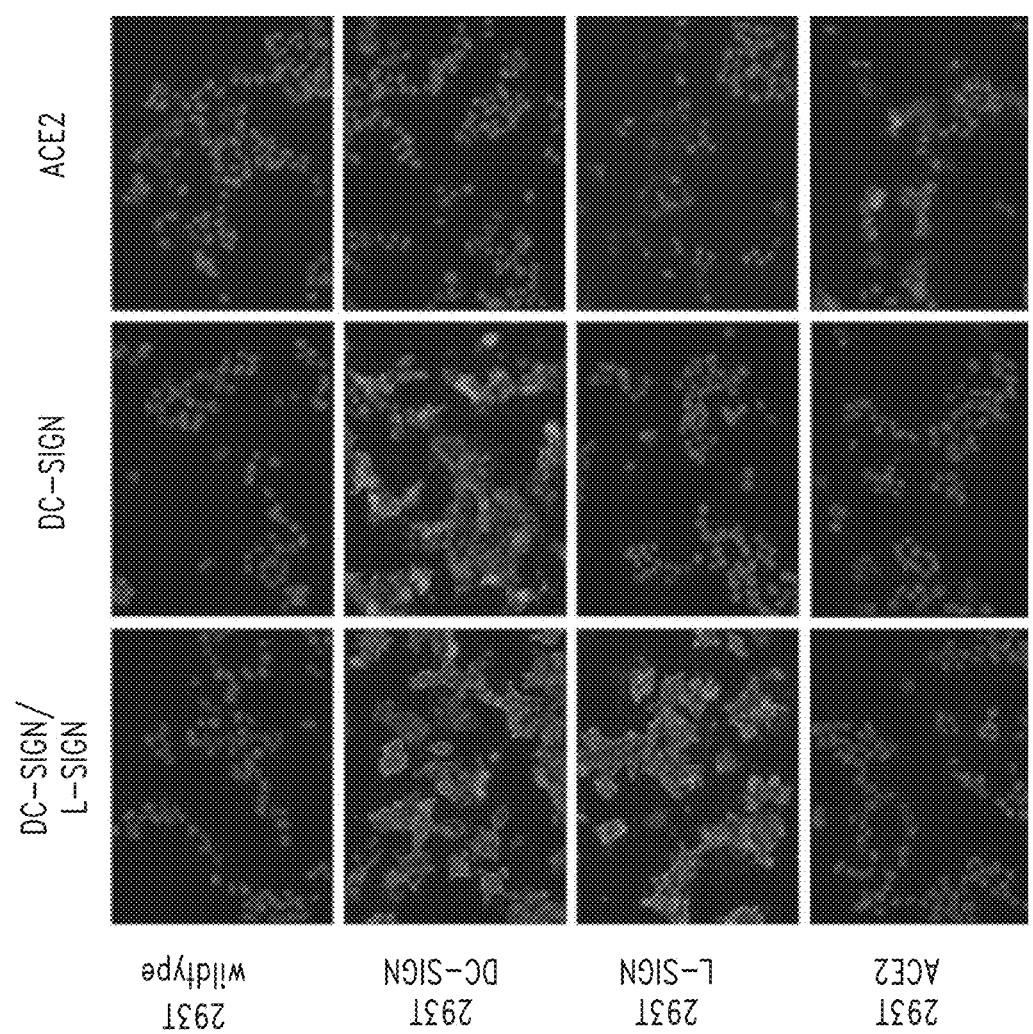

FIG. 60 shows expression (immunofluorescence) of DC-SIGN/L-SIGN, DC-SIGN, and ACE2 transgenes in HEK293T cells engineered to overexpress the indicated protein. See Example 37.

Figure 61:
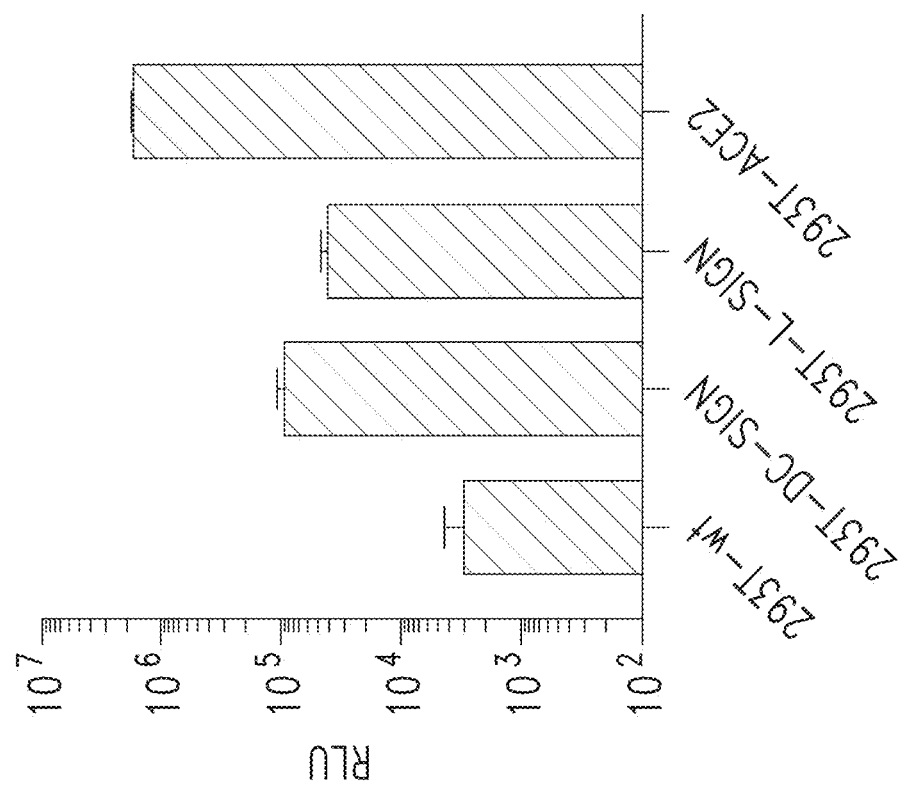

FIG. 61 shows VSV pseudovirus infection levels in wild-type HEK293T cells and in HEK293T cells engineered to overexpress DC-SIGN, L-SIGN, or ACE2. The pseudovirus expressed a recombinant SARS-CoV-2 spike protein with luciferase reporter. See Example 37.

Figure 62:
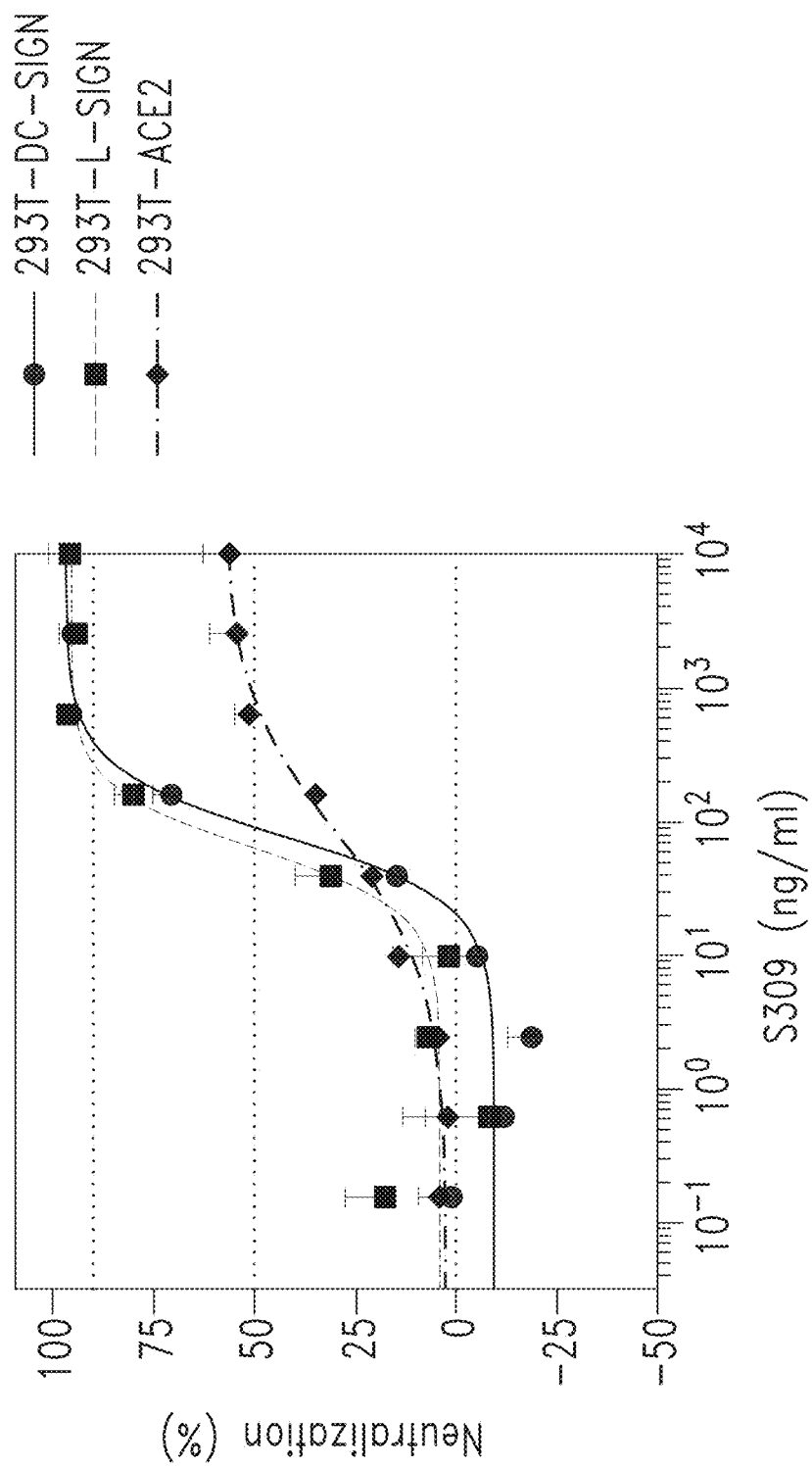

FIG. 62 shows neutralization by monoclonal antibody S309 (VH of SEQ ID NO.:105, VL of SEQ ID NO.:168) of VSV pseudovirus infection in HEK293T cells engineered to overexpress DC-SIGN, L-SIGN, or ACE2. In this example, antibody S309 includes M428L and N434S Fc mutations (EU numbering). See Example 37.

Figure 63:
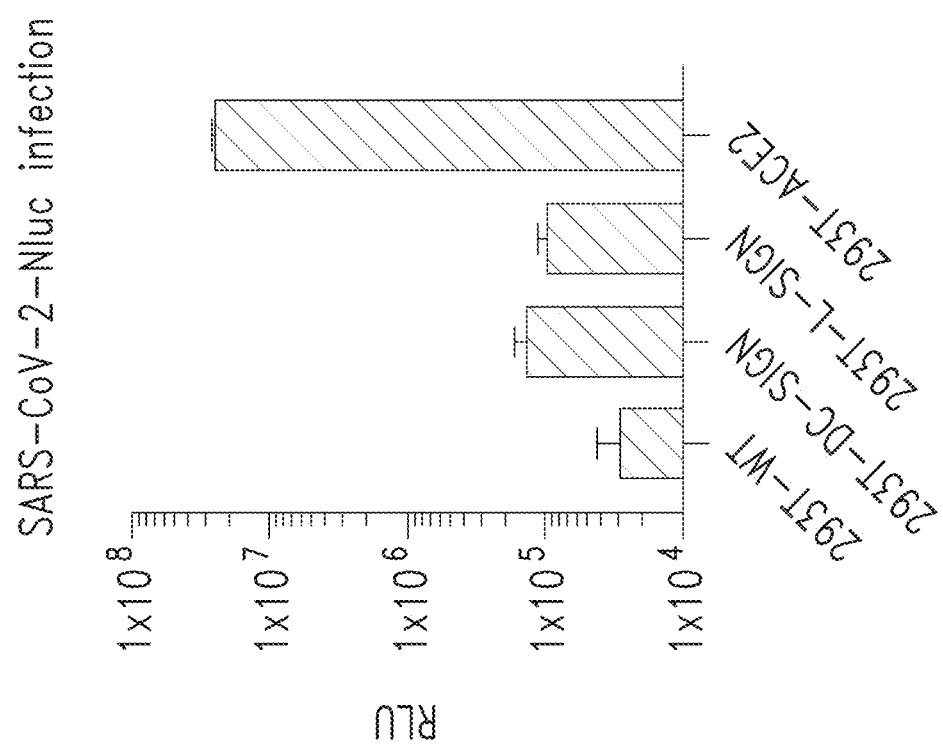

FIG. 63 shows live SARS-CoV-2 infection levels in wild-type HEK293T cells and in HEK293T cells engineered to overexpress DC-SIGN, L-SIGN, or ACE2. Infection was determined using a recombinant S protein with luciferase reporter. See Example 37.

Figure 64:
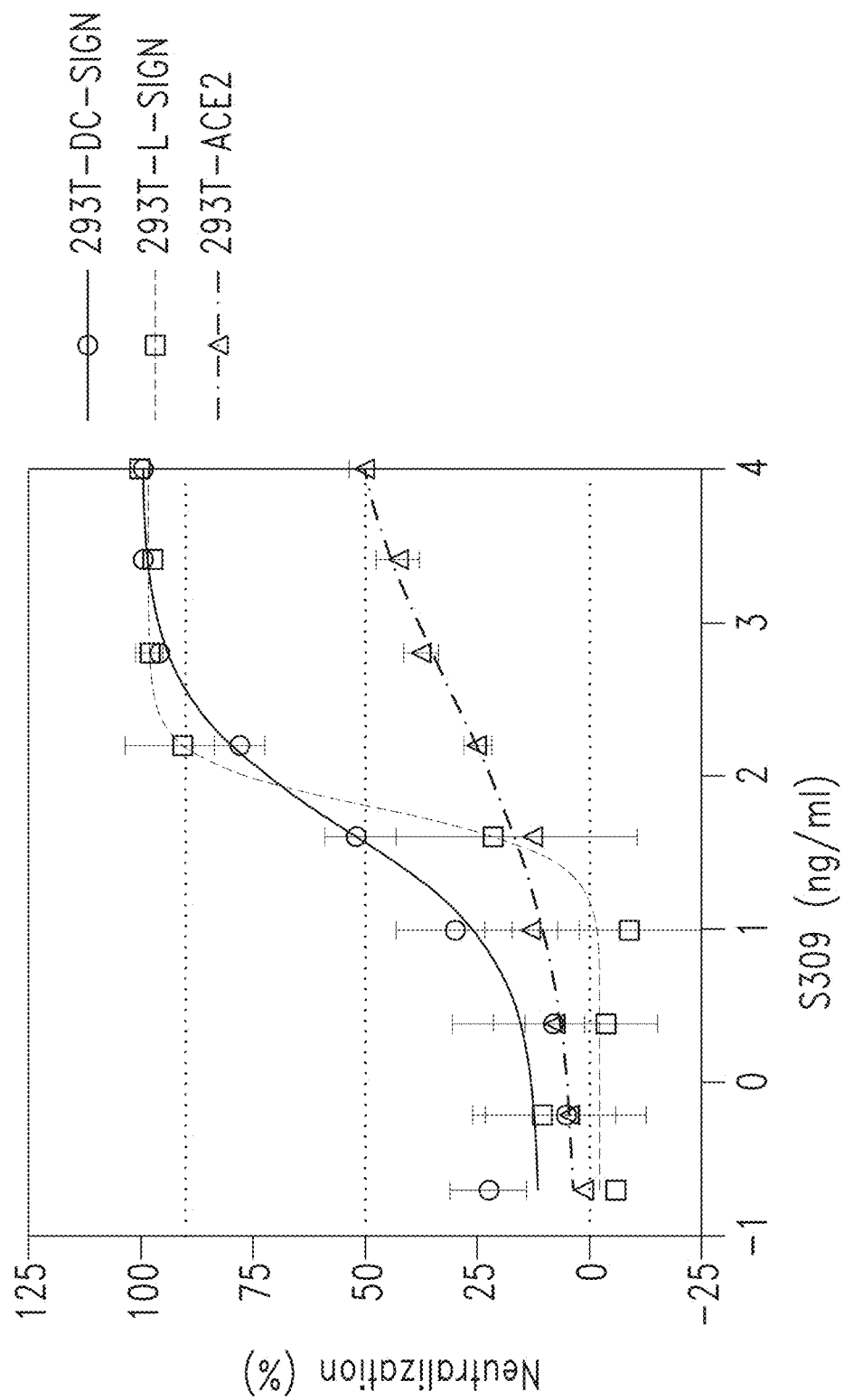

FIG. 64 shows neutralization by exemplary monoclonal antibody S309 (VH of SEQ ID NO.:105, VL of SEQ ID NO.:168) of live SARS-CoV-2 infection in HEK293T cells engineered to overexpress DC-SIGN, L-SIGN, or ACE2. In this example, antibody S309 includes M428L and N434S Fc mutations (EU numbering). See Example 37.

Figure 65:
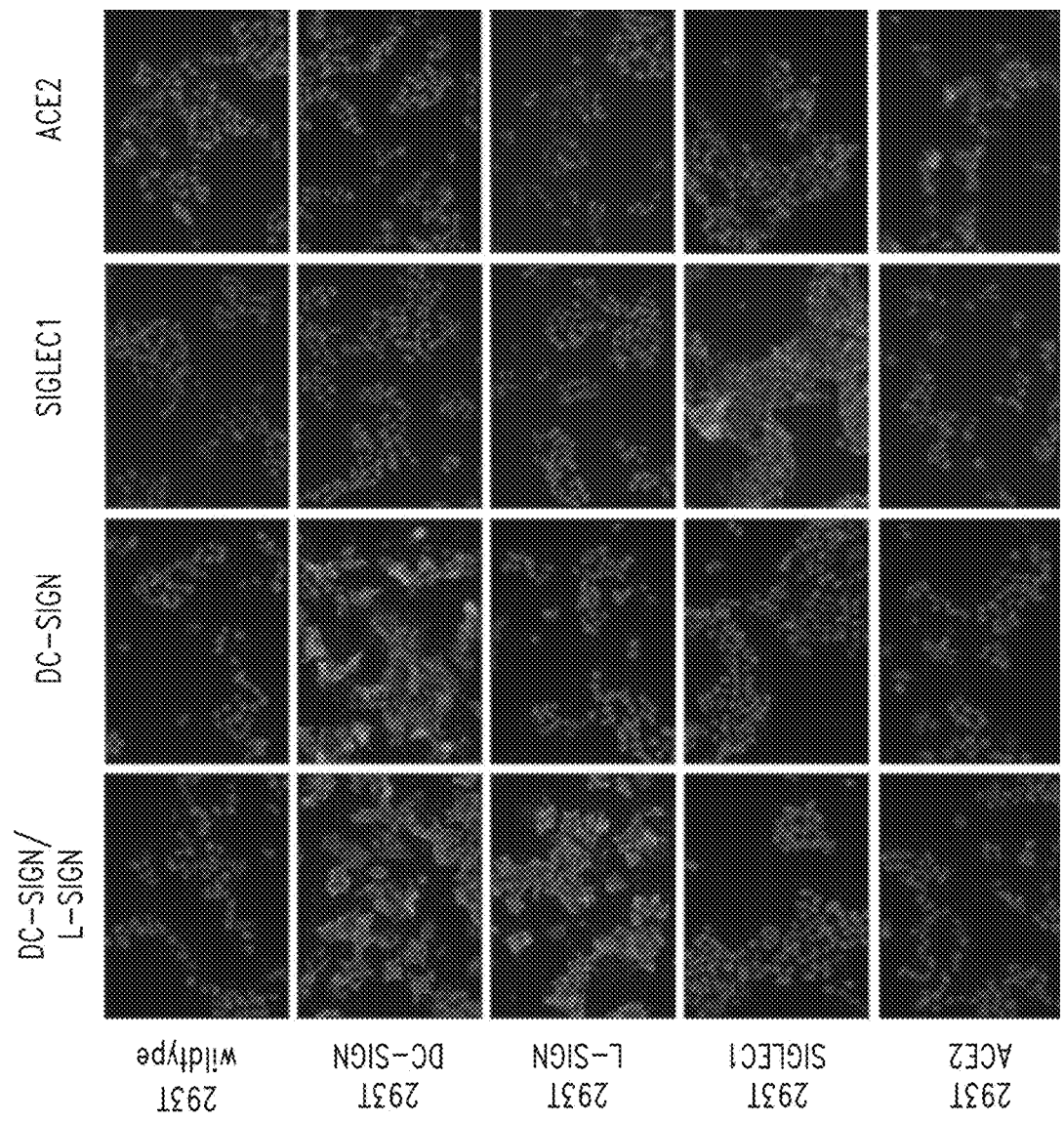

FIG. 65 shows expression (immunofluorescence) of L-SIGN, DC-SIGN, SIGLEC1, and ACE2 transgenes in HEK293T cells engineered to overexpress the indicated protein(s). See Example 37.

Figure 66:
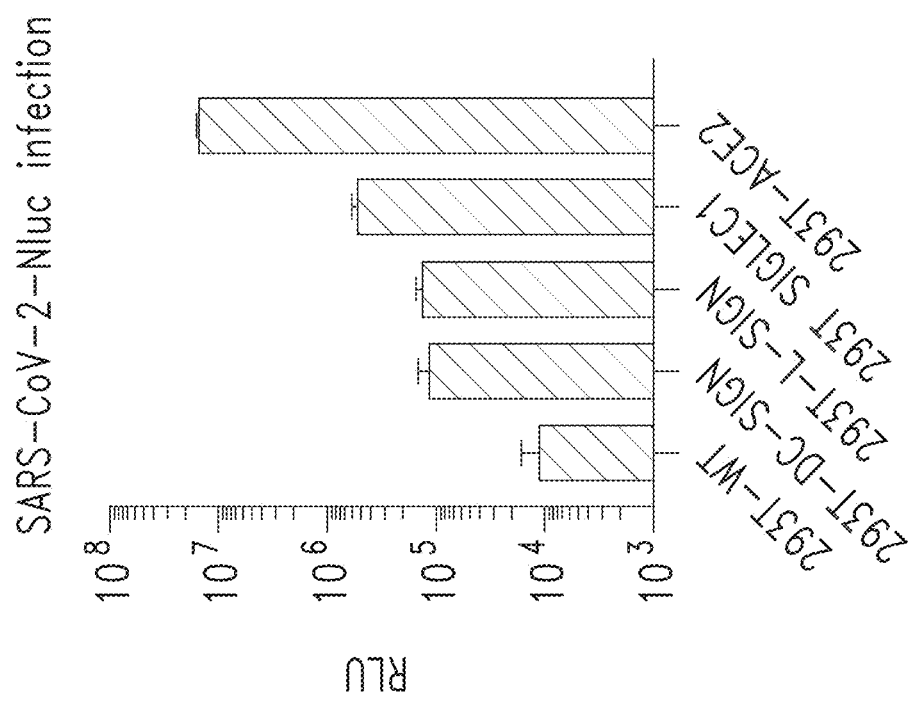

FIG. 66 shows live SARS-CoV-2 infection levels in wild-type HEK293T cells and in HEK293T cells engineered to overexpress DC-SIGN, L-SIGN, SIGLEC-1, or ACE2. Infection was determined using a recombinant S protein with luciferase reporter. See Example 37.

Figure 67:
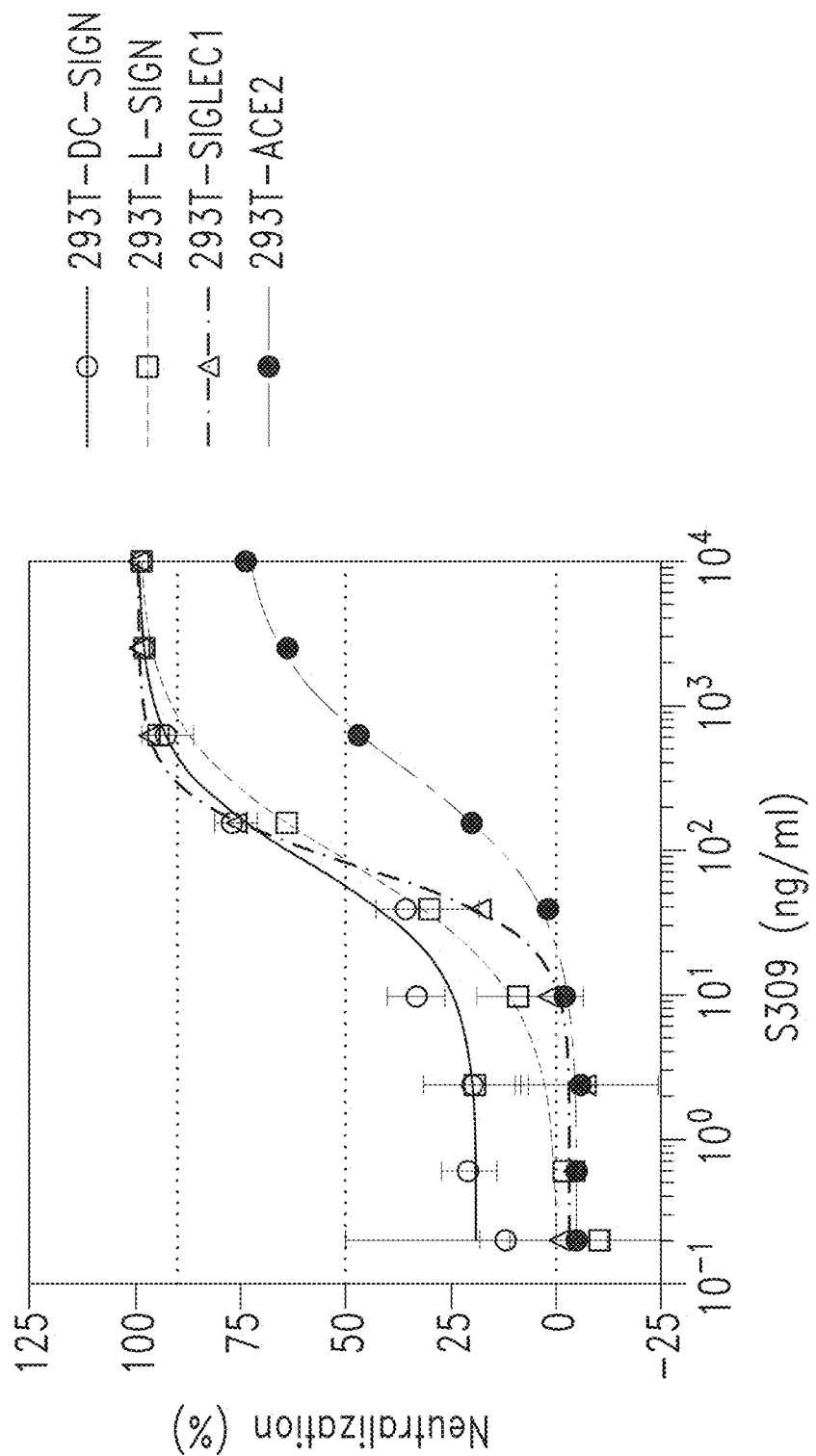

FIG. 67 shows neutralization by exemplary monoclonal antibody S309 (VH of SEQ ID NO.:105, VL of SEQ ID NO.:168) of live SARS-CoV-2 infection in HEK293T cells engineered to overexpress DC-SIGN, L-SIGN, SIGLEC-1, or ACE2. In this example, antibody S309 includes M428L and N434S Fc mutations (EU numbering). See Example 37.

Figure 68A:
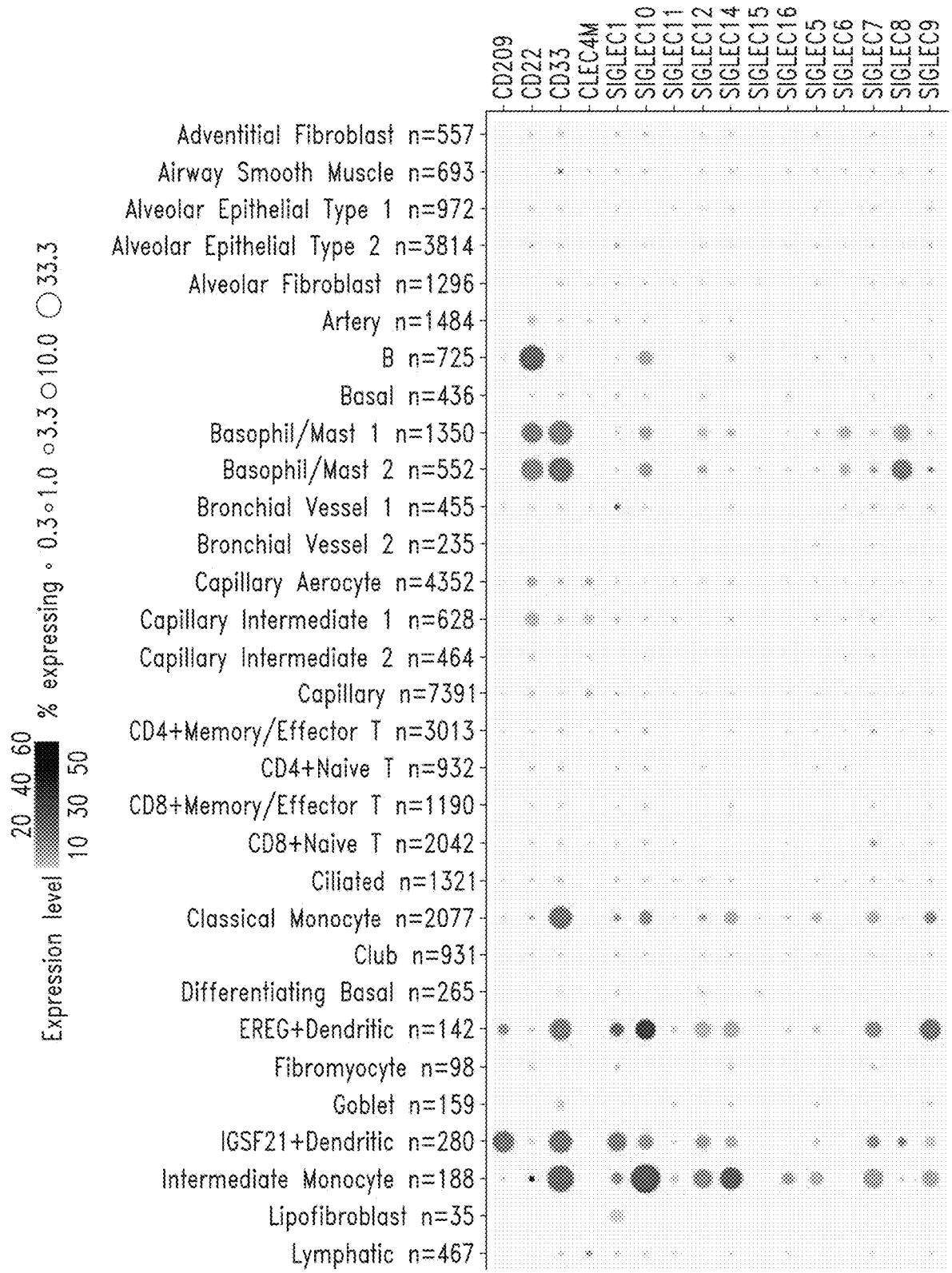
Figure 68B:
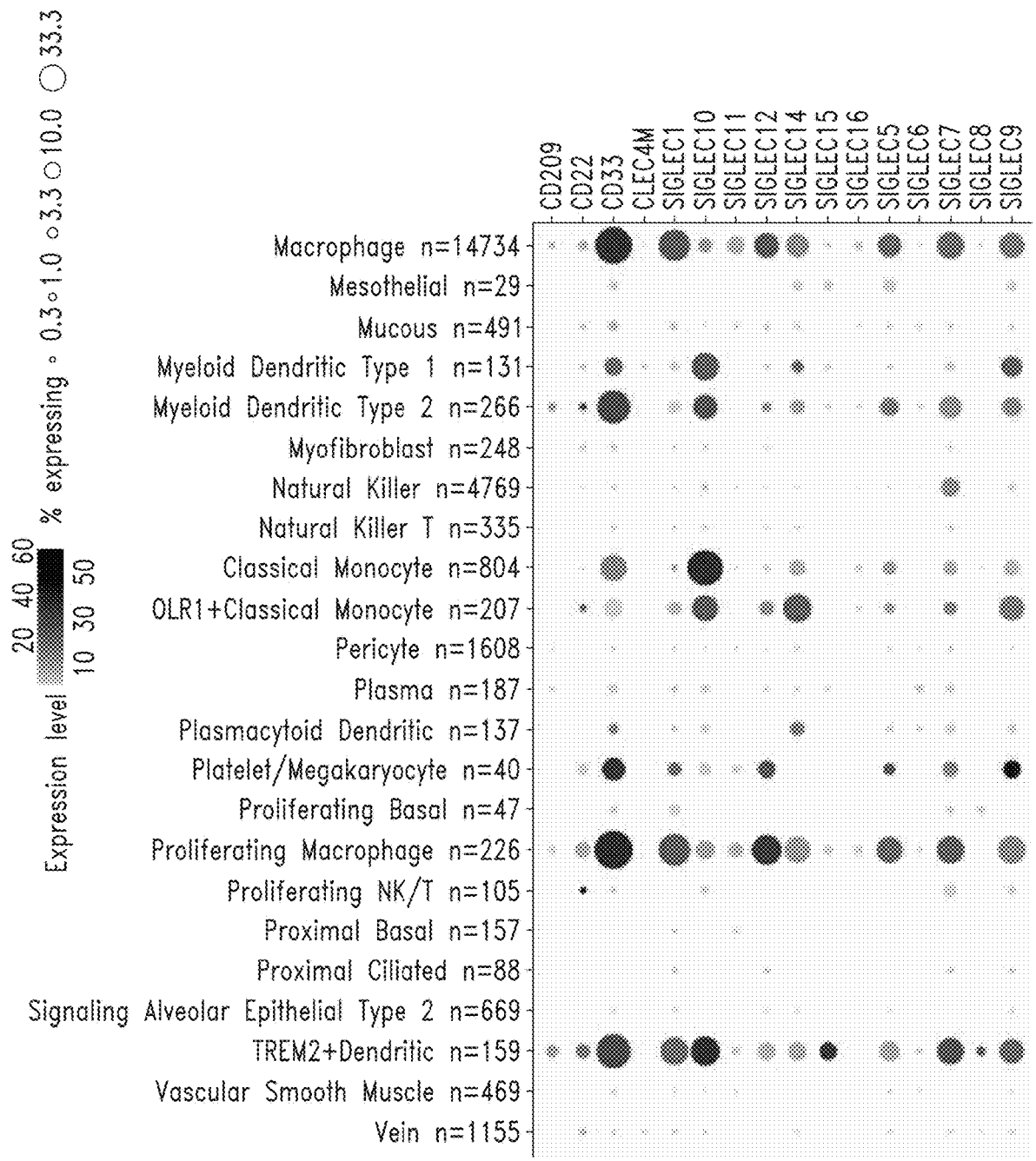

FIGS. 68A and 68B show expression analysis of receptor proteins including CD209 (DC-SIGN) and SIGLEC proteins in several cell types. Size of dot correlates with the percentage of cells of the indicated type that express the protein, and intensity of dot shading correlates with the expression level of the protein. See Example 37.

Figure 69:
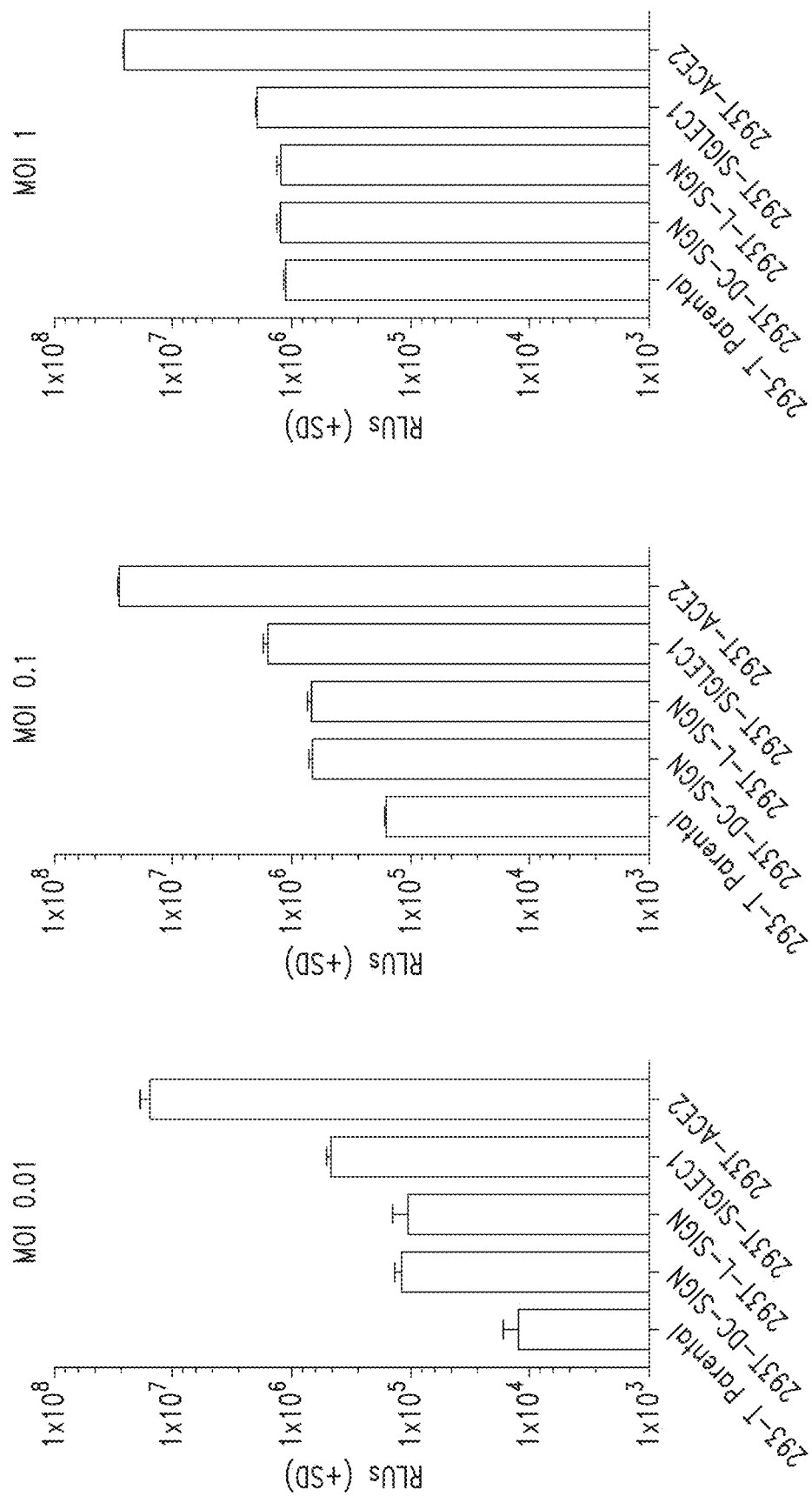

FIG. 69 shows infection by live SARS-CoV-2 expressing N-luciferase in HEK293T cells ("parental") or HEK293T cells stably expressing DC-SIGN, L-SIGN, SIGLEC-1, or ACE2. Data represent experiments testing SARS-CoV-2 at three multiplicities of infection (MOI). See Example 37.

Figure 70:
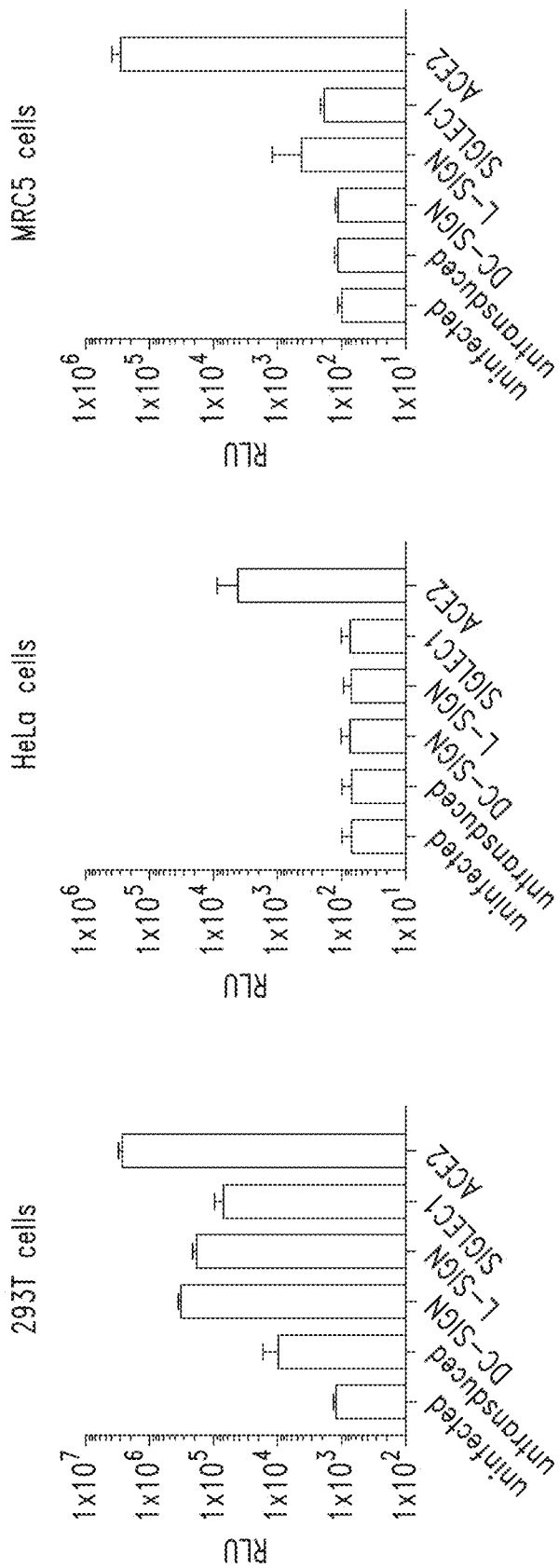

FIG. 70 shows infection by SARS-CoV-2 pseudotyped VSV in HEK293T cells, HeLa cells, and MRCS cells transiently transduced with lentivirus to express DC-SIGN, L-SIGN, SIGLEC-1, or ACE2. Uninfected cells are shown as negative control. See Example 37.

Figure 71A:
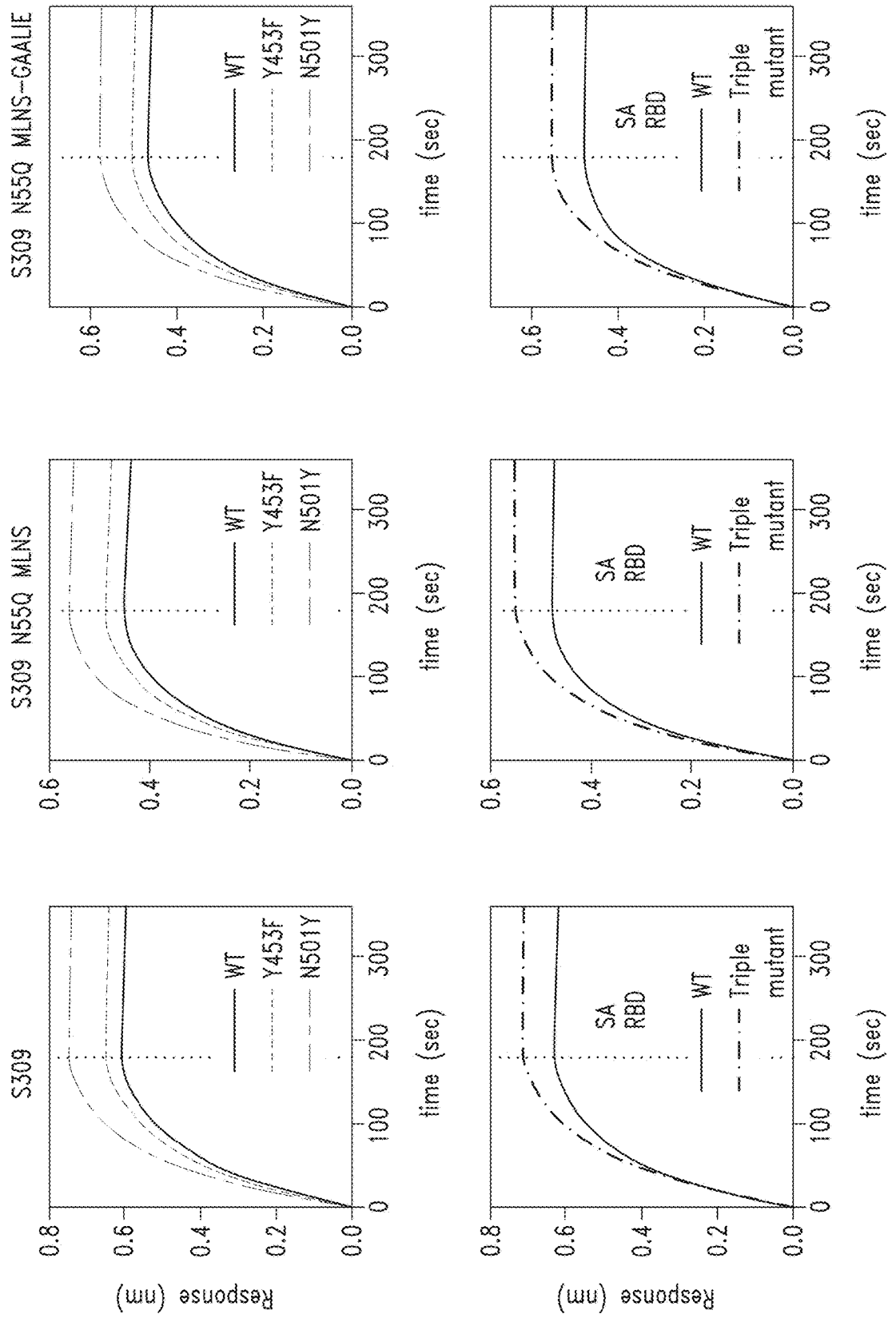
Figure 71B:
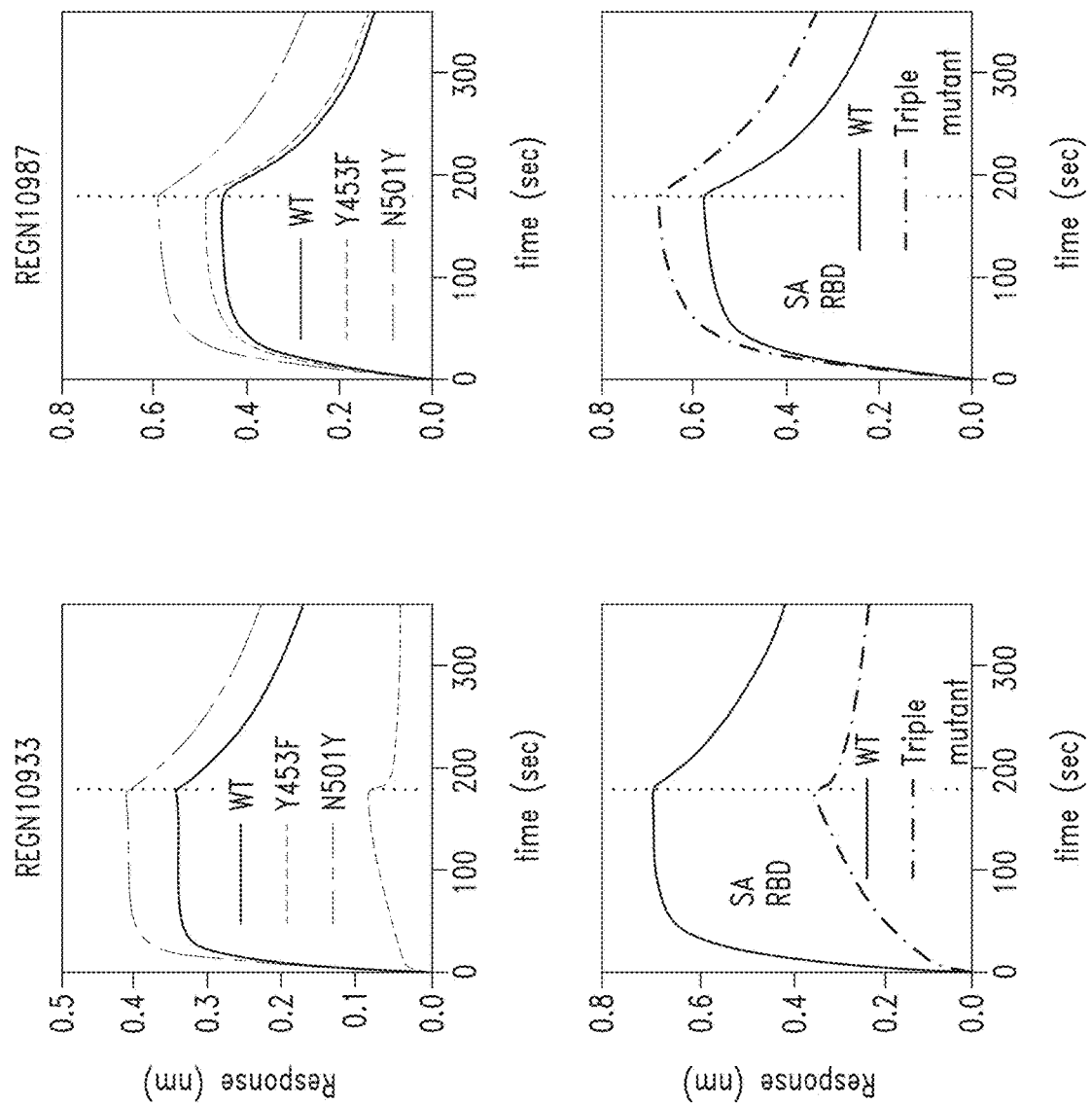

FIGS. 71A and 71B show binding (as measured by biolayer interferometry) of S309, S309 N55Q MLNS, S309 N55Q MLNS GAALIE (FIG. 71A), and comparator antibodies REGN10933 and REGN10987 (FIG. 71B) to WT and mutated variants of RBD. See Example 38.

Figure 72:
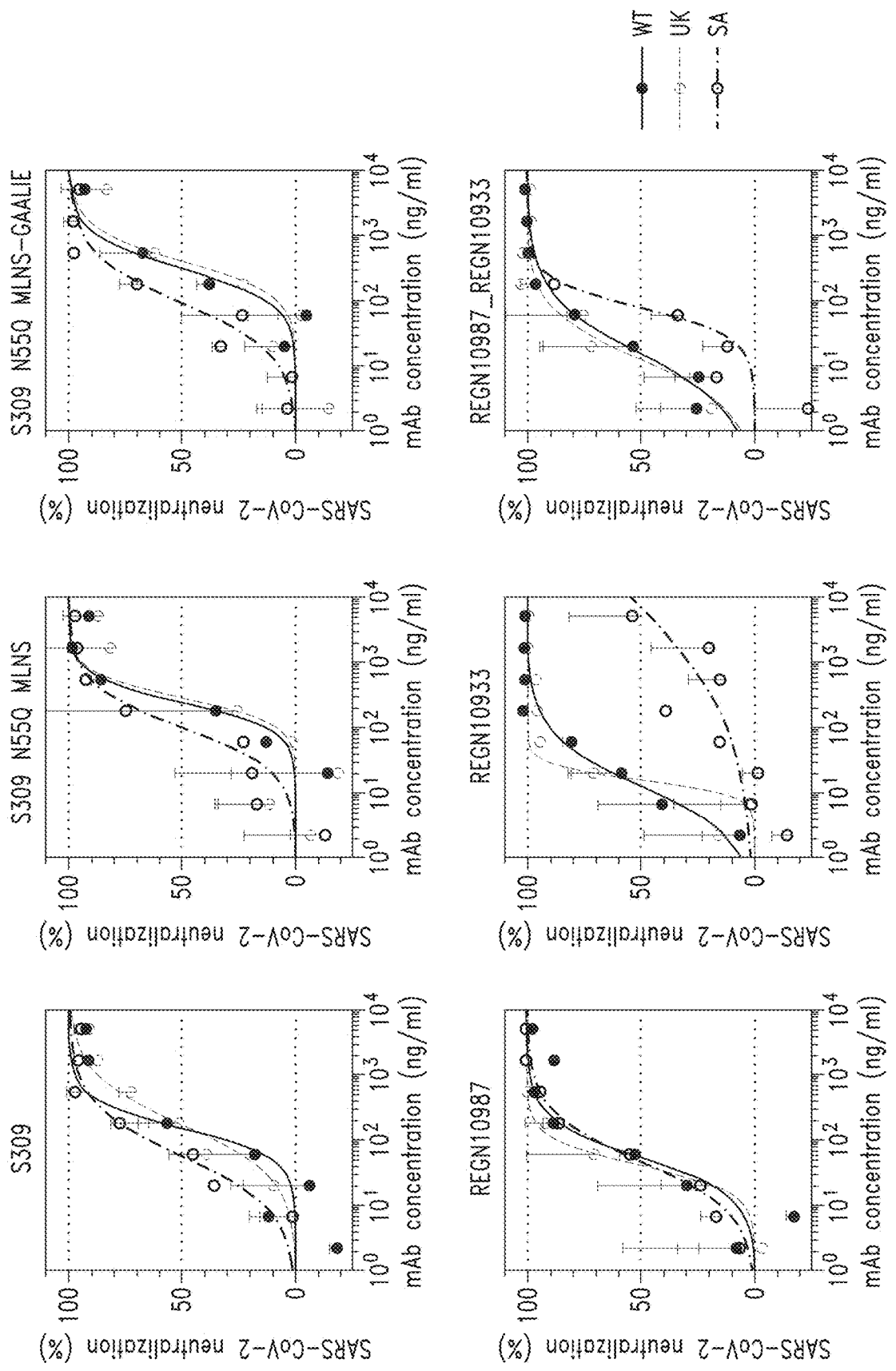

FIG. 72 shows neutralization of SARS-CoV-2 ("WT"=Wuhan-Hu-1; "UK"=SARS-CoV-2 variant B.1.1.7; and "SA"=variant B.1.351) MLV pseudovirus in Vero-E6 cells by S309 antibodies, as described in Example 39. Comparator antibodies REGN10987, REGN10933, and the combination of REGN10987+REGN10933 were also assessed.

FIGS. 73A-73D show that S309 (VH SEQ ID NO.:105; VL SEQ ID NO.:168) provides robust in vivo protection against SARS-CoV-2 challenge. Syrian hamsters were injected with the indicated amount of mAb 48 hours before intra-nasal challenge with SARS-CoV-2. (A) Quantification of viral RNA in the lungs 4 days post-infection. (B) Quantification of replicating virus in lung homogenates harvested 4 days post infection using a TCID50 assay. (C) Histological score of the lung tissue was assessed 4 days post infection. (D) The concentration of mAbs measured in the serum before infection (day 0) inversely correlates with the viral RNA load in the lung 4 days post infection. See Example 38.

DETAILED DESCRIPTION

Provided herein are antibodies and antigen-binding fragments that are capable binding to SARS-CoV-2 (e.g., a SARS-CoV-2 surface glycoprotein and/or RBD, as described herein, in a SARS-CoV-2 virion and/or expressed on the surface of a host cell, such as a cell infected by SARS-CoV-2). A host cell can be, for example, a lung cell, a CHO cell (such as, for example, an ExpiCHO cell transfected to express the surface glycoprotein), or the like. In certain embodiments, presently disclosed antibodies and antigen-binding fragments can neutralize a SARS-CoV-2 infection in an in vitro model of infection and/or in a human subject. Also provided are polynucleotides that encode the antibodies and antigen-binding fragments, vectors, host cells, and related compositions, as well as methods of using the antibodies, nucleic acids, vectors, host cells, and related compositions to treat (e.g., reduce, delay, eliminate, or prevent) a SARS-CoV-2 infection in a subject and/or in the manufacture of a medicament for treating a SARS-CoV-2 infection in a subject.

Prior to setting forth this disclosure in more detail, it may be helpful to an understanding thereof to provide definitions of certain terms to be used herein. Additional definitions are set forth throughout this disclosure.

As used herein, "SARS-CoV-2", also referred to herein as "Wuhan coronavirus", or "Wuhan seafood market pneumonia virus", or "Wuhan CoV", or "novel CoV", or "nCoV", or "2019 nCoV", or "Wuhan nCoV" is a betacoronavirus believed to be of lineage B (sarbecovirus). SARS-CoV-2 was first identified in Wuhan, Hubei province, China, in late 2019 and spread within China and to other parts of the world by early 2020. Symptoms of SARS-CoV-2 include fever, dry cough, and dyspnea.

The genomic sequence of SARS-CoV-2 isolate Wuhan-Hu-1 is provided in SEQ ID NO.:163 (see also GenBank MN908947.3, Jan. 23, 2020), and the amino acid translation of the genome is provided in SEQ ID NO.:164 (see also GenBank QHD43416.1, Jan. 23, 2020). Like other coronaviruses (e.g., SARS CoV), SARS-CoV-2 comprises a "spike" or surface ("S") type I transmembrane glycoprotein containing a receptor binding domain (RBD). RBD is believed to mediate entry of the lineage B SARS coronavirus to respiratory epithelial cells by binding to the cell surface receptor angiotensin-converting enzyme 2 (ACE2). In particular, a receptor binding motif (RBM) in the virus RBD is believed to interact with ACE2.

The amino acid sequence of the SARS-CoV-2 Wuhan-Hu-1 surface glycoprotein (S) is provided in SEQ ID NO.: 165. Antibodies and antigen-binding fragments of the present disclosure are capable of binding to a SARS CoV-2 surface glycoprotein (S), such as that of Wuhan-Hu-1. For example, in certain embodiments, an antibody or antigen-binding fragment binds to an epitope in Wuhan-Hu-1 S protein RBD.

The amino acid sequence of SARS-CoV-2 Wuhan-Hu-1 RBD is provided in SEQ ID NO.:166. SARS-CoV-2 Wuhan-Hu-1 S protein has approximately 73% amino acid sequence identity with SARS-CoV S protein. The amino acid sequence of SARS-CoV-2 Wuhan-Hu-1 RBM is provided in SEQ ID NO.:167. SARS-CoV-2 RBD has approximately 75% to 77% amino acid sequence similarity to SARS coronavirus RBD, and SARS-CoV-2 Wuhan Hu-1RBM has approximately 50% amino acid sequence similarity to SARS coronavirus RBM.

Unless otherwise indicated herein, SARS-CoV-2 Wuhan Hu-1 refers to a virus comprising the amino acid sequence set forth in any one or more of SEQ ID NOs.:164, 165, and 166, optionally with the genomic sequence set forth in SEQ ID NO.:163.

There have been a number of emerging SARS-CoV-2 variants. Some SARS-CoV-2 variants contain an N439K mutation, which has enhanced binding affinity to the human ACE2 receptor (Thomson, E. C., et al., *The circulating SARS-CoV-2 spike variant N439K maintains fitness while evading antibody-mediated immunity*. bioRxiv, 2020). Some SARS-CoV-2 variants contain an N501Y mutation, which is associated with increased transmissibility, including the lineages B.1.1.7 (also known as 20I/501Y.V1 and VOC 202012/01; (del69-70, del144, N501Y, A570D, D614G, P681H, T716I, S982A, and D1118H mutations)) and B.1.351 (also known as 20H/501Y.V2; L18F, D80A, D215G, R246I, K417N, E484K, N501Y, D614G, and A701V mutations), which were discovered in the United Kingdom and South Africa, respectively (Tegally, H., et al., *Emergence and rapid spread of a new severe acute respiratory syndrome-related coronavirus 2 (SARS-CoV-2) lineage with multiple spike mutations in South Africa*. medRxiv, 2020: p. 2020.12.21.20248640; Leung, K., et al., *Early empirical assessment of the N501Y mutant strains of SARS-CoV-2 in the United Kingdom, October to November 2020*. medRxiv, 2020: p. 2020.12.20.20248581). B.1.351 also include two other mutations in the RBD domain of SARS-CoV2 spike protein, K417N and E484K (Tegally, H., et al., *Emergence and rapid spread of a new severe acute respiratory syndrome-related coronavirus 2 (SARS-CoV-2) lineage with multiple spike mutations in South Africa*. medRxiv, 2020: p. 2020.12.21.20248640). Other SARS-CoV-2 variants include the Lineage B.1.1.28, which was first reported in Brazil; the Variant P.1, lineage B.1.1.28 (also known as 20J/501Y.V3), which was first reported in Japan; Variant L452R, which was first reported in California in the United States (Pan American Health Organization, Epidemiological update: Occurrence of variants of SARS-CoV-2 in the Americas, Jan. 20, 2021, available at reliefweb.int/sites/reliefweb.int/files/resources/2021-jan-20-phe-epi-update-SARS-CoV-2.pdf). Other SARS-CoV-2 variants include a SARS CoV-2 of clade 19A; SARS CoV-2 of clade 19B; a SARS CoV-2 of clade 20A; a SARS CoV-2 of clade 20B; a SARS CoV-2 of clade 20C; a SARS CoV-2 of clade 20D; a SARS CoV-2 of clade 20E (EU1); a SARS CoV-2 of clade 20F; a SARS CoV-2 of clade 20G; and SARS CoV-2 B1.1.207; and other SARS CoV-2 lineages described in Rambaut, A., et al., *A dynamic nomenclature proposal for SARS-CoV-2 lineages to assist genomic epidemiology*. Nat Microbiol 5, 1403-1407 (2020). The foregoing SARS-CoV-2 variants, and the amino acid and nucleotide sequences thereof, are incorporated herein by reference.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have," and "comprise" are used synonymously, which terms and variants thereof are intended to be construed as non-limiting.

"Optional" or "optionally" means that the subsequently described element, component, event, or circumstance may or may not occur, and that the description includes instances in which the element, component, event, or circumstance occurs and instances in which they do not.

In addition, it should be understood that the individual constructs, or groups of constructs, derived from the various combinations of the structures and subunits described herein, are disclosed by the present application to the same extent as if each construct or group of constructs was set forth individually. Thus, selection of particular structures or particular subunits is within the scope of the present disclosure.

The term "consisting essentially of" is not equivalent to "comprising" and refers to the specified materials or steps of a claim, or to those that do not materially affect the basic characteristics of a claimed subject matter. For example, a protein domain, region, or module (e.g., a binding domain) or a protein "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that functions in a manner similar to a naturally occurring amino acid.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s).

A "conservative substitution" refers to amino acid substitutions that do not significantly affect or alter binding characteristics of a particular protein. Generally, conservative substitutions are ones in which a substituted amino acid residue is replaced with an amino acid residue having a similar side chain. Conservative substitutions include a substitution found in one of the following groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W). Additionally or alternatively, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and Ile. Other conservative substitutions groups include: sulfur-containing: Met and Cysteine (Cys or C); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information can be found in Creighton (1984) Proteins, W.H. Freeman and Company.

As used herein, "protein" or "polypeptide" refers to a polymer of amino acid residues. Proteins apply to naturally occurring amino acid polymers, as well as to amino acid polymers in which one or more amino acid residue is an artificial chemical mimetic of a corresponding naturally occurring amino acid, and non-naturally occurring amino acid polymers. Variants of proteins, peptides, and polypeptides of this disclosure are also contemplated. In certain embodiments, variant proteins, peptides, and polypeptides comprise or consist of an amino acid sequence that is at least 70%, 75%, 80%, 85%, 90%, 91%, 92%, 93%, 94%, 95%, 96%, 97%, 98%, 99%, or 99.9% identical to an amino acid sequence of a defined or reference amino acid sequence as described herein.

"Nucleic acid molecule" or "polynucleotide" or "polynucleic acid" refers to a polymeric compound including covalently linked nucleotides, which can be made up of natural subunits (e.g., purine or pyrimidine bases) or non-natural subunits (e.g., morpholine ring). Purine bases include adenine, guanine, hypoxanthine, and xanthine, and pyrimidine bases include uracil, thymine, and cytosine. Nucleic acid molecules include polyribonucleic acid (RNA), which includes mRNA, microRNA, siRNA, viral genomic RNA, and synthetic RNA, and polydeoxyribonucleic acid (DNA), which includes cDNA, genomic DNA, and synthetic DNA, either of which may be single or double stranded. If single-stranded, the nucleic acid molecule may be the coding strand or non-coding (anti-sense) strand. A nucleic acid molecule encoding an amino acid sequence includes all nucleotide sequences that encode the same amino acid sequence. Some versions of the nucleotide sequences may also include intron(s) to the extent that the intron(s) would be removed through co- or post-transcriptional mechanisms. In other words, different nucleotide sequences may encode the same amino acid sequence as the result of the redundancy or degeneracy of the genetic code, or by splicing.

Variants of nucleic acid molecules of this disclosure are also contemplated. Variant nucleic acid molecules are at least 70%, 75%, 80%, 85%, 90%, and are preferably 95%, 96%, 97%, 98%, 99%, or 99.9% identical a nucleic acid molecule of a defined or reference polynucleotide as described herein, or that hybridize to a polynucleotide under stringent hybridization conditions of 0.015M sodium chloride, 0.0015M sodium citrate at about 65-68° C. or 0.015M sodium chloride, 0.0015M sodium citrate, and 50% formamide at about 42° C. Nucleic acid molecule variants retain the capacity to encode a binding domain thereof having a functionality described herein, such as binding a target molecule.

"Percent sequence identity" refers to a relationship between two or more sequences, as determined by comparing the sequences. Preferred methods to determine sequence identity are designed to give the best match between the sequences being compared. For example, the sequences are aligned for optimal comparison purposes (e.g., gaps can be introduced in one or both of a first and a second amino acid or nucleic acid sequence for optimal alignment). Further, non-homologous sequences may be disregarded for comparison purposes. The percent sequence identity referenced herein is calculated over the length of the reference sequence, unless indicated otherwise. Methods to determine sequence identity and similarity can be found in publicly available computer programs. Sequence alignments and percent identity calculations may be performed using a BLAST program (e.g., BLAST 2.0, BLASTP, BLASTN, or BLASTX). The mathematical algorithm used in the BLAST programs can be found in Altschul et al., *Nucleic Acids Res.* 25:3389-3402, 1997. Within the context of this disclosure, it will be understood that where sequence analysis software is used for analysis, the results of the analysis are based on the "default values" of the program referenced. "Default values" mean any set of values or parameters which originally load with the software when first initialized.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. "Isolated" can, in some embodiments, also describe an antibody, antigen-binding fragment, polynucleotide, vector, host cell, or composition that is outside of a human body.

The term "gene" means the segment of DNA or RNA involved in producing a polypeptide chain; in certain contexts, it includes regions preceding and following the coding region (e.g., 5' untranslated region (UTR) and 3' UTR) as well as intervening sequences (introns) between individual coding segments (exons).

A "functional variant" refers to a polypeptide or polynucleotide that is structurally similar or substantially structurally similar to a parent or reference compound of this disclosure, but differs slightly in composition (e.g., one base, atom or functional group is different, added, or removed), such that the polypeptide or encoded polypeptide is capable of performing at least one function of the parent polypeptide with at least 50% efficiency, preferably at least 55%, 60%, 70%, 75%, 80%, 85%, 90%, 95%, 96%, 97%, 98%, 99%, 99.9%, or 100% level of activity of the parent polypeptide. In other words, a functional variant of a polypeptide or encoded polypeptide of this disclosure has "similar binding," "similar affinity" or "similar activity" when the functional variant displays no more than a 50% reduction in performance in a selected assay as compared to the parent or reference polypeptide, such as an assay for measuring binding affinity (e.g., Biacore® or tetramer staining measuring an association ($K_a$) or a dissociation ($K_D$) constant).

As used herein, a "functional portion" or "functional fragment" refers to a polypeptide or polynucleotide that comprises only a domain, portion or fragment of a parent or reference compound, and the polypeptide or encoded polypeptide retains at least 50% activity associated with the domain, portion or fragment of the parent or reference compound, preferably at least 55%, 60%, 70%, 75%, 80%, 85%, 90%, 95%, 96%, 97%, 98%, 99%, 99.9%, or 100% level of activity of the parent polypeptide, or provides a biological benefit (e.g., effector function). A "functional portion" or "functional fragment" of a polypeptide or encoded polypeptide of this disclosure has "similar binding" or "similar activity" when the functional portion or fragment displays no more than a 50% reduction in performance in a selected assay as compared to the parent or reference polypeptide (preferably no more than 20% or 10%, or no more than a log difference as compared to the parent or reference with regard to affinity).

As used herein, the term "engineered," "recombinant," or "non-natural" refers to an organism, microorganism, cell, nucleic acid molecule, or vector that includes at least one genetic alteration or has been modified by introduction of an exogenous or heterologous nucleic acid molecule, wherein such alterations or modifications are introduced by genetic engineering (i.e., human intervention). Genetic alterations include, for example, modifications introducing expressible nucleic acid molecules encoding functional RNA, proteins, fusion proteins or enzymes, or other nucleic acid molecule additions, deletions, substitutions, or other functional disruption of a cell's genetic material. Additional modifications include, for example, non-coding regulatory regions in which the modifications alter expression of a polynucleotide, gene, or operon.

As used herein, "heterologous" or "non-endogenous" or "exogenous" refers to any gene, protein, compound, nucleic acid molecule, or activity that is not native to a host cell or a subject, or any gene, protein, compound, nucleic acid molecule, or activity native to a host cell or a subject that has been altered. Heterologous, non-endogenous, or exogenous includes genes, proteins, compounds, or nucleic acid molecules that have been mutated or otherwise altered such that the structure, activity, or both is different as between the native and altered genes, proteins, compounds, or nucleic acid molecules. In certain embodiments, heterologous, non-endogenous, or exogenous genes, proteins, or nucleic acid molecules (e.g., receptors, ligands, etc.) may not be endogenous to a host cell or a subject, but instead nucleic acids encoding such genes, proteins, or nucleic acid molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). The term "homologous" or "homolog" refers to a gene, protein, compound, nucleic acid molecule, or activity found in or derived from a host cell, species, or strain. For example, a heterologous or exogenous polynucleotide or gene encoding a polypeptide may be homologous to a native polynucleotide or gene and encode a homologous polypeptide or activity, but the polynucleotide or polypeptide may have an altered structure, sequence, expression level, or any combination thereof. A non-endogenous polynucleotide or gene, as well as the encoded polypeptide or activity, may be from the same species, a different species, or a combination thereof.

In certain embodiments, a nucleic acid molecule or portion thereof native to a host cell will be considered heterologous to the host cell if it has been altered or mutated, or a nucleic acid molecule native to a host cell may be considered heterologous if it has been altered with a heterologous expression control sequence or has been altered with an endogenous expression control sequence not normally associated with the nucleic acid molecule native to a host cell. In addition, the term "heterologous" can refer to a biological activity that is different, altered, or not endogenous to a host cell. As described herein, more than one heterologous nucleic acid molecule can be introduced into a host cell as separate nucleic acid molecules, as a plurality of individually controlled genes, as a polycistronic nucleic acid molecule, as a single nucleic acid molecule encoding an antibody or antigen-binding fragment (or other polypeptide), or any combination thereof.

As used herein, the term "endogenous" or "native" refers to a polynucleotide, gene, protein, compound, molecule, or activity that is normally present in a host cell or a subject.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof. An expressed nucleic acid molecule is typically operably linked to an expression control sequence (e.g., a promoter).

The term "operably linked" refers to the association of two or more nucleic acid molecules on a single nucleic acid fragment so that the function of one is affected by the other. For example, a promoter is operably linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As described herein, more than one heterologous nucleic acid molecule can be introduced into a host cell as separate nucleic acid molecules, as a plurality of individually controlled genes, as a polycistronic nucleic acid molecule, as a single nucleic acid molecule encoding a protein (e.g., a heavy chain of an antibody), or any combination thereof. When two or more heterologous nucleic acid molecules are introduced into a host cell, it is understood that the two or more heterologous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate nucleic acid molecules introduced into a host cell.

The term "construct" refers to any polynucleotide that contains a recombinant nucleic acid molecule (or, when the context clearly indicates, a fusion protein of the present disclosure). A (polynucleotide) construct may be present in a vector (e.g., a bacterial vector, a viral vector) or may be integrated into a genome. A "vector" is a nucleic acid molecule that is capable of transporting another nucleic acid molecule. Vectors may be, for example, plasmids, cosmids, viruses, a RNA vector or a linear or circular DNA or RNA molecule that may include chromosomal, non-chromosomal, semi-synthetic or synthetic nucleic acid molecules. Vectors of the present disclosure also include transposon systems (e.g., Sleeping Beauty, see, e.g., Geurts et al., *Mol. Ther.* 8:108, 2003: Matés et al., *Nat. Genet.* 41:753, 2009). Exemplary vectors are those capable of autonomous replication (episomal vector), capable of delivering a polynucleotide to a cell genome (e.g., viral vector), or capable of expressing nucleic acid molecules to which they are linked (expression vectors).

As used herein, "expression vector" or "vector" refers to a DNA construct containing a nucleic acid molecule that is operably linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself or deliver the polynucleotide contained in the vector into the genome without the vector sequence. In the present specification, "plasmid," "expression plasmid," "virus," and "vector" are often used interchangeably.

The term "introduced" in the context of inserting a nucleic acid molecule into a cell, means "transfection", "transformation," or "transduction" and includes reference to the incorporation of a nucleic acid molecule into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

In certain embodiments, polynucleotides of the present disclosure may be operatively linked to certain elements of a vector. For example, polynucleotide sequences that are needed to effect the expression and processing of coding sequences to which they are ligated may be operatively linked. Expression control sequences may include appropriate transcription initiation, termination, promoter, and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest.

In certain embodiments, the vector comprises a plasmid vector or a viral vector (e.g., a lentiviral vector or a γ-retroviral vector). Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox, and canarypox). Other viruses include, for example, Norwalk virus, togavirus, flavivirus, reoviruses, papovavirus, hepadnavirus, and hepatitis virus. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996).

"Retroviruses" are viruses having an RNA genome, which is reverse-transcribed into DNA using a reverse transcriptase enzyme, the reverse-transcribed DNA is then incorporated into the host cell genome. "Gammaretrovirus" refers to a genus of the retroviridae family. Examples of gammaretroviruses include mouse stem cell virus, murine leukemia virus, feline leukemia virus, feline sarcoma virus, and avian reticuloendotheliosis viruses.

"Lentiviral vectors" include HIV-based lentiviral vectors for gene delivery, which can be integrative or non-integrative, have relatively large packaging capacity, and can transduce a range of different cell types. Lentiviral vectors are usually generated following transient transfection of three (packaging, envelope, and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

In certain embodiments, the viral vector can be a gammaretrovirus, e.g., Moloney murine leukemia virus (MLV)-derived vectors. In other embodiments, the viral vector can be a more complex retrovirus-derived vector, e.g., a lentivirus-derived vector. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing transgenes are known in the art and have been previous described, for example, in: U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; and Verhoeyen et al., *Methods Mol. Biol.* 506:97, 2009. Retroviral and lentiviral vector constructs and expression systems are also commercially available. Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5:1517, 1998).

Other vectors that can be used with the compositions and methods of this disclosure include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as sleeping beauty or other transposon vectors).

When a viral vector genome comprises a plurality of polynucleotides to be expressed in a host cell as separate transcripts, the viral vector may also comprise additional sequences between the two (or more) transcripts allowing for bicistronic or multicistronic expression. Examples of such sequences used in viral vectors include internal ribosome entry sites (IRES), furin cleavage sites, viral 2A peptide, or any combination thereof.

Plasmid vectors, including DNA-based antibody or antigen-binding fragment-encoding plasmid vectors for direct administration to a subject, are described further herein.

As used herein, the term "host" refers to a cell or microorganism targeted for genetic modification with a heterologous nucleic acid molecule to produce a polypeptide of interest (e.g., an antibody of the present disclosure).

A host cell may include any individual cell or cell culture which may receive a vector or the incorporation of nucleic acids or express proteins. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. See, for example, Sambrook et al., *Molecular Cloning: A Laboratory Manual* 2d ed. (Cold Spring Harbor Laboratory, 1989).

In the context of a SARS-CoV-2 infection, a "host" refers to a cell or a subject (e.g., a human) infected with SARS-CoV-2.

"Antigen" or "Ag", as used herein, refers to an immunogenic molecule that provokes an immune response. This immune response may involve antibody production, activation of specific immunologically-competent cells, activation of complement, antibody dependent cytotoxicicity, or any combination thereof. An antigen (immunogenic molecule) may be, for example, a peptide, glycopeptide, polypeptide, glycopolypeptide, polynucleotide, polysaccharide, lipid, or the like. It is readily apparent that an antigen can be synthesized, produced recombinantly, or derived from a biological sample. Exemplary biological samples that can contain one or more antigens include tissue samples, stool samples, cells, biological fluids, or combinations thereof. Antigens can be produced by cells that have been modified or genetically engineered to express an antigen. Antigens can also be present in a SARS-CoV-2 (e.g., a surface glycoprotein or portion thereof), such as present in a virion, or expressed or presented on the surface of a cell infected by SARS-CoV-2.

The term "epitope" or "antigenic epitope" includes any molecule, structure, amino acid sequence, or protein determinant that is recognized and specifically bound by a cognate binding molecule, such as an immunoglobulin, or other binding molecule, domain, or protein. Epitopic determinants generally contain chemically active surface groupings of molecules, such as amino acids or sugar side chains, and can have specific three-dimensional structural characteristics, as well as specific charge characteristics. Where an antigen is or comprises a peptide or protein, the epitope can be comprised of consecutive amino acids (e.g., a linear epitope), or can be comprised of amino acids from different parts or regions of the protein that are brought into proximity by protein folding (e.g., a discontinuous or conformational epitope), or non-contiguous amino acids that are in close proximity irrespective of protein folding.

Antibodies and Antigen-Binding Fragments

In one aspect, the present disclosure provides an isolated antibody, or an antigen-binding fragment thereof, that comprises a heavy chain variable domain (VH) comprising a CDRH1, a CDRH2, and a CDRH3, and a light chain variable domain (VL) comprising a CDRL1, a CDRL2, and a CDRL3, and is capable of binding to a surface glycoprotein (S) of SARS-CoV-2. In certain embodiments, the antibody or antigen-binding fragment is capable of binding to a SARS-CoV-2 surface glycoprotein (S) expressed on a cell surface of a host cell and/or on a SARS-CoV-2 virion.

In certain embodiments, an antibody or antigen-binding fragment of the present disclosure associates with or unites with a SARS-CoV-2 surface glycoprotein epitope or antigen comprising the epitope, while not significantly associating or uniting with any other molecules or components in a sample.

In certain embodiments, an antibody or antigen-binding fragment of the present disclosure associates with or unites (e.g., binds) to a SARS-CoV-2 surface glycoprotein epitope, and can also associate with or unite with an epitope from another coronavirus (e.g., SARS CoV) present in the sample, but not significantly associating or uniting with any other molecules or components in the sample. In other words, in certain embodiments, an antibody or antigen binding fragment of the present disclosure is cross-reactive for SARS-CoV-2 and one or more additional coronavirus.

In certain embodiments, an antibody or antigen-binding fragment of the present disclosure specifically binds to a SARS-CoV-2 surface glycoprotein. As used herein, "specifically binds" refers to an association or union of an antibody or antigen-binding fragment to an antigen with an affinity or $K_a$ (i.e., an equilibrium association constant of a particular binding interaction with units of 1/M) equal to or greater than $10^5$ $M^{-1}$ (which equals the ratio of the on-rate $[K_{on}]$ to the off rate $[K_{off}]$ for this association reaction), while not significantly associating or uniting with any other molecules or components in a sample. Alternatively, affinity may be defined as an equilibrium dissociation constant ($K_d$) of a particular binding interaction with units of M (e.g., $10^{-5}$ M to $10^{-13}$ M). Antibodies may be classified as "high-affinity" antibodies or as "low-affinity" antibodies. "High-affinity" antibodies refer to those antibodies having a $K_a$ of at least $10^7 M^{-1}$, at least $10^8$ $M^{-1}$, at least $10^9$ $M^{-1}$, at least $10^{10}$ $M^{-1}$, at least $10^{11}$ $M^{-1}$, at least $10^{12} M^{-1}$, or at least $10^{13}$ $M^{-1}$. "Low-affinity" antibodies refer to those antibodies having a $K_a$ of up to $10^7 M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M).

In some contexts, antibody and antigen-binding fragments may be described with reference to affinity and/or to avidity for antigen. Unless otherwise indicated, avidity refers to the total binding strength of an antibody or antigen-binding fragment thereof to antigen, and reflects binding affinity, valency of the antibody or antigen-binding fragment (e.g., whether the antibody or antigen-binding fragment comprises one, two, three, four, five, six, seven, eight, nine, ten, or more binding sites), and, for example, whether another agent is present that can affect the binding (e.g., a non-competitive inhibitor of the antibody or antigen-binding fragment).

A variety of assays are known for identifying antibodies of the present disclosure that bind a particular target, as well as determining binding domain or binding protein affinities, such as Western blot, ELISA (e.g., direct, indirect, or sandwich), analytical ultracentrifugation, spectroscopy, and surface plasmon resonance (Biacore®) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent). Assays for assessing affinity or apparent affinity or relative affinity are also known.

In certain examples, binding can be determined by recombinantly expressing a SARS-CoV-2 antigen in a host cell (e.g., by transfection) and immunostaining the (e.g., fixed, or fixed and permeabilized) host cell with antibody and analyzing binding by flow cytometery (e.g., using a ZE5 Cell Analyzer (BioRad®) and FlowJo software (TreeStar). In some embodiments, positive binding can be defined by differential staining by antibody of SARS-CoV-2-expressing cells versus control (e.g., mock) cells.

In some embodiments an antibody or antigen-binding fragment of the present disclosure binds to SARS-CoV-2 S protein, as measured using biolayer interferometry. In certain embodiments, an antibody or antigen-binding fragment of the present disclosure binds to SARS-CoV-2 S protein with a $K_D$ of less than about $4.5 \times 10^{-9}$ M, less than about $5 \times 10^{-9}$ M, less than about $1 \times 10^{-10}$ M, less than about $5 \times 10^{-10}$ M, less than about $1 \times 10^{-11}$ M, less than about $5 \times 10^{-11}$ M, less than about $1 \times 10^{-12}$ M, or less than about $5 \times 10^{-12}$ M. In some embodiments, an antibody or antigen-binding fragment of the present disclosure binds to SARS-CoV-2 S protein RBD with a $K_D$ of less than about $4.5 \times 10^{-9}$ M, less than about $5 \times 10^{-9}$ M, less than about $1 \times 10^{-10}$ M, less than about $5 \times 10^{-10}$ M, less than about $1 \times 10^{-11}$ M, less than about $5 \times 10^{-11}$ M, less than about $1 \times 10^{-12}$ M, or less than about $5 \times 10^{-12}$ M. In certain embodiments, an antibody or antigen-binding fragment of the present disclosure binds to SARS-CoV-2 S protein (e.g., a glycosylated or a deglycosylated S protein RBD) with a $K_D$, a $k_a$, and/or a $k_d$ as shown in Table 8, Table 9, or Table 10 herein.

In particular embodiments, an antibody or antigen-binding fragment is capable of binding to a glycosylated S protein RBD with a $K_D$ of about 0.35 nM, about 0.36 nM, about 0.37 nM, about 0.38 nM, about 0.39 nM, about 0.40 nM, about 0.41 nM, about 0.42 nM, about 0.43 nM, about 0.44 nM, about 0.45 nM, about 0.46 nM, about 0.47 nM, about 0.48 nM, about 0.49 nM, about 0.50 nM, about 0.51 nM, or about 1.7 nM, optionally as measured by surface plasmon resonance, and/or with a $k_a$ of about 8.5e4 1/Ms, about 8.6e4 1/Ms, about 8.7e4 1/Ms, about 8.8e4 1/Ms, about 8.9e4 1/Ms, about 9.0e4 1/Ms, about 9.1e4 1/Ms, about 9.2e4 1/Ms, about 9.3e4 1/Ms, about 9.4e4 1/Ms, about 9.5e4 1/Ms, about 9.6e4 1/Ms, about 9.7e4 1/Ms, about 9.8e4 1/Ms, about 9.9e4 1/Ms, or about 1.0e5 1/Ms, optionally as measured by surface plasmon resonance, and/or with a $k_a$ of about 1.6e-4 1/S, about 3.3e-5 1/S, about 3.4e-5 1/S, about 3.5e-5 1/S, about 3.6e-5 1/S, about 3.7e-5 1/S, about 3.8e-5 1/S, about 3.9e-5 1/S, about 4.0e-5 1/S, about 4.1e-5 1/S, about 4.2e-5 1/S, about 4.3e-5 1/S, about 4.4e-5 1/S, about 4.5e-5 1/S, about 4.6e-5 1/S, about 4.7e-5 1/S, about 4.8e-5 1/S, about 4.9e-5 1/S, about 5.0e-5 1/S, about 5.1e-5 1/S, about 5.2e-5 1/S, about 5.3e-5 1/S, about 5.4e-5 1/S, about 5.5e-5 1/S, about 5.6e-5 1/S, about 5.7e-5 1/S, about 5.8e-5 1/S, about 5.9e-5 1/S, about 6.0e-5 1/S, about 6.1e-5 1/S, about 6.2e-5 1/S, about 6.3e-5 1/S, about 6.4e-5 1/S, or about 6.5e-5 1/S, optionally as measured by surface plasmon resonance.

In certain embodiments, an antibody or antigen-binding fragment is capable of binding to a deglycosylated S protein RBD with a $K_D$ of about 0.95, about 0.96 nM, about 0.97 nM, about 0.98 nM, about 0.99 nM, about 1.0 nM, about 1.1 nM, about 1.2 nM, about 1.3 nM, about 1.4 nM, about 1.5 nM, or about 1.6 nM, optionally as measured by surface plasmon resonance, and/or with a $k_a$ of about (1/S) about 2.5e5, about 2.6e5, about 2.7e5, about 2.8e5, about 2.9e5, about 3.0e5, about 3.1e5, optionally as measured by surface plasmon resonance, and/or with a $k_d$ of (1/S) about 2.8e-4, about 2.9e-4, about 3.0e-4, about 3.1e-4, about 3.2e-4, about 3.3e-4, about 3.4e-4, about 3.5e-4, about 3.6e-4, about 3.7e-4, about 3.8e-4, about 3.9e-4, about 4.0e-4, about 4.1e-4, about 4.2e-4, about 4.3e-4, about 4.4e-4, about 4.5e-4, about 4.6e-4, about 4.7e-4, about 4.8e-4, about 4.9e-4, or about 5.0e-4, optionally as measured by surface plasmon resonance.

In some embodiments for determining binding to RBD, surface plasmon resonance comprises using conducted using a sensor chip with anti-human Fc covalently immobilized (e.g., from GE). Buffer can be 10 mM HEPES pH 7.4, 150 mM NaCl, 3 mM EDTA, and 0.05% P20 detergent. SPR can be conducted at 25° C. Antibodies can be diluted from supernatant to approximately 2 µg/ml. RBD concentrations can be 0.8 nM, 3.1 nM, 12.5 nM, 50 nM, and/or 200 nM.

In some embodiments, an antibody or antigen-binding fragment is capable of binding to a Receptor Binding Domain (RBD) of the SARS-CoV-2 surface glycoprotein when the RBD is glycosylated and/or when the RBD is deglycosylated, wherein the binding is determined using surface plasmon resonance (SPR), wherein, optionally: (1) the SPR is performed using a Biacore T200 instrument using a single-cycle kinetics approach, further optionally with a 3 minute injection period and a 20 minute dissociation period; (2) the antibody or antigen-binding fragment is captured on a surface; (3) the RBD is present at a concentration of 0.8 nM, 3.1 nM, 12.5 nM, 50 nM, or 200 nM; (4) the antibody or antigen-binding fragment binds to the glycosylated RBD with a KD of about 2.0 nM, about 1.9 nM, about 1.8 nM, about 1.7 nM, about 1.6 nM, about 1.5 nM, about 1.4 nM, about 1.3 nM, about 1.2 nM, about 1.1 nM, about 1.0 nM, about 0.9 nM, about 0.8 nM, about 0.7 nM, about 0.6 nM, about 0.5 nM, or about 0.4 nM, or with a KD of 0.4 nM±0.05 nM, or with a KD of 0.45 nM±0.05 nM, or with a KD of 0.5 nM±0.05 nM, or with a KD of 0.6 nM±0.05 nM, or with a KD of 0.7 nM±0.05 nM, or with a KD of 1.7 nM±0.05 nM; and/or (5) the antibody or antigen-binding fragment binds to the deglycosylated RBD with a KD of about 37.0 nM, about 8.0 nM, about 2.0 nM, about 1.9 nM, about 1.8 nM, about 1.7 nM, about 1.6 nM, about 1.5 nM, about 1.4 nM, about 1.3 nM, about 1.2 nM, about 1.1 nM, about 1.0 nM, or about 0.9 nM, or with a KD of 37.0 nM±0.05 nM, or with a KD of 8.0 nM 0.05 nM, or with a KD of 1.0 nM±0.05 nM, or with a KD of 0.9 nM±0.05 nM, or with a KD of 1.3 nM±0.05 nM, or with a KD of 1.8 nM±0.05 nM, or with a KD of 1.7 nM±0.05 nM.

In certain embodiments, an antibody of the present disclosure is capable of neutralizing infection by SARS-CoV-2. As used herein, a "neutralizing antibody" is one that can neutralize, i.e., prevent, inhibit, reduce, impede, or interfere with, the ability of a pathogen to initiate and/or perpetuate an infection in a host. Neutralization may be quantified by, for example, assessing SARS-CoV-2 RNA levels in a(n e.g. lung) sample, assessing SARS-CoV-2 viral load in a(n e.g. lung) sample, assessing histopathology of a(n e.g. lung) sample, or the like. The terms "neutralizing antibody" and "an antibody that neutralizes" or "antibodies that neutralize" are used interchangeably herein. In any of the presently disclosed embodiments, the antibody or antigen-binding fragment is capable of preventing and/or neutralizing a SARS-CoV-2 infection in an in vitro model of infection and/or in an in vivo animal model of infection (e.g., using a Syrian hamster model with intranasal delivery of SARS-CoV-2) and/or in a human. In some embodiments, an antibody or antigen-binding fragment of the present disclosure is capable of neutralizing a SARS-CoV-2 infection with an IC90 of about 9 µg/ml. In some embodiments, an antibody or antigen-binding fragment of the present disclosure is capable of neutralizing a SARS-CoV-2 infection with an IC50 of about 16 to about 20 µg/ml. In some embodiments, an antibody or antigen-binding fragment is capable of neutralizing a SARS-CoV-2 infection, or a virus pseudotyped with SARS-CoV-2, with an IC50 of about 0.3 to about 0.4 µg/ml. In some embodiments, an antibody or antigen-binding fragment, or a composition comprising two or more antibodies or antigen-binding fragments, of the present disclosure is capable of neutralizing a SARS-CoV-2 infection, or a virus pseudotyped with SARS-CoV-2, with an IC50 of about 0.07 to about 0.08 µg/ml.

In certain embodiments, the antibody or antigen-binding fragment (i) recognizes an epitope in the ACE2 receptor binding motif (RBM, SEQ ID NO.:167) of SARS-CoV-2; (ii) is capable of blocking an interaction between SARS-CoV-2 and ACE2; (ii) is capable of binding to SARS-CoV-2 S protein with greater avidity than to SARS coronavirus S protein; (iv) is capable of staining about 30%, about 35%, about 40%, about 50%, about 55%, about 56%, about 57%, about 58%, about 59%, about 60%, or more of target cells expressing SARS-CoV-2 surface glycoprotein in a sample comprising about 50,000 of the target cells (e.g., ExpiCHO cells) in approximately 100 µL when the antibody or antigen-binding fragment is present at 10 µg/ml (e.g., staining as determined by a flow cytometry ELISA); (v) recognizes an epitope that is conserved in the ACE2 RBM of SARS-CoV-2 and in an ACE2 RBM of SARS coronavirus; (vi) is cross-reactive against SARS-CoV-2 and SARS coronavirus; (vii) recognizes an epitope in the SARS-CoV-2 surface glycoprotein that is not in the ACE2 RBM; or (viii) any combination of (i)-(vii).

In some embodiments, an antibody or antigen-binding fragment thereof is capable of capable of inhibiting an interaction between: (i) SARS-CoV-2 and a human DC-SIGN; (ii) SARS-CoV-2 and a human L-SIGN; (iii) SARS-CoV-2 and a human SIGLEC-1; or (iv) any combination of (i)-(iii). As disclosed herein, DC-SIGN, L-SIGN, and SIGLEC-1 can be involved in a SARS-CoV-2 infection, in roles comprising those of attachment receptors. Inhibiting an interaction between SARS-CoV-2 and DC-SIGN, L-SIGN, and/or SIGLEC-1 can, in some contexts, neutralize infection by the SARS-CoV-2.

In some embodiments, an antibody or antigen-binding fragment thereof is capable of binding to a surface glycoprotein of: (i) a SARS-CoV-2 Wuhan-Hu-1 (SEQ ID NO.: 165); (ii) a SARS-CoV-2 B.1.1.7; (iii) a SARS-CoV-2 B.1.351; (iv) a SARS-CoV-2 comprising any one or more of the following substitution mutations relative to SEQ ID NO.:165: N501Y; S477N; N439K; L452R; E484K; Y453F; A520S; K417N; K417V; S494P; N501T; S477R; V367F; P384L; A522S; A522V; V382L; P330S; T478I; S477I; P479S; or (v) any combination of (i)-(iv).

Terms understood by those in the art of antibody technology are each given the meaning acquired in the art, unless expressly defined differently herein. For example, the term "antibody" refers to an intact antibody comprising at least two heavy (H) chains and two light (L) chains inter-connected by disulfide bonds, as well as any antigen-binding portion or fragment of an intact antibody that has or retains the ability to bind to the antigen target molecule recognized by the intact antibody, such as an scFv, Fab, or Fab'2 fragment. Thus, the term "antibody" herein is used in the broadest sense and includes polyclonal and monoclonal antibodies, including intact antibodies and functional (antigen-binding) antibody fragments thereof, including fragment antigen binding (Fab) fragments, F(ab')2 fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific antibodies, diabodies, triabodies, tetrabodies, tandem di-scFv, and tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof (IgG1, IgG2, IgG3, IgG4), IgM, IgE, IgA, and IgD.

The terms "$V_L$" or "VL" and "$V_H$" or "VH" refer to the variable binding region from an antibody light chain and an antibody heavy chain, respectively. In certain embodiments, a VL is a kappa (κ) class (also "VK" herein). In certain embodiments, a VL is a lambda (λ) class. The variable binding regions comprise discrete, well-defined sub-regions known as "complementarity determining regions" (CDRs) and "framework regions" (FRs). The terms "complementarity determining region," and "CDR," are synonymous with "hypervariable region" or "HVR," and refer to sequences of amino acids within antibody variable regions, which, in general, together confer the antigen specificity and/or binding affinity of the antibody, wherein consecutive CDRs (i.e., CDR1 and CDR2, CDR2 and CDR3) are separated from one another in primary structure by a framework region. There are three CDRs in each variable region (HCDR1, HCDR2, HCDR3; LCDR1, LCDR2, LCDR3; also referred to as CDRHs and CDRLs, respectively). In certain embodiments, an antibody VH comprises four FRs and three CDRs as follows: FR1-HCDR1-FR2-HCDR2-FR3-HCDR3-FR4; and an antibody VL comprises four FRs and three CDRs as follows: FR1-LCDR1-FR2-LCDR2-FR3-LCDR3-FR4. In general, the VH and the VL together form the antigen-binding site through their respective CDRs.

As used herein, a "variant" of a CDR refers to a functional variant of a CDR sequence having up to 1-3 amino acid substitutions (e.g., conservative or non-conservative substitutions), deletions, or combinations thereof.

Numbering of CDR and framework regions may be according to any known method or scheme, such as the Kabat, Chothia, EU, IMGT, and AHo numbering schemes (see, e.g., Kabat et al., "Sequences of Proteins of Immunological Interest, US Dept. Health and Human Services, Public Health Service National Institutes of Health, 1991, 5$^{th}$ ed.; Chothia and Lesk, *J. Mol. Biol.* 196:901-917 (1987)); Lefranc et al., *Dev. Comp. Immunol.* 27:55, 2003; Honegger and Plückthun, *J. Mol. Bio.* 309:657-670 (2001)). Equivalent residue positions can be annotated and for different molecules to be compared using Antigen receptor Numbering And Receptor Classification (ANARCI) software tool (2016, Bioinformatics 15:298-300). Accordingly, identification of CDRs of an exemplary variable domain (VH or VL) sequence as provided herein according to one numbering scheme is not exclusive of an antibody comprising CDRs of the same variable domain as determined using a different numbering scheme. In certain embodiments, an antibody or antigen-binding fragment is provided that comprises CDRs from a VH sequence according to any one of SEQ ID NOs.:113, 1, 9-15, 23, 24, 27, 28-46, 55, 63, 79, 87, 95, 103, 105, 114-120, 129-146, 155, 172, 176-178, 194, 196, 198, 200, 202, 239, and 267, and from a VL sequence according to any one of SEQ ID NOs.:168, 5, 47-50, 59, 67, 71-72, 75, 76, 83, 91, 99, 109, 147-150, 159, 182, 190, 234, and 243, as determined using any known CDR numbering method, including the Kabat, Chothia, EU, IMGT, Martin (Enhanced Chothia), Contact, and AHo numbering methods. In certain embodiments, CDRs are according to the IMGT numbering method. In certain embodiments, CDRs are according to the antibody numbering method developed by the Chemical Computing Group (CCG); e.g., using Molecular Operating Environment (MOE) software (www.chemcomp.com).

In certain embodiments, an antibody or an antigen-binding fragment is provided that comprises a heavy chain variable domain (VH) comprising a CDRH1, a CDRH2, and a CDRH3, and a light chain variable domain (VL) comprising a CDRL1, a CDRL2, and a CDRL3, wherein: (i) the CDRH1 comprises or consists of the amino acid sequence according to any one of SEQ ID NOs.:106, 2, 56, 64, 80, 88, 96, 156, 179, 195, or 240, or a sequence variant thereof comprising one, two, or three acid substitutions, one or more of which substitutions is optionally a conservative substitution and/or is a substitution to a germline-encoded amino acid; (ii) the CDRH2 comprises or consists of the amino acid sequence according to any one of SEQ ID NOs.:121, 3, 16-22, 57, 65, 81, 89, 97, 107, 122-126, 157, 180, 197, 199, or 241, or a sequence variant thereof comprising one, two, or three amino acid substitutions, one or more of which substitutions is optionally a conservative substitution and/or is a substitution to a germline-encoded amino acid; (iii) the CDRH3 comprises or consists of the amino acid sequence according to any one of SEQ ID NOs.:108, 4, 25, 26, 58, 66, 82, 90, 98, 104, 127, 128, 158, 181, 201, 203, or 242, or a sequence variant thereof comprising one, two, or three amino acid substitutions, one or more of which substitutions is optionally a conservative substitution and/or is a substitution to a germline-encoded amino acid; (iv) the CDRL1 comprises or consists of the amino acid sequence according to any one of SEQ ID NOs.:169, 6, 51-54, 60, 68, 73, 74, 84, 92, 100, 110, 160, 183, 235, or 244, or a sequence variant thereof comprising one, two, or three amino acid substitutions, one or more of which substitutions is optionally a conservative substitution and/or is a substitution to a germline-encoded amino acid; (v) the CDRL2 comprises or consists of the amino acid sequence according to any one of SEQ ID NOs.:170, 7, 61, 69, 85, 93, 101, 111, 161, 184, 236, or 245, or a sequence variant thereof comprising one, two, or three amino acid substitutions, one or more of which substitutions is optionally a conservative substitution and/or is a substitution to a germline-encoded amino acid; and/or (vi) the CDRL3 comprises or consists of the amino acid sequence according to any one of SEQ ID NOs.:171, 8, 62, 70, 77, 78, 86, 94, 102, 112, 151, 152, 153, 154, 162, 185, 237, or 246, or a sequence variant thereof comprising having one, two, or three amino acid substitutions, one or more of which substitutions is optionally a conservative substitution and/or is a substitution to a germline-encoded amino acid, wherein the antibody or antigen binding fragment is capable of binding to a SARS-CoV-2 surface glycoprotein expressed on a cell surface of a host cell, on a virion, or both In some embodiments, an antibody or antigen-binding fragment comprises VH and VL amino acid sequences that are encoded by:

(i) a VH1-18 gene and a VK3-20 gene, respectively, or that are encoded by a polynucleotide having at least 90%, at least 91%, at least 92%, at least 93%, at least 94%, at least 95%, at least 96%, at least 97%, at least 98%, or at least 99% identity to VH1-18 and VK3-20, respectively;

(ii) a VH3-7 allele and a VL3-25 allele, respectively, or that are encoded by a polynucleotide having at least 90%, at least 91%, at least 92%, at least 93%, at least 94%, at least 95%, at least 96%, at least 97%, at least 98%, or at least 99% identity to VH3-7 and VL3-25, respectively;

(iii) a VH3-23 allele and a VK1-5 allele, respectively, or that are encoded by a polynucleotide having at least 90%, at least 91%, at least 92%, at least 93%, at least 94%, at least 95%, at least 96%, at least 97%, at least 98%, or at least 99% identity to VH3-23 and VK1-5, respectively;

(iv) a VH3-13 allele and a VK1-39 allele respectively, or that are encoded by a polynucleotide having at least 90%, at least 91%, at least 92%, at least 93%, at least 94%, at least 95%, at least 96%, at least 97%, at least 98%, or at least 99% identity to VH3-13 and VK1-39, respectively;

(v) a VH1-18 allele and a VK3-11 allele, respectively, or that are encoded by a polynucleotide having at least 90%, at least 91%, at least 92%, at least 93%, at least 94%, at least 95%, at least 96%, at least 97%, at least 98%, or at least 99% identity to VH1-18 and VK3-11, respectively; or (vi) a VH1-69 allele and a VL2-23 allele, respectively, or that are encoded by a polynucleotide having at least 90%, at least 91%, at least 92%, at least 93%, at least 94%, at least 95%, at least 96%, at least 97%, at least 98%, or at least 99% identity to VH1-69 and VL2-23, respectively.

In any of the presently disclosed embodiments, the antibody or antigen-binding fragment is capable of preventing and/or neutralizing a SARS-CoV-2 infection in an in vitro model of infection and/or in an in vivo animal model of infection and/or in a human.

In any of the presently disclosed embodiments, the antibody or antigen-binding fragment comprises CDRH1, CDRH2, CDRH3, CDRL1, CDRL2, and CDRL3 amino acid sequences according to SEQ ID NOs.: (i) 2-4 and 6-8 or 235-237, respectively; (ii) 2, any one of 16-22, 4, and 6-8 or 235-237, respectively; (iii) 2, 3, any one of 25-26, and 6-8 or 235-237, respectively; (iv) 2-4, 51, 7, and 8, respectively; (v) 2-4, 52, 7 or 236, and 8 or 237, respectively; (vi) 2-4, 53, 7 or 236, and 8 or 237, respectively; (vii) 2-5, 54, 7 or 236, and 8 or 237, respectively; (viii) 56-58 and 60-62, respectively; (ix) 64-66 and 68-70, respectively; (x) 64-66, 73 or 74, 69, and 70, respectively; (xi) 64-66, 68-69, and 77 or 78, respectively; (xii) 80-82 and 84-86, respectively; (xiii) 88-90 and 92-94, respectively; (xiv) 96-98 and 101-102, respectively; (xv) 96, 97, 104, and 100-102, respectively; (xvi) 106-108 and 110-112 or 169-171, respectively; (xvii) 106, any one of 121-126, 108, and 110-112, respectively; (xviii) 106, 107, 127 or 128, and 110-112, respectively; (xix) 106-108, 110, 111, and 151, respectively; (xx) 106-108, 110, 111, and 152, respectively; (xxi) 106-108, 110, 111, and 153, respectively; (xxii) 106-108, 110, 111, and 154, respectively; (xxiii) 106, 107 or any one of 121-126, 108 or 127 or 128, and 169-171, respectively; (xxiv) 156-158 and 160-162, respectively; (xxv) 106, 123, 127, and 169-171, respectively; (xxvi) 2, 17, 25, 6 or 235 or any one of 51-54, 7 or 236, and 8 or 237, respectively; (xxvii) 2, 20, 25, 6 or 235 or any one of 51-54, 7 or 236, and 8 or 237 respectively; (xxviii) 179-181 and 183-185, respectively, (xxix) 195, 180, 181 and 183-185, respectively; (xxx) 195, 197, 181 and 183-185, respectively; (xxxi) 195, 199, 181 and 183-185, respectively; (xxxii) 195, 197, 201 and 183-185, respectively; (xxxiii) 195, 197, 203 and 183-185, respectively;

(xxxiv) 195, 199, 201 and 183-185, respectively; (xxxv) 195, 199, 203 and 183-185, respectively; (xxxvi) 179, 180, 181 and 183-185, respectively; (xxxvii) 179, 197, 181 and 183-185, respectively; (xxxviii) 179, 199, 181 and 183-185, respectively; (xxxix) 179, 197, 201 and 183-185, respectively; (xxxx) 179, 197, 203 and 183-185, respectively; (xxxxi) 179, 199, 201 and 183-185, respectively; (xxxxii) 179, 199, 203 and 183-185, respectively; (xxxxiii) 179, 180, 201 and 183-185, respectively; (xxxxiv) 179, 180, 203 and 183-185, respectively; and (xxxxv) 240-242 and 244-246, respectively.

In certain embodiments, an antibody or an antigen-binding fragment of the present disclosure comprises CDRH1, CDRH2, CDRH3, CDRL1, CDRL2, and CDRL3 amino acid sequences as set forth in SEQ ID NOs: 80-82 and 84-86, respectively. In further embodiments, an antibody or antigen-binding fragment of the present disclosure binds to SARS-CoV-2 S protein with a $K_D$ of less than about $4.5 \times 10^{-9}$ M, less than about $5 \times 10^{-9}$ M, less than about $1 \times 10^{-10}$ M, less than about $5 \times 10^{-10}$ M, less than about $1 \times 10^{-11}$ M, less than about $5 \times 10^{-11}$ M, less than about $1 \times 10^{-12}$ M, or less than about $5 \times 10^{-12}$ M. In still further embodiments, an antibody or antigen-binding fragment of the present disclosure is capable of neutralizing a SARS-CoV-2 infection, and/or of neutralizing infection of a target cell by a virus pseudotyped with SARS-CoV-2, with an IC50 of about 16 to about 20 µg/ml.

In certain embodiments, an antibody or an antigen-binding fragment of the present disclosure comprises CDRH1, CDRH2, CDRH3, CDRL1, CDRL2, and CDRL3 amino acid sequences as set forth in SEQ ID NOs: 106-108 and 169-171 or 106, 121, 108, and 169-171, respectively. In further embodiments, an antibody or antigen-binding fragment of the present disclosure binds to SARS-CoV-2 S protein with a $K_D$ of less than about $4.5 \times 10^{-9}$ M, less than about $5-10^{-9}$ M, less than about $1 \times 10^{-10}$ M, less than about $5 \times 10^{-10}$ M, less than about $1 \times 10^{-11}$ M, less than about $5 \times 10^{-11}$ M, less than about $1 \times 10^{-12}$ M, or less than about $5 \times 10^{-12}$ M. In still further embodiments, an antibody or antigen-binding fragment of the present disclosure is capable of neutralizing a SARS-CoV-2 infection, and/or of neutralizing infection of a target cell by a virus pseudotyped with SARS-CoV-2, with an IC50 of about 0.3 to about 0.4 µg/ml.

In certain embodiments, an antibody or an antigen-binding fragment of the present disclosure comprises a CDRH1, a CDRH2, a CDRH3, a CDRL1, a CDRL2, and a CDRL3, wherein each CDR is independently selected from a corresponding CDR of SARS-CoV-2 S300 mAb, SARS-CoV-2 S300-v1 mAb, SARS-CoV-2 S300-v1.1 mAb, SARS-CoV-2 S300-v1.2 mAb, SARS-CoV-2 S300-v1.3 mAb, SARS-CoV-2 S300-v1.4 mAb, SARS-CoV-2 S300-v1.5 mAb, SARS-CoV-2 S300-v1.6 mAb, SARS-CoV-2 S300-v1.7 mAb, or SARS-CoV-2 S300-v1.8 mAb SARS-CoV-2 S300-v1.9 mAb, SARS-CoV-2 S300-v2 mAb, SARS-CoV-2 S300-v2.1 mAb, SARS-CoV-2 S300-v2.2 mAb, SARS-CoV-2 S300-v2.3 mAb, SARS-CoV-2 S300-v2.4 mAb, SARS-CoV-2 S300-v2.5 mAb, SARS-CoV-2 S300-v2.6 mAb, SARS-CoV-2 S300-v2.7 mAb, SARS-CoV-2 S300-v2.8 mAb, SARS-CoV-2 S300-v2.9 mAb, SARS-CoV-2 S300-v2.10, SARS-CoV-2 S300-v2.11, SARS-CoV-2 S300-v3 mAb, SARS-CoV-2 S300-v3.1 mAb, SARS-CoV-2 S300-v3.2 mAb, SARS-CoV-2 S300-v3.3 mAb, SARS-CoV-2 S300-v3.4 mAb, SARS-CoV-2 S300-v3.5 mAb, SARS-CoV-2 S300-v3.6 mAb, SARS-CoV-2 S300-v3.7 mAb, SARS-CoV-2 S300-v3.8 mAb, SARS-CoV-2 S300-v3.9 mAb, SARS-CoV-2 S300-v10 mAb, SARS-CoV-2 S300-v11 mAb, SARS-CoV-2 S300-v12 mAb, SARS-CoV-2 S300-v13 mAb, SARS-S300-v14 mAb, SARS-CoV-2 S302 mAb, SARS-CoV-2 S303 mAb, SARS-CoV-2 S303-v1 mAb, SARS-CoV-2 S303-v2 mAb, SARS-CoV-2 S303-v3 mAb, SARS-CoV-2 S303-v4 mAb, SARS-CoV-2 S303-v5 mAb, SARS-CoV-2 S304 mAb, SARS-CoV-2 S306 mAb, SARS-CoV-2 S307 mAb, SARS-CoV-2 S308 mAb, SARS-CoV-2 S308-v1 mAb, SARS-CoV-2 S308-v2 mAb, SARS-CoV-2 S309 mAb, SARS-CoV-2 S309-v1 mAb, SARS-CoV-2 S309-v1.1 mAb, SARS-CoV-2 S309-v1.2 mAb, SARS-CoV-2 S309-v1.3 mAb, SARS-CoV-2 S309-v1.4 mAb, SARS-CoV-2 S309-v1.5 mAb, SARS-CoV-2 S309-v1.6 mAb, SARS-CoV-2 S309-v1.7 mAb, SARS-CoV-2 S309-v1.8 mAb, SARS-CoV-2 S309-v2 mAb, SARS-CoV-2 S309-v2.1 mAb, SARS-CoV-2 S309-v2.2 mAb, SARS-CoV-2 S309-v2.3 mAb, SARS-CoV-2 S309-v2.4 mAb, SARS-CoV-2 S309-v2.5 mAb, SARS-CoV-2 S309-v2.6 mAb, SARS-CoV-2 S309-v2.7 mAb, SARS-CoV-2 S309-v2.8 mAb, SARS-CoV-2 309-v2.9 mAb, SARS-CoV-2 S309-v3 mAb, SARS-CoV-2 S309-v3.1 mAb, SARS-CoV-2 S309-v3.2 mAb, SARS-CoV-2 S309-v3.3 mAb, SARS-CoV-2 S309-v3.4 mAb, SARS-CoV-2 S309-v3.5 mAb, SARS-CoV-2 S309-v3.6 mAb, SARS-CoV-2 S309-v3.7 mAb, SARS-CoV-2 S309-v3.8 mAb, SARS-CoV-2 S309-v9 mAb, SARS-CoV-2 S309-v10 mAb, SARS-CoV-2 S309-v11 mAb, SARS-CoV-2 S309-v12 mAb, SARS-CoV-2 S309-v13 mAb, SARS-CoV-2 S310 mAb, SARS-CoV-2 S311 mAb, SARS-CoV-2 S312 mAb, SARS-CoV-2 S315-v1 mAb, SARS-CoV-2 S315-v2 mAb, SARS-CoV-2 S315-v3 mAb, SARS-CoV-2 S315-v4 mAb, SARS-CoV-2 S315-v5 mAb, SARS-CoV-2 S315-v6 mAb, or SARS-CoV-2 S315-v7 mAb, as provided in Table 2. That is, all combinations of CDRs from SARS-CoV-2 mAbs and the variant sequences thereof provided in Table 2 are contemplated.

Exemplary antibodies of the present disclosure include antibody S309 and engineered variants thereof. In particular embodiments, an antibody or antigen-binding fragment comprises a CDRH1, a CDRH2, a CDRH3, a CDRL1, a CDRL2, and a CDRL3 selected from any of the CDRH1, CDRH2, CDRH3, CDRL1, CDRL2, and CDRL3 amino acid sequences (respectively) provided in Table 1.

In some embodiments, an antibody or antigen-binding fragment comprises: a CDRH1, a CDRH2, and a CDRH3 of the VH amino acid sequence set forth in any one of SEQ ID NOs.:105, 113, 114, 115, 116, 117, 118, 119, 120, 129, 130, 131, 132, 133, 134, 135, 136, 137, 138, 139, 140, 141, 142, 143, 144, 145, 146, 172, and 267; and a CDRL1, a CDRL2, and a CDRL3 as set forth in SEQ ID NO.:168 (i.e., according to any CDR numbering or determination method known in the art, such as IMGT, Kabat, Chothia, AHo, North, Contact, CCG, EU, or Martin (Enhanced Chothia)).

In further embodiments, the antibody or antigen-binding fragment comprises a VH having at least 85% identity (i.e., 85%, 86, 87, 88, 89, 90, 91, 92, 93, 94, 95, 96, 97, 98, 99, or 100%) identity to a VH amino acid sequence provided in Table 1 and/or a VL having at least 85% identity (i.e., 85%, 86, 87, 88, 89, 90, 91, 92, 93, 94, 95, 96, 97, 98, 99, or 100%) identity to a VL amino acid sequence provided in Table 1. In still further embodiments, the antibody or antigen-binding fragment comprises a VH having at least 90% identity identity to a VH amino acid sequence provided in Table 1 and/or a VL having at least 90% identity to a VL amino acid sequence provided in Table 1. In still further embodiments, the antibody or antigen-binding fragment comprises a VH having at least 95% identity identity to a VH amino acid sequence provided in Table 1 and/or a VL having at least 95% identity to a VL amino acid sequence provided in Table 1. In still further embodiments, the antibody or antigen-binding fragment comprises a VH having at least 99% identity identity to a VH amino acid sequence provided in Table 1 and/or a VL having at least 99% identity to a VL amino acid sequence provided in Table 1. In some embodiments, the antibody or antigen-binding fragment comprises a VH amino acid sequence selected from the VH amino acid sequences provided in Table 1 and a VL amino acid sequence selected from the VL amino acid sequence provided in Table 1.

TABLE 1

CDR (IMGT) and Variable Region Amino Acid Sequences of Certain S309 Antibodies

CDRH1  GYPFTSYG (SEQ ID NO 106)

CDRH2  ISTYNGNT (SEQ ID NO.: 107);
       ISTYQGNT (SEQ ID NO.: 121);
       ISTYNSNT (SEQ ID NO.: 122);
       ISTYNANT (SEQ ID NO.: 123);
       ISTYNQNT (SEQ ID NO.: 124);
       ISTYLGNT (SEQ ID NO.: 125);
       ISTYTGNT (SEQ ID NO.: 126);

CDRH3  ARDYTRGAWFGESLIGGFDN (SEQ ID NO.: 108);
       ARDYTRGAFFGESLIGGFDN (SEQ ID NO.: 127);
       ARDYTRGAYFGESLIGGFDN (SEQ ID NO.: 128)

VH     QVQLVQSGAEVKKPGASVKVSCKASGYPFTSYGISWVRQAPGQGL
       EWMGWISTYNGNTNYAQKFQGRVTMTTDTSTTTGYMELRRLRSD
       DTAVYYCARDYTRGAWFGESLIGGFDNWGQGTLVTVSS
       (SEQ ID NO.: 105)
       QVQLVQSGAEVKKPGASVKVSCKASGYPFTSYGISWVRQAPGQGL
       EWMGWISTYQGNTNYAQKFQGRVTMTTDTSTTTGYMELRRLRSD
       DTAVYYCARDYTRGAWFGESLIGGFDNWGQGTLVTVSS
       (SEQ ID NO: 113)
       QVQLVQSGAEVKKPGASVKVSCKASGYPFTSYGISWVRQAPGQGL
       EWMGWISTYNSNTNYAQKFQGRVTMTTDTSTTTGYMELRRLRSDD
       TAVYYCARDYTRGAWFGESLIGGFDNWGQGTLVTVSS
       (SEQ ID NO.: 114)
       QVQLVQSGAEVKKPGASVKVSCKASGYPFTSYGISWVRQAPGQGL
       EWMGWISTYNANTNYAQKFQGRVTMTTDTSTTTGYMELRRLRSD
       DTAVYYCARDYTRGAWFGESLIGGFDNWGQGTLVTVSS
       (SEQ ID NO: 115)
       QVQLVQSGAEVKKPGASVKVSCKASGYPFTSYGISWVRQAPGQGL
       EWMGWISTYNQNTNYAQKFQGRVTMTTDTSTTTGYMELRRLRSD
       DTAVYYCARDYTRGAWFGESLIGGFDNWGQGTLVTVSS
       (SEQ ID NO.: 116)
       QVQLVQSGAEVKKPGASVKVSCKASGYPFTSYGISWVRQAPGQGL
       EWMGWISTYLGNTNYAQKFQGRVTMTTDTSTTTGYMELRRLRSD
       DTAVYYCARDYTRGAWFGESLIGGFDNWGQGTLVTVSS
       (SEQ ID NO.: 117)
       QVQLVQSGAEVKKPGASVKVSCKASGYPFTSYGISWVRQAPGQGL
       EWMGWISTYTGNTNYAQKFQGRVTMTTDTSTTTGYMELRRLRSD
       DTAVYYCARDYTRGAWFGESLIGGFDNWGQGTLVTVSS
       (SEQ ID NO.: 118)
       QVQLVQSGAEVKKPGASVKVSCKASGYPFTSYGISWVRQAPGQGL
       EWMGWISTYNGNTNYAQKFQGRVTMTTDTSTTTGYMELRRLRSD
       DTAVYYCARDYTRGAFFGESLIGGFDNWGQGTLVTVSS
       (SEQ ID NO.: 119)
       QVQLVQSGAEVKKPGASVKVSCKASGYPFTSYGISWVRQAPGQGL
       EWMGWISTYNGNTNYAQKFQGRVTMTTDTSTTTGYMELRRLRSD
       DTAVYYCARDYTRGAYFGESLIGGFDNWGQGTLVTVSS
       (SEQ ID NO.: 120)
       QVQLVQSGAEVKKPGASVKVSCKASGYPFTSYGISWVRQAPGQGL
       EWMGFISTYNGNTNYAQKFQGRVTMTTDTSTTTGYMELRRLRSDD
       TAVYYCARDYTRGAWFGESLIGGFDNWGQGTLVTVSS
       (SEQ ID NO.: 129)
       QVQLVQSGAEVKKPGASVKVSCKASGYPFTSYGISWVRQAPGQGL
       EWMGFISTYQGNTNYAQKFQGRVTMTTDTSTTTGYMELRRLRSDD
       TAVYYCARDYTRGAWFGESLIGGFDNWGQGTLVTVSS
       (SEQ ID NO.: 130)
       QVQLVQSGAEVKKPGASVKVSCKASGYPFTSYGISWVRQAPGQGL
       EWMGFISTYNSNTNYAQKFQGRVTMTTDTSTTTGYMELRRLRSDD
       TAVYYCARDYTRGAWFGESLIGGFDNWGQGTLVTVSS
       (SEQ ID NO.: 131)
       QVQLVQSGAEVKKPGASVKVSCKASGYPFTSYGISWVRQAPGQGL
       EWMGFISTYNANTNYAQKFQGRVTMTTDTSTTTGYMELRRLRSDD
       TAVYYCARDYTRGAWFGESLIGGFDNWGQGTLVTVSS
       (SEQ ID NO.: 132)
       QVQLVQSGAEVKKPGASVKVSCKASGYPFTSYGISWVRQAPGQGL
       EWMGFISTYNQNTNYAQKFQGRVTMTTDTSTTTGYMELRRLRSDD
       TAVYYCARDYTRGAWFGESLIGGFDNWGQGTLVTVSS
       (SEQ ID NO.: 133)

TABLE 1-continued

CDR (IMGT) and Variable Region Amino Acid Sequences of Certain S309 Antibodies

QVQLVQSGAEVKKPGASVKVSCKASGYPFTSYGISWVRQAPGQGL
       EWMGFISTYLGNTNYAQKFQGRVTMTTDTSTTTGYMELRRLRSDD
       TAVYYCARDYTRGAWFGESLIGGFDNWGQGTLVTVSS
       (SEQ ID NO.: 134)
       QVQLVQSGAEVKKPGASVKVSCKASGYPFTSYGISWVRQAPGQGL
       EWMGFISTYTGNTNYAQKFQGRVTMTTDTSTTTGYMELRRLRSDD
       TAVYYCARDYTRGAWFGESLIGGFDNWGQGTLVTVSS
       (SEQ ID NO.: 135)
       QVQLVQSGAEVKKPGASVKVSCKASGYPFTSYGISWVRQAPGQGL
       EWMGFISTYNGNTNYAQKFQGRVTMTTDTSTTTGYMELRRLRSDD
       TAVYYCARDYTRGAFFGESLIGGFDNWGQGTLVTVSS
       (SEQ ID NO.: 136)
       QVQLVQSGAEVKKPGASVKVSCKASGYPFTSYGISWVRQAPGQGL
       EWMGFISTYNGNTNYAQKFQGRVTMTTDTSTTTGYMELRRLRSDD
       TAVYYCARDYTRGAYFGESLIGGFDNWGQGTLVTVSS
       (SEQ ID NO.: 137)
       QVQLVQSGAEVKKPGASVKVSCKASGYPFTSYGISWVRQAPGQGL
       EWMGYISTYNGNTNYAQKFQGRVTMTTDTSTTTGYMELRRLRSDD
       TAVYYCARDYTRGAWFGESLIGGFDNWGQGTLVTVSS
       (SEQ ID NO.: 138)
       QVQLVQSGAEVKKPGASVKVSCKASGYPFTSYGISWVRQAPGQGL
       EWMGYISTYQGNTNYAQKFQGRVTMTTDTSTTTGYMELRRLRSDD
       TAVYYCARDYTRGAWFGESLIGGFDNWGQGTLVTVSS
       (SEQ ID NO.: 139)
       QVQLVQSGAEVKKPGASVKVSCKASGYPFTSYGISWVRQAPGQGL
       EWMGYISTYNSNTNYAQKFQGRVTMTTDTSTTTGYMELRRLRSDD
       TAVYYCARDYTRGAWFGESLIGGFDNWGQGTLVTVSS
       (SEQ ID NO.: 140)
       QVQLVQSGAEVKKPGASVKVSCKASGYPFTSYGISWVRQAPGQGL
       EWMGYISTYNANTNYAQKFQGRVTMTTDTSTTTGYMELRRLRSDD
       TAVYYCARDYTRGAWFGESLIGGFDNWGQGTLVTVSS
       (SEQ ID NO.: 141)
       QVQLVQSGAEVKKPGASVKVSCKASGYPFTSYGISWVRQAPGQGL
       EWMGYISTYNQNTNYAQKFQGRVTMTTDTSTTTGYMELRRLRSDD
       TAVYYCARDYTRGAWFGESLIGGFDNWGQGTLVTVSS
       (SEQ ID NO.: 142)
       QVQLVQSGAEVKKPGASVKVSCKASGYPFTSYGISWVRQAPGQGL
       EWMGYISTYLGNTNYAQKFQGRVTMTTDTSTTTGYMELRRLRSDD
       TAVYYCARDYTRGAWFGESLIGGFDNWGQGTLVTVSS
       (SEQ ID NO.: 143)
       QVQLVQSGAEVKKPGASVKVSCKASGYPFTSYGISWVRQAPGQGL
       EWMGYISTYTGNTNYAQKFQGRVTMTTDTSTTTGYMELRRLRSDD
       TAVYYCARDYTRGAWFGESLIGGFDNWGQGTLVTVSS
       (SEQ ID NO.: 144)
       QVQLVQSGAEVKKPGASVKVSCKASGYPFTSYGISWVRQAPGQGL
       EWMGYISTYNGNTNYAQKFQGRVTMTTDTSTTTGYMELRRLRSDD
       TAVYYCARDYTRGAFFGESLIGGFDNWGQGTLVTVSS
       (SEQ ID NO.: 145)
       QVQLVQSGAEVKKPGASVKVSCKASGYPFTSYGISWVRQAPGQGL
       EWMGYISTYNGNTNYAQKFQGRVTMTTDTSTTTGYMELRRLRSDD
       TAVYYCARDYTRGAYFGESLIGGFDNWGQGTLVTVSS
       (SEQ ID NO.: 146)
       QVQLVQSGAEVKKPGASVKVSCKASGYPFTSYGISWVRQAPGQGL
       EWMGFISTYNANTNYAQKFQGRVTMTTDTSTTTGYMELRRLRSDD
       TAVYYCARDYTRGAFFGESLIGGFDNWGQGTLVTVSS
       (SEQ ID NO.: 172)
       QVQLVQSGAEVKKPGASVKVSCKASGYPFTSYGISWVRQAPGQGL
       EWMGX$_1$ISTYX$_2$X$_3$NTNYAQKFQGRVTMTTDTSTTTGYMELRRLR
       SDDTAVYYCARDYTRGAX$_4$FGESLIGGFDNWGQGTLVTVSS
       wherein X$_1$ = W, F, or Y; X$_2$ = N, Q, L, or T;
       X$_3$ = G, S, A, or Q; X$_4$ = W, F, or Y
       (SEQ ID NO.: 267)

CDRL1  QTVSSTS (SEQ ID NO.: 169)

CDRL2  GAS (SEQ ID NO.: 170)

CDRL3  QQHDTSLT (SEQ ID NO.: 171)

VL     EIVLTQSPGTLSLSPGERATLSCRASQTVSSTSLAWYQQKPGQAP
       RLLIYGASSRATGIPDRFSGSGSGTDFTLTISRLEPEDFAVYYCQ
       QHDTSLTFGGGTKVEIK (SEQ ID NO.: 168)

In particular embodiments, the antibody or antigen-binding fragment comprises CDRH1, CDRH2, and CDRH3 according to SEQ ID NOs.:106, 107 or 121 or 122 or 123 or 124 or 125 or 126, and 108 or 127 or 128, respectively, and CDRL1, CDRL2, and CDRL3 according to SEQ ID NOs.: 169-171, respectively. In some embodiments, the antibody or antigen-binding fragment comprises the CDRH1, CDRH2, CDRH3, CDRL1, CDRL2, and CDRL3 amino acid sequences set forth in: (a) SEQ ID NOs.:106, 121, 108, 169, 170, and 171, respectively; (b) SEQ ID NOs.: 106, 121, 127, 169, 170, and 171, respectively; (c) SEQ ID NOs.: 106, 121, 128, 169, 170, and 171, respectively; (d) SEQ ID NOs.: 106, 107, 108, 169, 170, and 171, respectively; (e) SEQ ID NOs.: 106, 107, 127, 169, 170, and 171, respectively; (f) SEQ ID NOs.: 106, 107, 128, 169, 170, and 171, respectively; (g) SEQ ID NOs.: 106, 122, 108, 169, 170, and 171, respectively; (h) SEQ ID NOs.: 106, 122, 127, 169, 170, and 171, respectively; (i) SEQ ID NOs.: 106, 122, 128, 169, 170, and 171, respectively; (j) SEQ ID NOs.: 106, 123, 108, 169, 170, and 171, respectively; (k) SEQ ID NOs.: 106, 123, 127, 169, 170, and 171, respectively; (l)SEQ ID NOs.: 106, 123, 128, 169, 170, and 171, respectively; (m) SEQ ID NOs.: 106, 124, 108, 169, 170, and 171, respectively; (n) SEQ ID NOs.: 106, 124, 127, 169, 170, and 171, respectively; (o) SEQ ID NOs.: 106, 124, 128, 169, 170, and 171, respectively; (p) SEQ ID NOs.: 106, 125, 108, 169, 170, and 171, respectively; (q) SEQ ID NOs.: 106, 125, 127, 169, 170, and 171, respectively; (r) SEQ ID NOs.: 106, 125, 128, 169, 170, and 171, respectively; (s) SEQ ID NOs.: 106, 126, 108, 169, 170, and 171, respectively; (t) SEQ ID NOs.: 106, 126, 127, 169, 170, and 171, respectively; or (u) SEQ ID NOs.: 106, 126, 128, 169, 170, and 171, respectively.

In further embodiments, the VH comprises or consists of the amino acid sequence set forth in any one of SEQ ID NOs.:105, 113, 114, 115, 116, 117, 118, 119, 120, 129, 130, 131, 132, 133, 134, 135, 136, 137, 138, 139, 140, 141, 142, 143, 144, 145, 146, 172, and 267, and the VL comprises or consists of the amino acid sequence set forth in SEQ ID NO.:168.

The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM). The Fc region of an antibody heavy chain is described further herein. In any of the presently disclosed embodiments, an antibody or antigen-binding fragment of the present disclosure comprises any one or more of CL, a CH1, a CH2, and a CH3. In certain embodiments, a CL comprises an amino acid sequence having 90%, 91%, 92%, 93%, 94%, 95%, 96%, 975, 98%, 99%, or 100% identity to the amino acid sequence of SEQ ID NO.:174 or SEQ ID NO.:193. In certain embodiments, a CH1-CH2-CH3 comprises an amino acid sequence having 90%, 91%, 92%, 93%, 94%, 95%, 96%, 975, 98%, 99%, or 100% identity to the amino acid sequence of SEQ ID NO.:173 or SEQ ID NO.:175 or SEQ ID NO.:265 or SEQ ID NO.:266. It will be understood that, for example, production in a mammalian cell line can remove one or more C-terminal lysine of an antibody heavy chain (see, e.g., Liu et al. *mAbs* 6(5):1145-1154 (2014)). Accordingly, an antibody or antigen-binding fragment of the present disclosure can comprise a heavy chain, a CH1-CH3, a CH3, or an Fc polypeptide wherein a C-terminal lysine residue is present or is absent; in other words, encompassed are embodiments where the C-terminal residue of a heavy chain, a CH1-CH3, or an Fc polypeptide is not a lysine, and embodiments where a lysine is the C-terminal residue. In certain embodiments, a composition comprises a plurality of an antibody and/or an antigen-binding fragment of the present disclosure, wherein one or more antibody or antigen-binding fragment does not comprise a lysine residue at the C-terminal end of the heavy chain, CH1-CH3, or Fc polypeptide, and wherein one or more antibody or antigen-binding fragment comprises a lysine residue at the C-terminal end of the heavy chain, CH1-CH3, or Fc polypeptide.

A "Fab" (fragment antigen binding) is the part of an antibody that binds to antigens and includes the variable region and CH1 of the heavy chain linked to the light chain via an inter-chain disulfide bond. Each Fab fragment is monovalent with respect to antigen binding, i.e., it has a single antigen-binding site. Pepsin treatment of an antibody yields a single large F(ab')2 fragment that roughly corresponds to two disulfide linked Fab fragments having divalent antigen-binding activity and is still capable of cross-linking antigen. Both the Fab and F(ab')2 are examples of "antigen-binding fragments." Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them. Other chemical couplings of antibody fragments are also known.

Fab fragments may be joined, e.g., by a peptide linker, to form a single chain Fab, also referred to herein as "scFab." In these embodiments, an inter-chain disulfide bond that is present in a native Fab may not be present, and the linker serves in full or in part to link or connect the Fab fragments in a single polypeptide chain. A heavy chain-derived Fab fragment (e.g., comprising, consisting of, or consisting essentially of VH+CH1, or "Fd") and a light chain-derived Fab fragment (e.g., comprising, consisting of, or consisting essentially of VL+CL) may be linked in any arrangement to form a scFab. For example, a scFab may be arranged, in N-terminal to C-terminal direction, according to (heavy chain Fab fragment-linker-light chain Fab fragment) or (light chain Fab fragment-linker-heavy chain Fab fragment). Peptide linkers and exemplary linker sequences for use in scFabs are discussed in further detail herein.

A scFab can be comprise any combination of VH and VL sequences or any combination of the CDRH1, CDRH2, CDRH3, CDRL1, CDRL2, and CDRL3 sequences disclosed herein. In certain embodiments, a scFab comprises the VH sequence as provided in SEQ ID NO: 105 or SEQ ID NO: 113 and the VL sequence as provided in SEQ ID NO: 168. In certain embodiments, a scFab comprises a CDRH1 sequence as provided in SEQ ID NO: 106, a CDRH2 sequence as provided in SEQ ID NO: 107 or 121, a CDRH3 sequence as provided in SEQ ID NO: 108, a CDRL1 sequence as provided in SEQ ID NO: 169, a CDRL2 sequence as provided in SEQ ID NO: 170, and a CDRL3 sequence as provided in SEQ ID NO: 171. In certain embodiments, a scFab comprises an amino acid sequence having at least 90%, 91%, 92%, 93%, 94%, 95%, 96%, 97%, 98%, 99%, or 100% identity to the amino acid sequence provided in any one of SEQ ID NOs.: 218-219 or 226-227.

"Fv" is a small antibody fragment that contains a complete antigen-recognition and antigen-binding site. This fragment generally consists of a dimer of one heavy- and one light-chain variable region domain in tight, non-covalent association. However, even a single variable domain (or half of an Fv comprising only three CDRs specific for an antigen)

has the ability to recognize and bind antigen, although typically at a lower affinity than the entire binding site.

"Single-chain Fv" also abbreviated as "sFv" or "scFv", are antibody fragments that comprise the $V_H$ and $V_L$ antibody domains connected into a single polypeptide chain. In some embodiments, the scFv polypeptide comprises a polypeptide linker disposed between and linking the $V_H$ and $V_L$ domains that enables the scFv to retain or form the desired structure for antigen binding. Such a peptide linker can be incorporated into a fusion polypeptide using standard techniques well known in the art. Additionally or alternatively, Fv can have a disulfide bond formed between and stabilizing the VH and the VL. For a review of scFv, see Pluckthun in The Pharmacology of Monoclonal Antibodies, vol. 113, Rosenburg and Moore eds., Springer-Verlag, New York, pp. 269-315 (1994); Borrebaeck 1995, infra. In certain embodiments, the antibody or antigen-binding fragment comprises a scFv comprising a VH domain, a VL domain, and a peptide linker linking the VH domain to the VL domain. In particular embodiments, a scFv comprises a VH domain linked to a VL domain by a peptide linker, which can be in a VH-linker-VL orientation or in a VL-linker-VH orientation. Any scFv of the present disclosure may be engineered so that the C-terminal end of the VL domain is linked by a short peptide sequence to the N-terminal end of the VH domain, or vice versa (i.e., (N)VL(C)-linker-(N)VH(C) or (N)VH(C)-linker-(N)VL(C). Alternatively, in some embodiments, a linker may be linked to an N-terminal portion or end of the VH domain, the VL domain, or both.

Peptide linker sequences may be chosen, for example, based on: (1) their ability to adopt a flexible extended conformation; (2) their inability or lack of ability to adopt a secondary structure that could interact with functional epitopes on the first and second polypeptides and/or on a target molecule; and/or (3) the lack or relative lack of hydrophobic or charged residues that might react with the polypeptides and/or target molecule. Other considerations regarding linker design (e.g., length) can include the conformation or range of conformations in which the VH and VL can form a functional antigen-binding site. In certain embodiments, peptide linker sequences contain, for example, Gly, Asn and Ser residues. Other near neutral amino acids, such as Thr and Ala, may also be included in a linker sequence. Other amino acid sequences which may be usefully employed as linker include those disclosed in Maratea et al., Gene 40:39 46 (1985); Murphy et al., Proc. Natl. Acad. Sci. USA 83:8258 8262 (1986); U.S. Pat. Nos. 4,935,233, and 4,751,180. Other illustrative and non-limiting examples of linkers may include, for example, Glu-Gly-Lys-Ser-Ser-Gly-Ser-Gly-Ser-Glu-Ser-Lys-Val-Asp (SEQ ID NO: 215) (Chaudhary et al., Proc. Natl. Acad. Sci. USA 87:1066-1070 (1990)) and Lys-Glu-Ser-Gly-Ser-Val-Ser-Ser-Glu-Gln-Leu-Ala-Gln-Phe-Arg-Ser-Leu-Asp (SEQ ID NO: 216) (Bird et al., Science 242:423-426 (1988)) and the pentamer Gly-Gly-Gly-Gly-Ser (SEQ ID NO: 217) when present in a single iteration or repeated 1 to 5 or more times, or more; see, e.g., SEQ ID NO: 213. Any suitable linker may be used, and in general can be about 3, 4, 5, 6, 7, 8, 9, 10, 11, 12, 13, 14, 15, 16, 17, 18, 19, 20, 21, 22, 15 23, 24, 25, 26, 27, 28, 29, 30, 40, 50, 60, 70, 80, 90, 100 amino acids in length, or less than about 200 amino acids in length, and will preferably comprise a flexible structure (can provide flexibility and room for conformational movement between two regions, domains, motifs, fragments, or modules connected by the linker), and will preferably be biologically inert and/or have a low risk of immunogenicity in a human. Exemplary linkers include those comprising or consisting of the amino acid sequence set forth in any one or more of SEQ ID NOs: 206-217. In certain embodiments, the linker comprises or consists of an amino acid sequence having at least 75% (i.e., at least about 75%, 80%, 85%, 90%, 91%, 92%, 93%, 94%, 95%, 96%, 97%, 98%, 99%, or more) identity to the amino acid sequence set forth in any one of SEQ ID NOs: 206-217.

scFv can be constructed using any combination of the VH and VL sequences or any combination of the CDRH1, CDRH2, CDRH3, CDRL1, CDRL2, and CDRL3 sequences disclosed herein. In certain embodiments, a scFv comprises the VH sequence provided in SEQ ID NO: 105 or SEQ ID NO: 113 and the VL sequence provided in SEQ ID NO: 168. In certain embodiments, a scFab comprises a CDRH1 sequence as provided in SEQ ID NO: 106, a CDRH2 sequence as provided in SEQ ID NO: 107 or 121, a CDRH3 sequence as provided in SEQ ID NO: 108, a CDRL1 sequence as provided in SEQ ID NO: 169, a CDRL2 sequence as provided in SEQ ID NO: 170, and a CDRL3 sequence as provided in SEQ ID NO: 171. In certain embodiments, a scFv can comprise the amino acid sequence as provided in SEQ ID NO: 220-221 or SEQ ID NO: 228-229.

In some embodiments, linker sequences are not required; for example, when the first and second polypeptides have non-essential N-terminal amino acid regions that can be used to separate the functional domains and prevent steric interference.

During antibody development, DNA in the germline variable (V), joining (J), and diversity (D) gene loci may be rearranged and insertions and/or deletions of nucleotides in the coding sequence may occur. Somatic mutations may be encoded by the resultant sequence, and can be identified by reference to a corresponding known germline sequence. In some contexts, somatic mutations that are not critical to a desired property of the antibody (e.g., binding to a SARS-CoV-2 antigen), or that confer an undesirable property upon the antibody (e.g., an increased risk of immunogenicity in a subject administered the antibody), or both, may be replaced by the corresponding germline-encoded amino acid, or by a different amino acid, so that a desirable property of the antibody is improved or maintained and the undesirable property of the antibody is reduced or abrogated. Thus, in some embodiments, the antibody or antigen-binding fragment of the present disclosure comprises at least one more germline-encoded amino acid in a variable region as compared to a parent antibody or antigen-binding fragment, provided that the parent antibody or antigen binding fragment comprises one or more somatic mutations. Variable region and CDR amino acid sequences of exemplary anti-SARS-CoV-2 antibodies of the present disclosure are provided in Table 2 herein.

In certain embodiments, an antibody or antigen-binding fragment comprises an amino acid modification (e.g., a substitution mutation) to remove an undesired risk of oxidation, deamidation, and/or isomerization.

Also provided herein are variant antibodies that comprise one or more amino acid alterations in a variable region (e.g., VH, VL, framework or CDR) as compared to a presently disclosed ("parent") antibody, wherein the variant antibody is capable of binding to a SARS-CoV-2 antigen.

In certain embodiments, the VH comprises or consists of an amino acid sequence having at least 85% (i.e., 85%, 86, 87, 88, 89, 90, 91, 92, 93, 94, 95, 96, 97, 98, 99, or 100%) identity to the amino acid sequence according to any one of SEQ ID NOs.: 1, 9-15, 23, 24, 27, 28-46, 55, 63, 79, 87, 95, 103, 105, 113-120, 129-146, 155, 172, 176-178, 194, 196, 198, 200, 202, and 239, wherein the variation is optionally limited to one or more framework regions and/or the variation comprises one or more substitution to a germline-encoded amino acid; and/or (ii) the VL comprises or consists of an amino acid sequence having at least 85% (i.e., 85%, 86, 87, 88, 89, 90, 91, 92, 93, 94, 95, 96, 97, 98, 99, or 100%) identity to the amino acid sequence according to any one of SEQ ID NOs.: 5, 47-50, 59, 67, 71-72, 75, 76, 83, 91, 99, 109, 147-150, 159, 168, 182, 190, 234, and 243, wherein the variation is optionally limited to one or more framework regions and/or the variation comprises one or more substitution to a germline-encoded amino acid.

In some embodiments, an antibody or antigen-binding fragment comprises VH and VL amino acid sequences that are encoded by, or that are the same as VH and VL amino acid sequences that are encoded by:

(i) a VH1-18 gene and a VK3-20 gene, respectively, or that are encoded by a polynucleotide having at least 90%, at least 91%, at least 92%, at least 93%, at least 94%, at least 95%, at least 96%, at least 97%, at least 98%, or at least 99% identity to VH1-18 and VK3-20, respectively;

(ii) a VH3-7 allele and a VL3-25 allele, respectively, or that are encoded by a polynucleotide having at least 90%, at least 91%, at least 92%, at least 93%, at least 94%, at least 95%, at least 96%, at least 97%, at least 98%, or at least 99% identity to VH3-7 and VL3-25, respectively;

(iii) a VH3-23 allele and a VK1-5 allele, respectively, or that are encoded by a polynucleotide having at least 90%, at least 91%, at least 92%, at least 93%, at least 94%, at least 95%, at least 96%, at least 97%, at least 98%, or at least 99% identity to VH3-23 and VK1-5, respectively;

(iv) a VH3-13 allele and a VK1-39 allele respectively, or that are encoded by a polynucleotide having at least 90%, at least 91%, at least 92%, at least 93%, at least 94%, at least 95%, at least 96%, at least 97%, at least 98%, or at least 99% identity to VH3-13 and VK1-39, respectively;

(v) a VH1-18 allele and a VK3-11 allele, respectively, or that are encoded by a polynucleotide having at least 90%, at least 91%, at least 92%, at least 93%, at least 94%, at least 95%, at least 96%, at least 97%, at least 98%, or at least 99% identity to VH1-18 and VK3-11, respectively; or (vi) a VH1-69 allele and a VL2-23 allele, respectively, or that are encoded by a polynucleotide having at least 90%, at least 91%, at least 92%, at least 93%, at least 94%, at least 95%, at least 96%, at least 97%, at least 98%, or at least 99% identity to VH1-69 and VL2-23, respectively.

In certain embodiments, the VH comprises or consists of any VH amino acid sequence set forth in Table 2, and the VL comprises or consists of any VL amino acid sequence set forth in Table 2. In particular embodiments, the VH and the VL comprise or consist of the amino acid sequences according to SEQ ID NOs.: (i) 1 and 5 or 234, respectively; (ii) any one of 9-15 and 5 or 234, respectively; (iii) 23 or 24 and 5 or 234, respectively; (iv) 27 and 5 or 234, respectively; (v) any one of 28-46 and 5 or 234, respectively; (vi) 1 and any one of 47-50, respectively; (vii) any one of 9-15 and any one of 47-50, respectively; (viii) 23 or 24 and any one of 47-50, respectively; (ix) 27 and any one of 47-50, respectively; (x) any one of 28-46 and any one of 47-50, respectively; (xi) 55 and 59, respectively; (xii) 63 and 67, respectively; (xiii) 63 and 71 or 72, respectively; (xiv) 63 and 75 or 76, respectively; (xv) 79 and 83, respectively; (xvi) 87 and 91, respectively; (xvii) 95 and 99, respectively; (xviii) 103 and 99, respectively; (xiv) 105 and 109 or 168, respectively; (xx) any one of 113-120 and 109 or 168, respectively; (xxi) 129 and 109 or 168, respectively; (xxii) any one of 130-146 and 109 or 168, respectively; (xxiii) 105 and any one of 147-150, respectively; (xxiv) any one of 113-120 and any one of 147-150, respectively; (xxv) any one of 130-146 and any one of 147-150, respectively; (xxvi) 155 and 159, respectively; (xxvii) 172 and 168, respectively; (xxviii) 176 or 177 and 5 or any one of 47-50, respectively; (xxix) 178 and 182 or 190, respectively (i.e., 178 and 182, respectively, or 178 and 190, respectively); (xxx) 194 and 182, respectively; (xxxi) 196 and 182, respectively; (xxxii) 198 and 182, respectively; (xxxiii) 200 and 182, respectively; (xxxiv) 202 and 182, respectively; or (xxxv) 239 and 243, respectively.

In certain embodiments, an antigen or an antigen-binding fragment of the present disclosure comprises a VH comprising or consisting of the amino acid sequence according to SEQ ID NO.:79 and a VL comprising or consisting of the amino acid sequence according to SEQ ID NO.:83. In further embodiments, an antigen or an antigen-binding fragment of the present disclosure comprises a VH comprising or consisting of the amino acid sequence according to SEQ ID NO.:79 and a VL comprising or consisting of the amino acid sequence according to SEQ ID NO.:83 and binds to SARS-CoV-2 S protein with a $K_D$ of less than about 4.5× $10^{-9}$ M, less than about $5×10^{-9}$ M, less than about $1×10^{-10}$ M, less than about $5×10^{-10}$ M, less than about $1×10^{-11}$ M, less than about $5×10^{-11}$ M, less than about $1×10^{-12}$ M, or less than about $5×10^{-12}$ M. In still further embodiments, an antigen or an antigen-binding fragment of the present disclosure comprises a VH comprising or consisting of the amino acid sequence according to SEQ ID NO: 79 and a VL comprising or consisting of the amino acid sequence according to SEQ ID NO: 83 and is capable of neutralizing a SARS-CoV-2 infection, or a virus pseudotyped with SARS-CoV-2, with an IC50 of about 16 to about 20 µg/ml.

In certain embodiments, an antibody or an antigen-binding fragment of the present disclosure comprises a VH comprising or consisting of the amino acid sequence according to SEQ ID NO.:105 and a VL comprising or consisting of the amino acid sequence according to SEQ ID NO.:168. In further embodiments, an antibody or an antigen-binding fragment of the present disclosure comprises a VH comprising or consisting of the amino acid sequence according to SEQ ID NO.:105 and a VL comprising or consisting of the amino acid sequence according to SEQ ID NO.:168 and binds to SARS-CoV-2 S protein with a $K_D$ of less than about $4.5×10^{-9}$ M, less than about $5×10^{-9}$ M, less than about $1×10^{-10}$ M, less than about $5×10^{-10}$ M, less than about $1×10^{-11}$ M, less than about $5×10^{-11}$ M, less than about $1×10^{-12}$ M, or less than about $5×10^{-12}$ M. In still further embodiments, an antibody or an antigen-binding fragment of the present disclosure comprises a VH comprising or consisting of the amino acid sequence according to SEQ ID NO.:105 and a VL comprising or consisting of the amino acid sequence according to SEQ ID NO.:168 and is capable of neutralizing a SARS-CoV-2 infection, or a virus pseudotyped with SARS-CoV-2, with an IC50 of about 0.3 to about 0.4 µg/ml.

In certain embodiments, an antibody or an antigen-binding fragment of the present disclosure comprises a VH comprising or consisting of the amino acid sequence according to SEQ ID NO.:105 and a VL comprising or consisting of the amino acid sequence according to SEQ ID NO.:168 and binds to SARS-CoV-2 S protein RBD with an EC50 of about 11 to about 25 ng/ml. In certain embodiments, an antibody or an antigen-binding fragment of the present disclosure comprises a VH comprising or consisting of the amino acid sequence according to SEQ ID NO.:113 and a VL comprising or consisting of the amino acid sequence according to SEQ ID NO.:168 and binds to SARS-CoV-2 S protein RBD with an EC50 of about 9 to about 23 ng/ml. In certain embodiments, an antibody or an antigen-binding fragment of the present disclosure comprises a VH comprising or consisting of the amino acid sequence according to SEQ ID NO.:129 and a VL comprising or consisting of the amino acid sequence according to SEQ ID NO.:168 and binds to SARS-CoV-2 S protein RBD with an EC50 of about 8 to about 22 ng/ml. In certain embodiments, an antibody or an antigen-binding fragment of the present disclosure comprises a VH comprising or consisting of the sequence according to SEQ ID NO.:119 and a VL comprising or consisting of the sequence according to SEQ ID NO.:168 and binds to SARS-CoV-2 S protein RBD with an EC50 of about 8 to about 22 ng/ml. In certain embodiments, an antibody or an antigen-binding fragment of the present disclosure comprises a VH comprising or consisting of the amino acid sequence according to SEQ ID NO.:172 and a VL comprising or consisting of the amino acid sequence according to SEQ ID NO.:168 and binds to SARS-CoV-2 S protein RBD with an EC50 of about 7 to about 19 ng/ml.

In certain embodiments, an antibody or antigen-binding fragment of the present disclosure is monospecific (e.g., binds to a single epitope) or is multispecific (e.g., binds to multiple epitopes and/or target molecules). Antibodies and antigen binding fragments may be constructed in various formats. Exemplary antibody formats disclosed in Spiess et al., *Mol. Immunol.* 67(2):95 (2015), and in Brinkmann and Kontermann, *mAbs* 9(2):182-212 (2017), which formats and methods of making the same are incorporated herein by reference and include, for example, Bispecific T cell Engagers (BiTEs), DARTs, Knobs-Into-Holes (KIH) assemblies, scFv-CH3-KIH assemblies, KIH Common Light-Chain antibodies, TandAbs, Triple Bodies, TriBi Minibodies, Fab-scFv, scFv-CH-CL-scFv, F(ab')2-scFv2, tetravalent HCabs, Intrabodies, CrossMabs, Dual Action Fabs (DAFs) (two-in-one or four-in-one), DutaMabs, DT-IgG, Charge Pairs, Fab-arm Exchange, SEEDbodies, Triomabs, LUZ-Y assemblies, Fcabs, κλ-bodies, orthogonal Fabs, DVD-Igs (e.g., U.S. Pat. No. 8,258,268, which formats are incorporated herein by reference in their entirety), IgG(H)-scFv, scFv-(H)IgG, IgG (L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, Zybody, and DVI-IgG (four-in-one), as well as so-called FIT-Ig (e.g., PCT Publication No. WO 2015/103072, which formats are incorporated herein by reference in their entirety), so-called WuxiBody formats (e.g., PCT Publication No. WO 2019/057122, which formats are incorporated herein by reference in their entirety), and so-called In-Elbow-Insert Ig formats (IEI-Ig; e.g., PCT Publication Nos. WO 2019/024979 and WO 2019/025391, which formats are incorporated herein by reference in their entirety).

In certain embodiments, the antibody or antigen-binding fragment comprises two or more of VH domains, two or more VL domains, or both (i.e., two or more VH domains and two or more VL domains). In particular embodiments, an antigen-binding fragment comprises the format (N-terminal to C-terminal direction) VH-linker-VL-linker-VH-linker-VL, wherein the two VH sequences can be the same or different and the two VL sequences can be the same or different. Such linked scFvs can include any combination of VH and VL domains arranged to bind to a given target, and in formats comprising two or more VH and/or two or more VL, one, two, or more different epitopes or antigens may be bound. It will be appreciated that formats incorporating multiple antigen-binding domains may include VH and/or VL sequences in any combination or orientation. For example, the antigen-binding fragment can comprise the format VL-linker-VH-linker-VL-linker-VH, VH-linker-VL-linker-VL-linker-VH, or VL-linker-VH-linker-VH-linker-VL.

Monospecific or multispecific antibodies or antigen-binding fragments of the present disclosure can comprise any combination of the VH and VL sequences and/or any combination of the CDRH1, CDRH2, CDRH3, CDRL1, CDRL2, and CDRL3 sequences disclosed herein. In certain embodiments, an antibody or antigen-binding fragment comprises the VH sequence provided in SEQ ID NO.:105 or SEQ ID NO.:113 and the VL sequence provided in SEQ ID NO: 168. In certain embodiments, an antibody or antigen-binding fragment comprises a CDRH1 sequence as provided in SEQ ID NO.:106, a CDRH2 sequence as provided in SEQ ID NO.:107 or 121, a CDRH3 sequence as provided in SEQ ID NO.:108, a CDRL1 sequence as provided in SEQ ID NO.:169, a CDRL2 sequence as provided in SEQ ID NO.: 170, and a CDRL3 sequence as provided in SEQ ID NO.: 171. In certain embodiments, an antibody or antigen-binding fragment comprises the amino acid sequence as provided in any one of SEQ ID NOs.: 222-225 or 230-233. A bispecific or multispecific antibody or antigen-binding fragment may, in some embodiments, comprise one, two, or more antigen-binding domains (e.g., a VH and a VL) of the instant disclosure. Two or more binding domains may be present that bind to the same or a different SARS-CoV-2 epitope, and a bispecific or multispecific antibody or antigen-binding fragment as provided herein can, in some embodiments, comprise a further SARS-CoV-2 binding domain, and/or can comprise a binding domain that binds to a different antigen or pathogen altogether.

In any of the presently disclosed embodiments, the antibody or antigen-binding fragment can be multispecific; e.g., bispecific, trispecific, or the like.

In certain embodiments, the antibody or antigen-binding fragment comprises: (i) a first VH and a first VL; and (ii) a second VH and a second VL, wherein the first VH and the second VH are different and each independently comprise an amino acid sequence having at least 85% (i.e., 85%, 86%, 87%, 88%, 89%, 90%, 91%, 92%, 93%, 94%, 95%, 96%, 97%, 98%, 99%, or 100%) identity to the amino acid sequence set forth in any one of SEQ ID NOs.: 1, 9-15, 23, 24, 27-46, 55, 63, 79, 87, 95, 103, 105, 113-120, 129-146, 155, 172, 176-178, 194, 196, 198, 200, 202, and 239, and wherein the first VL and the second VL are different and each independently comprise an amino acid sequence having at least 85% (i.e., 85%, 86%, 87%, 88%, 89%, 90%, 91%, 92%, 93%, 94%, 95%, 96%, 97%, 98%, 99%, or 100%) identity to the amino acid sequence set forth in any one of SEQ ID NOs.: 5, 47-50, 59, 67, 71, 72, 75, 76, 83, 91, 99, 109, 147-150, 159, 168, 182, 190, 234, and 243, and wherein the first VH and the first VL together form a first antigen-binding site, and wherein the second VH and the second VL together form a second antigen-binding site.

In certain embodiments, the antibody or antigen-binding fragment comprises a Fc polypeptide, or a fragment thereof. The "Fc" comprises the carboxy-terminal portions (i.e., the CH2 and CH3 domains of IgG) of both antibody H chains held together by disulfides. Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation. As discussed herein, modifications (e.g., amino acid substitutions) may be made to an Fc domain in order to modify (e.g., improve, reduce, or ablate) one or more functionality of an Fc-containing polypeptide (e.g., an antibody of the present disclosure). Such functions include, for example, Fc receptor (FcR) binding, antibody half-life modulation (e.g., by binding to FcRn), ADCC function, protein A binding, protein G binding, and complement binding. Amino acid modifications that modify (e.g., improve, reduce, or ablate) Fc functionalities include, for example, the T250Q/M428L, M252Y/S254T/T256E, H433K/N434F, M428L/N434S, E233P/L234V/L235A/G236+A327G/A330S/P331S, E333A, S239D/A330L/I332E, P257I/Q311, K326W/E333S, S239D/I332E/G236A, N297Q, K322A, S228P, L235E+E318A/K320A/K322A, L234A/L235A (also referred to herein as "LALA"), and L234A/L235A/P329G mutations, which mutations are summarized and annotated in "Engineered Fc Regions", published by InvivoGen (2011) and available online at invivogen.com/PDF/review/review-Engineered-Fc-Regions-invivogen.pdf?utm_source=review&utm_medium=pdf&utm_campaign=review&utm_content=Engineered-Fc-Regions, and are incorporated herein by reference. Unless the context indicates otherwise, Fc amino acid residues are numbered herein according to the EU numbering system.

For example, to activate the complement cascade, the C1q protein complex can bind to at least two molecules of IgG1 or one molecule of IgM when the immunoglobulin molecule(s) is attached to the antigenic target (Ward, E. S., and Ghetie, V., *Ther. Immunol.* 2 (1995) 77-94). Burton, D. R., described (*Mol. Immunol.* 22 (1985) 161-206) that the heavy chain region comprising amino acid residues 318 to 337 is involved in complement fixation. Duncan, A. R., and Winter, G. (*Nature* 332 (1988) 738-740), using site directed mutagenesis, reported that Glu318, Lys320 and Lys322 form the binding site to C1q. The role of Glu318, Lys320 and Lys 322 residues in the binding of C1q was confirmed by the ability of a short synthetic peptide containing these residues to inhibit complement mediated lysis.

For example, FcR binding can be mediated by the interaction of the Fc moiety (of an antibody) with Fc receptors (FcRs), which are specialized cell surface receptors on cells including hematopoietic cells. Fc receptors belong to the immunoglobulin superfamily, and shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC; Van de Winkel, J. G., and Anderson, C. L., *J Leukoc. Biol.* 49 (1991) 511-524). FcRs are defined by their specificity for immunoglobulin classes; Fc receptors for IgG antibodies are referred to as FcγR, for IgE as FcεR, for IgA as FcαR and so on and neonatal Fc receptors are referred to as FcRn. Fc receptor binding is described for example in Ravetch, J. V., and Kinet, J. P., *Annu. Rev. Immunol.* 9 (1991) 457-492; Capel, P. J., et al., *Immunomethods* 4 (1994) 25-34; de Haas, M., et al., *J Lab. Clin. Med.* 126 (1995) 330-341; and Gessner, J. E., et al., *Ann. Hematol.* 76 (1998) 231-248.

Cross-linking of receptors by the Fc domain of native IgG antibodies (FcγR) triggers a wide variety of effector functions including phagocytosis, antibody-dependent cellular cytotoxicity, and release of inflammatory mediators, as well as immune complex clearance and regulation of antibody production. Fc moieties providing cross-linking of receptors (e.g., FcγR) are contemplated herein. In humans, three classes of FcγR have been characterized to-date, which are: (i) FcγRI (CD64), which binds monomeric IgG with high affinity and is expressed on macrophages, monocytes, neutrophils and eosinophils; (ii) FcγRII (CD32), which binds complexed IgG with medium to low affinity, is widely expressed, in particular on leukocytes, is believed to be a central player in antibody-mediated immunity, and which can be divided into FcγRIIA, FcγRIIB and FcγRIIC, which perform different functions in the immune system, but bind with similar low affinity to the IgG-Fc, and the ectodomains of these receptors are highly homolougous; and (iii) FcγRIII (CD16), which binds IgG with medium to low affinity and has been found in two forms: FcγRIIIA, which has been found on NK cells, macrophages, eosinophils, and some monocytes and T cells, and is believed to mediate ADCC; and FcγRIIIB, which is highly expressed on neutrophils.

FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. Importantly, it has been shown that 75% of all FcγRIIB is found in the liver (Ganesan, L. P. et al., 2012: "FcγRIIb on liver sinusoidal endothelium clears small immune complexes," Journal of Immunology 189: 4981-4988). FcγRIIB is abundantly expressed on Liver Sinusoidal Endothelium, called LSEC, and in Kupffer cells in the liver and LSEC are the major site of small immune complexes clearance (Ganesan, L. P. et al., 2012: FcγRIIb on liver sinusoidal endothelium clears small immune complexes. Journal of Immunology 189: 4981-4988).

In some embodiments, the antibodies disclosed herein and the antigen-binding fragments thereof comprise an Fc polypeptide or fragment thereof for binding to FcγRIIb, in particular an Fc region, such as, for example IgG-type antibodies. Moreover, it is possible to engineer the Fc moiety to enhance FcγRIIB binding by introducing the mutations S267E and L328F as described by Chu, S. Y. et al., 2008: Inhibition of B cell receptor-mediated activation of primary human B cells by coengagement of CD19 and FcgammaRIIb with Fc-engineered antibodies. Molecular Immunology 45, 3926-3933. Thereby, the clearance of immune complexes can be enhanced (Chu, S., et al., 2014: Accelerated Clearance of IgE In Chimpanzees Is Mediated By Xmab7195, An Fc-Engineered Antibody With Enhanced Affinity For Inhibitory Receptor FcγRIIb. Am J Respir Crit, American Thoracic Society International Conference Abstracts). In some embodiments, the antibodies of the present disclosure, or the antigen binding fragments thereof, comprise an engineered Fc moiety with the mutations S267E and L328F, in particular as described by Chu, S. Y. et al., 2008: Inhibition of B cell receptor-mediated activation of primary human B cells by coengagement of CD19 and FcgammaRIIb with Fc-engineered antibodies. Molecular Immunology 45, 3926-3933.

On B cells, FcγRIIB may function to suppress further immunoglobulin production and isotype switching to, for example, the IgE class. On macrophages, FcγRIIB is thought to inhibit phagocytosis as mediated through FcγRIIA. On eosinophils and mast cells, the B form may help to suppress activation of these cells through IgE binding to its separate receptor.

Regarding FcγRT binding, modification in native IgG of at least one of E233-G236, P238, D265, N297, A327 and P329 reduces binding to FcγRT. IgG2 residues at positions 233-236, substituted into corresponding positions IgG1 and IgG4, reduces binding of IgG1 and IgG4 to FcγRT by $10^3$-fold and eliminated the human monocyte response to antibody-sensitized red blood cells (Armour, K. L., et al. *Eur. J. Immunol.* 29 (1999) 2613-2624).

Regarding FcγRII binding, reduced binding for FcγRIIA is found, e.g., for IgG mutation of at least one of E233-G236, P238, D265, N297, A327, P329, D270, Q295, A327, R292 and K414.

Two allelic forms of human FcγRIIA are the "H131" variant, which binds to IgG1 Fc with high affinity, and the "R131" variant, which binds to IgG1 Fc with low affinity. See, e.g., Bruhns et al., *Blood* 113:3716-3725 (2009).

Regarding FcγRIII binding, reduced binding to FcγRIIIA is found, e.g., for mutation of at least one of E233-G236, P238, D265, N297, A327, P329, D270, Q295, A327, S239, E269, E293, Y296, V303, A327, K338 and D376. Mapping of the binding sites on human IgG1 for Fc receptors, the above-mentioned mutation sites, and methods for measuring binding to FcγRI and FcγRIIA, are described in Shields, R. L., et al., *J. Biol. Chem.* 276 (2001) 6591-6604.

Two allelic forms of human FcγRIIIA are the "F158" variant, which binds to IgG1 Fc with low affinity, and the "V158" variant, which binds to IgG1 Fc with high affinity. See, e.g., Bruhns et al., *Blood* 113:3716-3725 (2009).

Regarding binding to FcγRII, two regions of native IgG Fc appear to be involved in interactions between FcγRIIs and IgGs, namely (i) the lower hinge site of IgG Fc, in particular amino acid residues L, L, G, G (234-237, EU numbering), and (ii) the adjacent region of the CH2 domain of IgG Fc, in particular a loop and strands in the upper CH2 domain adjacent to the lower hinge region, e.g. in a region of P331 (Wines, B. D., et al., J. Immunol. 2000; 164: 5313-5318). Moreover, FcγRT appears to bind to the same site on IgG Fc, whereas FcRn and Protein A bind to a different site on IgG Fc, which appears to be at the CH2-CH3 interface (Wines, B. D., et al., J. Immunol. 2000; 164: 5313-5318).

Also contemplated are mutations that increase binding affinity of an Fc polypeptide or fragment thereof of the present disclosure to a (i.e., one or more) Fcγ receptor (e.g., as compared to a reference Fc polypeptide or fragment thereof or containing the same that does not comprise the mutation(s); e.g., a wild-type Fc polypeptide or fragment thereof (e.g., of the same isotype as the Fc polypeptide or fragment thereof that comprises the mutation or mutations) or a Fc polypeptide or fragment thereof that is otherwise identical or is substantially identical to the Fc polypeptide or fragment thereof that comprises the mutation or mutations). See, e.g., Delillo and Ravetch, Cell 161(5):1035-1045 (2015) and Ahmed et al., J. Struc. Biol. 194(1):78 (2016), the Fc mutations and techniques of which are incorporated herein by reference.

In any of the herein disclosed embodiments, an antibody or antigen-binding fragment can comprise a Fc polypeptide or fragment thereof comprising a mutation selected from G236A; S239D; A330L; and I332E; or a combination comprising any two or more of the same; e.g., S239D/I332E; S239D/A330L/I332E; G236A/S239D/I332E; G236A/A330L/I332E (also referred to herein as "GAALIE"); or G236A/S239D/A330L/I332E. In some embodiments, the Fc polypeptide or fragment thereof does not comprise S239D. In some embodiments, the Fc polypeptide or fragment thereof comprises S at position 239.

In certain embodiments, the Fc polypeptide or fragment thereof may comprise or consist of at least a portion of an Fc polypeptide or fragment thereof that is involved in binding to FcRn binding. In certain embodiments, the Fc polypeptide or fragment thereof comprises one or more amino acid modifications that improve binding affinity for (e.g., enhance binding to) FcRn (e.g., at a pH of about 6.0) and, in some embodiments, thereby extend in vivo half-life of a molecule comprising the Fc polypeptide or fragment thereof (e.g., as compared to a reference (e.g., wild-type) Fc polypeptide or fragment thereof or antibody that is otherwise the same but does not comprise the modification(s)). In certain embodiments, the Fc polypeptide or fragment thereof comprises or is derived from a IgG Fc and a half-life-extending mutation comprises any one or more of: M428L; N434S; N434H; N434A; N434S; M252Y; S254T; T256E; T250Q; P257I Q311I; D376V; T307A; E380A (EU numbering). In certain embodiments, a half-life-extending mutation comprises M428L/N434S (also referred to herein as "MLNS" or "LS"). In certain embodiments, a half-life-extending mutation comprises M252Y/S254T/T256E. In certain embodiments, a half-life-extending mutation comprises T250Q/M428L. In certain embodiments, a half-life-extending mutation comprises P257I/Q311I. In certain embodiments, a half-life-extending mutation comprises P257I/N434H. In certain embodiments, a half-life-extending mutation comprises D376V/N434H. In certain embodiments, a half-life-extending mutation comprises T307A/E380A/N434A.

In some embodiments, an antibody or antigen-binding fragment includes a Fc moiety that comprises the substitution mutations M428L/N434S. In some embodiments, an antibody or antigen-binding fragment includes a Fc polypeptide or fragment thereof that comprises the substitution mutations G236A/A330L/I332E. In certain embodiments, an antibody or antigen-binding fragment includes a (e.g., IgG) Fc moiety that comprises a G236A mutation, an A330L mutation, and a I332E mutation (GAALIE), and does not comprise a S239D mutation (e.g., comprises a native S at position 239). In particular embodiments, an antibody or antigen-binding fragment includes an Fc polypeptide or fragment thereof that comprises the substitution mutations: M428L/N434S and G236A/A330L/I332E, and optionally does not comprise S239D. In certain embodiments, an antibody or antigen-binding fragment includes a Fc polypeptide or fragment thereof that comprises the substitution mutations: M428L/N434S and G236A/S239D/A330L/I332E.

In certain embodiments, the antibody or antigen-binding fragment comprises a mutation that alters glycosylation, wherein the mutation that alters glycosylation comprises N297A, N297Q, or N297G, and/or the antibody or antigen-binding fragment is partially or fully a glycosylated and/or is partially or fully a fucosylated. Host cell lines and methods of making partially or fully a glycosylated or partially or fully a fucosylated antibodies and antigen-binding fragments are known (see, e.g., PCT Publication No. WO 2016/181357; Suzuki et al. *Clin. Cancer Res.* 13(6): 1875-82 (2007); Huang et al. *MAbs* 6:1-12 (2018)).

In certain embodiments, the antibody or antigen-binding fragment is capable of eliciting continued protection in vivo in a subject even once no detectable levels of the antibody or antigen-binding fragment can be found in the subject (i.e., when the antibody or antigen-binding fragment has been cleared from the subject following administration). Such protection is referred to herein as a vaccinal effect. Without wishing to be bound by theory, it is believed that dendritic cells can internalize complexes of antibody and antigen and thereafter induce or contribute to an endogenous immune response against antigen. In certain embodiments, an antibody or antigen-binding fragment comprises one or more modifications, such as, for example, mutations in the Fc comprising G236A, A330L, and I332E, that are capable of activating dendritic cells that may induce, e.g., T cell immunity to the antigen.

In any of the presently disclosed embodiments, the antibody or antigen-binding fragment comprises a Fc polypeptide or a fragment thereof, including a CH2 (or a fragment thereof, a CH3 (or a fragment thereof), or a CH2 and a CH3, wherein the CH2, the CH3, or both can be of any isotype and may contain amino acid substitutions or other modifications as compared to a corresponding wild-type CH2 or CH3, respectively. In certain embodiments, a Fc polypeptide of the present disclosure comprises two CH2-CH3 polypeptides that associate to form a dimer.

In any of the presently disclosed embodiments, the antibody or antigen-binding fragment can be monoclonal. The term "monoclonal antibody" (mAb) as used herein refers to an antibody obtained from a population of substantially homogeneous antibodies, i.e., individual antibodies comprising the population are identical except for possible naturally occurring mutations that may be present, in some cases in minor amounts. Monoclonal antibodies are highly specific, being directed against a single antigenic site. Furthermore, in contrast to polyclonal antibody preparations that include different antibodies directed against different epitopes, each monoclonal antibody is directed against a single epitope of the antigen. In addition to their specificity, the monoclonal antibodies are advantageous in that they may be synthesized uncontaminated by other antibodies. The term "monoclonal" is not to be construed as requiring production of the antibody by any particular method. For example, monoclonal antibodies useful in the present invention may be prepared by the hybridoma methodology first described by Kohler et al., Nature 256:495 (1975), or may be made using recombinant DNA methods in bacterial, eukaryotic animal, or plant cells (see, e.g., U.S. Pat. No. 4,816,567). Monoclonal antibodies may also be isolated from phage antibody libraries using the techniques described in Clackson et al., Nature, 352:624-628 (1991) and Marks et al., J. Mol. Biol., 222:581-597 (1991), for example. Monoclonal antibodies may also be obtained using methods disclosed in PCT Publication No. WO 2004/076677A2.

Antibodies and antigen-binding fragments of the present disclosure include "chimeric antibodies" in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, U.S. Pat. Nos. 4,816,567; 5,530,101 and 7,498,415; and Morrison et al., Proc. Natl. Acad. Sci. USA, 81:6851-6855 (1984)). For example, chimeric antibodies may comprise human and non-human residues. Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992). Chimeric antibodies also include primatized and humanized antibodies.

A "humanized antibody" is generally considered to be a human antibody that has one or more amino acid residues introduced into it from a source that is non-human. These non-human amino acid residues are typically taken from a variable domain. Humanization may be performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting non-human variable sequences for the corresponding sequences of a human antibody. Accordingly, such "humanized" antibodies are chimeric antibodies (U.S. Pat. Nos. 4,816,567; 5,530,101 and 7,498,415) wherein substantially less than an intact human variable domain has been substituted by the corresponding sequence from a non-human species. In some instances, a "humanized" antibody is one which is produced by a non-human cell or animal and comprises human sequences, e.g., $H_C$ domains.

A "human antibody" is an antibody containing only sequences that are present in an antibody that is produced by a human. However, as used herein, human antibodies may comprise residues or modifications not found in a naturally occurring human antibody (e.g., an antibody that is isolated from a human), including those modifications and variant sequences described herein. These are typically made to further refine or enhance antibody performance. In some instances, human antibodies are produced by transgenic animals. For example, see U.S. Pat. Nos. 5,770,429; 6,596,541 and 7,049,426.

In certain embodiments, an antibody or antigen-binding fragment of the present disclosure is chimeric, humanized, or human.

Polynucleotides, Vectors, and Host Cells

In another aspect, the present disclosure provides isolated polynucleotides that encode any of the presently disclosed antibodies or an antigen-binding fragment thereof, or a portion thereof (e.g., a CDR, a VH, a VL, a heavy chain, or a light chain). In certain embodiments, the polynucleotide is codon-optimized for expression in a host cell. Once a coding sequence is known or identified, codon optimization can be performed using known techniques and tools, e.g., using the GenScript® OptimiumGene™ tool or Gene Synthesis by GeneArt® (ThermoFisher); see also Scholten et al., Clin. Immunol. 119:135, 2006). Codon-optimized sequences include sequences that are partially codon-optimized (i.e., one or a plurality of codons is optimized for expression in the host cell) and those that are fully codon-optimized.

It will also be appreciated that polynucleotides encoding antibodies and antigen-binding fragments of the present disclosure may possess different nucleotide sequences while still encoding a same antibody or antigen-binding fragment due to, for example, the degeneracy of the genetic code, splicing, and the like.

In certain embodiments, the polynucleotide comprises a polynucleotide having at least 50% (i.e., 50%, 55%, 60%, 65%, 70%, 75%, 80%, 85%, 90%, 91%, 92%, 93%, 94%, 95%, 96%, 97%, 98%, 99%, or 100%) identity to the polynucleotide sequence according to any one or more of SEQ ID NOs.:186-189, 191-192, 238, 247, 248-250, 254-255, and 257-262.

It will be appreciated that in certain embodiments, a polynucleotide encoding an antibody or antigen-binding fragment is comprised in a polynucleotide that includes other sequences and/or features for, e.g., expression of the antibody or antigen-binding fragment in a host cell. Exemplary features include a promoter sequence, a polyadenylation sequence, a sequence that encodes a signal peptide (e.g., located at the N-terminus of a expressed antibody heavy chain or light chain), or the like. Accordingly, in some embodiments, a polynucleotide further comprises a polynucleotide sequence having at least 50% identity to, comprising, or consisting of the polynucleotide sequence set forth in any one of SEQ ID NOs.:251-253 and 263. In some embodiments, a polynucleotide comprises a sequence that encodes a signal peptide (also referred-to as a leader sequence) having at least 90% to, comprising, or consisting of the amino acid sequence set forth in SEQ ID NO.: 256 or SEQ ID NO.: 264.

In any of the presently disclosed embodiments, the polynucleotide can comprise deoxyribonucleic acid (DNA) or ribonucleic acid (RNA). In some embodiments, the RNA comprises messenger RNA (mRNA).

Vectors are also provided, wherein the vectors comprise or contain a polynucleotide as disclosed herein (e.g., a polynucleotide that encodes an antibody or antigen-binding fragment that binds to SARS-CoV-2). A vector can comprise any one or more of the vectors disclosed herein. In particular embodiments, a vector is provided that comprises a DNA plasmid construct encoding the antibody or antigen-binding fragment, or a portion thereof (e.g., so-called "DMAb"; see, e.g., Muthumani et al., *J Infect Dis.* 214(3):369-378 (2016); Muthumani et al., *Hum Vaccin Immunother* 9:2253-2262 (2013)); Flingai et al., *Sci Rep.* 5:12616 (2015); and Elliott et al., *NPJ Vaccines* 18 (2017), which antibody-coding DNA constructs and related methods of use, including administration of the same, are incorporated herein by reference). In certain embodiments, a DNA plasmid construct comprises a single open reading frame encoding a heavy chain and a light chain (or a VH and a VL) of the antibody or antigen-binding fragment, wherein the sequence encoding the heavy chain and the sequence encoding the light chain are optionally separated by polynucleotide encoding a protease cleavage site and/or by a polynucleotide encoding a self-cleaving peptide. In some embodiments, the substituent components of the antibody or antigen-binding fragment are encoded by a polynucleotide comprised in a single plasmid. In other embodiments, the substituent components of the antibody or antigen-binding fragment are encoded by a polynucleotide comprised in two or more plasmids (e.g., a first plasmid comprises a polynucleotide encoding a heavy chain, VH, or VH+CH, and a second plasmid comprises a polynucleotide encoding the cognate light chain, VL, or VL+CL). In certain embodiments, a single plasmid comprises a polynucleotide encoding a heavy chain and/or a light chain from two or more antibodies or antigen-binding fragments of the present disclosure. An exemplary expression vector is pVax1, available from Invitrogen®. A DNA plasmid of the present disclosure can be delivered to a subject by, for example, electroporation (e.g., intramuscular electroporation), or with an appropriate formulation (e.g., hyaluronidase). In some embodiments, a vector of the present disclosure comprises a nucleotide sequence encoding a signal peptide. The signal peptide may or may not be present (e.g., can be enzymatically cleaved from) on the mature antibody or antigen-binding fragment. In certain embodiments, the signal peptide is encoded by a nucleotide sequence as set forth in SEQ ID NO.: 252 or SEQ ID NO.: 263, and/or the signal peptide comprises or consists of the amino acid sequence set forth in SEQ ID NO.:256 or SEQ ID NO.: 264. In some embodiments, a vector of the present disclosure comprises a polyadenylation signal sequence. In certain embodiments, the polyadenylation signal sequence comprises or consists of the nucleotide sequence as set forth in SEQ ID NO.: 253.

In some embodiments, a vector of the present disclosure comprises a CMV promoter. In certain embodiments, the promoter comprises or consists of the nucleotide sequence as set forth in SEQ ID NO.: 251.

In a further aspect, the present disclosure also provides a host cell expressing an antibody or antigen-binding fragment according to the present disclosure; or comprising or containing a vector or polynucleotide according to the present disclosure. Examples of such cells include but are not limited to, eukaryotic cells, e.g., yeast cells, animal cells, insect cells, plant cells; and prokaryotic cells, including *E. coli*. In some embodiments, the cells are mammalian cells. In certain such embodiments, the cells are a mammalian cell line such as CHO cells (e.g., DHFR-CHO cells (Urlaub et al., *PNAS* 77:4216 (1980)), human embryonic kidney cells (e.g., HEK293T cells), PER.C6 cells, Y0 cells, Sp2/0 cells. NS0 cells, human liver cells, e.g. Hepa RG cells, myeloma cells or hybridoma cells. Other examples of mammalian host cell lines include mouse sertoli cells (e.g., TM4 cells); monkey kidney CV1 line transformed by SV40 (COS-7); baby hamster kidney cells (BHK); African green monkey kidney cells (VERO-76); monkey kidney cells (CV1); human cervical carcinoma cells (HELA); human lung cells (W138); human liver cells (Hep G2); canine kidney cells (MDCK; buffalo rat liver cells (BRL 3A); mouse mammary tumor (MMT 060562); TRI cells; MRC 5 cells; and FS4 cells. Mammalian host cell lines suitable for antibody production also include those described in, for example, Yazaki and Wu, *Methods in Molecular Biology*, Vol. 248 (B. K. C. Lo, ed., Humana Press, Totowa, N.J.), pp. 255-268 (2003).

In certain embodiments, a host cell is a prokaryotic cell, such as an *E. coli*. The expression of peptides in prokaryotic cells such as *E. coli* is well established (see, e.g., Pluckthun, A. *Bio/Technology* 9:545-551 (1991). For example, antibodies may be produced in bacteria, in particular when glycosylation and Fc effector function are not needed. For expression of antibody fragments and polypeptides in bacteria, see, e.g., U.S. Pat. Nos. 5,648,237; 5,789,199; and 5,840,523.

In particular embodiments, the cell may be transfected with a vector according to the present description with an expression vector. The term "transfection" refers to the introduction of nucleic acid molecules, such as DNA or RNA (e.g. mRNA) molecules, into cells, such as into eukaryotic cells. In the context of the present description, the term "transfection" encompasses any method known to the skilled person for introducing nucleic acid molecules into cells, such as into eukaryotic cells, including into mammalian cells. Such methods encompass, for example, electroporation, lipofection, e.g., based on cationic lipids and/or liposomes, calcium phosphate precipitation, nanoparticle based transfection, virus based transfection, or transfection based on cationic polymers, such as DEAE-dextran or polyethylenimine, etc. In certain embodiments, the introduction is non-viral.

Moreover, host cells of the present disclosure may be transfected stably or transiently with a vector according to the present disclosure, e.g. for expressing an antibody, or an antigen-binding fragment thereof, according to the present disclosure. In such embodiments, the cells may be stably transfected with the vector as described herein. Alternatively, cells may be transiently transfected with a vector according to the present disclosure encoding an antibody or antigen-binding fragment as disclosed herein. In any of the presently disclosed embodiments, a polynucleotide may be heterologous to the host cell.

Accordingly, the present disclosure also provides recombinant host cells that heterologously express an antibody or antigen-binding fragment of the present disclosure. For example, the cell may be of a species that is different to the species from which the antibody was fully or partially obtained (e.g., CHO cells expressing a human antibody or an engineered human antibody). In some embodiments, the cell type of the host cell does not express the antibody or antigen-binding fragment in nature. Moreover, the host cell may impart a post-translational modification (PTM; e.g., glysocylation or fucosylation) on the antibody or antigen-binding fragment that is not present in a native state of the antibody or antigen-binding fragment (or in a native state of a parent antibody from which the antibody or antigen binding fragment was engineered or derived). Such a PTM may result in a functional difference (e.g., reduced immunogenicity). Accordingly, an antibody or antigen-binding fragment of the present disclosure that is produced by a host cell as disclosed herein may include one or more post-translational modification that is distinct from the antibody (or parent antibody) in its native state (e.g., a human antibody produced by a CHO cell can comprise a more post-translational modification that is distinct from the antibody when isolated from the human and/or produced by the native human B cell or plasma cell).

Insect cells useful expressing a binding protein of the present disclosure are known in the art and include, for example, *Spodoptera frugiperda* Sf9 cells, *Trichoplusia ni* BTI-TN5B1-4 cells, and *Spodoptera frugiperda* SfSWT01 "Mimic™" cells. See, e.g., Palmberger et al., *J. Biotechnol.* 153(3-4):160-166 (2011). Numerous baculoviral strains have been identified which may be used in conjunction with insect cells, particularly for transfection of *Spodoptera frugiperda* cells.

Eukaryotic microbes such as filamentous fungi or yeast are also suitable hosts for cloning or expressing protein-encoding vectors, and include fungi and yeast strains with "humanized" glycosylation pathways, resulting in the production of an antibody with a partially or fully human glycosylation pattern. See Gerngross, *Nat. Biotech.* 22:1409-1414 (2004); Li et al., *Nat. Biotech.* 24:210-215 (2006).

Plant cells can also be utilized as hosts for expressing a binding protein of the present disclosure. For example, PLANTIBODIES™ technology (described in, for example, U.S. Pat. Nos. 5,959,177; 6,040,498; 6,420,548; 7,125,978; and 6,417,429) employs transgenic plants to produce antibodies.

In certain embodiments, the host cell comprises a mammalian cell. In particular embodiments, the host cell is a CHO cell, a HEK293 cell, a PER.C6 cell, a Y0 cell, a Sp2/0 cell, a NS0 cell, a human liver cell, a myeloma cell, or a hybridoma cell.

In a related aspect, the present disclosure provides methods for producing an antibody, or antigen-binding fragment, wherein the methods comprise culturing a host cell of the present disclosure under conditions and for a time sufficient to produce the antibody, or the antigen-binding fragment. Methods useful for isolating and purifying recombinantly produced antibodies, by way of example, may include obtaining supernatants from suitable host cell/vector systems that secrete the recombinant antibody into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen from its natural environment. Methods for large scale production of one or more of the isolated/recombinant antibody described herein include batch cell culture, which is monitored and controlled to maintain appropriate culture conditions. Purification of soluble antibodies may be performed according to methods described herein and known in the art and that comport with laws and guidelines of domestic and foreign regulatory agencies.

Compositions

Also provided herein are compositions that comprise any one or more of the presently disclosed antibodies, antigen-binding fragments, polynucleotides, vectors, or host cells, singly or in any combination, and can further comprise a pharmaceutically acceptable carrier, excipient, or diluent. Carriers, excipients, and diluents are discussed in further detail herein.

In certain embodiments, a composition comprises a plurality of an antibody and/or an antigen-binding fragment of the present disclosure, wherein one or more antibody or antigen-binding fragment does not comprise a lysine residue at the C-terminal end of the heavy chain, CH1-CH3, or Fc polypeptide, and wherein one or more antibody or antigen-binding fragment comprises a lysine residue at the C-terminal end of the heavy chain, CH1-CH3, or Fc polypeptide. In some embodiments, a composition comprises an antibody or an antigen-binding fragment thereof that comprises the amino acid sequence set forth in SEQ ID NO.:173, SEQ ID NO.:175, SEQ ID NO.:265, or SEQ ID NO.:266.

In certain embodiments, a composition comprises two or more different antibodies or antigen-binding fragments according to the present disclosure. In certain embodiments, antibodies or antigen-binding fragments to be used in a combination each independently have one or more of the following characteristics: neutralize naturally occurring SARS-CoV-2 variants; do not compete with one another for Spike protein binding; bind distinct Spike protein epitopes; have a reduced formation of resistance to SARS-CoV-2; when in a combination, have a reduced formation of resistance to SARS-CoV-2; potently neutralize live SARS-CoV-2 virus; exhibit additive or synergistic effects on neutralization of live SARS-CoV-2 virus when used in combination; exhibit effector functions; are protective in relevant animal model(s) of infection; are capable of being produced in sufficient quantities for large-scale production.

In certain embodiments, a composition comprises a first antibody or antigen-binding fragment, comprising a VH comprising or consisting of the amino acid sequence as set forth in SEQ ID NO.: 79 and a VL comprising or consisting of the amino acid sequence as set forth in SEQ ID NO.: 83; and a second antibody or antigen-binding fragment comprising, a VH comprising or consisting of the amino acid sequence as set forth in SEQ ID NO.: 105 and a VL comprising of consisting of the amino acid sequence as set forth in SEQ ID NO.: 168. In certain embodiments, a composition comprises a first antibody or antigen-binding fragment comprising a heavy chain variable domain (VH) comprising a CDRH1, a CDRH2, and a CDRH3, and a light chain variable domain (VL) comprising a CDRL1, a CDRL2, and a CDRL3, wherein the CDRH1, CDRH2, and CDRH3 comprise or consist of the amino acid sequences set forth in SEQ ID NOs.: 80-82, respectively, and the CDRL1, CDRL2, and CDRL3 comprise or consist of the amino acid sequences set forth in SEQ ID NOs.: 84-86, respectively, and a second antibody or antigen-binding fragment comprising a heavy chain variable domain (VH) comprising a CDRH1, a CDRH2, and a CDRH3, and a light chain variable domain (VL) comprising a CDRL1, a CDRL2, and a CDRL3, wherein the CDRH1, CDRH2, and CDRH3 comprise or consist of the amino acid sequences set forth in SEQ ID NOs.: 106-108, respectively, and the CDRL1, CDRL2, and CDRL3 comprise or consist of the amino acid sequences set forth in SEQ ID NOs.: 169-171, respectively. In further embodiments, a composition is capable of neutralizing a SARS-CoV-2 infection, or a virus pseudotyped with SARS-CoV-2, with an IC50 of about 0.07 to about 0.08 µg/ml. In certain embodiments, a composition comprises a first antibody or antigen-binding fragment, comprising a VH comprising or consisting of the amino acid sequence as set forth in SEQ ID NO: 178 and a VL comprising or consisting of the amino acid sequence as set forth in SEQ ID NO.: 182 or SEQ ID NO.: 190; and a second antibody or antigen-binding fragment comprising, a VH comprising or consisting of the amino acid sequence as set forth in SEQ ID NO.: 105 and a VL comprising of consisting of the amino acid sequence as set forth in SEQ ID NO.: 168. In certain embodiments, a composition comprises a first antibody or antigen-binding fragment comprising a heavy chain variable domain (VH) comprising a CDRH1, a CDRH2, and a CDRH3, and a light chain variable domain (VL) comprising a CDRL1, a CDRL2, and a CDRL3, wherein the CDRH1, CDRH2, and CDRH3 comprise or consist of the amino acid sequences set forth in SEQ ID NOs.: 179-181, respectively, and the CDRL1, CDRL2, and CDRL3 comprise or consist of the amino acid sequences set forth in SEQ ID NOs.: 183-185, respectively, and a second antibody or antigen-binding fragment comprising a heavy chain variable domain (VH) comprising a CDRH1, a CDRH2, and a CDRH3, and a light chain variable domain (VL) comprising a CDRL1, a CDRL2, and a CDRL3, wherein the CDRH1, CDRH2, and CDRH3 comprise or consist of the amino acid sequences set forth in SEQ ID NOs.: 106-108, respectively, and the CDRL1, CDRL2, and CDRL3 comprise or consist of the amino acid sequences set forth in SEQ ID NOs.: 169-171, respectively.

In certain embodiments, a composition comprises a first vector comprising a first plasmid, and a second vector comprising a second plasmid, wherein the first plasmid comprises a polynucleotide encoding a heavy chain, VH, or VH+CH, and a second plasmid comprises a polynucleotide encoding the cognate light chain, VL, or VL+CL of the antibody or antigen-binding fragment thereof. In certain embodiments, a composition comprises a polynucleotide (e.g., mRNA) coupled to a suitable delivery vehicle or carrier. Exemplary vehicles or carriers for administration to a human subject include a lipid or lipid-derived delivery vehicle, such as a liposome, solid lipid nanoparticle, oily suspension, submicron lipid emulsion, lipid microbubble, inverse lipid micelle, cochlear liposome, lipid microtubule, lipid microcylinder, or lipid nanoparticle (LNP) or a nanoscale platform (see, e.g., Li et al. *Wilery Interdiscip Rev. Nanomed Nanobiotechnol.* 11(2):e1530 (2019)). Principles, reagents, and techniques for designing appropriate mRNA and and formulating mRNA-LNP and delivering the same are described in, for example, Pardi et al. (*J Control Release* 2/7345-351 (2015)); Thess et al. (*Mol Ther* 23: 1456-1464 (2015)); Thran et al. (*EMBO Mol Med* 9(10):1434-1448 (2017); Kose et al. (Sci. *Immunol.* 4 eaaw6647 (2019); and Sabnis et al. (*Mol. Ther.* 26:1509-1519 (2018)), which techniques, include capping, codon optimization, nucleoside modification, purification of mRNA, incorporation of the mRNA into stable lipid nanoparticles (e.g., ionizable cationic lipid/phosphatidylcholine/cholesterol/PEG-lipid; ionizable lipid:distearoyl PC:cholesterol:polyethylene glycol lipid), and subcutaneous, intramuscular, intradermal, intravenous, intraperitoneal, and intratracheal administration of the same, are incorporated herein by reference.

Methods and Uses

Also provided herein are methods for use of an antibody or antigen-binding fragment, nucleic acid, vector, cell, or composition of the present disclosure in the diagnosis of SARS-CoV-2 (e.g., in a human subject, or in a sample obtained from a human subject).

Methods of diagnosis (e.g., in vitro, ex vivo) may include contacting an antibody, antibody fragment (e.g., antigen binding fragment) with a sample. Such samples may be isolated from a subject, for example an isolated tissue sample taken from, for example, nasal passages, sinus cavities, salivary glands, lung, liver, pancreas, kidney, ear, eye, placenta, alimentary tract, heart, ovaries, pituitary, adrenals, thyroid, brain, skin or blood. The methods of diagnosis may also include the detection of an antigen/antibody complex, in particular following the contacting of an antibody or antibody fragment with a sample. Such a detection step can be performed at the bench, i.e. without any contact to the human or animal body. Examples of detection methods are well-known to the person skilled in the art and include, e.g., ELISA (enzyme-linked immunosorbent assay), including direct, indirect, and sandwich ELISA.

Also provided herein are methods of treating a subject using an antibody or antigen-binding fragment of the present disclosure, or a composition comprising the same, wherein the subject has, is believed to have, or is at risk for having an infection by SARS-CoV-2. "Treat," "treatment," or "ameliorate" refers to medical management of a disease, disorder, or condition of a subject (e.g., a human or non-human mammal, such as a primate, horse, cat, dog, goat, mouse, or rat). In general, an appropriate dose or treatment regimen comprising an antibody or composition of the present disclosure is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay or prevention of disease progression; remission; survival; prolonged survival; or any combination thereof. In certain embodiments, therapeutic or prophylactic/preventive benefit includes reduction or prevention of hospitalization for treatment of a SARS-CoV-2 infection (i.e., in a statistically significant manner). In certain embodiments, therapeutic or prophylactic/preventive benefit includes a reduced duration of hospitalization for treatment of a SARS-CoV-2 infection (i.e., in a statistically significant manner). In certain embodiments, therapeutic or prophylactic/preventive benefit includes a reduced or abrogated need for respiratory intervention, such as intubation and/or the use of a respirator device. In certain embodiments, therapeutic or prophylactic/preventive benefit includes reversing a late-stage disease pathology and/or reducing mortality.

A "therapeutically effective amount" or "effective amount" of an antibody, antigen-binding fragment, polynucleotide, vector, host cell, or composition of this disclosure refers to an amount of the composition or molecule sufficient to result in a therapeutic effect, including improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; or prolonged survival in a statistically significant manner. When referring to an individual active ingredient, administered alone, a therapeutically effective amount refers to the effects of that ingredient or cell expressing that ingredient alone.

When referring to a combination, a therapeutically effective amount refers to the combined amounts of active ingredients or combined adjunctive active ingredient with a cell expressing an active ingredient that results in a therapeutic effect, whether administered serially, sequentially, or simultaneously. A combination may comprise, for example, two different antibodies that specifically bind a SARS-CoV-2 antigen, which in certain embodiments, may be the same or different Wuhan coronavirus antigen, and/or can comprise the same or different epitopes.

Accordingly, in certain embodiments, methods are provided for treating a SARS-CoV-2 infection in a subject, wherein the methods comprise administering to the subject an effective amount of an antibody, antigen-binding fragment, polynucleotide, vector, host cell, or composition as disclosed herein.

Subjects that can be treated by the present disclosure are, in general, human and other primate subjects, such as monkeys and apes for veterinary medicine purposes. Other model organisms, such as mice and rats, may also be treated according to the present disclosure. In any of the aforementioned embodiments, the subject may be a human subject. The subjects can be male or female and can be any suitable age, including infant, juvenile, adolescent, adult, and geriatric subjects.

A number of criteria are believed to contribute to high risk for severe symptoms or death associated with a SARS CoV-2 infection. These include, but are not limited to, age, occupation, general health, pre-existing health conditions, and lifestyle habits. In some embodiments, a subject treated according to the present disclosure comprises one or more risk factors.

In certain embodiments, a human subject treated according to the present disclosure is an infant, a child, a young adult, an adult of middle age, or an elderly person. In certain embodiments, a human subject treated according to the present disclosure is less than 1 year old, or is 1 to 5 years old, or is between 5 and 125 years old (e.g., 5, 10, 15, 20, 25, 30, 35, 40, 45, 50, 55, 60, 65, 70, 75, 80, 85, 90, 95, 100, 105, 110, 115, or 125 years old, including any and all ages therein or therebetween). In certain embodiments, a human subject treated according to the present disclosure is 0-19 years old, 20-44 years old, 45-54 years old, 55-64 years old, 65-74 years old, 75-84 years old, or 85 years old, or older. Persons of middle, and especially of elderly age are believed to be at particular risk. In particular embodiments, the human subject is 45-54 years old, 55-64 years old, 65-74 years old, 75-84 years old, or 85 years old, or older. In some embodiments, the human subject is male. In some embodiments, the human subject is female.

In certain embodiments, a human subject treated according to the present disclosure is a resident of a nursing home or a long-term care facility, is a hospice care worker, is a healthcare provider or healthcare worker, is a first responder, is a family member or other close contact of a subject diagnosed with or suspected of having a SARS-CoV-2 infection, is overweight or clinically obese, is or has been a smoker, has or had chronic obstructive pulmonary disease (COPD), is asthmatic (e.g., having moderate to severe asthma), has an autoimmune disease or condition (e.g., diabetes), and/or has a compromised or depleted immune system (e.g., due to AIDS/HIV infection, a cancer such as a blood cancer, a lymphodepleting therapy such as a chemotherapy, a bone marrow or organ transplantation, or a genetic immune condition), has chronic liver disease, has cardiovascular disease, has a pulmonary or heart defect, works or otherwise spends time in close proximity with others, such as in a factory, shipping center, hospital setting, or the like.

In certain embodiments, a subject treated according to the present disclosure has received a vaccine for SARS-CoV-2 and the vaccine is determined to be ineffective, e.g., by post-vaccine infection or symptoms in the subject, by clinical diagnosis or scientific or regulatory criteria.

In certain embodiments, treatment is administered as peri-exposure prophylaxis. In certain embodiments, treatment is administered to a subject with mild-to-moderate disease, which may be in an outpatient setting. In certain embodiments, treatment is administered to a subject with moderate-to-severe disease, such as requiring hospitalization.

Typical routes of administering the presently disclosed compositions thus include, without limitation, oral, topical, transdermal, inhalation, parenteral, sublingual, buccal, rectal, vaginal, and intranasal. The term "parenteral", as used herein, includes subcutaneous injections, intravenous, intramuscular, intrasternal injection or infusion techniques. In certain embodiments, administering comprises administering by a route that is selected from oral, intravenous, parenteral, intragastric, intrapleural, intrapulmonary, intrarectal, intradermal, intraperitoneal, intratumoral, subcutaneous, topical, transdermal, intracisternal, intrathecal, intranasal, and intramuscular. In particular embodiments, a method comprises orally administering the antibody, antigen-binding fragment, polynucleotide, vector, host cell, or composition to the subject.

Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described an antibody or antigen-binding in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain an effective amount of an antibody or antigen-binding fragment, polynucleotide, vector, host cell, or composition of the present disclosure, for treatment of a disease or condition of interest in accordance with teachings herein.

A composition may be in the form of a solid or liquid. In some embodiments, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi solid, semi liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the composition is in the form of a capsule, for example, a gelatin capsule, it may contain, in addition to materials of the above type, a liquid carrier such as polyethylene glycol or oil.

The composition may be in the form of a liquid, for example, an elixir, syrup, solution, emulsion or suspension. The liquid may be for oral administration or for delivery by injection, as two examples. When intended for oral administration, preferred compositions contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

Liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of an antibody or antigen-binding fragment as herein disclosed such that a suitable dosage will be obtained. Typically, this amount is at least 0.01% of the antibody or antigen-binding fragment in the composition. When intended for oral administration, this amount may be varied to be between 0.1 and about 70% of the weight of the composition. Certain oral pharmaceutical compositions contain between about 4% and about 75% of the antibody or antigen-binding fragment. In certain embodiments, pharmaceutical compositions and preparations according to the present invention are prepared so that a parenteral dosage unit contains between 0.01 to 10% by weight of antibody or antigen-binding fragment prior to dilution.

The composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

A composition may include various materials which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The composition in solid or liquid form may include an agent that binds to the antibody or antigen-binding fragment of the disclosure and thereby assists in the delivery of the compound. Suitable agents that may act in this capacity include monoclonal or polyclonal antibodies, one or more proteins or a liposome. The composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi phasic, or tri phasic systems in order to deliver the active ingredient(s). Delivery of the aerosol includes the necessary container, activators, valves, subcontainers, and the like, which together may form a kit. One of ordinary skill in the art, without undue experimentation, may determine preferred aerosols.

It will be understood that compositions of the present disclosure also encompass carrier molecules for polynucleotides, as described herein (e.g., lipid nanoparticles, nanoscale delivery platforms, and the like).

The pharmaceutical compositions may be prepared by methodology well known in the pharmaceutical art. For example, a composition intended to be administered by injection can be prepared by combining a composition that comprises an antibody, antigen-binding fragment thereof, or antibody conjugate as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the peptide composition so as to facilitate dissolution or homogeneous suspension of the antibody or antigen-binding fragment thereof in the aqueous delivery system.

In general, an appropriate dose and treatment regimen provide the composition(s) in an amount sufficient to provide therapeutic and/or prophylactic benefit (such as described herein, including an improved clinical outcome (e.g., a decrease in frequency, duration, or severity of diarrhea or associated dehydration, or inflammation, or longer disease-free and/or overall survival, or a lessening of symptom severity). For prophylactic use, a dose should be sufficient to prevent, delay the onset of, or diminish the severity of a disease associated with disease or disorder. Prophylactic benefit of the compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

Compositions are administered in an effective amount (e.g., to treat a SARS-CoV-2 infection), which will vary depending upon a variety of factors including the activity of the specific compound employed; the metabolic stability and length of action of the compound; the age, body weight, general health, sex, and diet of the subject; the mode and time of administration; the rate of excretion; the drug combination; the severity of the particular disorder or condition; and the subject undergoing therapy. In certain embodiments, following administration of therapies according to the formulations and methods of this disclosure, test subjects will exhibit about a 10% up to about a 99% reduction in one or more symptoms associated with the disease or disorder being treated as compared to placebo-treated or other suitable control subjects.

Generally, a therapeutically effective daily dose of an antibody or antigen binding fragment is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g). For polynucleotides, vectors, host cells, and related compositions of the present disclosure, a therapeutically effective dose may be different than for an antibody or antigen-binding fragment.

In certain embodiments, a method comprises administering the antibody, antigen-binding fragment, polynucleotide, vector, host cell, or composition to the subject at 2, 3, 4, 5, 6, 7, 8, 9, 10 times, or more.

In certain embodiments, a method comprises administering the antibody, antigen-binding fragment, or composition to the subject a plurality of times, wherein a second or successive administration is performed at about 6, about 7, about 8, about 9, about 10, about 11, about 12, about 24, about 48, about 74, about 96 hours, or more, following a first or prior administration, respectively.

In certain embodiments, a method comprises administering the antibody, antigen-binding fragment, polynucleotide, vector, host cell, or composition at least one time prior to the subject being infected by SARS-CoV-2.

Compositions comprising an antibody, antigen-binding fragment, polynucleotide, vector, host cell, or composition of the present disclosure may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising an antibody or antigen-binding fragment of the disclosure and each active agent in its own separate dosage formulation. For example, an antibody or antigen-binding fragment thereof as described herein and the other active agent can be administered to the patient together in a single oral dosage composition such as a tablet or capsule, or each agent administered in separate oral dosage formulations. Similarly, an antibody or antigen-binding fragment as described herein and the other active agent can be administered to the subject together in a single parenteral dosage composition such as in a saline solution or other physiologically acceptable solution, or each agent administered in separate parenteral dosage formulations. Where separate dosage formulations are used, the compositions comprising an antibody or antigen-binding fragment and one or more additional active agents can be administered at essentially the same time, i.e., concurrently, or at separately staggered times, i.e., sequentially and in any order; combination therapy is understood to include all these regimens.

In certain embodiments, a combination therapy is provided that comprises one or more anti-SARS-CoV-2 antibody (or one or more nucleic acid, host cell, vector, or composition) of the present disclosure and one or more anti-inflammatory agent and/or one or more anti-viral agent. In particular embodiments, the one or more anti-inflammatory agent comprises a corticosteroid such as, for example, dexamethasone, prednisone, or the like. In some embodiments, the one or more anti-inflammatory agents comprise a cytokine antagonist such as, for example, an antibody that binds to IL6 (such as siltuximab), or to IL-6R (such as tocilizumab), or to IL-1β, IL-7, IL-8, IL-9, IL-10, FGF, G-CSF, GM-CSF, IFN-γ, IP-10, MCP-1, MIP-1A, MIP1-B, PDGR, TNF-α, or VEGF. In some embodiments, anti-inflammatory agents such as ruxolitinib and/or anakinra are used. In some embodiments, the one or more anti-viral agents comprise nucleotide analogs or nucleotide analog prodrugs such as, for example, remdesivir, sofosbuvir, acyclovir, and zidovudine. In particular embodiments, an antiviral agent comprises lopinavir, ritonavir, favipiravir, or any combination thereof. In some embodiments, a combination therapy comprises leronlimab. Anti-inflammatory agents for use in a combination therapy of the present disclosure also include non-steroidal anti-inflammatory drugs (NSAIDS). It will be appreciated that in such a combination therapy, the one or more antibody (or one or more nucleic acid, host cell, vector, or composition) and the one or more anti-inflammatory agent and/or one or the more antiviral agent can be administered in any order and any sequence, or together.

In some embodiments, an antibody (or one or more nucleic acid, host cell, vector, or composition) is administered to a subject who has previously received one or more anti-inflammatory agent and/or one or more antiviral agent. In some embodiments, one or more anti-inflammatory agent and/or one or more antiviral agent is administered to a subject who has previously received an antibody (or one or more nucleic acid, host cell, vector, or composition).

In certain embodiments, a combination therapy is provided that comprises two or more anti-SARS-CoV-2 antibodies of the present disclosure. A method can comprise administering a first antibody to a subject who has received a second antibody, or can comprise administering two or more antibodies together. For example, in particular embodiments, a method is provided that comprises administering to the subject (a) a first antibody or antigen-binding fragment, when the subject has received a second antibody or antigen-binding fragment; (b) the second antibody or antigen-binding fragment, when the subject has received the first antibody or antigen-binding fragment; or (c) the first antibody or antigen-binding fragment, and the second antibody or antigen-binding fragment.

In a related aspect, uses of the presently disclosed antibodies, antigen-binding fragments, vectors, host cells, and compositions are provided.

In certain embodiments, an antibody, antigen-binding fragment, polynucleotide, vector, host cell, or composition is provided for use in a method of treating a SARS-CoV-2 infection in a subject.

In certain embodiments, an antibody, antigen-binding fragment, or composition is provided for use in a method of manufacturing or preparing a medicament for treating a SARS-CoV-2 infection in a subject.

The present disclosure also provides the following Embodiments.

Embodiment 1. An antibody, or an antigen-binding fragment thereof, comprising a heavy chain variable domain (VH) comprising a CDRH1, a CDRH2, and a CDRH3, and a light chain variable domain (VL) comprising a CDRL1, a CDRL2, and a CDRL3, wherein:

(i) the CDRH1 comprises or consists of the amino acid sequence set forth in any one of SEQ ID NOs.:106, 2, 56, 64, 80, 88, 96, 156, 179, 195, or 240, or a sequence variant thereof comprising one, two, or three acid substitutions, one or more of which substitutions is optionally a conservative substitution and/or is a substitution to a germline-encoded amino acid;

(ii) the CDRH2 comprises or consists of the amino acid sequence set forth in any one of SEQ ID NOs.:121, 3, 16-22, 57, 65, 81, 89, 97, 107, 122-126, 157, 180, 197, 199, or 241, or a sequence variant thereof comprising one, two, or three amino acid substitutions, one or more of which substitutions is optionally a conservative substitution and/or is a substitution to a germline-encoded amino acid;

(iii) the CDRH3 comprises or consists of the amino acid sequence set forth in any one of SEQ ID NOs.:108, 4, 25, 26, 58, 66, 82, 90, 98, 104, 127, 128, 158, 181, 201, 203, or 242, or a sequence variant thereof comprising one, two, or three amino acid substitutions, one or more of which substitutions is optionally a conservative substitution and/or is a substitution to a germline-encoded amino acid;

(iv) the CDRL1 comprises or consists of the amino acid sequence set forth in any one of SEQ ID NOs.:169, 6, 51-54, 60, 68, 73, 74, 84, 92, 100, 110, 160, 183, 235, or 244, or a sequence variant thereof comprising one, two, or three amino acid substitutions, one or more of which substitutions is optionally a conservative substitution and/or is a substitution to a germline-encoded amino acid;

(v) the CDRL2 comprises or consists of the amino acid sequence set forth in any one of SEQ ID NOs.:170, 7, 61, 69, 85, 93, 101, 111, 161, 184, 236 or 245, or a sequence variant thereof comprising one, two, or three amino acid substitutions, one or more of which substitutions is optionally a conservative substitution and/or is a substitution to a germline-encoded amino acid; and/or (vi) the CDRL3 comprises or consists of the amino acid sequence set forth in any one of SEQ ID NOs.:171, 8, 62, 70, 77, 78, 86, 94, 102, 112, 151-154, 162, 185, 237, or 246, or a sequence variant thereof comprising having one, two, or three amino acid substitutions, one or more of which substitutions is optionally a conservative substitution and/or is a substitution to a germline-encoded amino acid, wherein the antibody or antigen-binding fragment is capable of binding to a SARS-CoV-2 surface glycoprotein (S) expressed on a cell surface of a host cell, on a SARS-CoV-2 virion, or both.

Embodiment 2. The antibody or antigen-binding fragment of Embodiment 1, which is capable of neutralizing a SARS-CoV-2 infection in an in vitro model of infection and/or in an in vivo animal model of infection and/or in a human.

Embodiment 3. The antibody or antigen-binding fragment of any one of Embodiments 1-2, comprising the CDRH1, CDRH2, CDRH3, CDRL1, CDRL2, and CDRL3 amino acid sequences set forth in SEQ ID NOs.:

(i) 106, 121, 108, 169, 170, and 171, respectively;

(ii) 2-4 and 6-8 or 235-237, respectively;

(iii) 2, any one of 16-22, 4, and 6-8 or 235-237, respectively;

(iv) 2, 3, any one of 25-26, and 6-8 or 235-237, respectively;

(v) 2-4, 51, 7 or 236, and 8 or 237, respectively;

(vi) 2-4, 52, 7 or 236, and 8 or 237, respectively;

(vii) 2-4, 53, 7 or 236, and 8 or 237, respectively;

(viii) 2-5, 54, 7 or 236, and 8 or 237, respectively;

(ix) 56-58 and 60-62, respectively;

(x) 64-66 and 68-70, respectively;

(xi) 64-66, 73 or 74, 69, and 70, respectively;

(xii) 64-66, 68, 69, and 77 or 78, respectively;

(xiii) 80-82 and 84-86, respectively;

(xiv) 88-90 and 92-94, respectively;

(xv) 96-98 and 101-102, respectively;

(xvi) 96, 97, 104, and 100-102, respectively;

(xvii) 106-108 and 169-171, respectively;

(xviii) 106, any one of 121-126, 108, and 169-171, respectively;

(xix) 106, 107, 127 or 128, and 169-171, respectively;

(xx) 106, 107 or any one of 121-126, 108 and 169-171, respectively;

(xxi) 156-158 and 160-162, respectively;

(xxii) 106, 123, 127, and 169-171, respectively;

(xxiii) 2, 17, 25, 6 or 235 or any one of 51-54, 7 or 236, and 8 or 237, respectively;

(xxiv) 2, 20, 25, 6 or 235 or any one of 51-54, 7 or 236, and 8 or 237, respectively;

(xxv) 179-181 and 183-185, respectively (xxvi) 195, 180, 181 and 183-185, respectively;

(xxvii) 195, 197, 181 and 183-185, respectively;

(xxviii) 195, 199, 181 and 183-185, respectively;

(xxiv) 195, 197, 201 and 183-185, respectively;

(xxx) 195, 197, 203 and 183-185, respectively;

(xxxi) 195, 199, 201 and 183-185, respectively;

(xxxii) 195, 199, 203 and 183-185, respectively;

(xxxiii) 179, 180, 181 and 183-185, respectively;

(xxxiv) 179, 197, 181 and 183-185, respectively;

(xxxv) 179, 199, 181 and 183-185, respectively;

(xxxvi) 179, 197, 201 and 183-185, respectively;

(xxxvii) 179, 197, 203 and 183-185, respectively;

(xxxviii) 179, 199, 201 and 183-185, respectively;

(xxxix) 179, 199, 203 and 183-185, respectively;

(xxxx) 179, 180, 201 and 183-185, respectively;

(xxxxi) 179, 180, 203 and 183-185, respectively; or (xxxxii) 240-242 and 244-246, respectively.

Embodiment 4. The antibody or antigen-binding fragment of any one of Embodiments 1-3, comprising:

(i) the CDRH1 amino acid sequence set forth in SEQ ID NO.:106;

(ii) the CDRH2 amino acid sequence set forth in SEQ ID NO.:121, SEQ ID NO.:107, SEQ ID NO.:122, SEQ ID NO.:123, SEQ ID NO.:124, SEQ ID NO.:125, or SEQ ID NO.:126;

(iii) the CDRH3 amino acid sequence set forth in SEQ ID NO.:108, SEQ ID NO.:127, or SEQ ID NO.:128;

(iv) the CDRL1 amino acid sequence set forth in SEQ ID NO.:169;

(v) the CDRL2 amino acid sequence set forth in SEQ ID NO.:170; and (vi) the CDRL3 amino acid sequence set forth in SEQ ID NO.:171, wherein, optionally, the antibody or antigen-binding fragment comprises the CDRH1, CDRH2, CDRH3, CDRL1, CDRL2, and CDRL3 amino acid sequences set forth in:

(a) SEQ ID NOs.:106, 121, 108, 169, 170, and 171, respectively;

(b) SEQ ID NOs.: 106, 121, 127, 169, 170, and 171, respectively;

(c) SEQ ID NOs.: 106, 121, 128, 169, 170, and 171, respectively;

(d) SEQ ID NOs.: 106, 107, 108, 169, 170, and 171, respectively;

(e) SEQ ID NOs.: 106, 107, 127, 169, 170, and 171, respectively;

(f) SEQ ID NOs.: 106, 107, 128, 169, 170, and 171, respectively;

(g) SEQ ID NOs.: 106, 122, 108, 169, 170, and 171, respectively;

(h) SEQ ID NOs.: 106, 122, 127, 169, 170, and 171, respectively;

(i) SEQ ID NOs.: 106, 122, 128, 169, 170, and 171, respectively;

(j) SEQ ID NOs.: 106, 123, 108, 169, 170, and 171, respectively;

(k) SEQ ID NOs.: 106, 123, 127, 169, 170, and 171, respectively;

(l) SEQ ID NOs.: 106, 123, 128, 169, 170, and 171, respectively;

(m) SEQ ID NOs.: 106, 124, 108, 169, 170, and 171, respectively;

(n) SEQ ID NOs.: 106, 124, 127, 169, 170, and 171, respectively;

(o) SEQ ID NOs.: 106, 124, 128, 169, 170, and 171, respectively;

(p) SEQ ID NOs.: 106, 125, 108, 169, 170, and 171, respectively;

(q) SEQ ID NOs.: 106, 125, 127, 169, 170, and 171, respectively;

(r) SEQ ID NOs.: 106, 125, 128, 169, 170, and 171, respectively;

(s) SEQ ID NOs.: 106, 126, 108, 169, 170, and 171, respectively;

(t) SEQ ID NOs.: 106, 126, 127, 169, 170, and 171, respectively; or (u) SEQ ID NOs.: 106, 126, 128, 169, 170, and 171, respectively.

Embodiment 5. An antibody or an antigen-binding fragment thereof, comprising a heavy chain variable domain (VH) comprising the CDRH1 amino acid sequence set forth in SEQ ID NO.:106, the CDRH2 amino acid sequence set forth in SEQ ID NO.:121, and the CDRH3 amino acid sequence set forth in SEQ ID NO.:108, and a light chain variable domain (VL) comprising a CDRL1 amino acid sequence set forth in SEQ ID NO.:169, a CDRL2 amino acid sequence set forth in SEQ ID NO.:170, and the CDRL3 amino acid sequence set forth in SEQ ID NO.:171, wherein the antibody or antigen binding fragment is capable of binding to a SARS-CoV-2 surface glycoprotein (S): expressed on a cell surface of a host cell; on a virion; or both.

Embodiment 6. The antibody or antigen-binding fragment of Embodiment 5, which is capable of neutralizing a SARS-CoV-2 infection in an in vitro model of infection and/or in an in vivo animal model of infection and/or in a human.

Embodiment 7. The antibody or antigen-binding fragment of any one of Embodiments 1-6, wherein:

(i) the VH comprises or consists of an amino acid sequence having at least 85% identity to the amino acid sequence set forth in any one of SEQ ID NOs.:113, 1, 9-15, 23, 24, 27, 28-46, 55, 63, 79, 87, 95, 103, 105, 114-120, 129-146, 155, 172, 176-178, 194, 196, 198, 200, 202, 239, and 267, wherein the variation as compared to the reference VH amino acid sequence, if present, is optionally limited to one or more framework regions and/or the variation comprises one or more substitution to a germline-encoded amino acid; and/or (ii) the VL comprises or consists of an amino acid sequence having at least 85% identity to the amino acid sequence set forth in any one of SEQ ID NOs.:168, 5, 47-50, 59, 67, 71-72, 75, 76, 83, 91, 99, 109, 147-150, 159, 182, 190, 234, and 243, wherein the variation as compared to the reference VH amino acid sequence, if present, is optionally limited to one or more framework regions and/or the variation comprises one or more substitution to a germline-encoded amino acid.

Embodiment 8. The antibody or antigen-binding fragment of any one of Embodiments 1-7, wherein the VH comprises or consists of any VH amino acid sequence set forth in Table 2, and wherein the VL comprises or consists of any VL amino acid sequence set forth in Table 2, wherein, optionally, the VH and the VL comprise or consist of the amino acid sequences set forth in SEQ ID NOs.:

(i) 113 and 168, respectively;

(ii) 1 and 5 or 234, respectively;

(iii) any one of 9-15 and 5 or 234, respectively;

(iv) 23 or 24 and 5 or 234, respectively;

(v) 27 and 5 or 234, respectively;

(vi) any one of 28-46 and 5 or 234, respectively;

(vii) 1 and any one of 47-50, respectively;

(viii) any one of 9-15 and any one of 47-50, respectively;

(ix) 23 or 24 and any one of 47-50, respectively;

(x) 27 and any one of 47-50, respectively;

(xi) any one of 28-46 and any one of 47-50, respectively;

(xii) 55 and 59, respectively;

(xiii) 63 and 67, respectively;

(xiv) 63 and 71 or 72, respectively;

(xv) 63 and 75 or 76, respectively;

(xvi) 79 and 83, respectively;

(xvii) 87 and 91, respectively;

(xviii) 95 and 99, respectively;

(xix) 103 and 99, respectively;

(xx) 105 and 168, respectively;

(xxi) any one of 114-120 or 267 and 168, respectively;

(xxii) 129 and 168, respectively;

(xxiii) any one of 130-146 and 168, respectively;

(xxiv) 105 and any one of 147-150, respectively;

(xxv) any one of 113-120 and any one of 147-150, respectively;

(xxvi) any one of 130-146 and any one of 147-150, respectively;

(xxvii) 155 and 159, respectively;

(xxviii) 172 and 168, respectively;

(xxix) 176 or 177 and 5 or 234 or any one of 47-50, respectively;

(xxx) 178 and 182 or 190, respectively;

(xxxi) 194 and 182, respectively;

(xxxii) 196 and 182, respectively;

(xxxiii) 198 and 182, respectively;

(xxxiv) 200 and 182, respectively;

(xxxv) 202 and 182, respectively; or (xxxvi) 239 and 243, respectively.

Embodiment 9. An antibody, or an antigen-binding fragment thereof, comprising a heavy chain variable domain (VH) and a light chain variable domain (VL), wherein the VH comprises or consists of the amino acid sequence set forth in SEQ ID NO.:113 and the VL comprises or consists of the amino acid sequence set forth in SEQ ID NO.:168.

Embodiment 10. An antibody, or an antigen-binding fragment thereof, comprising a heavy chain variable domain (VH) and a light chain variable domain (VL), wherein the VH comprises or consists of the amino acid sequence set forth in any one of SEQ ID NOs.:105, 114-120, 129-146, 172, and 267, and the VL comprises or consists of the amino acid sequence set forth in SEQ ID NO.:168.

Embodiment 11. An antibody, or antigen-binding fragment thereof, comprising a heavy chain variable domain (VH) and a light chain variable domain (VL), wherein the VH comprises or consists of the amino acid sequence set forth in SEQ ID NO.:79 and the VL comprises or consists of the amino acid sequence set forth in SEQ ID NO.:83.

Embodiment 12. An antibody, or antigen-binding fragment thereof, comprising a heavy chain variable domain (VH) comprising a CDRH1, a CDRH2, and a CDRH3, and a light chain variable domain (VL) comprising a CDRL1, a CDRL2, and a CDRL3, wherein the CDRH1, CDRH2, and CDRH3 comprise or consist of the amino acid sequences set forth in SEQ ID NOs.:80-82, respectively, and the CDRL1, CDRL2, and CDRL3 comprise or consist of the amino acid sequences set forth in SEQ ID NOs.:84-86, respectively, wherein the antibody or antigen-binding fragment is capable of binding to a SARS-CoV-2 surface glycoprotein (S) expressed on a cell surface of a host cell, on a SARS-CoV-2 virion, or both.

Embodiment 13. An antibody, or antigen-binding fragment thereof, comprising a heavy chain variable domain (VH) and a light chain variable domain (VL), wherein the VH comprises or consists of the amino acid sequence set forth in SEQ ID NO.:105 and the VL comprises or consists of the amino acid sequence set forth in SEQ ID NO.:168.

Embodiment 14. An antibody, or antigen-binding fragment thereof, comprising a heavy chain variable domain (VH) comprising a CDRH1, a CDRH2, and a CDRH3, and a light chain variable domain (VL) comprising a CDRL1, a CDRL2, and a CDRL3, wherein the CDRH1, CDRH2, and CDRH3 comprise or consist of the amino acid sequences set forth in SEQ ID NOs.:106-108, respectively, and the CDRL1, CDRL2, and CDRL3 comprise or consist of the amino acid sequences set forth in SEQ ID NOs.: 169-171, respectively, wherein the antibody or antigen-binding fragment is capable of binding to a SARS-CoV-2 surface glycoprotein (S) expressed on a cell surface of a host cell, on a SARS-CoV-2 virion, or both.

Embodiment 15. An antibody, or antigen-binding fragment thereof, comprising a heavy chain variable domain (VH) and a light chain variable domain (VL), wherein the VH comprises or consists of the amino acid sequence set forth in SEQ ID NO: 178 and the VL comprises or consists of the amino acid sequence set forth in SEQ ID NO.: 182 or SEQ ID NO.:190.

Embodiment 16. An antibody, or antigen-binding fragment thereof, comprising a heavy chain variable domain (VH) comprising a CDRH1, a CDRH2, and a CDRH3, and a light chain variable domain (VL) comprising a CDRL1, a CDRL2, and a CDRL3, wherein the CDRH1, CDRH2, and CDRH3 comprise or consist of the amino acid sequences set forth in SEQ ID NOs.:179-181, respectively, and the CDRL1, CDRL2, and CDRL3 comprise or consist of the amino acid sequences set forth in SEQ ID NOs.: 183-185, respectively, wherein the antibody or antigen-binding fragment is capable of binding to a SARS-CoV-2 surface glycoprotein (S) expressed on a cell surface of a host cell, on a SARS-CoV-2 virion, or both.

Embodiment 17. The antibody or antigen-binding fragment of any one of Embodiments 1-16, which:

(i) recognizes an epitope in the ACE2 receptor binding motif (RBM, SEQ ID NO.:167) of a SARS-CoV-2;

(ii) is capable of blocking an interaction between SARS-CoV-2 (e.g., a SARS-CoV-2 RBM) and ACE2;

(ii) is capable of binding to SARS-CoV-2 S protein with greater avidity than to SARS coronavirus S protein;

(iii) recognizes an epitope that is conserved in the ACE2 RBM of SARS-CoV-2 and in an ACE2 RBM of SARS coronavirus;

(vi) is cross-reactive against SARS-CoV-2 and SARS coronavirus;

(vii) recognizes an epitope in the SARS-CoV-2 surface glycoprotein that is not in the ACE2 RBM;

or (viii) any combination of (i)-(vii).

Embodiment 18. The antibody or antigen-binding fragment of any one of Embodiments 1-17, which is capable of inhibiting an interaction between SARS-CoV-2 and any one or more of DC-SIGN, L-SIGN, and SIGLEC-1.

Embodiment 19. The antibody or antigen-binding fragment of any one of Embodiments 1-18, which is capable of inhibiting an interaction between SARS-CoV-2 and any one or more of: DC-SIGN; L-SIGN; SIGLEC-1; CD22; CD33; CLEC4M, SIGLEC-16; SIGLEC-15; SIGLEC-14; SIGLEC-12; SIGLEC-11; SIGLEC-10; SIGLEC-9; SIGLEC-8; SIGLEC-7; SIGLEC-6; SIGLEC-5; or any combination thereof.

Embodiment 20. The antibody or antigen-binding fragment of any one of Embodiments 1-19, which is a IgG, IgA, IgM, IgE, or IgD isotype.

Embodiment 21. The antibody or antigen-binding fragment of any one of Embodiments 1-20, which is an IgG isotype selected from IgG1, IgG2, IgG3, and IgG4.

Embodiment 22. The antibody or antigen-binding fragment of any one of Embodiments 1-21, which is human, humanized, or chimeric.

Embodiment 23. The antibody or antigen-binding fragment of any one of Embodiments 1-22, wherein the antibody, or the antigen-binding fragment, comprises a human antibody, a monoclonal antibody, a purified antibody, a single chain antibody, a Fab, a Fab', a F(ab')2, a Fv, a scFv, or a scFab.

Embodiment 24. The antibody or antigen-binding fragment of Embodiment 23, wherein the scFab comprises:

(i) the amino acid sequence set forth in any one of SEQ ID NOs.:218-219 and 226-227;

(ii) a VL comprising the amino acid sequence set forth in SEQ ID NO.:168 and a VH comprising the amino acid sequence set forth in SEQ ID NO.: 105 or SEQ ID NO.:113; or (iii) a CDRH1 comprising the amino acid sequence set forth in SEQ ID NO.: 106, a CDRH2 comprising the amino acid sequence set forth in SEQ ID NO.:107 or 121, a CDRH3 comprising the amino acid sequence set forth in SEQ ID NO.:108, a CDRL1 comprising the amino acid sequence set forth in SEQ ID NO.:169, a CDRL2 comprising the amino acid sequence set forth in SEQ ID NO.:170, and a CDRL3 comprising the amino acid sequence set forth in SEQ ID NO.:171.

Embodiment 25. The antibody or antigen-binding fragment of Embodiment 23, wherein the scFv comprises:

(i) the amino acid sequence set forth in any one of SEQ ID NOs.:220-221 or 228-229;

(ii) a VL comprising the amino acid sequence set forth in SEQ ID NO.:168 and a VH comprising the amino acid sequence set forth in SEQ ID NO.:105 or SEQ ID NO.:113; or (iii) a CDRH1 comprising the amino acid sequence set forth in SEQ ID NO.:106, a CDRH2 comprising the amino acid sequence set forth in SEQ ID NO.:107 or 121, a CDRH3 comprising the amino acid sequence set forth in SEQ ID NO.:108, a CDRL1 comprising the amino acid sequence set forth in SEQ ID NO.:169, a CDRL2 comprising the amino acid sequence set forth in SEQ ID NO.:170, and a CDRL3 comprising the amino acid sequence set forth in SEQ ID NO.:171.

Embodiment 26. The antibody or antigen-binding fragment of Embodiment 25, wherein the scFv comprises more than one VH domain and more than one VL domain.

Embodiment 27. The antibody or antigen-binding fragment of Embodiment 26, wherein the scFv comprises:
(i) the amino acid sequence as set forth in any one of SEQ ID NOs.:222-225 or SEQ ID NOs.:230-233;
(ii) two VL domains, each comprising the amino acid sequence as set forth in SEQ ID NO.:168, and two VH domains, each comprising the amino acid sequence as set forth in SEQ ID NO.:105 or SEQ ID NO.:113; or
(iii) two VL domains, each comprising a CDRL1 comprising the amino acid sequence set forth in SEQ ID NO.: 169, a CDRL2 comprising the amino acid sequence set forth in SEQ ID NO.:170, and a CDRL3 comprising the amino acid sequence set forth in SEQ ID NO.:171, and two VH domains, each comprising a CDRH1 comprising the amino acid sequence set forth in SEQ ID NO.:106, a CDRH2 comprising the amino acid sequence set forth in SEQ ID NO.:107 or 121, a CDRH3 comprising the amino acid sequence set forth in SEQ ID NO.:108.

Embodiment 28. The antibody or antigen-binding fragment of any one of Embodiments 1-27, wherein the antibody or antigen-binding fragment is a multi-specific antibody or antigen-binding fragment.

Embodiment 29. The antibody or antigen-binding fragment of Embodiment 28, wherein the antibody or antigen-binding fragment is a bispecific antibody or antigen-binding fragment.

Embodiment 30. The antibody or antigen-binding fragment of Embodiment 28 or 29, comprising:
(i) a first VH and a first VL; and
(ii) a second VH and a second VL,
wherein the first VH and the second VH are different and each independently comprise an amino acid sequence having at least 85% identity to the amino acid sequence set forth in any one of SEQ ID NOs.:113, 1, 9-15, 23, 24, 27-46, 55, 63, 79, 87, 95, 103, 105, 114-120, 129-146, 155, 172, 176-178, 194, 196, 198, 200, 202, 239, and 267,
wherein the first VL and the second VL are different and each independently comprise an amino acid sequence having at least 85% identity to the amino acid sequence set forth in any one of SEQ ID NOs.:168, 5, 47-50, 59, 67, 71, 72, 75, 76, 83, 91, 99, 109, 147-150, 159, 182, 190, 234, and 243;
and wherein the first VH and the first VL together form a first antigen-binding site, and wherein the second VH and the second VL together form a second antigen-binding site.

Embodiment 31. The antibody or antigen-binding fragment of any one of Embodiments 1-30, wherein the antibody or antigen-binding fragment further comprises a Fc polypeptide or a fragment thereof.

Embodiment 32. The antibody or antigen-binding fragment of Embodiment 31, wherein the Fc polypeptide or fragment thereof comprises:
(i) a mutation that enhances binding to a FcRn as compared to a reference Fc polypeptide that does not comprise the mutation; and/or
(ii) a mutation that enhances binding to a FcγR as compared to a reference Fc polypeptide that does not comprise the mutation.

Embodiment 33. The antibody or antigen-binding fragment of Embodiment 32, wherein the mutation that enhances binding to a FcRn comprises: M428L; N434S; N434H; N434A; N434S; M252Y; S254T; T256E; T250Q; P257I; Q311I; D376V; T307A; E380A; or any combination thereof.

Embodiment 34. The antibody or antigen-binding fragment of Embodiment 32 or 33, wherein the mutation that enhances binding to FcRn comprises:
(i) M428L/N434S;
(ii) M252Y/S254T/T256E;
(iii) T250Q/M428L;
(iv) P257I/Q311I;
(v) P257I/N434H;
(vi) D376V/N434H;
(vii) T307A/E380A/N434A; or
(viii) any combination of (i)-(vii).

Embodiment 35. The antibody or antigen-binding fragment of any one of Embodiments 32-34, wherein the mutation that enhances binding to FcRn comprises M428L/N434S.

Embodiment 36. The antibody or antigen-binding fragment of any one of Embodiments 32-35, wherein the mutation that enhances binding to a FcγR comprises S239D; I332E; A330L; G236A; or any combination thereof.

Embodiment 37. The antibody or antigen-binding fragment of any one of Embodiments 32-36, wherein the mutation that enhances binding to a FcγR comprises:
(i) S239D/I332E;
(ii) S239D/A330L/I332E;
(iii) G236A/S239D/I332E; or
(iv) G236A/A330L/I332E.

Embodiment 38. The antibody or antigen-binding fragment of any one of Embodiments 1-37:
which comprises a mutation that alters glycosylation, wherein the mutation that alters glycosylation comprises N297A, N297Q, or N297G; and/or
which is a glycosylated and/or a fucosylated.

Embodiment 39. The antibody or antigen-binding fragment of any one of Embodiments 31-38, wherein the Fc polypeptide comprises a L234A mutation and a L235A mutation.

Embodiment 40. The antibody or antigen-binding fragment of any one of Embodiments 1-39, wherein the antibody or antigen-binding fragment binds to the SARS-CoV-2 S protein, as measured using biolayer interferometry.

Embodiment 41. The antibody or antigen-binding fragment of Embodiment 40, wherein the antibody or antigen-binding fragment binds to the SARS-CoV-2 S protein with a KD of less than about $4.5 \times 10^{-9}$ M, such as less than $4.5 \times 10^{-9}$ M.

Embodiment 42. The antibody or antigen-binding fragment of Embodiment 40 or 41, wherein the antibody or antigen-binding fragment binds to the SARS-CoV-2 S protein with a KD of less than about $1.0 \times 10^{-10}$ M, such as less than $1.0 \times 10^{-10}$ M.

Embodiment 43. The antibody or antigen-binding fragment of any one of Embodiments 40-42, wherein the antibody or antigen-binding fragment binds to the SARS-CoV-2 S protein with a KD of less than about $1.0 \times 10^{-11}$ M, such less than $1.0 \times 10^{-11}$ M.

Embodiment 44. The antibody or antigen-binding fragment of any one of Embodiments 40-43, wherein the antibody or antigen-binding fragment binds to the SARS-CoV-2 S protein with a KD of less than about $1 \times 10^{-12}$ M, such as less than $1 \times 10^{-12}$ M.

Embodiment 45. The antibody or antigen-binding fragment of any one of Embodiments 1-44, wherein the antibody or antigen-binding fragment is capable of neutralizing a SARS-CoV-2 infection and/or of neutralizing an infection of a target cell with an IC50 of about 16 to about 20 µg/ml.

Embodiment 46. The antibody or antigen-binding fragment of any one of Embodiments 1-45, wherein the antibody or antigen-binding fragment is capable of neutralizing a SARS-CoV-2 infection and/or of neutralizing an infection of a target cell with an IC50 of about 0.3 to about 0.4 µg/ml or about 3 to about 4 nM.

Embodiment 47. The antibody or antigen-binding fragment of any one of Embodiments 1-46, wherein the antibody or antigen-binding fragment is capable of inducing antibody-dependent cell-mediated cytotoxicity (ADCC) and/or antibody dependent cellular phagocytosis (ADCP) against a target cell infected by a SARS-CoV-2.

Embodiment 48. The antibody or antigen-binding fragment of any one of Embodiments 40-47, wherein a Fab of the antibody or antigen-binding fragment is capable of binding to SARS-CoV-2 S protein with a KD of $2.0 \times 10^{-9}$ or less, $1.9 \times 10^{-9}$ or less, or $1.8 \times 10^{-9}$ or less.

Embodiment 49. The antibody or antigen-binding fragment of any one of Embodiments 1-48, wherein the antibody or antigen-binding fragment is capable of neutralizing infection by the SARS-CoV-2 and does not compete with a human ACE2 for binding to the SARS-CoV-2 S protein, wherein, optionally, the neutralizing comprises neutralizing infection in an in vitro model of infection.

Embodiment 50. The antibody or antigen-binding fragment of any one of Embodiments 1-49, wherein the antibody or antigen-binding fragment is capable of neutralizing infection by the SARS-CoV-2 with an IC50 of 3.0 nM, 3.1 nM, 3.2 nM, 3.3 nM, 3.4 nM, 3.5 nM, 3.6 nM, 3.7 nM, 3.8 nM, 3.9 nM, or 4.0 nM.

Embodiment 51. The antibody or antigen-binding fragment of any one of Embodiments 47-50, wherein the inducing ADCC comprises activating a Natural Killer cell that comprises a V158 FcγRIIIa variant, a Natural Killer cell that comprises a F158 FcγRIIIa variant, or both.

Embodiment 52. The antibody or antigen-binding fragment of any one of Embodiments 47-51, wherein the ADCP comprises engaging a FcγRIIa and/or a FcγRIIIa expressed on the surface of a phagocytic cell, such as a monocyte, a macrophage, or a dendritic cell.

Embodiment 53. An antibody, or an antigen-binding fragment thereof, that competes for binding to a SARS-CoV-2 surface glycoprotein with the antibody or antigen-binding fragment of any one of Embodiments 1-52, wherein, optionally, the antibody or antigen-binding fragment is capable of inhibiting an interaction between SARS-CoV-2 and any one or more of DC-SIGN, L-SIGN, and SIGLEC-1.

Embodiment 54. An antibody, or an antigen-binding fragment thereof, that competes for binding to a SARS-CoV-2 surface glycoprotein with antibody S309 (VH SEQ ID NO.:105; VL SEQ ID NO.:168) and/or antibody S303 (VH SEQ ID NO.:63; VL SEQ ID NO.:67), wherein, optionally, the antibody or antigen-binding fragment is capable of inhibiting an interaction between SARS-CoV-2 and any one or more of DC-SIGN, L-SIGN, and SIGLEC-1.

Embodiment 55. An antibody, or an antigen-binding fragment thereof, that competes for binding to a SARS-CoV-2 surface glycoprotein with antibody S304 (VH SEQ ID NO.:79; VL SEQ ID NO.:81) and/or antibody S315 (VH SEQ ID NO.:178; VL SEQ ID NO.:182).

Embodiment 56. The antibody or antigen-binding fragment of any one of Embodiments 1-55, which is capable of binding to the SARS-CoV-2 surface glycoprotein when the SARS-CoV-2 surface glycoprotein is comprised in a prefusion trimer.

Embodiment 57. The antibody or antigen-binding fragment of any one of Embodiments 1-56, which is capable of binding to a Receptor Binding Domain (RBD) of the SARS-CoV-2 surface glycoprotein when the RBD is glycosylated and/or when the RBD is deglycosylated, wherein the binding is determined using surface plasmon resonance (SPR), wherein, optionally:

(1) the SPR is performed using a Biacore T200 instrument using a single-cycle kinetics approach, further optionally with a 3 minute injection period and a 20 minute dissociation period;

(2) the antibody or antigen-binding fragment is captured on a surface;

(3) the RBD is present at a concentration of were 0.8 nM, 3.1 nM, 12.5 nM, 50 nM, or 200 nM;

(4) the antibody or antigen-binding fragment binds to the glycosylated RBD with a KD of about 2.0 nM, about 1.9 nM, about 1.8 nM, about 1.7 nM, about 1.6 nM, about 1.5 nM, about 1.4 nM, about 1.3 nM, about 1.2 nM, about 1.1 nM, about 1.0 nM, about 0.9 nM, about 0.8 nM, about 0.7 nM, about 0.6 nM, about 0.5 nM, about 0.4 nM, or about 0.3 nM, or with a KD of 0.4 nM±0.05 nM, or with a KD of 0.45 nM±0.05 nM, or with a KD of 0.5 nM±0.05 nM, or with a KD of 0.6 nM±0.05 nM, or with a KD of 0.7 nM±0.05 nM, or with a KD of 1.7 nM±0.05 nM; and/or (5) the antibody or antigen-binding fragment binds to the deglycosylated RBD with a KD of about 37.0 nM, about 8.0 nM, about 2.0 nM, about 1.9 nM, about 1.8 nM, about 1.7 nM, about 1.6 nM, about 1.5 nM, about 1.4 nM, about 1.3 nM, about 1.2 nM, about 1.1 nM, about 1.0 nM, or about 0.9 nM, or with a KD of 37.0 nM±0.05 nM, or with a KD of 8.0 nM±0.05 nM, or with a KD of 1.0 nM±0.05 nM, or with a KD of 0.9 nM±0.05 nM, or with a KD of 1.3 nM±0.05 nM, or with a KD of 1.8 nM 0.05 nM, or with a KD of 1.7 nM±0.05 nM.

Embodiment 58. The antibody or antigen-binding fragment of any one of Embodiments 1-57, which is capable of neutralizing an infection by the SARS-CoV-2 in a human lung cell, wherein, optionally, the human lung cell comprises a Calu-3 cell, wherein, further optionally, the antibody or antigen-binding fragment has a neutralization IC50 of about 97 ng/mL.

Embodiment 59. The antibody or antigen-binding fragment of any one of Embodiments 1-58, which is capable of binding to a human complement component C1q, wherein, optionally, binding to the C1q is determined using biolayer interferometry (BLI), such as using an Octet instrument.

Embodiment 60. The antibody or antigen-binding fragment of any one of Embodiments 1-59, which is capable of inhibiting SARS-CoV-2 surface glycoprotein-mediated cell-cell fusion.

Embodiment 61. The antibody or antigen-binding fragment of any one of Embodiments 1-60, which does not cause antibody-mediated enhancement of SARS-CoV-2 replication in a human donor-derived peripheral blood mononuclear cell (PBMC) or a dendritic cell.

Embodiment 62. The antibody or antigen-binding fragment of any one of Embodiments 1-61, comprising:

(i) a CH1-CH3 comprising or consisting of the amino acid sequence set forth in SEQ ID NO.:173 or 175; and/or (ii) a CL comprising of consisting of the amino acid sequence set forth in SEQ ID NO.:174 or SEQ ID NO.:193.

Embodiment 63. An isolated antibody, or an antigen-binding fragment thereof, comprising a heavy chain variable domain (VH) that comprises the complementarity determining region (CDR)H1 amino acid sequence set forth in SEQ ID NO.:106, the CDRH2 amino acid sequence set forth in SEQ ID NO.:121, and the CDRH3 amino acid sequence set forth in SEQ ID NO.:108, and a light chain variable domain (VL) that comprises the CDRL1 amino acid sequence set forth in SEQ ID NO.:169, the CDRL2 amino acid sequence set forth in SEQ ID NO.:170, and the CDRL3 amino acid sequence set forth in SEQ ID NO.:171, wherein the antibody or antigen-binding fragment is capable of binding to a SARS-CoV-2 surface glycoprotein (S): expressed on a cell surface of a host cell; on a SARS-CoV-2 virion; or both.

Embodiment 64. The isolated antibody or antigen-binding fragment of any one of Embodiments 1-63, which is capable of binding to a surface glycoprotein (S) of:
(i) a SARS-CoV-2 Wuhan-Hu-1 (SEQ ID NO.:165);
(ii) a SARS-CoV-2 B.1.1.7;
(iii) a SARS-CoV-2 B.1.351;
(iv) a SARS-CoV-2 comprising any one or more of the following substitution mutations relative to SEQ ID NO.:165: N501Y; S477N; N439K; L452R; E484K; Y453F; A520S; K417N; K417V; S494P; N501T; S477R; V367F; P384L; A522S; A522V; V382L; P330S; T478I; S477I; P479S; or
(v) any combination of (i)-(iv).

Embodiment 65. The isolated antibody or antigen-binding fragment of Embodiment 63 or 64, which is capable of neutralizing a SARS-CoV-2 infection:
(i) in an in vitro model of infection;
(ii) in an in vivo animal model of infection;
(iii) in a human; or
(iv) any combination of (i)-(iii).

Embodiment 66. The isolated antibody or antigen-binding fragment of Embodiment any one of Embodiments 63-65, wherein:
(i) the VH comprises or consists of an amino acid sequence having at least 85% identity to the amino acid sequence set forth in SEQ ID NO.:113; and/or
(ii) the VL comprises or consists of an amino acid sequence having at least 85% identity to the amino acid sequence set forth in SEQ ID NO.:168.

Embodiment 67. The isolated antibody or antigen-binding fragment of any one of Embodiments 63-66, wherein:
(i) the VH comprises or consists of an amino acid sequence having at least 90% identity to the amino acid sequence set forth in SEQ ID NO.:113; and/or
(ii) the VL comprises or consists of an amino acid sequence having at least 90% identity to the amino acid sequence set forth in SEQ ID NO.:168.

Embodiment 68. The isolated antibody or antigen-binding fragment of any one of Embodiments 63-67, wherein:
(i) the VH comprises or consists of an amino acid sequence having at least 95% identity to the amino acid sequence set forth in SEQ ID NO.:113; and/or
(ii) the VL comprises or consists of an amino acid sequence having at least 95% identity to the amino acid sequence set forth in SEQ ID NO.:168.

Embodiment 69. The isolated antibody or antigen-binding fragment any one of Embodiments 63-68, wherein:
(i) the VH comprises or consists of an amino acid sequence having at least 99% identity to the amino acid sequence set forth in SEQ ID NO.:113; and/or
(ii) the VL comprises or consists of an amino acid sequence having at least 99% identity to the amino acid sequence set forth in SEQ ID NO.:168.

Embodiment 70. The isolated antibody or antigen-binding fragment of any one of Embodiments 63-69, which is capable of inhibiting an interaction between:
(i) SARS-CoV-2 and a human DC-SIGN;
(ii) SARS-CoV-2 and a human L-SIGN;
(iii) SARS-CoV-2 and a human SIGLEC-1; or
(iv) any combination of (i)-(iii).

Embodiment 71. The isolated antibody or antigen-binding fragment of any one of Embodiments 63-70, wherein the antibody or antigen-binding fragment comprises a human antibody, a monoclonal antibody, a purified antibody, a single chain antibody, a Fab, a Fab', a F(ab')2, a Fv, a scFv, or a scFab.

Embodiment 72. The isolated antibody or antigen-binding fragment of any one of Embodiments 63-71, wherein the antibody or antigen-binding fragment further comprises a Fc polypeptide or a fragment thereof.

Embodiment 73. The isolated antibody or antigen-binding fragment of any one of Embodiments 63-72, which is a IgG, IgA, IgM, IgE, or IgD isotype.

Embodiment 74. The isolated antibody or antigen-binding fragment of Embodiment 72 or 73, wherein the Fc polypeptide or fragment thereof comprises:
(i) a mutation that enhances binding to a FcRn as compared to a reference Fc polypeptide that does not comprise the mutation; and/or
(ii) a mutation that enhances binding to a FcγR as compared to a reference Fc polypeptide that does not comprise the mutation.

Embodiment 75. The isolated antibody or antigen-binding fragment of Embodiment 74, wherein the mutation that enhances binding to a FcRn comprises:
(i) M428L/N434S;
(ii) M252Y/S254T/T256E;
(iii) T250Q/M428L;
(iv) P257I/Q311I;
(v) P257I/N434H;
(vi) D376V/N434H;
(vii) T307A/E380A/N434A; or
(viii) any combination of (i)-(vii).

Embodiment 76. The isolated antibody or antigen-binding fragment of Embodiment 75, wherein the mutation that enhances binding to FcRn comprises M428L/N434S.

Embodiment 77. The isolated antibody or antigen-binding fragment of any one of Embodiments 74-76, wherein the mutation that enhances binding to a FcγR comprises S239D, I332E, A330L, G236A, or any combination thereof.

Embodiment 78. The isolated antibody or antigen-binding fragment of Embodiment 77, wherein the mutation that enhances binding to a FcγR comprises:
(i) S239D/I332E;
(ii) S239D/A330L/I332E;
(iii) G236A/S239D/I332E; or
(iv) G236A/A330L/I332E.

Embodiment 79. The isolated antibody or antigen-binding fragment of any one of Embodiments 63-78, further comprising a CH1-CH3 that comprises or consists of the amino acid sequence set forth in SEQ ID NO.:265 or 266.

Embodiment 80. An isolated antibody, or an antigen-binding fragment thereof, comprising a heavy chain variable domain (VH) and a light chain variable domain (VL), wherein the VH comprises or consists of the amino acid sequence set forth in SEQ ID NO.:113 and the VL comprises or consists of the amino acid sequence set forth in SEQ ID NO.:168.

Embodiment 81. The isolated antibody or antigen-binding fragment of Embodiment 80, which is capable of neutralizing a SARS-CoV-2 infection:
(i) in an in vitro model of infection;
(ii) in an in vivo animal model of infection;
(iii) in a human; or
(iv) any combination of (i)-(iii).

Embodiment 82. The isolated antibody or antigen-binding fragment of Embodiment 80 or 81, which is capable of inhibiting an interaction between:
(i) SARS-CoV-2 and a human DC-SIGN;
(ii) SARS-CoV-2 and a human L-SIGN;
(iii) SARS-CoV-2 and a human SIGLEC-1; or
(iv) any combination of (i)-(iii).

Embodiment 83. The isolated antibody or antigen-binding fragment of any one of Embodiments 80-82, wherein the antibody or antigen-binding fragment further comprises a Fc polypeptide or a fragment thereof.

Embodiment 84. The isolated antibody or antigen-binding fragment of any one of Embodiments 80-83, which is a IgG, IgA, IgM, IgE, or IgD isotype.

Embodiment 85. The isolated antibody or antigen-binding fragment of any one of Embodiments 83 or 84, wherein the Fc polypeptide or fragment thereof comprises:
(i) a mutation that enhances binding to a FcRn as compared to a reference Fc polypeptide that does not comprise the mutation; and/or
(ii) a mutation that enhances binding to a FcγR as compared to a reference Fc polypeptide that does not comprise the mutation.

Embodiment 86. The isolated antibody or antigen-binding fragment of Embodiment 85, wherein the mutation that enhances binding to a FcRn comprises:
(i) M428L/N434S;
(ii) M252Y/S254T/T256E;
(iii) T250Q/M428L;
(iv) P257I/Q311I;
(v) P257I/N434H;
(vi) D376V/N434H;
(vii) T307A/E380A/N434A; or
(viii) any combination of (i)-(vii).

Embodiment 87. The isolated antibody or antigen-binding fragment of Embodiment 86, wherein the mutation that enhances binding to FcRn comprises M428L/N434S.

Embodiment 88. The isolated antibody or antigen-binding fragment of any one of Embodiments 85-87, wherein the mutation that enhances binding to a FcγR comprises S239D, I332E, A330L, G236A, or any combination thereof.

Embodiment 89. The isolated antibody or antigen-binding fragment of Embodiment 88, wherein the mutation that enhances binding to a FcγR comprises:
(i) S239D/I332E;
(ii) S239D/A330L/I332E;
(iii) G236A/S239D/I332E; or
(iv) G236A/A330L/I332E.

Embodiment 90. The isolated antibody or antigen-binding fragment of any one of Embodiments 80-89, further comprising a CH1-CH3 that comprises or consists of the amino acid sequence set forth in SEQ ID NO.:265 or 266.

Embodiment 91. An isolated antibody that comprises:
(i) a heavy chain comprising (i)(1) a VH that comprises or consists of the amino acid sequence set forth in SEQ ID NO.:113, and (i)(2) a CH1-CH3 that comprises or consists of the amino acid sequence set forth in SEQ ID NO.:173; and
(ii) a light chain comprising (ii)(1) a VL that comprises or consists of the amino acid sequence set forth in SEQ ID NO.:168, and (ii)(2) a CL that comprises or consists of the amino acid sequence set forth in SEQ ID NO.:174.

Embodiment 92. An isolated antibody, or an antigen-binding fragment thereof, that is capable of binding to a SARS-CoV-2 surface glycoprotein (S) and inhibiting an interaction between a SARS-CoV-2 and a human DC-SIGN, a human L-SIGN, a human SIGLEC-1, or any combination thereof.

Embodiment 93. An isolated antibody that comprises:
(i) a heavy chain comprising (i)(1) a VH that comprises or consists of the amino acid sequence set forth in SEQ ID NO.:113, and (i)(2) a CH1-CH3 that comprises or consists of the amino acid sequence set forth in SEQ ID NO.:175; and
(ii) a light chain comprising (ii)(1) a VL that comprises or consists of the amino acid sequence set forth in SEQ ID NO.: 168, and (ii)(2) a CL that comprises or consists of the amino acid sequence set forth in SEQ ID NO.:174.

Embodiment 94. An isolated antibody, or an antigen-binding fragment thereof, comprising a heavy chain variable domain (VH) that comprises the complementarity determining region (CDR)H1 amino acid sequence set forth in SEQ ID NO.:106, the CDRH2 amino acid sequence set forth in SEQ ID NO.:121, and the CDRH3 amino acid sequence set forth in SEQ ID NO.:108, and a light chain variable domain (VL) that comprises the CDRL1 amino acid sequence set forth in SEQ ID NO.:169, the CDRL2 amino acid sequence set forth in SEQ ID NO.:170, and the CDRL3 amino acid sequence set forth in SEQ ID NO.:171,
wherein the antibody or antigen-binding fragment is capable of binding to a SARS-CoV-2 surface glycoprotein (S): expressed on a cell surface of a host cell; on a SARS-CoV-2 virion; or both.

Embodiment 95. The antibody or antigen-binding fragment of Embodiment 94, which is capable of neutralizing a SARS-CoV-2 infection:
(i) in an in vitro model of infection;
(ii) in an in vivo animal model of infection;
(iii) in a human; or
(iv) any combination of (i)-(iii).

Embodiment 96. The antibody or antigen-binding fragment of Embodiment 94 or 95, wherein:
(i) the VH comprises or consists of an amino acid sequence having at least 85% identity to the amino acid sequence set forth in SEQ ID NO.:113; and/or
(ii) the VL comprises or consists of an amino acid sequence having at least 85% identity to the amino acid sequence set forth in SEQ ID NO.:168.

Embodiment 97. The antibody or antigen-binding fragment of any one of Embodiments 94-96, wherein the VH comprises or consists of the amino acid sequence set forth in SEQ ID NO.:113 and the VL comprises or consists of the amino acid sequence set forth in SEQ ID NO.:168.

Embodiment 98. The antibody or antigen-binding fragment of any one of Embodiments 94-97, which:
(i) is capable of binding to SARS-CoV-2 surface glycoprotein with greater avidity than to a SARS coronavirus S protein;
(ii) is cross-reactive against SARS-CoV-2 and SARS coronavirus;
(iii) recognizes an epitope in the SARS-CoV-2 surface glycoprotein that is not in the ACE2 RBM; or
(iv) any combination of (i)-(iii).

Embodiment 99. The antibody or antigen-binding fragment of any one of Embodiments 94-98, which is a IgG, IgA, IgM, IgE, or IgD isotype, and is preferably an IgG isotype selected from IgG1, IgG2, IgG3, and IgG4.

Embodiment 100. The antibody or antigen-binding fragment of any one of Embodiments 94-99:
(i) which is human, humanized, or chimeric;
(ii) wherein the antibody or the antigen-binding fragment comprises a human antibody, a monoclonal antibody, a purified antibody, a single chain antibody, a Fab, a Fab', a F(ab')2, a Fv, a scFv, or a scFab; and/or (iii) wherein the antibody or antigen-binding fragment is a multi-specific antibody or antigen-binding fragment, wherein, optionally, the antigen-binding fragment is a bispecific antibody or antigen-binding fragment.

Embodiment 101. The antibody or antigen-binding fragment of any one of Embodiments 94-100, wherein the antibody or antigen-binding fragment further comprises a Fc polypeptide or a fragment thereof.

Embodiment 102. The antibody or antigen-binding fragment of Embodiment 101, wherein the Fc polypeptide or fragment thereof comprises:

(1) a mutation that enhances binding to a FcRn as compared to a reference Fc polypeptide that does not comprise the mutation, wherein, optionally, the mutation that enhances binding to a FcRn comprises M428L, N434S, N434H, N434A, N434S, M252Y, S254T, T256E, T250Q, P257I, Q311I, D376V, T307A, E380A, or any combination thereof, wherein, further optionally, the mutation that enhances binding to a FcRn comprises: (i) M428L/N434S; (ii) M252Y/S254T/T256E; (iii) T250Q/M428L; (iv) P257I/Q311I; (v) P257I/N434H; (vi) D376V/N434H; (vii) T307A/E380A/N434A; or (viii) any combination of (i)-(vii); and/or (2) a mutation that enhances binding to a FcγR as compared to a reference Fc polypeptide that does not comprise the mutation, wherein, optionally, the mutation that enhances binding to a FcγR comprises S239D, I332E, A330L, G236A, or any combination thereof, wherein, further optionally, the mutation that enhances binding to a FcγR comprises: (i) S239D/I332E; (ii) S239D/A330L/I332E; (iii) G236A/S239D/I332E; or (iv) G236A/A330L/I332E.

Embodiment 103. The antibody or antigen-binding fragment of Embodiment 102, wherein the mutation that enhances binding to a FcRn comprises M428L/N434S and/or the mutation that enhances binding to a FcγR comprises G236A/A330L/I332E.

Embodiment 104. The antibody or antigen-binding fragment of any one of Embodiments 94-103, comprising:

(i) a CH1-CH3 having 90%, 91%, 92%, 93%, 94%, 95%, 96%, 97%, 98%, 99%, or 100% identity to SEQ ID NO.:173 or 175; and/or (ii) a CL comprising an amino acid sequence having 90%, 91%, 92%, 93%, 94%, 95%, 96%, 97%, 98%, 99%, or 100% identity to the amino acid sequence of SEQ ID NO.:174.

Embodiment 105. The antibody or antigen-binding fragment of any one of Embodiments 94-104, which comprises a mutation that alters glycosylation of the antibody or antigen-binding fragment, wherein the mutation that alters glycosylation of the antibody or antigen-binding fragment comprises N297A, N297Q, or N297G, and/or wherein the antibody or antigen-binding fragment is a glycosylated and/or a fucosylated.

Embodiment 106. The antibody or antigen-binding fragment of any one of Embodiments 94-4105, wherein the antibody or antigen-binding fragment binds to a SARS-CoV-2 surface glycoprotein or an RBD thereof with a KD of less than about $4.5 \times 10^{-9}$ M, less than about $5 \times 10^{-9}$ M, less than about $1 \times 10^{-10}$ M, less than about $5 \times 10^{-10}$ M, less than about $1 \times 10^{-11}$ M, less than about $5 \times 10^{-11}$ M, or less than about $1 \times 10^{-12}$ M, as measured by biolayer interferometry, wherein, optionally, the antibody or antigen-binding fragment binds to the SARS-CoV-2 surface glycoprotein with a KD of less than $1 \times 10^{-12}$ M, as measured by biolayer interferometry (e.g., by immobilizing the antibody or antigen-binding fragment on sensors and dipping the sensors into wells containing different concentrations of SARS-CoV-2 or RBD, recording kinetics of antibody binding during the association phase, after which the sensors are dipped into buffer without antibody to observe kinetics of antibody detaching from the SARS-CoV-2 or RBD during the dissociation phase. Protein A biosensors (Pall ForteBio) can be used to immobilize recombinant antibodies at 2.7 ug/ml for 1 minute, after a hydration step for 10 minutes with Kinetics Buffer (KB; 0.01% endotoxin-free BSA, 0.002^Tween-20, 0.005% NaN3 in PBS). Association curves can be recorded for 5 minutes by incubating the antibody-coated sensors with different concentrations of SARS-CoV-1 RBD (Sino Biological) or SARS-CoV-2 RBD (produced in house in Expi-CHO cells; residues 331-550 of spike from BetaCoV/Wuhan-Hu-1/2019, accession number MN908947). SARS-CoV-2 or RBD concentration tested can be 10 ug/ml, then 1:2.5 serially diluted. Dissociation can be recorded for 9 minutes by moving the sensors to wells containing KB. Affinities, represented by KD values, can be calculated using a global fit model (Octet). Octet Red96 (ForteBio) equipment was used).

Embodiment 107. The antibody or antigen-binding fragment of any one of Embodiments 94-106, wherein the antibody or antigen-binding fragment is capable of inducing antibody-dependent cell-mediated cytotoxicity (ADCC) and/or antibody dependent cellular phagocytosis (ADCP) against a target cell infected by a SARS-CoV-2, wherein, optionally, the inducing ADCC comprises activating a Natural Killer cell that comprises a V158 FcγRIIIa variant, a Natural Killer cell that comprises a F158 FcγRIIIa variant, or both, and/or the inducing ADCP comprises engaging a FcγRIIa expressed on the surface of a phagocytic cell, such as a monocyte, a macrophage, or a dendritic cell.

Embodiment 108. The antibody or antigen-binding fragment of any one of Embodiments 94-107, wherein the antibody or antigen-binding fragment is a Fab and the Fab is capable of binding to a SARS-CoV-2 surface glycoprotein with a KD of $2.0 \times 10^{-9}$ M or less, $1.9 \times 10^{-9}$ M or less, or $1.8 \times 10^{-9}$ M or less, as measured by biolayer interferometry.

Embodiment 109. The antibody or antigen-binding fragment of any one of Embodiments 94-108, wherein the antibody or antigen-binding fragment is capable of neutralizing infection by the SARS-CoV-2 and does not compete with a human ACE2 for binding to the SARS-CoV-2 surface glycoprotein.

Embodiment 110. An antibody, or an antigen-binding fragment thereof, that competes for binding to a SARS-CoV-2 surface glycoprotein with the antibody or antigen-binding fragment of any one of Embodiments 94-109.

Embodiment 111. The antibody or antigen-binding fragment of any one of Embodiments 94-110, which is capable of binding to the SARS-CoV-2 surface glycoprotein when the SARS-CoV-2 surface glycoprotein is comprised in a prefusion trimer.

Embodiment 112. The antibody or antigen-binding fragment of any one of Embodiments 94-111, which is capable of binding to a Receptor Binding Domain (RBD) of the SARS-CoV-2 surface glycoprotein when the RBD is glycosylated and/or when the RBD is deglycosylated, wherein the binding is determined using surface plasmon resonance (SPR), wherein, optionally:

(1) the SPR is performed using a Biacore T200 instrument using a single-cycle kinetics approach, further optionally with a 3 minute injection period and a 20 minute dissociation period;

(2) the antibody or antigen-binding fragment is captured on a surface;

(3) the RBD is present at a concentration of 0.8 nM, 3.1 nM, 12.5 nM, 50 nM, or 200 nM;

(4) the antibody or antigen-binding fragment binds to the glycosylated RBD with a KD of about about 0.6 nM, about 0.5 nM, about 0.4 nM, or about 0.3 nM, or with a KD of 0.3 nM±0.05 nM, or with a KD of 0.4 nM±0.05 nM, or with a KD of 0.45 nM±0.05 nM, or with a KD of 0.5 nM±0.05 nM, or with a KD of 0.6 nM±0.05 nM; and/or (5) the antibody or antigen-binding fragment binds to the deglycosylated RBD with a KD of about 1.6 nM, about 1.5 nM, about 1.4 nM, about 1.3 nM, about 1.2 nM, about 1.1 nM, about 1.0.

Embodiment 113. The antibody or antigen-binding fragment of any one of Embodiments 94-112, which is capable of neutralizing an infection by the SARS-CoV-2 in a human lung cell, wherein, optionally, the human lung cell comprises a Calu-3 cell, wherein, further optionally, the antibody or antigen-binding fragment has a neutralization IC50 of about 97 ng/mL.

Embodiment 114. The antibody or antigen-binding fragment of any one of Embodiments 94-113, which is capable of binding to a human complement component C1q, wherein, optionally, binding to the C1q is determined using biolayer interferometry (BLI), such as using an Octet instrument.

Embodiment 115. The antibody or antigen-binding fragment of any one of Embodiments 94-114, which is capable of inhibiting SARS-CoV-2 surface glycoprotein-mediated cell-cell fusion.

Embodiment 116. The antibody or antigen-binding fragment of any one of Embodiments 94-115, which does not cause antibody-mediated enhancement of SARS-CoV-2 replication in a human donor-derived peripheral blood mononuclear cell (PBMC) or a dendritic cell.

Embodiment 117. The antibody or antigen-binding fragment of any one of Embodiments 94-116, which is capable of inhibiting an interaction between:

(i) SARS-CoV-2 and a human DC-SIGN;
(ii) SARS-CoV-2 and a human L-SIGN;
(iii) SARS-CoV-2 and a human SIGLEC-1; or
(iv) any combination of (i)-(iii).

Embodiment 118. The antibody or antigen-binding fragment of any one of Embodiments 94-117, which is capable of binding to a surface glycoprotein of:

(i) a SARS-CoV-2 Wuhan-Hu-1 (SEQ ID NO.:165);
(ii) a SARS-CoV-2 B.1.1.7;
(iii) a SARS-CoV-2 B.1.351;
(iv) a SARS-CoV-2 comprising any one or more of the following substitution mutations relative to SEQ ID NO.: 165: N501Y; S477N; N439K; L452R; E484K; Y453F; A520S; K417N; K417V; S494P; N501T; S477R; V367F; P384L; S522S; A522V; V382L; P330S; T478I; S477I; P479S; or
(v) any combination of (i)-(iv).

Embodiment 119. The antibody or antigen-binding fragment of any one of Embodiments 94-118, wherein the antibody or antigen-binding fragment is capable of neutralizing infection by the SARS-CoV-2 with an IC50 of 3.0 nM, 3.1 nM, 3.2 nM, 3.3 nM, 3.4 nM, 3.5 nM, 3.6 nM, 3.7 nM, 3.8 nM, 3.9 nM, or 4.0 nM.

Embodiment 120. The antibody or antigen-binding fragment of any one of Embodiments 94-119, comprising:

(i) a heavy chain comprising (i)(1) a VH that comprises or consists of the amino acid sequence set forth in SEQ ID NO.:113, and (i)(2) a CH1-CH3 that comprises or consists of the amino acid sequence set forth in SEQ ID NO.:173; and (ii) a light chain comprising (ii)(1) a VL that comprises or consists of the amino acid sequence set forth in SEQ ID NO.: 168, and (ii)(2) a CL that comprises or consists of the amino acid sequence set forth in SEQ ID NO.:174.

Embodiment 121. The antibody or antigen-binding fragment of any one of Embodiments 94-120, comprising:

(i) a heavy chain comprising (i)(1) a VH that comprises or consists of the amino acid sequence set forth in SEQ ID NO.:113, and (i)(2) a CH1-CH3 that comprises or consists of the amino acid sequence set forth in SEQ ID NO.:175; and (ii) a light chain comprising (ii)(1) a VL that comprises or consists of the amino acid sequence set forth in SEQ ID NO.: 168, and (ii)(2) a CL that comprises or consists of the amino acid sequence set forth in SEQ ID NO.:174.

Embodiment 122. The antibody or antigen-binding fragment of any one of Embodiments 94-121, comprising a CH1-CH3 that comprises or consists of the amino acid sequence set forth in SEQ ID NO.:265 or 266.

Embodiment 123. An isolated polynucleotide encoding the antibody or antigen-binding fragment of any one of Embodiments 1-122, or encoding a VH, a heavy chain, a VL, and/or a light chain of the antibody or the antigen-binding fragment.

Embodiment 124. The isolated polynucleotide of Embodiment 123, wherein the polynucleotide comprises deoxyribonucleic acid (DNA) or ribonucleic acid (RNA), wherein the RNA optionally comprises messenger RNA (mRNA).

Embodiment 125. The isolated polynucleotide of Embodiment 123 or 124, which is codon-optimized for expression in a host cell.

Embodiment 126. The isolated polynucleotide of any one of Embodiments 123-125, comprising a polynucleotide having at least 50% identity to the polynucleotide sequence according to any one or more of SEQ ID NOs.:186-189, 191-192, 238, 247, 248-255 and 257-262.

Embodiment 127. The isolated polynucleotide of any one of Embodiments 123-126, comprising the polynucleotide sequence set forth in any one or more of SEQ ID NOs.:249, 250, and 257-262.

Embodiment 128. A recombinant vector comprising the polynucleotide of any one of Embodiments 123-127.

Embodiment 129. A host cell comprising the polynucleotide of any one of Embodiments 123-127 and/or the vector of Embodiment 128, wherein the polynucleotide is heterologous to the host cell.

Embodiment 130. A human B cell comprising the polynucleotide of any one of Embodiments 123-129, wherein polynucleotide is heterologous to the human B cell and/or wherein the human B cell is immortalized.

Embodiment 131. A composition comprising:

(i) the antibody or antigen-binding fragment of any one of Embodiments 1-122;
(ii) the polynucleotide of any one of Embodiments 123-127;
(iii) the recombinant vector of Embodiment 128;
(iv) the host cell of Embodiment 129; and/or
(v) the human B cell of Embodiment 130, and a pharmaceutically acceptable excipient, carrier, or diluent.

Embodiment 132. The composition of Embodiment 131, comprising two or more antibodies or antigen-binding fragments of any one of Embodiments 1-122.

Embodiment 133. The composition of Embodiment 132, comprising:

(i) a first antibody or antigen-binding fragment, comprising a VH comprising or consisting of the amino acid sequence set forth in SEQ ID NO.:79 and a VL comprising or consisting of the amino acid sequence set forth in SEQ ID NO.:83; and (ii) a second antibody or antigen-binding fragment comprising, a VH comprising or consisting of the amino acid sequence set forth in SEQ ID NO.:105 and a VL comprising of consisting of the amino acid sequence set forth in SEQ ID NO.:168.

Embodiment 134. The composition of Embodiment 132, comprising:

(i) a first antibody or antigen-binding fragment comprising a heavy chain variable domain (VH) comprising a CDRH1, a CDRH2, and a CDRH3, and a light chain variable domain (VL) comprising a CDRL1, a CDRL2, and a CDRL3, wherein the CDRH1, CDRH2, and CDRH3 comprise or consist of the amino acid sequences set forth in SEQ ID NOs.:80-82, respectively, and the CDRL1, CDRL2, and CDRL3 comprise or consist of the amino acid sequences set forth in SEQ ID NOs.:84-86, respectively; and (ii) a second antibody or antigen-binding fragment comprising a heavy chain variable domain (VH) comprising a CDRH1, a CDRH2, and a CDRH3, and a light chain variable domain (VL) comprising a CDRL1, a CDRL2, and a CDRL3, wherein the CDRH1, CDRH2, and CDRH3 comprise or consist of the amino acid sequences set forth in SEQ ID NOs.:106-108, respectively, and the CDRL1, CDRL2, and CDRL3 comprise or consist of the amino acid sequences set forth in SEQ ID NOs.:169-171, respectively.

Embodiment 135. The composition of Embodiment 132, comprising:

(i) a first antibody or antigen-binding fragment, comprising a VH comprising or consisting of the amino acid sequence set forth in SEQ ID NO.:178 and a VL comprising or consisting of the amino acid sequence set forth in SEQ ID NO.:182 or SEQ ID NO.:190; and (ii) a second antibody or antigen-binding fragment comprising, a VH comprising or consisting of the amino acid sequence set forth in SEQ ID NO.:105 and a VL comprising of consisting of the amino acid sequence set forth in SEQ ID NO.:168.

Embodiment 136. The composition of Embodiment 135, comprising:

(i) a first antibody or antigen-binding fragment comprising a heavy chain variable domain (VH) comprising a CDRH1, a CDRH2, and a CDRH3, and a light chain variable domain (VL) comprising a CDRL1, a CDRL2, and a CDRL3, wherein the CDRH1, CDRH2, and CDRH3 comprise or consist of the amino acid sequences set forth in SEQ ID NOs.:179-181, respectively, and the CDRL1, CDRL2, and CDRL3 comprise or consist of the amino acid sequences set forth in SEQ ID NOs.:183-185, respectively; and (ii) a second antibody or antigen-binding fragment comprising a heavy chain variable domain (VH) comprising a CDRH1, a CDRH2, and a CDRH3, and a light chain variable domain (VL) comprising a CDRL1, a CDRL2, and a CDRL3, wherein the CDRH1, CDRH2, and CDRH3 comprise or consist of the amino acid sequences set forth in SEQ ID NOs.:106-108, respectively, and the CDRL1, CDRL2, and CDRL3 comprise or consist of the amino acid sequences set forth in SEQ ID NOs.:169-171, respectively.

Embodiment 137. The composition of Embodiment 132, comprising:

(i) a first antibody or antigen-binding fragment comprising a VH comprising or consisting of the amino acid sequence set forth in SEQ ID NO.:178 and a VL comprising or consisting of the amino acid sequence set forth in SEQ ID NO.:182 or SEQ ID NO.:190; and (ii) a second antibody or antigen-binding fragment comprising a VH comprising or consisting of the amino acid sequence set forth in SEQ ID NO.:63 and a VL comprising or consisting of the amino acid sequence set forth in SEQ ID NO.:67, any one of SEQ ID NOs.:71-71, or any one of SEQ ID NOs:75-76.

Embodiment 138. The composition of Embodiment 132, comprising:

(i) a first antibody or antigen-binding fragment comprising a heavy chain variable domain (VH) comprising a CDRH1, a CDRH2, and a CDRH3, and a light chain variable domain (VL) comprising a CDRL1, a CDRL2, and a CDRL3, wherein the CDRH1, CDRH2, and CDRH3 comprise or consist of the amino acid sequences set forth in SEQ ID NOs.:179-181, respectively, and the CDRL1, CDRL2, and CDRL3 comprise or consist of the amino acid sequences set forth in SEQ ID NOs.:183-185, respectively; and (ii) a second antibody or antigen-binding fragment comprising a heavy chain variable domain (VH) comprising a CDRH1, a CDRH2, and a CDRH3, and a light chain variable domain (VL) comprising a CDRL1, a CDRL2, and a CDRL3, wherein the CDRH1, CDRH2, and CDRH3 comprise or consist of the amino acid sequences set forth in SEQ ID NOs.:64-66, respectively, the CDRL1 comprises or consists of the amino acid sequences set forth in any one of SEQ ID NO.:68, SEQ ID NO.:73, or SEQ ID NO.:74, the CDRL2 comprises or consists of the amino acid sequences set forth in SEQ ID NO.:69, and the CDRL3 comprises or consists of the amino acid sequences set forth in SEQ ID NO.:70, SEQ ID NO.:77, or SEQ ID NO.:78.

Embodiment 139. A composition comprising (i) the antibody or antigen-binding fragment of Embodiment 8 or 9 and (ii) the antibody or antigen-binding fragment of Embodiment 10 or 11, wherein the composition is capable of neutralizing a SARS-CoV-2 infection with an IC50 of about 0.07 to about 0.08 µg/ml.

Embodiment 140. A composition comprising the polynucleotide of any one of Embodiments 123-127 encapsulated in a carrier molecule, wherein the carrier molecule optionally comprises a lipid, a lipid-derived delivery vehicle, such as a liposome, a solid lipid nanoparticle, an oily suspension, a submicron lipid emulsion, a lipid microbubble, an inverse lipid micelle, a cochlear liposome, a lipid microtubule, a lipid microcylinder, lipid nanoparticle (LNP), or a nanoscale platform.

Embodiment 141. A method of treating a SARS-CoV-2 infection in a subject, the method comprising administering to the subject an effective amount of:

(i) the antibody or antigen-binding fragment of any one of Embodiments 1-122;

(ii) the polynucleotide of any one of Embodiments 123-127;

(iii) the recombinant vector of Embodiment 128;

(iv) the host cell of Embodiment 129;

(v) the human B cell of Embodiment 130; and/or (vi) the composition of any one of Embodiments 131-140.

Embodiment 142. A method of inhibiting a SARS-CoV-2 infection in a subject, the method comprising administering to the subject an effective amount of:

(i) the antibody or antigen-binding fragment of any one of Embodiments 1-122;
(ii) the polynucleotide of any one of Embodiments 123-127;
(iii) the recombinant vector of Embodiment 128;
(iv) the host cell of Embodiment 129;
(v) the human B cell of Embodiment 130; and/or
(vi) the composition of any one of Embodiments 131-140.

Embodiment 143. The antibody or antigen-binding fragment of any one of Embodiments 1-122, the polynucleotide of any one of Embodiments 123-127, the recombinant vector of Embodiment 128, the host cell of Embodiment 129, the human B cell of Embodiment 130, and/or the composition of any one of Embodiments 131-140 for use in a method of treating a SARS-CoV-2 infection in a subject.

Embodiment 144. The antibody or antigen-binding fragment of any one of Embodiments 1-122, the polynucleotide of any one of Embodiments 123-127, the recombinant vector of Embodiment 128, the host cell of Embodiment 129, the human B cell of Embodiment 130, and/or the composition of any one of Embodiments 131-140 for use in a method of inhibiting a SARS-CoV-2 infection in a subject.

Embodiment 145. The antibody or antigen-binding fragment of any one of Embodiments 1-122, the polynucleotide of any one of Embodiments 123-127, the recombinant vector of Embodiment 128, the host cell of Embodiment 129, the human B cell of Embodiment 130, and/or the composition of any one of Embodiments 131-140, for use in the preparation of a medicament for the treatment of a SARS-CoV-2 infection in a subject.

Embodiment 146. A method for in vitro diagnosis of a SARS-CoV-2 infection, the method comprising:
(i) contacting a sample from a subject with an antibody or antigen-binding fragment of any one of Embodiments 1-122; and
(ii) detecting a complex comprising an antigen and the antibody, or comprising an antigen and the antigen binding fragment.

Embodiment 147. The method of Embodiment 146, wherein the sample comprises blood isolated from the subject.

Embodiment 148. A combination or composition comprising:
(i) an antibody or antigen-binding fragment comprising
(i)(a) a CDRH1 amino acid sequence GYPFTSYG, a CDRH2 amino acid sequence ISTYNGNT or ISTYQGNT, a CDRH3 amino acid sequence ARDYTRGAWFGESLIGGFDN; a CDRL1 amino acid sequence or QTVSSTS, a CDRL2 amino acid sequence GAS, and a CDRL3 amino acid sequence QHDTSLT; or
(i)(b) a VH amino acid sequence comprising or consisting of QVQLVQSGAEVKKPGASVKVSCKASGYPFT-SYGISWVRQAPGQGLEWMGWIS TYNGNTNYA-QKFQGRVTMTTDTSTTTGYMELRRLRSDD-TAVYYCARDYTRG AWFGESLIGGFDNWGQG-TLVTVSS
or comprising or consisting of QVQLVQSGAEVKKP-GASVKVSCKASGYPFTSYGISWVRQAPGQ-GLEWMGWIS TYQGNTNYAQKFQGRVTMTTDT-STTTGYMELRRLRSDDTAVYYCARDYTRG AWFGESLIGGFDNWGQGTLVTVSS,
and a VL amino acid sequence comprising or consisting of EIVLTQSPGTLSLSPGERATLSCRASQTVSST-SLAWYQQKPGQAPRLLIYGASSR ATGIPDRFSGSGSGTDFTLTISRLEPED-FAVYYCQQHDTSLTFGGGTKVEIK;

and
(ii) an antibody or antigen-binding fragment comprising:
(ii)(a) VH and VL amino acid sequences according to SEQ ID NOs.:79 and 83, respectively;
(ii)(b) CDRH1, CDRH2, CDRH3, CDRL1, CDRL2, and CDRL3 amino acid sequences according to SEQ ID NOS.:80-82 and 84-86, respectively;
(ii)(c) VH and VL amino acid sequences according to SEQ ID NOs.:178 or 194 or 196 or 198 or 200 or 202 and 182 or 190, respectively; or
(ii)(d) CDRH1, CDRH2, CDRH3, CDRL1, CDRL2, and CDRL3 amino acid sequences according to SEQ ID NOs.:179 or 195, 180 or 197 or 199, 181, 201 or 203, and 183-185, respectively.

Embodiment 149. A method of preventing or treating or neutralizing a coronavirus infection in a subject, the method comprising administering to the subject the combination or composition of Embodiment 148, wherein, optionally, the antibody or antigen binding fragment of (i) and the antibody or antigen binding fragment of (ii) are administered concurrently, simultaneously, or consecutively.

Embodiment 150. A method of preventing or treating or neutralizing a coronavirus infection in a subject, the method comprising administering to a subject who has received a first antibody or antigen binding fragment comprising:
(a) VH and VL amino acid sequences according to SEQ ID NOs.:79 and 83, respectively; or
(b) CDRH1, CDRH2, CDRH3, CDRL1, CDRL2, and CDRL3 amino acid sequences according to SEQ ID NOs.:80-82 and 84-86, respectively; and a second antibody or antigen binding fragment comprising:
(a) a VH amino acid sequence according to SEQ ID NO.:105 or 113, and a VL amino acid sequence according to SEQ ID NO: 168; or
(b) CDRH1, CDRH2, and CDRH3 amino acids according to SEQ ID NOs.: 106-108, respectively, or SEQ ID NOs.:106, 121, and 108, respectively, and CDRL1, CDRL2, and CDRL3 amino acid sequences according to SEQ ID NOs.:169-171, respectively.

Embodiment 151. A method of preventing or treating or neutralizing a coronavirus infection in a subject, the method comprising administering to a subject who has received a first antibody or antigen binding fragment comprising:
(a) a VH amino acid sequence according to SEQ ID NOs.:105 or 113, and a VL amino acid sequence according to SEQ ID NO.:168; or
(b) CDRH1, CDRH2, and CDRH3 amino acids according to SEQ ID NOs.: 106-108, respectively, or SEQ ID NOs.: 106, 121, and 108, respectively, and CDRL1, CDRL2, and CDRL3 amino acid sequences according to SEQ ID NOS.: 169-171, respectively;
a second antibody or antigen binding fragment comprising:
(a) VH and VL amino acid sequences according to SEQ ID NOs.:79 and 83, respectively; or
(b) CDRH1, CDRH2, CDRH3, CDRL1, CDRL2, and CDRL3 amino acid sequences according to SEQ ID NOS.:80-82 and 84-86, respectively.

Embodiment 152. A method of preventing or treating or neutralizing a coronavirus infection in a subject, the method comprising administering to a subject who has received a first antibody or antigen binding fragment comprising:
(a) VH and VL amino acid sequences according to SEQ ID NOs.:178 or 194 or 196 or 198 or 200 or 202 and 182 or 190, respectively; or (b) CDRH1, CDRH2, CDRH3, CDRL1, CDRL2, and CDRL3 amino acid sequences according to SEQ ID NOS.: 179 or 195, 180 or 197 or 199, 181 201 or 203, and 183-185, respectively;
a second antibody or antigen binding fragment comprising:
(a) a VH amino acid sequence according to SEQ ID NOs.:105 or 113, and a VL amino acid sequence according to SEQ ID NO: 168; or
(b) CDRH1, CDRH2, and CDRH3 amino acids according to SEQ ID NOs.: 106-108, respectively, or SEQ ID NOs.: 106, 121, and 108, respectively, and CDRL1, CDRL2, and CDRL3 amino acid sequences according to SEQ ID NOS.:169-171, respectively.

Embodiment 153. A method of preventing or treating or neutralizing a coronavirus infection in a subject, the method comprising administering to a subject who has received a first antibody or antigen binding fragment comprising:
(a) a VH amino acid sequence according to SEQ ID NOs.:105 or 113, and a VL amino acid sequence according to SEQ ID NO: 168; or
(b) CDRH1, CDRH2, and CDRH3 amino acids according to SEQ ID NOs.: 106-108, respectively, or SEQ ID NOs.: 106, 121, and 108, respectively, and CDRL1, CDRL2, and CDRL3 amino acid sequences according to SEQ ID NOS.: 169-171, respectively;
a second antibody or antigen binding fragment comprising:
(a) VH and VL amino acid sequences according to SEQ ID NOs.:178 or 194 or 196 or 198 or 200 or 202 and 182 or 190, respectively; or
(b) CDRH1, CDRH2, CDRH3, CDRL1, CDRL2, and CDRL3 amino acid sequences according to SEQ ID NOS.:179 or 195, 180 or 197 or 199, 181 201 or 203, and 183-185, respectively.

TABLE 2

Sequences

| Sequence Description | SEQ ID NO. | Sequence |
|---|---|---|
| SARS-CoV-2 S300-v1 mAb VH (aa) | 1 | QVQLVQSGAEVKKPGASVKVSCKASGYTFT DYYIHWVRQAPGQGPEWLGWVNGYSGATR YAQKYQGRVTMTRDTSISTAYMQLSRLRPDD TAVYYCARDRPSHEWAMYFFDNWGQGTLV TVSS |
| SARS-CoV-2 S300-v1 mAb CDRH1 (aa) | 2 | GYTFTDYY |
| SARS-CoV-2 S300-v1 mAb CDRH2 (aa) | 3 | VNGYSGAT |
| SARS-CoV-2 S300-v1 mAb CDRH3 (aa) | 4 | ARDRPSHEWAMYFFDN |
| SARS-CoV-2 S300-v1 mAb VL (VK) (aa) | 5 | QIVLTQSPGTLSLSPGERATLSCRASQSVPSSC LAWYQQKPGQAPRLLIYGASGRATGIPDRFS GSGSGTDFTLTIRRLEPEDFAVYYCQQYGSSP PLTFGGGTKVEIK |
| SARS-CoV-2 S300-v1 mAb CDRL1 (aa) | 6 | QSVPSSC |
| SARS-CoV-2 S300-v1 mAb CDRL2 (aa) | 7 | GAS |

TABLE 2-continued

| Sequence Description | SEQ ID NO. | Sequence |
|---|---|---|
| SARS-CoV-2 S300-v1 mAb CDRL3 (aa) | 8 | QQYGSSPPLT |
| SARS-CoV-2 S300-v1.1 mAb VH (aa) | 9 | QVQLVQSGAEVKKPGASVKVSCKASGYTFTDYYIHWVRQAPGQGPEWLGWVQGYSGATRYAQKYQGRVTMTRDTSISTAYMQLSRLRPDDTAVYYCARDRPSHEWAMYFFDNWGQGTLVTVSS |
| SARS-CoV-2 S300-v1.2 mAb VH (aa) | 10 | QVQLVQSGAEVKKPGASVKVSCKASGYTFTDYYIHWVRQAPGQGPEWLGWVNAYSGATRYAQKYQGRVTMTRDTSISTAYMQLSRLRPDDTAVYYCARDRPSHEWAMYFFDNWGQGTLVTVSS |
| SARS-CoV-2 S300-v1.3 mAb VH (aa) | 11 | QVQLVQSGAEVKKPGASVKVSCKASGYTFTDYYIHWVRQAPGQGPEWLGWVNSYSGATRYAQKYQGRVTMTRDTSISTAYMQLSRLRPDDTAVYYCARDRPSHEWAMYFFDNWGQGTLVTVSS |
| SARS-CoV-2 S300-v1.4 mAb VH (aa) | 12 | QVQLVQSGAEVKKPGASVKVSCKASGYTFTDYYIHWVRQAPGQGPEWLGWVNPYSGATRYAQKYQGRVTMTRDTSISTAYMQLSRLRPDDTAVYYCARDRPSHEWAMYFFDNWGQGTLVTVSS |
| SARS-CoV-2 S300-v1.5 mAb VH (aa) | 13 | QVQLVQSGAEVKKPGASVKVSCKASGYTFTDYYIHWVRQAPGQGPEWLGWVNQYSGATRYAQKYQGRVTMTRDTSISTAYMQLSRLRPDDTAVYYCARDRPSHEWAMYFFDNWGQGTLVTVSS |
| SARS-CoV-2 S300-v1.6 mAb VH (aa) | 14 | QVQLVQSGAEVKKPGASVKVSCKASGYTFTDYYIHWVRQAPGQGPEWLGWVLGYSGATRYAQKYQGRVTMTRDTSISTAYMQLSRLRPDDTAVYYCARDRPSHEWAMYFFDNWGQGTLVTVSS |
| SARS-CoV-2 S300-v1.7 mAb VH (aa) | 15 | QVQLVQSGAEVKKPGASVKVSCKASGYTFTDYYIHWVRQAPGQGPEWLGWVTGYSGATRYAQKYQGRVTMTRDTSISTAYMQLSRLRPDDTAVYYCARDRPSHEWAMYFFDNWGQGTLVTVSS |
| SARS-CoV-2 S300-v1.1 mAb CDRH2 (aa) | 16 | VQGYSGAT |
| SARS-CoV-2 S300-v1.2 mAb CDRH2 (aa) | 17 | VNAYSGAT |

TABLE 2-continued

Sequences

| Sequence Description | SEQ ID NO. | Sequence |
|---|---|---|
| SARS-CoV-2 S300-v1.3 mAb CDRH2 (aa) | 18 | VNSYSGAT |
| SARS-CoV-2 S300-v1.4 mAb CDRH2 (aa) | 19 | VNPYSGAT |
| SARS-CoV-2 S300-v1.5 mAb CDRH2 (aa) | 20 | VNQYSGAT |
| SARS-CoV-2 S300-v1.6 mAb CDRH2 (aa) | 21 | VLGYSGAT |
| SARS-CoV-2 S300-v1.7 mAb CDRH2 (aa) | 22 | VTGYSGAT |
| SARS-CoV-2 S300-v1.8 mAb VH (aa) | 23 | QVQLVQSGAEVKKPGASVKVSCKASGYTFT DYYIHWVRQAPGQGPEWLGWVNGYSGATR YAQKYQGRVTMTRDTSISTAYMQLSRLRPDD TAVYYCARDRPSHEFAMYFFDNWGQGTLV TVSS |
| SARS-CoV-2 S300-v1.9 mAb VH (aa) | 24 | QVQLVQSGAEVKKPGASVKVSCKASGYTFT DYYIHWVRQAPGQGPEWLGWVNGYSGATR YAQKYQGRVTMTRDTSISTAYMQLSRLRPDD TAVYYCARDRPSHEYAMYFFDNWGQGTLV TVSS |
| SARS-CoV-2 S300-v1.8 mAb CDRH3 (aa) | 25 | ARDRPSHEFAMYFFDN |
| SARS-CoV-2 S300-v1.9 mAb CDRH3 (aa) | 26 | ARDRPSHEYAMYFFDN |
| SARS-CoV-2 | 27 | QVQLVQSGAEVKKPGASVKVSCKASGYTFT DYYIHWVRQAPGQGPEWLGFVNGYSGATRY |

TABLE 2-continued

Sequences

| Sequence Description | SEQ ID NO. | Sequence |
|---|---|---|
| S300-v2 mAb VH (aa) | | AQKYQGRVTMTRDTSISTAYMQLSRLRPDDT AVYYCARDRPSHEWAMYFFDNWGQGTLVTVSS |
| SARS-CoV-2 S300-v2.1 mAb VH (aa) | 28 | QVQLVQSGAEVKKPGASVKVSCKASGYTFTDYYIHWVRQAPGQGPEWLGFVQGYSGATRYAQKYQGRVTMTRDTSISTAYMQLSRLRPDDTAVYYCARDRPSHEWAMYFFDNWGQGTLVTVSS |
| SARS-CoV-2 S300-v2.2 mAb VH (aa) | 29 | QVQLVQSGAEVKKPGASVKVSCKASGYTFTDYYIHWVRQAPGQGPEWLGFVNAYSGATRYAQKYQGRVTMTRDTSISTAYMQLSRLRPDDTAVYYCARDRPSHEWAMYFFDNWGQGTLVTVSS |
| SARS-CoV-2 S300-v2.3 mAb VH (aa) | 30 | QVQLVQSGAEVKKPGASVKVSCKASGYTFTDYYIHWVRQAPGQGPEWLGFVNSYSGATRYAQKYQGRVTMTRDTSISTAYMQLSRLRPDDTAVYYCARDRPSHEWAMYFFDNWGQGTLVTVSS |
| SARS-CoV-2 S300-v2.4 mAb VH (aa) | 31 | QVQLVQSGAEVKKPGASVKVSCKASGYTFTDYYIHWVRQAPGQGPEWLGFVNPYSGATRYAQKYQGRVTMTRDTSISTAYMQLSRLRPDDTAVYYCARDRPSHEWAMYFFDNWGQGTLVTVSS |
| SARS-CoV-2 S300-v2.5 mAb VH (aa) | 32 | QVQLVQSGAEVKKPGASVKVSCKASGYTFTDYYIHWVRQAPGQGPEWLGFVNQYSGATRYAQKYQGRVTMTRDTSISTAYMQLSRLRPDDTAVYYCARDRPSHEWAMYFFDNWGQGTLVTVSS |
| SARS-CoV-2 S300-v2.6 mAb VH (aa) | 33 | QVQLVQSGAEVKKPGASVKVSCKASGYTFTDYYIHWVRQAPGQGPEWLGFVLGYSGATRYAQKYQGRVTMTRDTSISTAYMQLSRLRPDDTAVYYCARDRPSHEWAMYFFDNWGQGTLVTVSS |
| SARS-CoV-2 S300-v2.7 mAb VH (aa) | 34 | QVQLVQSGAEVKKPGASVKVSCKASGYTFTDYYIHWVRQAPGQGPEWLGFVTGYSGATRYAQKYQGRVTMTRDTSISTAYMQLSRLRPDDTAVYYCARDRPSHEWAMYFFDNWGQGTLVTVSS |
| SARS-CoV-2 S300-v2.8 mAb VH (aa) | 35 | QVQLVQSGAEVKKPGASVKVSCKASGYTFTDYYIHWVRQAPGQGPEWLGFVNGYSGATRYAQKYQGRVTMTRDTSISTAYMQLSRLRPDDTAVYYCARDRPSHEFAMYFFDNWGQGTLVTVSS |
| SARS-CoV-2 S300-v2.9 mAb VH (aa) | 36 | QVQLVQSGAEVKKPGASVKVSCKASGYTFTDYYIHWVRQAPGQGPEWLGFVNGYSGATRYAQKYQGRVTMTRDTSISTAYMQLSRLRPDDTAVYYCARDRPSHEYAMYFFDNWGQGTLVTVSS |
| SARS-CoV-2 S300-v3 mAb VH (aa) | 37 | QVQLVQSGAEVKKPGASVKVSCKASGYTFTDYYIHWVRQAPGQGPEWLGYVNGYSGATRYAQKYQGRVTMTRDTSISTAYMQLSRLRPDDTAVYYCARDRPSHEWAMYFFDNWGQGTLVTVSS |

TABLE 2-continued

Sequences

| Sequence Description | SEQ ID NO. | Sequence |
|---|---|---|
| SARS-CoV-2 S300-v3.1 mAb VH (aa) | 38 | QVQLVQSGAEVKKPGASVKVSCKASGYTFT DYYIHWVRQAPGQGPEWLGYVQGYSGATR YAQKYQGRVTMTRDTSISTAYMQLSRLRPDD TAVYYCARDRPSHEWAMYFFDNWGQGTLV TVSS |
| SARS-CoV-2 S300-v3.2 mAb VH (aa) | 39 | QVQLVQSGAEVKKPGASVKVSCKASGYTFT DYYIHWVRQAPGQGPEWLGYVNAYSGATR YAQKYQGRVTMTRDTSISTAYMQLSRLRPDD TAVYYCARDRPSHEWAMYFFDNWGQGTLV TVSS |
| SARS-CoV-2 S300-v3.3 mAb VH (aa) | 40 | QVQLVQSGAEVKKPGASVKVSCKASGYTFT DYYIHWVRQAPGQGPEWLGYVNSYSGATRY AQKYQGRVTMTRDTSISTAYMQLSRLRPDDT AVYYCARDRPSHEWAMYFFDNWGQGTLVT VSS |
| SARS-CoV-2 S300-v3.4 mAb VH (aa) | 41 | QVQLVQSGAEVKKPGASVKVSCKASGYTFT DYYIHWVRQAPGQGPEWLGYVNPYSGATRY AQKYQGRVTMTRDTSISTAYMQLSRLRPDDT AVYYCARDRPSHEWAMYFFDNWGQGTLVT VSS |
| SARS-CoV-2 S300-v3.5 mAb VH (aa) | 42 | QVQLVQSGAEVKKPGASVKVSCKASGYTFT DYYIHWVRQAPGQGPEWLGYVNQYSGATR YAQKYQGRVTMTRDTSISTAYMQLSRLRPDD TAVYYCARDRPSHEWAMYFFDNWGQGTLV TVSS |
| SARS-CoV-2 S300-v3.6 mAb VH (aa) | 43 | QVQLVQSGAEVKKPGASVKVSCKASGYTFT DYYIHWVRQAPGQGPEWLGYVLGYSGATR YAQKYQGRVTMTRDTSISTAYMQLSRLRPDD TAVYYCARDRPSHEWAMYFFDNWGQGTLV TVSS |
| SARS-CoV-2 S300-v3.7 mAb VH (aa) | 44 | QVQLVQSGAEVKKPGASVKVSCKASGYTFT DYYIHWVRQAPGQGPEWLGYVTGYSGATR YAQKYQGRVTMTRDTSISTAYMQLSRLRPDD TAVYYCARDRPSHEWAMYFFDNWGQGTLV TVSS |
| SARS-CoV-2 S300-v3.8 mAb VH (aa) | 45 | QVQLVQSGAEVKKPGASVKVSCKASGYTFT DYYIHWVRQAPGQGPEWLGYVNGYSGATR YAQKYQGRVTMTRDTSISTAYMQLSRLRPDD TAVYYCARDRPSHEFAMYFFDNWGQGTLV TVSS |
| SARS-CoV-2 S300-v3.9 mAb VH (aa) | 46 | QVQLVQSGAEVKKPGASVKVSCKASGYTFT DYYIHWVRQAPGQGPEWLGYVNGYSGATR YAQKYQGRVTMTRDTSISTAYMQLSRLRPDD TAVYYCARDRPSHEYAMYFFDNWGQGTLV TVSS |
| SARS-CoV-2 S300-v10 mAb VL (VK) (aa) | 47 | QIVLTQSPGTLSLSPGERATLSCRASQSVPSSY LAWYQQKPGQAPRLLIYGASGRATGIPDRFS GSGSGTDFTLTIRRLEPEDFAVYYCQQYGSSP PLTFGGGTKVEIK |

TABLE 2-continued

Sequences

| Sequence Description | SEQ ID NO. | Sequence |
|---|---|---|
| SARS-CoV-2 S300-v11 mAb VL (VK) (aa) | 48 | QIVLTQSPGTLSLSPGERATLSCRASQSVPSSS LAWYQQKPGQAPRLLIYGASGRATGIPDRFS GSGSGTDFTLTIRRLEPEDFAVYYCQQYGSSP PLTFGGGTKVEIK |
| SARS-CoV-2 S300-v12 mAb VL (VK) (aa) | 49 | QIVLTQSPGTLSLSPGERATLSCRASQSVPSST LAWYQQKPGQAPRLLIYGASGRATGIPDRFS GSGSGTDFTLTIRRLEPEDFAVYYCQQYGSSP PLTFGGGTKVEIK |
| SARS-CoV-2 S300-v13 mAb VL (VK) (aa) | 50 | QIVLTQSPGTLSLSPGERATLSCRASQSVPSSA LAWYQQKPGQAPRLLIYGASGRATGIPDRFS GSGSGTDFTLTIRRLEPEDFAVYYCQQYGSSP PLTFGGGTKVEIK |
| SARS-CoV-2 S300-v10 mAb CDRL1 (aa) | 51 | QSVPSSY |
| SARS-CoV-2 S300-v11 mAb CDRL1 (aa) | 51 | QSVPSSS |
| SARS-CoV-2 S300-v12 mAb CDRL1 (aa) | 53 | QSVPSST |
| SARS-CoV-2 S300-v13 mAb CDRL1 (aa) | 54 | QSVPSSA |
| SARS-CoV-2 S302 mAb VH (aa) | 55 | QVQLVESGGGVVQPGRSLRLSCAASGFTFSS YGMHWVRQAPGKGLEWVAVISYDGSNKYY ADSVKGRFTISRDNSKNTLYLQMNSLRAEDT AVYYCAKDISSGWDRVFDYWGQGTLVTVSS |
| SARS-CoV-2 S302 mAb CDRH1 (aa) | 56 | GFTFSSYG |

TABLE 2-continued

Sequences

| Sequence Description | SEQ ID NO. | Sequence |
|---|---|---|
| SARS-CoV-2 S302 mAb CDRH2 (aa) | 57 | ISYDGSNK |
| SARS-CoV-2 S302 mAb CDRH3 (aa) | 58 | AKDISSGWDRVFDY |
| SARS-CoV-2 S302 mAb VL (VK) (aa) | 59 | EILLTQSPGTLSLSPGERATLSCRTSQSVGSSY LAWYQQKPGQAPRLLIYAASRAIGIPDRFSG SGSGTDFTLTISRLEPEDFAVYYCQQYGSSPW TFGQGTKVEIK |
| SARS-CoV-2 S302 mAb CDRL1 (aa) | 60 | QSVGSSY |
| SARS-CoV-2 S302 mAb CDRL2 (aa) | 61 | AAS |
| SARS-CoV-2 S302 mAb CDRL3 (aa) | 62 | QQYGSSPWT |
| SARS-CoV-2 S303-v1 mAb VH (aa) | 63 | EVQLVESGGGLVKPGGSLRLSCAASGFTFLT YSMNWVRQTPGKRLQWVSAISGSGGATYY ADSVKGRFTISRDNSKNTLYLQMNTVTADDT AIYFCARERDDIFPMGLNAFDIWGQGAMVI VSS |
| SARS-CoV-2 S303-v1 mAb CDRH1 (aa) | 64 | GFTFLTYS |
| SARS-CoV-2 S303-v1 mAb CDRH2 (aa) | 65 | ISGSGGAT |
| SARS-CoV-2 S303-v1 mAb CDRH3 (aa) | 66 | ARERDDIFPMGLNAFDI |

TABLE 2-continued

Sequences

| Sequence Description | SEQ ID NO. | Sequence |
|---|---|---|
| SARS-CoV-2 S303-v1 mAb VL (VK) (aa) | 67 | DIQMTQSPSTLSASVGDRVTITCRASQSISNW LAWYQQKPGKAPKLLIYKASSLESGVPSRFS GSGSGTEFTLTISSLQPDDSATYYCQQYDTYS WTFGQGTKVEIK |
| SARS-CoV-2 S303-v1 mAb CDRL1 (aa) | 68 | QSISNW |
| SARS-CoV-2 S303-v1 mAb CDRL2 (aa) | 69 | KAS |
| SARS-CoV-2 S303-v1 mAb CDRL3 (aa) | 70 | QQYDTYSWT |
| SARS-CoV-2 S303-v2 mAb VL (VK) (aa) | 71 | DIQMTQSPSTLSASVGDRVTITCRASQSISNFL AWYQQKPGKAPKLLIYKASSLESGVPSRFSGS GSGTEFTLTISSLQPDDSATYYCQQYDTYSW TFGQGTKVEIK |
| SARS-CoV-2 S303-v3 mAb VL (VK) (aa) | 72 | DIQMTQSPSTLSASVGDRVTITCRASQSISNYL AWYQQKPGKAPKLLIYKASSLESGVPSRFSGS GSGTEFTLTISSLQPDDSATYYCQQYDTYSW TFGQGTKVEIK |
| SARS-CoV-2 S303-v2 mAb CDRL1 (aa) | 73 | QSISNF |
| SARS-CoV-2 S303-v3 mAb CDRL1 (aa) | 74 | QSISNY |
| SARS-CoV-2 S303-v4 mAb VL (VK) (aa) | 75 | DIQMTQSPSTLSASVGDRVTITCRASQSISNW LAWYQQKPGKAPKLLIYKASSLESGVPSRFS GSGSGTEFTLTISSLQPDDSATYYCQQYDTYS FTFGQGTKVEIK |
| SARS-CoV-2 S303-v5 mAb VL (VK) (aa) | 76 | DIQMTQSPSTLSASVGDRVTITCRASQSISNW LAWYQQKPGKAPKLLIYKASSLESGVPSRFS GSGSGTEFTLTISSLQPDDSATYYCQQYDTYS YTFGQGTKVEIK |

TABLE 2-continued

Sequences

| Sequence Description | SEQ ID NO. | Sequence |
|---|---|---|
| SARS-CoV-2 S303-v4 mAb CDRL3 (aa) | 77 | QQYDTYSFT |
| SARS-CoV-2 S303-v5 mAb CDRL3 (aa) | 78 | QQYDTYSYT |
| SARS-CoV-2 S304 mAb VH (aa) | 79 | EVQLVESGGGLVQPGGSLRLSCAASGTFSSYDMHWVRQTTGKGLEWVSTIGTAGDTYYPDSVKGRFTISREDAKNSLYLQMNSLRAGDTAVYYCARGDSSGYYYYFDYWGQGTLLTVSS |
| SARS-CoV-2 S304 mAb CDRH1 (aa) | 80 | GFTFSSYD |
| SARS-CoV-2 S304 mAb CDRH2 (aa) | 81 | IGTAGDT |
| SARS-CoV-2 S304 mAb CDRH3 (aa) | 82 | ARGDSSGYYYYFDY |
| SARS-CoV-2 S304 mAb VL (VK) (aa) | 83 | DIQMTQSPSSLSAAVGDRVTITCRASQSIGSYLNWYQQKPGKAPKLLIYAASSLQSGVPSRFSGSGSGTDFTLTISSLQPEDFAIYYCQQSYVSPTYTFGPGTKVDIK |
| SARS-CoV-2 S304 mAb CDRL1 (aa) | 84 | QSIGSY |
| SARS-CoV-2 S304 mAb CDRL2 (aa) | 85 | AAS |
| SARS-CoV-2 S304 mAb CDRL3 (aa) | 86 | QQSYVSPTYT |

TABLE 2-continued

Sequences

| Sequence Description | SEQ ID NO. | Sequence |
|---|---|---|
| SARS-CoV-2 S306 mAb VH (aa) | 87 | QVQLVQSGAEVKKPGASVKVSCKASTYTFTSFGISWVRQAPGQGLEWMGWITTYSGDTNYAQKFQGRVTMTTDTSTNTAYMELRSLRSDDTAVYYCASDYFDSSGYYHSFDYWGQGTLVTVSS |
| SARS-CoV-2 S306 mAb CDRH1 (aa) | 88 | TYTFTSFG |
| SARS-CoV-2 S306 mAb CDRH2 (aa) | 89 | ITTYSGDT |
| SARS-CoV-2 S306 mAb CDRH3 (aa) | 90 | ASDYFDSSGYYHSFDY |
| SARS-CoV-2 S306 mAb VL (VK) (aa) | 91 | EIVLTQSPDTLSLSPGERATLSCRASQSVSSYLAWYQQRPGQAPRLLIYDASKRATGIPARFSGSGSGTDFTLTISSLEPEDFAVYYCQQRSNWPPGCSFGQGTKVEIK |
| SARS-CoV-2 S306 mAb CDRL1 (aa) | 92 | QSVSSY |
| SARS-CoV-2 S306 mAb CDRL2 (aa) | 93 | DAS |
| SARS-CoV-2 S306 mAb CDRL3 (aa) | 94 | QQRSNWPPGCS |
| SARS-CoV-2 S308-v1 mAb VH (aa) | 95 | QVQLVESGGGVVQPGRSLRLSCAASRFTFSSYGMHWVRQAPGKGLEWVAVIWHDGNNKHYGDSVKGRVTISRDNSKNTLYLQMTSLRAEDTAVYYCARAVTTFKGSGRARMRGMDVWGQGTTVTVSS |
| SARS-CoV-2 S308-v1 mAb CDRH1 (aa) | 96 | RFTFSSYG |

TABLE 2-continued

| Sequences | | |
|---|---|---|
| Sequence Descrip- tion | SEQ ID NO. | Sequence |
| SARS-CoV-2 S308-v1 mAb CDRH2 (aa) | 97 | IWHDGNNK |
| SARS-CoV-2 S308-v1 mAb CDRH3 (aa) | 98 | ARAVTTFKGSGRARMRGMDV |
| SARS-CoV-2 S308-v1 mAb VL (VK) (aa) | 99 | DIQLTQSPSFLSASVGDRVTITCRASQGINTYL AWYQQKPGKAPKLLIYAASTLQSGVPSRFSG SGSGTEFTLTISSLQPEDFATYYCQHLDTYPF TFGPGTKVDIK |
| SARS-CoV-2 S308-v1 mAb CDRL1 (aa) | 100 | QGINTY |
| SARS-CoV-2 S308-v1 mAb CDRL2 (aa) | 101 | AAS |
| SARS-CoV-2 S308-v1 mAb CDRL3 (aa) | 102 | QHLDTYPFT |
| SARS-CoV-2 S308-v2 mAb VH (aa) | 103 | QVQLVESGGGVVQPGRSLRLSCAASRFTFSS YGMHWVRQAPGKGLEWVAVIWHDGNNKH YGDSVKGRVTISRDNSKNTLYLQMTSLRAED TAVYYCARAVTTFKGSGRARLRGMDVWG QGTTVTVSS |
| SARS-CoV-2 S308-v2 mAb CDRH3 (aa) | 104 | ARAVTTFKGSGRARLRGMDV |
| SARS-CoV-2 S309-v1 mAb VH (aa) | 105 | QVQLVQSGAEVKKPGASVKVSCKASGYPFT SYGISWVRQAPGQGLEWMGWISTYNGNTNY AQKFQGRVTMTTDTSTTTGYMELRRLRSDDT AVYYCARDYTRGAWFGESLIGGFDNWGQG |
| SARS-CoV-2 S309-v1 mAb CDRH1 (aa) | 106 | GYPFTSYG |

TABLE 2-continued

Sequences

| Sequence Description | SEQ ID NO. | Sequence |
|---|---|---|
| SARS-CoV-2 S309-v1 mAb CDRH2 (aa) | 107 | ISTYNGNT |
| SARS-CoV-2 S309-v1 mAb CDRH3 (aa) | 108 | ARDYTRGAWFGESLIGGFDN |
| SARS-CoV-2 S309-v1 mAb VL (VK) (aa) (non-productive) | 109 | DIQMTQSPSSLSTSVGDRVTITCRASQGINNY VAWYQQKPGKVPKLLIYGASTLQSGVPSRFR GSGSGTGFTLTISSLQPEDVASYYCRKYNSAP WTFGQGTRVEIK |
| SARS-CoV-2 S309-v1 mAb CDRL1 (aa) (non-productive) | 110 | QGINNY |
| SARS-CoV-2 S309-v1 mAb CDRL2 (aa) (non-productive) | 111 | GAS |
| SARS-CoV-2 S309-v1 mAb CDRL3 (aa) (non-productive) | 112 | RKYNSAPWT |
| SARS-CoV-2 S309-v1.1 mAb VH (aa) | 113 | QVQLVQSGAEVKKPGASVKVSCKASGYPFT SYGISWVRQAPGQGLEWMGWISTYQGNTN YAQKFQGRVTMTTDTSTTTGYMELRRLRSD DTAVYYCARDYTRGAWFGESLIGGFDNWG QGTLVTVSS |
| SARS-CoV-2 S309-v1.2 mAb VH (aa) | 114 | QVQLVQSGAEVKKPGASVKVSCKASGYPFT SYGISWVRQAPGQGLEWMGWISTYNSNTNY AQKFQGRVTMTTDTSTTTGYMELRRLRSDDT AVYYCARDYTRGAWFGESLIGGFDNWGQG TLVTVSS |

TABLE 2-continued

Sequences

| Sequence Description | SEQ ID NO. | Sequence |
|---|---|---|
| SARS-CoV-2 S309-v1.3 mAb VH (aa) | 115 | QVQLVQSGAEVKKPGASVKVSCKASGYPFT SYGISWVRQAPGQGLEWMGWISTYNANTNY AQKFQGRVTMTTDTSTTTGYMELRRLRSDDT AVYYCARDYTRGAWFGESLIGGFDNWGQG TLVTVSS |
| SARS-CoV-2 S309-v1.4 mAb VH (aa) | 116 | QVQLVQSGAEVKKPGASVKVSCKASGYPFT SYGISWVRQAPGQGLEWMGWISTYNQNTNY AQKFQGRVTMTTDTSTTTGYMELRRLRSDDT AVYYCARDYTRGAWFGESLIGGFDNWGQG TLVTVSS |
| SARS-CoV-2 S309-v1.5 mAb VH (aa) | 117 | QVQLVQSGAEVKKPGASVKVSCKASGYPFT SYGISWVRQAPGQGLEWMGWISTYLGNTNY AQKFQGRVTMTTDTSTTTGYMELRRLRSDDT AVYYCARDYTRGAWFGESLIGGFDNWGQG TLVTVSS |
| SARS-CoV-2 S309-v1.6 mAb VH (aa) | 118 | QVQLVQSGAEVKKPGASVKVSCKASGYPFT SYGISWVRQAPGQGLEWMGWISTYTGNTNY AQKFQGRVTMTTDTSTTTGYMELRRLRSDDT AVYYCARDYTRGAWFGESLIGGFDNWGQG TLVTVSS |
| SARS-CoV-2 S309-v1.7 mAb VH (aa) | 119 | QVQLVQSGAEVKKPGASVKVSCKASGYPFT SYGISWVRQAPGQGLEWMGWISTYNGNTNY AQKFQGRVTMTTDTSTTTGYMELRRLRSDDT AVYYCARDYTRGAFFGESLIGGFDNWGQG TLVTVSS |
| SARS-CoV-2 S309-v1.8 mAb VH (aa) | 120 | QVQLVQSGAEVKKPGASVKVSCKASGYPFT SYGISWVRQAPGQGLEWMGWISTYNGNTNY AQKFQGRVTMTTDTSTTTGYMELRRLRSDDT AVYYCARDYTRGAYFGESLIGGFDNWGQG TLVTVSS |
| SARS-CoV-2 S309-v1.1 mAb CDRH2 (aa) | 121 | ISTYQGNT |
| SARS-CoV-2 S309-v1.2 mAb CDRH2 (aa) | 122 | ISTYNSNT |
| SARS-CoV-2 S309-v1.3 mAb CDRH2 (aa) | 123 | ISTYNANT |
| SARS-CoV-2 S309-v1.4 mAb CDRH2 (aa) | 124 | ISTYNQNT |

TABLE 2-continued

Sequences

| Sequence Description | SEQ ID NO. | Sequence |
|---|---|---|
| SARS-CoV-2 S309-v1.5 mAb CDRH2 (aa) | 125 | ISTYLGNT |
| SARS-CoV-2 S309-v1.6 mAb CDRH2 (aa) | 126 | ISTYTGNT |
| SARS-CoV-2 S309-v1.7 mAb CDRH3 (aa) | 127 | ARDYTRGAFFGESLIGGFDN |
| SARS-CoV-2 S309-v1.8 mAb CDRH3 (aa) | 128 | ARDYTRGAYFGESLIGGFDN |
| SARS-CoV-2 S309-v2 mAb VH (aa) | 129 | QVQLVQSGAEVKKPGASVKVSCKASGYPFTSYGISWVRQAPGQGLEWMGFISTYNGNTNYAQKFQGRVTMTTDTSTTTGYMELRRLRSDDTAVYYCARDYTRGAWFGESLIGGFDNWGQGTLVTVSS |
| SARS-CoV-2 S309-v2.1 mAb VH (aa) | 130 | QVQLVQSGAEVKKPGASVKVSCKASGYPFTSYGISWVRQAPGQGLEWMGFISTYQGNTNYAQKFQGRVTMTTDTSTTTGYMELRRLRSDDTAVYYCARDYTRGAWFGESLIGGFDNWGQGTLVTVSS |
| SARS-CoV-2 S309-v2.2 mAb VH (aa) | 131 | QVQLVQSGAEVKKPGASVKVSCKASGYPFT SYGISWVRQAPGQGLEWMGFISTYNSNTNYAQKFQGRVTMTTDTSTTTGYMELRRLRSDDTAVYYCARDYTRGAWFGESLIGGFDNWGQGTLVTVSS |
| SARS-CoV-2 S309-v2.3 mAb VH (aa) | 132 | QVQLVQSGAEVKKPGASVKVSCKASGYPFTSYGISWVRQAPGQGLEWMGFISTYNANTNYAQKFQGRVTMTTDTSTTTGYMELRRLRSDDTAVYYCARDYTRGAWFGESLIGGFDNWGQGTLVTVSS |
| SARS-CoV-2 S309-v2.4 mAb VH (aa) | 133 | QVQLVQSGAEVKKPGASVKVSCKASGYPFTSYGISWVRQAPGQGLEWMGFISTYNQNTNYAQKFQGRVTMTTDTSTTTGYMELRRLRSDDTAVYYCARDYTRGAWFGESLIGGFDNWGQGTLVTVSS |
| SARS-CoV-2 S309-v2.5 mAb VH (aa) | 134 | QVQLVQSGAEVKKPGASVKVSCKASGYPFTSYGISWVRQAPGQGLEWMGFISTYLGNTNYAQKFQGRVTMTTDTSTTTGYMELRRLRSDDTAVYYCARDYTRGAWFGESLIGGFDNWGQGTLVTVSS |

TABLE 2-continued

Sequences

| Sequence Description | SEQ ID NO. | Sequence |
|---|---|---|
| SARS-CoV-2 S309-v2.6 mAb VH (aa) | 135 | QVQLVQSGAEVKKPGASVKVSCKASGYPFT SYGISWVRQAPGQGLEWMGFISTYTGNTNY AQKFQGRVTMTTDTSTTTGYMELRRLRSDDT AVYYCARDYTRGAWFGESLIGGFDNWGQG TLVTVSS |
| SARS-CoV-2 S309-v2.7 mAb VH (aa) | 136 | QVQLVQSGAEVKKPGASVKVSCKASGYPFT SYGISWVRQAPGQGLEWMGFISTYNGNTNY AQKFQGRVTMTTDTSTTTGYMELRRLRSDDT AVYYCARDYTRGAFFGESLIGGFDNWGQG TLVTVSS |
| SARS-CoV-2 S309-v2.8 mAb VH (aa) | 137 | QVQLVQSGAEVKKPGASVKVSCKASGYPFT SYGISWVRQAPGQGLEWMGFISTYNGNTNY AQKFQGRVTMTTDTSTTTGYMELRRLRSDDT AVYYCARDYTRGAYFGESLIGGFDNWGQG TLVTVSS |
| SARS-CoV-2 S309-v3 mAb VH (aa) | 138 | QVQLVQSGAEVKKPGASVKVSCKASGYPFT SYGISWVRQAPGQGLEWMGYISTYNGNTNY AQKFQGRVTMTTDTSTTTGYMELRRLRSDDT AVYYCARDYTRGAWFGESLIGGFDNWGQG TLVTVSS |
| SARS-CoV-2 S309-v3.1 mAb VH (aa) | 139 | QVQLVQSGAEVKKPGASVKVSCKASGYPFT SYGISWVRQAPGQGLEWMGYISTYQGNTNY AQKFQGRVTMTTDTSTTTGYMELRRLRSDDT AVYYCARDYTRGAWFGESLIGGFDNWGQG TLVTVSS |
| SARS-CoV-2 S309-v3.2 mAb VH (aa) | 140 | QVQLVQSGAEVKKPGASVKVSCKASGYPFT SYGISWVRQAPGQGLEWMGYISTYNSNTNY AQKFQGRVTMTTDTSTTTGYMELRRLRSDDT AVYYCARDYTRGAWFGESLIGGFDNWGQG TLVTVSS |
| SARS-CoV-2 S309-v3.3 mAb VH (aa) | 141 | QVQLVQSGAEVKKPGASVKVSCKASGYPFT SYGISWVRQAPGQGLEWMGYISTYNANTNY AQKFQGRVTMTTDTSTTTGYMELRRLRSDDT AVYYCARDYTRGAWFGESLIGGFDNWGQG TLVTVSS |
| SARS-CoV-2 S309-v3.4 mAb VH (aa) | 142 | QVQLVQSGAEVKKPGASVKVSCKASGYPFT SYGISWVRQAPGQGLEWMGYISTYNQNTNY AQKFQGRVTMTTDTSTTTGYMELRRLRSDDT AVYYCARDYTRGAWFGESLIGGFDNWGQG TLVTVSS |
| SARS-CoV-2 S309-v3.5 mAb VH (aa) | 143 | QVQLVQSGAEVKKPGASVKVSCKASGYPFT SYGISWVRQAPGQGLEWMGYISTYLGNTNY AQKFQGRVTMTTDTSTTTGYMELRRLRSDDT AVYYCARDYTRGAWFGESLIGGFDNWGQG TLVTVSS |
| SARS-CoV-2 S309-v3.6 mAb VH (aa) | 144 | QVQLVQSGAEVKKPGASVKVSCKASGYPFT SYGISWVRQAPGQGLEWMGYISTYTGNTNY AQKFQGRVTMTTDTSTTTGYMELRRLRSDDT AVYYCARDYTRGAWFGESLIGGFDNWGQG TLVTVSS |

TABLE 2-continued

Sequences

| Sequence Description | SEQ ID NO. | Sequence |
|---|---|---|
| SARS-CoV-2 S309-v3.7 mAb VH (aa) | 145 | QVQLVQSGAEVKKPGASVKVSCKASGYPFT SYGISWVRQAPGQGLEWMGYISTYNGNTNY AQKFQGRVTMTTDTSTTTGYMELRRLRSDDT AVYYCARDYTRGAFFGESLIGGFDNWGQG TLVTVSS |
| SARS-CoV-2 S309-v3.8 mAb VH (aa) | 146 | QVQLVQSGAEVKKPGASVKVSCKASGYPFT SYGISWVRQAPGQGLEWMGYISTYNGNTNY AQKFQGRVTMTTDTSTTTGYMELRRLRSDDT AVYYCARDYTRGAYFGESLIGGFDNWGQG TLVTVSS |
| SARS-CoV-2 S309-v9 mAb VL(VK) (aa) (non-productive) | 147 | DIQMTQSPSSLSTSVGDRVTITCRASQGINNY VAWYQQKPGKVPKLLIYGASTLQSGVPSRFR GSGSGTGFTLTISSLQPEDVASYYCRKYNSAP GTFGQGTRVEIK |
| SARS-CoV-2 S309-v10 mAb VL (VK) (aa) (non-productive) | 148 | DIQMTQSPSSLSTSVGDRVTITCRASQGINNY VAWYQQKPGKVPKLLIYGASTLQSGVPSRFR GSGSGTGFTLTISSLQPEDVASYYCRKYNSAP RTFGQGTRVEIK |
| SARS-CoV-2 S309-v11 mAb VL (VK) (aa) (non-productive) | 149 | DIQMTQSPSSLSTSVGDRVTITCRASQGINNY VAWYQQKPGKVPKLLIYGASTLQSGVPSRFR GSGSGTGFTLTISSLQPEDVASYYCRKYNSAP FTFGQGTRVEIK |
| SARS-CoV-2 S309-v12 mAb VL (VK) (aa) (non-productive) | 150 | DIQMTQSPSSLSTSVGDRVTITCRASQGINNY VAWYQQKPGKVPKLLIYGASTLQSGVPSRFR GSGSGTGFTLTISSLQPEDVASYYCRKYNSAP YTFGQGTRVEIK |
| SARS-CoV-2 S309-v9 mAb CDRL3 (aa) (non-productive) | 151 | RKYNSAPGT |
| SARS-CoV-2 S309-v10 mAb CDRL3 | 152 | RKYNSAPRT |

TABLE 2-continued

Sequences

| Sequence Description | SEQ ID NO. | Sequence |
|---|---|---|
| (aa) (non-productive) | | |
| SARS-CoV-2 S309-v11 mAb CDRL3 (aa) (non-productive) | 153 | RKYNSAPFT |
| SARS-CoV-2 S309-v12 mAb CDRL3 (aa) (non-productive) | 154 | RKYNSAPYT |
| SARS-CoV-2 S310 mAb VH (aa) | 155 | QVQLVQSGAELKKPGSSVKVSCKASGGTFNSYSFNWVRQAPGQGLEWLGGIIPVLGTSNYAQKFQGRVAVTADEFTTTAYMELSSLRSEDTAVYYCATRTYDSSGYRPYYYGLDVWGQGTPVTVSS |
| SARS-CoV-2 S310 mAb CDRH1 (aa) | 156 | GGTFNSYS |
| SARS-CoV-2 S310 mAb CDRH2 (aa) | 157 | IIPVLGTS |
| SARS-CoV-2 S310 mAb CDRH3 (aa) | 158 | ATRTYDSSGYRPYYYGLDV |
| SARS-CoV-2 S310 mAb VL (VK) (aa) | 159 | QSALTQPASVSGSPGQSITISCTGTSSDVGSYNLVSWYQQRPGKAPELMIYEVTKRPSGLSNRFSGSKSGNTASLTISGLQAEDEADYYCCSYAGSDTVIFGGGTKVTVL |
| SARS-CoV-2 S310 mAb CDRL1 (aa) | 160 | SSDVGSYNL |

TABLE 2-continued

Sequences

| Sequence Description | SEQ ID NO. | Sequence |
|---|---|---|
| SARS-CoV-2 S310 mAb CDRL2 (aa) | 161 | EVT |
| SARS-CoV-2 S310 mAb CDRL3 (aa) | 162 | CSYAGSDTVI |

| Wuhan seafood market pneumonia virus isolate Wuhan-Hu-1 genomic sequence (GenBank: MN 908947.3; Jan. 23, 2020) | 163 |
|---|---|

```
   1 attaaaggtt tataccttcc caggtaacaa accaaccaac tttcgatctc ttgtagatct
  61 gttctctaaa cgaactttaa aatctgtgtg gctgtcactc ggctgcatgc ttagtgcact
 121 cacgcagtat aattaataac taattactgt cgttgacagg acacgagtaa ctcgtctatc
 181 ttctgcaggc tgcttacggt ttcgtccgtg ttgcagccga tcatcagcac atctaggttt
 241 cgtccgggtg tgaccgaaag gtaagatgga gagccttgtc cctggtttca acgagaaaac
 301 acacgtccaa ctcagtttgc ctgttttaca ggttcgcgac gtgctcgtac gtggctttgg
 361 agactccgtg gaggaggtct tatcagaggc cgtcaacat cttaaagatg gcacttgtgg
 421 cttagtagaa gttgaaaaag gcgttttgcc tcaacttgaa cagccctatg tgttcatcaa
 481 acgttcggat gctcgaactg cacctcatgg tcatgttatg gttgagctgg tagcagaact
 541 cgaaggcatt cagtacggtc gtagtggtga gacacttggt gtccttgtcc ctcatgtggg
 601 cgaaatacca gtggcttacc gcaaggttct tcttcgtaag aacggtaata aaggagctgg
 661 tggccatagt tacggcgccg atctaaagtc atttgactta ggcgacgagc ttggcactga
 721 tccttatgaa gattttcaag aaaactggaa cactaaacat agcagtggtg ttacccgtga
 781 actcatgcgt gagcttaacg gaggggcata cactcgctat gtcgataaca acttctgtgg
 841 ccctgatggc taccctcttg agtgcattaa agaccttcta gcacgtgctg gtaaagcttc
 901 atgcactttg tccgaacaac tggactttat tgacactaag aggggtgtat actgctgccg
 961 tgaacatgag catgaaattg cttggtacac ggaacgttct gaaagagct atgaattgca
1021 gacacctttt gaaattaaat tggcaaagaa atttgacact ttcaatgggg aatgtccaaa
1081 ttttgtattt cccttaaatt ccataatcaa gactattcaa ccaagggttg aaaagaaaaa
1141 gcttgatggc tttatgggta gaattcgatc tgtctatcca gttgcgtcac caaatgaatg
1201 caaccaaatg tgcctttcaa ctctcatgaa gtgtgatcat tgtggtgaaa cttcatggca
1261 gacgggcgat tttgttaaag ccacttgcga attttgtggc actgagaatt tgactaaaga
1321 aggtgccact acttgtggtt acttaccca aaatgctgtt gttaaaattt attgtccagc
1381 atgtcacaat tcagaagtag gacctgagca tagtcttgcc gaataccata tgaatctgg
1441 cttgaaaacc attcttcgta agggtggtcg cactattgcc tttggaggct gtgtgttctc
1501 ttatgttggt tgccataaca gtgtgccta ttggggttca cgtgctagcg ctaacatagg
1561 ttgtaaccat acaggtgttg ttggagaagg ttccgaaggt cttaatgaca accttcttga
1621 aatactccaa aaagagaaag tcaacatcaa tattgttggt gactttaaac ttaatgaaga
1681 gatcgccatt attttggcat cttttttctgc ttccacaagt gcttttgtgg aaactgtgaa
1741 aggtttggat tataaagcat tcaaacaaat tgttgaatcc tgtggtaatt ttaaagttac
1801 aaaaggaaaa gctaaaaaag gtgcctggaa tattggtgaa cagaaatcaa tactgagtcc
1861 tctttatgca tttgcatcag aggctgctcg tgttgtacga tcaatttttct cccgcactct
1921 tgaaactgct caaaattctg tgcgtgtttt acagaaggcc gctataacaa tactagatgg
1981 aatttcacag tattcactga gactcattga tgctatgatg ttcacatctg atttggctac
2041 taacaatcta gttgtaatgg cctacattac aggtggtgtt gttcagttga cttcgcagtg
2101 gctaactaac atctttgca ctgtttatga aaaactcaaa cccgtccttg attggcttga
2161 agagaagttt aaggaagtg tagagtttct tagagacggt tgggaaattg ttaaatttat
2221 ctcaacctgt gcttgtgaaa ttgtcggtgg acaaattgtc acctgtgcaa aggaaattaa
2281 ggagagtgtt cagacattct ttaagcttgt aaataaattt ttggcttttgt gtgctgactc
2341 tatcattatt ggtggagcta aacttaaagc cttgaattta ggtgaaacat ttgtcacgca
2401 ctcaaaggga ttgtacagaa agtgtgttaa atccagagaa gaaactggcc tactcatgcc
2461 tctaaaagcc ccaaaagaaa ttatcttctt agagggagaa acacttccca cagaagtgtt
2521 aacagagaa gttgtcttga aactggtga tttacaacaa ttagaacaac ctactcagtga
2581 agctgttgaa gctccattgg ttggtacacc agtttgtatt aacgggctta tgttgctcga
2641 aatcaaagac acagaaaagt actgtgccct tgcaccaat atgatggtaa caaacaatac
2701 cttcacactc aaaggcggtg caccaacaaa ggttactttt ggtgatgaca ctgtgataga
2761 agtgcaaggt tacaagagtg tgaatatcac ttttgaactt gatgaaaggt ttgataaagt
2821 acttaatgag aagtgctctg cctatacagt tgaactcggt acagaagtaa atgagttcgc
2881 ctgtgttgtg gcagatgctg tcataaaaac tttgcaacca gtatctgaat tacttacacc
2941 actgggcatt gatttagatg agtggagtat ggctacatac tactatttg atgagtctgg
3001 tgagtttaaa ttggcttcac atatgtattg ttctttctac cctccagatg aggatgaaga
3061 agaaggtgat tgtgaagaag aagagtttga gccatcaact caatatgagt atggtactga
3121 agatgattac caaggtaaac ctttggaatt tggtgccact tctgctgctc ttcaacctga
3181 agaagagcaa gaagaagatt ggttagatga tgatagtcaa caaactgttg tcaacaaga
3241 cggcagtgag gacaatcaga caactactat tcaaacaatt gttgaggttc aacctgacat
3301 tgatgatgaa cttacaccag ttgttcagac tattgaagtg aatagtttta gtggttattt
3361 aaaacttact gacaatgtat acattaaaaa tgcagacatt gtggaagaag ctaaaaaggt
3421 aaaaccaaca gtggttgtta atgcagccaa tgtttacctt aaacatggag gaggtgttgc
3481 aggagcctta aataaggcta ctaacaatgc catgcaagtt gaatctgatg attacatagc
3541 tactaatgga ccacttaaag tgggtggtag ttgtgtttta agcggacaca atcttgctaa
```

TABLE 2-continued

Sequences

| Sequence Description | SEQ ID NO. | Sequence |
|---|---|---|

```
3601 acactgtctt catgttgtcg gcccaaatgt taacaaaggt gaagacattc aacttcttaa
3661 gagtgcttat gaaaatttta atcagcacga agttctactt gcaccattat tatcagctgg
3721 tattttttggt gctgacccta tacattcttt aagagtttgt gtagatactg ttcgcacaaa
3781 tgtctactta gctgtctttg ataaaaatct ctatgacaaa cttgtttcaa gcttttttgga
3841 aatgaagagt gaaaagcaag ttgaacaaaa gatcgctgag attcctaaag aggaagttaa
3901 gccatttata actgaaaagta aaccttcagt tgaacagaga aaacaagatg ataagaaaat
3961 caaagcttgt gttgaagaag ttacaacaac tctggaagaa actaagttcc tcacagaaaa
4021 cttgttactt tatattgaca ttaatggcaa tcttcatcca gattctgcca ctcttgttag
4081 tgacattgac atcactttct taaagaaaga tgctccatat atagtggggtg atgttgttca
4141 agagggtgtt ttaactgctg tggttatacc tactaaaaag gctggtggca ctactgaaat
4201 gctagcgaaa gctttgagaa aagtgccaac agacaattat ataaccactt acccgggtca
4261 gggtttaaat ggttacactg tagaggaggc aaagacagtg cttaaaaagt gtaaaagtgc
4321 cttttacatt ctaccatcta ttatctctaa tgagaagcaa gaaattcttg gaactgtttc
4381 ttggaatttg cgagaaatgc ttgcacatgc agaagaaaca cgcaaattaa tgcctgtctg
4441 tgtggaaact aaagccatag tttcaactat acagcgtaaa tataagggta ttaaaataca
4501 agagggtgtg gttgattatg tgctagatt ttacttttac accagtaaaa caactgtagc
4561 gtcacttatc aacacactta acgatctaaa tgaaactctt gttacaatgc cacttggcta
4621 tgtaacacat ggcttaaatt tggaagaagc tgctcggtat atgagatctc tcaaagtgcc
4681 agctacagtt tctgtttctt cacctgatgc tgttacagcg tataatggtt atcttacttc
4741 ttcttctaaa acacctgaag aacattttat tgaaaccatc tcacttgctg gttcctataa
4801 agattggtcc tattctggac aatctacaca actaggtata gaatttctta agagaggtga
4861 taaaagtgta tattacacta gtaatcctac cacattccac ctagatggtg aagttatcac
4921 ctttgacaat cttaagcacg ttctttcttt gagagaagtg aggactatta aggtgtttac
4981 aacagtagac aacattaacc tccacacgca agttgtggac atgtcaatga catatggaca
5041 acagtttggt ccaacttatt tggatggagc tgatgttact aaaataaaac ctcataattc
5101 acatgaaggt aaaacatttt atgttttacc taatgatgac actctacgtg ttgaggcttt
5161 tgagtactac cacacaactg atcctagttt tctgggtagg tacatgtcag cattaaatca
5221 cactaaaaag tggaaatacc cacaagttaa tggtttaact tctattaaat gggcagataa
5281 caactgttat cttgccactg cattgttaac actccaacaa atagagttga agtttaatcc
5341 acctgctcta caagatgctt attacagagc aagggctggt gaagctgcta acttttgtgc
5401 acttatctta gcctactgta ataagacagt aggtgagtta ggtgatgtta gagaaacaat
5461 gagttacttg tttcaacatg ccaatttaga ttcttgcaaa agagtcttga acgtggtgtg
5521 taaaacttgt ggacaacagc agacaaccct taagggtgta gaagctgtta tgtacatggg
5581 cacactttct tatgaacaat ttaagaaagg tgttcagata ccttgtacgt gtggtaaaca
5641 agctacaaaa tatctagtac aacaggagtc acctttgtt atgatgtcag caccacctgc
5701 tcagtatgaa cttaagcatg gtacatttac ttgtgctagt gagtacactg gtaattacca
5761 gtgtggtcac tataaacata taacttctaa agaaactttg tattgcatag acggtgcttt
5821 acttacaaag tcctcagaat acaaaggtcc tattacggat gttttctaca agaaaacag
5881 ttacacaaca accataaaac cagttactta taaattggat ggtgttgttt gtacagaaat
5941 tgaccctaag ttggacaatt attataagaa agacaattct tatttcacag agcaaccaat
6001 tgatcttgta ccaaaccaac catatccaaa cgcaagcttc gataattta agtttgtatg
6061 tgataatatc aaatttgctg atgatttaaa ccagttaact ggttataaga aacctgcttc
6121 aagagagctt aaagttacat ttttccctga cttaaatggt gatgtggtgg ctattgatta
6181 taaacactac acaccctctt ttaagaaagg agctaaattg ttacataaac ctattgtttg
6241 gcatgttaac aatgcaacta ataaagccac gtataaacca aatacctggt gtatacgttg
6301 tctttggagc acaaaaccag ttgaaacatc aaattcgttt gatgtactga agtcagagga
6361 cgcgcaggga atggataatc ttgcctgcga agatctaaaa ccagtctctg aagaagtagt
6421 ggaaaatcct accatacaga aagacgttct tgagtgtaat gtgaaaacta ccgaagttgt
6481 aggagacatt atacttaaac cagcaaataa tagtttaaaa attacagaag aggttggcca
6541 cacagatcta atggctgctt atgtagacaa ttctgtctct actattaaga aacctaatga
6601 attatctaga gtattaggtt tgaaaaccct tgctactcat ggtttagctg ctgttaatag
6661 tgtcccttgg gatactatag ctaattatgc taagcttttt cttaacaaag ttgttagtac
6721 aactactaac atagttacac ggtgtttata ccgtgtttgt actaattata tgcctttattt
6781 ctttactta ttgctacaat tgtgtacttt tactagaagt acaaattcta gaattaaagc
6841 atctatgccg actactatag caaagaatac tgttaagagt gtcggtaaat tttgtctaga
6901 ggcttcattt aattatttga agtcacctaa ttttttctaaa ctgataaata ttataatttg
6961 gtttttacta ttaagtgttt gcctaggttc tttaatctac tcaaccgctg cttaggtgt
7021 tttaatgtct aatttaggca tgccttctta ctgtactgga acagagaag gctatttgaa
7081 ctctactaat gtcactattg caacctactg tactggttct ataccttgta gtgtttgtct
7141 tagtggttta gattcttag acacctatcc ttctttagaa actatacaaa ttaccatttc
7201 atcttttaaa tgggatttaa ctgcttttgg cttagttgca gagtggtttt tggcatatat
7261 tctttttcact aggttttttct atgtacttgg attggctgca atcatgcaat tgttttttcag
7321 ctatttttgca gtacatttta ttagtaattc ttggcttatg tggttaataa ttaatcttgt
7381 acaaatggcc ccgatttcag ctatggttag aatgtacatc ttctttgcat catttttatta
7441 tgtatggaaa agttatgtgc attgtgtaga cggttgtaat tcatcaactt gtatgatgtg
7501 ttacaaacgt aatagagcaa caagagtcga atgtacaact attgttaatg tgttagaag
7561 gtcctttat gtctatgcta atggaggtaa aggcttttgc aaactacaca attggaattg
7621 tgttaattgt gatacattct gtgctgtag tacatttatt agtgatgaag ttgcgagaga
7681 tttgtcacta cagttaaaaa gaccaataaa tcctactgac cagtcttctt acatcgttga
7741 tagtgttaca gtgaagaatg gttccatcca tctttacttt gataaagctg tcaaaagac
7801 ttatgaaaga cattctctct ctcattttgt taacttagac aacctgagag ctaataacac
7861 taaaggttca ttgcctatta atgttatagt ttttgatggt aaatcaaaat gtgaagaatc
7921 atctgcaaaa tcagcgtctg tttactacag tcagcttatg tgtcaaccta tactgttact
7981 agatcaggca ttagtgtctg atgttggtga tagtgcggaa gttgcagtta aaatgtttga
```

TABLE 2-continued

Sequences

| Sequence Description | SEQ ID NO. | Sequence |
|---|---|---|

```
 8041 tgcttacgtt aatacgtttt catcaacttt taacgtacca atggaaaaac tcaaaacact
 8101 agttgcaact gcagaagctg aacttgcaaa gaatgtgtcc ttagacaatg tcttatctac
 8161 ttttatttca gcagctcggc aagggtttgt tgattcagat gtagaaacta aagatgttgt
 8221 tgaatgtctt aaattgtcac atcaatctga catagaagtt actggcgata gttgtaataa
 8281 ctatatgctc acctataaca aagttgaaaa catgacaccc cgtgaccttg gtgcttgtat
 8341 tgactgtagt gcgcgtcata ttaatgcgca ggtagcaaaa agtcacaaca ttgctttgat
 8401 atggaacgtt aaagatttca tgtcattgtc tgaacaacta cgaaaacaaa tacgtagtgc
 8461 tgctaaaaag aataacttac cttttaagtt gacatgtgca actactagac aagttgttaa
 8521 tgttgtaaca acaaagatag cacttaaggg tggtaaaatt gttaataatt ggttgaagca
 8581 gttaattaaa gttacacttg tgttcctttt tgttgctgct attttctatt taataacacc
 8641 tgttcatgtc atgtctaaac atactgactt ttcaagtgaa atcataggat acaaggctat
 8701 tgatggtggt gtcactcgtg acatagcatc tacagatact tgttttgcta acaaacatgc
 8761 tgattttgac acatggttta gccagcgtgg tggtagttat actaatgaca aagcttgccc
 8821 attgattgct gcagtcataa caagagaagt gggttttgtc gtgcctggtt tgcctggcac
 8881 gatattacgc acaactaatg gtgacttttt gcatttctta cctagagttt ttagtgcagt
 8941 tggtaacatc tgttacacac catcaaaact tatagagtac actgactttg caacatcagc
 9001 ttgtgttttg gctgctgaat gtacaatttt taaagatgct tctggtaagc cagtaccata
 9061 ttgttatgat accaatgtac tagaaggttc tgttgcttat gaaagtttac gccctgacac
 9121 acgttatgtg ctcatggatg gctctattat tcaattttcct aacacctacc ttgaaggttc
 9181 tgttagagtg gtaacaactt ttgattctga gtactgtagg cacggcactt gtgaaagatc
 9241 agaagctggt gttttgtgtat ctactagtgg tagatgggta cttaacaatg attattacag
 9301 atctttacca ggagttttct gtggtagtaga tgctgtaaat ttacttacta atatgtttac
 9361 accactaatt caacctattg gtgctttgga catatcagca tctatagtag ctggtggtat
 9421 tgtagctatc gtagtaacat gccttgccta ctattttatg aggtttagaa gagcttttgg
 9481 tgaatacagt catgtagttg ccttaatac tttactattc cttatgtcat tcactgtact
 9541 ctgtttaaca ccagtttact cattcttacc tggtgtttat tctgttattt acttgtactt
 9601 gacattttat cttactaatg atgtttctt tttagcacat attcagtgga tggttatgtt
 9661 cacaccttta gtaccttct ggataacaat tgcttatatc atttgtattt ccacaaagca
 9721 tttctattgg ttcttttagta attacctaaa gagacgtgta gtctttaatg gtgtttcctt
 9781 tagtactttt gaagaagctg cgctgtgcac ctttttgtta aataaagaaa tgtatctaaa
 9841 gttgcgtagt gatgtgctat tacctcttac gcaatataat agatacttag ctctttataa
 9901 taagtacaag tattttagtg gagcaatgga tacaactagc tacagagaag ctgctttgttg
 9961 tcatctcgca aaggctctca atgacttcag taactcaggt tctgatgttc tttaccaacc
10021 accacaaacc tctatcacct cagctgtttt gcagagtggt tttagaaaaa tggcattccc
10081 atctggtaaa gttgagggtt gtatggtaca agtaacttgt ggtacaacta cacttaacgg
10141 tctttggctt gatgacgtag tttactgtcc aagacatgtg atctgcacct ctgaagacat
10201 gcttaaccct aattatgaag atttactcat tcgtaagtct aatcataatt tcttggtaca
10261 ggctggtaat gttcaactca gggttattgg acattctatg caaaattgtg tacttaagct
10321 taaggttgat acagccaatc ctaagacacc taagtataag tttgttcgca ttcaaccagg
10381 acagacttttt tcagtgttag cttgttacaa tggttcacca tctggtgttt accaatgtgc
10441 tatgaggccc aattctcacta ttaagggttc attccttaat ggttcatgtg gtagtgttgg
10501 tttaacata gattatgact gtgtctcttt ttgttacatg caccatatgg aattaccaac
10561 tggagttcat gctggcacag acttagaagg taacttttat ggacctttttg ttgacaggca
10621 aacagcacaa gcagctgtga cggacacaac tattacagtt aatgttttag cttggttgta
10681 cgctgctgtt ataaatggag acaggtggtt tctcaatcga tttaccacaa ctcttaatga
10741 ctttaacctt gtggctatga agtacaatta tgaacctcta acacaagacc atgttgacat
10801 actaggacct ctttctgctc aaactggaat tgccgtttta gatatgtgtg cttcattaaa
10861 agaattactg caaaatggta tgaatggaca taccatattg ggtagtgctt tattagaaga
10921 tgaatttaca ccttttgatg ttgttagaca atgctcaggt gttactttcc aaagtgcagt
10981 gaaaagaaca atcaagggta cacaccactg gttgttactc acaatttga cttcactttt
11041 agttttagtc cagagtactc aatggtctttt gttctttttt ttgtatgaaa atgcctttttt
11101 acctttgct atgggtatta ttgctatgtc tgcttttgca atgatgtttg tcaaacataa
11161 gcatgcattt ctctgttttgt ttttgttacc ttctcttgcc actgtagctt attttaatat
11221 ggtctatatg cctgctagtt gggtgatgcg tattatgaca tggttggata tggttgatac
11281 tagtttgtct ggtttttaagc taaaagactg tgttatgtat gcatcagctg tagtgttact
11341 aatccttatg acagcaagaa ctgtgtatga tgatggtgct aggagagtgt ggacacttat
11401 gaatgtcttg acactcgttt ataaagttta ttatggtaat gctttagatc aagccattttc
11461 catgtgggct cttataatct ctgttacttc taactactca ggtgtagtta caactgtcat
11521 gttttggcc agaggtattg ttttatgtg tgttgagtat tgccctattt tcttcataac
11581 tggtaataca cttcagtgta taatgctagt ttattgtttc ttaggctatt tttgtacttg
11641 ttacttggc ctcttttgtt tactcaaccg ctacttttga ctgactcttg gtgtttatga
11701 ttacttagtt tctacacagg agtttatagata tatgaattca cagggactac tcccacccaa
11761 gaatagcata gatgccttca aactcaacat taaattgttg ggtgttggtg gcaaaccttg
11821 tatcaaagta gccactgtac agtctaaaat gtcagatgta aagtgcacat cagtagtctt
11881 actctcagtt ttgcaacaac tcagagtaga atcatcatct aaattgtggg ctcaatgtgt
11941 ccagttacac aatgacattc tcttagctaa agatactact gaagcctttg aaaaaatggt
12001 ttcactactt tctgttttgc tttccatgca gggtgctgta gacataaaca agctttgtga
12061 agaaatgctg gacaacaggg caaccttaca agctatagcc tcagagttta gttcccttcc
12121 atcatatgca gcttttgtct ctgctcaaga agcttatgag caggctgttg ctaatggtga
12181 ttctgaagtt gttcttaaaa agttgaagaa gtcctttgaat gtggctaaat ctgaatttga
12241 ccgtgatgca gccatgcaac gtaagtggga aaagatggct gatcaagcta tgacccaaat
12301 gtataacag ctagatctg aggacaagag ggcaaagtt actagtgcta tgcagacaat
12361 gcttttcact atgcttagaa agttggataa tgatgcactc aacaacatta tcaacaatgc
12421 aagagatggt tgtgttccct tgaacataat acctctacca acagcagcca aactaatggt
```

TABLE 2-continued

Sequences

| Sequence Description | SEQ ID NO. | Sequence |
|---|---|---|

```
12481 tgtcatacca gactataaca catataaaaa tacgtgtgat ggtacaacat ttacttatgc
12541 atcagcattg tgggaaatcc aacaggttgt agatgcagat agtaaaattg ttcaacttag
12601 tgaaattagt atggacaatt cacctaattt agcatgcct cttattgtaa cagctttaag
12661 ggccaattct gctgtcaaat tacagaataa tgagcttagt cctgttgcac tacgacagat
12721 gtcttgtgct gccggtacta cacaaactgc ttgcactgat gacaatgcgt tagcttacta
12781 caacacaaca aagggaggta ggtttgtact tgcactgtta tccgatttac aggatttgaa
12841 atgggctaga ttccctaaga gtgatggaac tggtactatc tatacagaac tggaaccacc
12901 ttgtaggttt gttacagaca cacctaaagg tcctaaagtg aagtatttat actttattaa
12961 aggattaaac aacctaaata gaggtatggt acttggtagt ttagctgcca cagtacgtct
13021 acaagctggt aatgcaacag aagtgcctgc caattcaact gtattatctt tctgtgctt
13081 tgctgtagat gctgctaaag cttacaaaga ttatctgct agtgggggac aaccaatcac
13141 taattgtgtt aagatgttgt gtacacacac tggtactggt caggcaataa cagttacacc
13201 ggaagccaat atggatcaag aatcctttgg tggtgcatcg tgttgtctgt actgccgttg
13261 ccacatagat catccaaatc ctaaaggatt ttgtgactta aaaggtaagt atgtacaaat
13321 acctacaact tgtgctaatg accctgtggg ttttacactt aaaaacacag tctgtaccgt
13381 ctgcggtatg tggaaaggtt atggctgtag ttgtgatcaa ctccgcgaac ccatgcttca
13441 gtcagctgat gcacaatcgt ttttaaacgg gtttgcggtg taagtgcagc ccgtcttaca
13501 ccgtgcggca caggcactag tactgatgtc gtatacaggg cttttgacat ctacaatgat
13561 aaagtagctg gttttgctaa attcctaaaa actaattgtt gtcgcttcca agaaaaggac
13621 gaagatgaca atttaattga ttcttacttt gtagttaaga gacacactt ctctaactac
13681 caacatgaag aaacaattta aatttacttt aaggattgtc cagctgttgc taaacatgac
13741 ttctttaagt ttagaataga cggtgacatg gtaccacata tatcacgtca acgtcttact
13801 aaatacacaa tggcagacct cgtctatgct ttaaggcatt ttgatgaagg taattgtgac
13861 acattaaaag aaatacttgt cacatacaat tgttgtgatg atgattattt caataaaaag
13921 gactggtatg attttgtaga aaacccagat atattacgcg tatacgccaa cttaggtgaa
13981 cgtgtacgcc aagctttgtt aaaaacagta caattctgtg atgccatgcg aaatgctggt
14041 attgttggtg tactgacatt agataatcaa gatctcaatg gtaactggta tgatttcggt
14101 gatttcatac aaaccacgcc aggtagtgga gttcctgttg tagattccta ttattcattg
14161 ttaatgccta tattaacctt gaccagggct ttaactgcag agtcacatgt tgacactgac
14221 ttaacaaagc cttacattaa gtgggatttg ttaaaatatg acttcacgga agagaggtta
14281 aaactctttg accgttattt taaatattgg gatcagacat accacccaaa ttgtgttaac
14341 tgtttggatg acagatgcat tctgcattgt gcaaacttta atgttttatt ctctacagtg
14401 ttcccaccta caagttttgg accactagtg agaaaaatat ttgttgatgg tgttccattt
14461 gtagtttcaa ctggatacca cttcagagag ctaggtgttg tacataatca ggatgtaaac
14521 ttacatagct ctagacttag ttttaaggaa ttacttgtgt atgctgctga ccctgctatg
14581 cacgctgctt ctggtaatct attactagat aaacgcacta cgtgctttc agtagctgca
14641 cttactaaca atgttgcttt tcaaactgtc aaaccggta attttaacaa agacttctat
14701 gactttgctg tgtctaaggg tttctttaag gaaggaagtt ctgttgaatt aaaacacttc
14761 ttctttgctc aggatggtaa tgctgctatc agcgattatg actactatcg ttataatcta
14821 ccaacaatgt gtgatatcag acaactacta tttgtagttg aagttgttga taagtacttt
14881 gattgttacg atggtggctg tattaatgct aaccaagtca tcgtcaacaa cctagacaaa
14941 tcagctggtt ttccatttaa taaatggggt aaggctagac tttattatga ttcaatgagt
15001 tatgaggatc aagatgcact tttcgcatat acaaaacgta atgtcatccc tactataact
15061 caaatgaatc ttaagtatgc cattagtgca aagaatagag ctcgcaccgt agctgtgtc
15121 tctatctgta gtactatgac caatagacag tttcatcaaa aattattgaa atcaatagcc
15181 gccactagag gagctactgt agtaattgga acaagcaaat tctatggtgg ttggcacaac
15241 atgttaaaaa ctgtttatag tgatgtagaa aaccctcacc ttatgggttg ggattatcct
15301 aaatgtgata gagccatgcc taacatgctt agaattatgg cctcacttgt tcttgctcgc
15361 aaacatacaa cgtgttgtag cttgtcacac cgtttctata gattagctaa tgagtgtgct
15421 caagtattga gtgaaatggt catgtgtggc ggtcactat atgttaaacc aggtggaacc
15481 tcatcaggag atgccacaac tgcttatgct aatagtgttt taacatttg tcaagctgtc
15541 acggccaatg ttaatgcact tttatctact gatggtaaca aaattgccga taagtatgtc
15601 cgcaatttac aacacagact ttatgagtgt ctctataga atagagatgt tgacacagac
15661 tttgtgaatg agttttacgc atatttgcgt aaacatttct caatgatgat actctctgac
15721 gatgctgttg tgtgtttcaa tagcacttat gcatctcaag gtctagtggc tagcataaag
15781 aactttaagt cagttcttta ttatcaaaac aatgttttta tgtctgaagc aaaatgttgg
15841 actgagactg accttactaa aggacctcat gaattttgct ctcaactac aatgctagtt
15901 aaacagggtg atgattatgt gtaccttcct tacccagatc catcaagaat cctaggggcc
15961 ggctgttttg tagatgatat cgtaaaaaca gatggtacac ttatgattga acgttcgtg
16021 tctttagcta tagatgctta cccacttact aaacatccta atcaggagta tgctgatgtc
16081 tttcatttgt acttacaata cataagaaag ctacatgtta gttaacgag acacatgtta
16141 gacatgtatt ctgttatgct tactaatgat aacacttcaa ggtattggga acctgagttt
16201 tatgaggcta tgtacacacc gcatacagtc ttacaggctg ttggggcttg tgttctttgc
16261 aattcacaga cttcattaag atgtggtgct tgcatacgta gaccattctt atgttgtaaa
16321 tgctgttacg accatgtcat atcaacatca cataaattag tcttgtctgt taatccgtat
16381 gtttgcaatg ctccaggttg tgatgtcaca gatgtgactc aactttactt aggaggtatg
16441 agctattatt gtaaatcaca taaaccaccc attagttttc cattgtgtgc taatggacaa
16501 gttttggt tatataaaaa tacatgtgtt ggtagcgata atgttactga ctttaatgca
16561 attgcaacat gtgactggac aaatgctggt gattacatcc tagctaacac ctgtactgaa
16621 agactcaagc ttttttgcagc agaaacgctc aaagctactg aggagacatt taaactgtct
16681 tatggtattg ctactgtacg tgaagtgctg tctgcagag aattacatct ttcatgggaa
16741 gttggtaaac ctagaccacc acttaaccga aattatgtct ttactggtta tcgtgtaact
16801 aaaaacagta aagtacaaat aggagagtac acctttgaaa aagtgactab tggtgatgct
16861 gttgtttacc gaggtacaac aacttacaaa ttaaatgttg gtgattattt tgtgctgaca
```

TABLE 2-continued

Sequences

| Sequence Description | SEQ ID NO. | Sequence |
|---|---|---|

```
16921 tcacatacag taatgccatt aagtgcacct acactagtgc cacaagagca ctatgttaga
16981 attactggct tatacccaac actcaatatc tcagatgagt tttctagcaa tgttgcaaat
17041 tatcaaaagg ttggtatgca aaagtattct acactccagg gaccacctgg tactggtaag
17101 agtcattttg ctattggcct agctctctac tacccttctg ctcgcatagt gtatacagct
17161 tgctctcatg ccgctgttga tgcactatgt gagaaggcat taaaatattt gcctatagat
17221 aaatgtagta gaattatacc tgcacgtgct cgtgtagagt gttttgataa attcaaagtg
17281 aattcaacat tagaacagta tgtcttttgt actgtaaatg cattgcctga gacgacagca
17341 gatatagttg tctttgatga aatttcaatg gccacaaatt atgatttgag tgttgtcaat
17401 gccagattac gtgctaagca ctatgtgtac attggcgacc ctgctcaatt acctgcacca
17461 cgcacattgc taactaaggg cacactagaa ccagaatatt tcaattcagt gtgtagactt
17521 atgaaaacta taggtccaga catgttcctc ggaacttgtc ggcgttgtcc tgctgaaatt
17581 gttgacactg tgagtgcttt ggtttatgat aataagctta aagcacataa agacaaatca
17641 gctcaatgct ttaaaatgtt ttataagggt gttatcacgc atgatgtttc atctgcaatt
17701 aacaggccac aaataggcgt ggtaagagaa ttccttacac gtaaccctgc ttggagaaaa
17761 gctgtctttta tttcaccttaa taattcacag aatgctgtag cctcaaagat tttgggacta
17821 ccaactcaaa ctgttgattc atcacagggc tcagaatatg actatgtcat attcactcaa
17881 accactgaaa cagctcactc ttgtaatgta aacagattta atgttgtcat taccagagca
17941 aaagtaggca tactttgcat aatgtctgat agagaccttt atgacaagtt gcaatttaca
18001 agtcttgaaa ttccacgtag aatgtggca actttacaag ctgaaaatgt aacaggactc
18061 tttaaagatt gtagtaaggt aatcactggg ttacatccta cacaggcacc tacacacctc
18121 agtgttgaca ctaaattcaa aactgaaggt ttatgtgttg acatacctgg catacctaag
18181 gacatgacct atagaagact catctctatg atgggtttta aaatgaatta tcaagttaat
18241 ggttacccta acatgtttat cacccgcgaa gaagctataa gacatgtacg tgcatggatt
18301 ggcttcgatg tcgagggtg tcatgctact agagaagctg ttggtaccaa tttaccttta
18361 cagctaggtt tttctacagg tgttaaccta gttgctgtac ctacaggtta tgttgataca
18421 cctaataata cagatttttc cagagttagt gctaaaccac cgcctggaga tcaatttaaa
18481 caccctcatac cacttatgta caaaggactt ccttggaatg tagtgcgtat aaagattgta
18541 caaatgttaa gtgacacact taaaaatctc tctgacagag tcgtatttgt cttatgggca
18601 catggctttg agttgacatc tatgaagtat tttgtgaaaa taggacctga gcgcacctgt
18661 tgtctatgtg atagacgtgc cacatgcttt tccactgctt cagacactta tgcctgttgg
18721 catcattcta ttggatttga ttacgtctat aatccgttta tgattgatgt tcaacaatgg
18781 ggttttacag gtaacctaca aagcaaccat gatctgtatt gtcaagtcca tggtaatgca
18841 catgtagcta gttgtgatgc aatcatgact aggtgtcag ctgtccacga gtgctttgtt
18901 aagcgtgttg actggactat tgaatatcct ataattggtg atgaactgaa gattaatgcg
18961 gcttgtagaa aggttcaaca catggttgtt aaagctgcat tattagcaga caaattccca
19021 gttcttcacg acattggtaa ccctaaagct attaagtgta tacctcaagc tgatgtagaa
19081 tggaagttct atgatgcaca gccttgtagt gacaaagctt ataaaataga agaattattc
19141 tattcttatg ccacacattc tgacaaattc acagatggtg tatgcctatt ttggaattgc
19201 aatgtcgata gatatcctgc taattccatt gtttgtagat ttgacactag agtgctatct
19261 aaccttaact tgcctggttg tgatggtggc agtttgtatg taaataaaca tgcattccac
19321 acaccagctt ttgataaaag tgctttttgtt aatttaaaac aattaccatt tttctattac
19381 tctgacagtc catgtgagtc tcatggaaaa caagtagtgt cagatataga ttatgtacca
19441 ctaaagtctg ctacgtgtat aacacgttgc aatttaggtg gtgctgtctg tagacatcat
19501 gctaatgagt acagattgta tctcgatgct tataacatga tgatctcagc tggctttagc
19561 ttgtgggttt acaaacaatt tgatacttat aacctctgga acacttttac aagacttcag
19621 agtttagaaa atgtggcttt taatgttgta aataagggac acttttgatgg acaacagggt
19681 gaagtaccag tttctatcat taataacact gtttacacaa aagttgatgg tgttgatgta
19741 gaattgtttg aaaataaaac aacattacct gttaatgtag catttgagct ttgggctaag
19801 cgcaacatta accagtacc agaggtgaaa atactcaata atttgggtgt ggacattgct
19861 gctaatactg tgatctggga ctacaaaaga gatgctccag cacatatatc tactattggt
19921 gtttgttcta tgactgacat agccaagaaa ccaactgaaa cgatttgtgc accactcact
19981 gtctttttttg atggtagagt tgatggtcaa gtagacttat ttagaaatgc ccgtaatggt
20041 gttcttatta cagaaggtag tgttaaaggt ttacaaccat ctgtaggtcc caaacaagct
20101 agtcttaatg gagtcacatt aattggagaa gccgtaaaaa cacagttcaa ttattataag
20161 aaagttgatg gtgttgtcca acaattacct gaaacttact ttactcagag tagaaattta
20221 caagaattta aacccaggag tcaaatggaa attgatttct tagaattagc tatggatgaa
20281 ttcattgaac ggtataaatt agaaggctat gccttcgaac atatcgttta tggagatttt
20341 agtcatagtc agttaggtgg tttacatcta ctgattggac tagctaaacg ttttaaggaa
20401 tcacctttg aattagaaga tttttattcct atggacagta cagttaaaaaa ctatttcata
20461 acagatgcgc aaacaggttc atctaagtgt gtgtgttctg ttattgattt attacttgat
20521 gattttgttg aaataataaaa atcccaagat ttatctgtag tttctaaagt tgtcaaagtg
20581 actattgact atacagaaat ttcatttatg ctttggtgta aagatggcca tgtagaaaca
20641 ttttacccaa aattacaatc tagtcaagcg tggcaaccgg tgttgctat gcctaatctt
20701 tacaaaatgc aaagaatgct attagaaaag tgtgaccttc aaaattatgg tgatagtgca
20761 acattaccta aaggcataat gatgaatgtc gcaaaatata ctcaactgtg tcaatatttta
20821 aacacattaa cattagctgt accctataat atgagagtta tacattttg tgctggtctt
20881 gataaaggag ttgcaccagg tacagctgtt ttaagacagt ggttgcctac gggtacgctg
20941 cttgtcgatt cagatcttaa tgactttgtc tctgatgcag attcaacttt gattggtgat
21001 tgtgcaactg tacatacgga taataatgg tcagtgatac tacgaccct
21061 aagactaaaa atgttacaaa agaaaatgg tctaaagagg gtttttcac ttacatttgt
21121 gggtttatac aacaaaagct agctcttgga ggttccgtgg ctataaagat aacagaacat
21181 tcttgaatg ctgatcttta taagctcatg ggacacttcg catggtggac agcctttgtt
21241 actaatgtga atgcgtcatc atctgaagca ttttaattg gatgtaatta tcttggcaaa
21301 ccacgcgaac aaatagatgg ttatgtcatg catgcaaatt acatattttg gaggaataca
```

TABLE 2-continued

Sequences

| Sequence Description | SEQ ID NO. | Sequence |
|---|---|---|

```
21361 aatccaattc agttgtcttc ctattctttta tttgacatga gtaaatttcc ccttaaatta
21421 aggggtactg ctgttatgtc tttaaaagaa ggtcaaatca atgatatgat tttatctctt
21481 cttagtaaag gtagacttat aattagagaa aacaacagag ttgttatttc tagtgatgtt
21541 cttgttaaca actaaacgaa caatgtttgt ttttcttgtt ttattgccac tagtctctag
21601 tcagtgtgtt aatcttacaa ccagaactca attacccct gcatacacta attctttcac
21661 acgtggtgtt tattaccctg acaaagtttt cagatcctca gttttacatt caactcagga
21721 cttgttctta cctttcttt ccaatgttac ttggttccat gctatacatg tctctgggac
21781 caatggtact aagaggtttg ataaccctgt cctaccattt aatgatggtg tttattttgc
21841 ttccactgag aagtctaaca taataagagg ctggatttt ggtactactt tagattcgaa
21901 gacccagtcc ctacttattg ttaataacgc tactaatgtt gttattaaag tctgtgaatt
21961 tcaattttgt aatgatccat ttttgggtgt ttattaccac aaaaacaaca aaagttggat
22021 ggaaagtgag ttcagagttt attctagtgc gaataattgc acttttgaat atgtctctca
22081 gccttttctt atggaccttg aaggaaaaca gggtaatttc aaaaatctta gggaatttgt
22141 gtttaagaat attgatggtt attttaaaat atattctaag cacacgccta ttaatttagt
22201 gcgtgatctc cctcagggtt tttcggcttt agaaccattg gtagatttgc caataggtat
22261 taacatcact aggtttcaaa ctttacttgc tttacataga agttatttga ctcctggtga
22321 ttcttcttca ggttggacag ctggtgctgc agcttattat gtgggttatc ttcaacctag
22381 gacttttcta ttaaaatata atgaaaatgg aaccattaca gatgctgtag actgtgcact
22441 tgaccctctc tcagaaacaa agtgtacgtt gaaatccttc actgtagaaa aaggaatcta
22501 tcaaacttct aactttagg tccaaccaac agaatctatt gttagatttc ctaatattac
22561 aaacttgtgc ccttttggtg aagtttttaa cgccaccaga tttgcatctg tttatgcttg
22621 gaacaggaag agaatcagca actgtgttgc tgattattct gtcctatata attccgcatc
22681 attttccact tttaagtgtt atggagtgtc tcctactaaa ttaaatgatc tctgctttac
22741 taatgtctat gcagattcat ttgtaattag aggtgatgaa gtcagacaaa tcgctccagg
22801 gcaaactgga aagattgctg attataatta taaattacca gatgattta caggctgcgt
22861 tatagcttgg aattctaaca atcttgattc taaggttggt ggtaattata attacctgta
22921 tagattgttt aggaagtcta atctcaaacc ttttgagaga gatatttcaa ctgaaatcta
22981 tcaggccggt agcacacctt gtaatggtgt tgaaggtttt aattgttact ttccttaca
23041 atcatatggt ttccaaccca ctaatggtgt tggttaccaa ccatacagag tagtagtact
23101 ttcttttgaa cttctacatg caccagcaac tgtttgtgga cctaaaaagt ctactaattt
23161 ggttaaaaac aaatgtgtca atttcaactt caatggttta acaggcacag gtgttcttac
23221 tgagtctaac aaaaagttc tgccttttcca acaatttgga agagacattg ctgacactac
23281 tgatgctgtc cgtgatccac agacacttga gattcttgac attacaccat gttcttttgg
23341 tggtgtcagt gttataacac caggaacaaa tacttctaac caggttgctg ttctttatca
23401 ggatgttaac tgcacagaag tccctgttgc tattcatgca gatcaactta ctcctacttg
23461 gcgtgtttat tctacaggtt ctaatgtttt tcaaacacgt gcaggctgtt taataggggc
23521 tgaacatgtc aacaactcat atgagtgtga catacccatt ggtgcaggta tatgcgctag
23581 ttatcagact cagactaatt ctcctcggcg ggcacgtagt gtagctagtc aatccatcat
23641 tgcctacact atgtcacttg gtgcagaaaa ttcagttgct tactctaata actctattgc
23701 catacccaca aattttacta ttagtgttac cacagaaatt ctaccagtgt ctatgaccaa
23761 gacatcagta gattgtacaa tgtacatttg tggtgattca actgaatgca gcaatccttt
23821 gttgcaatat ggcagttttt gtacacaatt aaaccgtgct ttaactggaa tagctgttga
23881 acaagacaaa aacacccaag aagtttttgc acaagtcaaa caaattaca aaacaccacc
23941 aattaaagat tttggtggtt ttaattttc acaaatatta ccagatccat caaaaccaag
24001 caagaggtca tttattgaag atctactttt caacaaagtg acacttgcag atgctggctt
24061 catcaaacaa tatggtgatt gccttggtga tattgctgct agagacctca tttgtgcaca
24121 aaagtttaac ggccttactg tttttgccacc tttgctcaca gatgaaatga ttgctcaata
24181 cacttctgca ctgttagcgg gtacaatcac ttctggttgg acctttggtg caggtgctgc
24241 attacaaata ccatttgcta tgcaaatggc ttataggttt aatggtattg gagttacaca
24301 gaatgttctc tatgagaacc aaaaattgat tgccaaccaa tttaatagtg ctattggcaa
24361 aattcaagac tcactttctt ccacagcaag tgcacttgga aaacttcaag atgtggtcaa
24421 ccaaaatgca caagcttaa acacgcttgt taaacaactt agctccaatt ttggtgcaat
24481 ttcaagtgtt ttaaatgata tccttctcacg tcttgacaaa gttgaggctg aagtgcaaat
24541 tgataggttg atcacaggca gacttcaaag tttgcagaca tatgtgactc aacaattaat
24601 tagagctgca gaaatcagag cttctgctaa tcttgctgct actaaaatgt cagagtgtgt
24661 acttggacaa tcaaaaagag ttgatttttg tggaaagggc tatcatctta tgtccttccc
24721 tcagtcagca cctcatggtg tagtcttctt gcatgtgact tatgtccctg cacaagaaaa
24781 gaacttcaca actgctcctg ccatttgtca tgatggaaaa gcacactttc ctcgtgaagg
24841 tgtcttttgtt tcaaatggca cacactggtt tgtaacacaa aggaattttt atgaaccaca
24901 aatcattact acagacaaca catttgtgtc tggtaactgt gatgttgtaa taggaattgt
24961 caacaacaca gtttatgatc ctttgcaacc tgaattagat tcattcaagg aggagttaga
25021 taaatatttt aagaatcata catcaccaga tgttgattta ggtgacatct ctggcattaa
25081 tgcttcagtt gtaaacattc aaaaagaaat tgaccgcctc aatgaggttg ccaagaattt
25141 aaatgaatct ctcatcgatc tccaagaact tggaaagtat gagcagtata taaaatggcc
25201 atggtacatt tggctaggtt ttatagctgg cttgattgcc atagtaatgg tgacaattat
25261 gctttgctgt atgaccagtt gctgtagttg tctcaagggc tgttgttctt gtggatcctg
25321 ctgcaaattt gatgaagacg actctgagcc agtgctcaaa ggagtcaaat tacattacac
25381 ataaacgaac ttatggattt gtttatgaga atcttcacaa ttggaactgt aactttgaag
25441 caaggtgaaa tcaaggatgc tactccttca gattttgttc gcgctactgc aacaataccg
25501 atacaagcct cactcccttt cggatggctt attgttggcg ttgcacttct gctgtttttt
25561 cagagcgctt ccaaaatcat aaccctcaaa aagagatggc aactagcact ctccaagggt
25621 gttcactttg tttgcaactt gctgttgttg tttgtaacag tttactcaca ccttttgctc
25681 gttgctgctg gccttgaagc ccctttttctc tatcttatg ctttagtcta cttcttgcag
25741 agtataaact tgtaagaat aataatgagg ctttggcttt gctggaaatg ccgttccaaa
```

TABLE 2-continued

Sequences

| Sequence Description | SEQ ID NO. | Sequence |
|---|---|---|
| | | 25801 aacccattac tttatgatgc caactatttt ctttgctggc atactaattg ttacgactat |
| | | 25861 tgtataccttt acaatagtgt aacttcttca attgtcatta cttcaggtga tggcacaaca |
| | | 25921 agtcctatttt ctgaacatga ctaccagatt ggtggttata ctgaaaaatg ggaatctgga |
| | | 25981 gtaaaagact gtgttgtatt acacagttac ttcacttcag actattacca gctgtactca |
| | | 26041 actcaattga gtacagacac tggtgttgaa catgttacct tcttcatcta caataaaatt |
| | | 26101 gttgatgagc tgaagaaca tgtccaaatt cacacaatcg acggttcatc cggagttgtt |
| | | 26161 aatccagtaa tggaaccaat ttatgatgaa ccgacgacga ctactagcgt gccttttgtaa |
| | | 26221 gcacaagctg atgagtacga acttatgtac tcattcgttt cggaagagac aggtacgtta |
| | | 26281 atagttaata gcgtacttct ttttcttgct ttcgtggtat tcttgctagt tacactagcc |
| | | 26341 atccttactg cgcttcgatt gtgtgcgtac tgctgcaata ttgttaacgt gagtcttgta |
| | | 26401 aaaccttctt tttacgttta ctctcgtgtt aaaaatctga attcttctag agttcctgat |
| | | 26461 cttctggtct aaacgaacta aatattatat tagttttct gtttggaact ttaattttag |
| | | 26521 ccatggcaga ttccaacggt actattaccg ttgaagagct taaaaagctc cttgaacaat |
| | | 26581 ggaacctagt aataggtttc ctattcctta catggatttg tcttctacaa tttgcctatg |
| | | 26641 ccaacaggaa taggttttg tatataatta agttaatttt cctctggctg ttatggccag |
| | | 26701 taactttagc ttgttttgtg cttgctgctg tttacagaat aaattggatc accggtggaa |
| | | 26761 ttgctatcgc aatgcttgt cttgtaggct tgatgtggct cagctacttc attgcttett |
| | | 26821 tcagactgtt tgcgcgtacg cgttccatgt ggtcattcaa tccagaaact aacattcttc |
| | | 26881 tcaacgtgcc actccatggc actattctga ccagaccgct tctagaaagt gaactcgtaa |
| | | 26941 tcggagctgt gatccttcgt ggacatcttc gtattgctgg acaccatcta ggacgctgtg |
| | | 27001 acatcaagga cctgcctaaa gaaatcactg ttgctacatc acgaacgctt tcttattaca |
| | | 27061 aattgggagc ttcgcagcgt gtagcaggtg actcaggttt tgctgcatac agtcgctaca |
| | | 27121 ggattggcaa ctataaatta aacacagacc attccagtag cagtgacaat attgctttgc |
| | | 27181 ttgtacagta agtgacaaca gatgtttcat ctcgttgact ttcaggttac tatagcagag |
| | | 27241 atattactaa ttattatgag gactttttaaa gttccatttt ggaatcttga ttacatcata |
| | | 27301 aacctcataa ttaaaaattt atctaagtca ctaactgaga ataaatattc tcaattagat |
| | | 27361 gaagagcaac caatggagat tgattaaacg aacatgaaaa ttattctttt cttggcactg |
| | | 27421 ataacactcg ctacttgtga gcttatcac taccaagagt gtgttagagg tacaacagta |
| | | 27481 cttttaaaag aaccttgctc ttctgaaca tacgagggca attcaccatt tcatcctcta |
| | | 27541 gctgataaca aatttgcact gacttgcttt agcactcaat ttgctttgc ttgtcctgac |
| | | 27601 ggcgtaaaac acgtctatca gttacgtgcc agatcagttt cacctaaaact gttcatcaga |
| | | 27661 caagaggaag ttcaagaact ttactctcca attttctta ttgttgcggc aatagtgttt |
| | | 27721 ataacactttt gcttcacact caaaagaaag acagaatgat tgaactttca ttaattgact |
| | | 27781 tctatttgtg cttttagcc tttctgctat tccttgtttt aattatgctt attatcttttt |
| | | 27841 ggttctcact tgaactgcaa gatcataatg aaacttgtca cgcctaaacg aacatgaaat |
| | | 27901 ttcttgtttt cttaggaatc atcaaactg tcaccaagaa tgtagtttac |
| | | 27961 agtcatgtac tcaacatcaa ccatatgtag ttgatgaccc gtgtcctatt cacttctatt |
| | | 28021 ctaaatggta tattagagta ggagctagaa aatcagcacc tttaattgaa ttgtgcgtgg |
| | | 28081 atgaggctgg ttctaaatca cccattcagt acatcgatat cggtaattat acagtttcct |
| | | 28141 gtttaccttt tacaattaat tgccaggaac ctaaattggg tagtcttgta gtgcgttgtt |
| | | 28201 cgttctatga agactttta gagtatcatg acgttcgtgt tgttttagat ttcatctaaa |
| | | 28261 cgaacaaact aaaatgtctg ataatggacc ccaaaatcag cgaaatgcac cccgcattac |
| | | 28321 gtttggtgga ccctcagatt caactggcag taaccagaat ggagaacgca gtggggcgcg |
| | | 28381 atcaaaacaa cgtcggcccc aaggtttacc caataatact gcgtcttgtt tcaccgctct |
| | | 28441 cactcaacat ggcaaggaag accttaaatt ccctcgagga caaggcgttc caattaacac |
| | | 28501 caatagcagt ccagatgacc aaattggcta ctaccgaaga gctaccagac gaattcgtgg |
| | | 28561 tggtgacggt aaaatgaaag atctcagtcc aagatggtat ttctactacc taggaactgg |
| | | 28621 gccagaagct ggacttccct atggtgctaa caaagacgc atcatatggt ttgcaactga |
| | | 28681 gggagccttg aatacaccaa aagatcacat tggcaccgc aatcctgcta acaatgctgca |
| | | 28741 aatcgtgcta caacttcctc aaggaacaac attgccaaaa ggcttctacg cagaagggag |
| | | 28801 cagaggcggc agtcaagcct cttctcgttc ctcatcacgt agtcgcaaca gttcaagaaa |
| | | 28861 ttcaactcca ggcagcagta ggggaacttc tcctgctaga atggctggca atggcggtga |
| | | 28921 tgctgctctt gctttgctgc tgcttgacag attgaaccag cttgagagca aaatgtctgg |
| | | 28981 taaaggccaa caacaacaag gccaaactgt cactaagaaa tctgctgctg aggcttctaa |
| | | 29041 gaagcctcgg caaaaacgta ctgccactaa agcatacaat gtaacacaag ctttcggcag |
| | | 29101 acgtggtcca gaacaaaccc aaggaaattt tggggaccag gaactaatca gacaaggaac |
| | | 29161 tgattacaaa cattggccgc aaattgcaca aatttgcccc cagcgcttcag cgttcttcgg |
| | | 29221 aatgtcgcgc attggcatgg aagtcacacc ttcgggaacg tggttgacct acacaggtgt |
| | | 29281 catcaaattg gatgacaaag atccaaattt caaagatcaa gtcatttgc tgaataagca |
| | | 29341 tattgacgca tacaaaacat tcccaccaac agagcctaaa aaggacaaaa agaagaaggc |
| | | 29401 tgatgaaact caagcctac cgcagagaca gaagaaacag caaactgtga ctcttcttcc |
| | | 29461 tgctgcagat ttggatgatt ctccaaaca attgcaacaa tccatgagca gtgctgactc |
| | | 29521 aactcaggcc taaactcatg cagaccacac aaggcagatg ggctatataa acgttttcgc |
| | | 29581 ttttccgttt acgatatata gtctactctt gtgcagaatg aattctcgta actacatagc |
| | | 29641 acaagtagat gtagttaact ttaatctcac atagcaatct ttaatcagtg tgtaacatta |
| | | 29701 gggaggactt gaaagagcca ccacatttc accgaggcca cgcggagtac gatcgagtgt |
| | | 29761 acagtgaaca atgctaggga gagctgccta tatggaagag ccctaatgtg taaaattaat |
| | | 29821 tttagtagtg ctatccccat gtgattttaa tagcttctta ggagaatgac aaaaaaaaaa |
| | | 29881 aaaaaaaaaa aaaaaaaaaa aaa |
| Wuhan seafood market pneumonia | 164 | MESLVPGFNEKTHVQLSLPVLQVRDVLVRGF GDSVEEVLSEARQHLKDGTCGLVEVEKGVLP QLEQPYVFIKRSDARTAPHGHVMVELVAELE GIQYGRSGETLGVLVPHVGEIPVAYRKVLLR |

TABLE 2-continued

Sequences

| Sequence Description | SEQ ID NO. | Sequence |
|---|---|---|
| virus isolate Wuhan-Hu-1 genomic sequence (GenBank: MN 908947.3; Jan. 23, 2020) - amino acid translation | | KNGNKGAGGHSYGADLKSFDLGDELGTDPY EDFQENWNTKHSSGVTRELMRELNGGAYTR YVDNNFCGPDGYPLECIKDLLARAGKASCTL SEQLDFIDTKRGVYCCREHEHEIAWYTERSEK SYELQTPFEIKLAKKFDTFNGECPNFVFPLNSII KTIQPRVEKKKLDGFMGRIRSVYPVASPNECN QMCLSTLMKCDHCGETSWQTGDFVKATCEF CGTENLTKEGATTCGYLPQNAVVKIYCPACH NSEVGPEHSLAEYHNESGLKTILRKGGRTIAF GGCVFSYVGCHNKCAYWVPRASANIGCNHT GVVGEGSEGLNDNLLEILQKEKVNINIVGDFK LNEEIAIILASFSASTSAFVETVKGLDYKAFKQ IVESCGNFKVTKGKAKKGAWNIGEQKSILSPL YAFASEAARVVRSIFSRTLETAQNSVRVLQKA AITILDGISQYSLRLIDAMMFTSDLATNNLVV MAYITGGVVQLTSQWLTNIFGTVYEKLKPVL DWLEEKFKEGVEFLRDGWEIVKFISTCACEIV GGQIVTCAKEIKESVQTFFKLVNKFLALCADS IIIGGAKLKALNLGETFVTHSKGLYRKCVKSR EETGLLMPLKAPKEIIFLEGETLPTEVLTEEVV LKTGDLQPLEQPTSEAVEAPLVGTPVCINGLM LLEIKDTEKYCALAPNMMVTNNTFTLKGGAP TKVTFGDDTVIEVQGYKSVNITFELDERIDKV LNEKCSAYTVELGTEVNEFACVVADAVIKTL QPVSELLTPLGIDLDEWSMATYYLFDESGEFK LASHMYCSFYPPDEDEEEGDCEEEEFEPSTQY EYGTEDDYQGKPLEFGATSAALQPEEEQEED WLDDDSQQTVGQQDGSEDNQTTTIQTIVEVQ PQLEMELTPVVQTIEVNSFSGYLKLTDNVYIK NADIVEEAKKVKPTVVVNAANVYLKHGGGV AGALNKATNNAMQVESDDYIATNGPLKVGG SCVLSGHNLAKHCLHVVGPNVNKGEDIQLLK SAYENFNQHEVLLAPLLSAGIFGADPIHSLRV CVDTVRTNVYLAVFDKNLYDKLVSSFLEMKS EKQVEQKIAEIPKEEVKPFITESKPSVEQRKQD DKKIKACVEEVTTTLEETKFLTENLLLYIDING NLHPDSATLVSDIDITFLKKDAPYIVGDVVQE GVLTAVVIPTKKAGGTTEMLAKALRKVPTDN YITTYPGQGLNGYTVEEAKTVLKKCKSAFYIL PSIISNEKQEILGTVSWNLREMLAHAEEETRKL MPVCVETKAIVSTIQRKYKGIKIQEGVVDYGA RFYFYTSKTTVASLINTLNDLNETLVTMPLGY VTHGLNEEAARYMRSLKVPATVSVSSPDAV TAYNGYLTSSSKTPEEHFIETISLAGSYKDWS YSGQSTQLGIEFLKRGDKSVYYTSNPTTFHLD GEVITFDNLKTLLSLREVRTIKVFTTVDNINLH TQVVDMSMTYGQQFGPTYLDGADVTKIKPH NSHEGKTFYVLPNDDTLRVEAFEYYHTTDPS FLGRYMSALNHTKKWKYPQVNGLTSIKWAD NNCYLATALLTLQQIELKFNPPALQDAYYRA RAGEAANFCALILAYCNKTVGELGDVRETMS YLFQHANLDSCKRVLNVVCKTCGQQQTTLK GVEAVMYGTLSYEQFKKGVQIPCTCGKQA TKYLVQQESPFVMMSAPPAQYELKHGTFTCA SEYTGNYQCGHYKHITSKETLYCIDGALLTKS SEYKGPITDVFYKENSYTTTIKPVTYKLDGVV CTEIDPKLDNYYKKDNSYFTEQPIDLVPNQPY PNASFDNFKFVCDNIKFADDLNQLTGYKKPA SRELKVTFFPDLNGDVVAIDYKHYTPSFKKG AKLLHKPIVWHVNNATNKATYKPNTWCIRC LWSTKPVETSNSFDVLKSEDAQGMDNLACED LKPVSEEVVENPTIQKDVLECNVKTTEVVGDI ILKPANNSLKITEEVGHTDLMAAYVDNSSLTI KKPNELSRVLGLKTLATHGLAAVNSVPWDTI ANYAKPFLNKVVSTTTNIVTRCLNRVCTNYM PYFFTLLLQLCTFTRSTNSRIKASMPTTIAKNT VKSVGKFCLEASFNYLKSPNFSKLINIIIWFLL LSVCLGSLIYSTAALGVLMSNLGMPSYCTGY REGYLNSTNVTIATYCTGSIPCSVCLSGLDSLD TYPSLETIQITISSFKWDLTAFGLVAEWFLAYI LFTRFFYVLGLAAIMQLFFSYFAVHFISNSWL MWLIINLVQMAPISAMVRMYIFFASFYYVWK SYVHVVDGCNSSTCMMCYKRNRATRVECTT IVNGVRRSFYVYANGGKGFCKLHNWNCVNC |

TABLE 2-continued

Sequences

| Sequence Description | SEQ ID NO. | Sequence |
|---|---|---|
| | | DTFCAGSTFISDEVARDLSLQFKRPINPTDQSS |
| | | YIVDSVTVKNGSIHLYFDKAGQKTYERHSLS |
| | | HFVNLDNLRANNTKGSLPINVIVFDGKSKCEE |
| | | SSAKSASVYYSQLMCQPILLLDQALVSDVGD |
| | | SAEVAVKMFDAYVNTFSSTFNVPMEKLKTLV |
| | | ATAEAELAKNVSLDNVLSTFISAARQGFVDS |
| | | DVETKDVVECLKLSHQSDIEVTGDSCNNYML |
| | | TYNKVENMTPRDLGACIDCSARHINAQVAKS |
| | | HNIALIWNVKDFMSLSEQLRKQIRSAAKKNN |
| | | LPFKLTCATTRQVVNVVTTKIALKGGKIVNN |
| | | WLKQLIKVTLVFLFVAAIFYLITPVHVMSKHT |
| | | DFSSEIIGYKAIDGGVTRDIASTDTCFANKHA |
| | | DFDTWFSQRGGSYTNDKACPLIAAVITREVGF |
| | | VVPGLPGTILRTTNGDFLHFLPRVFSAVGNIC |
| | | YTPSKLIEYTDFATSACVLAAECTIFKDASGK |
| | | PVPYCYDTNVLEGSVAYESLRPDTRYVLMDG |
| | | SIIQFPNTYLEGSVRVVTTFDSEYCRHGTCERS |
| | | EAGVCVSTSGRWVLNNDYYRSLPGVFCGVD |
| | | AVNLLTNMFTPLIQPIGALDISASIVAGGIVAI |
| | | VVTCLAYYFMRFRRAFGEYSHVVAFNTLLFL |
| | | MSFTVLCLTPVYSFLPGVYSVIYLYLTFYLTN |
| | | DVSFLAHIQWMVMFTPLVPFWITIAYIICISTK |
| | | HFYWFFSNYLKRRVVFNGVSFSTFEEAALCTF |
| | | LLNKEMYLKLRSDVLLPLTQYNRYLALYNK |
| | | YKYFSGAMDTTSYREAACCHLAKALNDFSNS |
| | | GSDVLYQPPQTSITSAVLQSGFRKMAFPSGKV |
| | | EGCMVQVTCGTTTLNGLWLDDVVYCPRHVI |
| | | CTSEDMLNPNYEDLLIRKSNHNFLVQAGNVQ |
| | | LRVIGHSMQNCVLKLKVDTANPKTPKYKFVR |
| | | IQPGQTFSVLACYNGSPSGVYQCAMRPNFTIK |
| | | GSFLNGSCGSVGFNIDYDCVSFCYMHHMELP |
| | | TGVHAGTDLEGNFYGPFVDRQTAQAAGTDT |
| | | TITVNVLAWLYAAVINGDRWFLNRFTTTLND |
| | | FNLVAMKYNYEPLTQDHVDILGPLSAQTGIA |
| | | VLDMCASLKELLQNGMNGRTILGSALLEDEF |
| | | TPFDVVRQCSGVTFQSAVKRTIKGTHHWLLL |
| | | TILTSLLVLVQSTQWSLFFFLYENAFLPFAMGI |
| | | IAMSAFAMMFVKHKHAFLCLFLLPSLATVAY |
| | | FNMVYMPASWVMRIMTWLDMVDTSLSGFK |
| | | LKDCVMYASAVVLLILMTARTVYDDGARRV |
| | | WTLMNVLTLVYKVYYGNALDQAISMWALII |
| | | SVTSNYSGVVTTVMFLARGIVFMCVEYCPIFF |
| | | ITGNTLQCIMLVYCFLGYFCTCYFGLFCLLNR |
| | | YFRLTLGVYDYLVSTQEFRYMNSQGLLPPKN |
| | | SIDAFKLNIKLLGVGGKPCIKVATVQSKMSDV |
| | | KCTSVVLLSVLQQLRVESSSKLWAQCVQLHN |
| | | DILLAKDTTEAFEKMVSLLSVLLSMQGAVDI |
| | | NKLCEEMLDNRATLQAIASEFSSLPSYAAFAT |
| | | AQEAYEQAVANGDSEVVLKKLKKSLNVAKS |
| | | EFDRDAAMQRKLEKMADQAMTQMYKQARS |
| | | EDKRAKVTSAMQTMLFTMLRKLDNDALNNII |
| | | NNARDGCVPLNIIPLTTAAKLMVVIPDYNTYK |
| | | NTCDGTTFTYASALWEIQQVVDADSKIVQLS |
| | | EISMDNSPNLAWPLIVTALRANSAVKLQNNE |
| | | LSPVALRQMSCAAGTTQTACTDDNALAYYN |
| | | TTKGGRFVLALLSDLQDLKWARFPKSDGTGT |
| | | IYTELEPPCRFVTDTPKGPKVKYLYFIKGLNN |
| | | LNRGMVLGSLAATVRLQAGNATEVPANSTV |
| | | LSFCAFAVDAAKAYKDYLASGGQPITNCVK |
| | | MLCTHTGTGQAITVTPEANMDQESFGGASCC |
| | | LYCRCHIDHPNPKGFCDLKGKYVQIPTTCAN |
| | | DPVGFTLKNTVCTVCGMWKGYGCSCDQLRE |
| | | PMLQSADAQSFLNRVCGVSAARLTPCGTGTS |
| | | TDVVYRAFDIYNDKVAGFAKFLKTNCCRFQE |
| | | KDEDDNLIDSYFVVKRHTFSNYQHEETIYNLL |
| | | KDCPAVAKHDFFKFRIDGDMVPHISRQRLTK |
| | | YTMADLVYALRHFDEGNCDTLKEILVTYNCC |
| | | DDDYFNKKDWYDFVENPDILRVYANLGERV |
| | | RQALLKTVQFCDAMRNAGIVGVLTLDNQDL |
| | | NGNWYDFGDFIQTTPGSGVPVV |
| | | DSYYSLLMPILTLTRALTAESHVDTDLTKPYI |
| | | KWDLLKYDFTEERLKLFDRYFKYWDQTYHP |
| | | NCVNCLDDRCILHCANFNVLFSTVFPPTSFGP |
| | | LVRKIFVDGVPFVVSTGYHFRELGVVHNQDV |

TABLE 2-continued

Sequences

| Sequence Description | SEQ ID NO. | Sequence |
|---|---|---|
| | | NLHSSRLSFKELLVYAADPAMHAASGNLLLD KRTTCFSVAALTNNVAFQTVKPGNFNKDFYD FAVSKGFFKEGSSVELKHFFFAQDGNAAISDY DYYRYNLPTMCDIRQLLFVVEVVDKYFDCY DGGCINANQVIVNNLDKSAGFPFNKWGKARL YYDSMSYEDQDALFAYTKRNVIPTITQMNLK YAISAKNRARTVAGVSICSTMTNRQFHQKLL KSIAATRGATVVIGTSKFYGGWHNMLKTVYS DVENPHLMGWDYPKCDRAMPNMLRIMASL VLARKHTTCCSLSHRFYRLANECAQVLSEMV MCGGSLYVKPGGTSSGDATTAYANSVFNICQ AVTANVNALLSTDGNKIADKYVRNLQHRLY ECLYRNRDVDTDFVNEFYAYLRKHFSMMILS DDAVVCFNSTYASQGLVASIKNFKSVLYYQN NVFMSEAKCWTETDLTKGPHEFCSQHTMLV KQGDDYVYLPYPDPSRILGAGCFVDDIVKTD GTLMIERFVSLAIDAYPLTKHPNQEYADVFHL YLQYIRKLHDELTGHMLDMYSVMLTNDNTS RYWEPEFYEAMYTPHTVLQAVGACVLCNSQ TSLRCGACIRRPFLCCKCCYDHVISTSHKLVL SVNPYVCNAPGCDVTDVTQLYLGGMSYYCK SHKPPISFPLCANGQVFGLYKNTCVGSDNVTD FNAIATCDWTNAGDYILANTCTERLKLFAAE TLKATEETFKLSYGIATVREVLSDRELHLSWE VGKPRPPLNRNYVFTGYRVTKNSKVQIGEYT FEKGDYGDAVVYRGTTTYKLNVGDYFVLTS HTVMPLSAPTLVPQEHYVRITGLYPTLNISDE FSSNVANYQKVGMQKYSTLQGPPGTGKSHF AIGLALYYPSARIVYTACSHAAVDALCEKAL KYLPIDKCSRIIPARARVECFDKFKVNSTLEQY VFCTVNALPETTADIVVFDEISMATNYDLSVV NARLRAKHYVYIGDPAQLPAPRTLLTKGTLE PEYFNSVCRLMKTIGPDMFLGTCRRCPAEIVD TVSALVYDNKLKAHKDKSAQCFKMFYKGVI THDVSSAINRPQIGVVREFLTRNPAWRKAVFI SPYNSQNAVASKILGLPTQTVDSSQGSEYDYV IFTQTTETAHSCNVNRFNVAITRAKVGILCIMS DRDLYDKLQFTSLEIPRRNVATLQAENVTGLF KDCSKVITGLHPTQAPTHLSVDTKFKTEGLCV DIPGIPKDMTYRRLISMMGFKMNYQVNGYPN MFITREEAIRHVRAWIGFDVEGCHATREAVG TNLPLQLGFSTGVNLVAVPTGYVDTPNNTDF SRVSAKPPPGDQFKHLIPLMYKGLPWNVVRI KIVQMLSDTLKNLSDRVVFVLWAHGFELTSM KYFVKIGPERTCCLCDRRATCFSTASDTYAC WHHSIGFDYVYNPFMIDVQQWGFTGNLQSN HDLYCQVHGNAHVASCDAIMTRCLAVHECF VKRVDWTIEYPIIGDELKINAACRKVQHMVV KAALLADKFPVLHDIGNPKAIKCVPQADVEW KFYDAQPCSDKAYKIEELFYSYATHSDKFTD GVCLFWNCNVDRYPANSIVCRFDTRVLSNLN LPGCDGGSLYVNKHAFHTPAFDKSAFVNLKQ LPFFYYSDSPCESHGKQVVSDIDYVPLKSATCI TRCNLGGAVCRHHANEYRLYLDAYNMMISA GFSLWVYKQFDTYNLWNTFTRLQSLENVAF NVVNKGHFDGQQGEVPVSIINNTVYTKVDGV DVELFENKTTLPVNVAFELWAKRNIKPVPEV KILNNLGVDIAANTVIWDYKRDAPAHISTIGV CSMTDIAKKPTETICAPLTVFFDGRVDGQVDL FRNARNGVLITEGSVKGLQPSVGPKQASLNG VTLIGEAVKTQFNYYKKVDGVVQQLPETYFT QSRNLQEFKPRSQMEIDFLELAMDEFIERYKL EGYAFEHIVYGDFSHSQLGGLHLLIGLAKRFK ESPFELEDFIPMDSTVKNYFITDAQTGSSKCVC SVIDLLLDDFVEIIKSQDLSVVSKVVKVTIDYT EISFMLWCKDGHVETFYPKLQSSQAWQPGVA MPNLYKMQRMLLEKCDLQNYGDSATLPKGI MMNVAKYTQLCQYLNTLTLAVPYNMRVIHF GAGSDKGVAPGTAVLRQWLPTGTLLVDSDL NDFVSDADSTLIGDCATVHTANKWDLIISDM YDPKTKNVTKENDSKEGFFTYICGFIQQKLAL GGSVAIKITEHSWNADLYKLMGHFAWWTAF |

TABLE 2-continued

Sequences

| Sequence Description | SEQ ID NO. | Sequence |
|---|---|---|
| | | VTNVNASSSEAFLIGCNYLGKPREQIDGYVM<br>HANYIFWRNTNPIQLSSYSLFDMSKFPLKLRG<br>TAVMSLKEGQINDMILSLLSKGRLIIRENNRV<br>VISSDVLVNN |
| surface glycoprotein [Wuhan seafood market pneumonia virus]; GenBank: QHD 43416.1; Jan. 23, 2020 | 165 |     1 mfvflvllpl vssqcvnltt rtqlppaytn sftrgvyypd kvfrssvlhs tqdlflpffs<br>  61 nvtwfhaihv sgtngtkrfd npvlpfndgv yfasteksni irgwifgttl dsktqslliv<br>121 nnatnvvikv cefqfcndpf lgvyyhknnk swmesefrvy ssannctfey vsqpflmdle<br>181 gkqgnfknlr efvfknidgy fkiyskhtpi nlvrdlpqgf saleplvdlp iginitrfqt<br>241 llalhrsylt pgdsssgwta gaaayyvgyl qprtfllkyn engtitdavd caldplsetk<br>301 ctlksftvek giyqtsnfrv qptesivrfp nitnlcpfge vfnatrfasv yawnrkrisn<br>361 cvadysvlyn sasfstfkcy gvsptklndl cftnvyadsf virgdevrqi apgqtgkiad<br>421 ynyklpddft gcviawnsnn ldskvggnyn ylyrlfrksn lkpferdist eiyqagstpc<br>481 ngvegfncyf plqsygfqpt ngvgyqpyrv vvlsfellha patvcgpkks tnlvknkcvn<br>541 fnfngltgtg vltesnkkfl pfqqfgrdia dttdavrdpq tleilditpc sfggvsvitp<br>601 gtntsnqvav lyqdvnctev pvaihadqlt ptwrvystgs nvfqtragcl igaehvnnsy<br>661 ecdipigagi casyqtqtns prrarsvasq siiaytmslg aensvaysnn siaiptnfti<br>721 svtteilpvs mtktsvdctm yicgdstecs nlllqygsfc tqlnraltgi aveqdkntqe<br>781 vfaqvkqiyk tppikdfggf nfsqilpdps kpskrsfied llfnkvtlad agfikqygdc<br>841 lgdiaardli caqkfngltv lppllttdemi aqytsallag titsgwtfga gaalqipfam<br>901 qmayrfngig vtqnvlyenq klianqfnsa igkiqdslss tasalgklqd vvnqnaqaln<br>961 tlvkqlssnf gaissvlndi lsrldkveae vqidrlitgr lqslqtyvtq qliraaeira<br>1021 sanlaatkms ecvlgqskrv dfcgkgyhlm sfpqsaphgv vflhvtyvpa qeknfttapa<br>1081 ichdgkahfp regvfsngt hwfvtqrnfy epqiittdnt fvsgncdvvi givnntvydp<br>1141 lqpeldsfke eldkyfknht spdvdlgdis ginasvvniq keidrlneva knlneslidl<br>1201 qelgkyeqyi kwpwyiwlgf iagliaivmv timlccmtsc csclkgccsc gscckfdedd<br>1261 sepvlkgvkl hyt |
| surface glycoprotein RBD [Wuhan seafood market pneumonia virus]; GenBank: QHD 43416.1; Jan. 23, 2020 | 166 | nitnlcpfgevfnatrfasvyawnrkrisncvadysvlynsasfstfkc<br>ygvsptklndlcftnvyadsfvirgdevrqiapgqtgkiadynyklpd<br>dftgcviawnsnnldskvggnynylyrlfrksnlkpferdisteiyqa<br>gstpcngvegfncyfplqsygfqptngvgyqpyrvvvlsfellhapa<br>tvcgpkkstnlvknkcvnfnfngltgtg |
| Receptor Binding Motif (RBM) in surface glycoprotein RBD [Wuhan seafood market pneumonia virus]; GenBank: QHD 43416.1; Jan. 23, 2020 | 167 | Nsnnldskvggnynylyrlfrksnlkpferdisteiyqagstpcngve<br>gfncyfplqsygfqptngvgyqpy |
| SARS-CoV-2 S309-v13 mAb VL (VK) (aa) | 168 | EIVLTQSPGTLSLSPGERATLSCRASQTVSSTS<br>LAWYQQKPGQAPRLLIYGASSRATGIPDRFSG<br>SGSGTDFTLTISRLEPEDFAVYYCQQHDTSLT<br>FGGGTKVEIK |

TABLE 2-continued

Sequences

| Sequence Description | SEQ ID NO. | Sequence |
|---|---|---|
| SARS-CoV-2 S309-v13 mAb CDRL1 (aa) | 169 | QTVSSTS |
| SARS-CoV-2 S309-v13 mAb CDRL2 (aa) | 170 | GAS |
| SARS-CoV-2 S309-v13 mAb CDRL3 (aa) | 171 | QQHDTSLT |
| SARS-CoV-2 S309-v2.9 mAb VH (aa) | 172 | QVQLVQSGAEVKKPGASVKVSCKASGYPFT SYGISWVRQAPGQGLEWMGFISTYNANTNY AQKFQGRVTMTTDTSTTTGYMELRRLRSDDT AVYYCARDYTRGAFFGESLIGGFDNWGQG TLVTVSS |
| SARS-CoV-2 CH1-CH3 G1m17; IgG1*01 LS (aa) | 173 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLGGPSVFLFPP KPKDTLMISRTPEVTCVVVDVSHEDPEVKFN WYVDGVEVHNAKTKPREEQYNSTYRVVSVL TVLHQDWLNGKEYKCKVSNKALPAPIEKTIS KAKGQPREPQVYTLPPSRDELTKNQVSLTCL VKGFYPSDIAVEWESNGQPENNYKTTPPVLD SDGSFFLYSKLTVDKSRWQQGNVFSCSVLHE ALHSHYTQKSLSLSPGK |
| SARS-CoV-2 mAb CL (Ck) IgKC *01 klm3 (aa) | 174 | RTVAAPSVFIFPPSDEQLKSGTASVVCLLNNF YPREAKVQWKVDNALQSGNSQESVTEQDSK DSTYSLSSTLTLSKADYEKHKVYACEVTHQG LSSPVTKSFNRGEC |
| SARS-CoV-2 CH1-CH3 G1m17; IgG1*01 LS GAALIE (aa) | 175 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLAGPSVFLFPP KPKDTLMISRTPEVTCVVVDVSHEDPEVKFN WYVDGVEVHNAKTKPREEQYNSTYRVVSVL TVLHQDWLNGKEYKCKVSNKALPLPEEKTIS KAKGQPREPQVYTLPPSRDELTKNQVSLTCL VKGFYPSDIAVEWESNGQPENNYKTTPPVLD SDGSFFLYSKLTVDKSRWQQGNVFSCSVLHE ALHSHYTQKSLSLSPGK |
| SARS-CoV-2 S300-v2.10 mAb VH (aa) | 176 | QVQLVQSGAEVKKPGASVKVSCKASGYTFT DYYIHWVRQAPGQGPEWLGFVNAYSGATRY AQKYQGRVTMTRDTSISTAYMQLSRLRPDDT AVYYCARDRPSHEFAMYFFDNWGQGTLVT VSS |
| SARS-CoV-2 S300-v2.11 mAb VH (aa) | 177 | QVQLVQSGAEVKKPGASVKVSCKASGYTFT DYYIHWVRQAPGQGPEWLGFVQGYSGATRY AQKYQGRVTMTRDTSISTAYMQLSRLRPDDT AVYYCARDRPSHEFAMYFFDNWGQGTLVT VSS |

TABLE 2-continued

Sequences

| Sequence Description | SEQ ID NO. | Sequence |
|---|---|---|
| SARS-CoV-2 S315-v1 mA TABLE 2-continued Sequences

| Sequence Description | SEQ ID NO. | Sequence |
|---|---|---|
| SARS-CoV-2 S315-v1 mAb VH (nt-codon optimized) | 188 | GAAGTGCAGCTTGTCGAGAGCGGCGGAGG CCTCGTTCAGCCAGG TABLE 2-continued Sequences

| Sequence Description | SEQ ID NO. | Sequence |
|---|---|---|
| SARS-CoV-2 S315-v4 mAb VH (aa) | 196 | EVQLVESGGGLVQPGGSLRLSCAASGFTFSN YWMTWVRQAPGKGLEWVANIKQDASEKY YVDSVKGRFTISRDNAKNSLYLQMNSLRAED TAVYYCARDLWWNDQAHYYGMDVWGQG TTVTVSS |
| SARS-CoV-2 S315-v4 mAb CDRH2 (aa) | 197 | IKQDASEK |
| SARS-CoV-2 S315-v5 mAb VH (aa) | 198 | EVQLVESGGGLVQPGGSLRLSCAASGFTFSN YWMTWVRQAPGKGLEWVANIKQEGSEKY YVDSVKGRFTISRDNAKNSLYLQMNSLRAED TAVYYCARDLWWNDQAHYYGMDVWGQG TTVTVSS |
| SARS-CoV-2 S315-v5 mAb CDRH2 (aa) | 199 | IKQEGSEK |
| SARS-CoV-2 S315-v6 mAb VH (aa) | 200 | EVQLVESGGGLVQPGGSLRLSCAASGFTFSN YWMTWVRQAPGKGLEWVANIKQDGSEKY YVDSVKGRFTISRDNAKNSLYLQMNSLRAED TAVYYCARDLFWNDQAHYYGMDVWGQGT TVTVSS |
| SARS-CoV-2 S315-v6 mAb CDRH3 (aa) | 201 | ARDLFWNDQAHYYGMDV |
| SARS-CoV-2 S315-v7 mAb VH (aa) | 202 | EVQLVESGGGLVQPGGSLRLSCAASGFTFSN YWMTWVRQAPGKGLEWVANIKQDGSEKY YVDSVKGRFTISRDNAKNSLYLQMNSLRAED TAVYYCARDLWFNDQAHYYGMDVWGQGT TVTVSS |
| SARS-CoV-2 S315-v7 mAb CDRH3 (aa) | 203 | ARDLWFNDQAHYYGMDV |
| SARS-CoV-2 Heavy Chain IgHG1*01 Fd (aa) | 204 | QVQLVQSGAEVKKPGASVKVSCKASGYPFT SYGISWVRQAPGQGLEWMGWISTYNGNTNY AQKFQGRVTMTTDTSTTTGYMELRRLSDDT AVYYCARDYTRGAWFGESLIGGFDNWGQG TLVTVSSASTKGPSVFPLAPSSKSTSGGTAAL LQSSGLYSLSSVVTVPSSSLGTQTYICNVNHK PSNTKVDKRVEPKSC |
| SARS-CoV-2 Light Chain IgKC*01 (aa) | 205 | EIVLTQSPGTLSLSPGERATLSCRASQTVSSTS LAWYQQKPGQAPRLLIYGASSRATGIPDRFSG SGSGTDFTLTISRLEPEDFAVYYCQQHDTSLT FGGGTKVEIKRTVAAPSVFIFPPSDEQLKSGTA SVVCLLNNFYPREAKVQWKVDNALQSGNSQ ESVTEQDSKDSTYSLSSTLTLSKADYEKHKVY ACEVTHQGLSSPVTKSFNRGEC |
| Linker (aa) | 206 | GSTSGSGKPGSGEGSTKG |
| Linker (aa) | 207 | GSGKPGSGEG |

TABLE 2-continued

Sequences

| Sequence Description | SEQ ID NO. | Sequence |
|---|---|---|
| Linker (aa) | 208 | GKPGSGEG |
| Linker (aa) | 209 | SGKPGSGE |
| Linker (aa) | 210 | BPXXXZ, wherein each X is independently a glycine (G) or serine (S), B is a positively charged amino acid and Z is glycine (G) or a negatively charged amino acid |
| Linker (aa) | 211 | (GxS)y, wherein x is 1-10 and y is 1-10 |
| Linker (aa) | 212 | GGGGSGGGGSGGGGS |
| Linker (aa) | 213 | GGGGSGGGGSGGGGSGGGGSGGGGSGGGGSGGGGSGGGGSGGGGS |
| Linker (aa) | 214 | GSTSGGGSGGGSGGGGSS |
| Linker (aa) | 215 | EGKSSGSGSESKVD |
| Linker (aa) | 216 | KESGSVSSEQLAQFRSLD |
| Linker (aa) | 217 | GGGGS |
| SARS-CoV-2 S309-scFab (H-L) (aa) | 218 | QVQLVQSGAEVKKPGASVKVSCKASGYPFT SYGISWVRQAPGQGLEWMGWISTYNGNTNY AQKFQGRVTMTTDTSTTTGYMELRRLRSDDT AVYYCARDYTRGAWFGESLIGGFDNWGQG TLVTVSSASTKGPSVFPLAPSSKSTSGGTAAL GCLVKDYFPEPVTVSWNSGALTSGVHTFPAV LQSSGLYSLSSVVTVPSSSLGTQTYICNVNHK PSNTKVDKRVEPKSCGGGGSGGGGSGGGGS GGGGSGGGGSGGGGSGGGGSGGGGSGGGGS GGGGSEIVLTQSPGTLSLSPGERATLSCRASQ TVSSTSLAWYQQKPGQAPRLLIYGASSRATGI PDRFSGSGSGTDFTLTISRLEPEDFAVYYCQQ HDTSLTFGGGTKVEIKRTVAAPSVFIFPPSDE QLKSGTASVVCLLNNFYPREAKVQWKVDNA LQSGNSQESVTEQDSKDSTYSLSSTLTLSKAD YEKHKVYACEVTHQGLSSPVTKSFNRGEC |
| SARS-CoV-2 S309-scFab (L-H) (aa) | 219 | EIVLTQSPGTLSLSPGERATLSCRASQTVSSTS LAWYQQKPGQAPRLLIYGASSRATGIPDRFSG SGSGTDFTLTISRLEPEDFAVYYCQQHDTSLT FGGGTKVEIKRTVAAPSVFIFPPSDEQLKSGTA SVVCLLNNFYPREAKVQWKVDNALQSGNSQ ESVTEQDSKDSTYSLSSTLTLSKADYEKHKVY ACEVTHQGLSSPVTKSFNRGECGGGGSGGGG SGGGGSGGGGSGGGGSGGGGSGGGGSGGGG SGGGGSGGGGSQVQLVQSGAEVKKPGASVK VSCKASGYPFTSYGISWVRQAPGQGLEWMG WISTYNGNTNYAQKFQGRVTMTTDTSTTTG YMELRRLRSDDTAVYYCARDYTRGAWFGE SLIGGFDNWGQGTLVTVSSASTKGPSVFPLA PSSKSTSGGTAALGCLVKDYFPEPVTVSWNS GALTSGVHTFPAVLQSSGLYSLSSVVTVPSSS LGTQTYICNVNHKPSNTKVDKRVEPKSC |
| SARS-CoV-2 S309-scFv (VH-VL) (aa) | 220 | QVQLVQSGAEVKKPGASVKVSCKASGYPFT SYGISWVRQAPGQGLEWMGWISTYNGNTNY AQKFQGRVTMTTDTSTTTGYMELRRLRSDDT AVYYCARDYTRGAWFGESLIGGFDNWGQG TLVTVSSGGGGSGGGGSGGGGSEIVLTQSPGT LSLSPGERATLSCRASQTVSSTSLAWYQQKP GQAPRLLIYGASSRATGIPDRFSGSGSGTDFTL TISRLEPEDFAVYYCQQHDTSLTFGGGTKVEI K |
| SARS-CoV-2 S309-scFv | 221 | EIVLTQSPGTLSLSPGERATLSCRASQTVSSTS LAWYQQKPGQAPRLLIYGASSRATGIPDRFSG SGSGTDFTLTISRLEPEDFAVYYCQQHDTSLT FGGGTKVEIKGGGGSGGGGSGGGGSQVQLV |

| Sequence Description | SEQ ID NO. | Sequence |
|---|---|---|
| (VL-VH) (aa) | | QSGAEVKKPGASVKVSCKASGYPFTSYGISW VRQAPGQGLEWMGWISTYNGNTNYAQKFQ GRVTMTTDTSTTTGYMELRRLRSDDTAVYY CARDYTRGAWFGESLIGGFDNWGQGTLVT VSS |
| SARS-CoV-2 S309-scFv (VH-VL) (aa) | 222 | QVQLVQSGAEVKKPGASVKVSCKASGYPFT SYGISWVRQAPGQGLEWMGWISTYNGNTNY AQKFQGRVTMTTDTSTTTGYMELRRLRSDDT AVYYCARDYTRGAWFGESLIGGFDNWGQG TLVTVSSGGGGSGGGGSGGGGSEIVLTQSPGT LSLSPGERATLSCRASQTVSSTSLAWYQQKP GQAPRLLIYGASSRATGIPDRFSGSGSGTDFTL TISRLEPEDFAVYYCQQHDTSLTFGGGTKVEI KGGGGSGGGGSGGGGSGGGGSQVQLVQSGA EVKKPGASVKVSCKASGYPFTSYGISWVRQA PGQGLEWMGWISTYNGNTNYAQKFQGRVT MTTDTSTTTGYMELRRLRSDDTAVYYCARD YTRGAWFGESLIGGFDNWGQGTLVTVSSGG GGSGGGGSGGGGSEIVLTQSPGTLSLSPGERA TLSCRASQTVSSTSLAWYQQKPGQAPRLLIY GASSRATGIPDRFSGSGSGTDFTLTISRLEPED FAVYYCQQHDTSLTFGGGTKVEIK |
| SARS-CoV-2 S309-scFv-(VH-VL)-(VL-VH) (aa) | 223 | QVQLVQSGAEVKKPGASVKVSCKASGYPFT SYGISWVRQAPGQGLEWMGWISTYNGNTNY AQKFQGRVTMTTDTSTTTGYMELRRLRSDDT AVYYCARDYTRGAWFGESLIGGFDNWGQG TLVTVSSGGGGSGGGGSGGGGSEIVLTQSPGT LSLSPGERATLSCRASQTVSSTSLAWYQQKP GQAPRLLIYGASSRATGIPDRFSGSGSGTDFTL TISRLEPEDFAVYYCQQHDTSLTFGGGTKVEI KGGGGSGGGGSGGGGSGGGGSEIVLTQSPGT LSLSPGERATLSCRASQTVSSTSLAWYQQKP GQAPRLLIYGASSRATGIPDRFSGSGSGTDFTL TISRLEPEDFAVYYCQQHDTSLTFGGGTKVEI KGGGGSGGGGSGGGGSQVQLVQSGAEVKKP GASVKVSCKASGYPFTSYGISWVRQAPGQGL EWMGWISTYNGNTNYAQKFQGRVTMTTDT STTTGYMELRRLRSDDTAVYYCARDYTRGA WFGESLIGGFDNWGQGTLVTVSS |
| SARS-CoV-2 S309-scFv-(VL-VH) (VH-VL) (aa) | 224 | EIVLTQSPGTLSLSPGERATLSCRASQTVSSTS LAWYQQKPGQAPRLLIYGASSRATGIPDRFSG SGSGTDFTLTISRLEPEDFAVYYCQQHDTSLT FGGGTKVEIKGGGGSGGGGSGGGGSQVQLV QSGAEVKKPGASVKVSCKASGYPFTSYGISW VRQAPGQGLEWMGWISTYNGNTNYAQKFQ GRVTMTTDTSTTTGYMELRRLRSDDTAVYY CARDYTRGAWFGESLIGGFDNWGQGTLVT VSSGGGGSGGGGSGGGGSGGGGSQVQLVQS GAEVKKPGASVKVSCKASGYPFTSYGISWVR QAPGQGLEWMGWISTYNGNTNYAQKFQGR VTMTTDTSTTTGYMELRRLRSDDTAVYYCA RDYTRGAWFGESLIGGFDNWGQGTLVTVSS GGGGSGGGGSGGGGSEIVLTQSPGTLSLSPGE RATLSCRASQTVSSTSLAWYQQKPGQAPRLL IYGASSRATGIPDRFSGSGSGTDFTLTISRLEPE DFAVYYCQQHDTSLTFGGGTKVEIK |
| SARS-CoV-2 S309-scFv-(VL-VH)-(VL-VH) (aa) | 225 | EIVLTQSPGTLSLSPGERATLSCRASQTVSSTS LAWYQQKPGQAPRLLIYGASSRATGIPDRFSG SGSGTDFTLTISRLEPEDFAVYYCQQHDTSLT FGGGTKVEIKGGGGSGGGGSGGGGSQVQLV QSGAEVKKPGASVKVSCKASGYPFTSYGISW VRQAPGQGLEWMGWISTYNGNTNYAQKFQ GRVTMTTDTSTTTGYMELRRLRSDDTAVYY CARDYTRGAWFGESLIGGFDNWGQGTLVT VSSGGGGSGGGGSGGGGSGGGGSEIVLTQSP GTLSLSPGERATLSCRASQTVSSTSLAWYQQ KPGQAPRLLIYGASSRATGIPDRFSGSGSGTDF |

TABLE 2-continued

Sequences

| Sequence Description | SEQ ID NO. | Sequence |
|---|---|---|
| | | TLTISRLEPEDFAVYYCQQHDTSLTFGGGTK VEIKGGGGSGGGGSGGGGSQVQLVQSGAEV KKPGASVKVSCKASGYPFTSYGISWVRQAPG QGLEWMGWISTYNGNTNYAQKFQGRVTMT TDTSTTTGYMELRRLRSDDTAVYYCARDYT RGAWFGESLIGGFDNWGQGTLVTSS |
| SARS-CoV-2 S309-scFab-(H-L) v1.1 (aa) | 226 | QVQLVQSGAEVKKPGASVKVSCKASGYPFT SYGISWVRQAPGQGLEWMGWISTYQGNTN YAQKFQGRVTMTTDTSTTTGYMELRRLRSD DTAVYYCARDYTRGAWFGESLIGGFDNWG QGTLVTVSSASTKGPSVFPLAPSSKSTSGGTA ALGCLVKDYFPEPVTVSWNSGALTSGVHTFP AVLQSSGLYSLSSVVTVPSSSLGTQTYICNVN HKPSNTKVDKRVEPKSCGGGGSGGGGSGGG GSGGGGSGGGGSGGGGSGGGGSGGGGSGGG GSGGGGSEIVLTQSPGTLSLSPGERATLSCRAS QTVSSTSLAWYQQKPGQAPRLLIYGASRAT GIPDRFSGSGSGTDFTLTISRLEPEDFAVYYCQ QHDTSLTFGGGTKVEIKRTVAAPSVFIFPPSD EQLKSGTASVVCLLNNFYPREAKVQWKVDN ALQSGNSQESVTEQDSKDSTYSLSSTLTLSKA DYEKHKVYACEVTHQGLSSPVTKSFNRGEC |
| SARS-CoV-2 S309-scFab-(L-H) v1.1 (aa) | 227 | EIVLTQSPGTLSLSPGERATLSCRASQTVSSTS LAWYQQKPGQAPRLLIYGASRATGIPDRFSG SGSGTDFTLTISRLEPEDFAVYYCQQHDTSLT FGGGTKVEIKRTVAAPSVFIFPPSDEQLKSGTA SVVCLLNNFYPREAKVQWKVDNALQSGNSQ ESVTEQDSKDSTYSLSSTLTLSKADYEKHKVY ACEVTHQGLSSPVTKSFNRGECGGGGSGGGG SGGGGSGGGGSGGGGSGGGGSGGGGSGGGG SGGGGSGGGGSQVQLVQSGAEVKKPGASVK VSCKASGYPFTSYGISWVRQAPGQGLEWMG WISTYQGNTNYAQKFQGRVTMTTDTSTTTG YMELRRLRSDDTAVYYCARDYTRGAWFGE SLIGGFDNWGQGTLVTVSSASTKGPSVFPLA PSSKSTSGGTAALGCLVKDYFPEPVTVSWNS GALTSGVHTFPAVLQSSGLYSLSSVVTVPSSS LGTQTYICNVNHKPSNTKVDKRVEPKSC |
| SARS-CoV-2 S309-scFv-(VH-VL) v1.1 (aa) | 228 | QVQLVQSGAEVKKPGASVKVSCKASGYPFT SYGISWVRQAPGQGLEWMGWISTYQGNTN YAQKFQGRVTMTTDTSTTTGYMELRRLRSD DTAVYYCARDYTRGAWFGESLIGGFDNWG QGTLVTVSSGGGGSGGGGSGGGGSEIVLTQS PGTLSLSPGERATLSCRASQTVSSTSLAWYQQ KPGQAPRLLIYGASSRATGIPDRFSGSGSGTDF TLTISRLEPEDFAVYYCQQHDTSLTFGGGTK VEIK |
| SARS-CoV-2 S309-scFv-(VL-VH) v1.1 (aa) | 229 | EIVLTQSPGTLSLSPGERATLSCRASQTVSSTS LAWYQQKPGQAPRLLIYGASRATGIPDRFSG SGSGTDFTLTISRLEPEDFAVYYCQQHDTSLT FGGGTKVEIKGGGGSGGGGSGGGGSQVQLV QSGAEVKKPGASVKVSCKASGYPFTSYGISW VRQAPGQGLEWMGWISTYQGNTNYAQKFQ GRVTMTTDTSTTTGYMELRRLRSDDTAVYY CARDYTRGAWFGESLIGGFDNWGQGTLVT VSS |
| SARS-CoV-2 S309-scFv-(VH-VL)-(VH-VL) v1.1 (aa) | 230 | QVQLVQSGAEVKKPGASVKVSCKASGYPFT SYGISWVRQAPGQGLEWMGWISTYQGNTN YAQKFQGRVTMTTDTSTTTGYMELRRLRSD DTAVYYCARDYTRGAWFGESLIGGFDNWG QGTLVTVSSGGGGSGGGGSGGGGSEIVLTQS PGTLSLSPGERATLSCRASQTVSSTSLAWYQQ KPGQAPRLLIYGASSRATGIPDRFSGSGSGTDF TLTISRLEPEDFAVYYCQQHDTSLTFGGGTK VEIKGGGSGGGGSGGGGSGGGGSQVQLVQ SGAEVKKPGASVKVSCKASGYPFTSYGISWV |

TABLE 2-continued

Sequences

| Sequence Description | SEQ ID NO. | Sequence |
|---|---|---|
| | | RQAPGQGLEWMGWISTYQGNTNYAQKFQG RVTMTTDTSTTTGYMELRRLRSDDTAVYYC ARDYTRGAWFGESLIGGFDNWGQGTLVTV SSGGGGSGGGGSGGGGSEIVLTQSPGTLSLSP GERATLSCRASQTVSSTSLAWYQQKPGQAPR LLIYGASSRATGIPDRFSGSGSGTDFTLTISRLE PEDFAVYYCQQHDTSLTFGGGTKVEIK |
| SARS-CoV-2 S309-scFv-(VH-VL)-(VL-VH) v1.1 (aa) | 231 | QVQLVQSGAEVKKPGASVKVSCKASGYPFT SYGISWVRQAPGQGLEWMGWISTYQGNTN YAQKFQGRVTMTTDTSTTTGYMELRRLRSD DTAVYYCARDYTRGAWFGESLIGGFDNWG QGTLVTVSSGGGGSGGGGSGGGGSEIVLTQS PGTLSLSPGERATLSCRASQTVSSTSLAWYQQ KPGQAPRLLIYGASSRATGIPDRFSGSGSGTDF TLTISRLEPEDFAVYYCQQHDTSLTFGGGTK VEIKGGGGSGGGGSGGGGSGGGGSEIVLTQS PGTLSLSPGERATLSCRASQTVSSTSLAWYQQ KPGQAPRLLIYGASSRATGIPDRFSGSGSGTDF TLTISRLEPEDFAVYYCQQHDTSLTFGGGTK VEIKGGGGSGGGGSGGGGSQVQLVQSGAEV KKPGASVKVSCKASGYPFTSYGISWVRQAPG QGLEWMGWISTYQGNTNYAQKFQGRVTMT TDTSTTTGYMELRRLRSDDTAVYYCARDYT RGAWFGESLIGGFDNWGQGTLVTVSS |
| SARS-CoV-2 S309-scFv-(VL-VH)-(VH-VL) v1.1 (aa) | 232 | EIVLTQSPGTLSLSPGERATLSCRASQTVSSTS LAWYQQKPGQAPRLLIYGASSRATGIPDRFSG SGSGTDFTLTISRLEPEDFAVYYCQQHDTSLT FGGGTKVEIKGGGGSGGGGSGGGGSQVQLV QSGAEVKKPGASVKVSCKASGYPFTSYGISW VRQAPGQGLEWMGWISTYQGNTNYAQKFQ GRVTMTTDTSTTTGYMELRRLRSDDTAVYY CARDYTRGAWFGESLIGGFDNWGQGTLVT VSSGGGGSGGGGSGGGGSGGGGSQVQLVQS GAEVKKPGASVKVSCKASGYPFTSYGISWVR QAPGQGLEWMGWISTYQGNTNYAQKFQGR VTMTTDTSTTTGYMELRRLRSDDTAVYYCA RDYTRGAWFGESLIGGFDNWGQGTLVTVSS GGGGSGGGGSGGGGSEIVLTQSPGTLSLSPGE RATLSCRASQTVSSTSLAWYQQKPGQAPRLL IYGASSRATGIPDRFSGSGSGTDFTLTISRLEPE DFAVYYCQQHDTSLTFGGGTKVEIK |
| SARS-CoV-2 S309-scFv-(VL-VH)-(VL-VH) v1.1 (aa) | 233 | EIVLTQSPGTLSLSPGERATLSCRASQTVSSTS LAWYQQKPGQAPRLLIYGASSRATGIPDRFSG SGSGTDFTLTISRLEPEDFAVYYCQQHDTSLT FGGGTKVEIKGGGGSGGGGSGGGGSQVQLV QSGAEVKKPGASVKVSCKASGYPFTSYGISW VRQAPGQGLEWMGWISTYQGNTNYAQKFQ GRVTMTTDTSTTTGYMELRRLRSDDTAVYY CARDYTRGAWFGESLIGGFDNWGQGTLVT VSSGGGGSGGGGSGGGGSGGGGSEIVLTQSP GTLSLSPGERATLSCRASQTVSSTSLAWYQQ KPGQAPRLLIYGASSRATGIPDRFSGSGSGTDF TLTISRLEPEDFAVYYCQQHDTSLTFGGGTK VEIKGGGGSGGGGSGGGGSQVQLVQSGAEV KKPGASVKVSCKASGYPFTSYGISWVRQAPG QGLEWMGWISTYQGNTNYAQKFQGRVTMT TDTSTTTGYMELRRLRSDDTAVYYCARDYT RGAWFGESLIGGFDNWGQGTLVTVSS |
| SARS-CoV-2 S300-v14 mAb VL (VK) (aa) | 234 | DIVMTQSPDSLAVSLGERATINCKSSQSVLYS SNNKNYLAWYQQKPGQPPKLLISWASTRESG VPDRFSGSGSGTDFTLTISSLQAEDVAVYYCQ QYYSAPGITFGQGTRLEIK |

TABLE 2-continued

Sequences

| Sequence Description | SEQ ID NO. | Sequence |
|---|---|---|
| SARS-CoV-2 S300-v14 mAb CDRL1 (aa) | 235 | QSVLYSSNNKNY |
| SARS-CoV-2 S300-v14 mAb CDRL2 (aa) | 236 | WAS |
| SARS-CoV-2 S300-v14 mAb CDRL3 (aa) | 237 | QQYYSAPGIT |
| SARS-CoV2 S300-v14 mAb VL (VK) (nt) | 238 | GACATCGTGATGACCCAGTCTCCAGACTCA CTGGCTGTGTCTCTGGGCGAGAGGGCCACC ATCAACTGTAAGTCCAGCCAGAGTGTTTTA TACAGCTCCAACAATAAGAACTACTTAGC TTGGTACCAGCAGAAACCAGGACAGCCTCC TAAGCTGCTCATTTCCTGGGCTTCTACCCG GGAATCCGGGGTCCCTGACCGATTCAGTGG CAGCGGGTCTGGGACAGATTTCACTCTCAC CATCAGCAGCCTGCAGGCTGAAGATGTGGC AGTTTATTACTGTCAACAATATTATAGTGC TCCCGGGATCACCTTCGGCCAGGGGACAC GACTGGAGATTAAAC |
| SARS-CoV2 S307 mAb VH (aa) | 239 | QVQLQESGPGLVKPSETLSLTCTVSGGSVTSG SYYWSWIRQPPGKGLEWIGYMYYSGSTNYN PSLKSRVTISVDTSKNQFSLKLSSVTAADTAV YYCARAGCTGITCLRYDYYYGLDVWGQGT TVTVSS |
| SARS-CoV2 S307 mAb CDRH1 (aa) | 240 | GGSVTSGSYY |
| SARS-CoV2 S307 mAb CDRH2 (aa) | 241 | MYYSGST |
| SARS-CoV2 S307 mAb CDRH3 (aa) | 242 | ARAGCTGITCLRYDYYYGLDV |
| SARS-CoV2 S307 mAb VL (VK) (aa) | 243 | EIVLTQSPGTLSLSPGKRATLSCRASQSVSSSY LAWYQQRPGQAPRLLIYGASSRAAGIPDRFS GSGSGTDFTLTISRLEPEDFAVYYCQQYGSSS WTFGQGTKVEIK |

TABLE 2-continued

Sequences

| Sequence Description | SEQ ID NO. | Sequence |
|---|---|---|
| SARS-CoV2 S307 mAb CDRL1 (aa) | 244 | QSVSSSY |
| SARS-CoV2 S307 mAb CDRL2 (aa) | 245 | GAS |
| SARS-CoV2 S307 mAb CDRL3 (aa) | 246 | QQYGSSSWT |
| SARS-CoV2 S307 mAb VH (nt) | 247 | CAGGTGCAGCTGCAGGAGTCGGGCCCAGGACTGGTGAAGCCTTCGGAGACCCTGTCCCTCACCTGCACTGTCTCTGGTGGCTCCGTCACCAGTGGTAGTTACTACTGGAGCTGGATCCGGCAGCCCCCAGGGAAGGGACTGGAGTGGATTGGGTATATGTATTACAGTGGGAGCACCAATTACAACCCCTCCCTCAAGAGTCGAGTCACCATATCAGTAGACACGTCCAAGAACCAGTTCTCCCTGAAGCTGAGCTCTGTGACCGCTGCGGACACGGCCGTGTATTACTGTGCGAGGGCAGGTTGTACTGGTATCACCTGCTTACGTTACGACTACTACTACGGTCTGGACGTCTGGGGCCAAGGGACCACGGTCACCGTCTCCTCA |
| SARS-CoV2 S307 mAb VL (VK) (nt) | 248 | GAAATTGTGTTGACGCAGTCTCCAGGCACCCTGTCTTTGTCTCCAGGGAAAGAGCCACCCTCTCCTGCAGGGCCAGTCAGAGTGTTAGCAGCAGCTACTTAGCCTGGTACCAGCAGAGACCTGGCCAGGCTCCCAGGCTCCTCATCTATGGTGCATCCAGCAGGGCCGCTGGCATCCCAGACAGGTTCAGTGGCAGTGGGTCTGGGACAGACTTCACTCTCACCATCAGCAGACTGGAGCCTGAAGATTTTGCAGTGTATTACTGTCAGCAGTATGGTAGCTCATCGTGGACGTTCGGCCAAGGGACCAAGGTGGAAATCAAAC |
| SARS-CoV-2 S309-v1 mAb VH (nt) | 249 | CAGGTTCAGCTGGTGCAGTCTGGAGCTGAGGTGAAGAAGCCTGGGGCCTCAGTGAAGGTCTCCTGCAAGGCTTCTGGTTACCCCTTTACCAGTTATGGTATCAGCTGGGTGCGACAGGCCCCTGGACAAGGGCTTGAGTGGATGGGATGGATCAGCACTTACAATGGTAACACAAATTATGCACAGAAGTTCCAGGGCAGAGTCACCATGACCACAGACACATCCACGACCACAGGCTACATGGAGCTGAGGAGGCTGAGATCTGACGACACGGCCGTGTATTACTGTGCGAGAGATTATACTCGTGGTGCTTGGTTCGGGGAGTCATTGATAGGGGCTTTGACAACTGGGGCCAGGGAACCCTGGTCACCGTCTCCTCA |
| SARS-CoV-2 S309-v13 mAb VL (VK) (nt) | 250 | GAAATTGTGTTGACGCAGTCTCCAGGCACCCTGTCTTTGTCTCCAGGGGAAAGAGCCACCCTCTCCTGCAGGGCCAGTCAGACTGTTAGCAGCACCTCCTTAGCCTGGTACCAGCAGAAACCTGGCCAGGCTCCCAGGCTCCTCATCTATGGTGCATCCAGCAGGGCCACTGGCATCCCAGACAGGTTCAGCGGCAGTGGGTCTGGGACAGACTTCACTCTCACCATCAGCAGACTGGAG |

TABLE 2-continued

| Sequences | | |
|---|---|---|
| Sequence Descrip-tion | SEQ ID NO. | Sequence |
| | | CCTGAAGATTTTGCAGTGTATTACTGTCAGC AGCATGATACCTCACTCACTTTCGGCGGAG GGACCAAGGTGGAGATCAAAC |
| CMV promoter (nt) | 251 | GACATTGATTATTGACTAGTTATTAATAGTA ATCAATTACGGGGTCATTAGTTCATAGCCC ATATATGGAGTTCCGCGTTACATAACTTAC GGTAAATGGCCCGCCTGGCTGACCGCCCAA CGACCCCCGCCCATGACGTCAATAATGACG TATGTTCCCATAGTAACGCCAATAGGGACT TTCCATTGACGTCAATGGGTGGAGTATTTA CGGTAAACTGCCCACTTGGCAGTACATCAA GTGTATCATATGCCAAGTACGCCCCCTATT GACGTCAATGACGGTAAATGGCCCGCCTGG CATTATGCCCAGTACATGACCTTATGGGAC TTTCCTACTTGGCAGTACATCTACGTATTAG TCATCGCTATTACCATGGTGATGCGGTTTTG GCAGTACATCAATGGGCGTGGATAGCGGTT TGACTCACGGGGATTTCCAAGTCTCCACCC CATTGACGTCAATGGGAGTTTGTTTTGGCA CCAAAATCAACGGGACTTTCCAAAATGTCG TAACAACTCCGCCCCATTGACGCAAATGGG CGGTAGGCGTGTACGGTGGGAGGTCTATAT AAGCAGAGCTCGTTTAGTGAACCGTCAGAT CGCCTGGAGACGCCATCCACGCTGTTTTGA CCTCCATAGAAGACACCGGGACCGATCCAG CCTCCGCGGCCGGGAACGGTGCATTGGAAC GCGGATTCCCCGTGCCAAGAGTGACGTAAG TACCGCCTATAGAGTCTATAGGCCCACCCC CTTGGCTTCGTTAG |
| Signal peptide (nt) | 252 | ATGGGATGGTCATGTATCATCCTTTTTCTAG TAGCAACTGCAACCGGTGT |
| Poly-adenyla-tion signal sequence (nt) | 253 | AACTTGTTTATTGCAGCTTATAATGGTTACA AATAAAGCAATAGCATCACAAATTTCACAA ATAAAGCATTTTTTTCACTGCATTCTAGTTG TGGTTTGTCCAAACTCATCAATGTATCTTAT CATGTCTGGATC |
| SARS-CoV-2 Light Chain IgKC*01 (nt) | 254 | GTACGGTGGCTGCACCATCTGTCTTCATCTT CCCGCCATCTGATGAGCAGTTGAAATCTGG AACTGCCTCTGTTGTGTGCCTGCTGAATAAC TTCTATCCCAGAGAGGCCAAAGTACAGTGG AAGGTGGATAACGCCCTCCAATCGGGTAAC TCCCAGGAGAGTGTCACAGAGCAGGACAG CAAGGACAGCACCTACAGCCTCAGCAGCAC CCTGACGCTGAGCAAAGCAGACTACGAGA AACACAAAGTCTACGCCTGCGAAGTCACCC ATCAGGGCCTGAGCTCGCCCGTCACAAAGA GCTTCAACAGGGGAGAGTGTTAG |
| SARS-CoV-2 CH1-CH3 Glm17; IgG1*01 (nt) | 255 | GCGTCGACCAAGGGCCCATCGGTCTTCCCC CTGGCACCCTCCTCCAAGAGCACCTCTGGG GGCACAGCGGCCCTGGGCTGCCTGGTCAAG GACTACTTCCCCGAACCTGTGACGGTCTCG TGGAACTCAGGCGCCCTGACCAGCGGCGTG CACACCTTCCCGGCTGTCCTACAGTCCTCAG GACTCTACTCCCTCAGCAGCGTGGTGACCG TGCCCTCCAGCAGCTTGGGCACCCAGACCT ACATCTGCAACGTGAATCACAAGCCCAGCA ACACCAAGGTGGACAAGAGAGTTGAGCCC AAATCTTGTGACAAAACTCACACATGCCCA CCGTGCCCAGCACCTGAACTCCTGGGGGGA CCGTCAGTCTTCCTCTTCCCCCCAAAACCCA AGGACACCCTCATGATCTCCCGGACCCCTG AGGTCACATGCGTGGTGGTGGACGTGAGCC ACGTGGACGGCGTGGAGGTGCATAATGCCA AGACAAAGCCGCGGGAGGAGCAGTACAAC AGCACGTACCGTGTGGTCAGCGTCCTCACC GTCCTGCACCAGGACTGGCTGAATGGCAAG |

TABLE 2-continued

Sequences

| Sequence Description | SEQ ID NO. | Sequence |
|---|---|---|
| | | GAGTACAAGTGCAAGGTCTCCAACAAAGCC<br>CTCCCAGCCCCCATCGAGAAAACCATCTCC<br>AAAGCCAAAGGGCAGCCCCGAGAACCACA<br>GGTGTACACCCTGCCCCCATCCCGGGAGGA<br>GATGACCAAGAACCAGGTCAGCCTGACCTG<br>CCTGGTCAAAGGCTTCTATCCCAGCGACAT<br>CGCCGTGGAGTGGGAGAGCAATGGGCAGC<br>CGGAGAACAACTACAAGACCACGCCTCCCG<br>TGCTGGACTCCGACGGCTCCTTCTTCCTCTA<br>TAGCAAGCTCACCGTGGACAAGAGCAGGTG<br>GCAGCAGGGGAACGTCTTCTCATGCTCCGT<br>GATGCATGAGGCTCTGCACAACCACTACAC<br>GCAGAAGAGCCTCTCCCTGTCCCCGGGTAA<br>ATGA |
| Signal peptide (aa) | 256 | MGWSCIILFLVATATG |
| SARS-CoV-2 S309-v1.1 mAb CH1-CH3 Glm17; IgGHG1*01 LS; GAALIE; signal peptide (nt-CO) | 257 | <u>atgggctggtcctgtatcatcctgttcctggtcgccacagccaccggagt<br>gcacagcc</u>aagtgcagctggtccagagcggcgccgaggtgaagaag<br>cccggcgctagcgtgaaggtgtcctgtaaagccagcggatatccttta<br>ccagctacggcatctcctgggtgcggcaggcccctggccagggcctg<br>gaatggatgggctggatcagcacctaccagggaaataccaactacgc<br>ccagaagttccagggaagagtgacaatgaccacagatacatctacaac<br>caccggctacatggaactgaggcggctgagaagcgacgacaccgcc<br>gtgtactactgcgccagagattacaccagaggcgcttggttcggcgag<br>agcctgatcggcggcttcgacaactgggccagggaaccctggtgac<br>agtgtctagcgcttctaccaaaggcccttctgtctttcctctggccccttct<br>agcaagtctacaagcggaggcaccgccgccctgggctgcctggtgaa<br>ggactactttccccgagcccgtgaccgtgagctggaatagcggcgccct<br>gacaagcggcgtgcacaccttcccagctgtgctgcagagcagcggcc<br>tgtatagcctgagcagcgtggtcaccgtgcccagcagcagcctggga<br>acacagacctacatctgcaacgtgaaccacaagccttctaataccaagg<br>tggataagaaggtggaacctaagagctgcgacaaaacacacacatgc<br>cctccatgtcctgctccagagctgctggccggccccagcgttttttctgttc<br>ccccccaaacctaaagacaccctgatgatcagcagaacccctgaggtg<br>acctgtgtggtggtggacgtgtcccacgaagatcctgaggtgaagttca<br>actggtacgtggatggagtggaagtgcacaacgccaagaccaaacct<br>agagaagagcagtacaacagcacatatagagtcgtgtccgtgcttaca<br>gtgctgcaccaggactggctgaatggaaaggaatacaagtgcaaggt<br>gtccaacaaggccctgcctctgcctgaggagaagacaatctctaaagc<br>caagggccaacctcgggaacctcaggtgtacacactgcccccagcc<br>gggacgagctgaccaagaaccaggtgtccctgacctgcctggtcaag<br>ggcttctacccctctgatatcgccgtggaatgggagagcaacggccaa<br>cctgagaacaactacaagaccacccctccagtgctggacagcgacgg<br>cagcttcttcctgtacagcaagctgaccgttgacaagtccagatggcag<br>cagggcaacgtgttcagctgtagcgtcctgcacgaggccctgcattctc<br>actacacccagaagagcctgtccctcagccctggcaagtga |
| SARS-CoV-2 S309-v1.1 mAb CH1-CH3 Glm17; IgGHG1*01 LS; GAALIE; (nt-CO) | 258 | caagtgcagctggtccagagcggcgccgaggtgaagaagcccggcg<br>ctagcgtgaaggtgtcctgtaaagccagcggatatccttttaccagctac<br>ggcatctcctgggtgcggcaggcccctggccagggcctggaatggat<br>gggctggatcagcacctaccagggaaataccaactacgcccagaagtt<br>ccagggaagagtgacaatgaccacagatacatctacaaccaccggct<br>acatggaactgaggcggctgagaagcgacgacaccgccgtgtactac<br>tgcgccagagattacaccagaggcgcttggttcggcgagagcctgatc<br>ggcggcttcgacaactgggccagggaaccctggtgacagtgtctag<br>cgcttctaccaaaggcccttctgtctttcctctggccccttctagcaagtct<br>acaagcggaggcaccgccgccctgggctgcctggtgaaggactactt<br>ccccgagcccgtgaccgtgagctggaatagcggcgccctgacaagc<br>ggcgtgcacaccttcccagctgtgctgcagagcagcggcctgtatagc<br>ctgagcagcgtggtcaccgtgcccagcagcagcctgggaacacaga<br>cctacatctgcaacgtgaaccacaagccttctaataccaaggtggataa<br>gaaggtggaacctaagagctgcgacaaaacacacacatgccctccat<br>gtcctgctccagagctgctggccggccccagcgttttttctgttcccccc<br>aaacctaaagacaccctgatgatcagcagaacccctgaggtgacctgt<br>gtggtggtggacgtgtcccacgaagatcctgaggtgaagttcaactggt<br>acgtggatggagtggaagtgcacaacgccaagaccaaacctagagaa<br>gagcagtacaacagcacatatagagtcgtgtccgtgcttacagtgctgc<br>accaggactggctgaatggaaaggaatacaagtgcaaggtgtccaac<br>aaggccctgcctctgcctgaggagaagacaatctctaaagccaaggg |

TABLE 2-continued

Sequences

| Sequence Description | SEQ ID NO. | Sequence |
|---|---|---|
| | | ccaacctcgggaacctcaggtgtacacactgcccccagccgggacg<br>agctgaccaagaaccaggtgtccctgacctgcctggtcaagggcttcta<br>cccctctgatatcgccgtggaatgggagagcaacggccaacctgaga<br>acaactacaagaccaccctccagtgctggacagcgacggcagcttct<br>tcctgtacagcaagctgaccgttgacaagtccagatggcagcagggca<br>acgtgttcagctgtagcgtcctgcacgaggccctgcattctcactacacc<br>cagaagagcctgtccctcagccctggcaagtga |
| SARS-CoV-2 S309-v1.1 mAb CH1-CH3 Glm17; IgGHG1*01 LS; signal peptide (nt-CO) | 259 | <u>atgggctggtcctgtatcatcctgttcctggtcgccacagccaccggagt</u><br><u>gcacagcc</u>aagtgcagctggtccagagcggcgccgaggtgaagaag<br>cccggcgctagcgtgaaggtgtcctgtaaagccagcggatatccttta<br>ccagctacggcatctcctgggtgcggcaggcccctggccagggcctg<br>gaatggatgggctggatcagcacctaccagggaaataccaactacgc<br>ccagaagttccagggaagagtgacaatgaccacagatacatctacaac<br>caccggctacatggaactgaggcggctgagaagcgacgacaccgcc<br>gtgtactactgcgccagagattacaccagaggcgcttggttcggcgag<br>agcctgatcggcggcttcgacaactggggccagggaaccctggtgac<br>agtgtctagcgcttctaccaaaggcccttctgtctttcctctggccccttct<br>agcaagtctacaagcggaggcaccgccgccctgggctgcctggtgaa<br>ggactacttccccgagcccgtgaccgtgagctggaatagcggcgccct<br>gacaagcggcgtgcacaccttcccagctgtgctgcagagcagcggcc<br>tgtatagcctgagcagcgtggtcaccgtgcccagcagcagcctggga<br>acacagacctacatctgcaacgtgaaccacaagccttctaataccaagg<br>tggataagaaggtggaacctaagagctgcgacaaaacacacacatgc<br>cctccatgtcctgctccagagctgctgggcggccccagcgttttctgtt<br>ccccccaaacctaaagacacccctgatgatcagcagaaccccctgaggt<br>gacctgtgtggtggtggacgtgtcccacgaagatcctgaggtgaagttc<br>aactggtacgtggatggagtggaagtgcacaacgccaagaccaaacc<br>tagagaagagcagtacaacagcacatatagagtcgtgtccgtgcttaca<br>gtgctgcaccaggactggctgaatggaaaggaatacaagtgcaaggt<br>gtccaacaaggcccctgcctgcccctatcgagaagacaatctctaaagc<br>caagggccaacctcgggaacctcaggtgtacacactgcccccagcc<br>gggacgagctgaccaagaaccaggtgtccctgacctgcctggtcaag<br>ggcttctaccccctctgatatcgccgtggaatgggagagcaacggccaa<br>cctgagaacaactacaagaccaccctccagtgctggacagcgacgg<br>cagcttcttcctgtacagcaagctgaccgttgacaagtccagatggcag<br>cagggcaacgtgttcagctgtagcgtcctgcacgaggccctgcattctc<br>actacacccagaagagcctgtccctcagccctggcaagtga |
| SARS-CoV-2 S309-v1.1 mAb CH1-CH3 Glm17; IgGHG1*01 LS (nt-CO) | 260 | caagtgcagctggtccagagcggcgccgaggtgaagaagcccggcg<br>ctagcgtgaaggtgtcctgtaaagccagcggatatcctttaccagctac<br>ggcatctcctgggtgcggcaggcccctggccagggcctggaatggat<br>gggctggatcagcacctaccagggaaataccaactacgcccagaagtt<br>ccagggaagagtgacaatgaccacagatacatctacaaccaccggct<br>acatggaactgaggcggctgagaagcgacgacaccgccgtgtactac<br>tgcgccagagattacaccagaggcgcttggttcggcgagagcctgatc<br>ggcggcttcgacaactggggccagggaaccctggtgacagtgtctag<br>cgcttctaccaaaggcccttctgtctttcctctggccccttctagcaagtct<br>acaagcggaggcaccgccgccctgggctgcctggtgaaggactactt<br>ccccgagcccgtgaccgtgagctggaatagcggcgccctgacaagc<br>ggcgtgcacaccttcccagctgtgctgcagagcagcggcctgtatagc<br>ctgagcagcgtggtcaccgtgcccagcagcagcctgggaacacaga<br>cctacatctgcaacgtgaaccacaagccttctaataccaaggtggataa<br>gaaggtggaacctaagagctgcgacaaaacacacacatgccctccat<br>gtcctgctccagagctgctgggcggccccagcgttttctgttcccccc<br>aaacctaaagacacccctgatgatcagcagaaccccctgaggtgacctgt<br>gtggtggtggacgtgtcccacgaagatcctgaggtgaagttcaactggt<br>acgtggatggagtggaagtgcacaacgccaagaccaaacctagaaa<br>gagcagtacaacagcacatatagagtcgtgtccgtgcttacagtgctgc<br>aaggccctgcctgcccctatcgagaagacaatctctaaagccaagggc<br>caacctcgggaacctcaggtgtacacactgcccccagccgggacga<br>gctgaccaagaaccaggtgtccctgacctgcctggtcaagggcttctac<br>ccctctgatatcgccgtggaatgggagagcaacggccaacctgagaa<br>caactacaagaccaccctccagtgctggacagcgacggcagcttctt<br>cctgtacagcaagctgaccgttgacaagtccagatggcagcagggca<br>acgtgttcagctgtagcgtcctgcacgaggccctgcattctcactacacc<br>cagaagagcctgtccctcagccctggcaagtga |
| S309-v13 Light chain | 261 | <u>tgggctggtcctgcatcatcctgttcctggtggccacagccaccggcgt</u><br><u>gcacagc</u>gagatcgtcctgacacagagccccggcacactgagcctct<br>ccccaggcgagcgggctacactgtcttgtagagcttctcagaccgtgtc<br>cagcaccagcctggcctggtatcagcagaaacctggccaggcccta |

TABLE 2-continued

Sequences

| Sequence Description | SEQ ID NO. | Sequence |
|---|---|---|
| klm3; IgKC*01; signal peptide (nt-CO) | | gactgctgatctacggcgccagcagcagagccaccggcatccctgat agattcagcggcagcggatctggaaccgacttcaccctgaccatcagc cggctggaacccgaggactttgccgtgtactactgccagcaacacgac accagcctgaccttcggcggcggaacaaaggtggaaatcaagagaac cgtggccgcccctagcgtgttcatcttccccccccagcgacgagcagct gaagagcggtacagcttctgtggtgtgcctgctgaacaacttctacccg cgggaagccaaggtgcagtggaaggtggacaacgccctgcagagcg gcaacagccaggagagcgtgacagagcaggacagcaaggacagca cctacagcctgagcagcaccctgaccctgagcaaggccgactacgag aagcacaaggtgtacgcctgtgaagtgacccaccagggcctgtctagc cctgtgaccaagtcttttaacagaggcgagtgctga |
| S309-v13 Light chain klm3; IgKC*01; (nt-CO) | 262 | Gagatcgtcctgacacagagccccggcacactgagcctctccccagg cgagcgggctacactgtcttgtagagcttctcagaccgtgtccagcacc agcctggcctggtatcagcagaaacctggccaggcccctagactgctg atctacggcgccagcagcagagccaccggcatccctgatagattcagc ggcagcggatctggaaccgacttcaccctgaccatcagccggctgga acccgaggactttgccgtgtactactgccagcaacacgacaccagcct gaccttcggcggcggaacaaaggtggaaatcaagagaaccgtggcc gcccctagcgtgttcatcttccccccccagcgacgagcagctgaagagc ggtacagcttctgtggtgtgcctgctgaacaacttctacccgcggggaag ccaaggtgcagtggaaggtggacaacgccctgcagagcggcaacag ccaggagagcgtgacagagcaggacagcaaggacagcacctacag cctgagcagcaccctgaccctgagcaaggccgactacgagaagcac aaggtgtacgcctgtgaagtgacccaccagggcctgtctagccctgtg accaagtcttttaacagaggcgagtgctga |
| Signal peptide (nt-CO) | 263 | Atgggctggtcctgcatcatcctgttcctggtggccacagccaccggc gtgcacagc |
| Signal peptide (aa) | 264 | MGWSCIILFLVATATGVHS |
| SARS-CoV-2 CH1-CH3 G1m17; IgG1*01 LS no C-term Lys (aa) | 265 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLGGPSVFLFPP KPKDTLMISRTPEVTCVVVDVSHEDPEVKFN WYVDGVEVHNAKTKPREEQYNSTYRVVSVL TVLHQDWLNGKEYKCKVSNKALPAPIEKTIS KAKGQPREPQVYTLPPSRDELTKNQVSLTCL VKGFYPSDIAVEWESNGQPENNYKTTPPVLD SDGSFFLYSKLTVDKSRWQQGNVFSCSVLHE ALHSHYTQKSLSLSPG |
| SARS-CoV-2 CH1-CH3 G1m17; IgG1*01 LS GAALIE no C-term Lys (aa) | 266 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLAGPSVFLFPP KPKDTLMISRTPEVTCVVVDVSHEDPEVKFN WYVDGVEVHNAKTKPREEQYNSTYRVVSVL TVLHQDWLNGKEYKCKVSNKALPLPEEKTIS KAKGQPREPQVYTLPPSRDELTKNQVSLTCL VKGFYPSDIAVEWESNGQPENNYKTTPPVLD SDGSFFLYSKLTVDKSRWQQGNVFSCSVLHE ALHSHYTQKSLSLSPG |
| SARS-CoV-2 S309 VH consensus sequence | 267 | QVQLVQSGAEVKKPGASVKVSCKASGYPFT SYGISWVRQAPGQGLEWMGX$_1$ISTYX$_2$X$_3$NTN YAQKFQGRVTMTTDTSTTTGYMELRRLRSD DTAVYYCARDYTRGAX$_4$FGESLIGGFDNWG QGTLVTVSS wherein X$_1$ = W, F, or Y; X$_2$ = N, Q, L, or T; X$_3$ = G, S, A, or Q; X$_4$ = W, F, or Y |

EXAMPLES

Example 1

Human Monoclonal Antibodies that Bind Spike Protein of SARS-CoV-2

B cells from a donor with previous SARS-CoV infection were sorted and immortalized with EBV and screened in 384-well plates (method described in European patent EP1597280B1, which method is incorporated herein by reference).

Figure 4A:
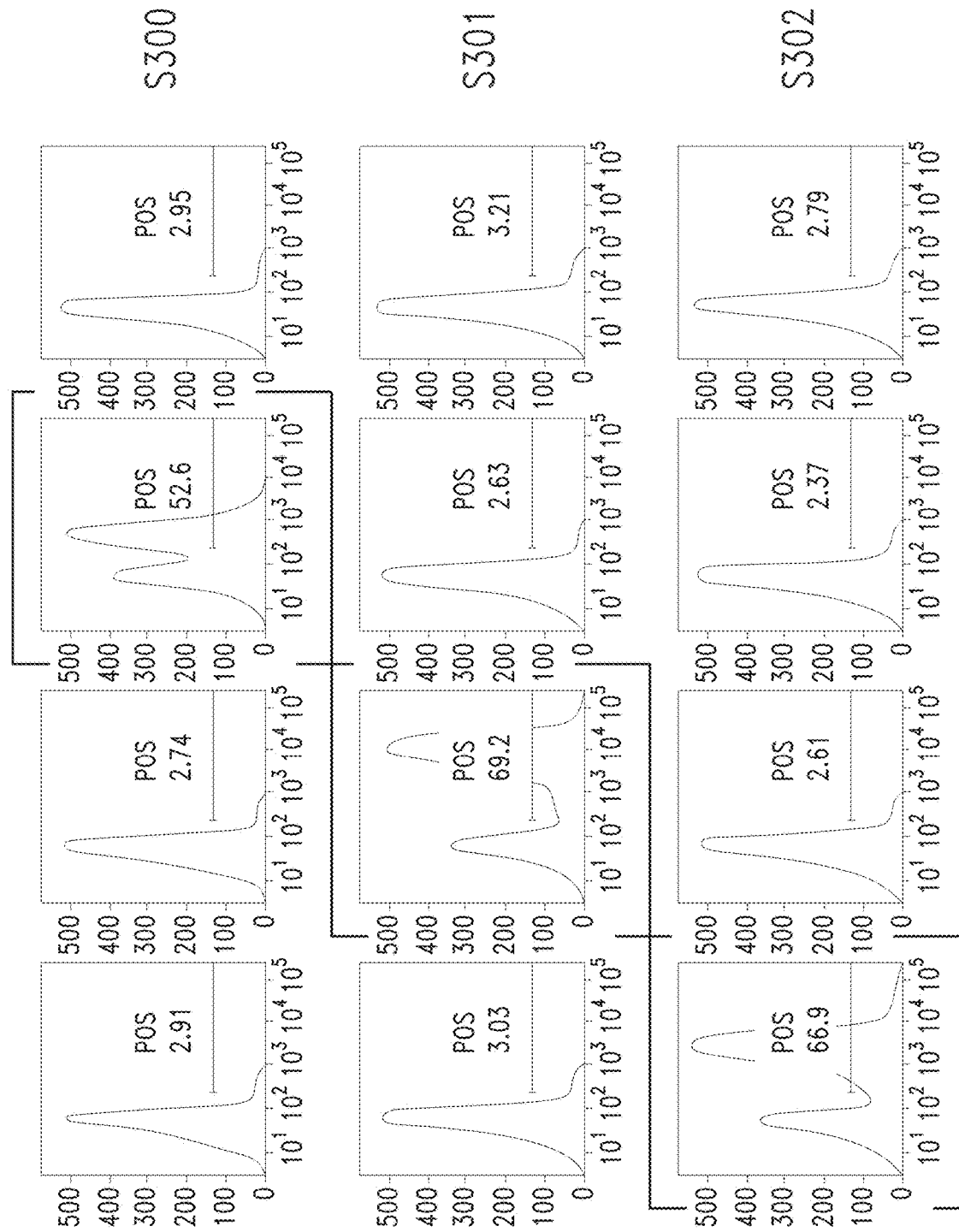
FIGS. 4A and 4B show binding of antibody-containing B cell supernatant to SARS-CoV-2 S protein expressed on ExpiCHO cells, as described in Example 1. Graphs showing binding profiles of antibodies S300-S310 are indicated with boxes.
Figure 4A:
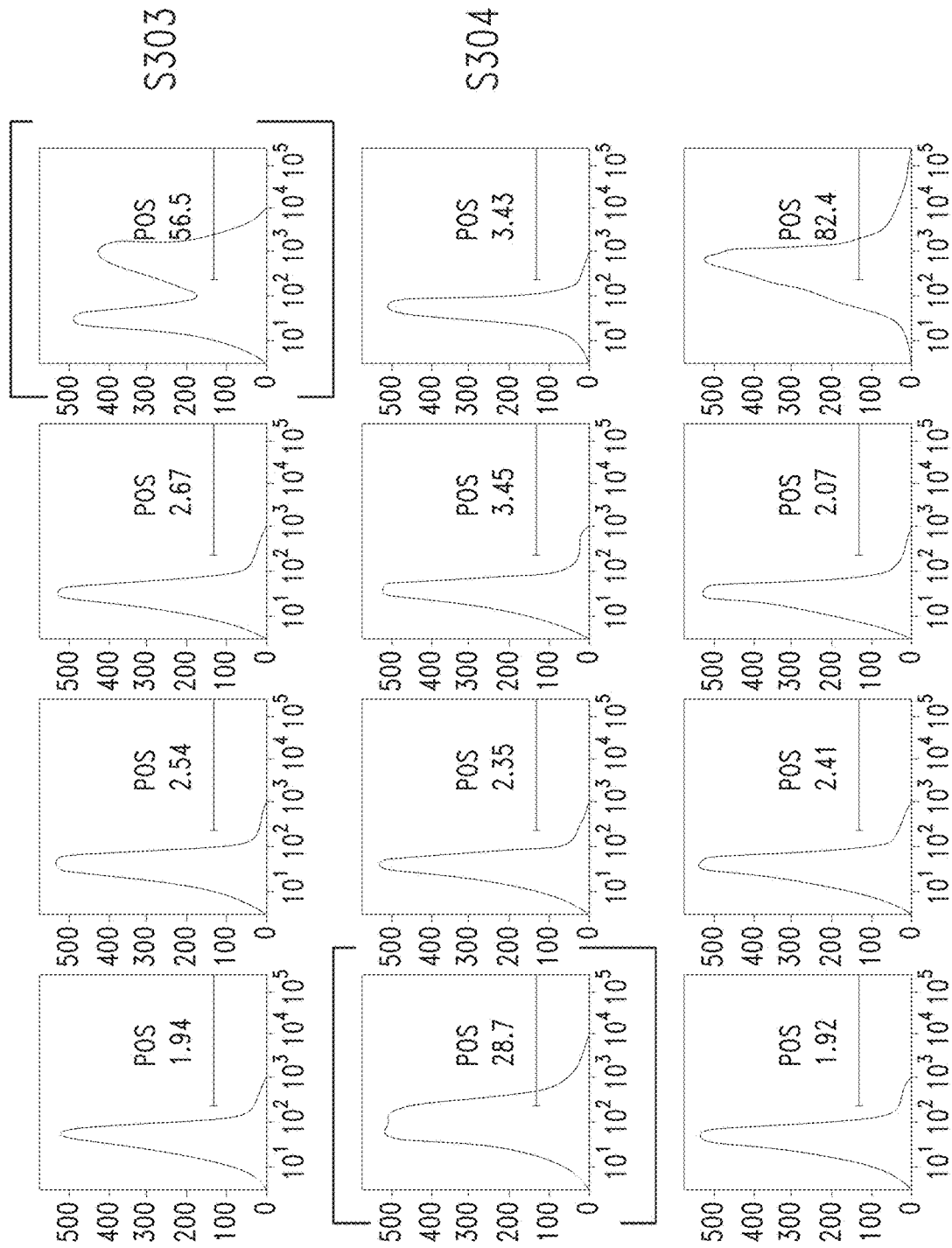
Figure 4A:
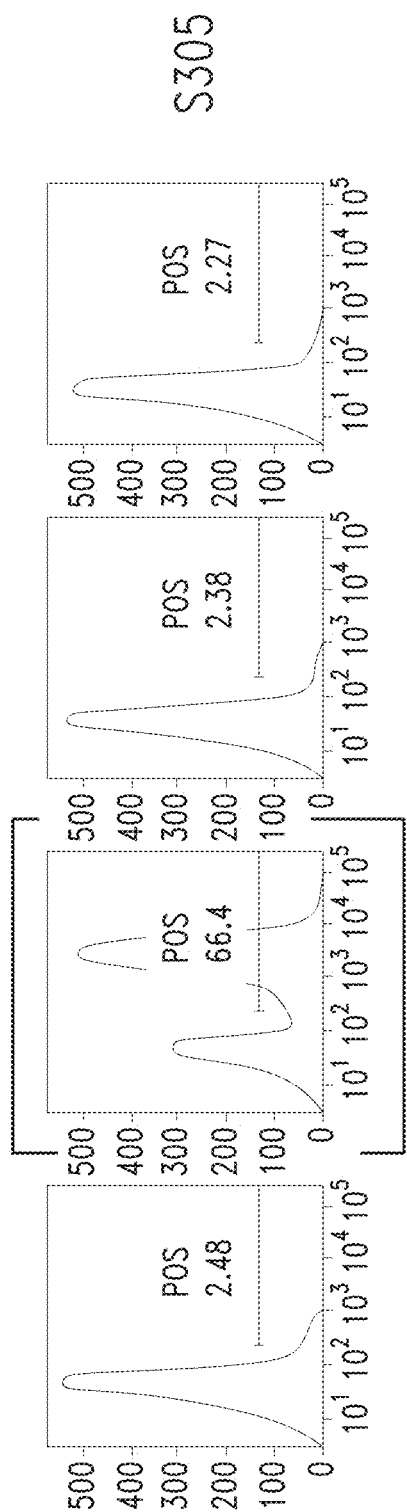
Figure 4B:
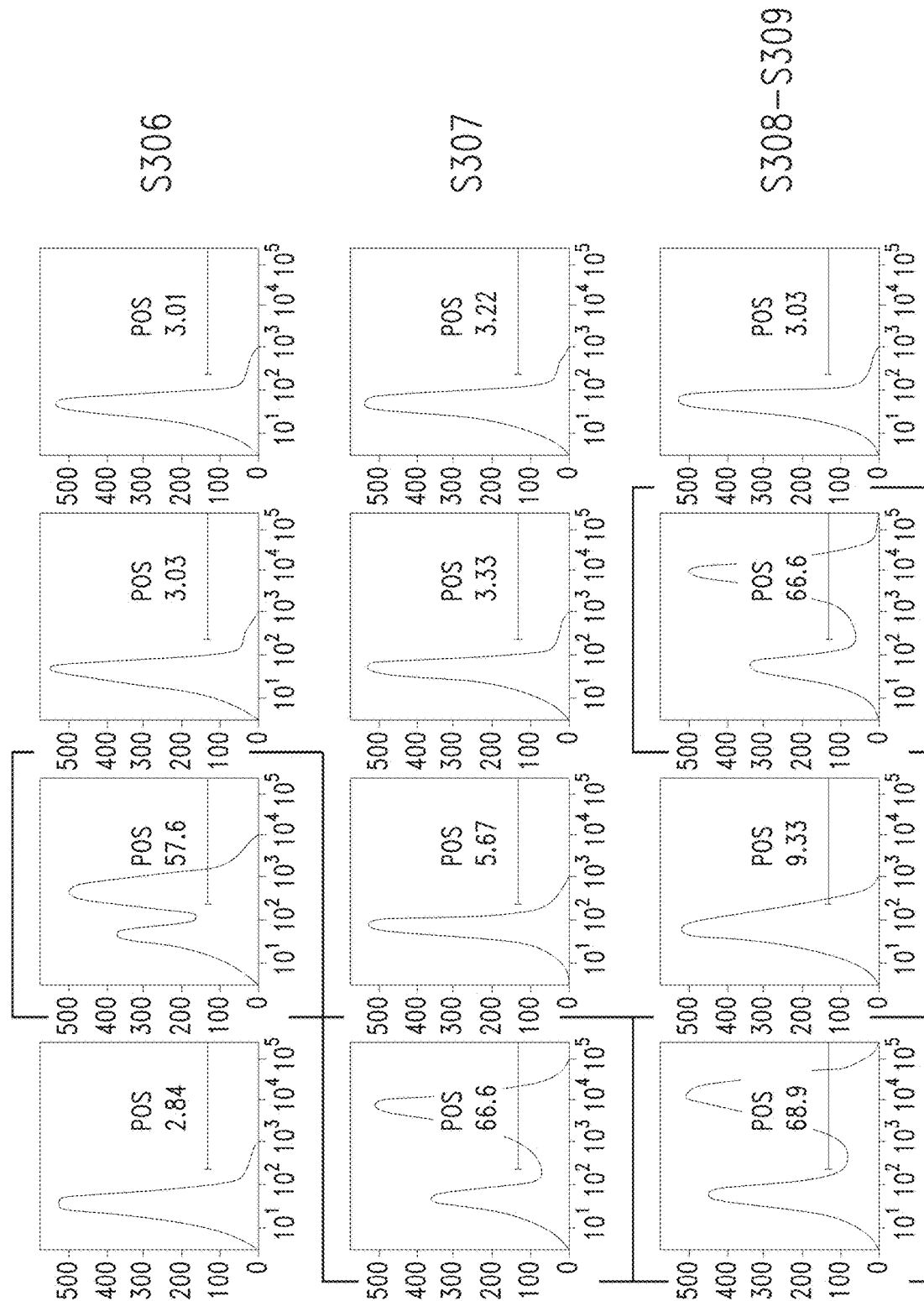
Figure 4B:
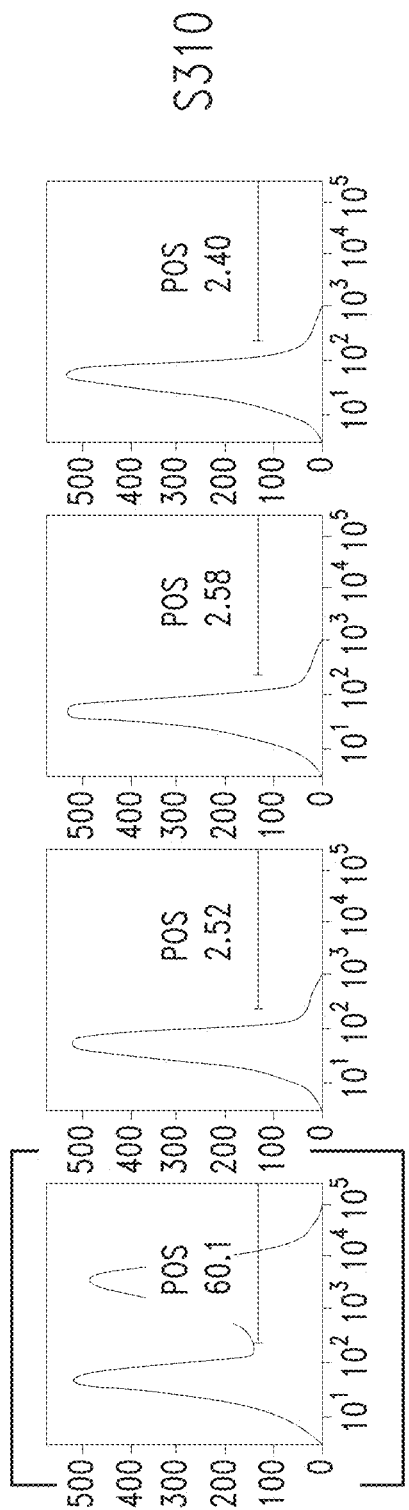

Two weeks after immortalization, supernatants of immortalized B cells were tested for antibody binding to SARS-CoV-2 Spike ("S") protein using a flow cytometry-based method. Briefly, ExpiCHO cells were transfected with S protein of SARS-CoV-2 (strain BetaCoV/Wuhan-Hu-1/2019), or with an empty plasmid as a negative control. Fourteen monoclonal antibodies were identified that bind SARS-CoV-2 S, and were termed SARS-CoV-2 S300 through SARS-CoV-2 S312 and SARS-CoV-2 S315, respectively. Binding data for SARS-CoV-2 S300 through SARS-CoV-2 S310 are shown in FIGS. 4A and 4B (in these figures, the antibodies are identified as "S300"-"S310", respectively). Graphs showing positive binding are indicated with boxes.

The heavy chain complementarity determining region (CDR)3 and light chain (L)CDR3 amino acid sequences of certain of these antibodies, along with the percent identity of the variable region gene sequences to germline (IMGT; imgt.org), are provided in Table 3.

Example 2

Binding of Antibodies to RBD of SARS-CoV-2 Using Octet

Strepavidin biosensors (Pall ForteBio) were used to immobilize anti-Strep Tag II antibody at 3 ug/ml (clone 5A9F9, Biotin, LabForce AG, Muttenz CH), after a hydration step for 10 minutes with Kinetics Buffer (KB; 0.01% endotoxin-free BSA, 0.002^Tween-20, 0.005% NaN3 in PBS). SARS-CoV-2 RBD with a Strep Tag II (produced in-house) was then loaded for 6 min at a concentration of 4 μg/ml in KB. Antibodies from B cell supernatant were allowed to associate for 1620 seconds (27 minutes). To observe dissociation, sensors were moved from the antibody solution into KB and antibody dissociation was monitored.

The "S303" mAb comprises the S303-v1 VH and VL amino acid sequences provided in Table 2 (SEQ ID NOs.:63 and 67, respectively). The "S309" mAb comprises the S309-v1 VH and S309-v13 VL amino acid sequences provided in Table 2 (SEQ ID NOs.: 105 and 168, respectively). The alleles encoding SEQ ID NOs.:109 and 147-150 from S309 B cell were determined to be non-productive; SEQ ID NO.:168 was the productive allele.

Figure 1A:
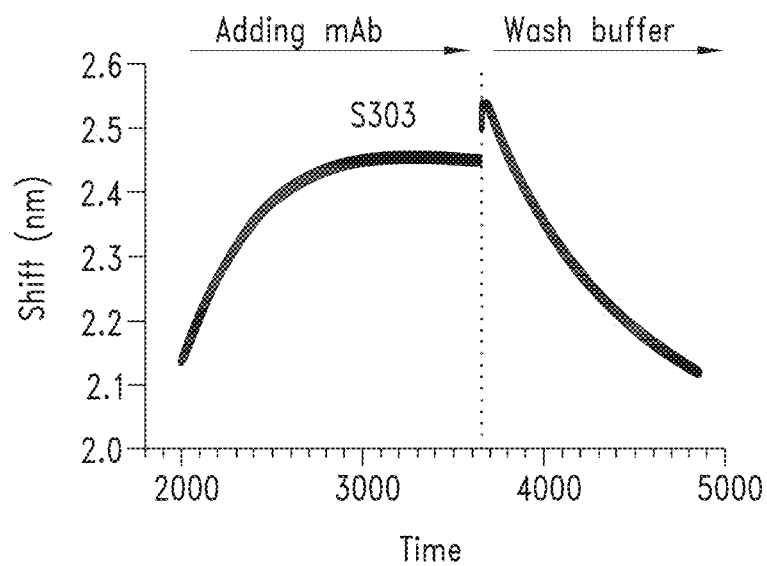
FIGS. 1A and 1B show binding by antibodies (1A) S303 (VH SEQ ID NO.:63; VL SEQ ID NO.:67) and (1B) S309 (VH SEQ ID NO.:105; VL SEQ ID NO.:168) of the present disclosure to recombinant SARS-CoV-2 RBD, as described in Example 2.
Figure 1B:
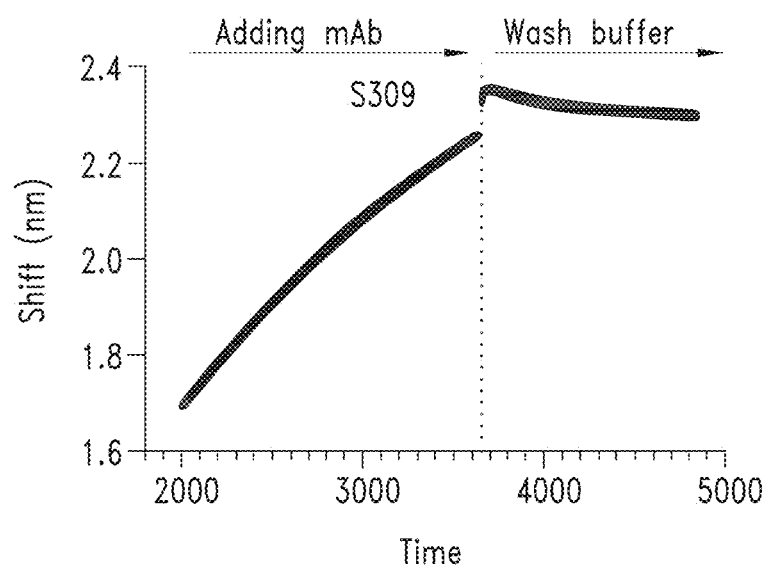

Comparison of the binding curves for S303 and S309 mAbs to SARS-CoV-2 RBD (FIGS. 1A and 1B) indicates that S303 has both a faster on-rate and a faster off-rate than S309, suggesting that S309 may bind to SARS-CoV-2 RBD with higher affinity.

Example 3

Assessing Binding of Antibodies to RBD of SARS-CoV-2 and SARS-CoV-1 Using Octet Unless the context clearly indicates otherwise (e.g., that antibodies were present in B cell supernatant, or an antibody Fab fragment was used), antibodies of the present disclosure are described in this and the subsequent Examples as recombinantly expressed human IgG1, in some cases with amino acid mutations in the Fc, as described herein.

TABLE 3

| mAb | Blood sample date | VH (% identity) | HCDR3 length | HCDR3 sequence | VL (% identity) | LCDR3 sequence | SARS-CoV | SARS-CoV-2 | Specificity |
|---|---|---|---|---|---|---|---|---|---|
| S309 | 2013 | VH1-18 (97.22) | 20 | ARDYTRGAWFGES LIGGFDN (SEQ ID NO.: 108) | VK3-20 (97.52) | QQHDTSLT (SEQ ID NO.: 171) | + | + | RBD |
| S315 | 2013 | VH3-7 (97.92) | 17 | ARDLWWNDQAHY YGMDV (SEQ ID NO.: 181) | VL3-25 (97.57) | QSADSSGTV (SEQ ID NO.: 185) | + | + | RBD |
| S303 | 2013 | VH3-23 (90.28) | 17 | ARERDDIFPMGLNA FDI (SEQ ID NO.: 66) | VK1-5 (97.49) | QQYDTYSWT (SEQ ID NO.: 70) | + | + | RBD |
| S304 | 2013 | VH3-13 (97.89) | 14 | ARGDSSGYYYYFD Y (SEQ ID NO.: 82) | VK1-39 (93.55) | QQSYVSPTYT (SEQ ID NO.: 86) | + | + | RBD |
| S306 | 2013 | VH1-18 (95.49) | 16 | ASDYDFSSGYYHSF DY (SEQ ID NO.: 90) | VK3-11 (98.92) | QQRSNWPPGCS (SEQ ID NO.: 94) | + | + | Non-RBD |
| S310 | 2013 | VH1-69 (92.71) | 19 | ATRTYDSSGYRPY YYGLDV (SEQ ID NO.: 158) | VL2-23 (97.57) | CSYAGSDTVI (SEQ ID NO.: 162) | + | + | Non-RBD |

Binding affinity of three SARS-CoV/SARS-CoV-2 cross-reactive recombinant antibodies (S303 rIgG1, S304 rIgG1, S309 rIgG1) and two SARS-CoV-1 specific antibodies (S109 rIgG1, S230 rIgG1) was tested by biolayer interferometry (BLI) using Octet. Affinity was measured by immobilizing the antibody on sensors and dipping the sensors into wells containing different concentrations of RBD.

Kinetics of antibody binding to RBD were recorded during the association phase, after which the sensors were dipped into buffer without antibody to observe kinetics of antibody detaching from the RBD during the dissociation phase. Briefly, protein A biosensors (Pall ForteBio) were used to immobilize recombinant antibodies at 2.7 ug/ml for 1 minute, after a hydration step for 10 minutes with Kinetics Buffer (KB; 0.01% endotoxin-free BSA, 0.002^Tween-20, 0.005% NaN3 in PBS). Association curves were recorded for 5 minutes by incubating the antibody-coated sensors with different concentrations of SARS-CoV-1 RBD (Sino Biological) or SARS-CoV-2 RBD (produced in house in Expi-CHO cells; residues 331-550 of spike from BetaCoV/Wuhan-Hu-1/2019, accession number MN908947). The highest RBD concentration tested was 10 ug/ml, then 1:2.5 serially diluted. Dissociation was recorded for 9 minutes by moving the sensors to wells containing KB. Affinities, represented by KD values, were calculated using a global fit model (Octet). Octet Red96 (ForteBio) equipment was used.

FIGS. 6A-6E show association and dissociation curves for antibodies using the highest RBD concentration tested (10 m/ml). The switch from RBD solution to buffer is indicated with a vertical dashed line. Three cross-reactive antibodies (S303 rIgG1, S304 rIgG1 (VH of SEQ ID NO.: 79, VL of SEQ ID NO.:73), S309 rIgG1 (VH of SEQ ID NO.:105, VL of SEQ ID NO.:168) and two SARS-CoV-1 specific antibodies (S230 and S109) were tested. All antibodies showed strong binding to SARS-CoV-1 RBD. S230 and S109 did not bind to SARS-CoV-2 RBD. Binding of S303 rIgG1, S304 rIgG1, and S309 rIGg1 to SARS-CoV-2 RBD was in the nanomolar to sub-picomolar range, with S309 rIgG1 showing the highest affinity. KD values are indicated below the graphs in FIGS. 6A-6E. KD values are estimates (KD=<$1.0\times10^{-12}$M) if the antibody binding is very strong and dissociation is slow. An exact KD for S309 rIgG1 could not be measured by this assay since the dissociation was too slow.

Example 4

Neutralization of SARS-CoV-2 Infection

Replication-incompetent viruses pseudotyped with the SARS-CoV-2 S gene (isolate BetaCoV/Wuhan-Hu-1/2019; accession number MN908947) were produced using methods as previously described (Temperton N J, et al. (2005) Longitudinally profiling neutralizing antibody response to SARS coronavirus with pseudotypes. *Emerg Infect Dis* 11(3):411-416). Briefly, HEK293T/17 cells were cotransfected with a SARS-CoV-2 S-expressing plasmid (phCMV1, Genlantis) and with a complementing viral-genome reporter gene vector, pNL4-3. Luc+.E-R+. A single-cycle infectivity assay was used to measure the neutralization of luciferase-encoding virions pseudotyped with the SARS-CoV-2 S protein, as previously described (Temperton N J, et al. (2007) A sensitive retroviral pseudotype assay for influenza H5N1-neutralizing antibodies. *Influenza Other Respi Viruses* 1(3):105-112.). Briefly, appropriate dilutions of the virion-containing culture supernatants were preincubated at 37° C. for 1 h with antibodies at various concentrations, and the virus-mAb mixtures were then added to Vero E6 cells that had been seeded the day before infection. The cells were then lysed with Steady-Glo reagent (Promega, E2520), and the relative luminescence units (RLU) in the cell lysates were determined on a luminometer microplate reader (Synergy H1 Hybrid Multi-Mode Reader; Biotek). The reduction of infectivity was determined by comparing the RLU in the presence and absence of antibody and expressed as percentage of neutralization.

Figure 2A:
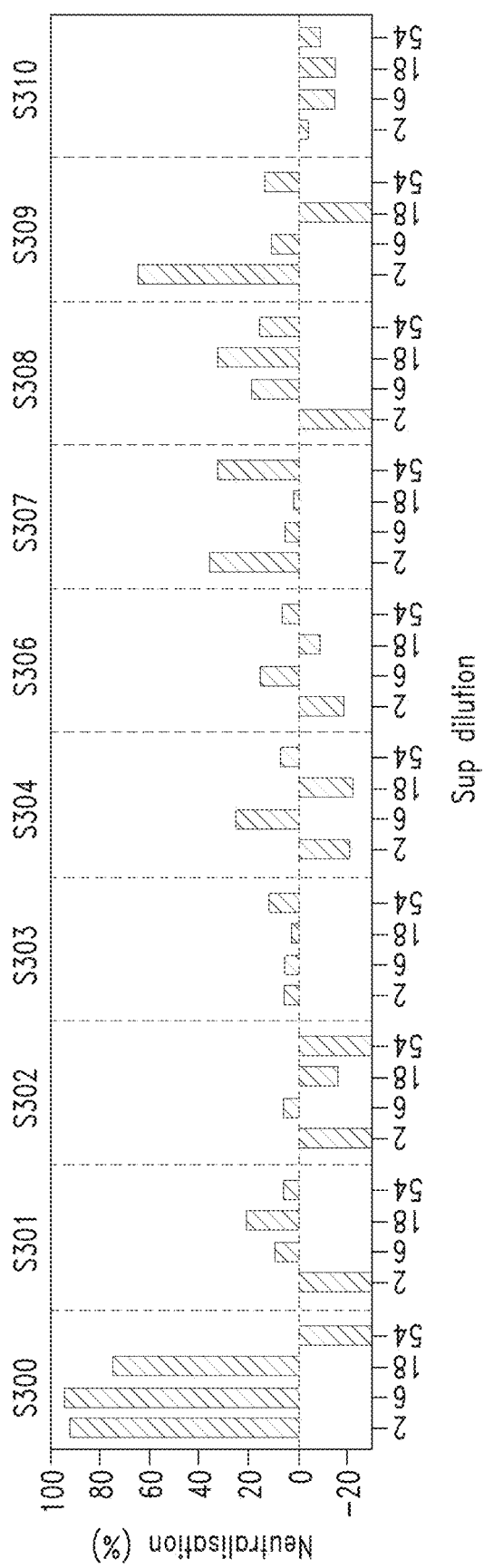
FIGS. 2A and 2B show SARS-CoV-2 neutralization of infection by certain antibodies of the present disclosure, as described in Example 4.
Figure 2B:
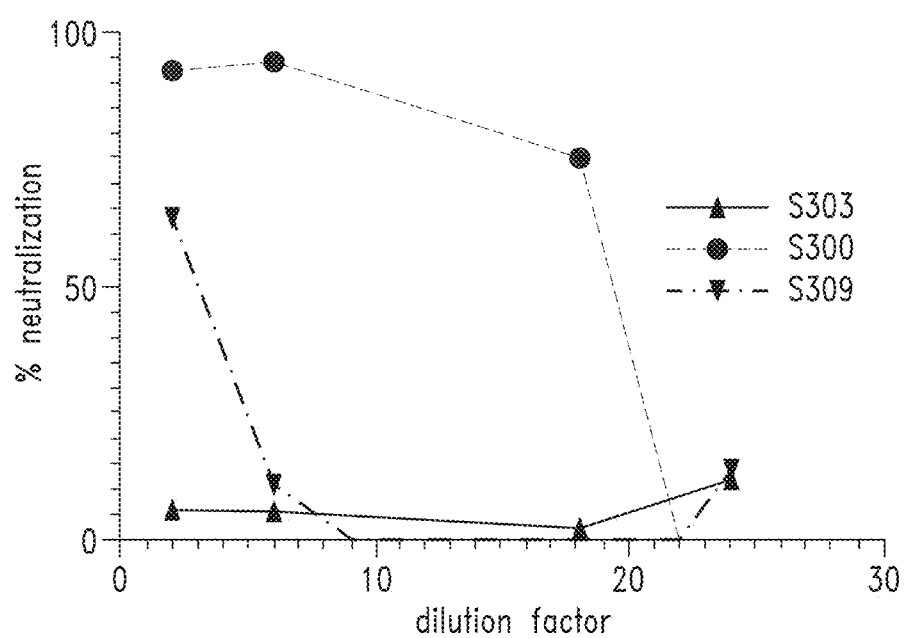

Antibodies S300-v1 (VH: SEQ ID NO.:1; VL: SEQ ID NO.:5), S301, S302, S303-v1 (VH SEQ ID NO.:63; VL SEQ ID NO.:67), S304 (VH SEQ ID NO.:79; VL SEQ ID NO.:83), S306 (VH SEQ ID NO.:87; VL SEQ ID NO.:91), S307 (VH SEQ ID NO.:239; VL SEQ ID NO.:243), S308-v1, S309 (comprising the S309-v1 VH sequence set forth in SEQ ID NO: 105 and the S309-v13 VL sequence set forth in SEQ ID NO: 168), and S310 were tested for neutralization function (Table 4, FIG. 2A). Antibodies SARS-CoV-2 S300-v1 and SARS-CoV-2 S309 neutralized SARS-CoV-2 infection (FIGS. 2A and 2B).

TABLE 4

Percent neutralization of infection by antibodies (titration series)

| Dilution | S300 | S301 | S302 | S303 | S304 | S306 | S307 | S308 | S309 | S310 |
|---|---|---|---|---|---|---|---|---|---|---|
| 2 | 93 | −31 | −47 | 6 | −21 | −19 | 36 | −46 | 65 | −4 |
| 6 | 94 | 10 | 6 | 5 | 25 | 15 | 5 | 19 | 11 | −15 |
| 18 | 75 | 21 | −16 | 2 | −22 | −9 | 2 | 32 | −29 | −15 |
| 54 | −41 | 7 | −60 | 12 | 7 | 6 | 32 | 16 | 14 | −6 |

Figure 3A:
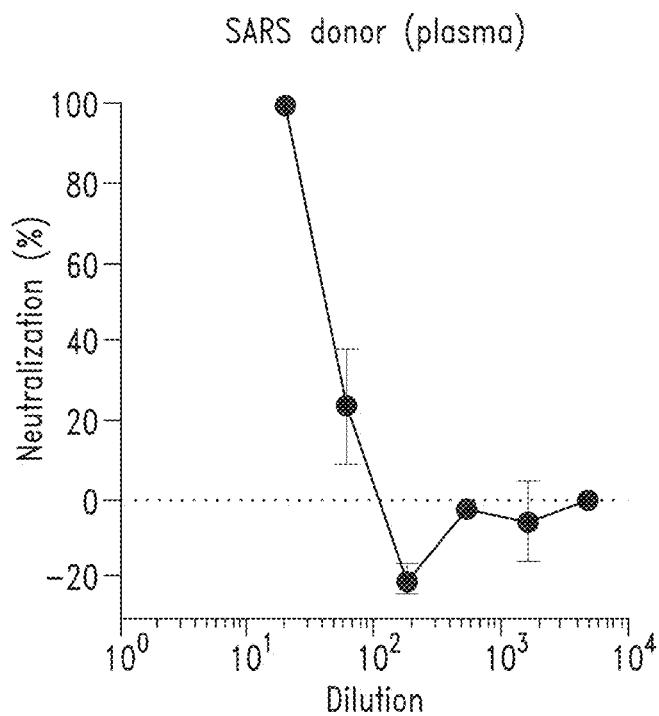
FIGS. 3A-3I show SARS-CoV-2 neutralization of infection, as described in Example 4.
Figure 3B:
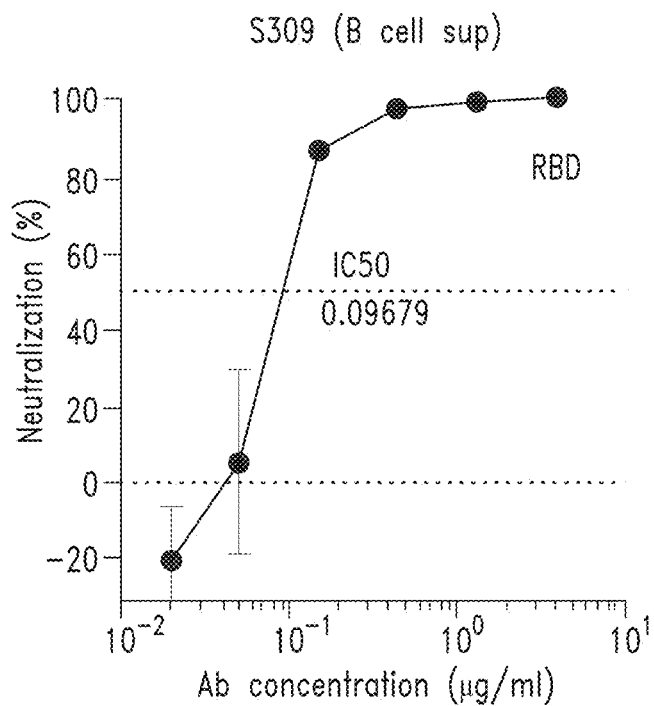
Figure 3C:
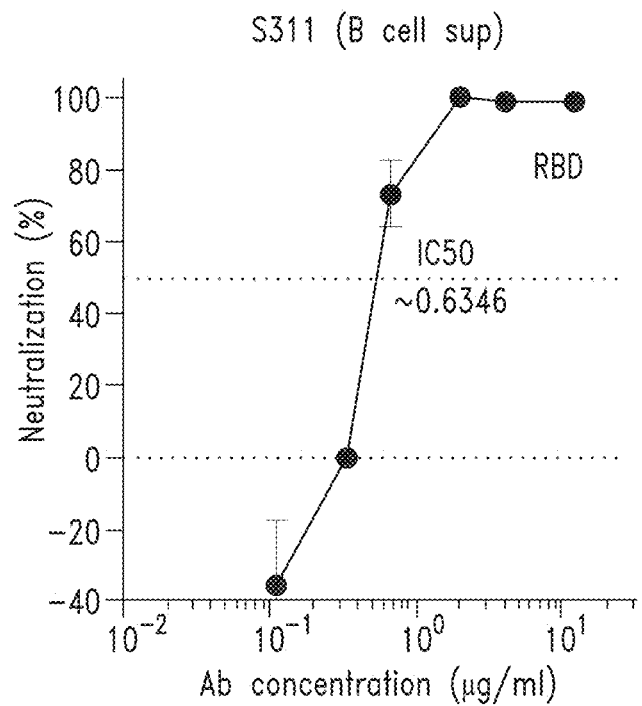
Figure 3D:
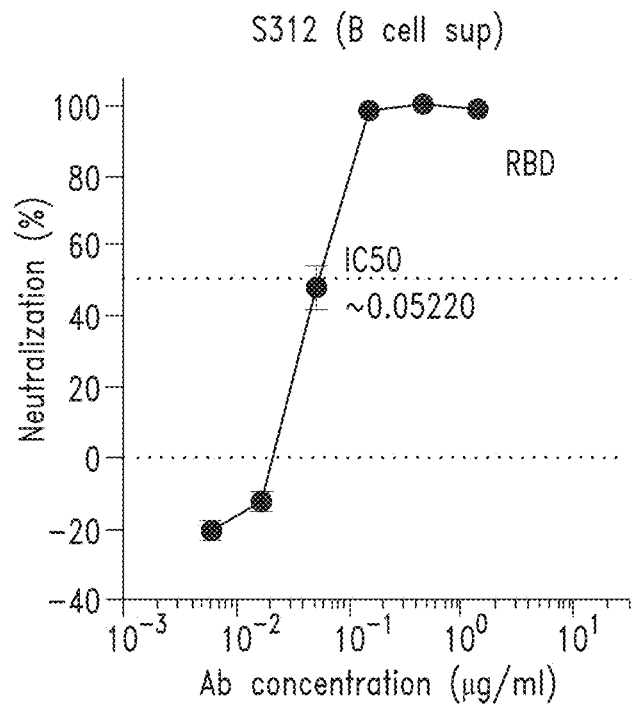
Figure 3E:
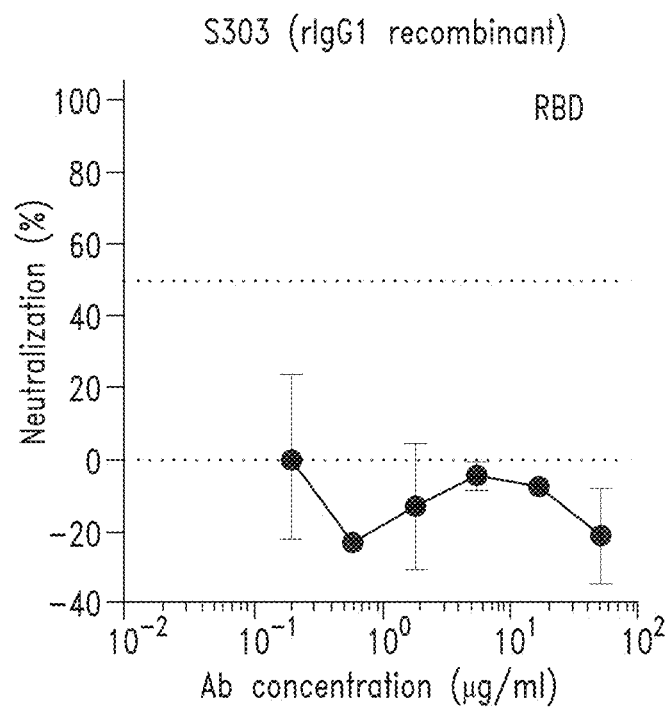
Figure 3F:
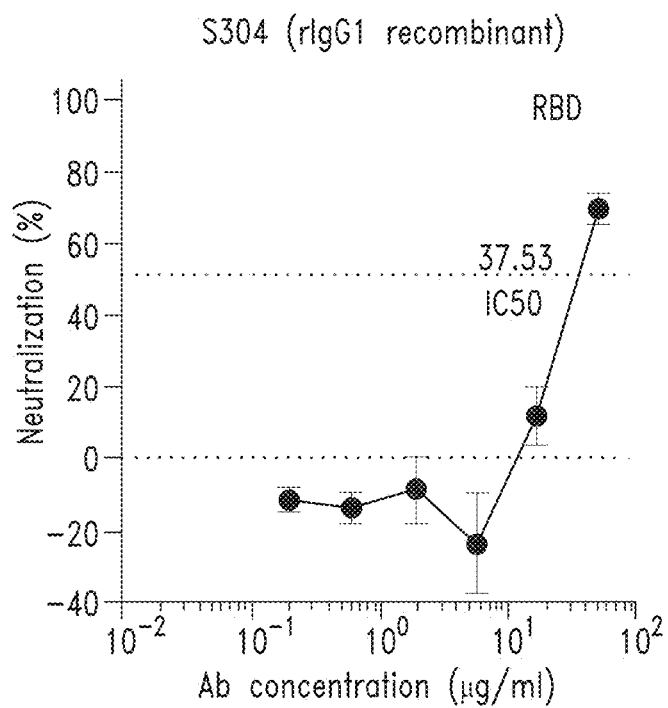
Figure 3G:
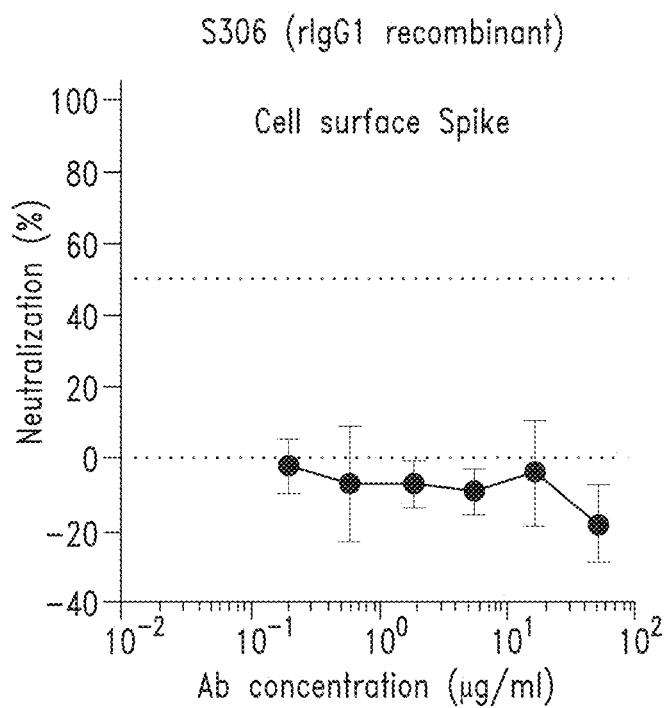
Figure 3H:
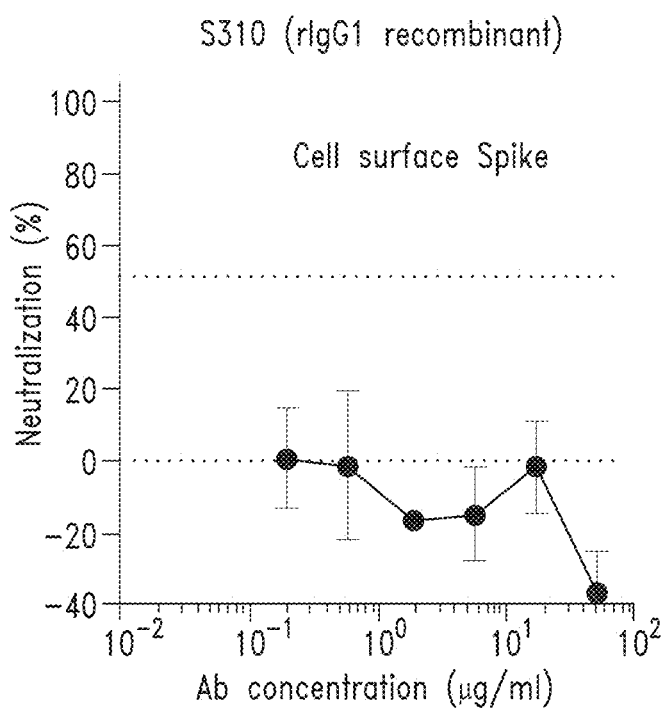
Figure 3I:
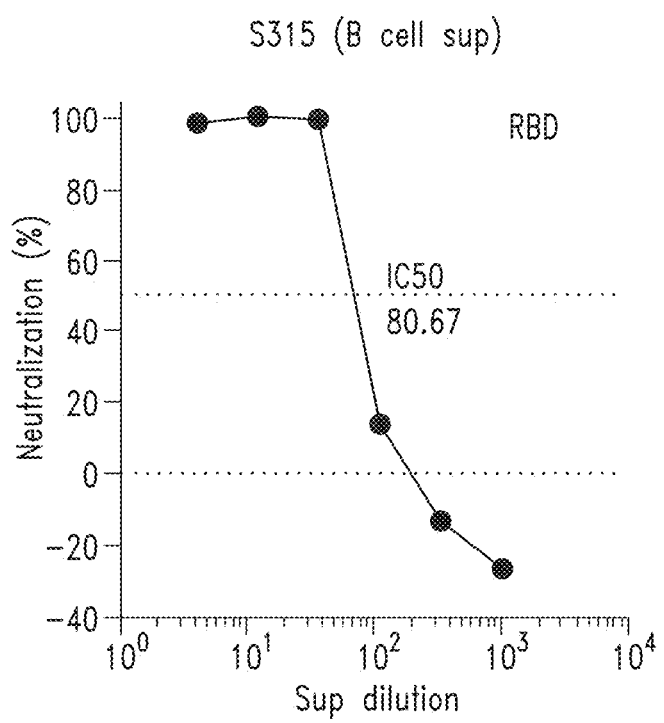

Additional neutralization assays were carried out using plasma from SARS CoV-1 survivors and antibodies SARS-CoV-2 S309, S311, S312, S303-v1 (rIgG1), S304 (rIgG1), S306 (rIgG1), S310 (rIgG1), and S315 (FIG. 3A-3I). FIG. 3A shows neutralizing activity of SARS-CoV donor plasma. FIGS. 3B-3D and 3I show neutralizing activity of supernatant from B cells producing S309, S311, S312, and S315, respectively. FIGS. 3E-3H show neutralizing activity of recombinant antibody at various concentrations. Using this assay, supernatant containing antibody S309, S311, S312, or S315 neutralizes SARS-CoV-2 infection.

Figure 13:
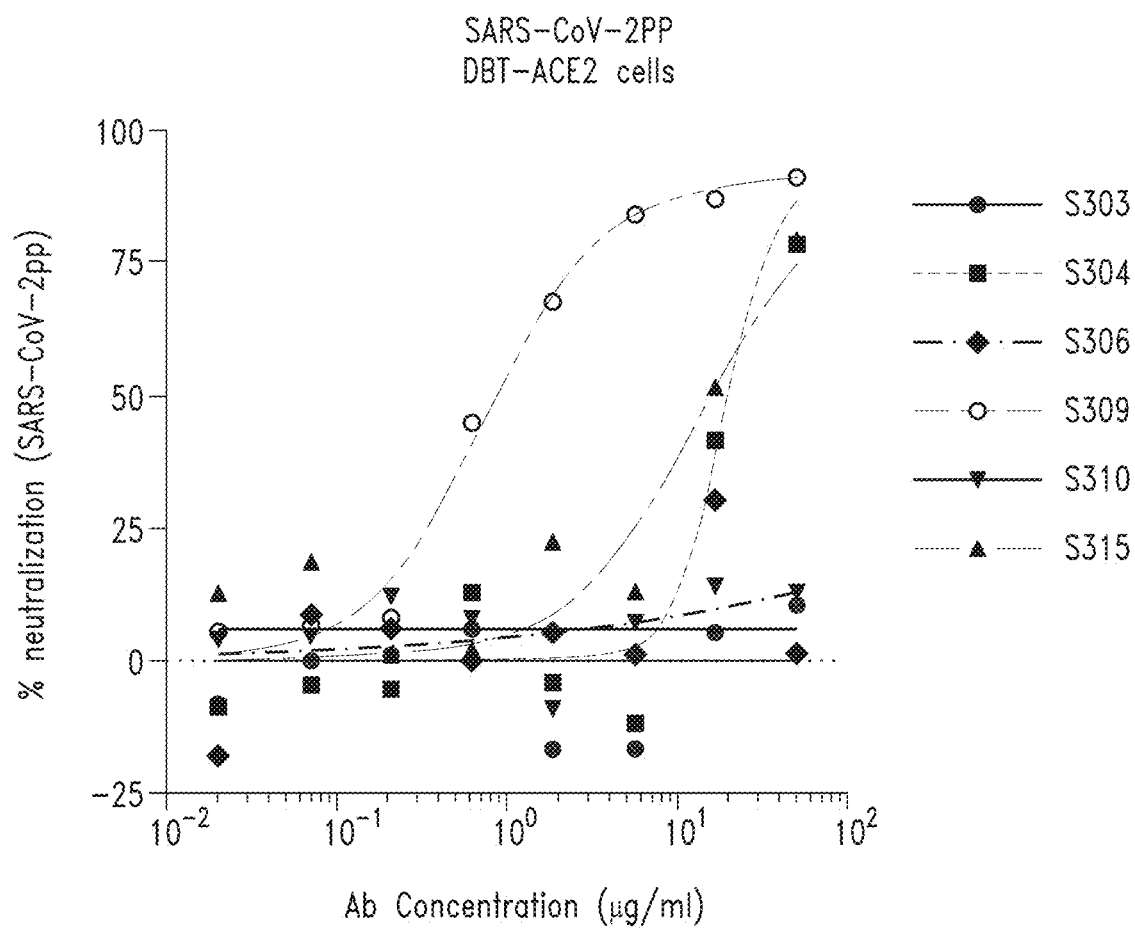
FIG. 13 shows neutralization of infection by antibodies S303 (VH SEQ ID NO.:63; VL SEQ ID NO:67), S304 (VH SEQ ID NO.:79; VL SEQ ID NO.:83), S306 (VH SEQ ID NO.:87; VL SEQ ID NO.:91), S309 (VH SEQ ID NO.:105; VL SEQ ID NO.:168), S310 (VH SEQ ID NO.:155; VL SEQ ID NO.:159), and S315 (VH SEQ ID NO.:178; VL SEQ ID NO.:182) against SARS-CoV-2 pseudotyped virus, as described in Example 4.
Figure 14A:
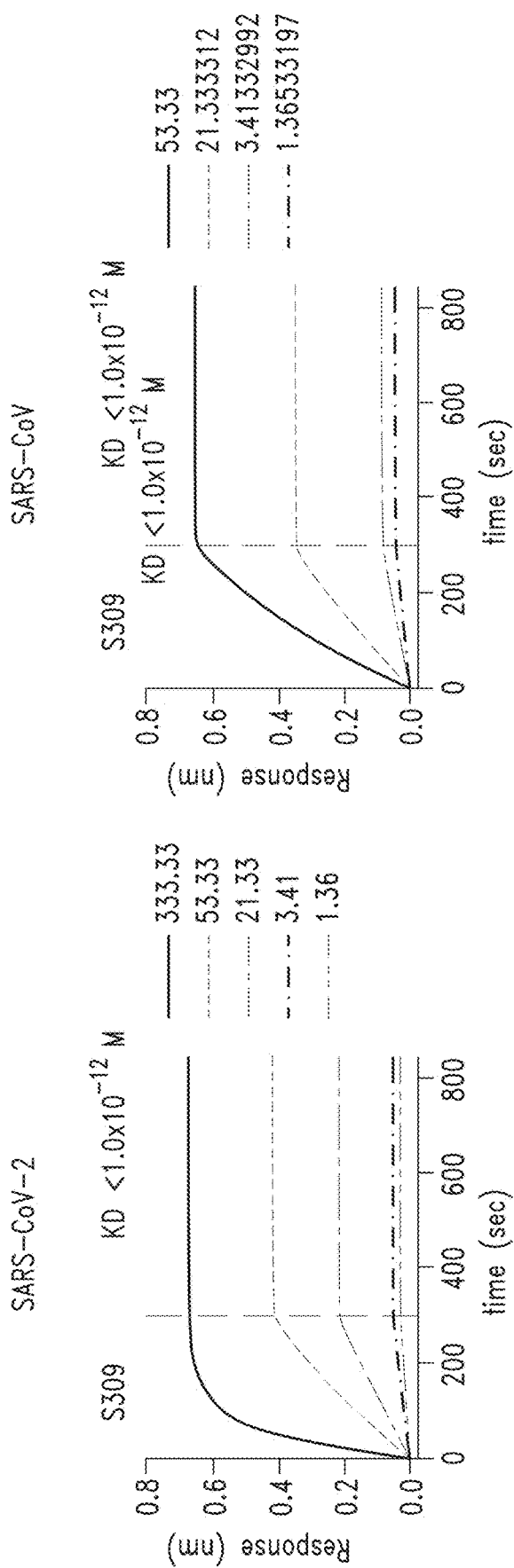
FIGS. 14A-14D show binding affinity/avidity of antibodies S309 (VH SEQ ID NO.:105; VL SEQ ID NO.:168), S303 (VH SEQ ID NO.:63; VL SEQ ID NO:67), S304 (VH SEQ ID NO.:79; VL SEQ ID NO.:83), and S315 (VH SEQ ID NO.:178; VL SEQ ID NO.:182) to RBD of SARS-CoV-1 (right panels) and SARS-CoV-2 (left panels), as described in Example 10.
Figure 14B:
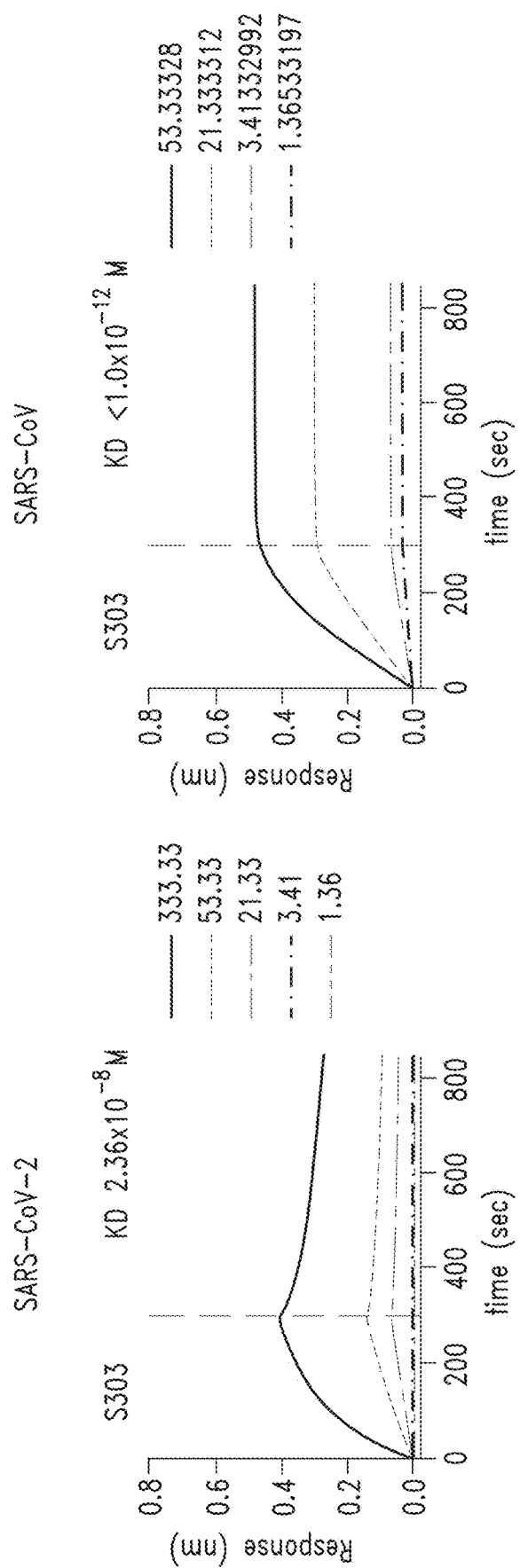
Figure 14C:
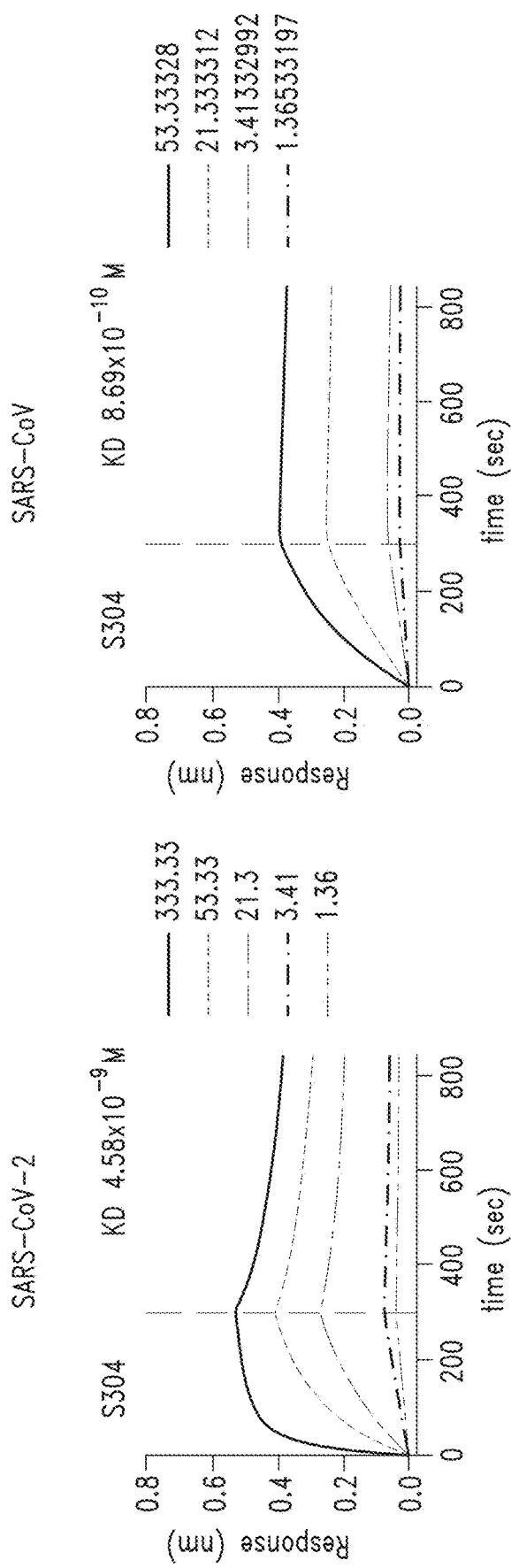
Figure 14D:
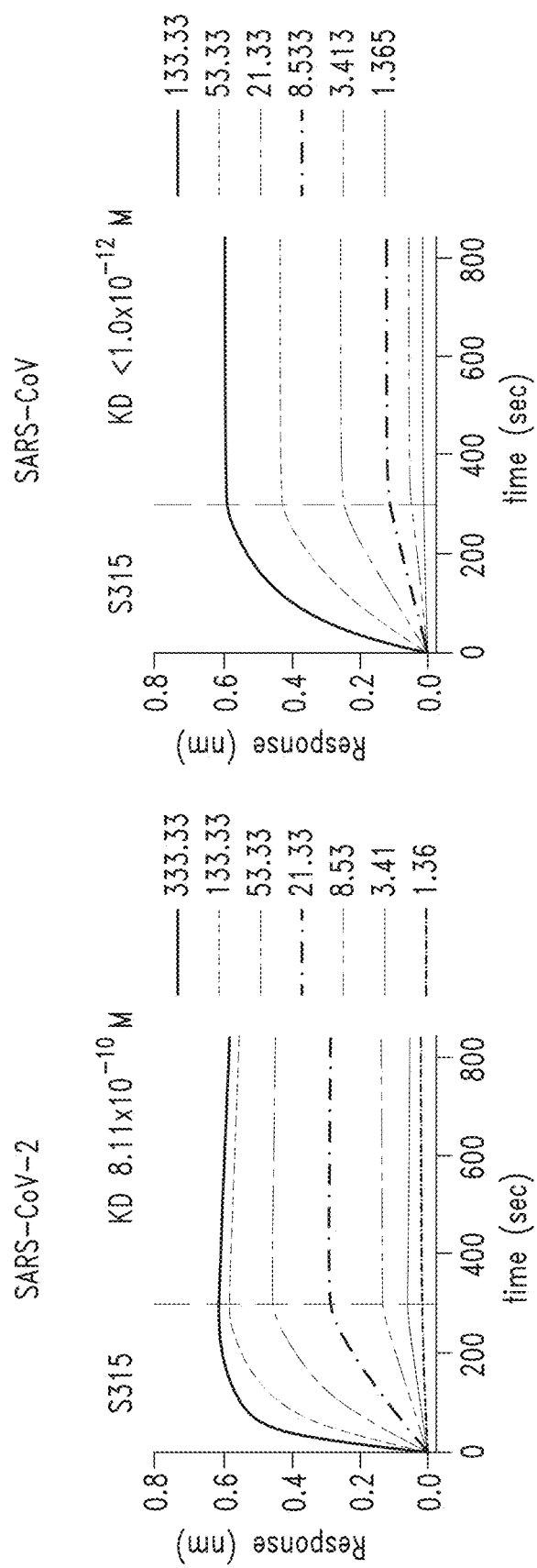
Figure 34:
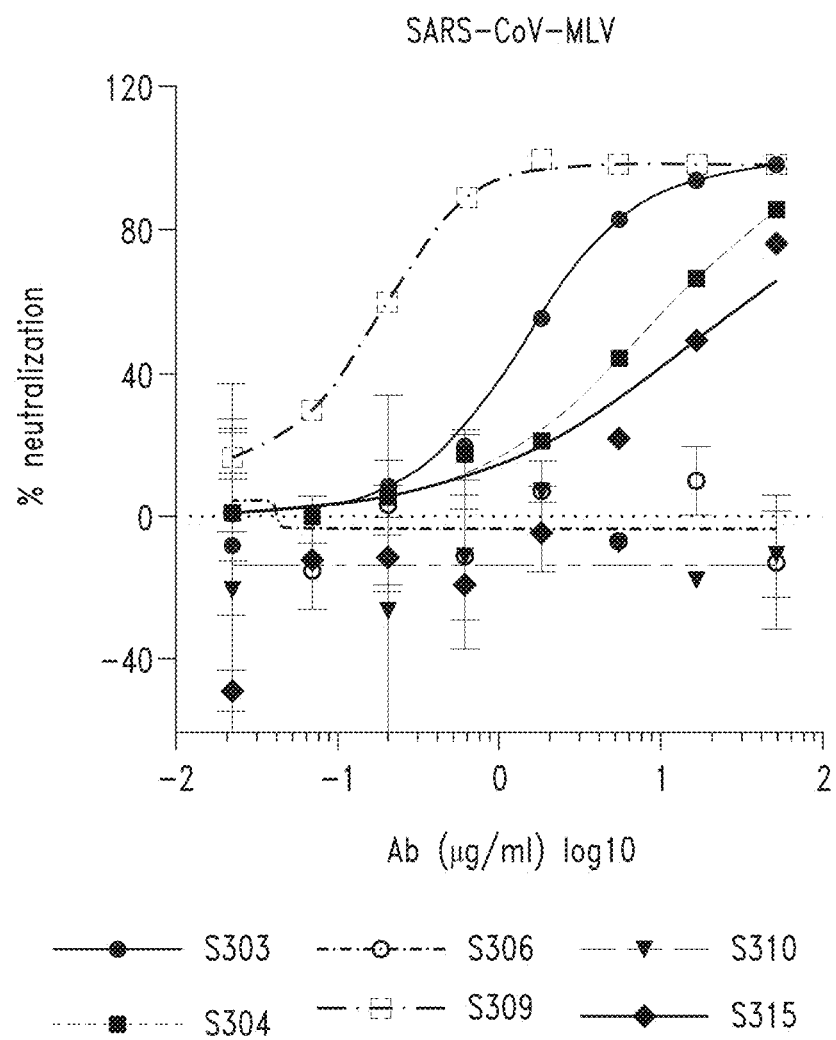
FIG. 34 shows neutralization of infection by exemplary antibodies S303 (VH SEQ ID NO.:63; VL SEQ ID NO:67), S304 (VH SEQ ID NO.:79; VL SEQ ID NO.:83), S306 (VH SEQ ID NO.:87; VL SEQ ID NO.:91), S309 (VH SEQ ID NO.:105; VL SEQ ID NO.:168), S310 (VH SEQ ID NO.: 155; VL SEQ ID NO.:159), and S315 (VH SEQ ID NO.: 178; VL SEQ ID NO.:182) against SARS-CoV-1 pseudotyped virus. See Example 4.
Figure 36:
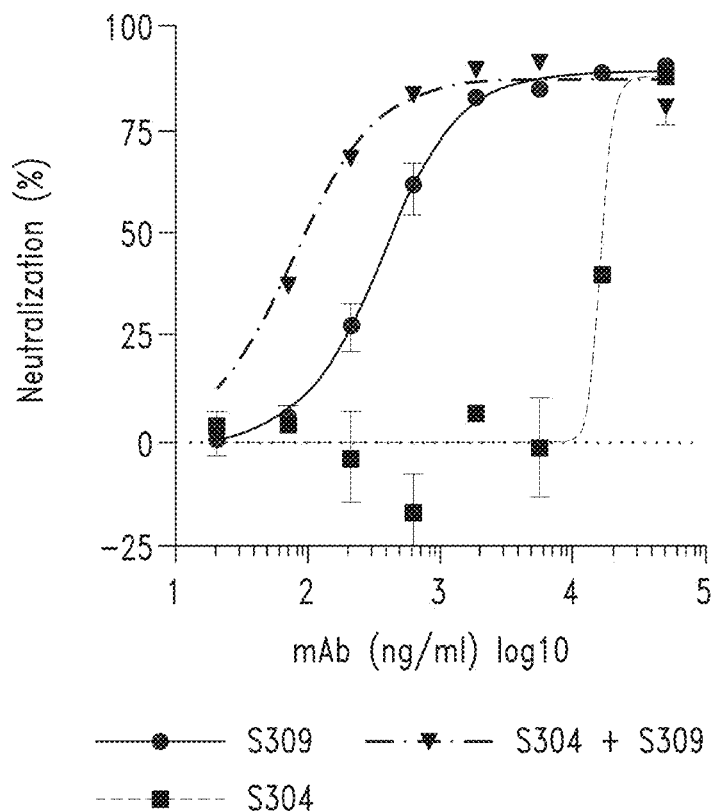
FIG. 36 shows neutralization of SARS-CoV-2-MLV by antibody S309 (VH SEQ ID NO.:105; VL SEQ ID NO.:168) combined with an equimolar amount of antibody S304 (VH SEQ ID NO.:79; VL SEQ ID NO.:83). For antibody cocktails, the concentration shown on the x axis is that of the individual antibodies. See Example 4.
Figure 37:
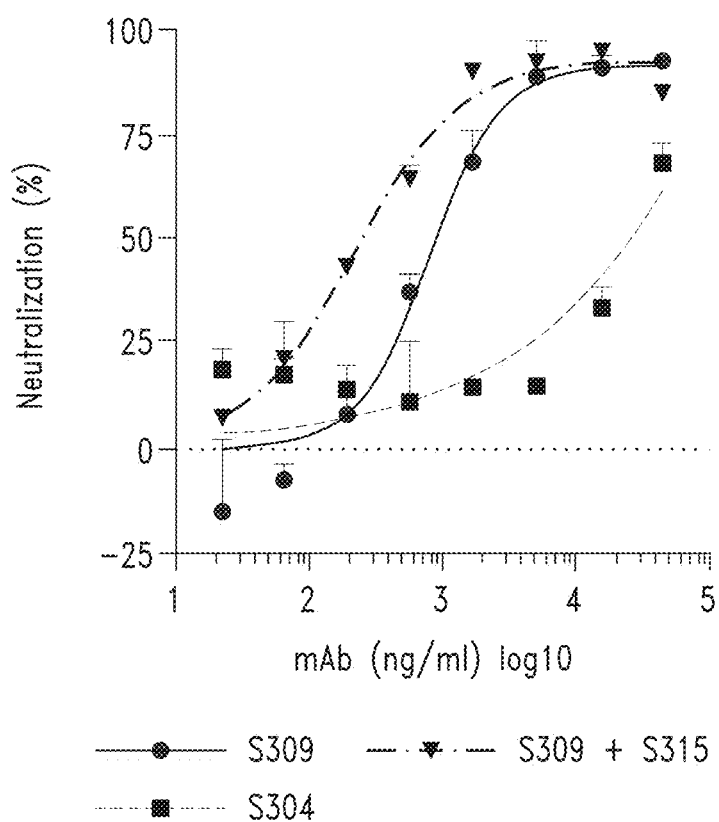
FIG. 37 shows neutralization of SARS-CoV2-MLV by S309 (VH SEQ ID NO.:105; VL SEQ ID NO.:168) combined with an equimolar amount of antibody S315 (VH SEQ ID NO.:178; VL SEQ ID NO.:182) antibodies. For antibody cocktails, the concentration shown on the x axis is that of the individual antibodies. See Example 4.

Additional neutralization assays were carried out using antibodies S303, S304, S306, S309 (VH SEQ ID NO.:105; VL SEQ ID NO.:168), S310, and S315. FIG. 13 shows neutralizing activity of these antibodies at various concentrations against SARS-CoV-2 pseudotyped MLV. DBT cells stably transfected with ACE2 (DBT-ACE2) were used as target cells. FIG. 34 shows neutralizing activity against SARS-CoV-1 pseudotyped MLV by these antibodies at various concentrations. Additional neutralization data for S304, S309, S304+S309, S315, and S315+S309 are shown in FIGS. 36 and 37.

Example 5

Neutralization of SARS-CoV-2 Infection

Neutralizing activity of two SARS-CoV-1 and SARS-CoV-2 cross-neutralizing antibodies, S304 rIgG1 and S309 (VH: SEQ ID NO.:105; VL: SEQ ID NO.:168) rIgG1, against SARS-CoV-2 pseudotyped viruses (SARS-CoV-2pp) was assessed.

Murine leukemia virus (MLV) pseudotyped with SARS-CoV-2 Spike protein (SARS-CoV-2pp) was used. DBT cells stably transfected with ACE2 (DBT-ACE2) were used as target cells. SARS-CoV-2pp was activated with trypsin TPCK at 10 µg/ml. Activated SARS-CoV-2pp was added to a dilution series of antibodies (starting with 50 µg/ml final concentration per antibody, 3-fold dilution). Antibodies were tested at concentrations from 50 µg/ml to 0.02 µg/ml. For the combination of S304 rIgG1 and S309 rIgG1, starting concentrations were 50 µg/ml for each antibody, i.e. the total starting antibody concentration was 100 µg/ml. DBT-ACE2 cells were added to the antibody-virus mixtures and incubated for 48 hours. Luminescence was measured after aspirating cell culture supernatant and adding steady-GLO substrate (Promega).

Figure 7:
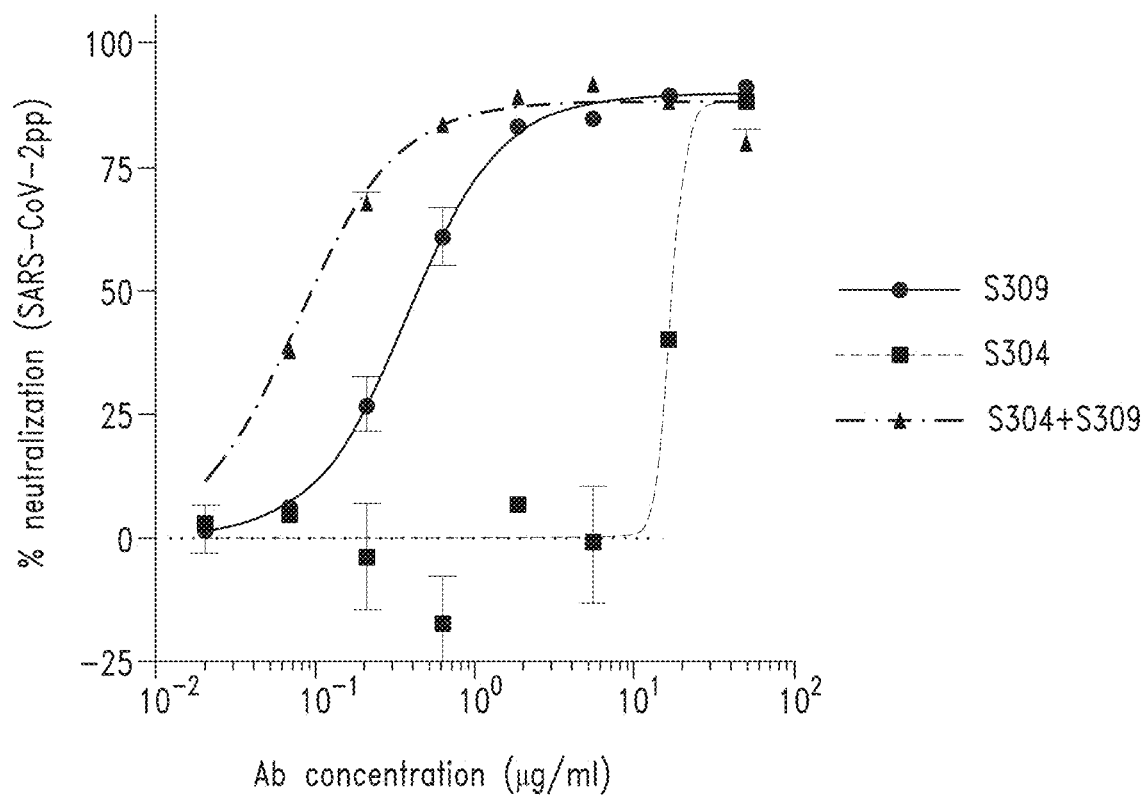
FIG. 7 shows neutralization of infection by S304 (VH SEQ ID NO.:79; VL SEQ ID NO.:83) and S309 (VH SEQ ID NO.:105; VL SEQ ID NO.:168) antibodies, alone or in combination, against SARS-CoV-2 pseudotyped virus, as described in Example 5.
Figure 8A:
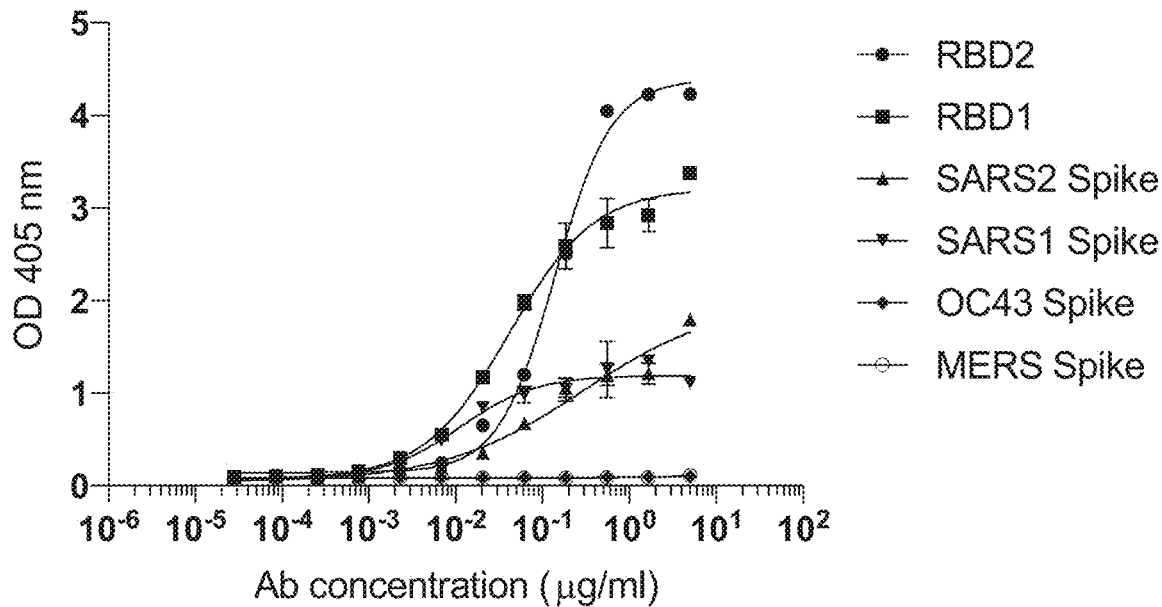
FIGS. 8A-8K show binding curves of certain antibodies for RBD of SARS-CoV-1, RBD of SARS-CoV-2, and ectodomains of various coronaviruses, as measured by ELISA. See Example 8.
Figure 8B:
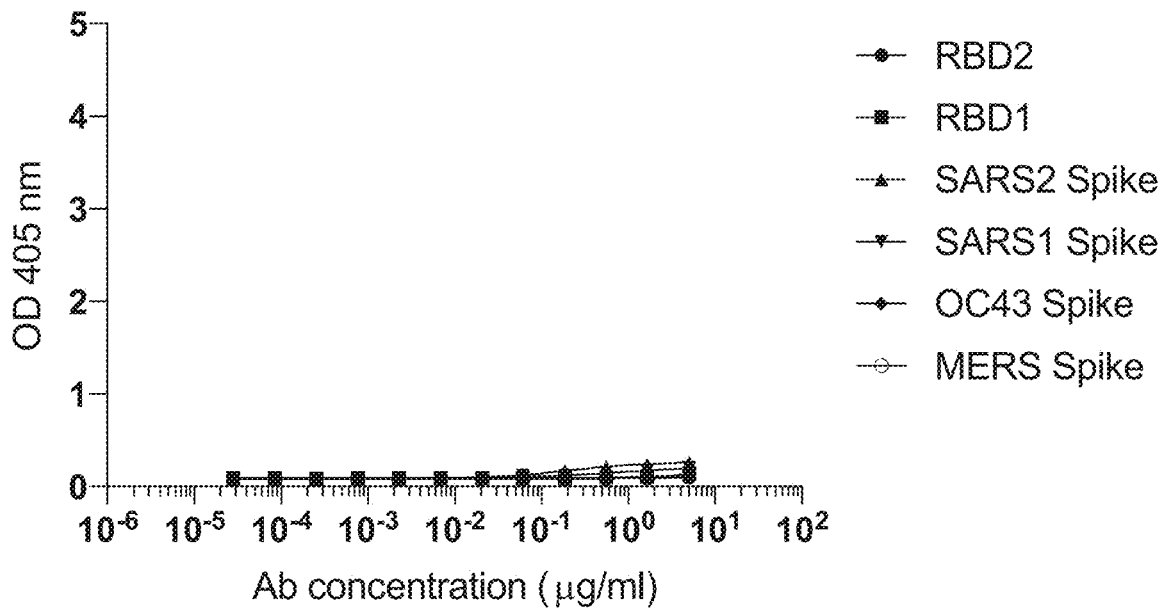
Figure 8C:
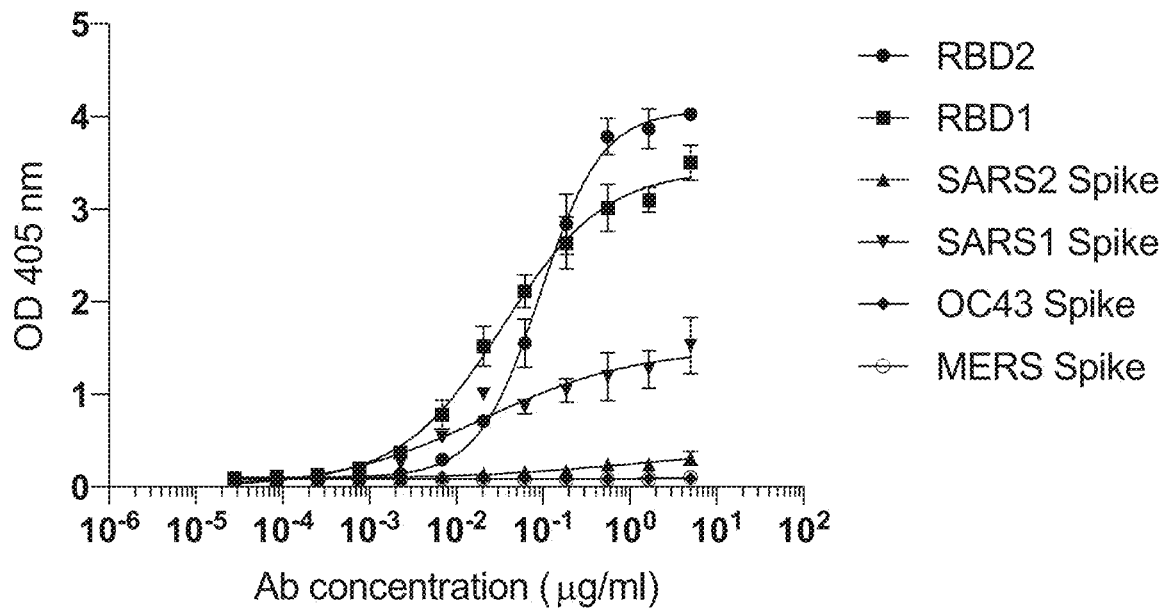
Figure 8D:
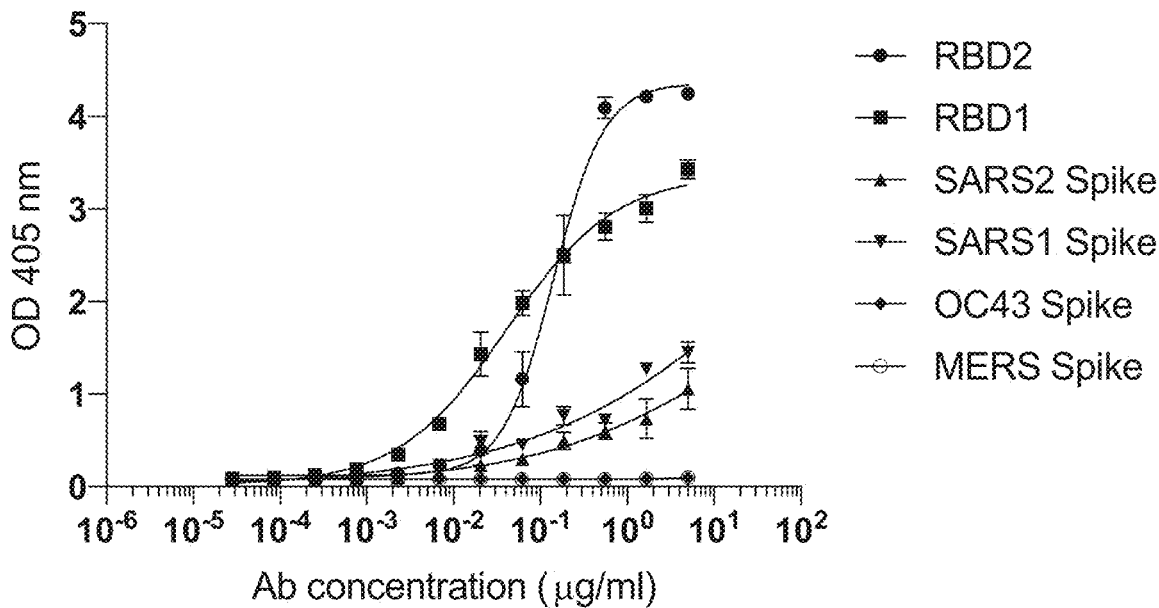
Figure 8E:
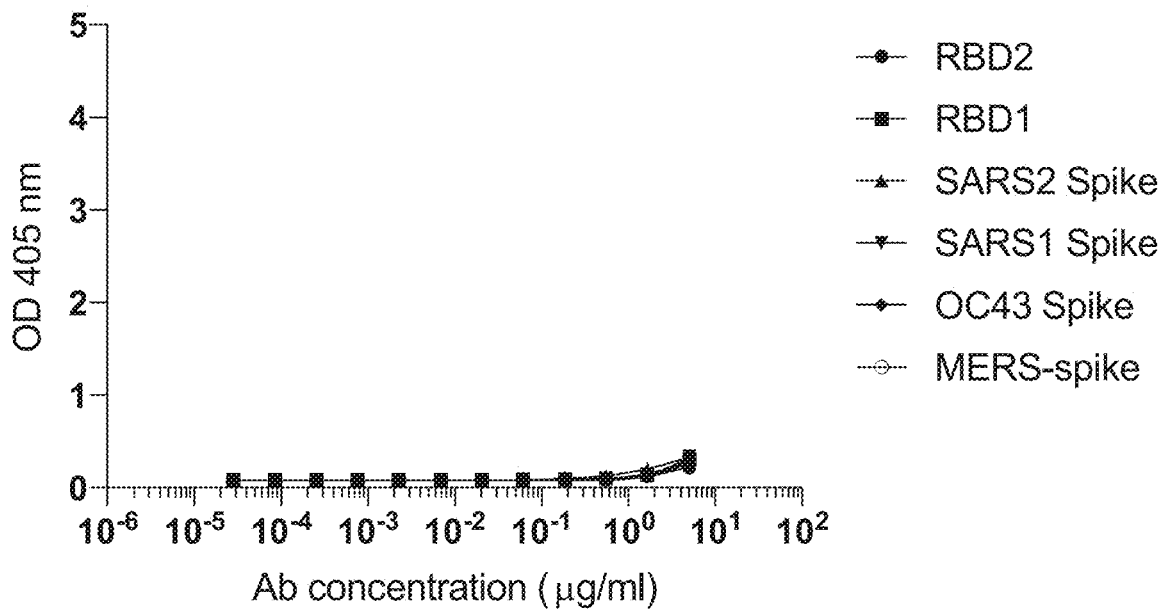
Figure 8F:
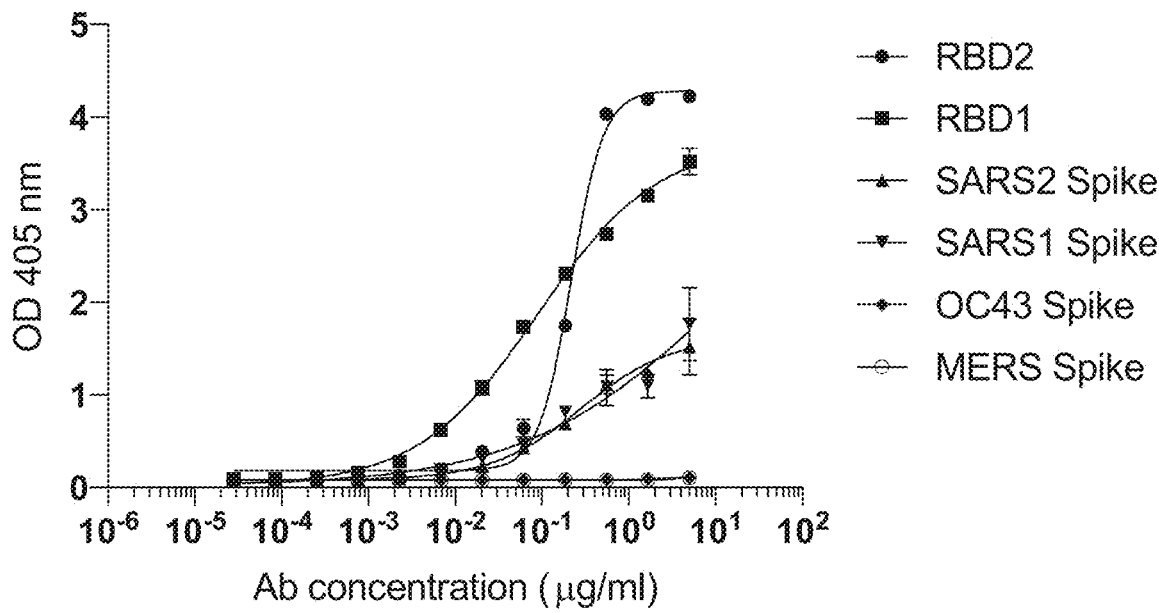
Figure 8G:
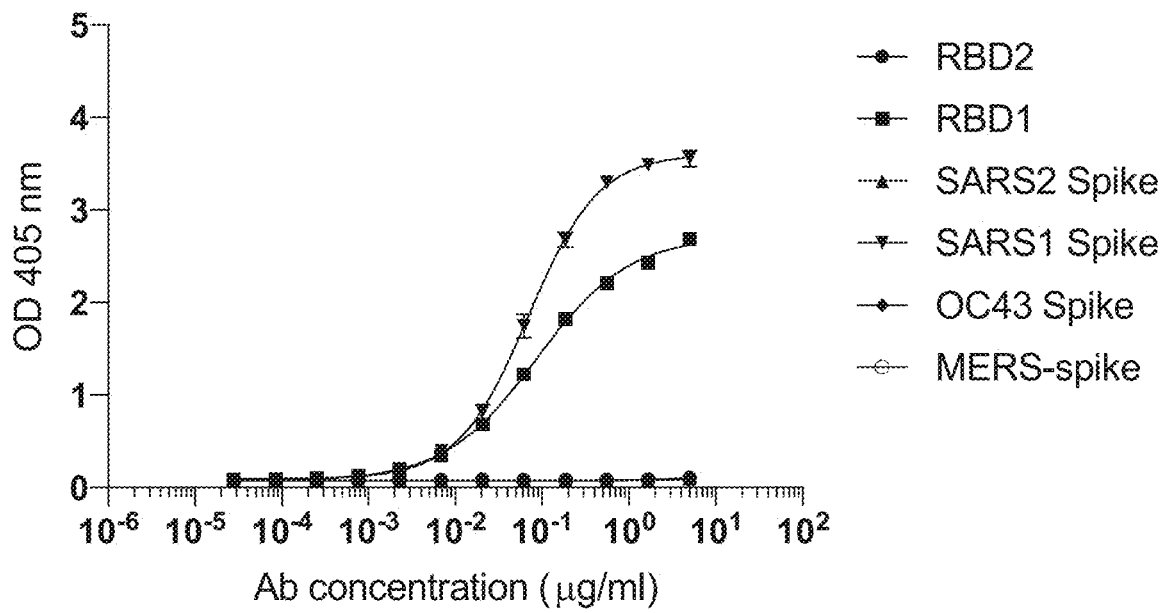
Figure 8H:
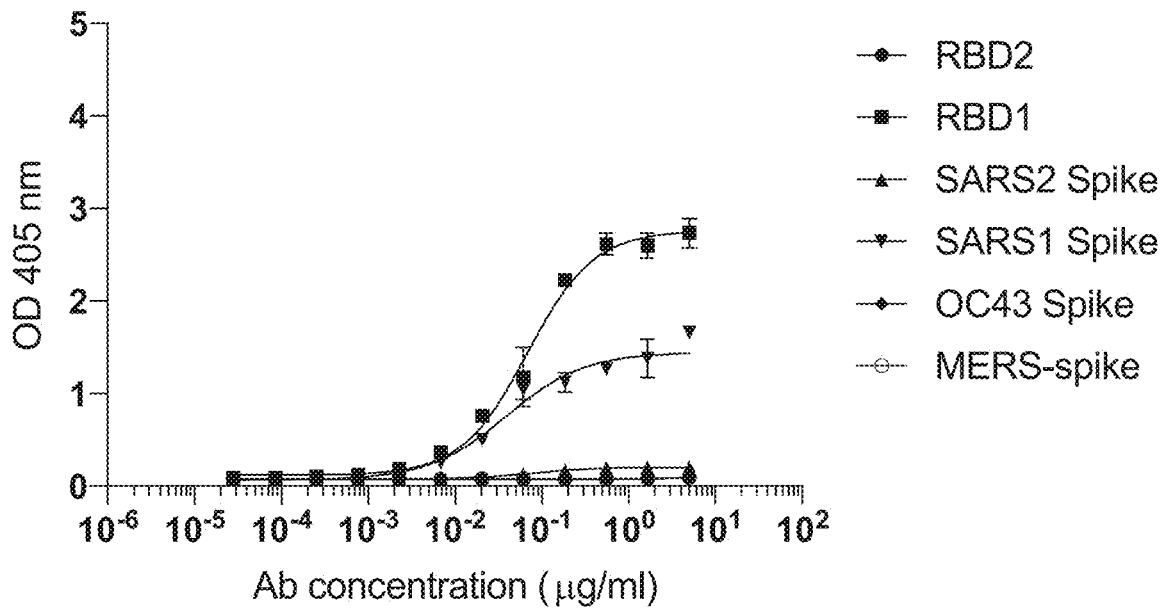
Figure 8I:
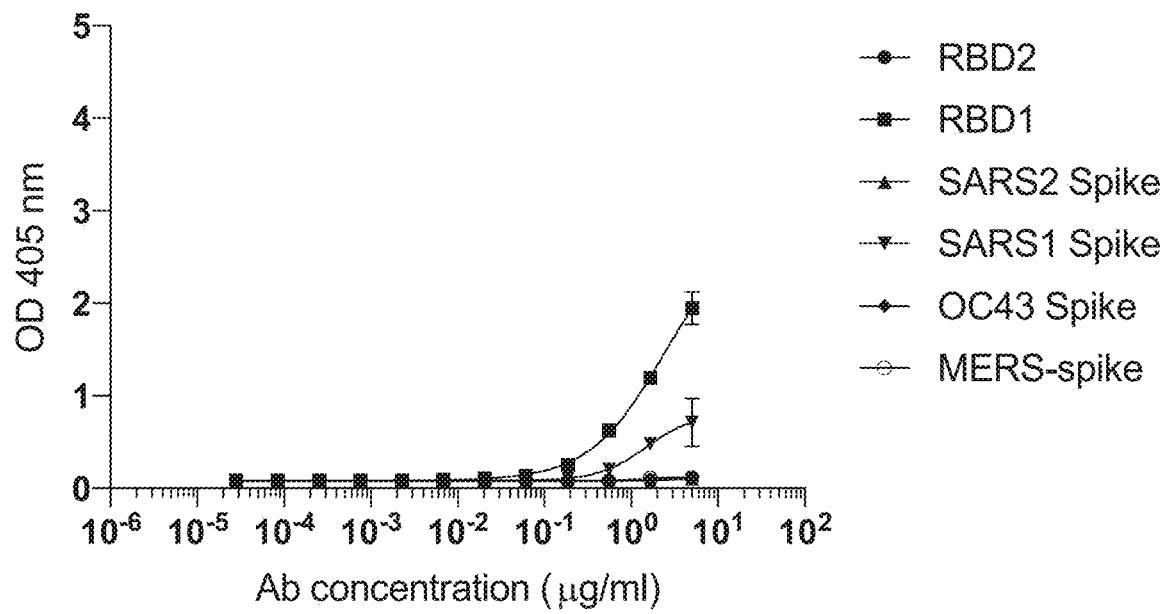
Figure 8J:
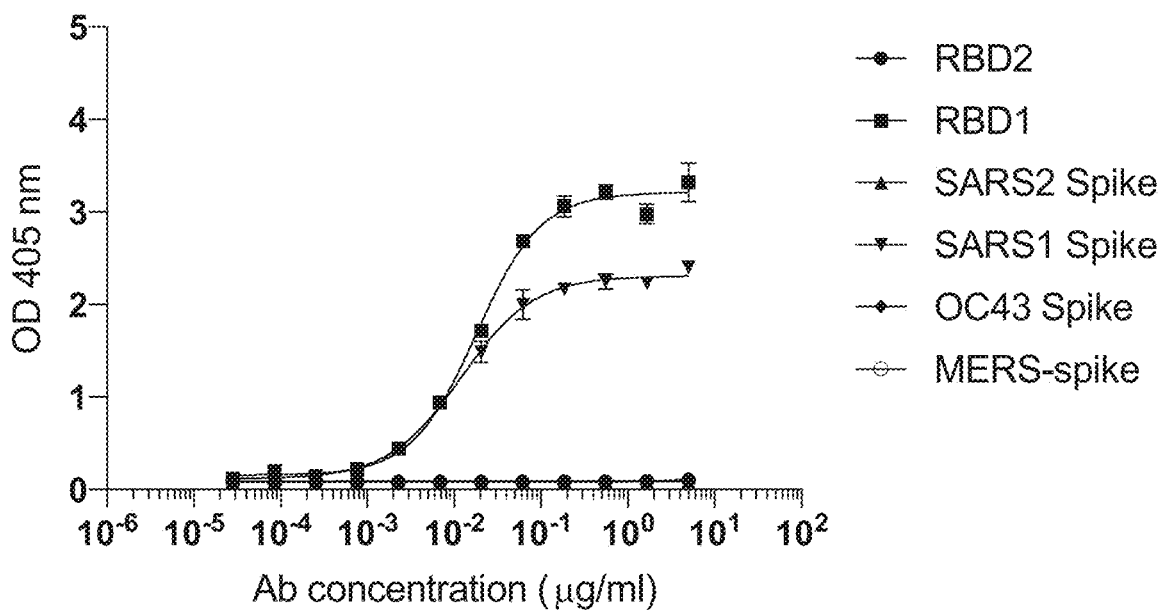
Figure 8K:
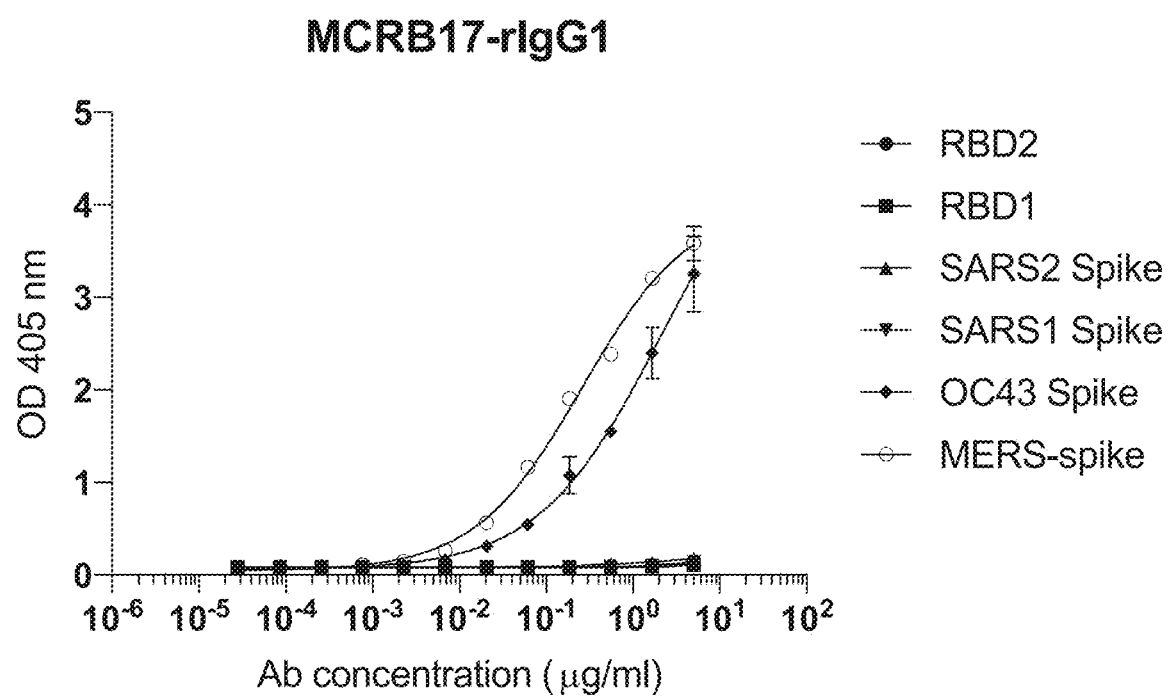

In this assay, S309 rIgG1 exhibited a neutralization of infection IC50 of 0.37 µg/ml, and S304 rIgG1 exhibited an IC50 of approximately 17 µg/ml. A combination of these two antibodies exhibited an IC50 of 0.077 µg/ml. See FIG. 7 and Table 5.

TABLE 5

| IC50 (µg/ml) of antibodies | | | |
|---|---|---|---|
| | S309 | S304 | S304 + S309 |
| IC50 | 0.3707 | ~16.95 | 0.07704 |

Figure 23:
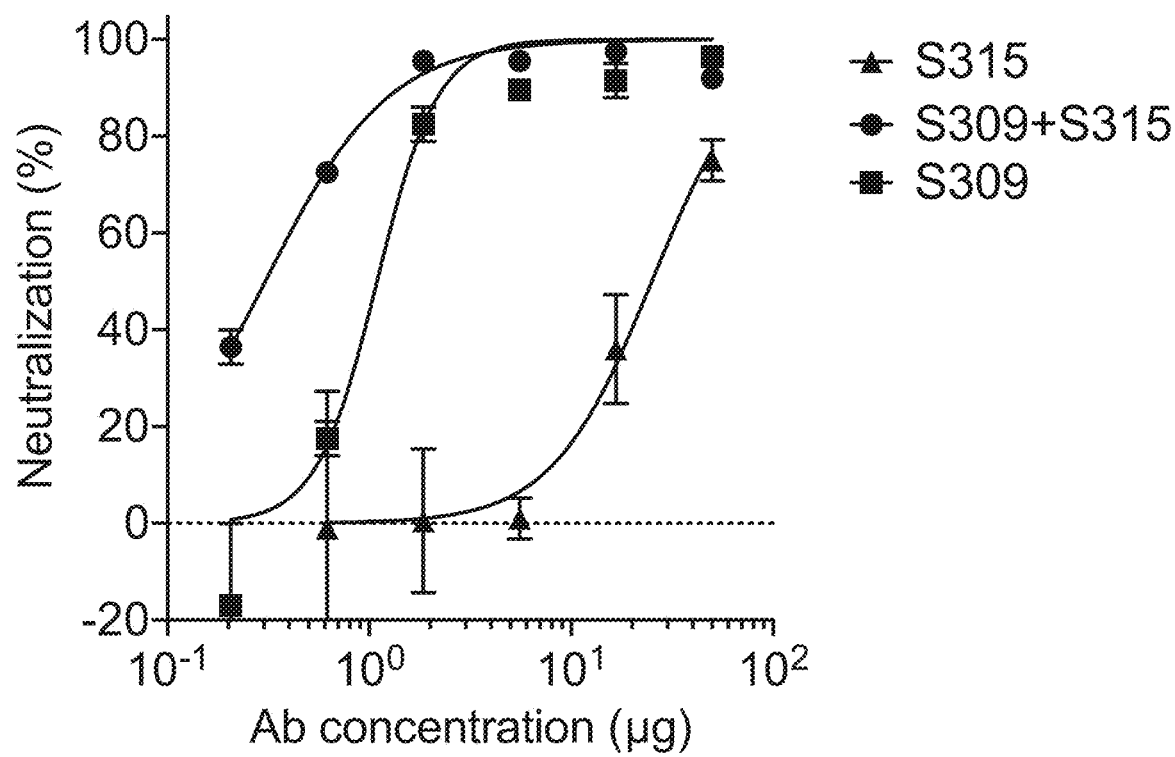
FIG. 23 shows neutralization of infection by antibodies S309 (VH SEQ ID NO.:105; VL SEQ ID NO.:168) and S315 (VH SEQ ID NO.:178; VL SEQ ID NO.:182), alone or in combination, against SARS-CoV-2 pseudotyped virus, as described in Example 5.

Further neutralization assays were carried out using the same procedure for recombinant monoclonal antibodies S309 and S315, singly and in combination. In this assay, S309 exhibited an IC50 of 1.091 µg/ml, and S315 exhibited an IC50 of 25.1 µg/ml. The combination of both of these antibodies exhibited an IC50 of 0.3047 µg/ml. See FIG. 23 and Table 6.

TABLE 6

| IC50 (µg/ml) of antibodies and antibody combination | | |
|---|---|---|
| S309 + S315 | S309 | S315 |
| IC50 0.3047 | 1.091 | 25.10 |

Example 6

Reactivity of Human Monoclonal Antibodies Against SARS-CoV and SARS-CoV-2

Reactivity of additional human mAbs "S311" and "S312" against the spike S1 subunit protein and the RBD of SARS-CoV and SARS-CoV-2 protein was assessed by enzyme-linked immunosorbent assay (ELISA).

96-well plates were coated with recombinant SARS-CoV-2 Spike S1 Subunit Protein (Sino Biological), SARS-CoV-2 RBD (Sino Biological or produced in house; residues 331-550 of spike from BetaCoV/Wuhan-Hu-1/2019, accession number MN908947), recombinant SARS-CoV Spike S1 Subunit Protein (Sino Biological), or SARS-CoV RBD (Sino Biological).

Wells were washed and blocked with PBS+1% BSA for 1 hour at room temperature, and were then incubated with serially diluted mAbs for 1 hour at room temperature. Bound mAbs were detected by incubating alkaline phosphatase-conjugated goat anti-human IgG (Southern Biotechnology: 2040-04) for 1 hour at room temperature, and were developed by 1 mg/ml p-nitrophenylphosphate substrate in 0.1 M glycine buffer (pH 10.4) for 30 min at room temperature. Optical density (OD) values were measured at a wavelength of 405 nm in an ELISA reader (Powerwave 340/96 spectrophotometer, BioTek).

Figure 5A:
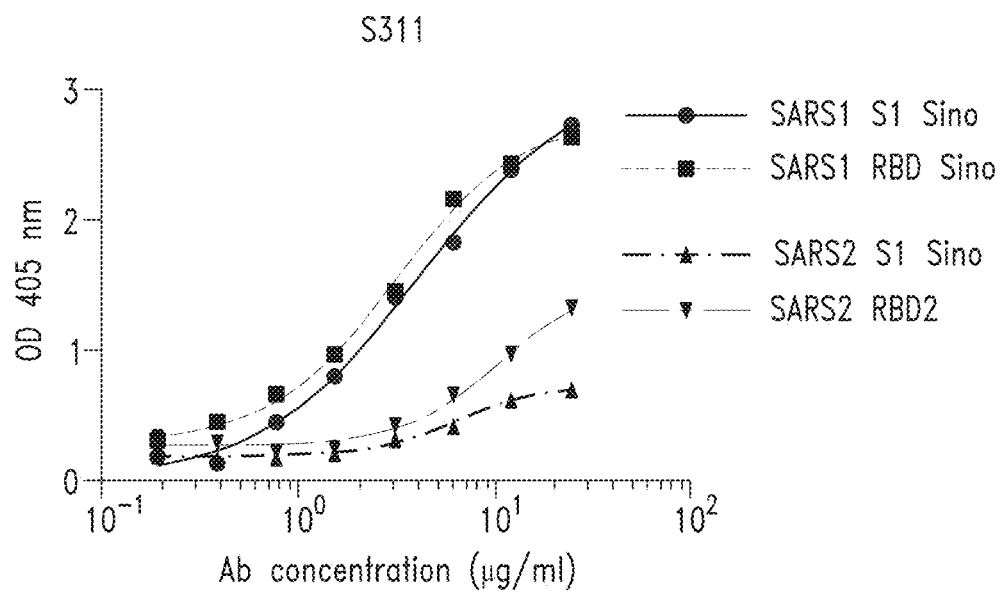
FIGS. 5A and 5B show binding of antibodies S311 and S312 in the supernatant of cultured B cells to SARS-CoV-1 and SARS-CoV-2, as described in Example 6. Antibody concentrations are estimates. SARS S1 Sino: protein from Sino Biological. RBD2: RBD of SARS-CoV-2 produced in-house.
Figure 5B:
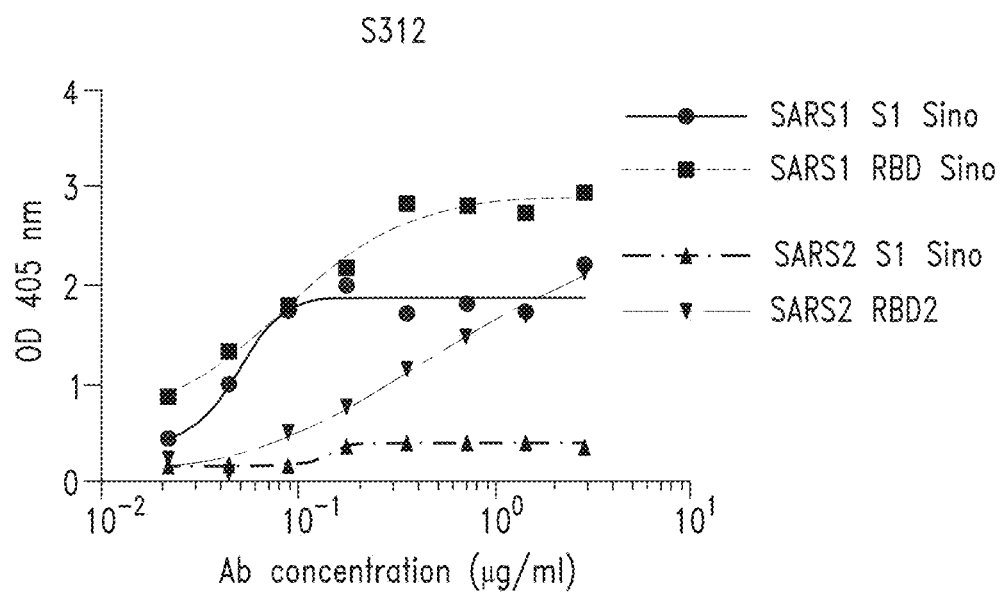
Figure 6A:
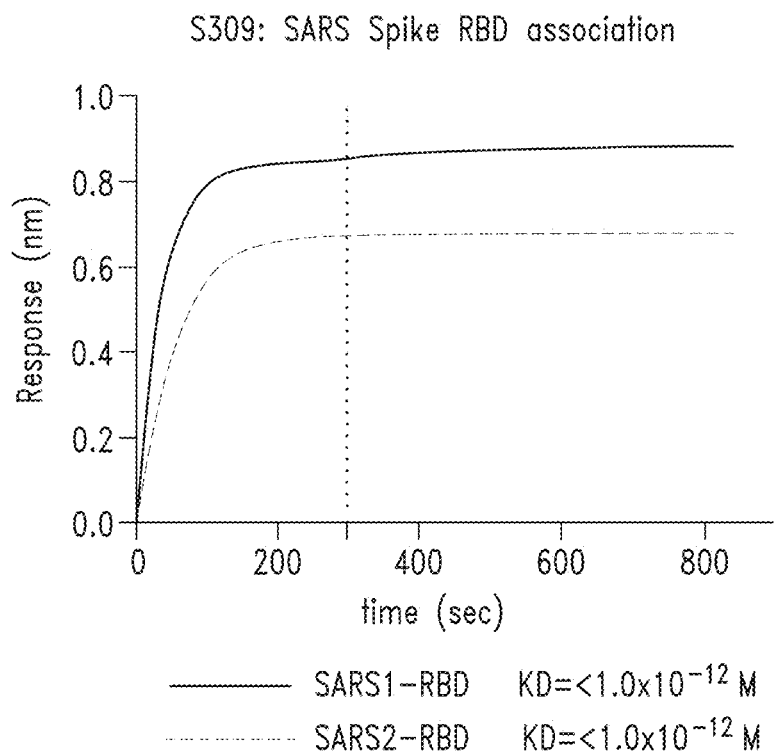
FIGS. 6A-6E show (top) binding curves of certain antibodies of the present disclosure for SARS-CoV-1 (SARS1) RBD and SARS-CoV-2 (SARS2) RBD, as measured by Octet, and (bottom) KD values. KD values for antibodies (e.g., $<1.0\times10^{-12}$ M) with very strong binding and slow dissociation are estimates. These data and experiments are described further in Example 3.
Figure 6B:
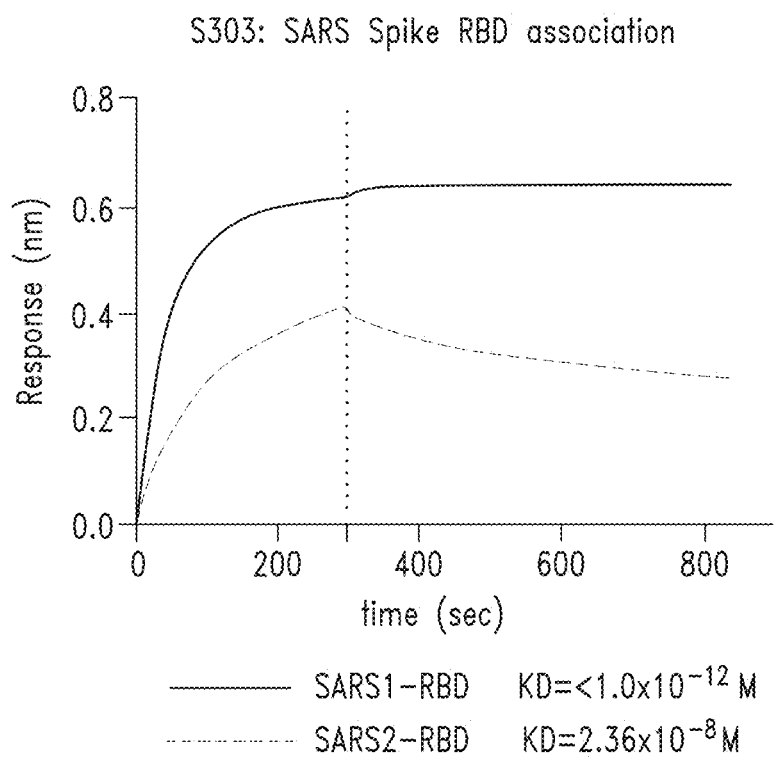
Figure 6C:
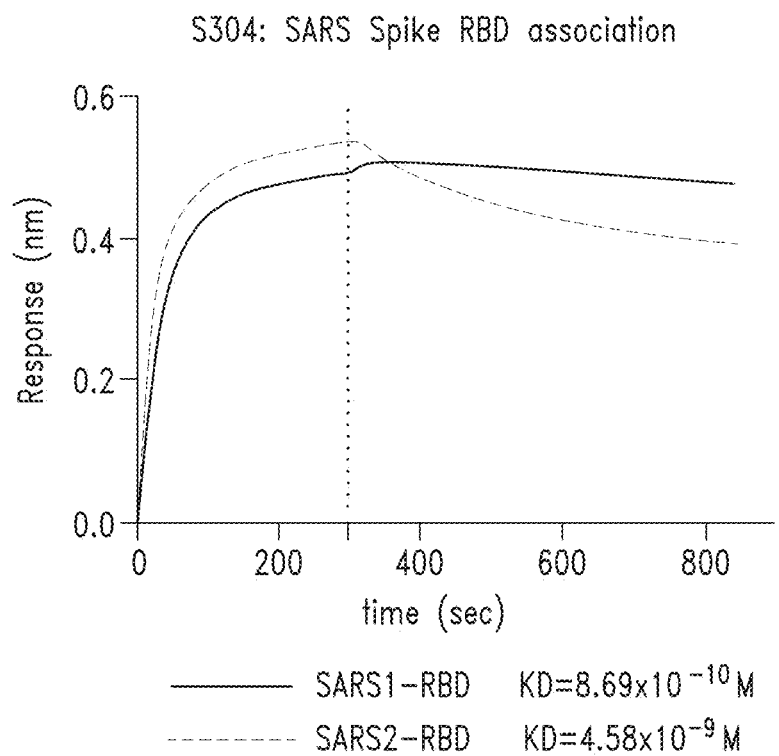
Figure 6D:
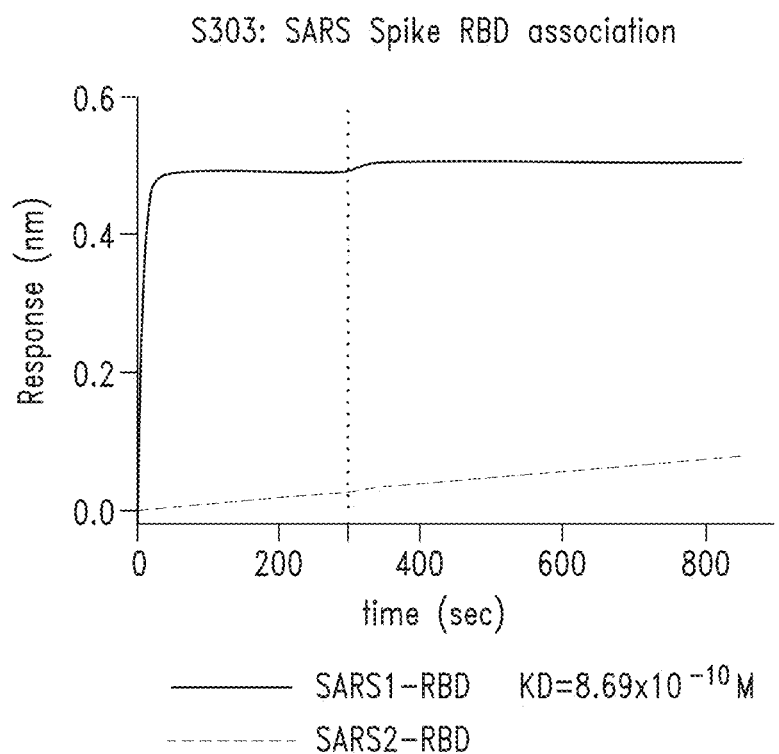
Figure 6E:
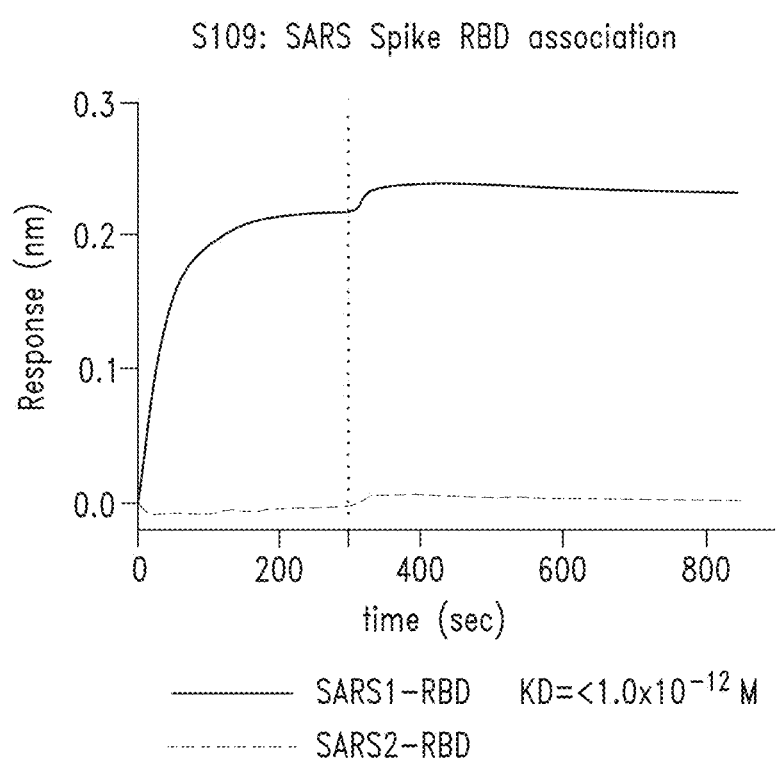

Results are shown in FIG. 5A (SARS-CoV-2 S311) and FIG. 5B (SARS-CoV-2 S312).

Figure 38A:
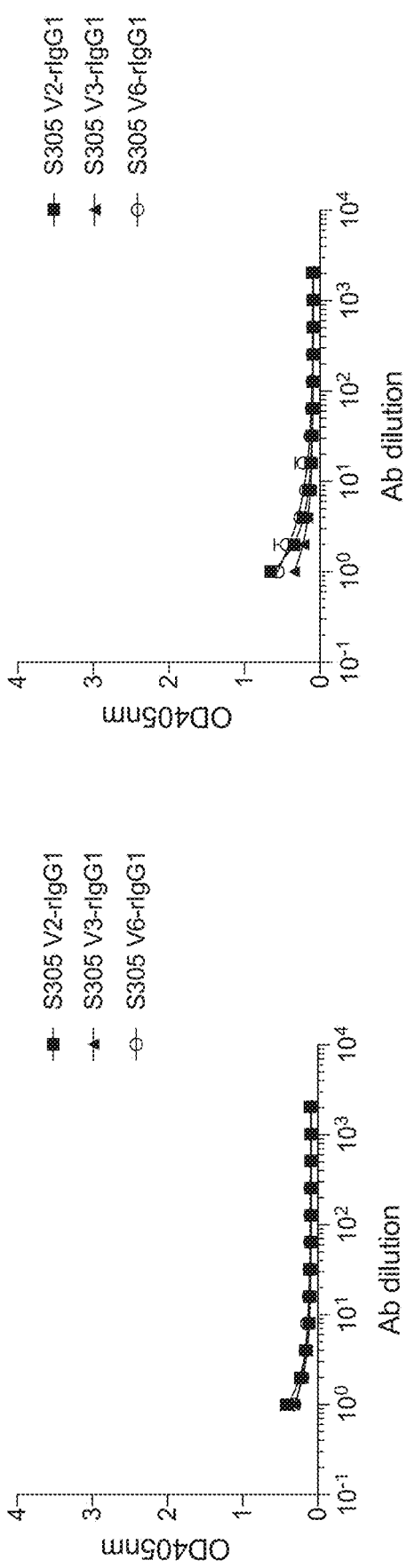
FIGS. 38A-38D show binding of certain antibodies to RBD of SARS-CoV-2 and SARS-CoV-1, as described in Example 6. Antibodies were expressed recombinantly and binding was assayed using ELISA. 96-well ELISA plates were coated with SARS-CoV-2 RBD (produced in house; residues 331-550 of Spike protein from BetaCoV/Wuhan-Hu-1/2019, accession number MN908947) at 10 µg/ml and SARS-CoV-1 RBD (Sino Biological, 40150-V08B1) at 1 µg/ml. After blocking with 1% BSA in PBS, antibodies were added to the plates and incubated at room temperature for one hour. Plates were washed and secondary antibody goat anti-human IgG-AP (Southern Biotechnology, 2040-04) was added. Substrate p-nitrophynylphosphate (pNPP, Sigma-Aldrich, 337 71768) was used for color development. OD405 was analyzed on an ELx808IU plate reader (Biotek). Left panel of each figure shows binding to SARS-CoV-2 RBD and right panel shows binding to SARS-CoV-1 RBD.
Figure 38B:
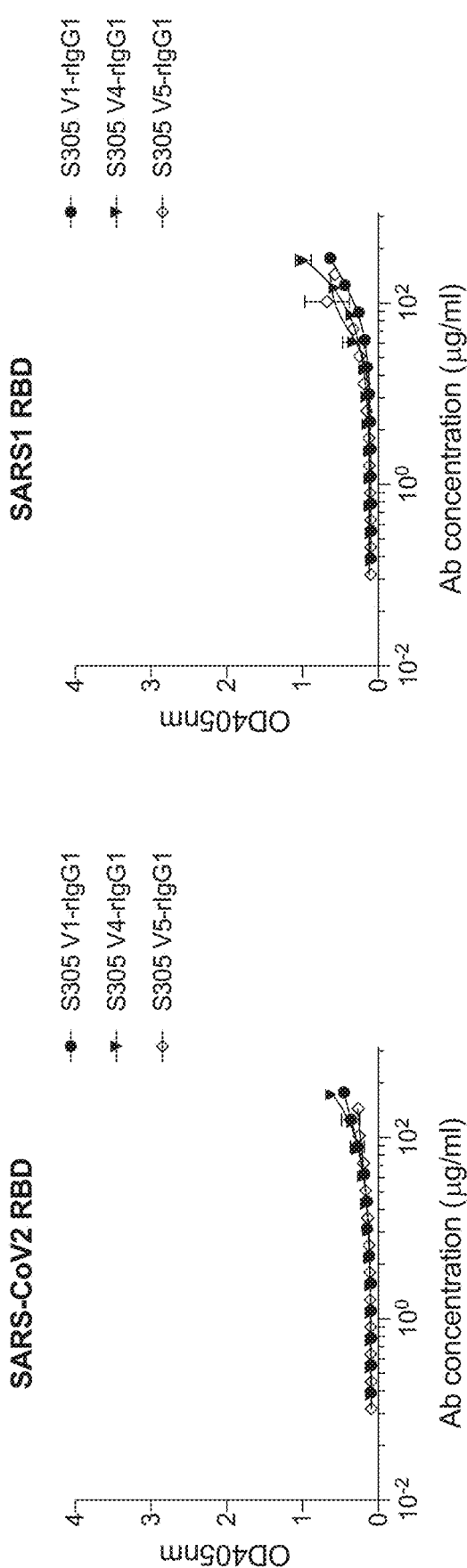
Figure 38C:
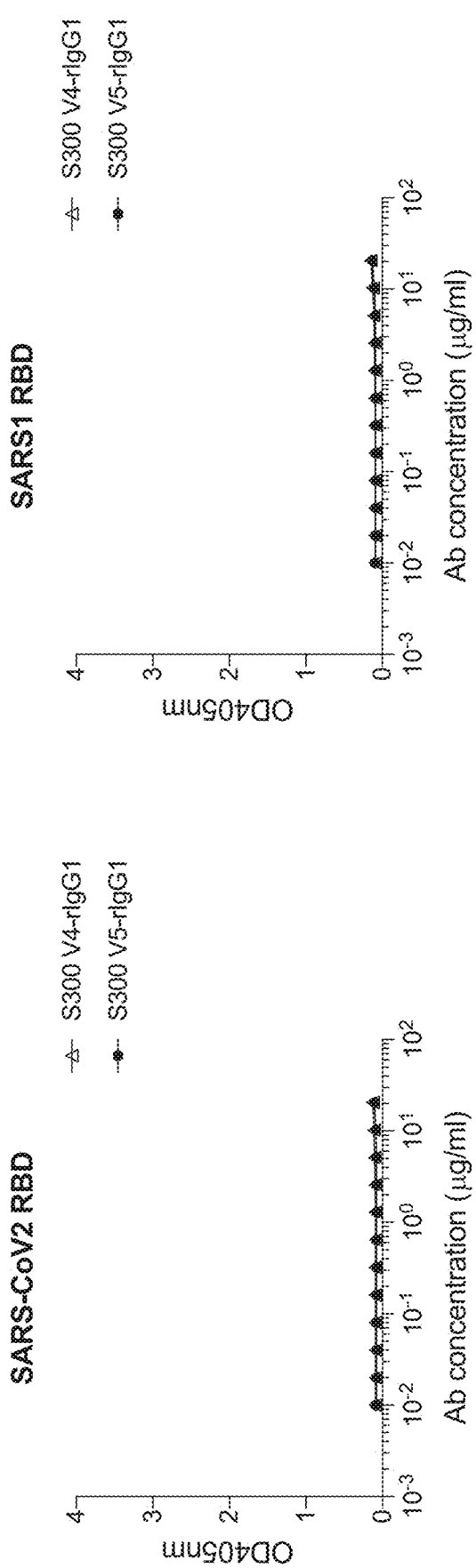
Figure 38D:
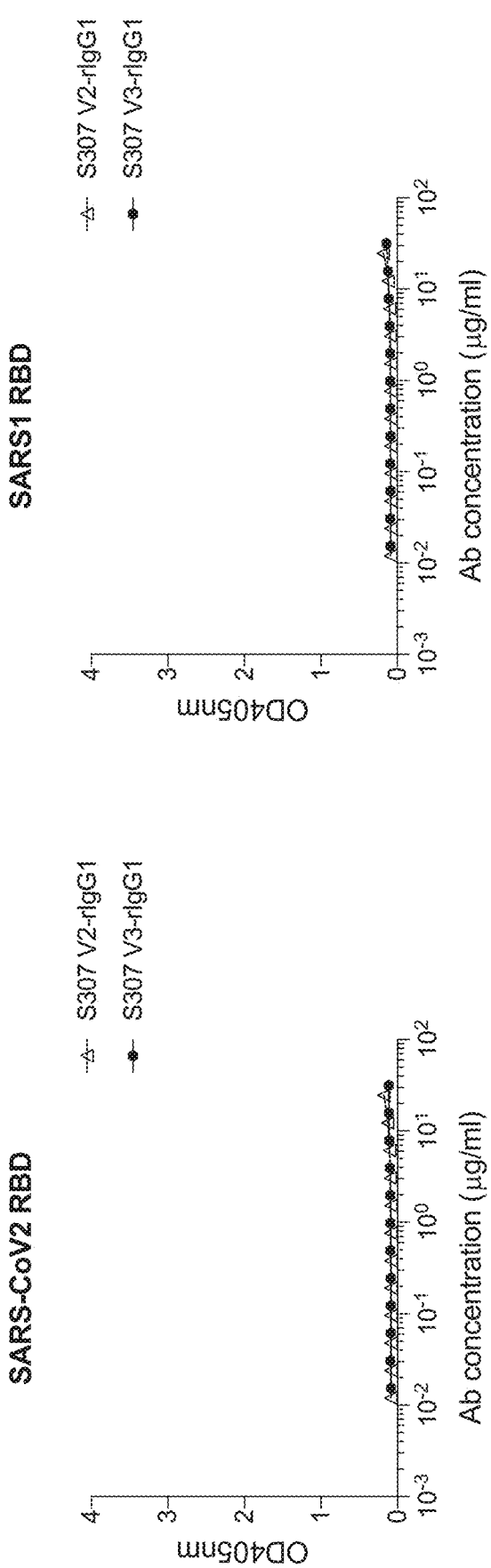
Figure 39A:
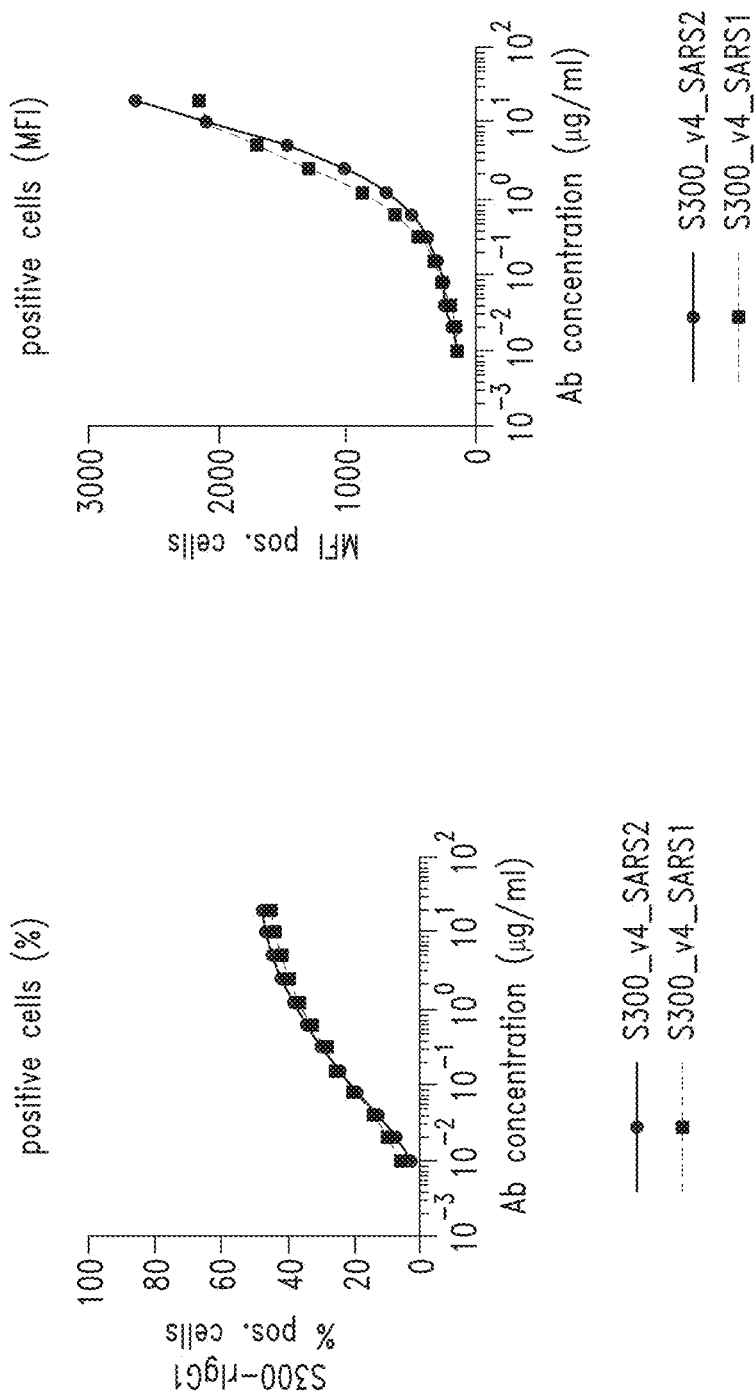
FIGS. 39A and 39B show binding of certain antibodies to Spike protein of SARS-CoV-2 and SARS-CoV-1, as described in Example 9. Expi-CHO cells were transiently transfected with phCMV1-SARS-CoV-2-S, SARS-spike-pcDNA.3 (strain SARS) or empty phCMV1 using Expifectamine CHO Enhancer. Two days after transfection, cells were collected for immunostaining with antibodies. An Alexa647-labelled secondary antibody anti-human IgG Fc was used for detection. Binding of antibodies to transfected cells was analyzed by flow cytometry using a ZE5 Cell Analyzer (BioRad).
Figure 39B:
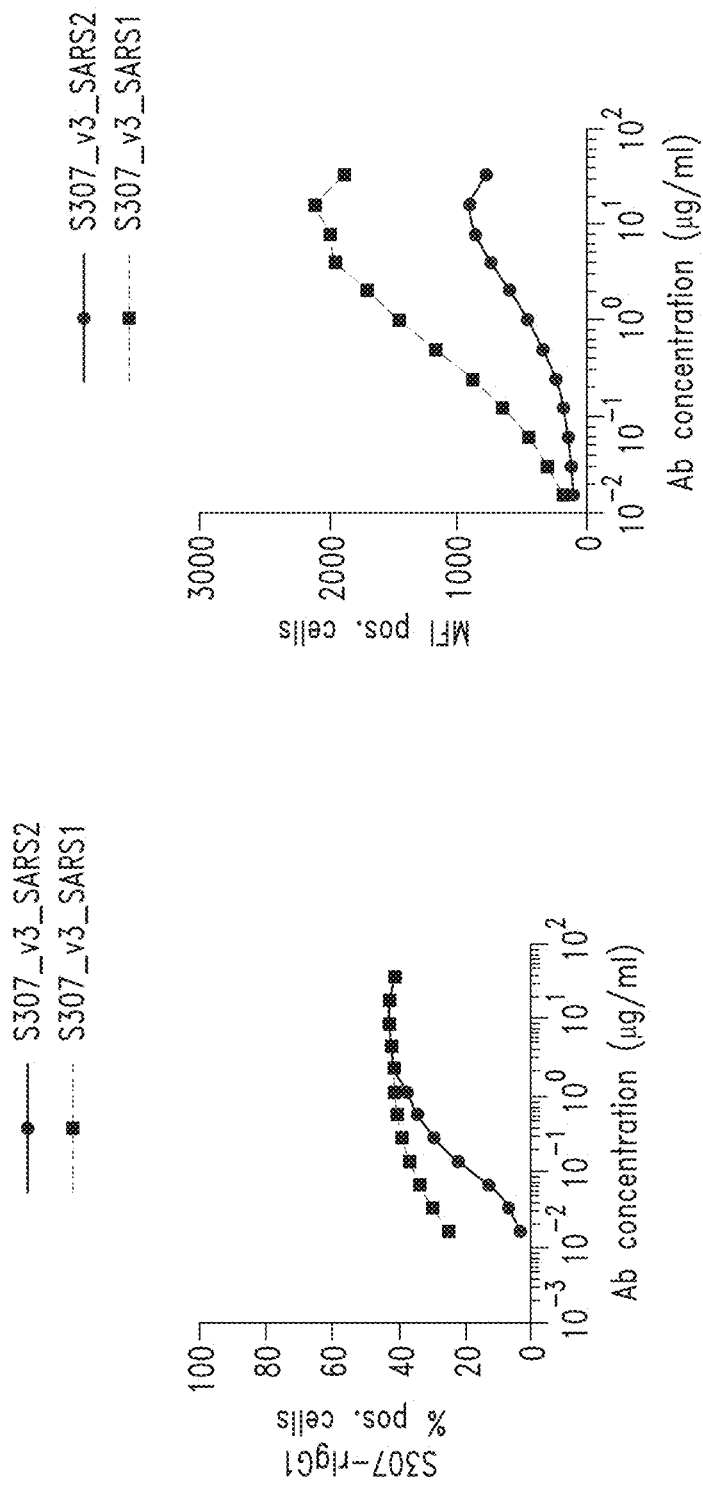
Figure 40A:
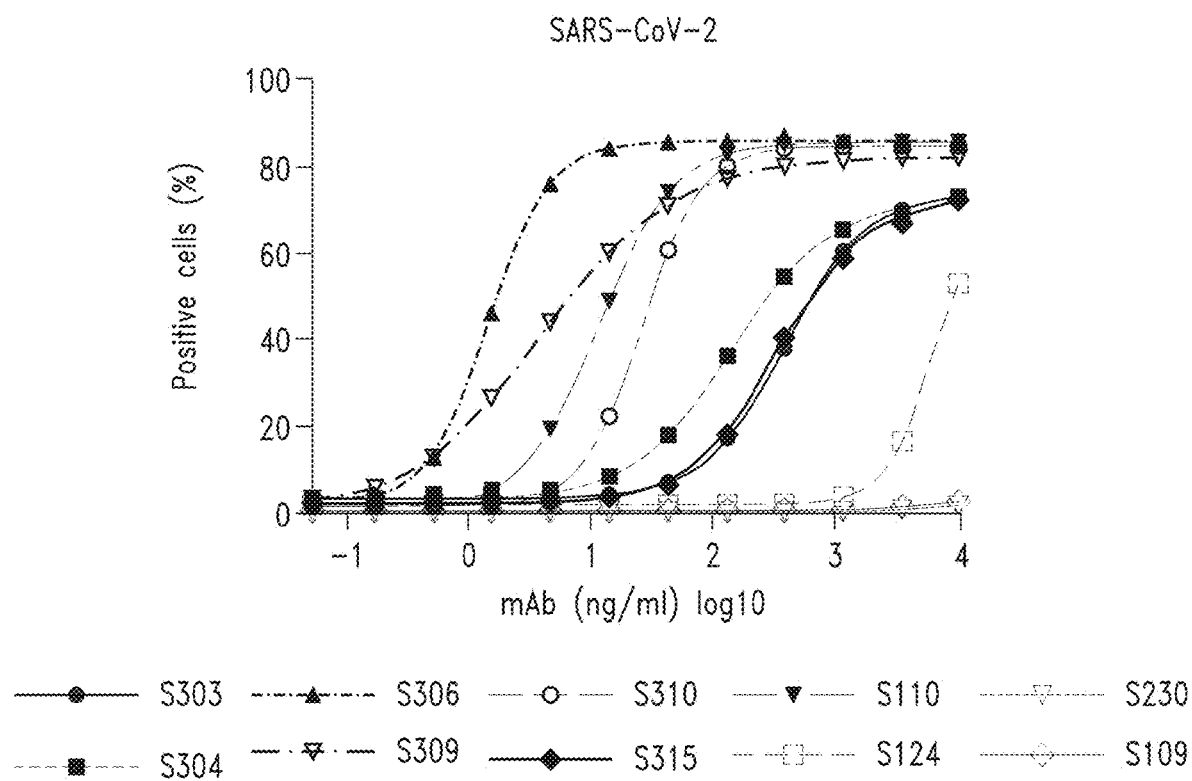
FIGS. 40A and 40B show binding of exemplary antibodies to S glycoproteins of SARS-CoV-2 (FIG. 40A) or SARS-CoV-1 (FIG. 40B) expressed at the surface of ExpiCHO cells, as described in Example 9. Symbols are means of duplicates from one experiment.
Figure 40B:
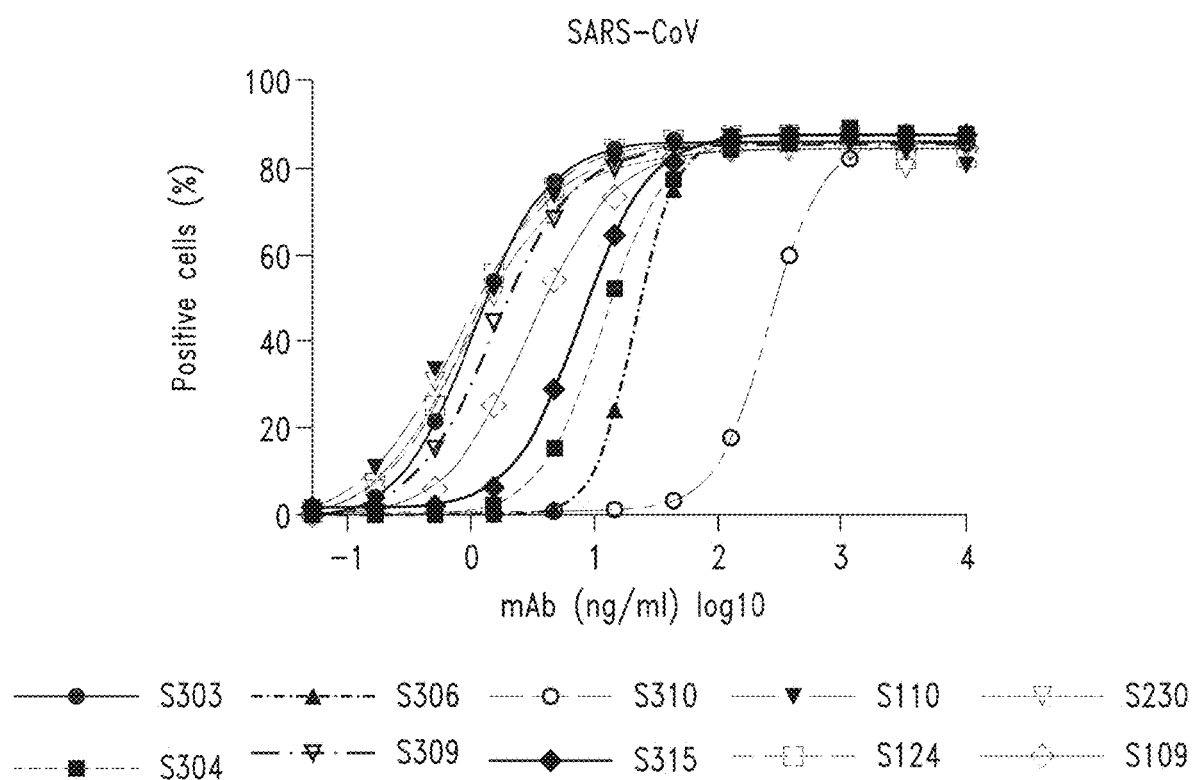

Further assays were performed to investigate reactivity of antibody variants engineered from S300, S305, or S307 to RBD of SARS-CoV-2 and SARS-CoV-1, using the same procedure described above in this Example. Results are shown in FIGS. 38A-38D. Antibody "S300 V4-rIgG1," as shown in FIG. 38C, comprises a VH comprising the amino acid sequence of SEQ ID NO.:1 and a VL (Vκ) comprising the amino acid sequence of SEQ ID NO.:234. Antibody "S307 V3-rIgG1," as shown in FIG. 38D, comprises a VH comprising the amino acid sequence of SEQ ID NO.: 239 and a VL(Vκ) comprising the amino acid sequence of SEQ ID NO.:243.

Example 7

Neutralization of SARS-CoV-2 Infection by S309 and S315

Neutralizing activity of recombinant antibodies S309 (VH: SEQ ID NO.:105; VL SEQ ID NO.:168) rIgG1-MLNS and S315 rIgG1-MLNS against SARS-CoV-2 pseudotyped viruses (SARS-CoV-2pp) was determined. These recombinant antibodies included M428L and N434S mutations in the Fc domain (see, e.g., Zalevsky et al., *Nat. Biotechnol.* 28(2):157-159 (2010); this combination of Fc mutations is also referred-to as "MLNS" or "LS" in the present disclosure, including in the drawings).

Figure 9:
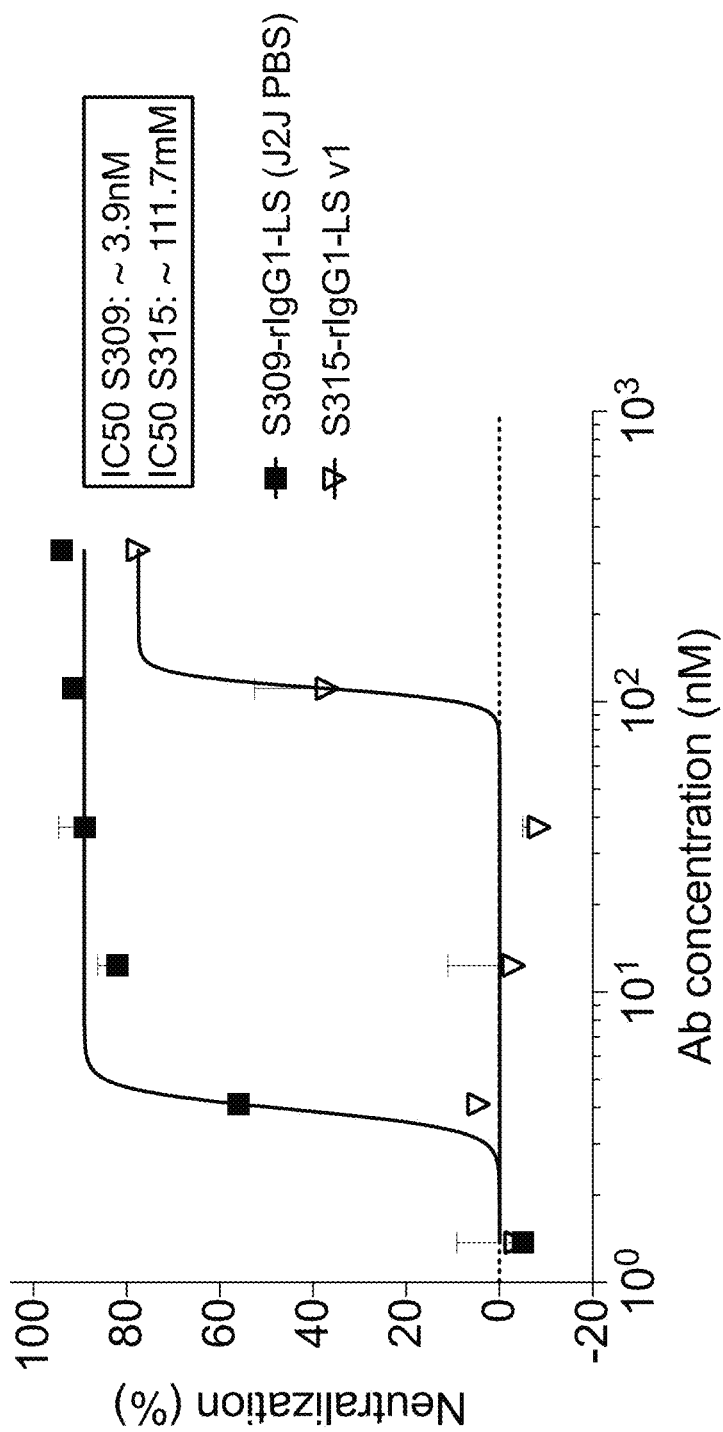
FIG. 9 shows neutralization of infection by S309 rIgG1 (VH SEQ ID NO.:105; VL SEQ ID NO.:168) and S315 rIgG1 (VH SEQ ID NO.:178; VL SEQ ID NO.:182) against SARS-CoV-2 pseudotyped virus, as described in Example 7.

Murine leukemia virus (MLV) pseudotyped with SARS-CoV-2 Spike protein (SARS-CoV-2pp) was used. DBT cells stably transfected with ACE2 (DBT-ACE2) were used as target cells. SARS-CoV-2pp was activated with trypsin TPCK at 10 µg/ml. Activated SARS-CoV-2pp was added to a dilution series of the tested antibody. DBT-ACE2 cells were added to the antibody-virus mixtures and incubated for 48 hours. Luminescence was measured after aspirating cell culture supernatant and adding steady-GLO substrate (Promega). Luciferase signal of infected cells was used to calculate the percentage of neutralization relative to a no-antibody control. S309 rIgG1 MLNS ("S309-rIgG1-LS" in FIG. 9) exhibited a neutralization of infection IC50 of approximately 3.9 nM, and S315 rIgG1 MLNS ("S315-rIgG1-LSv1" in FIG. 9) exhibited an IC50 of approximately 111.7 mM. See FIG. 9.

Figure 10:
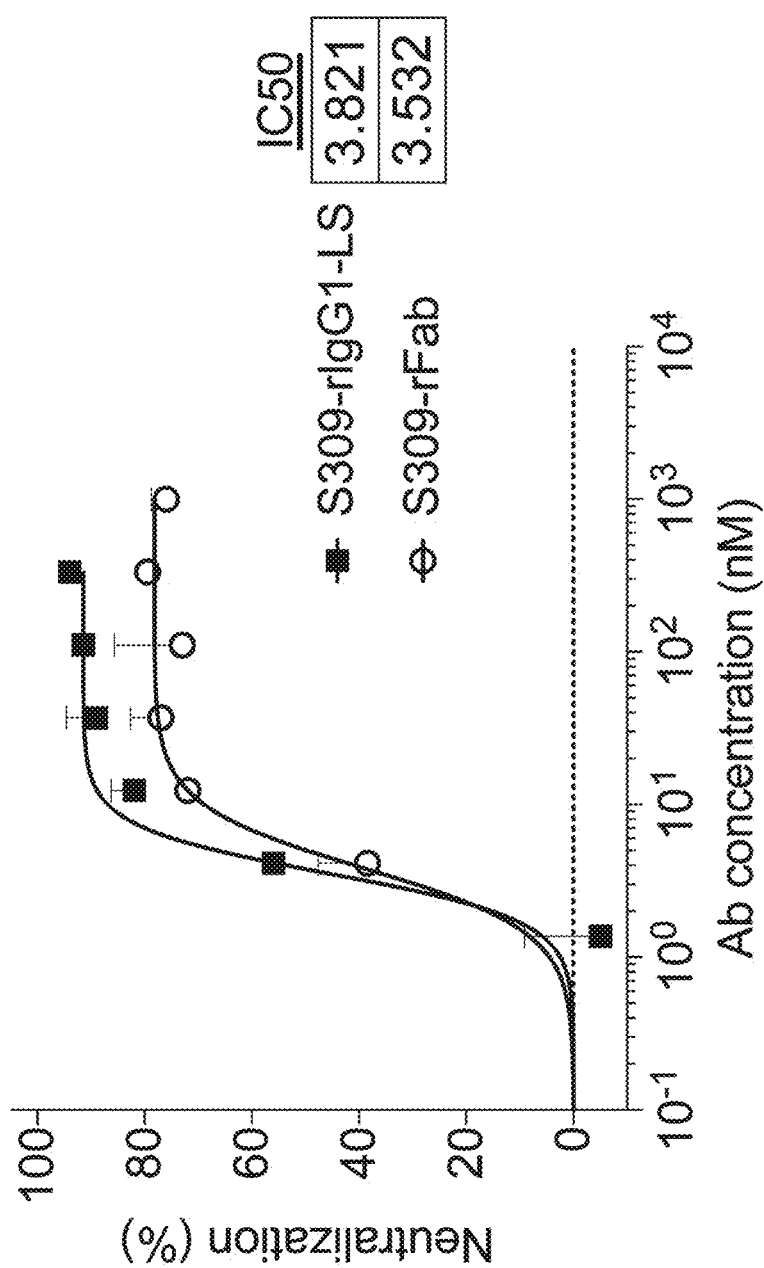
FIG. 10 shows neutralization of infection by S309 full-length rIgG1 and S309 rFab (both of which comprise a VH of SEQ ID NO.:105 and a VL of SEQ ID NO.:168) against SARS-CoV-2 pseudotyped virus, as described in Example 7.
Figure 11:
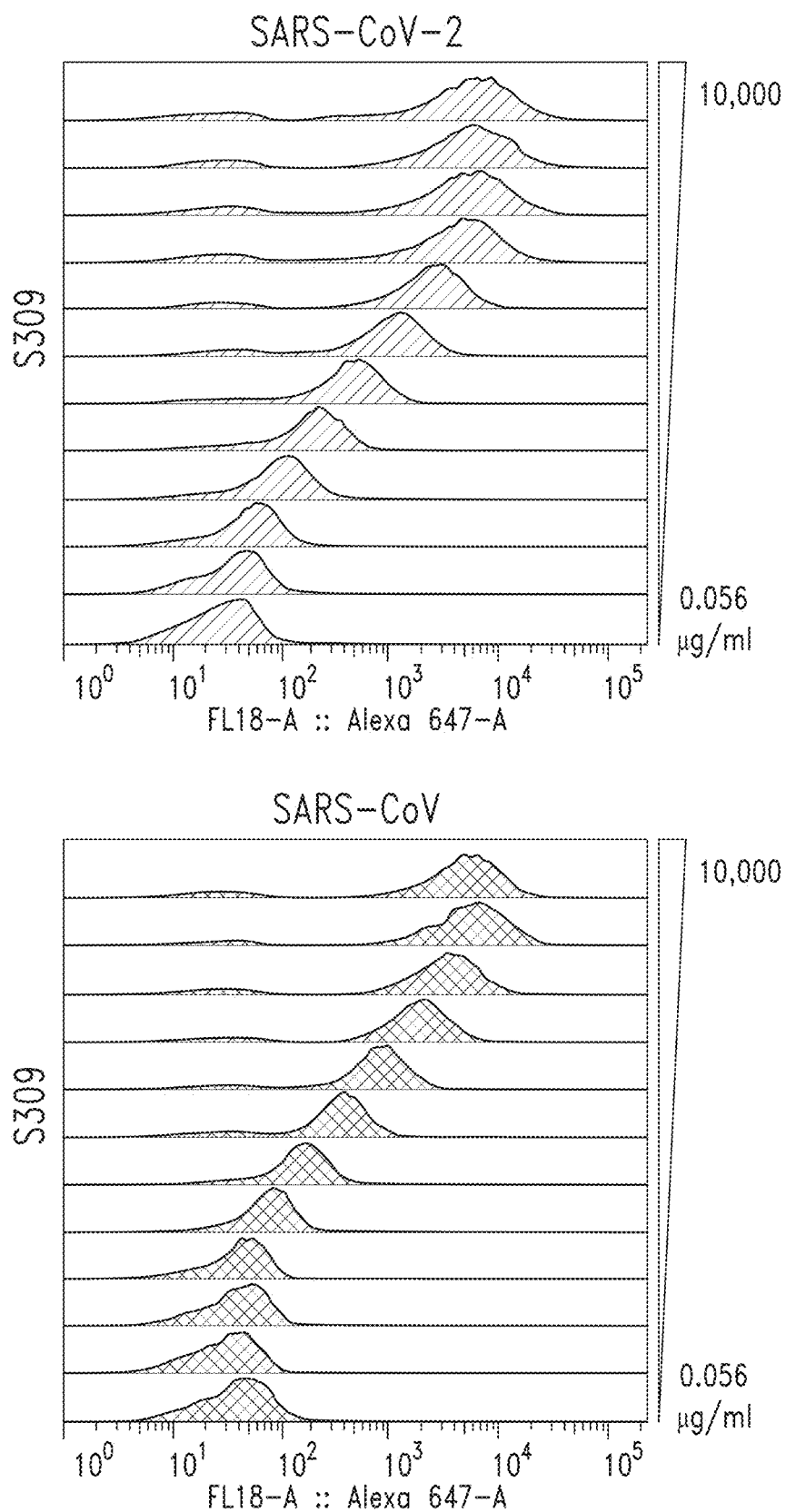
FIG. 11 shows binding of antibody S309 (VH SEQ ID NO.:105; VL SEQ ID NO.:168) to SARS-CoV-1 and SARS-CoV-2 spike protein expressed on ExpiCHO cells, as described in Example 9. Stacked histograms of flow cytometry graphs show antibody dose-dependent binding of S309 to SARS-CoV and SARS-CoV-2.
Figure 12A:
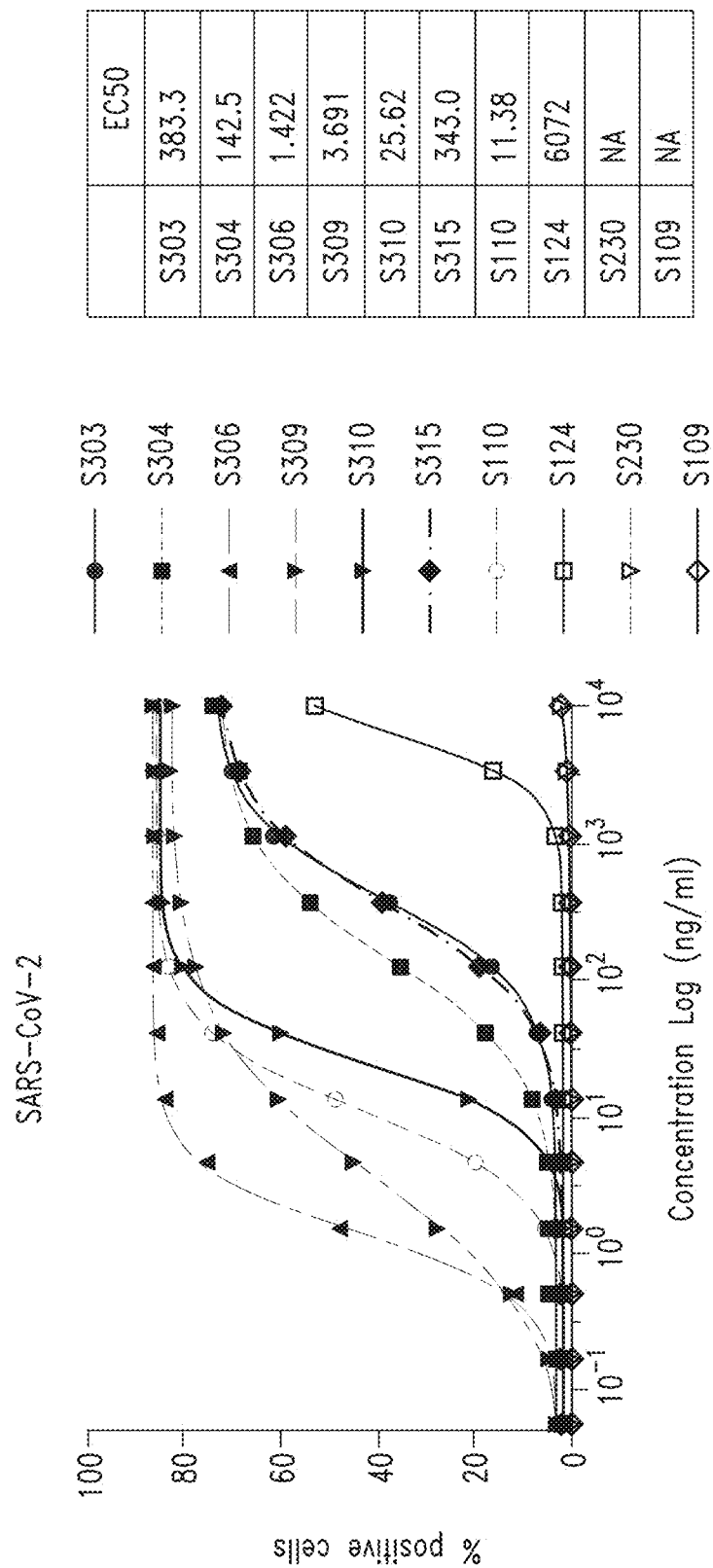

Neutralizing activity of S309-rFab was compared to that of full-length S309 rIgG1 MLNS ("S309-rIgG1-LS" in FIG. 10). Full-length S309 rIgG-LS exhibited an IC50 of 3.821 nM, while S309-rFab exhibited an IC50 of 3.532 nM. See FIG. 10.

Example 8

Reactivity of Antibodies Against RBD of SARS-CoV-1, RBD of SARS-CoV-2, and Ectodomains of Various Coronaviruses Reactivity of monoclonal antibodies against the RBDs of SARS-CoV-1 and SARS-CoV-2 and the Spike proteins of SARS-CoV-1, SARS-CoV-2, OC43 coronavirus, and MERS coronavirus was studied by enzyme-linked immunosorbent assay (ELISA). 384-well shallow ELISA plates were coated with stabilized prefusion Spike protein trimer of SARS-CoV-1, SARS-CoV-2, OC43, or MERS at 1 µg/ml, or with SARS-CoV-2 RBD (produced in house; residues 331-550 of spike from BetaCoV/Wuhan-Hu-1/2019, accession number MN908947) at 10 μg/ml, or SARS-CoV-1 RBD (Sino Biological) at 1 μg/ml.

Wells were washed and blocked with PBS+1% BSA for 1 hour at room temperature, and were then incubated with serially diluted antibody for 1-2 hours at room temperature. Antibodies were tested at a concentration range of 5 to 0.00028 μg/ml. Plates were washed and bound antibodies were detected by incubating alkaline phosphatase-conjugated goat anti-human IgG (Southern Biotechnology: 2040-04) for 1 hour at room temperature followed by color development using 1 mg/ml p-nitrophenylphosphate substrate (Sigma-Aldrich 71768) in 0.1 M glycine buffer (pH 10.4) for 30 min at room temperature. The optical density (OD) values were measured at a wavelength of 405 nm in an ELISA reader (Powerwave 340/96 spectrophotometer, BioTek).

The ELISA assay results are shown in FIGS. 8A-8K and 18A-18J. Recombinant antibodies, some bearing MLNS Fc mutations, are indicated with rIgG1.

Example 9

Binding of Antibodies to Spike Protein of SARS-CoV-1 and SARS-CoV-2

ExpiCHO cells were transfected with phCMV1-SARS-CoV-2-S, SARS-spike_pcDNA.3 (strain SARS), or empty phCMV1 using Expifectamine CHO Enhancer. Two days after transfection, cells were collected for immunostaining with antibody. An Alexa647-labelled secondary antibody anti-human IgG Fc was used for detection. Binding of monoclonal antibody to transfected cells was analyzed by flow cytometry using a ZE5 Cell Analyzer (Biorard) and FlowJo software (TreeStar). Positive binding was defined by differential staining of CoV-S transfectants versus mock transfectants. Antibody S309 (VH of SEQ ID NO.:105; VL of SEQ ID NO.:168) was tested by flow cytometry at 10 μg/ml for the ability to stain ExpiCHO cells expressing the S protein of SARS-CoV-1 or SARS-CoV-2. Stacked histograms of flow cytometry graphs show antibody dose-dependent binding by S309 to SARS-CoV-1 or SARS-CoV-2 S protein. Results are shown in FIG. 11.

Binding of monoclonal antibodies S303, S304, S306, S309, S310, S315, S110, S124, S230, and S109 (all expressed as rIgG1) to SARS-CoV-1 S protein and SARS-CoV-2 S protein was measured by flow cytometry. Results are shown in FIGS. 12A, 12B, 40A, and 40B. Eight of the tested antibodies exhibited EC50 values ranging between 1.4 ng/ml and 6,100 ng/ml for SARS-CoV-2 S protein binding and between 0.8 ng/ml and 254 ng/ml for SARS-CoV-1 S protein binding.

Further binding assays using the same procedure were carried out for S309 and four engineered variants of S309 bearing different mutations in VH (N55Q, W50F, W105F, or W50F+G56A+W105F). Results are shown in FIG. 27. EC50 values for each antibody tested in these assays are shown in Table 7; the numbers enclosed in parentheses in the "Antibody" column in Table 7 correspond to the figure key in FIG. 27.

TABLE 7

| Antibody | VH SEQ ID NO. | VL SEQ ID NO. | EC50 (ng/ml)-Exp. 1 | EC50 (ng/ml)-Exp. 2 |
|---|---|---|---|---|
| S309 WT ("11") | 105 | 168 | 23.1 | 11.5 |
| S309 N55Q ("12") | 113 | 168 | 22.3 | 9.6 |
| S309 W50F ("13") | 129 | 168 | 21.8 | 8.9 |
| S309 W105F ("14") | 119 | 168 | 21.4 | 8.4 |
| S309 W50F-G56A-W105F ("15") | 172 | 168 | 18.8 | 7.8 |

Additional binding assays using the same procedure were carried out using antibodies S303, S304, S306, S309, S310, S315, and comparator antibodies S109, S110, S124, and S230. Results are shown in FIGS. 33A and 42A (binding to SARS-CoV-2 S protein), and 33B and 42B (binding to SARS-CoV-1 S protein). MFI: mean fluorescence intensity as measured by flow cytometry.

The same assay was performed using recombinant antibodies S300 and S307. Results for antibody S300-rIgG1, which comprises a VH comprising the amino acid sequence of SEQ ID NO.:1 and a VL (Vκ) comprising the amino acid sequence of SEQ ID NO.:234, are shown in FIG. 39A. Results for antibody S307-rIgG1, which comprises a VH comprising the amino acid sequence of SEQ ID NO.: 239 and a VL (Vκ) comprising the amino acid sequence of SEQ ID NO.:24, are shown in FIG. 39B.

Example 10

Binding of Antibodies S309, S303, S304, and S315 to RBD of SARS-CoV-2 and SARS-CoV-1

Affinity of recombinant antibodies S309, S303, S304, and S315 for RBD of CoV-1 and CoV-2 was tested using biolayer interferometry (BLI; Octet). Briefly, His-tagged RBD of SARS-CoV-1 or SARS-CoV-2 was loaded at 3 μg/ml in kinetics buffer (KB) for 15 minutes onto anti-HIS (HIS2) biosensors (Molecular Devices, ForteBio). Association of full-length antibodies was performed in KB at 15 μg/ml for 5 minutes. Association of Fab fragments was performed in KB at 5 μg/mL for 5 minutes. Dissociation in KB was measured for 10 minutes. Affinities, represented by KD values, were calculated using a global fit model (Octet). Octet Red96 (ForteBio) equipment was used.

FIGS. 14A-14D show association and dissociation curves for S309, S303, S304, and S315, respectively. Each of these antibodies bound to SARS-CoV-2 and SARS-CoV-1 RBD with nanomolar to sub-picomolar affinity. FIGS. 20A and 20B show association and dissociation curves for S309 IgG and S309 Fab, respectively. In these figures, the switch from antibody (or Fab) solution to buffer is indicated with a vertical dashed line.

Example 11

Binding of S309 IgG and S309 Fab to SARS-CoV-2 S Protein Ectodomain Trimer and RBD Affinity and avidity determination of IgG1 and Fab fragment: biotinylated RBD of SARS-CoV-2 (produced in-house; amino acid residues 331-550 of spike protein from BetaCoV/Wuhan-Hu-1/2019, accession number MN908947, biotinylated with EZ-Link NHS-PEG4-Biotin from ThermoFisher) and biotinylated SARS-CoV-2 2P S avi-tagged were loaded at 7.5 μg/ml in Kinetics Buffer (KB;

0.01% endotoxin-free BSA, 0.002% Tween-20, 0.005% NaN3 in PBS) for 8 minutes onto Streptavidin biosensors (Molecular Devices, ForteBio). Association of IgG1 and Fab with target was performed in KB at 100, 33, 11, 3.6, 1.2 nM for 5 minutes. Dissociation in KB was measured for 10 minutes. KD values were calculated using a 1:1 global fit model (Octet).

Figure 41A:
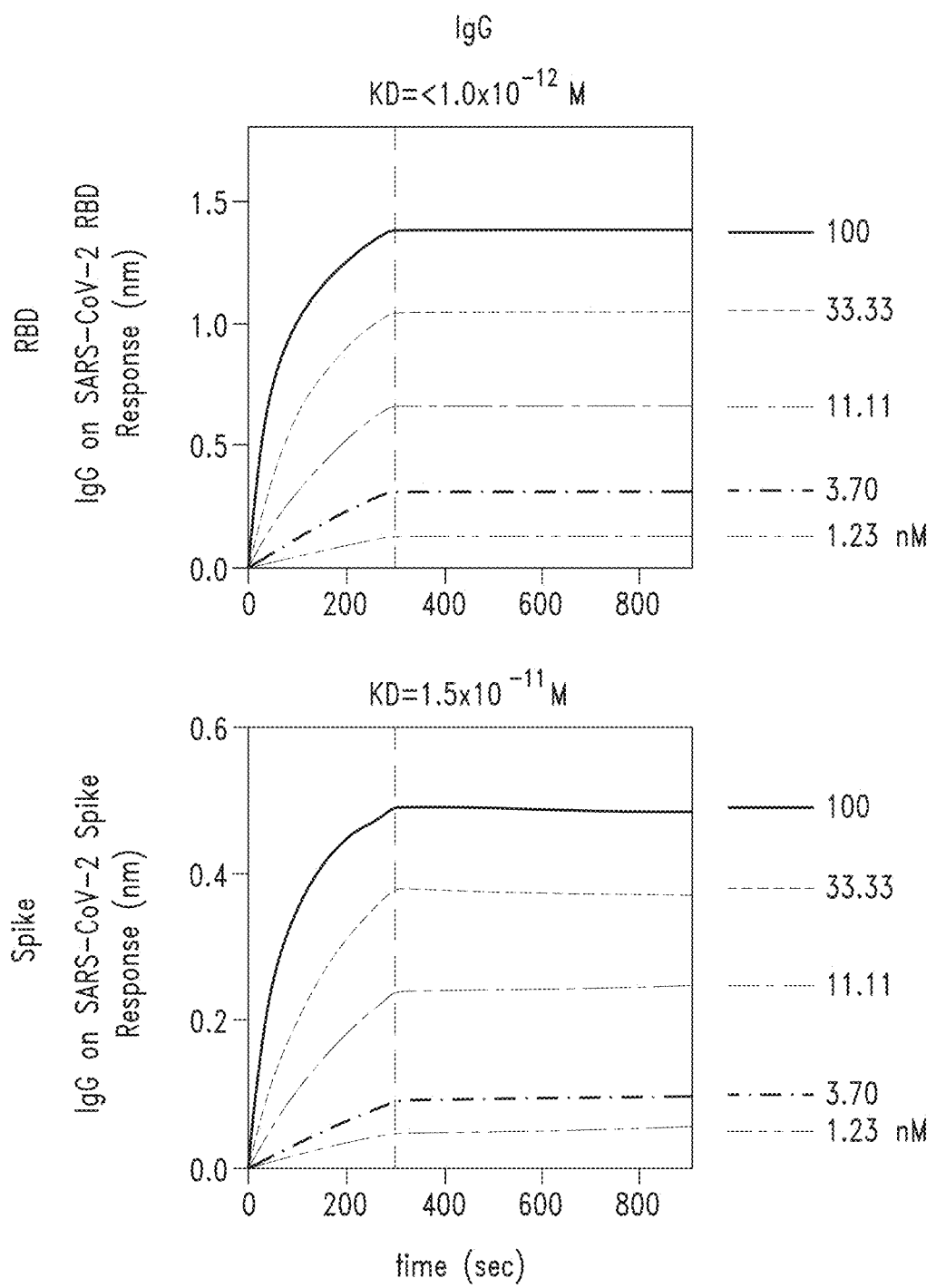
FIGS. 41A and 41B show binding affinity and avidity of S309 IgG (FIG. 41A) and S309 Fab (FIG. 41B) for SARS-CoV-2 RBD (top panel) or SARS-CoV-2 Spike protein (bottom panel). For both IgG and Fab: VH SEQ ID NO.:105 and VL SEQ ID NO.:168. See Example 11. Biotinylated RBD of SARS-CoV-2 or biotinylated SARS-CoV-2 prefusion S ectodomain trimer were loaded onto Streptavidin biosensors, and association of different concentrations of S309-IgG-MLNS (comprising M428L and N434S Fc mutations (EU numbering)) or S309 Fab was measured. Vertical dashed lines indicate the start of the dissociation phase when biosensors were switched to buffer.
Figure 41B:
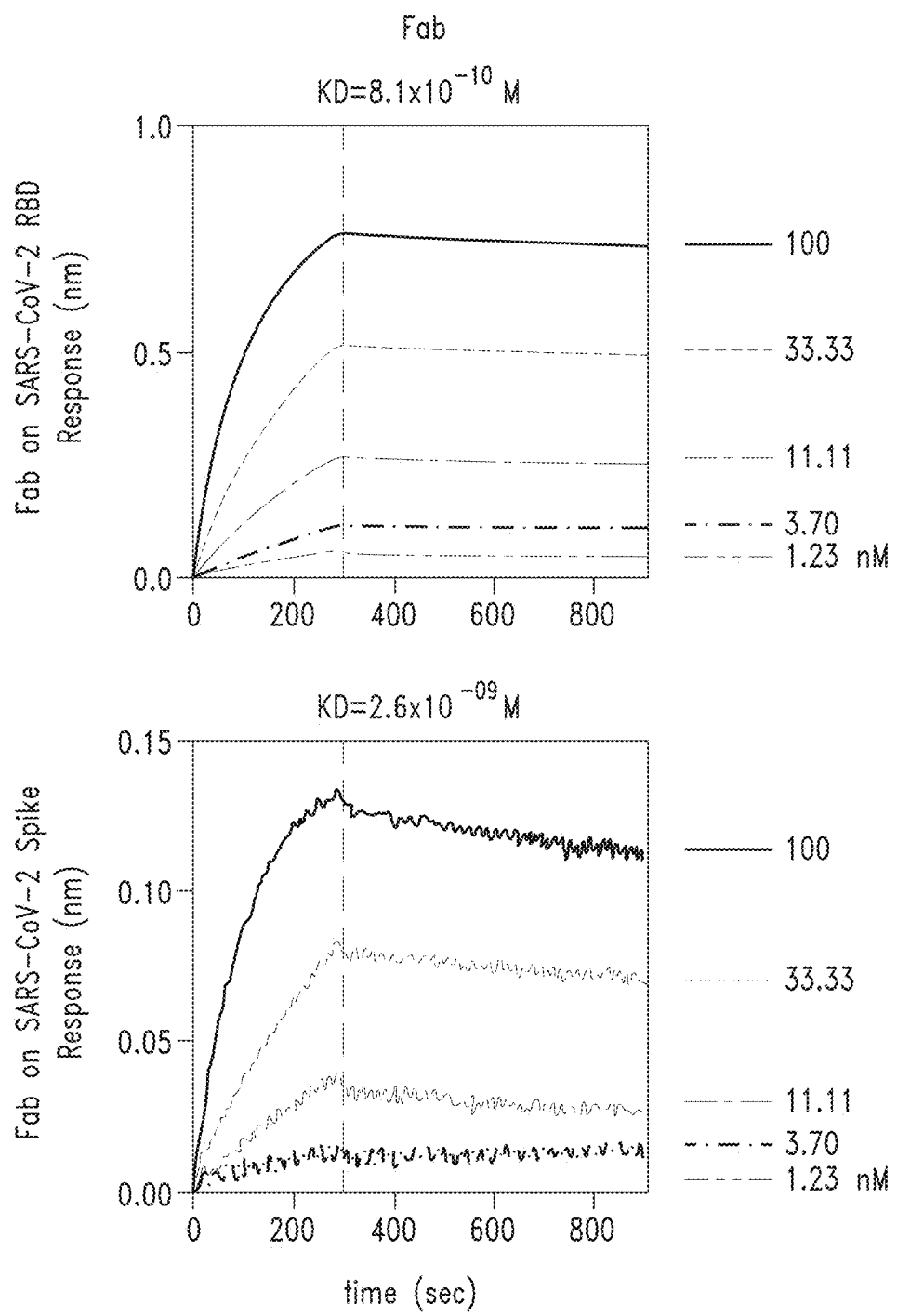
Figure 42A:
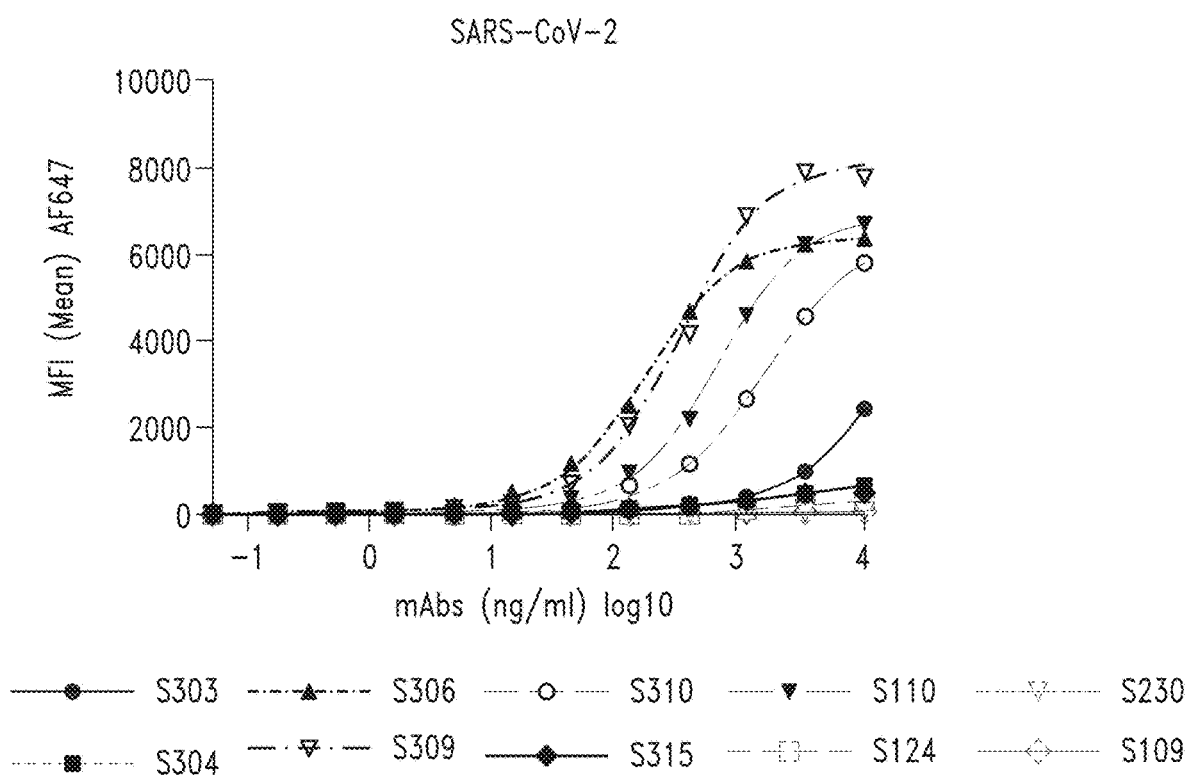
FIGS. 42A and 42B show binding of antibodies S303, S304, S306, S309, S310, and S315, along with comparator antibodies S110, S124, S230, and S109, to S protein expressed on a cell surface. See Example 9.
Figure 42B:
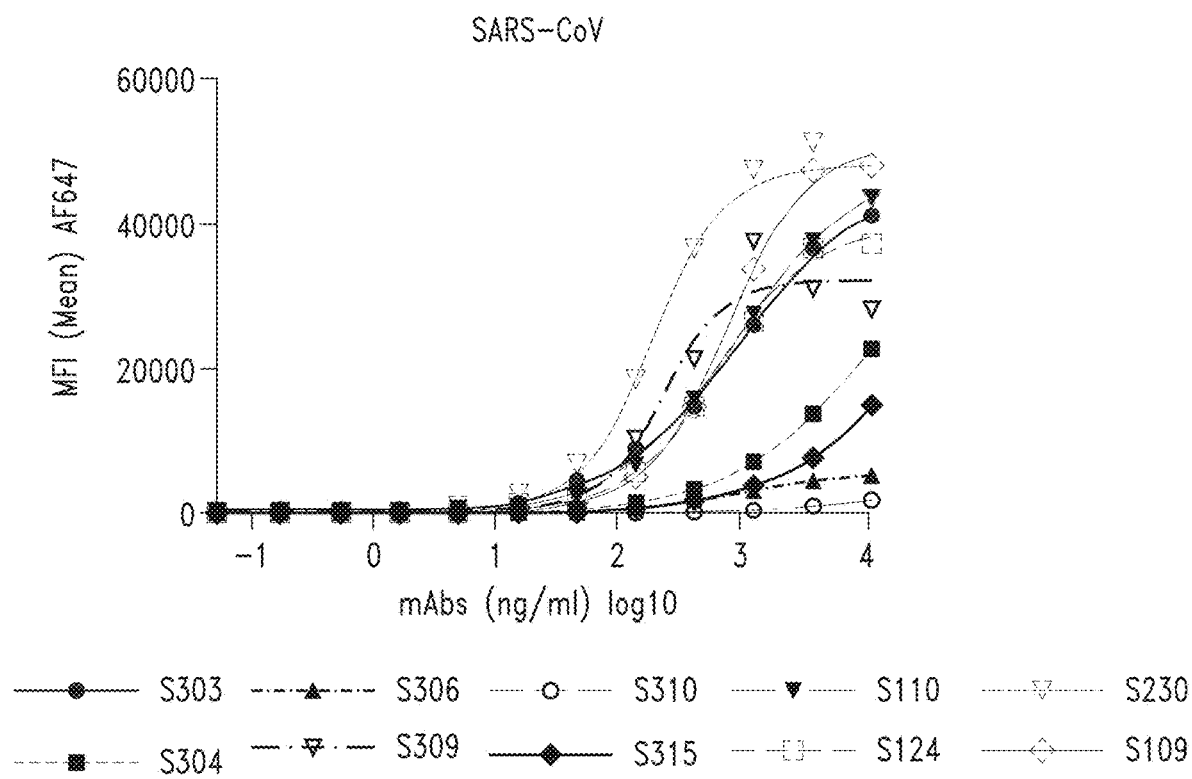

Results are shown in FIGS. 41A and 41B. In this assay, S309 IgG bound to the SARS-CoV-2 RBD and to the S ectodomain trimer with sub-picomolar and picomolar avidities, respectively. S309 Fab bound to both the SARS-CoV-2 RBD and the S ectodomain trimer with nanomolar to sub-nanomolar affinities.

Example 12

Competitive Binding of Antibodies to RBD of SARS-CoV-1 or SARS-CoV-2

Competitive binding of pairs of monoclonal antibodies to SARS-CoV-1 RBD or SARS-CoV-2 RBD was measured to identify respective binding sites of the antibodies.

Figure 15A:
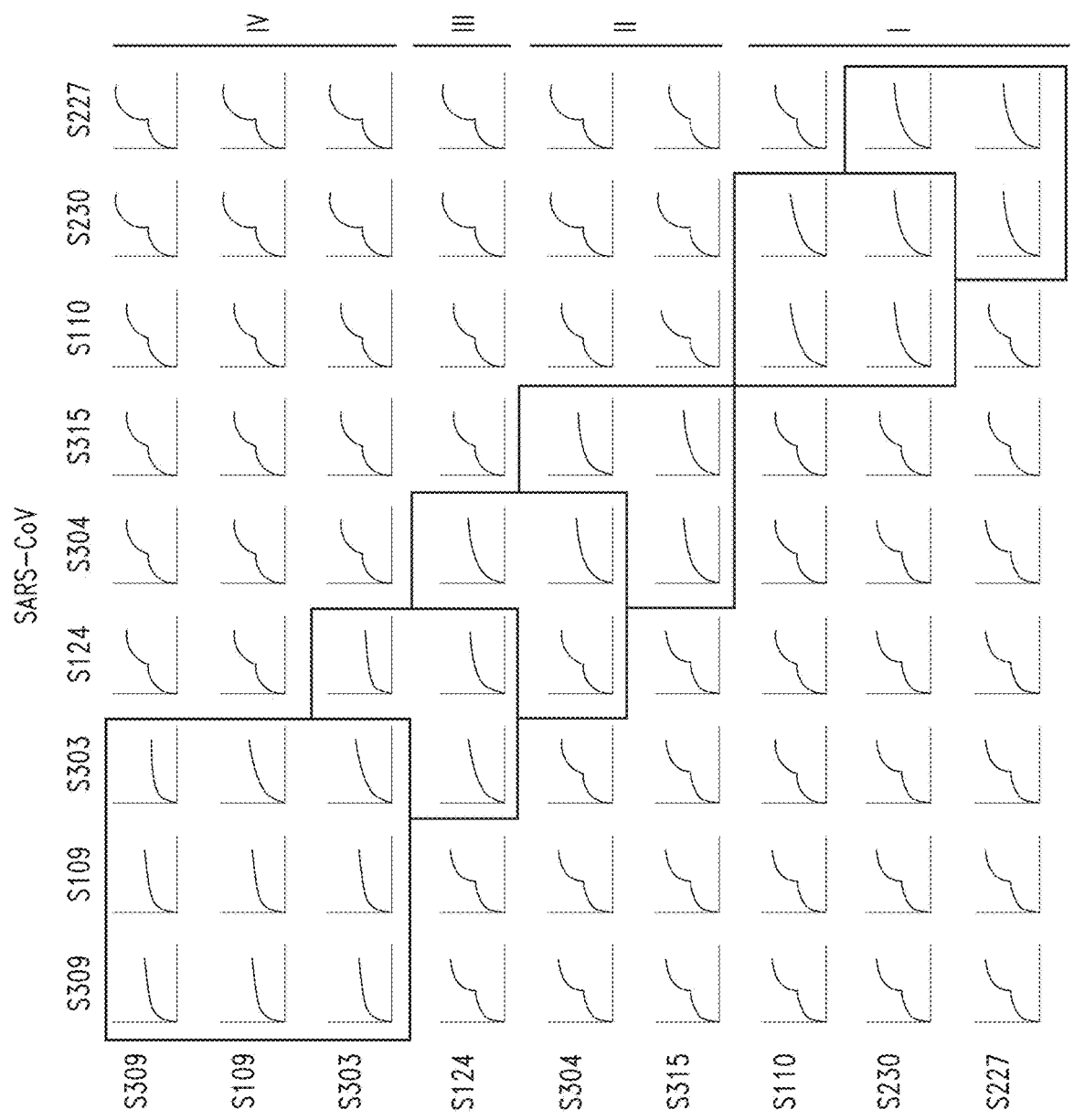
FIGS. 15A and 15B show competition of pairs of antibodies of the present disclosure for binding to the RBD of SARS-CoV-1 (FIG. 15A) and SARS-CoV-2 (FIG. 15B), as described in Example 12. For each graph, the x-axis shows time (0 to 1000 seconds), and the y-axis shows the binding to RBD as measured by BLI (0 to 3 nm). The first antibody is indicated on the left of the matrix and the second antibody is indicated on the top of the matrix. The dashed vertical lines in FIG. 15B show the switch from the first antibody to the second antibody. At right ("I"-"IV" in FIG. 15A, "II" and "IV" in FIG. 15B) are antigenic sites as determined by structural information, escape mutant analysis, and BLI-based epitope binning.
Figure 15B:
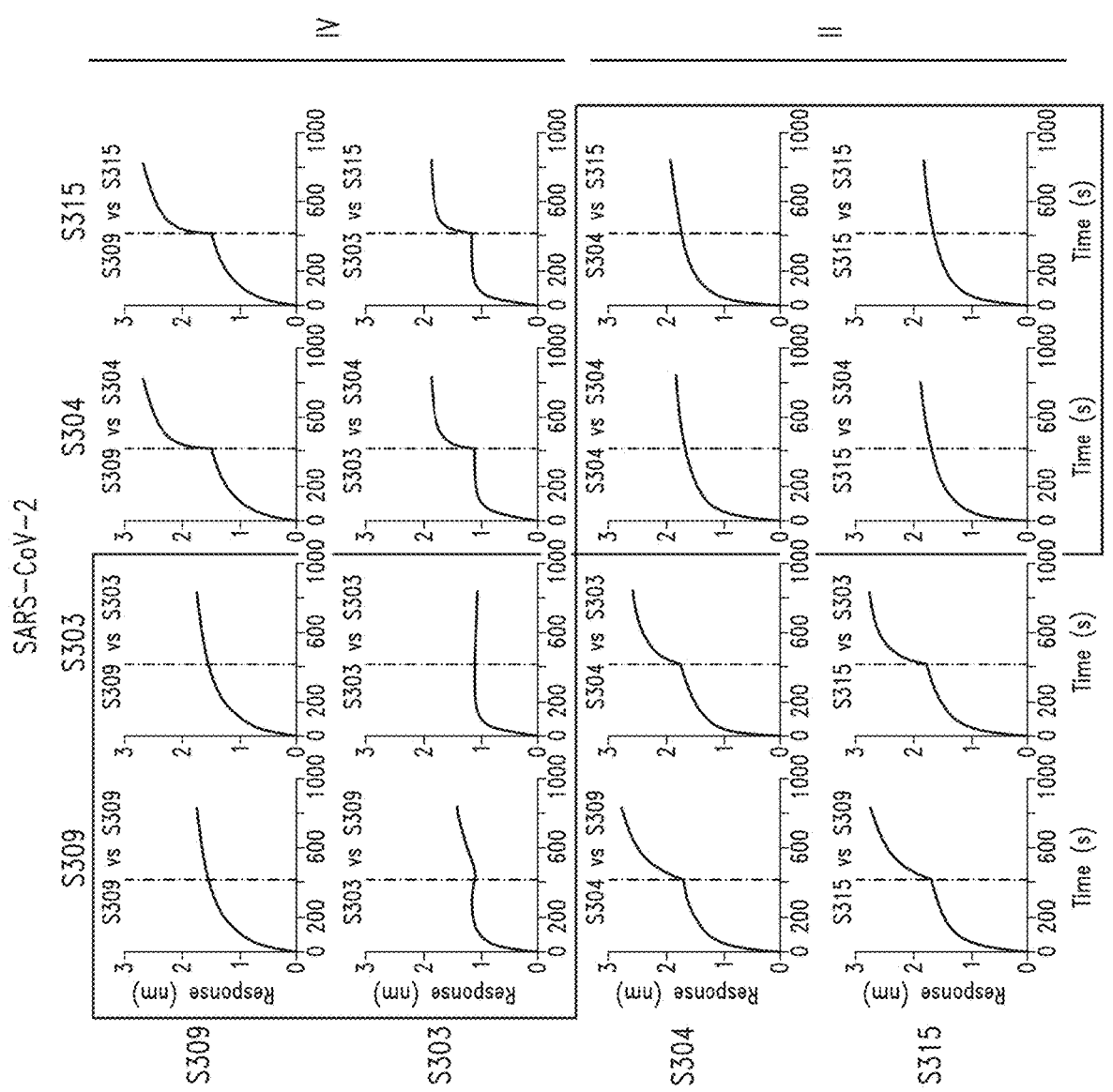

Strepavidin biosensors (Pall ForteBio) were used to immobilize anti-Strep Tag II antibody at 3 ug/ml (clone 5A9F9, Biotin, LabForce AG, Muttenz CH), after a hydration step for 10 min with Kinetics Buffer (KB; 0.01% endotoxin-free BSA, 0.002^Tween-20, 0.005% NaN3 in PBS). Either SARS-CoV-1 or SARS-CoV-2 RBD with a Strep Tag II (produced in-house) was then loaded for 6 min at a concentration of 4 µg/ml in KB. The first antibody was allowed to associate for a period of time, and then the second antibody was allowed to associate for 7 minutes (420 seconds). FIG. 15A shows competition of antibody pairs for binding to the RBD of SARS-CoV-1. FIG. 15B shows competition of antibody pairs for binding to the RBD of SARS-CoV-2. The dashed vertical lines in FIGS. 15A and 15B indicate the switch from the first antibody, indicated on the left of the matrix, to the second antibody, indicated on top of the matrix. Using these and other data, four antigenic regions or sites (I-IV in FIGS. 15A and 15B) were identified.

Example 13

Interference with RBD:Human ACE2 Binding

Figure 16:
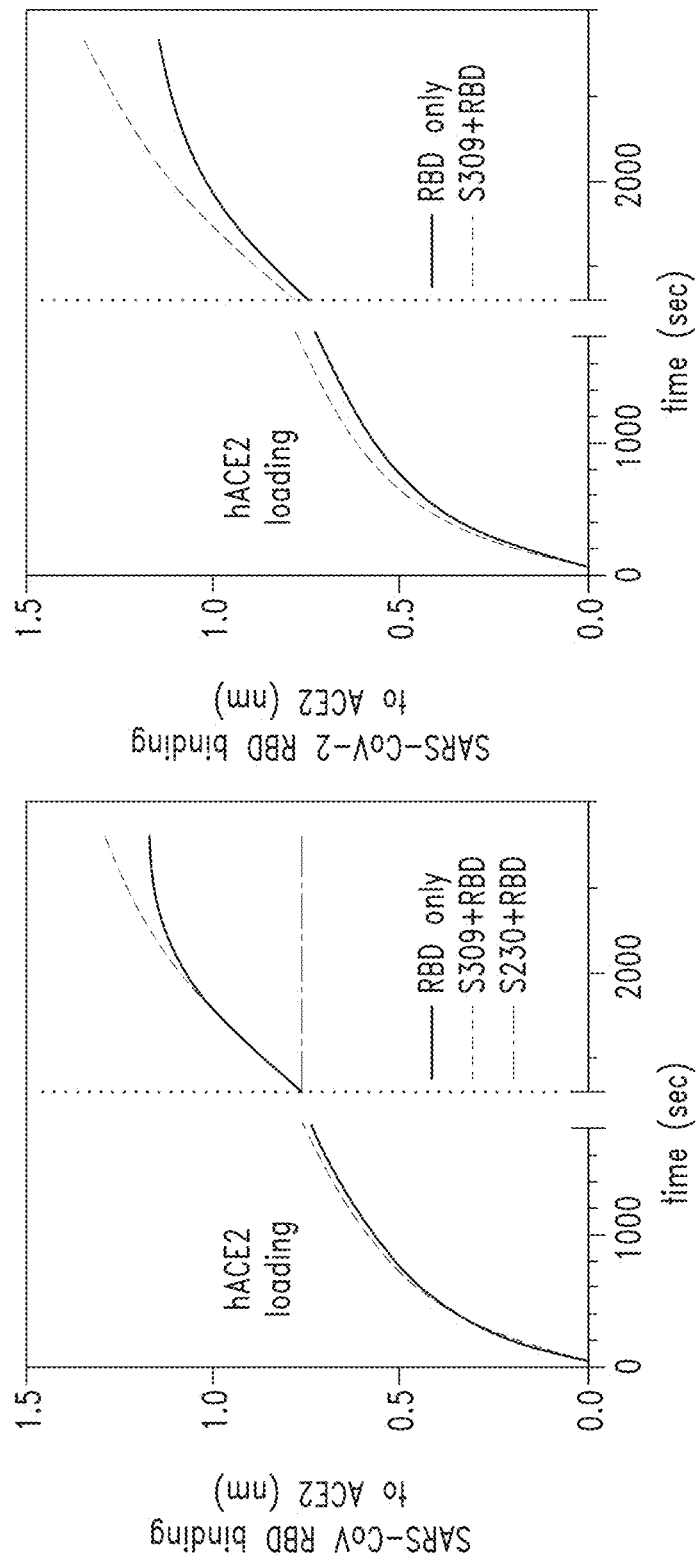
FIG. 16 shows the ability of S309 to interfere with RBD of SARS-CoV-1 (left) or SARS-CoV-2 (right) binding to human ACE2 (hACE2), as described in Example 13. hACE2 was loaded onto BLI sensors, followed by incubation of the sensors with RBD alone or RBD in combination with antibody. The vertical dashed line indicates the start of the association of RBD with or without antibody. In the graph at left, antibody S230 was used as a positive control of inhibition of SARS-CoV-1 RBD binding to ACE2 based on previous studies (see. Walls et al., *Cell* 176(5):1023-1039.e15 (2019)).
Figure 19A:
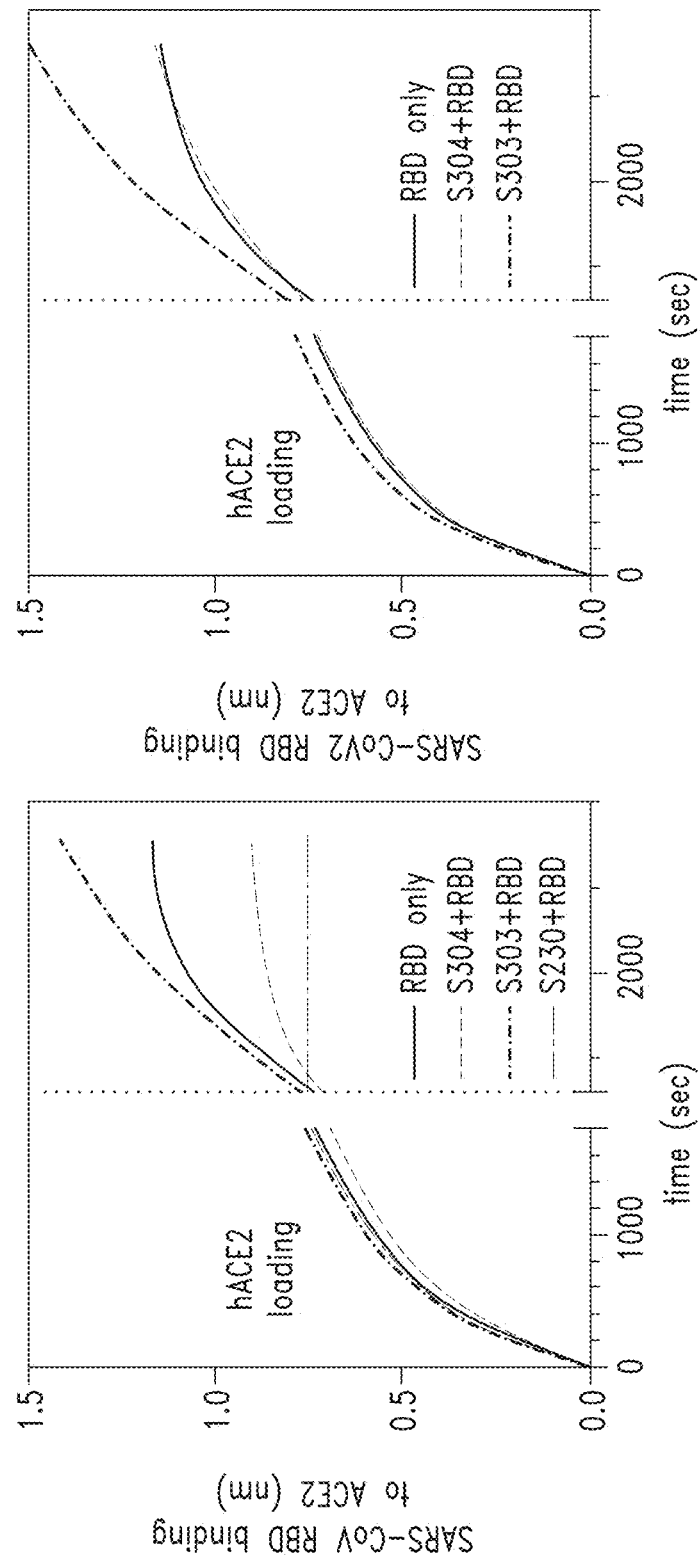
FIGS. 19A and 19B show ability of certain antibodies to interfere with RBD binding to human ACE2, as described in Example 13. Human ACE2 (hACE2) was loaded onto BLI sensors, followed by incubation of the sensors with RBD alone or RBD in combination with recombinant antibody. The vertical dashed line indicates the start of the loading of RBD with or without antibody. RBD: Receptor binding domain.
Figure 19B:
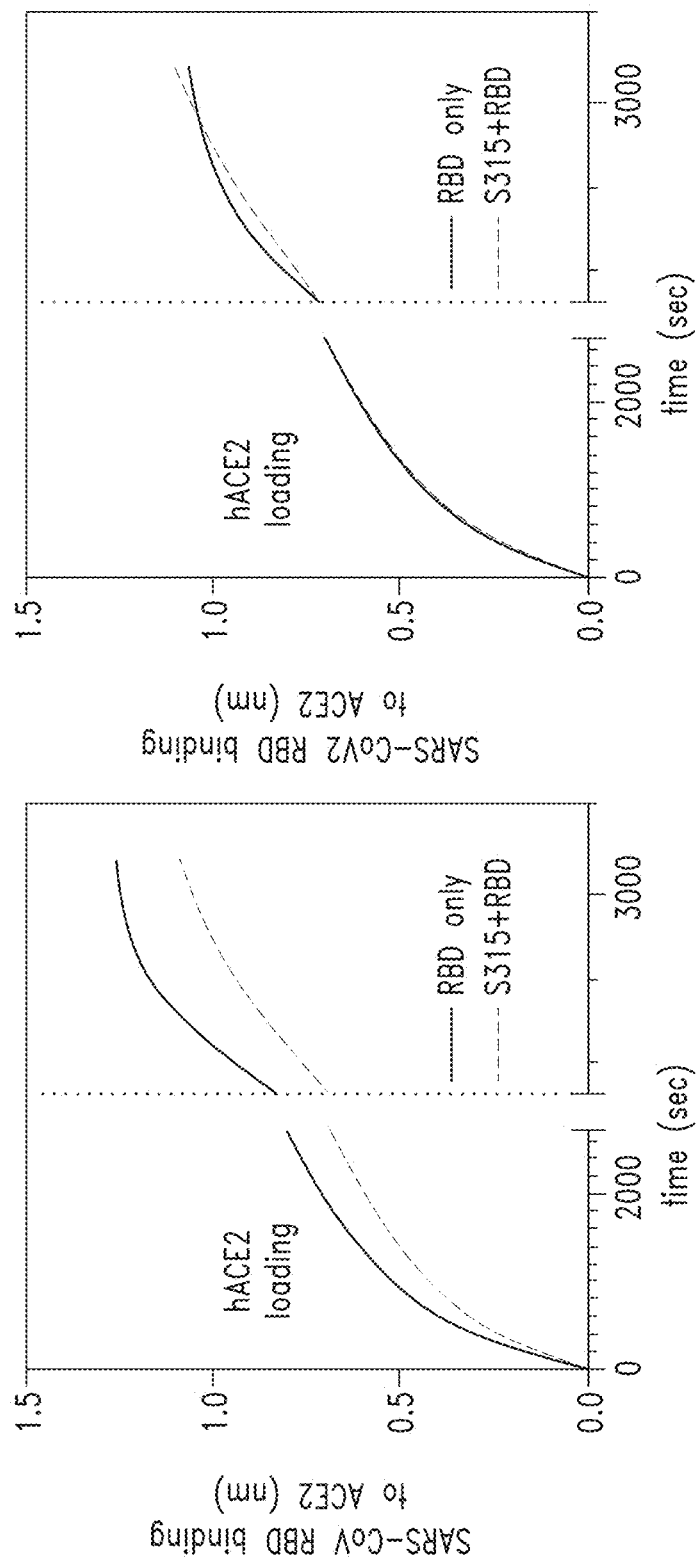
Figure 20A:
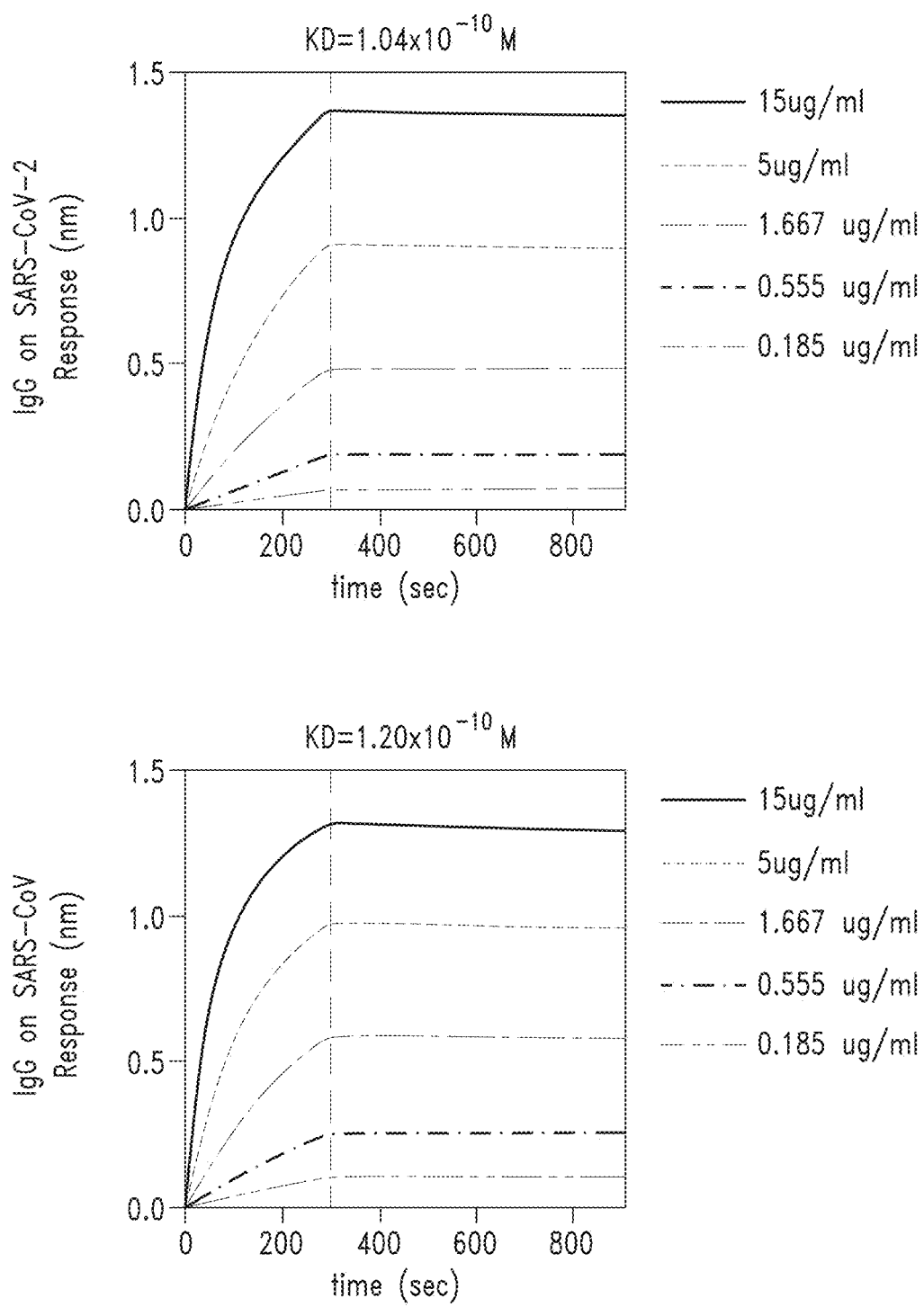
FIGS. 20A and 20B show binding affinity and avidity of antibody S309 IgG (FIG. 20A) versus S309 Fab (FIG. 20B) for SARS-CoV-1 RBD (bottom of each figure) and SARS-CoV-2 RBD (top of each figure), as described in Example 10. For both the IgG and the Fab: VH SEQ ID NO.:105; VL SEQ ID NO.:168. RBD was loaded to BLI pins and association of different concentrations of S309-IgG-MLNS or S309 Fab was measured. Vertical dashed lines indicate the start of the dissociation phase when BLI pins were switched to buffer.
Figure 20B:
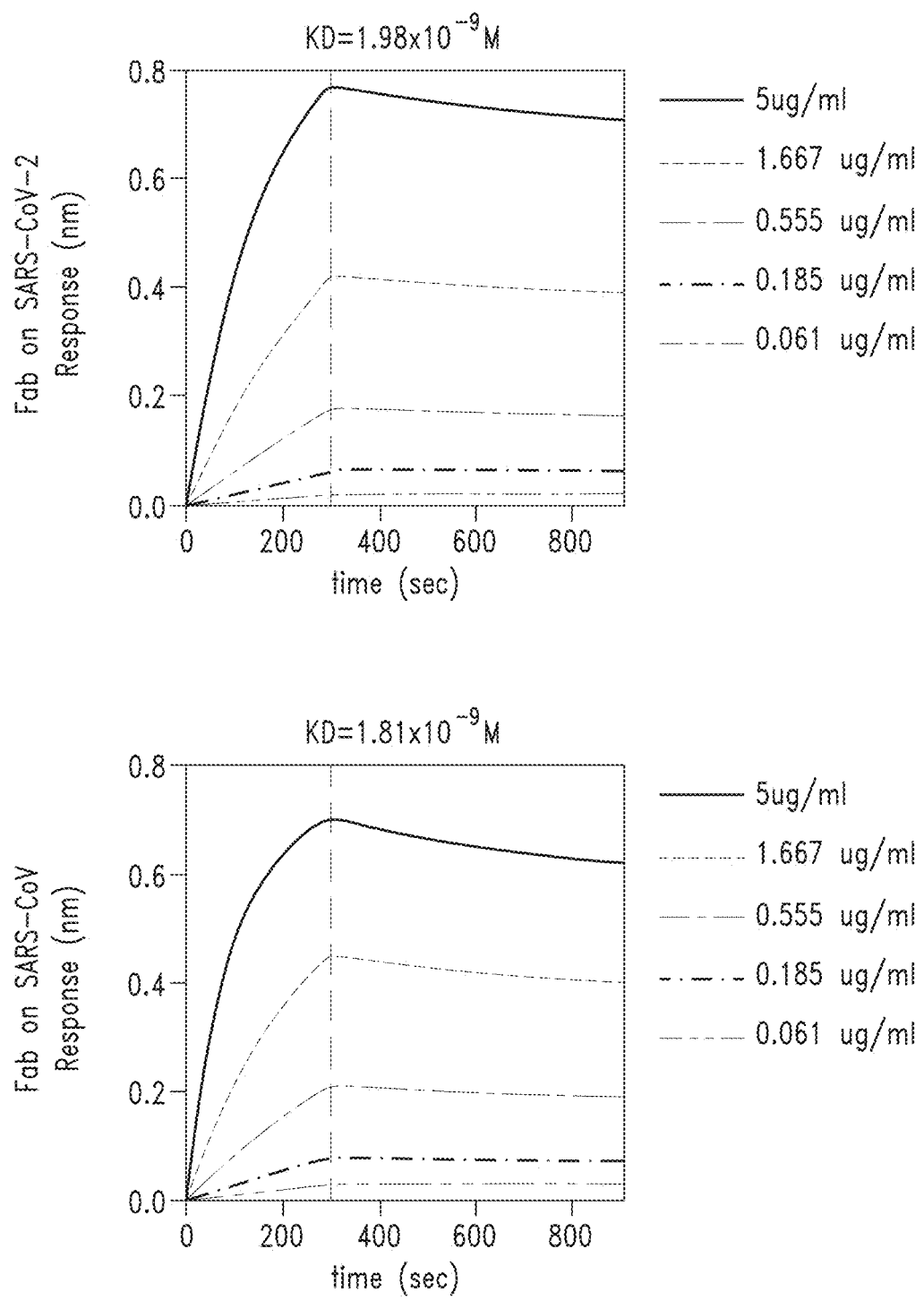

The ability of antibodies to interfere with RBD binding to human ACE2 was measured. ACE2-His (Bio-Techne AG) was loaded for 30 minutes at 5 µg/ml in kinetics buffer (KB) onto anti-HIS (HIS2) biosensors (molecular Devices-ForteBio) SARS-CoV-1 RBD-rabbit Fc or SARS-CoV-2 RBD-mouse Fc (Sino Biological Europe GmbH) at 1 µg/ml was associated for 15 minutes, after a preincubation with or without antibody at 30 µg/ml for 30 minutes. Dissociation was monitored for 5 minutes. FIG. 16 shows data obtained using antibody S309 or S230. FIGS. 19A and 19B show data obtained using antibodies S304, S303, or S230 (FIG. 19A), or RBD and antibody S315 (FIG. 19B). The vertical dashed line in each of FIGS. 16, 19A, and 19B indicates the start of the loading of RBD with or without antibody.

Example 14

Effector Function of Antibodies

Natural killer (NK)-mediated antibody-dependent cell cytotoxicity (ADCC) can contribute to viral control by killing infected cells displaying viral protein on their surface. To investigate the ability of antibodies to leverage this function, ADCC was interrogated in vitro using human NK cells (isolated from fresh blood of healthy donors using the MACSxpress NK Isolation Kit (Miltenyi Biotec, Cat. Nr.: 130-098-185)) as effector cells and SARS-CoV-2 S-transfected ExpiCHO cells as target cells. Target cells were incubated with different amounts of antibody and after 10 minutes were incubated with primary human NK cells as effector cells at a target:effector ratio of 9:1. Antibody-dependent cell killing was measured using a LDH release assay (Cytotoxicity Detection Kit (LDH) (Roche; Cat. Nr.: 11644793001)) after 4 hours of incubation at 37° C.

Macrophage- or dendritic cell-mediated antibody-dependent cellular phagocytosis (ADCP) can also contribute to viral control by clearing infected cells and by potentially stimulating T cell response with viral antigen presentation. ADCP was tested using peripheral blood mononuclear cells as phagocytes and ExpiCHO transfected with SARS-CoV-2 S fluorescently labeled with PKH67 Fluorescent Cell Linker Kits (Sigma Aldrich, Cat. Nr.: MINI67) as target cells. Target cells were incubated with different amounts of antibody for 10 minutes, followed by incubation with human PBMCs isolated from healthy donors that were fluorescently labeled with Cell Trace Violet (Invitrogen, Cat. Nr.: C34557) at an effector:target ratio of 20:1. After an overnight incubation at 37° C., cells were stained with anti-human CD14-APC antibody (BD Pharmingen, Cat. Nr.: 561708, Clone M5E2) to stain phagocytic cells. Antibody-mediated phagocytosis was determined by flow cytometry, measuring the % of monocytes that were positive for PKH67 fluorescence.

Antibodies S309 (VH SEQ ID NO.:105; VL SEQ ID NO.:168), S304, S306, S315, S230, and the combination of S309 and S304, were tested.

Figure 17A:
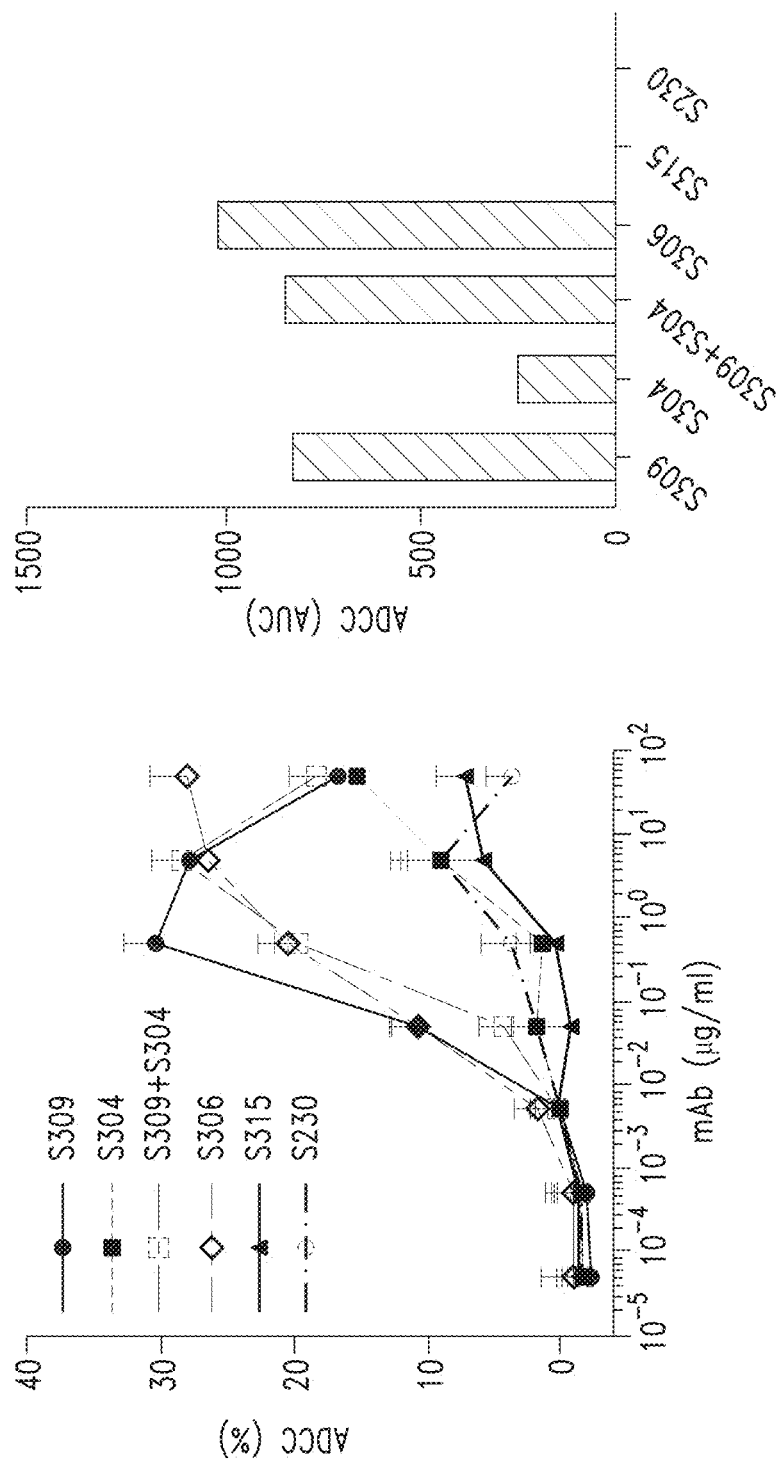
FIGS. 17A and 17B show antibody-dependent effects of certain antibodies of the present disclosure against model infected cells, as described in Example 14.
Figure 17B:
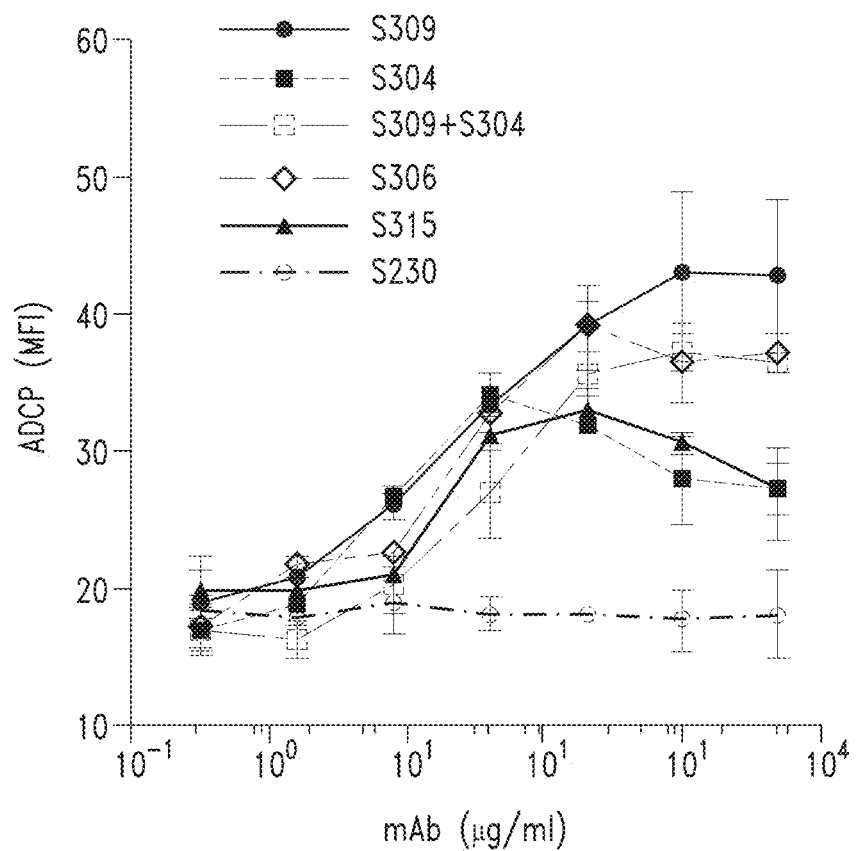
Figure 18A:
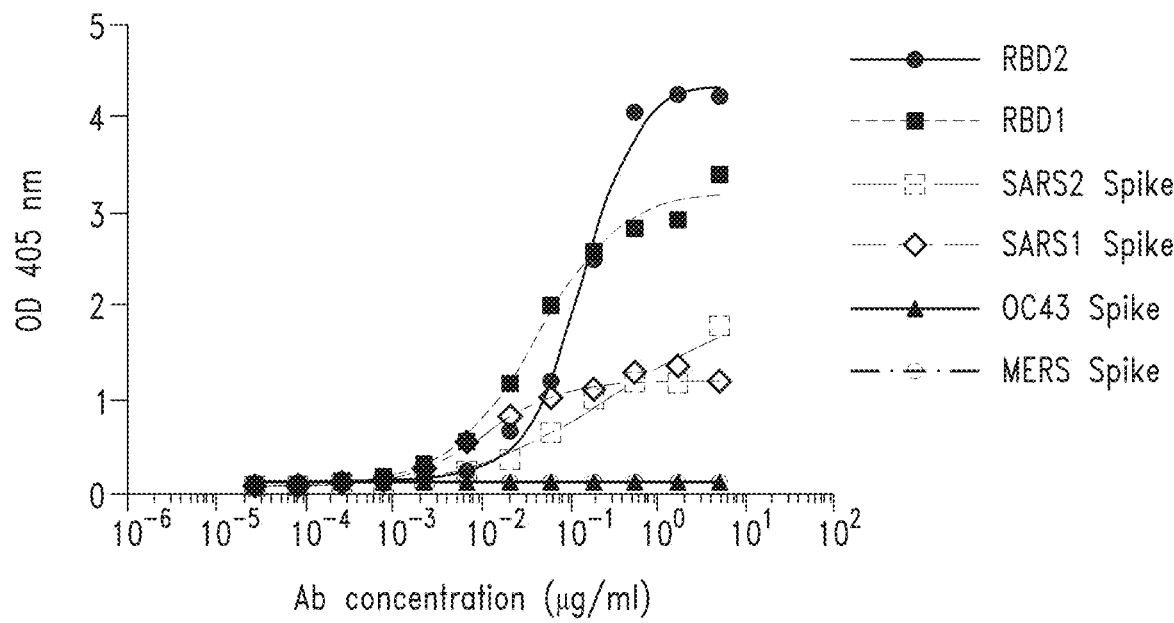
FIGS. 18A-18J show binding curves of certain recombinant antibodies for RBD of SARS-CoV-1, RBD of SARS-CoV-2, and ectodomains of various coronavirus strains, as measured by ELISA. See Example 8. Recombinant mAbs were tested by ELISA at a concentration range of 5 to 0.00028 mg/ml. RBD2: Receptor binding domain of SARS-CoV-2. RBD1: Receptor binding domain of SARS-CoV (also referred-to herein as SARS-CoV-1). Spike: stabilized prefusion trimer of the indicated coronavirus. Some antibodies were recombinantly expressed as IgG1 (rIgG1), and some antibodies were recombinantly expressed as IgG1 with the MLNS mutation (M428L and N434S (EU numbering)) in the Fc (rIgG1-LS).
Figure 18B:
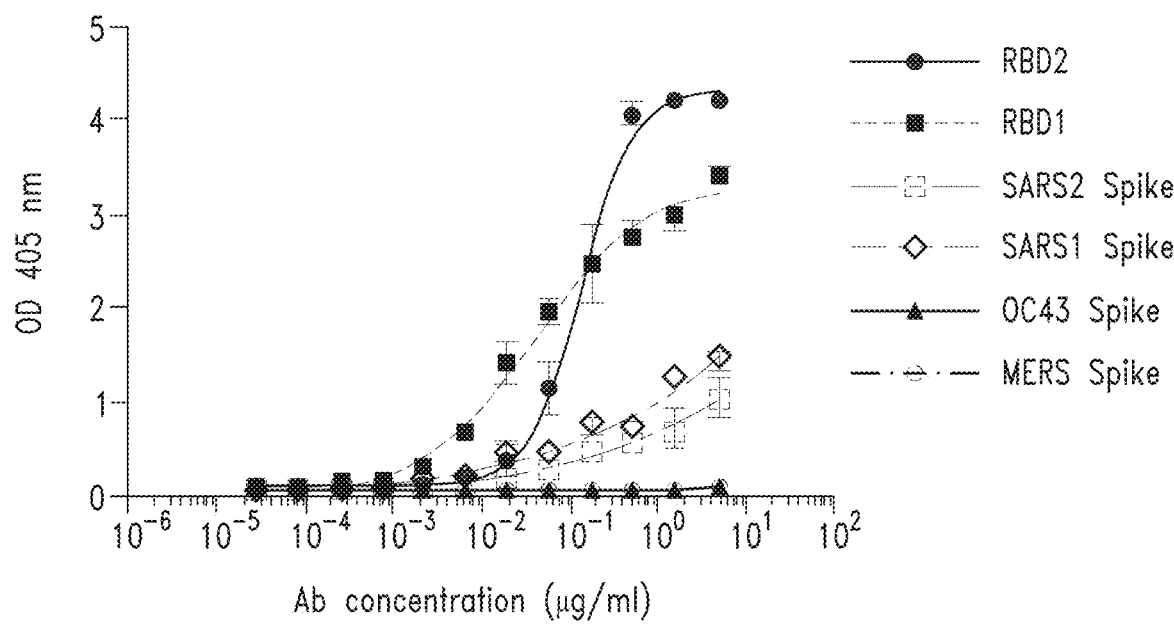
Figure 18C:
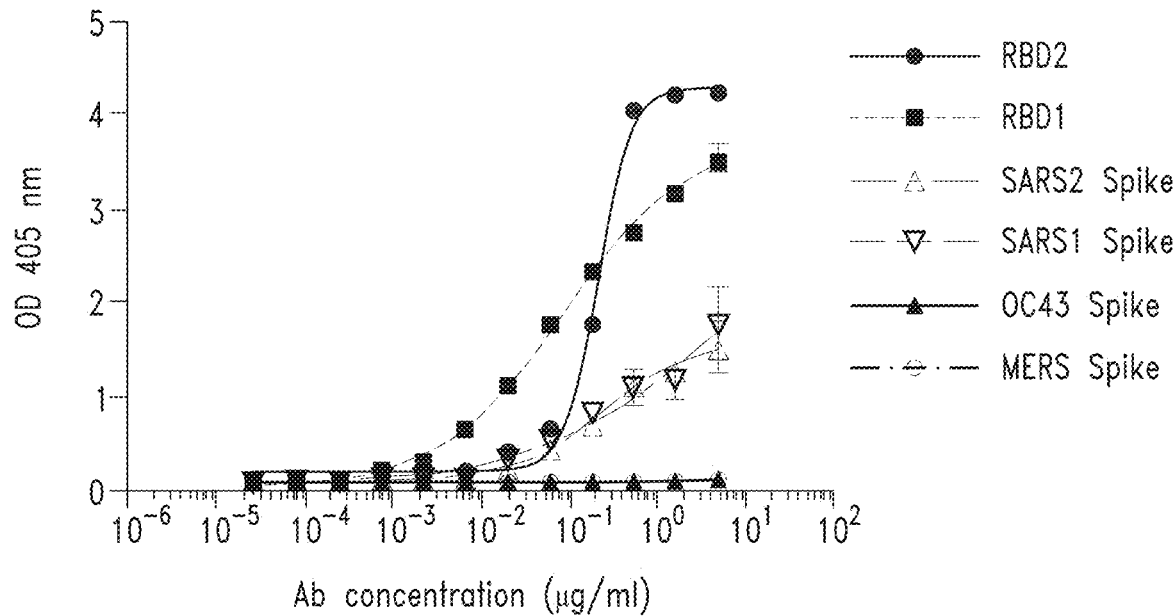
Figure 18D:
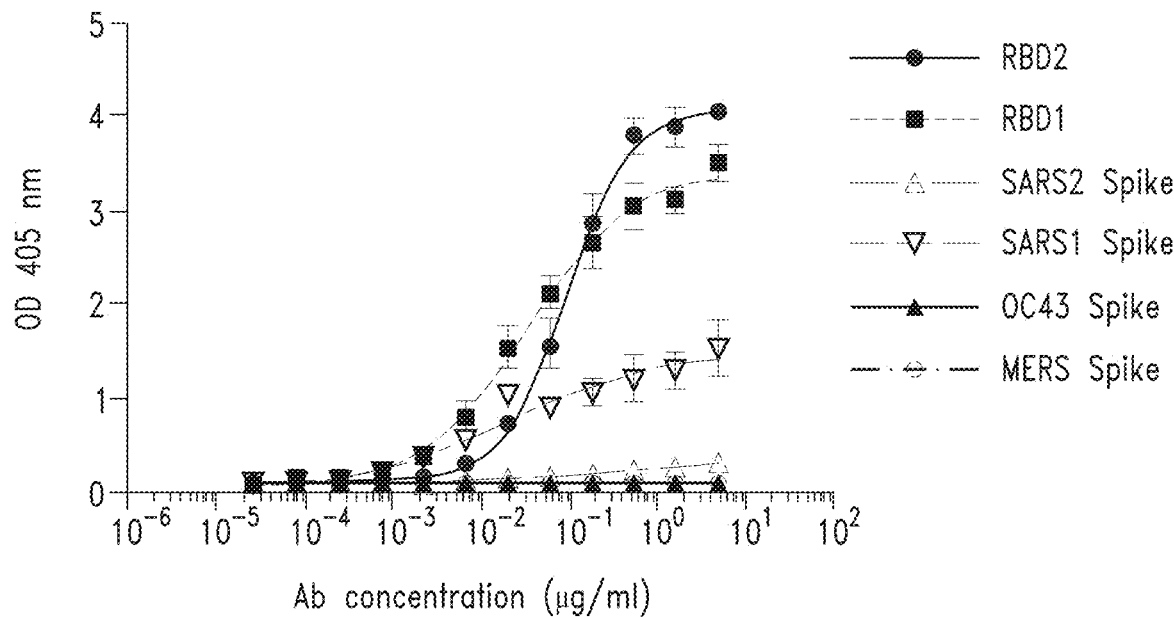
Figure 18E:
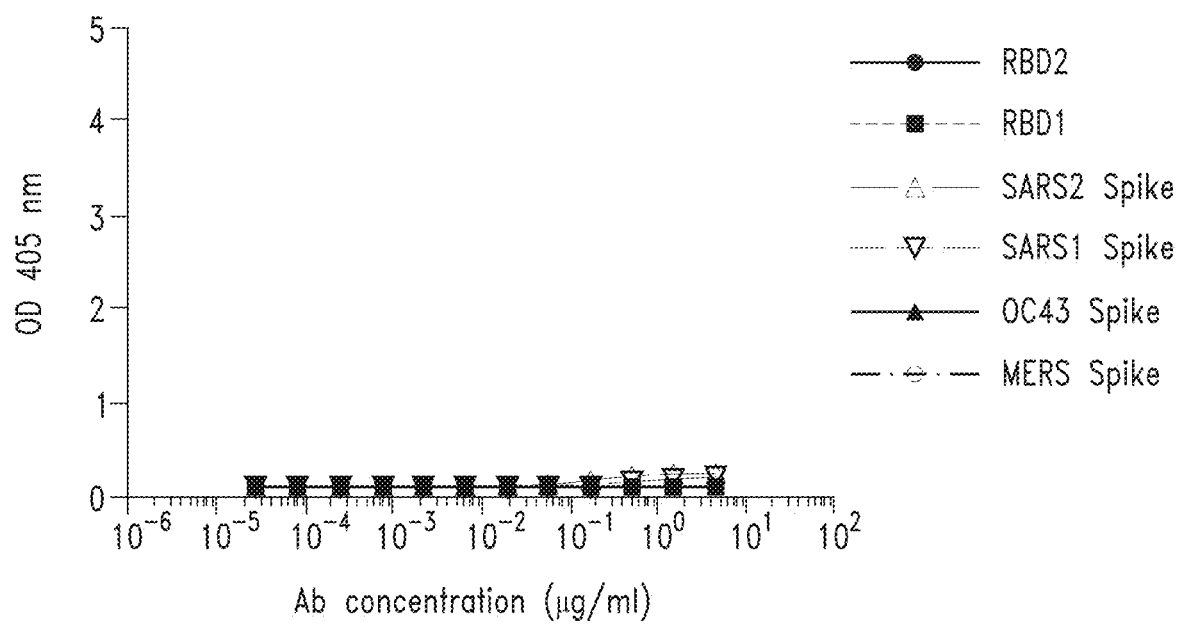
Figure 18F:
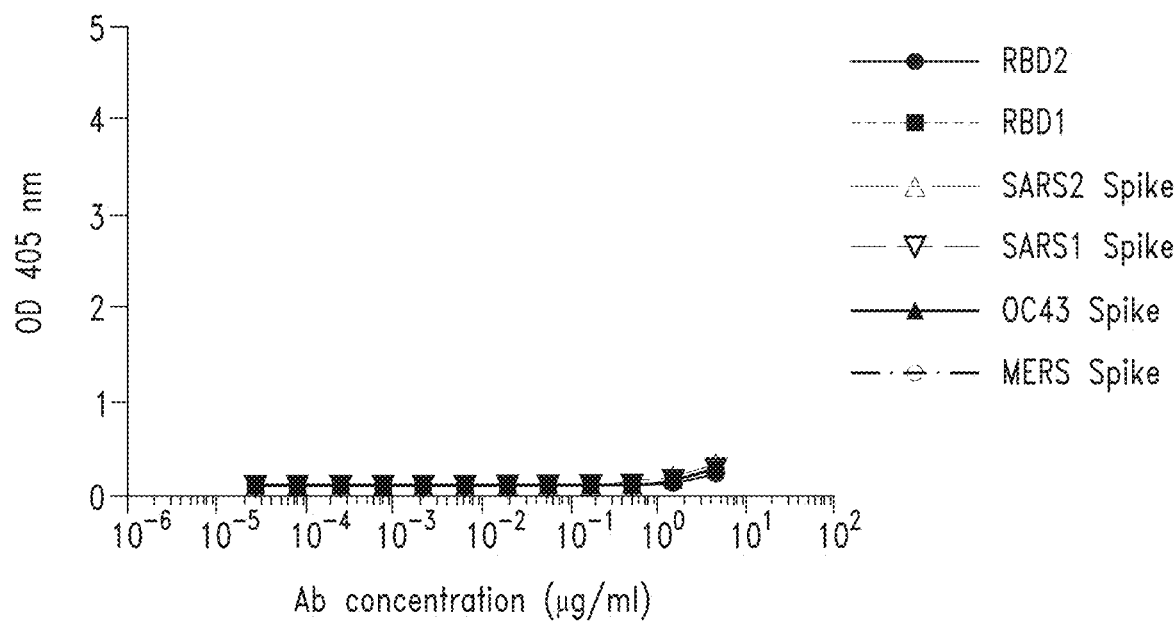
Figure 18G:
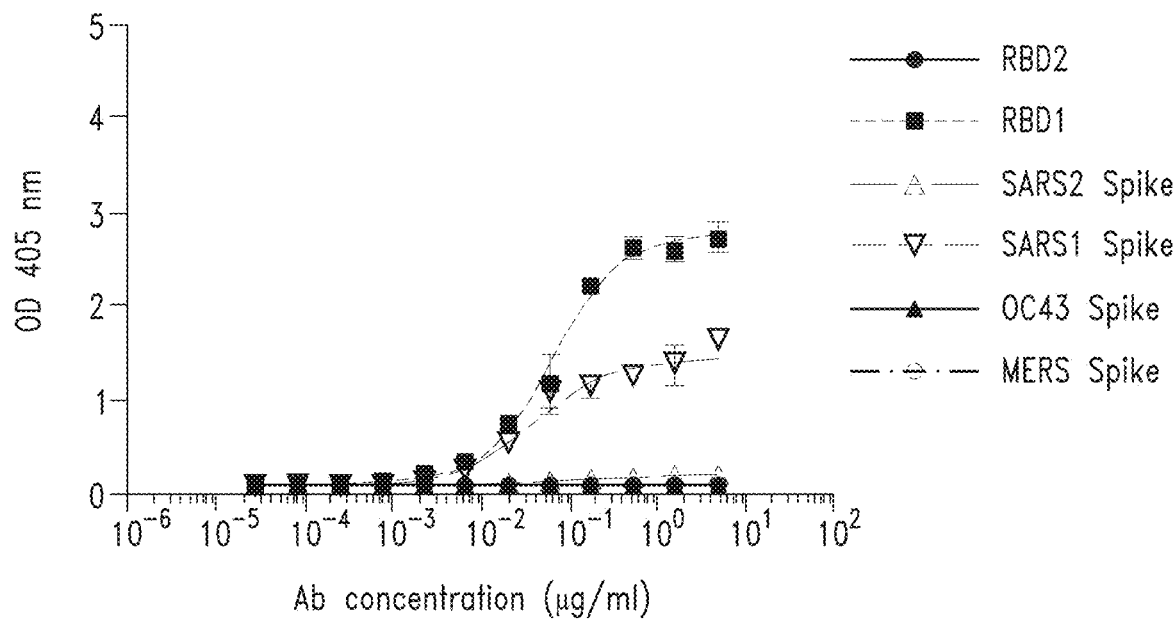
Figure 18H:
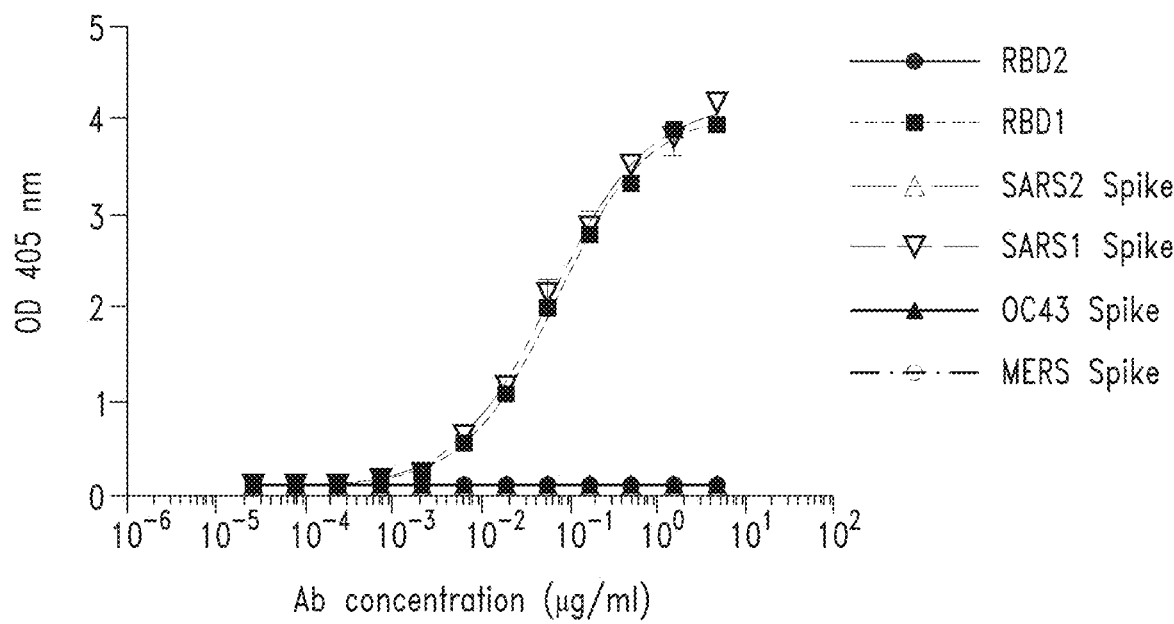
Figure 18I:
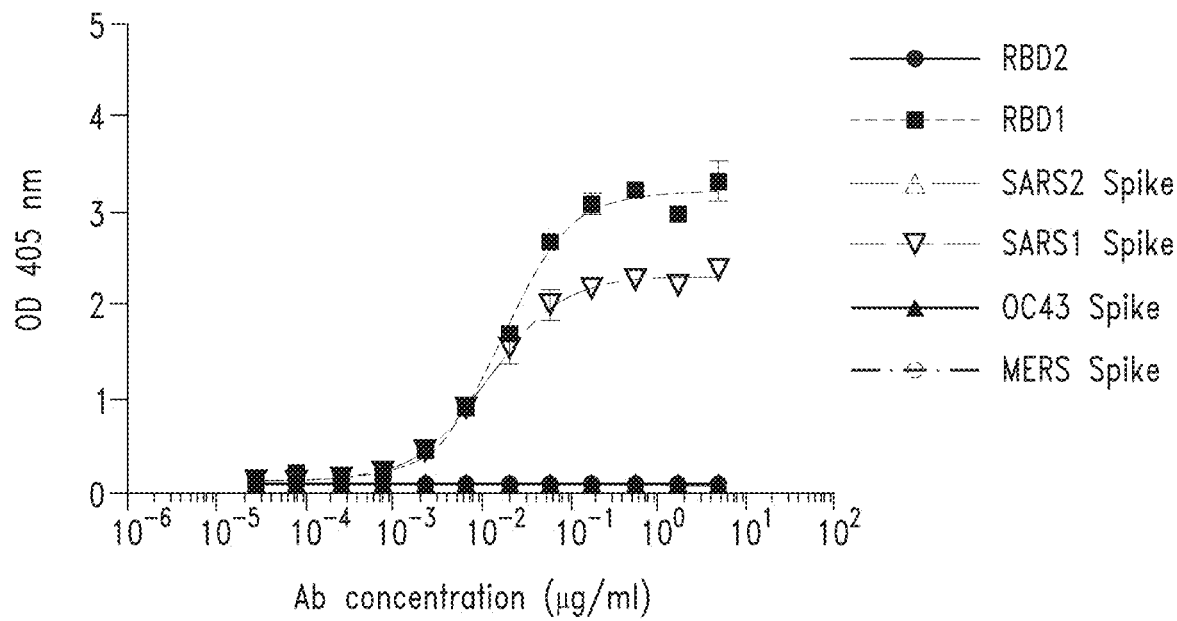
Figure 18J:
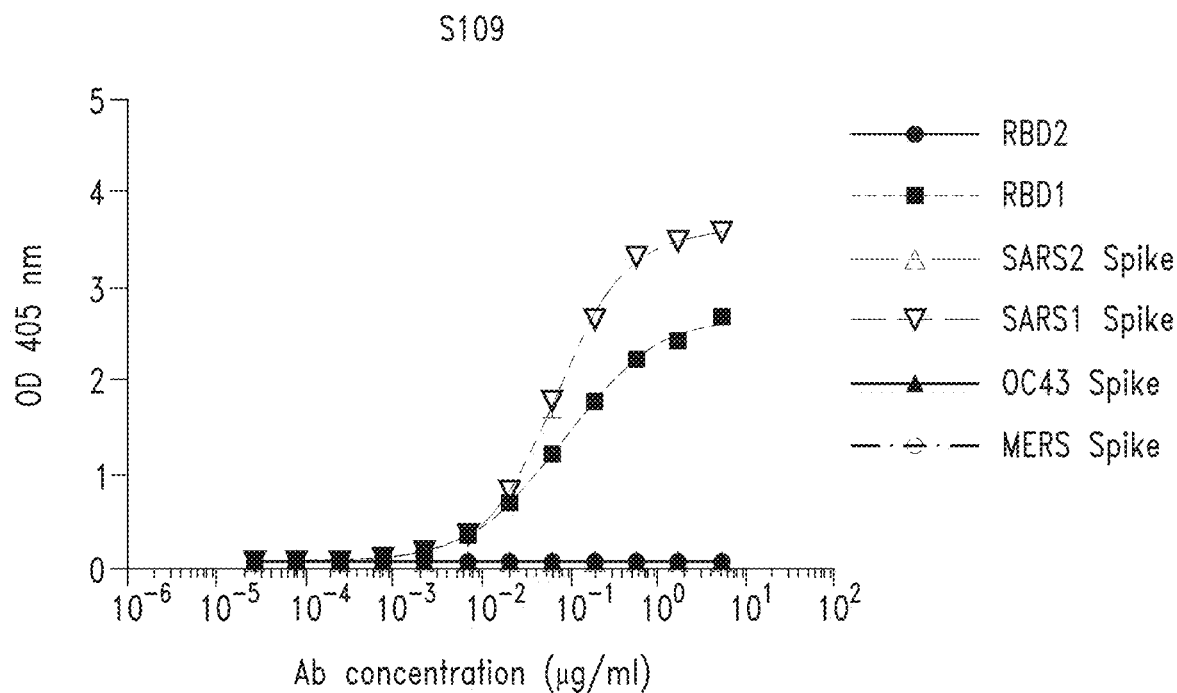

FIG. 17A shows ADCC function of antibodies using primary NK effector cells and SARS-CoV-2 S-expressing ExpiCHO as target cells. Symbols show means±SD of duplicate measurements. FIG. 17B shows ADCP function of antibodies using PBMCs as phagocytic cells and PKF67-labelled SARS-CoV-2 S-expressing ExpiCHO as target cells. Symbols show means±SD of duplicate measurements.

Figure 45:
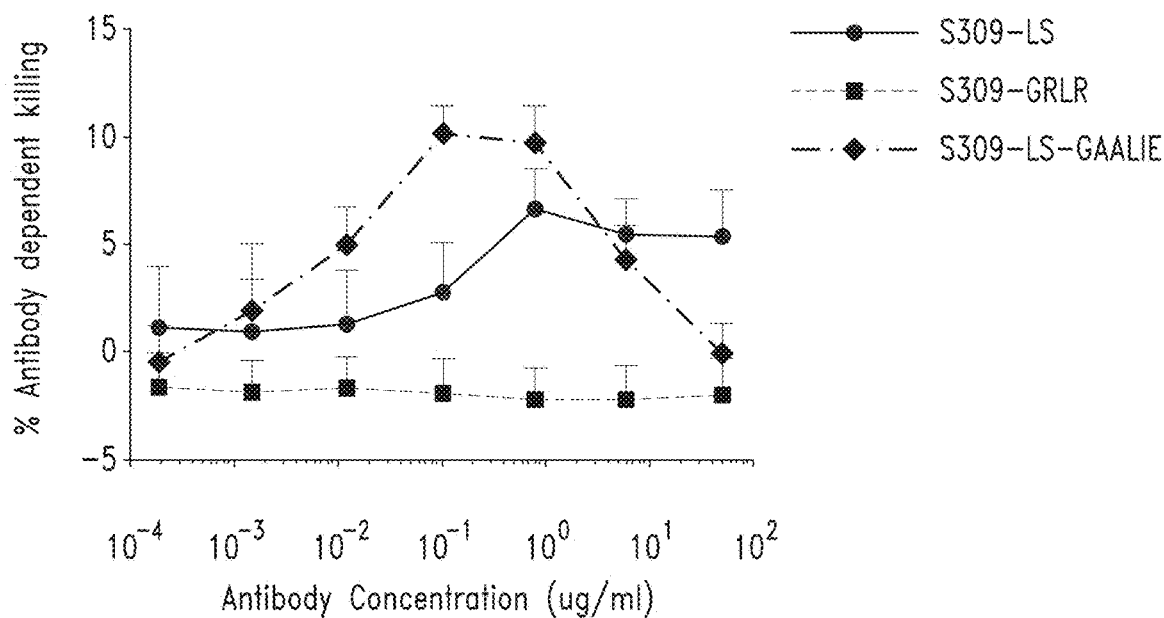
FIG. 45 shows antibody-dependent cytotoxicity of certain antibodies of the present disclosure using primary NK cells as effector cells and SARS-CoV-2-expressing ExpiCHO cells as target cells. See Example 14. The graph shows the % killing of target cells after incubation with antibodies S309 LS (also referred to herein as S309 MLNS), S309 GRLR (G236R/L328R; non-FcR binding variant), or S309 LS GAALIE (also referred to herein as S309 MLNS GAALIE, comprising G236A, A330L, I332E, M428L, and N434S Fc mutations (EU numbering)).

Fc variants of S309 were tested for ADCC. S309-LS includes the M428L and N434S Fc mutations. S309-GRLR includes the G236R/L328R Fc mutation, which exhibits minimal binding to FcγRs. S309-LS-GAALIE includes the MLNS and GAALIE (G236A/A330L/I332E) Fc mutations. Results are shown in FIG. 45.

Figure 24A:
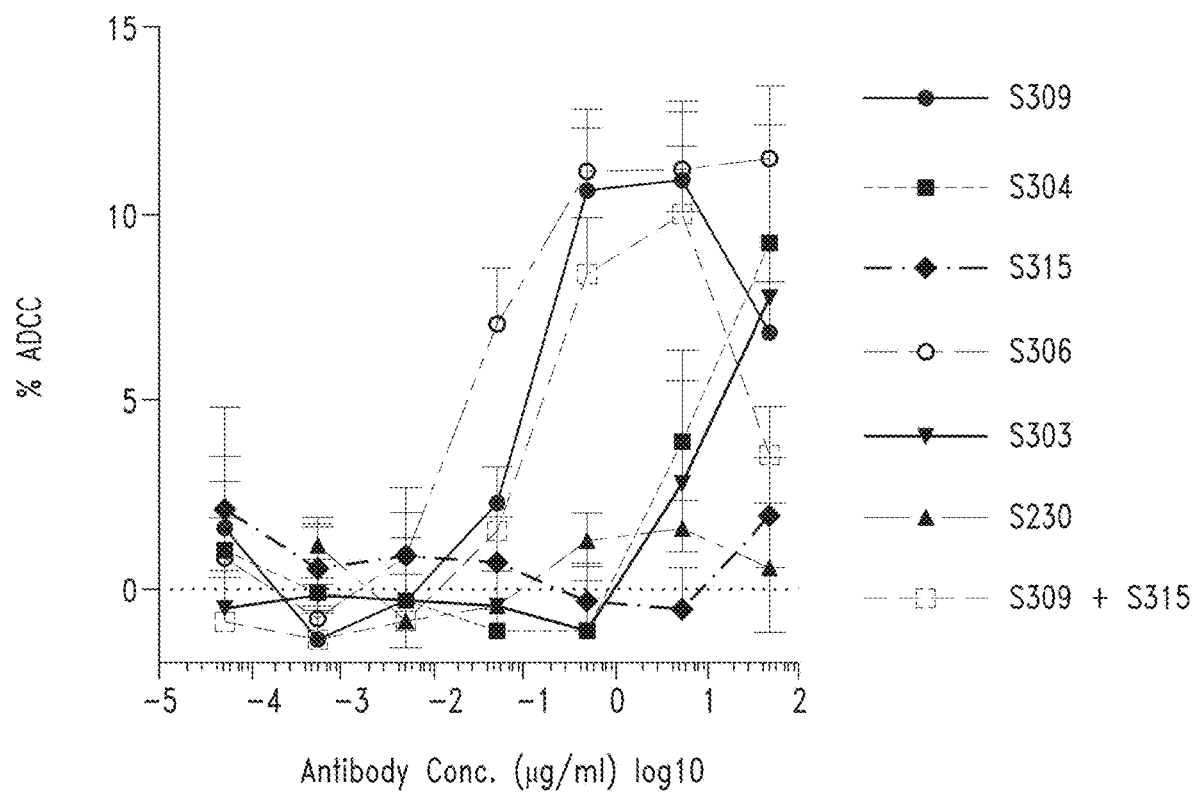
FIGS. 24A and 24B show antibody-dependent effects of certain antibodies of the present disclosure against model infected cells, as described in Example 14.
Figure 24B:
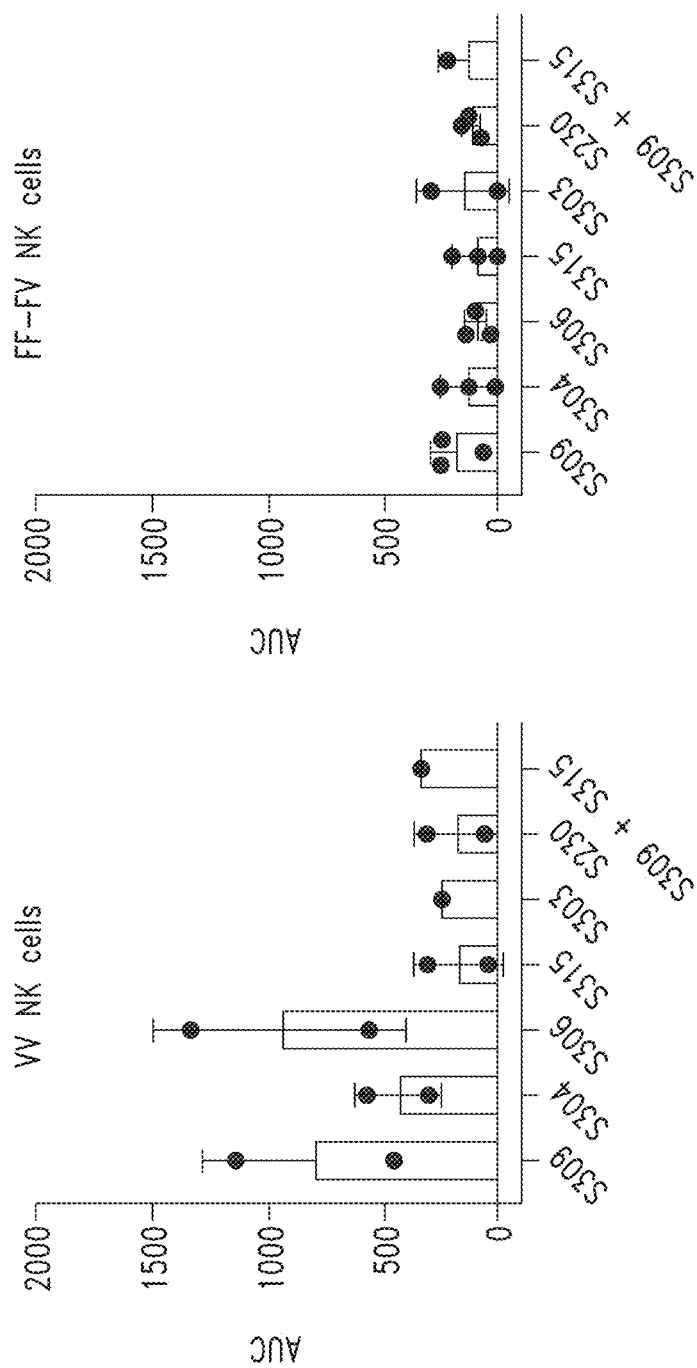
Figure 25A:
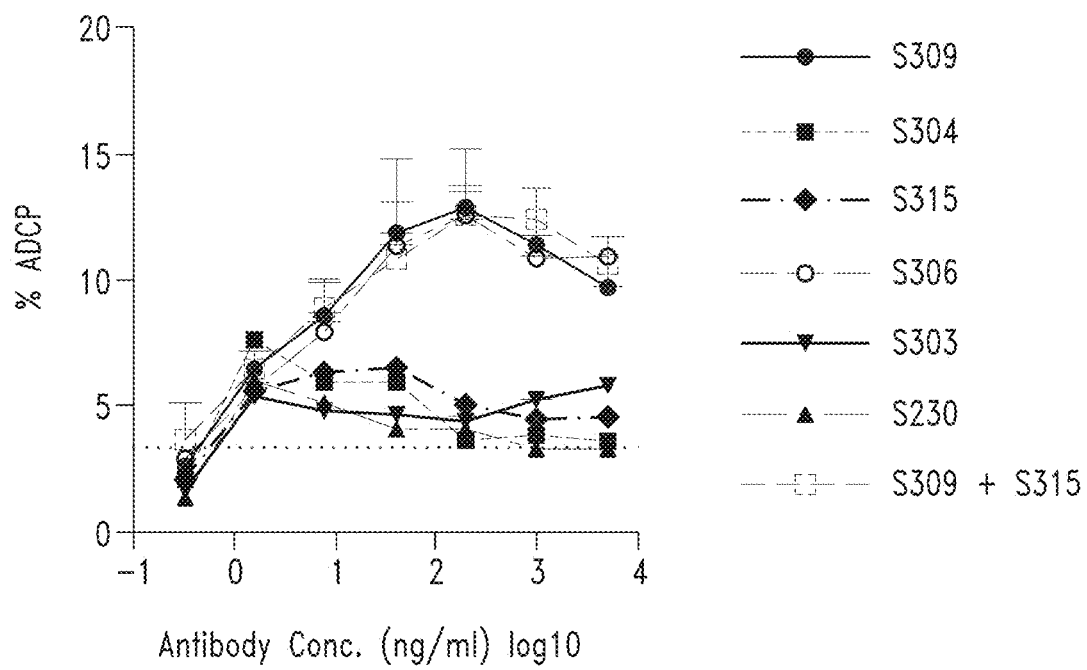
FIGS. 25A and 25B show further antibody-dependent effects of certain antibodies of the present disclosure, as described in Example 14.
Figure 25B:
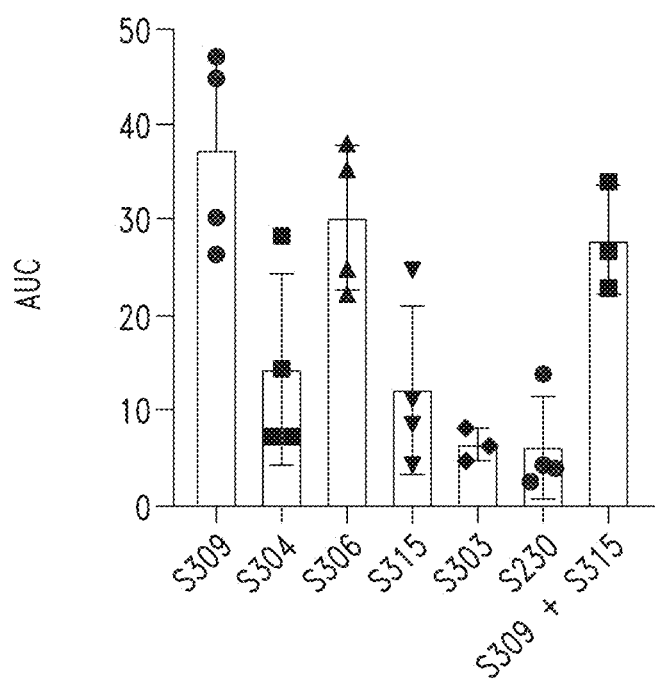
Figure 26:
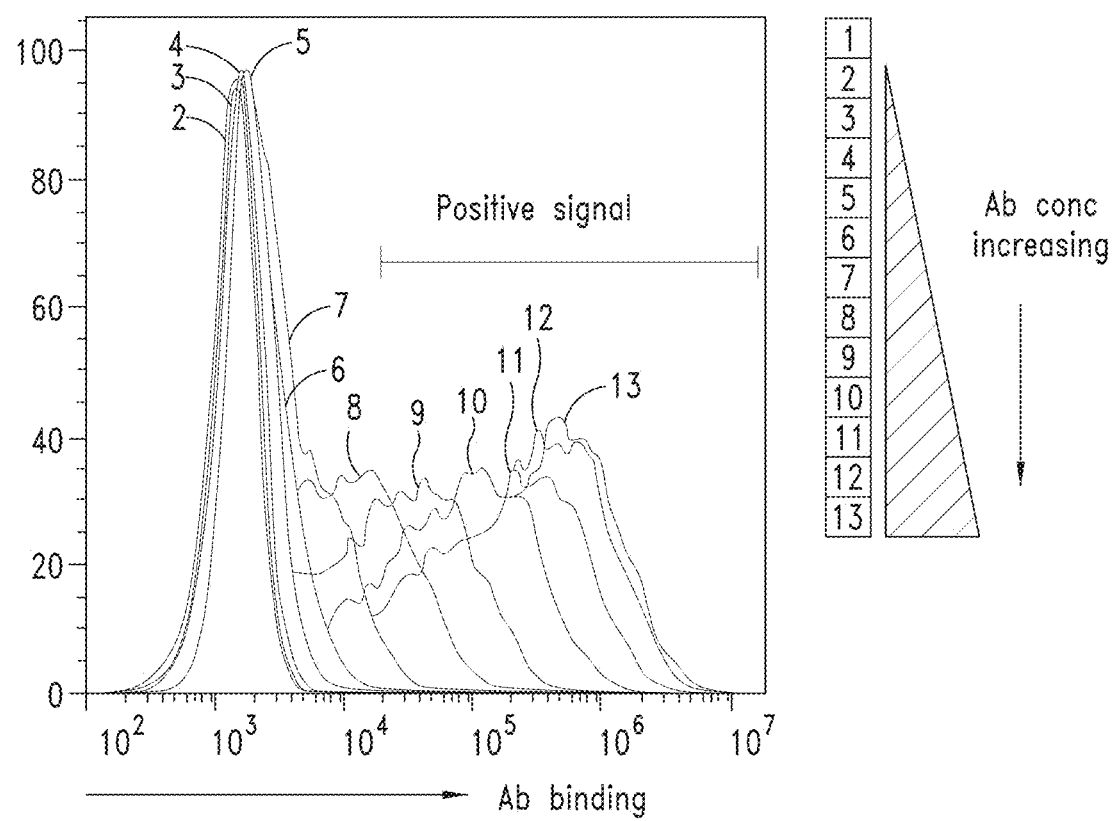
FIG. 26 shows antibody binding as measured by flow cytometry. Binding of antibody S309 to SARS-CoV-2 Spike protein expressed in Expi-CHO cells was detected with a fluorescently labeled secondary antibody.
Figure 27:
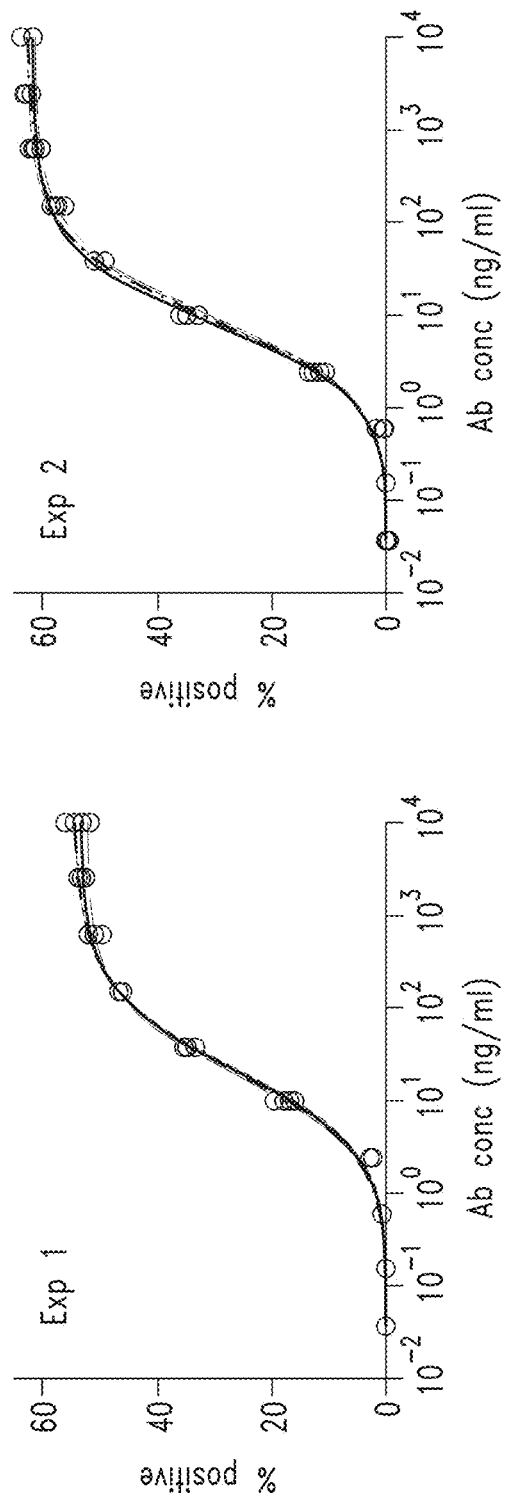
FIG. 27 shows binding of antibody S309 (labeled as "11" in the figure key) and four engineered variants of S309 (labeled as "12" through "15", respectively) to S protein, as measured by flow cytometry. See Example 9. The four engineered variant antibodies are as follows: S309 N55Q comprises an N55Q mutation in CDRH2, resulting in a variant VH sequence (SEQ ID NO.:113), and the wild-type VL sequence (SEQ ID NO.:168) of S309; S309 W50F comprises a W50F variant VH sequence (SEQ ID NO: 129) and the wild-type VL sequence (SEQ ID NO.:168) of S309; S309 W105F comprises a W105F variant VH sequence (SEQ ID NO: 119) and the wild-type VL sequence (SEQ ID NO.:168) of S309; and S309 W50F/G56A/W105F comprises a W50F/G56A/W105F variant VH sequence (SEQ ID NO.:172) and the wild-type VL sequence of S309.
Figure 27:
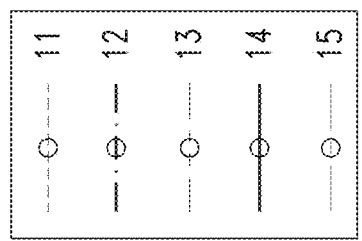

Antibodies S303, S304, S306, S309, S315, and the combination of S309 and S315 were assayed for ADCC and ADCP function. FIG. 24A shows ADCC of antibodies using primary NK effector cells and SARS-CoV- or SARS-CoV-2 S-expressing ExpiCHO as target cells. The graph in FIG. 24A shows the % killing determined for one representative donor homozygous for the high affinity FcγRIIIa (symbols show mean±SD). FIG. 24B shows area under the curve (AUC) for the responses of cells from donors homozygous for the high affinity FcγRIIIa variant 158V (VV), compared to cells from donors heterozygous for 158V (FV) or homozygous for the low affinity variant 158F (FF) (mean±SD). FIG. 25A shows ADCP using PBMCs as phagocytic cells and PKH67-labelled SARS-CoV-2 S-expressing ExpiCHO as target cells, for one representative donor. % ADCP indicates the percentage of monocytes positive for PKH67. FIG. 25B shows the area under the curve (AUC) for the responses from multiple donors.

Example 15

Reactivity of Antibodies to Cell Lysate of SARS-CoV-2-Infected Cells

Figure 21A:
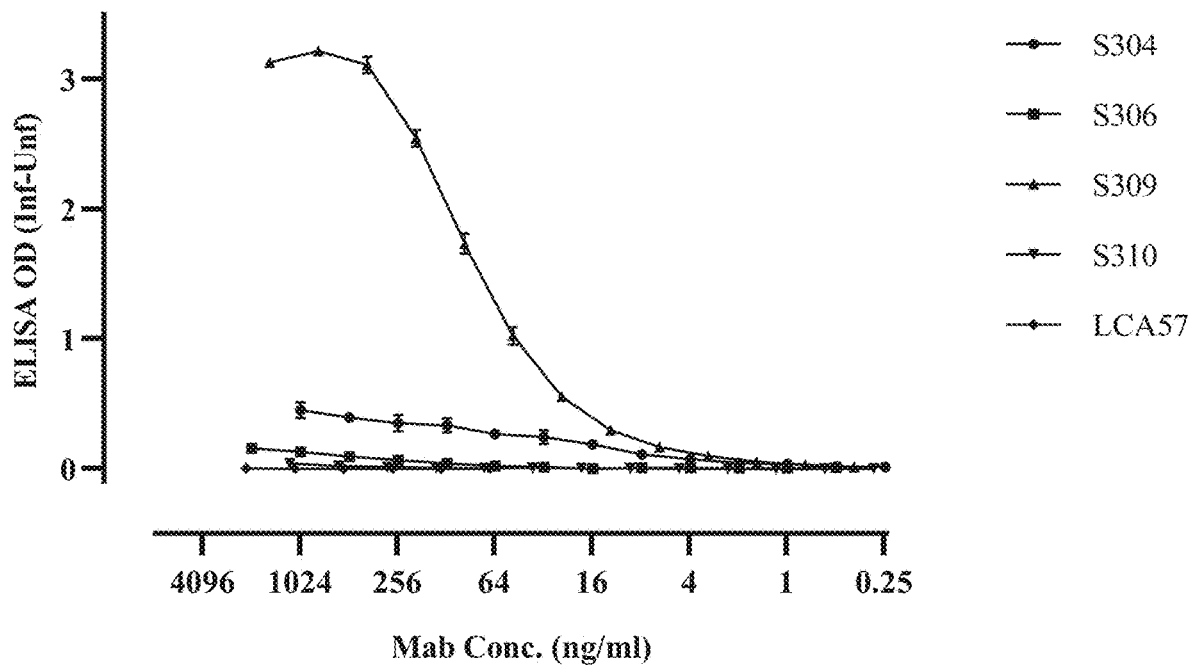
Figure 21B:
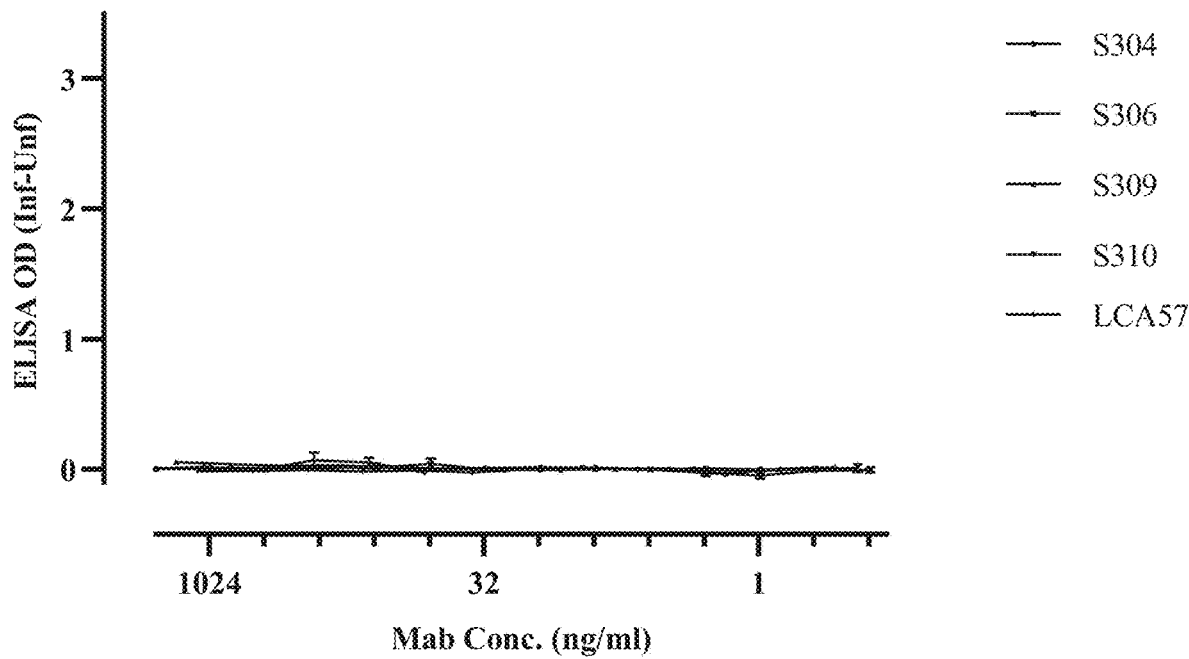
Figure 22A:
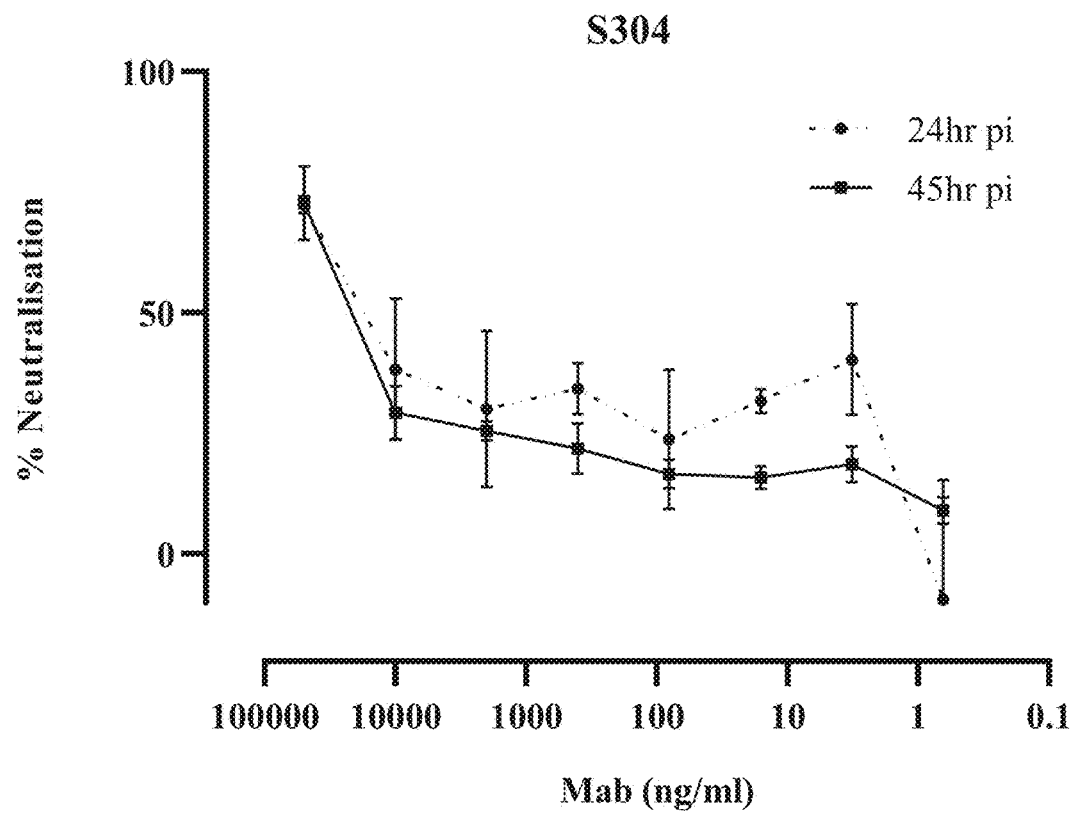
FIG. 22A-22D show neutralization of SARS-CoV-2 infection by antibodies as assessed by inhibition of nucleoprotein (NP) expression at 24 and 45 hours post infection. See Example 16.
Figure 22B:
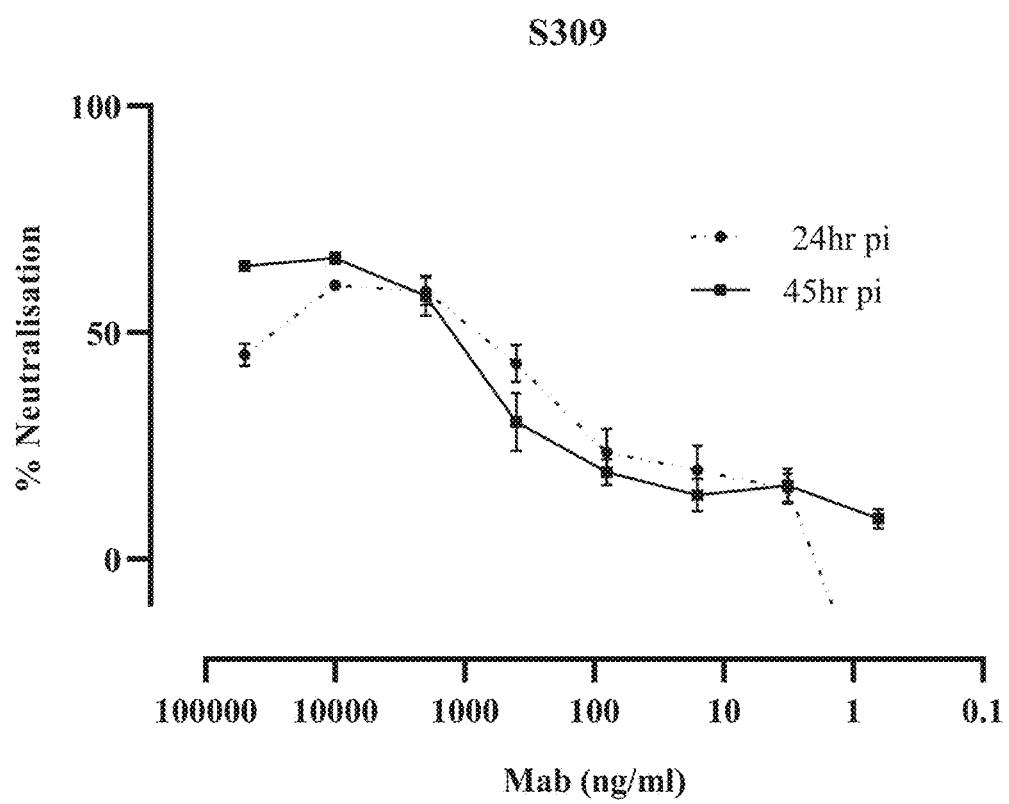
Figure 22C:
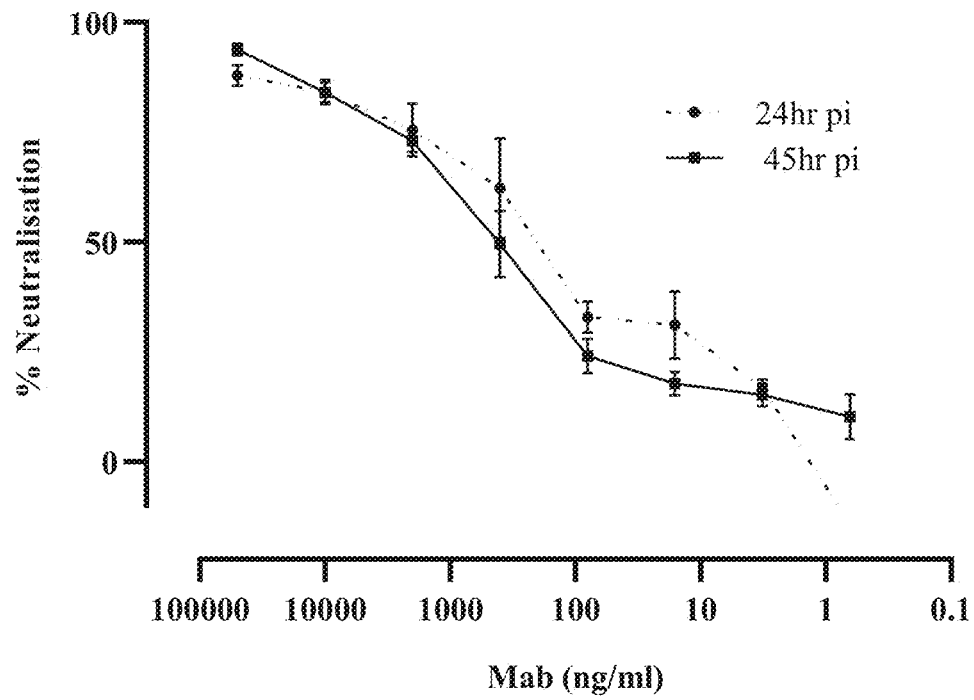
Figure 22D:
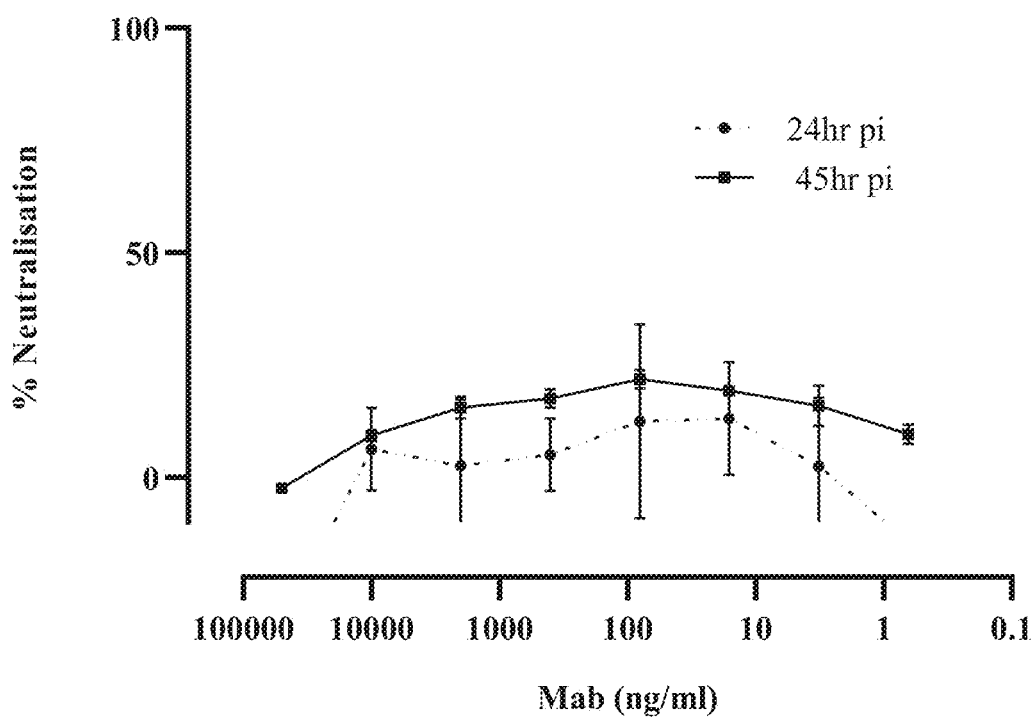

Reactivity of antibodies S304, S306, S309, and S310 against cell lysate of SARS-CoV-2-infected VeroE6 cells was measured. FIG. 21A shows reactivity of the antibodies, as measured by indirect ELISA S against TX100-extracted lysate of SARS-CoV-2-infected VeroE6 cells. FIG. 21B shows reactivity of the antibodies, as measured by indirect ELISA S against SDS extracted (denatured) lysate of SARS-CoV-2-infected VeroE6 cells. FIG. 21C shows reactivity of human SARS-CoV-1 convalescent serum, as measured by indirect ELISA S against TX100-extracted or SDS-extracted lysate of SARS-CoV-2-infected VeroE6 cells.

Example 16

Neutralization of SARS-CoV-2 Infection by Antibodies S304 and S309, Alone or in Combination Neutralization of SARS-CoV-2 infection by monoclonal antibodies S304 and S309 was assessed using a SARS-CoV-2 live virus assay. The live virus neutralization assay quantifies the number of infected cells by staining for viral nucleoprotein (NP) with an NP-specific polyclonal rabbit serum. Inhibition was assessed by measuring NP expression at 24 and 45 hours post infection. Enzyme immunoassay (EIA) was used to quantify the level of infection for each antibody dilution tested.

Data are shown in FIGS. 22A-22D. Neutralization was carried out for one hour at room temperature at the indicated antibody concentrations using Vero E6 cells in monolayer in 96-well plates. Wells were infected with 100 TCID50 of virus. After 24 or 45 hours, monolayers were fixed and stained for inhibition of NP expression. When combined, S304 and S309 show a synergistic enhancement of neutralization.

Example 17

Production of S309 RIgG Variant Antibodies

Recombinant IgG1 antibodies were produced using the VH and VL sequences of antibody S309. In this example, antibodies are referred-to as "S309-11", "S309-12", "S309-13", "S309-14", and "S309-15", respectively. "S309-11" comprises the wild-type VH sequence (SEQ ID NO: 105) and the wild-type VL sequence (SEQ ID NO: 168) of S309. "S309-12" comprises an N55Q mutation in CDRH2, providing a VH variant sequence (SEQ ID NO: 113) and the wild-type VL sequence (SEQ ID NO: 168) of S309. "S309-13" comprises a W50F mutation in VH (SEQ ID NO: 129) and the wild-type VL sequence (SEQ ID NO: 168) of S309. "S309-14" comprises a W105F VH variant sequence (SEQ ID NO: 119) and the wild-type VL sequence (SEQ ID NO: 168) of S309. "S309-15" comprises a W50F/G56A/W105F VH variant (SEQ ID NO: 172) and the wild-type VL sequence of S309 (SEQ ID NO: 168). S309 recombinant antibody (S309-11) and each of the four variants S309-12-S309-15 were produced by transient transfection and expression of a plasmid vector encoding the recombinant antibody in HD 293F cells (GenScript). A plasmid vector encoding the S309 antibodies also encoded a signal peptide as set forth in SEQ ID NO.:252. This signal peptide provided superior antibody production as compared to other signal peptides tested. Data not shown. Cells were harvested on day 4 and IgG expression was validated by Western blot and protein A titer analysis.

Example 18

Binding of S309 RIgG and Variants to SARS-CoV-2 RBD

Binding of recombinant monoclonal antibody S309 and the four S309 variants described in Example 17 (S309-12-S309-15) to RBD was measured using surface plasmon resonance (SPR). SPR experiments were carried out with a Biacore T200 instrument using a single-cycle kinetics approach. Antibody expressed as IgG was captured on the surface and increasing concentrations of purified SARS-CoV-2 RBD, either glycosylated or deglycosylated form, were injected. SPR was conducted using a sensor chip with anti-human Fc covalently immobilized (GE). Buffer used was 10 mM HEPES pH 7.4, 150 mM NaCl, 3 mM EDTA, and 0.05% P20 detergent. Assays were conducted at 25° C. Recombinant antibodies were diluted from supernatant to approximately 2 µg/ml. RBD concentrations were 0.8 nM, 3.1 nM, 12.5 nM, 50 nM, and 200 nM. Glycosylated RBD was obtained by expression in HEK293 cells and purified using one-step Ni affinity purification. Deglycosylated RBD was obtained by expression in-house in Expi293 cells grown in the presence of kifunensine, purification using one-step Ni affinity purification, and treatment with endoglycosidase H. Single-cycle kinetics assays were carried out with 3 minute injections and 20 minute dissociation periods. Association and dissociation kinetics were monitored and fit to a binding model to determine affinity. Results are shown in FIGS. 30A-30F and Table 8.

TABLE 8

| mAb Supernatant S309 WT or variant | Glycosylated RBD | | | Deglycosylated RBD | | |
| --- | --- | --- | --- | --- | --- | --- |
| | $K_D$ | $K_a$ (1/Ms) | $K_d$ (1/s) | $K_D$ | $K_a$ (1/Ms) | $K_d$ (1/s) |
| S309-11 (WT) | 0.50 nM | 10.0e4 | 5.0e−5 | 0.91 nM | 3.0e5 | 2.8e−4 |
| S309-11 (WT) replicate | 0.68 nM | 9.5e4 | 6.5e−5 | 0.98 nM | 2.9e5 | 2.9e−4 |
| S309-12 (N55Q) | 0.46 nM | 9.2e4 | 4.2e−5 | 1.3 nM | 2.7e5 | 3.6e−4 |
| S309-13 (W50F) | 0.51 nM | 9.9e4 | 5.0e−5 | 1.8 nM | 3.0e5 | 5.3e−4 |
| S309-14 (W105F) | 0.38 nM | 1.0e5 | 3.9e−5 | 7.9 nM | 9.8e5 | 7.7e−3 |
| S309-15 (W50F/G56A/W105F) | 1.7 nM | 9.9e4 | 1.6e−4 | >10 nM | estimated Kd with steady-state fit | |

Figure 30A:
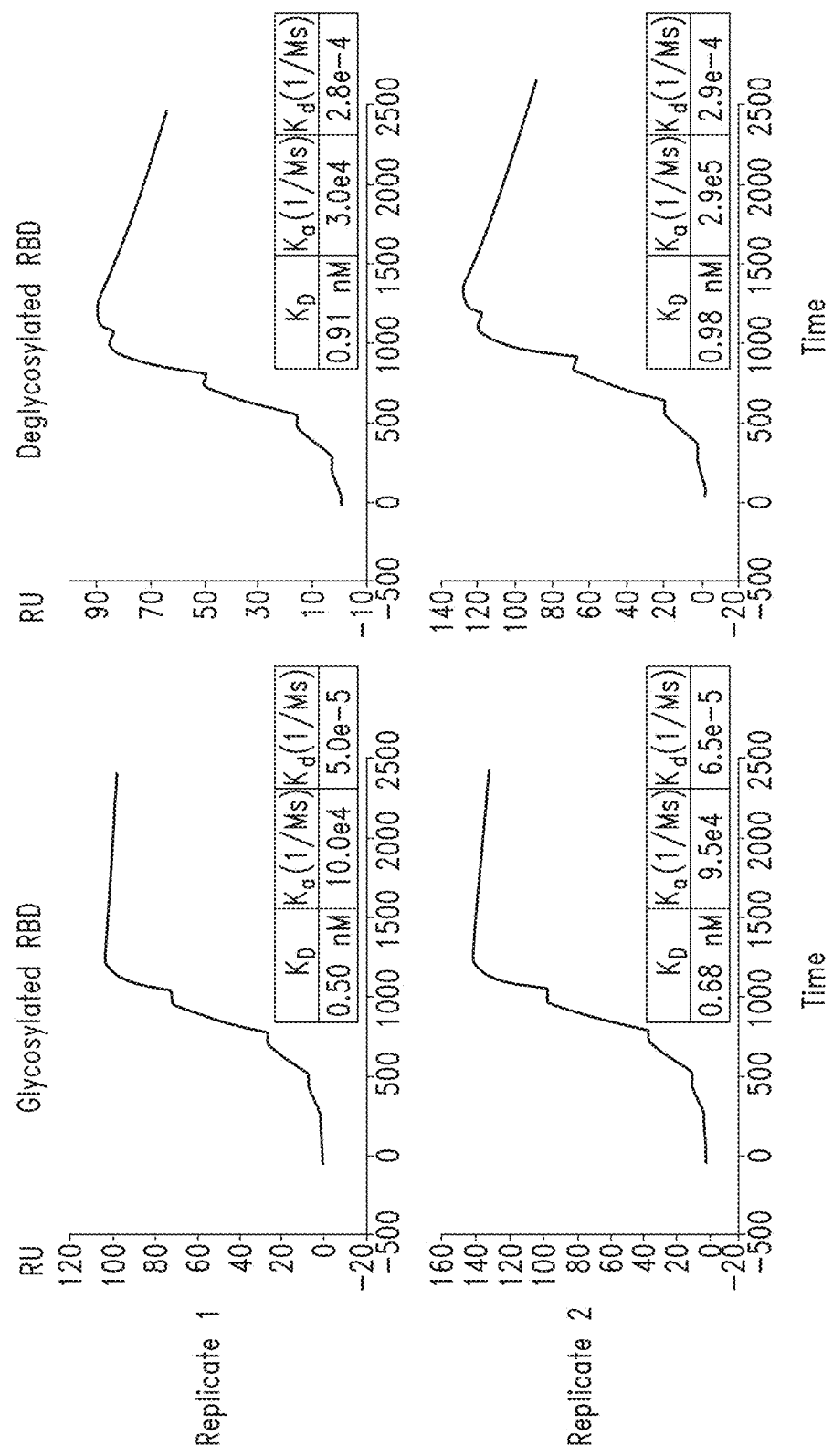
FIGS. 30A-30F show binding kinetics of exemplary antibodies to SARS-CoV-2 glycosylated or deglycosylated RBD as measured by SPR. See Example 18. Antibodies S309 (having S309 wild-type VH (SEQ ID NO.:105) and VL (SEQ ID NO.: 168) amino acid sequences), S309 N55Q, S309 W50F, S309 W105F, and S309 W50F/G56A/W105F were tested.
Figure 30B:
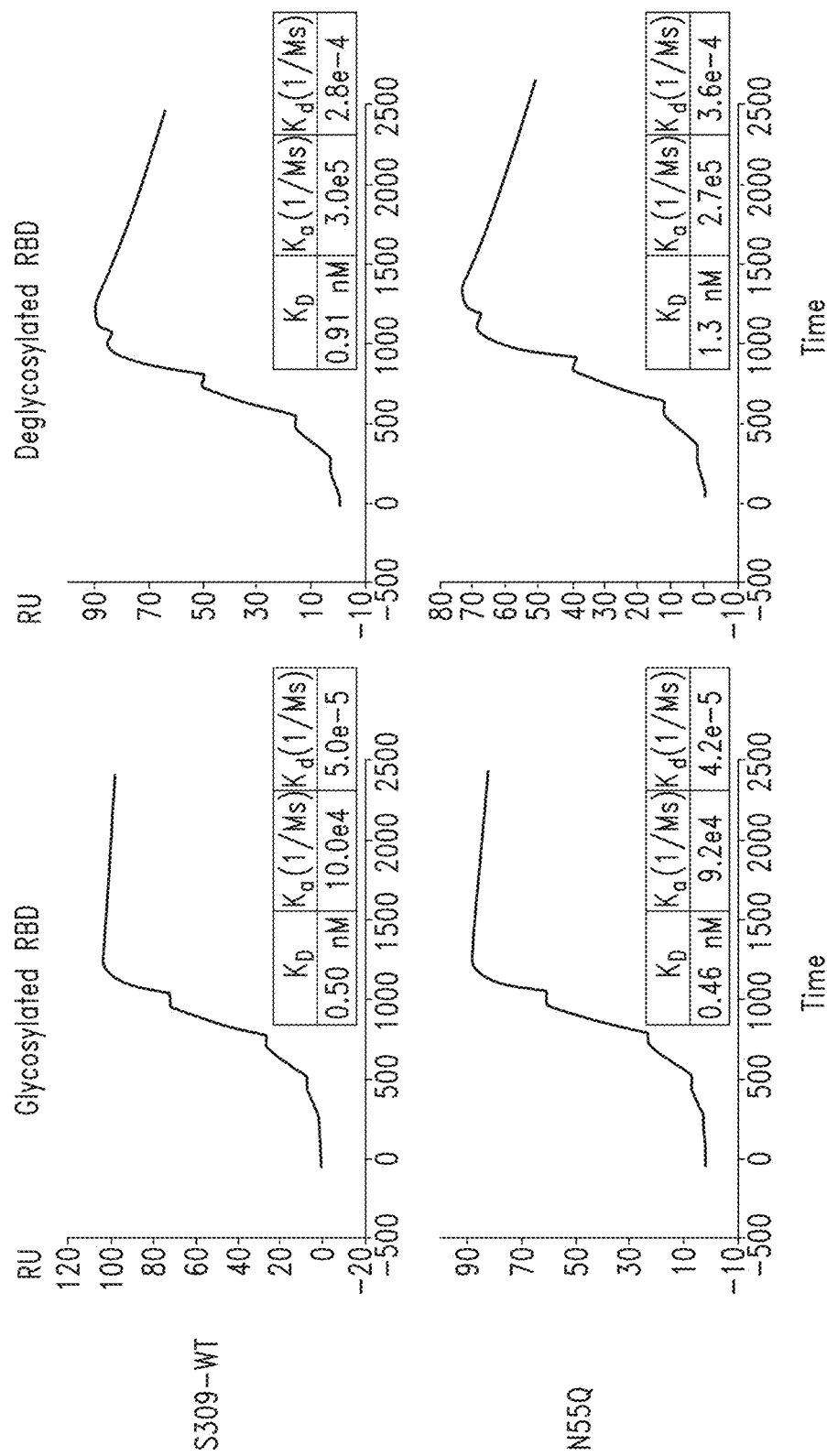
Figure 30C:
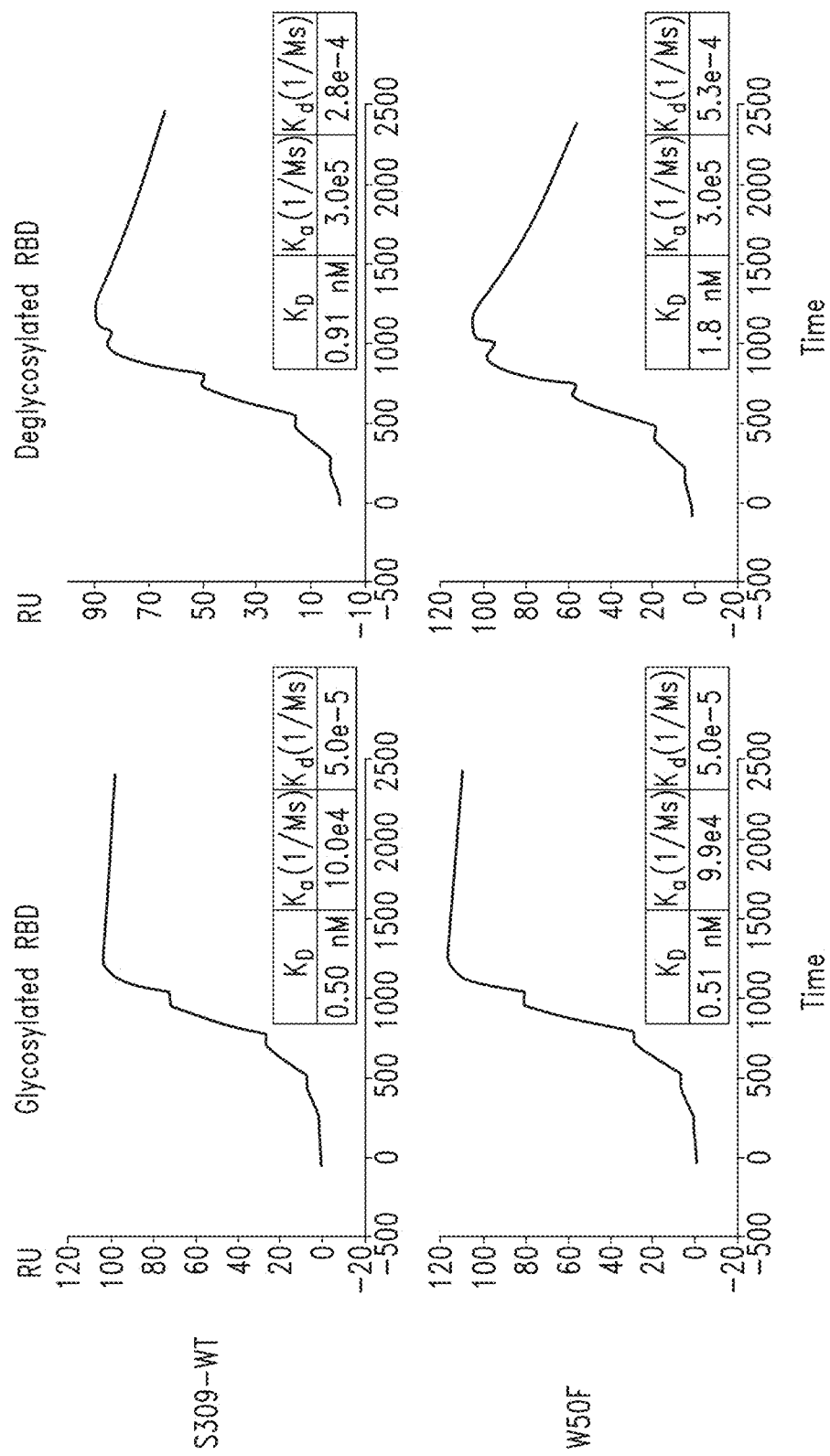
Figure 30D:
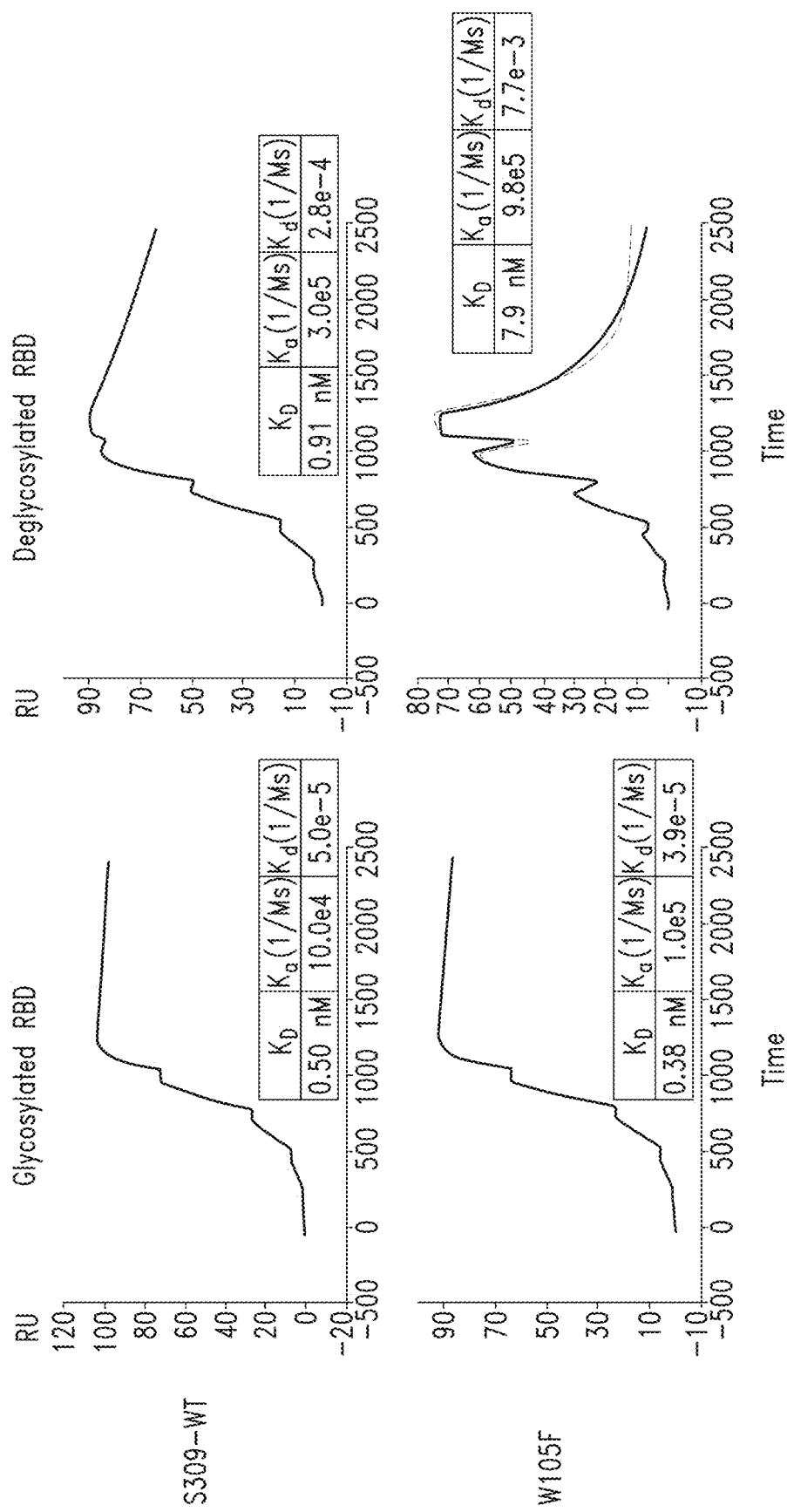
Figure 30E:
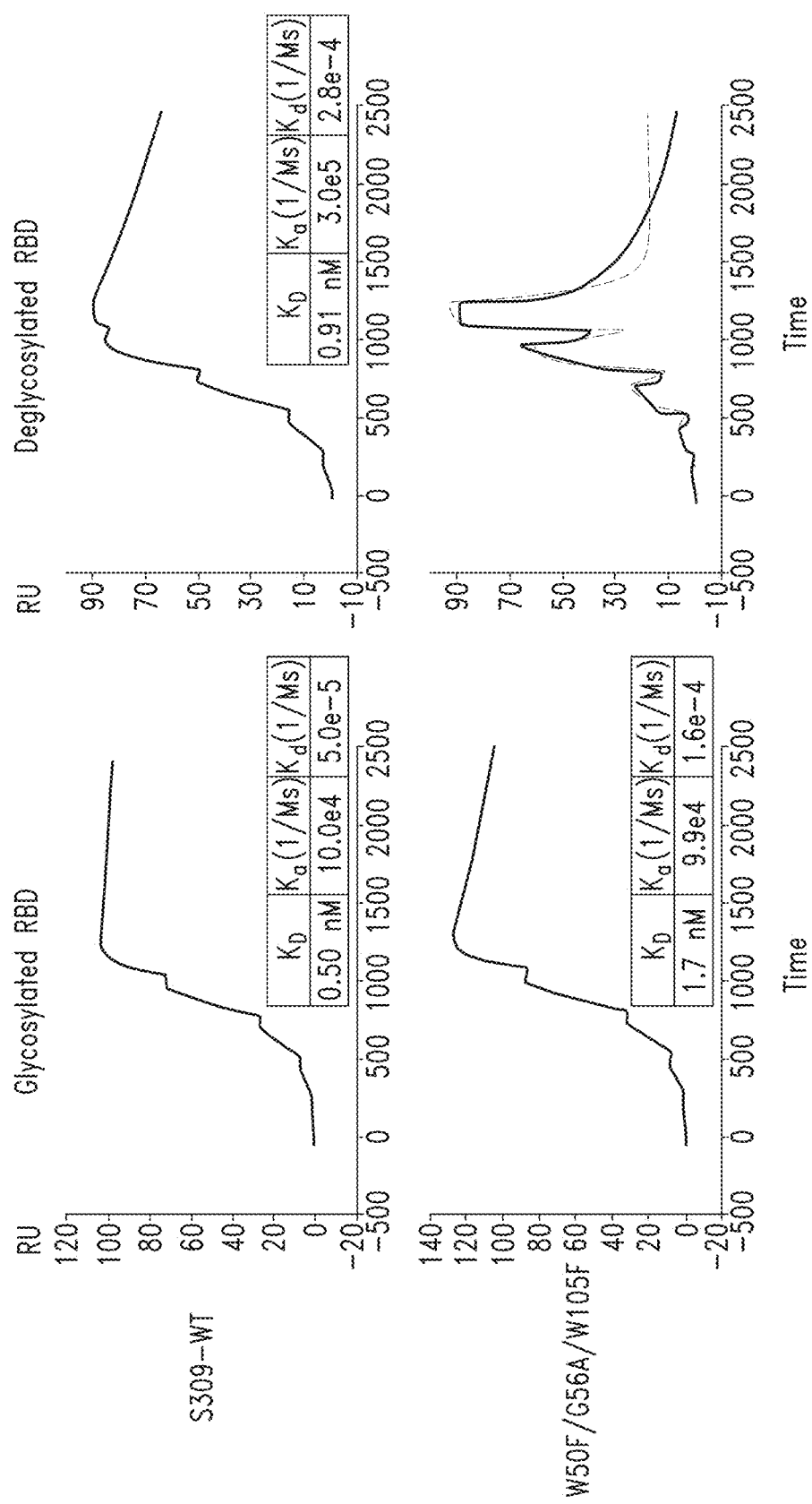
Figure 30F:
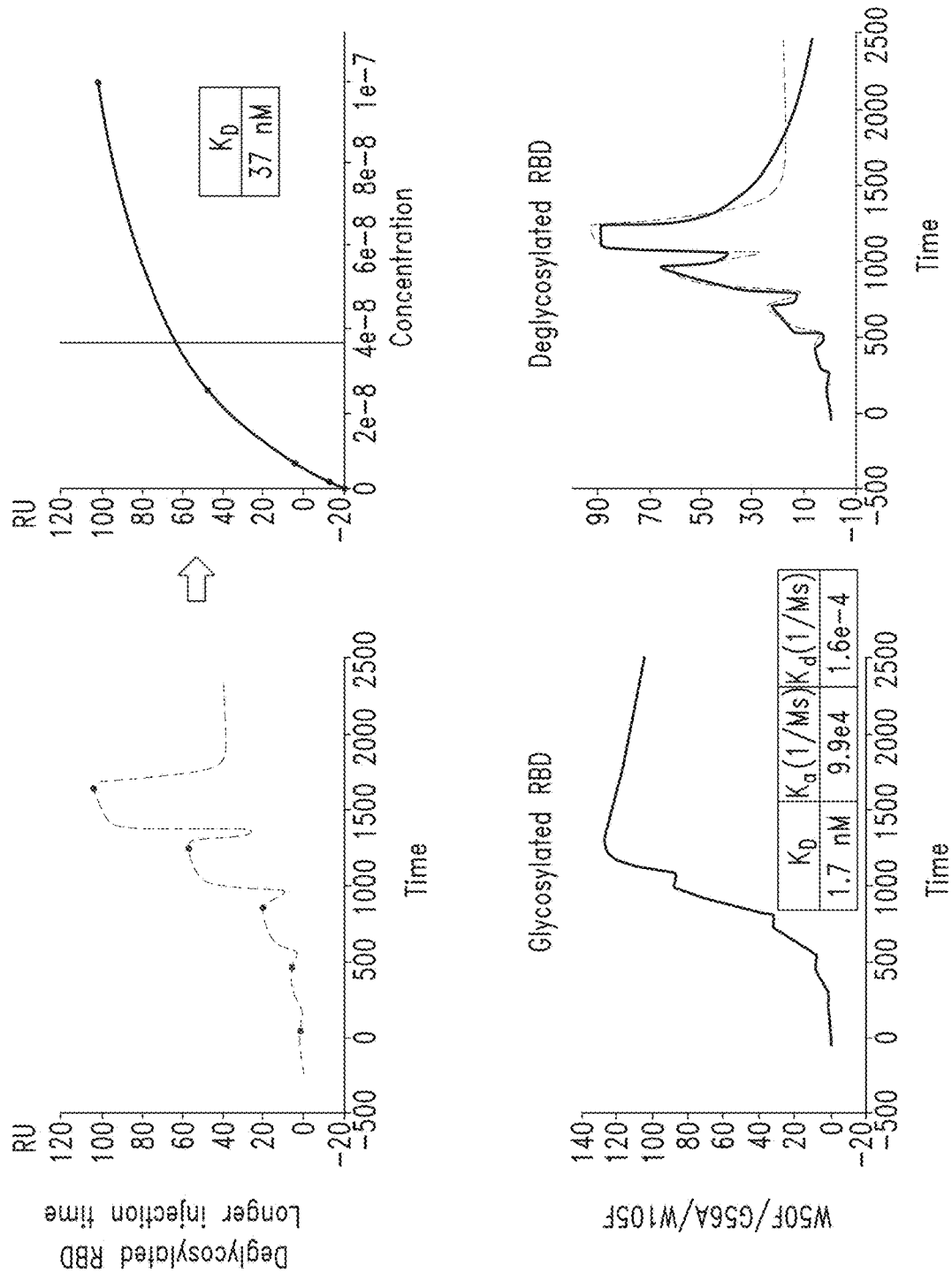

Binding to deglycosylated RBD was measured in two different SPR assays using different parameters. Experiment 1 used 10-minute injections and an RBD concentration series of 4-fold dilutions from 100 nM. Experiment 2 used 3-minute injections and a concentration series of 4-fold dilutions from 200 nM, as described above. Results are shown in Table 9. Results of Experiment 1 for S309-15 are also shown in FIG. 30F, top two panels.

TABLE 9

| mAb Supernatant S309 WT or variant | Experiment 1 | | | Experiment 2 | | |
|---|---|---|---|---|---|---|
| | $K_D$ | $K_a$ (1/Ms) | $K_d$ (1/s) | $K_D$ | $K_a$ (1/Ms) | $K_d$ (1/s) |
| S309-11 (WT) | 0.83 nM | 3.0e5 | 2.5e−4 | 0.91 nM | 3.0e5 | 2.8e−4 |
| S309-11 (WT) replicate | 0.91 nM | 3.0e5 | 2.7e−4 | 0.98 nM | 2.9e5 | 2.9e−4 |
| S309-12 (N55Q) | 1.2 nM | 2.7e5 | 3.2e−4 | 1.3 nM | 2.7e5 | 3.6e−4 |
| S309-13 (W50F) | 1.7 nM | 2.8e5 | 4.6e−4 | 1.8 nM | 3.0e5 | 5.3e−4 |
| S309-14 (W105F) | 14 nM | Fit to steady state | | 7.9 nM | 9.8e5 | 7.7e−3 |
| S309-15 (W50F/G56A/ W105F) | 37 nM | Fit to steady state | | Steady-state fit not possible | | |

Binding of recombinant antibody S309 and the four engineered variants to RBD was measured by surface plasmon resonance (SPR) using the same procedure described above, except using purified recombinant antibodies rather than cell culture supernatant. Results are shown in Table 10.

TABLE 10

| S309 WT or variant VH | Glycosylated RBD | | | Deglycosylated RBD | | |
|---|---|---|---|---|---|---|
| | $K_D$ | $K_a$ (1/Ms) | $K_d$ (1/s) | $K_D$ | $K_a$ (1/Ms) | $K_d$ (1/s) |
| S309-11 (WT) | 0.26 nM | 9.3e4 | 2.4e−5 | 0.67 nM | 3.4e5 | 2.3e−4 |
| S309-12 (N55Q) | 0.39 nM | 8.5e4 | 3.3e−5 | 1.1 nM | 3.1e5 | 3.2e−4 |
| S309-13 (W50F) | 0.39 nM | 9.2e4 | 3.6e−5 | 1.4 nM | 3.5e5 | 4.9e−4 |
| S309-14 (W105F) | 0.35 nM | 9.6e5 | 3.4e−5 | 5.1 nM | 1.5e6 | 7.9e−3 |
| S309-15 (W50F/G56A/ W105F) | 1.6 nM | 9.4e4 | 1.5e−4 | >10 nM | estimate Kd with steady-state fit | |
| S309 G56A | 0.54 nM | 9.3e4 | 5.1e−5 | 0.70 nM | 3.4e5 | 2.4e−4 |

Example 19

Neutralization of SARS-CoV-2 Infection by S309 Antibodies

Figures 28, 29:
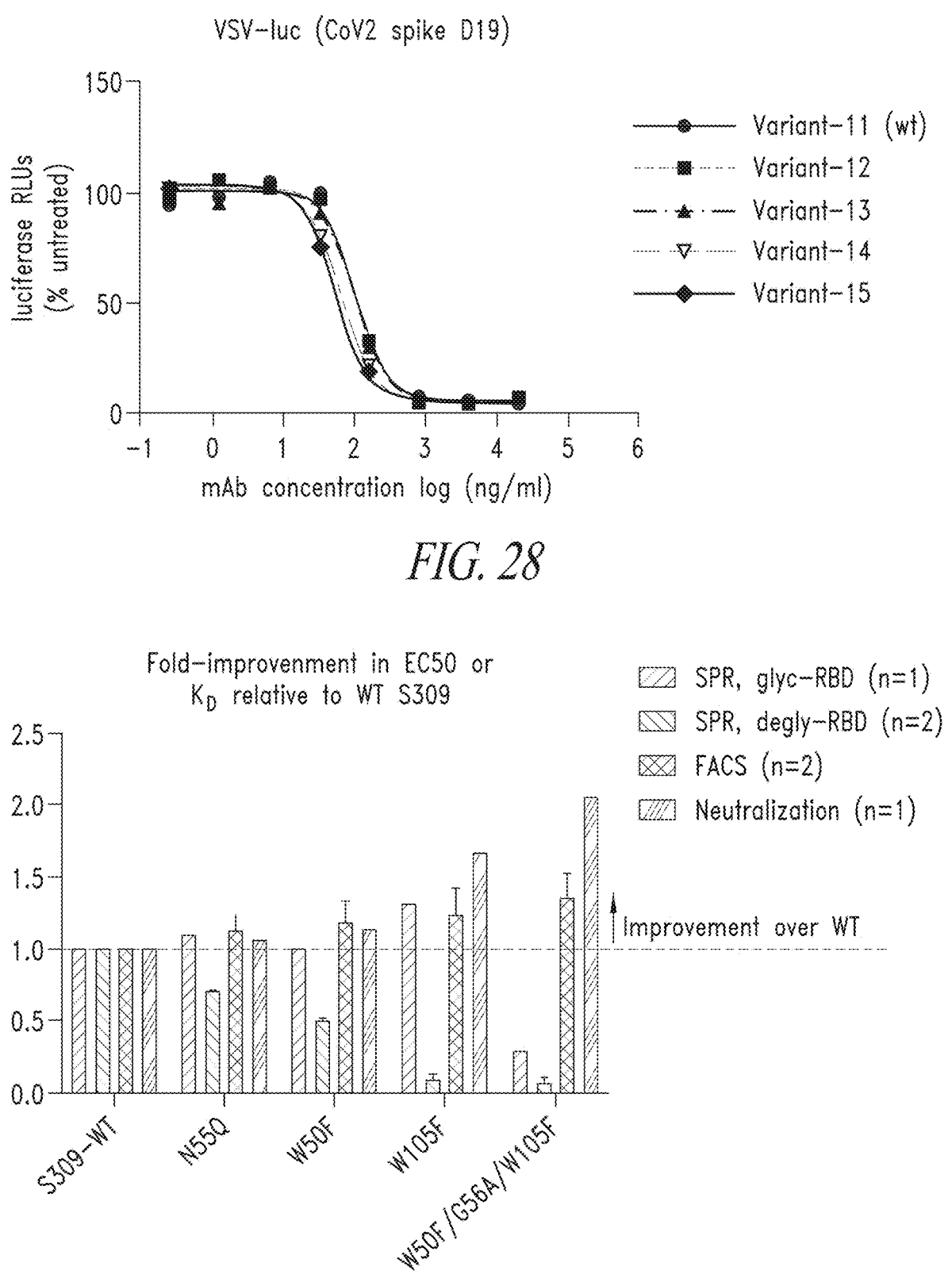

Neutralizing activity of S309 and the four engineered S309 variants described in Examples 17 and 18 ("S309-12"-"S309-15") was determined using a VSV-based luciferase reporter pseudotyping system (Kerafast). VSV pseudoparticles and antibody were mixed in DMEM and allowed to incubate for 30 minutes at 37° C. The infection mixture was then allowed to incubate with Vero E6 cells for 1 h at 3TC, followed by the addition of DMEM with Pen-Strep and 10% FBS (infection mixture is not removed). The cells were incubated at 37° C. for 18-24 hours. Luciferase was measured using an Ensight Plate Reader (Perkin Elmer) after the addition of Bio-Glo reagent (Promega). Results are shown in FIG. 28. In FIG. 28, Variants-11-15 correspond to S309-11-S309-15, respectively. Calculated EC50 values based on this experiment are shown in Table 11.

TABLE 11

| Antibody | EC50 (ng/ml) |
|---|---|
| S309-11 (WT VH) | 109 |
| S309-12 (N55Q VH) | 103 |
| S309-13 (W50F VH) | 97 |
| S309-14 (W105F VH) | 65 |
| S309-15 (W50F/G56A/W105F VH) | 53 |

Example 20

Antibody-Dependent Activation of Human FcγRIIIa or FcγRIIa

Figure 31:
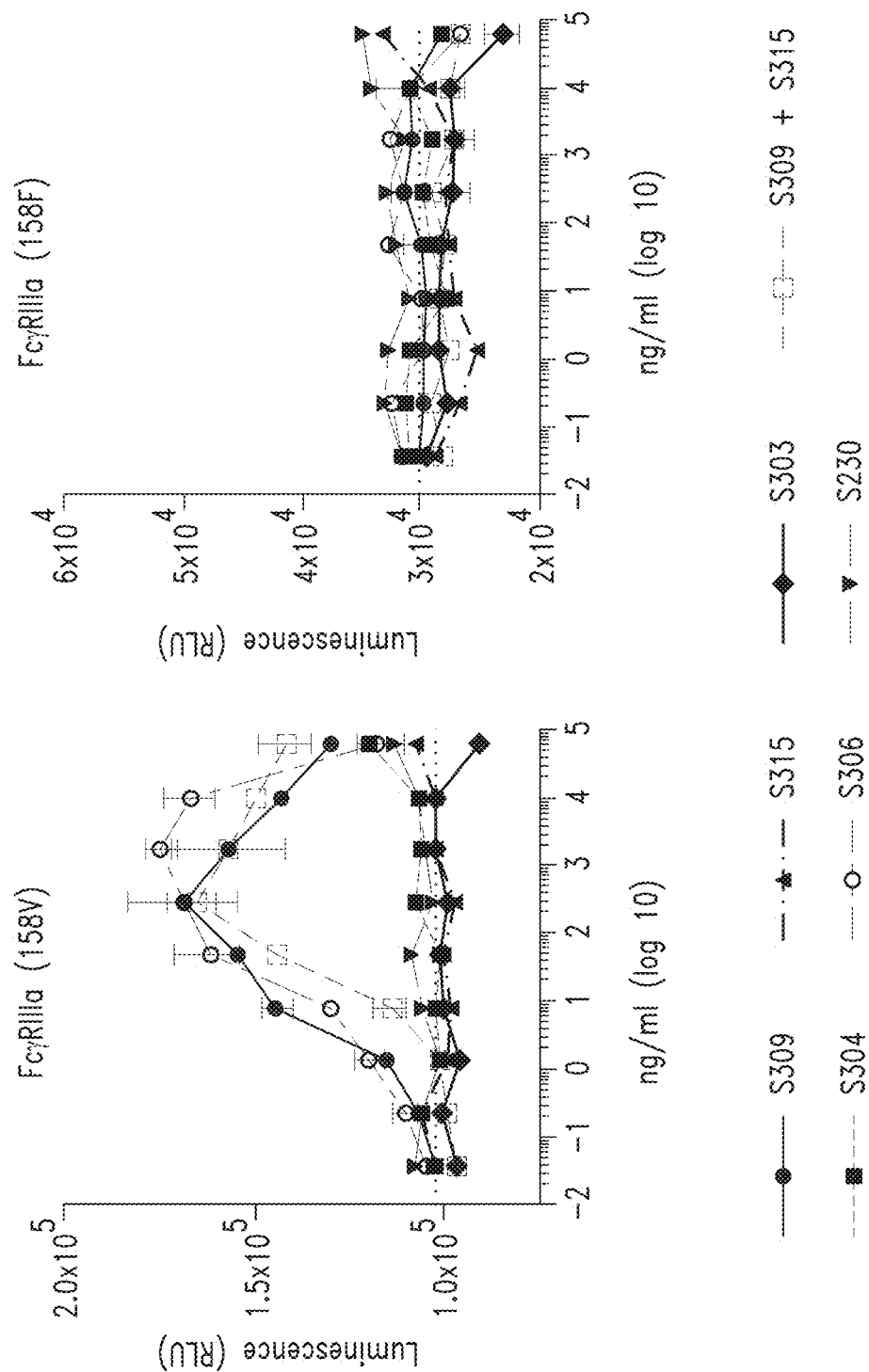
FIG. 31 shows activation of high affinity (158V) FcγRIIIa (left panel) or low affinity (158F) FcγRIIIa (right panel) by antibodies S303 (VH SEQ ID NO.:63; VL SEQ ID NO:67), S304 (VH SEQ ID NO.:79; VL SEQ ID NO.:83), S306 (VH SEQ ID NO.:87; VL SEQ ID NO.:91), S309 (VH SEQ ID NO.:105; VL SEQ ID NO.:168), and a combination of S309 and S315, along with comparator antibody S230. See Example 20. Activation was measured using SARS-CoV-2 S-expressing ExpiCHO cells as target cells and Jurkat reporter cells stably transfected with NFAT-driven luciferase reporter gene. Activation of FcγRIIIa results in NFAT-mediated expression of the luciferase reporter gene. Results are from one experiment, one or two measurements per mAb.
Figure 32:
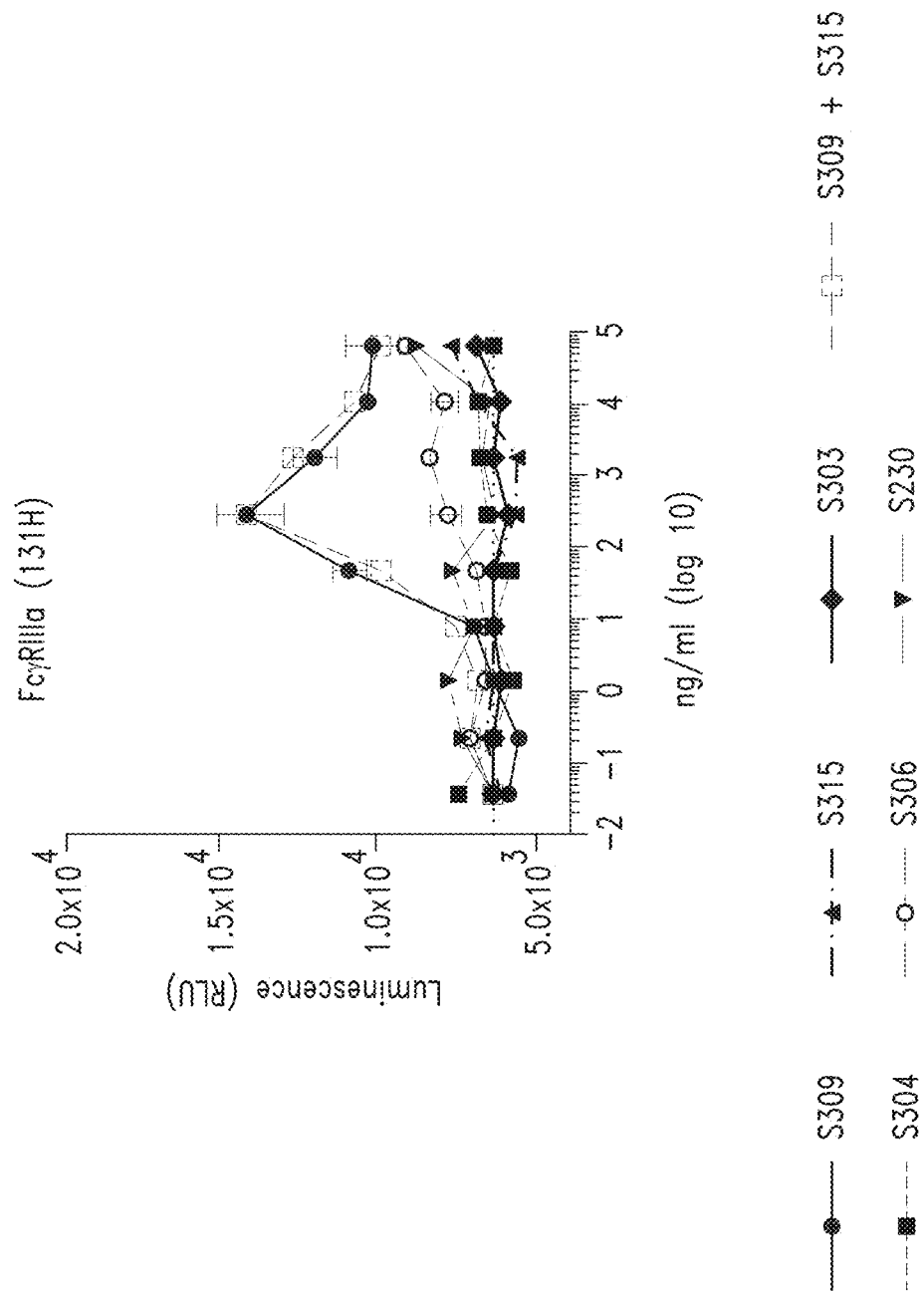
FIG. 32 shows activation of FcγRIIa by exemplary antibodies S303 (VH SEQ ID NO.:63; VL SEQ ID NO.:67), S304 (VH SEQ ID NO.:79; VL SEQ ID NO.:83), S306 (VH SEQ ID NO.:87; VL SEQ ID NO.:91), S309 (VH SEQ ID NO.:105; VL SEQ ID NO.:168), and a combination of S309 and S315, along with comparator monoclonal antibody S230. See Example 20. Activation was measured using SARS-CoV-2 S-expressing ExpiCHO cells as target cells and Jurkat reporter cells stably transfected with NFAT-driven luciferase reporter gene. Activation of FcγRIIa results in NFAT-mediated expression of the luciferase reporter gene.
Figure 33A:
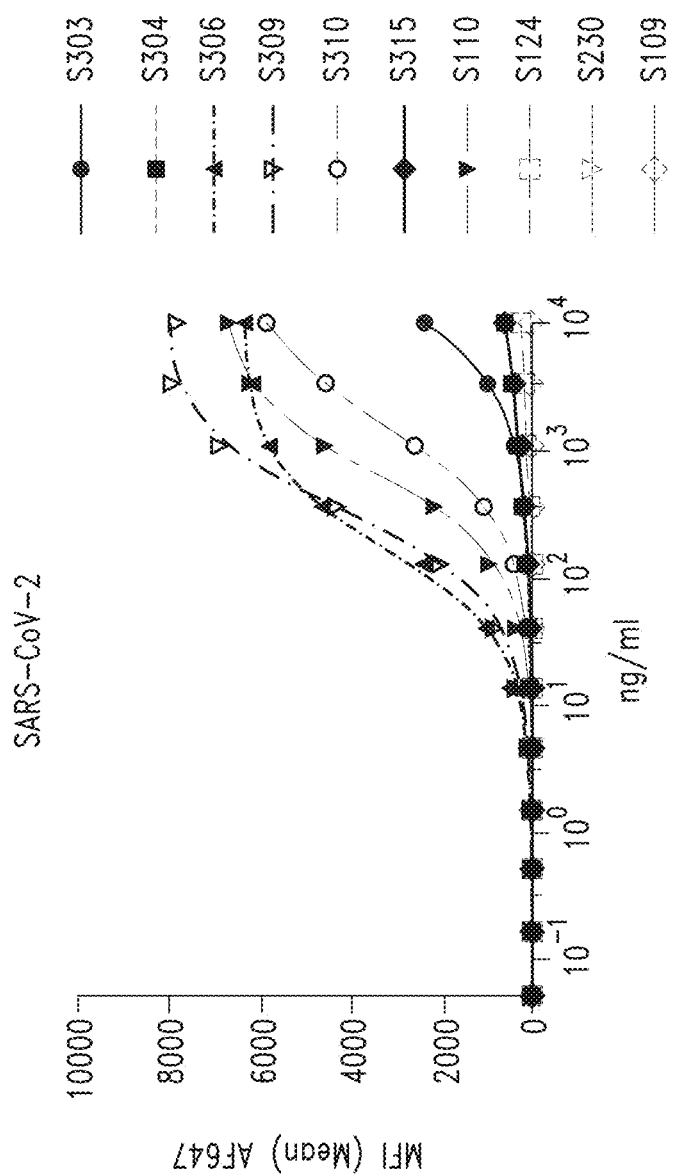
FIGS. 33A and 33B show binding of antibodies S303 (VH SEQ ID NO.:63; VL SEQ ID NO:67), S304 (VH SEQ ID NO.:79; VL SEQ ID NO.:83), S306 (VH SEQ ID NO.:87; VL SEQ ID NO.:91), S309 (VH SEQ ID NO.:105; VL SEQ ID NO.:168), S310 (VH SEQ ID NO.:155; VL SEQ ID NO.:159), and S315 (VH SEQ ID NO.:178; VL SEQ ID NO.:182), along with comparator antibodies S110, S230, and S109, to S protein expressed on a cell surface. See Example 9.
Figure 33B:
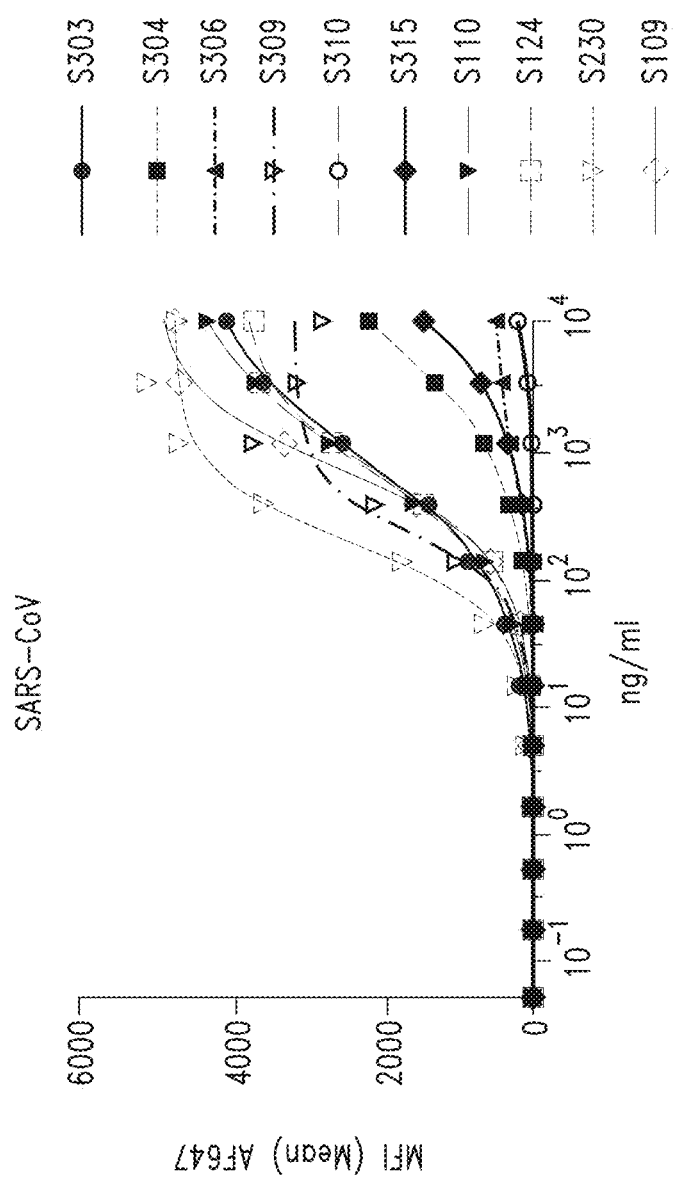

Antibody-dependent activation of human FcγRIIIa or FcγRIIa was examined. ExpiCHO cells were transiently transfected with SARS-CoV-2 S (BetaCoV/Wuhan-Hu-1/2019), and incubated with titrated concentrations of antibody for 10 minutes. ExpiCHO cells were then incubated with Jurkat cells expressing FcγRIIIa or FcγRIIa on their surface and stably transfected with NFAT-driven luciferase gene (Promega, Cat. Nr.: G9798 and G7018) at an effector to target ratio of 6:1 for FcγRIIIa and 5:1 for FcγRIIa. Activation of human FcγRs in this bioassay results in the NFAT-mediated expression of the luciferase reporter gene. Luminescence was measured after 21 hours of incubation at 37° C. with 5% $CO_2$, using the Bio-Glo-TM Luciferase Assay Reagent according to the manufacturer's instructions. Antibodies S303, S304, S306, S309, S315, and a combination of S309 and S315 were assayed, along with comparator antibody S230. Results are shown in FIGS. 31 and 32.

Example 21

Analysis of SARS-CoV-2 S Glycoprotein Sequences

Figure 35A:
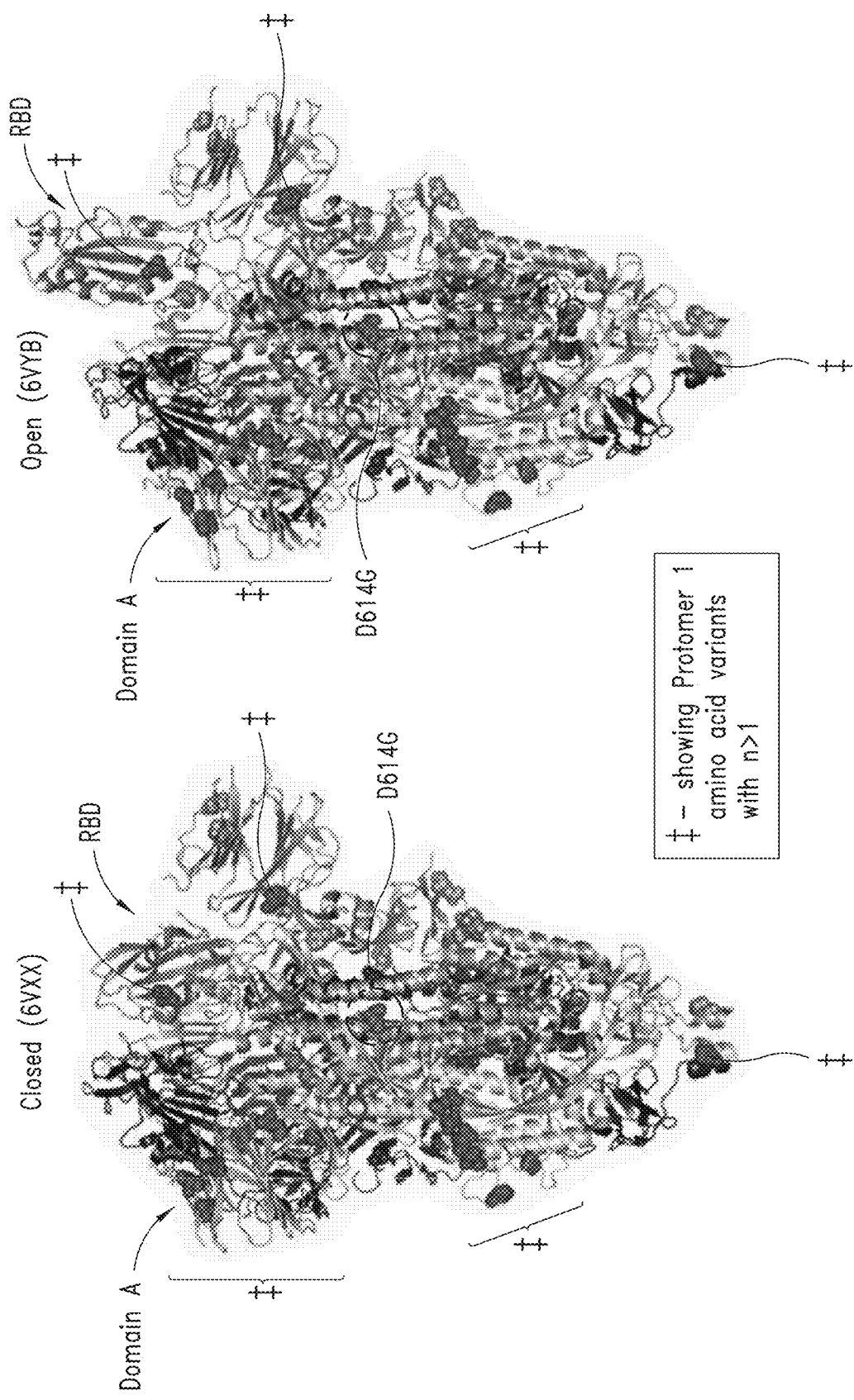
FIGS. 35A and 35B show conservation of Spike protein residues, as described in Example 21.
Figure 35B:
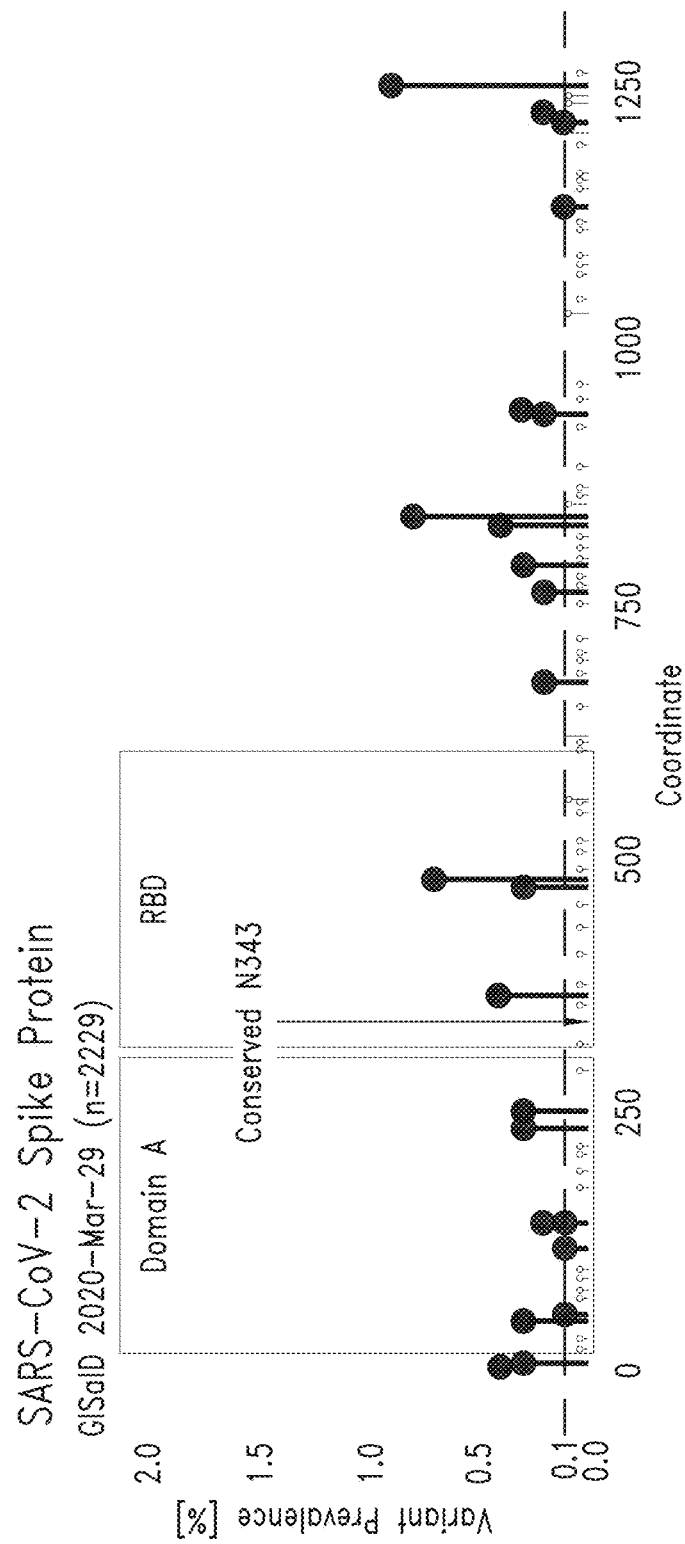

Analysis of the S glycoprotein sequences of 2,229 SARS-CoV-2 isolates indicated that several mutations have occurred with variable frequency on the SARS-CoV-2 S ectodomain. FIG. 35A shows Spike protein variants occurring with a frequency of n>1 as spheres mapped onto the closed and open form of the full trimeric Spike ectodomain. The RBD and other Spike protein domains are shown as indicated. 40 mutations (out of 2229 total) are shown. Due to lack of detail in the PDB structures, only residue 367 (n=8) is highlighted in the RBD, and residues 476 (n=7) and 483 (n=17) are not. FIG. 35B shows the prevalence of variants in Spike glycoprotein by amino acid. Each dot is a distinct variant. The locations of Domain A and RBD are shown. Variants passing a frequency threshold of 0.1% are as indicated.

Figure 43:
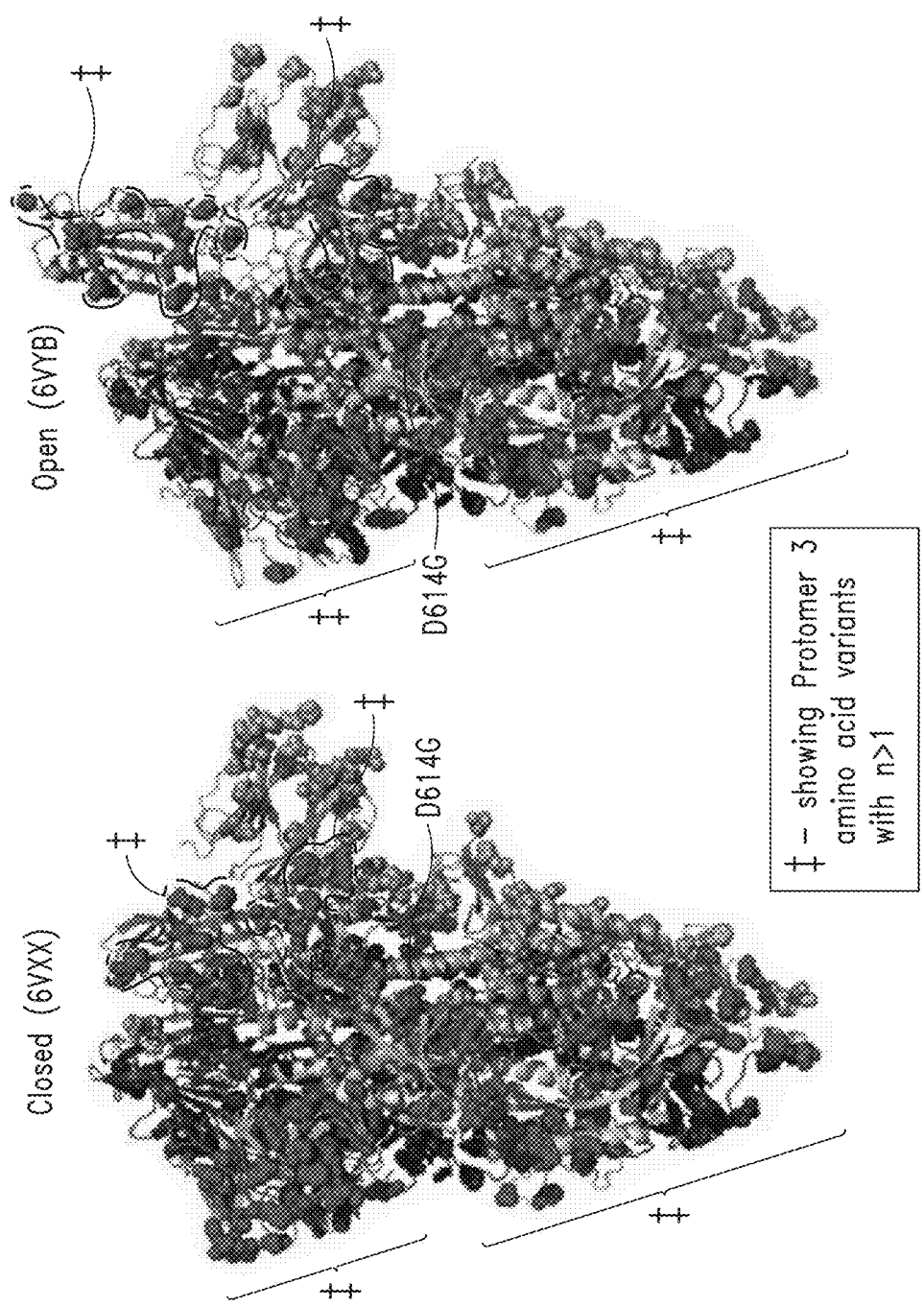
FIG. 43 shows conservation of Spike protein residues, as described in Example 21. Spike protein variants supported by at least two sequences as indicated spheres mapped onto the closed (left) and open (right) form of the full trimeric Spike ectodomain. The RBD and other Spike protein domains are shown as indicated. 171 variants (out of 11,839 total Spike protein sequences analyzed) are shown.

Further analysis of the S glycoprotein sequences was carried out using 11,839 SARS-CoV-2 isolates. FIG. 43 shows variants supported by at least two sequences (prevalence greater than 0.01%) rendered as indicated spheres mapped onto the closed (left) and open (right) form of the full trimeric Spike ectodomain. Each dot is a distinct variant. FIG. 43 shows Spike protein variants supported by at least two sequences as indicated spheres mapped onto the closed (left) and open (right) form of the full trimeric Spike ectodomain. The RBD and other Spike protein domains are shown in the colors indicated. 171 variants (out of 11,839 total Spike protein sequences analyzed) are shown. Variants are labeled if their prevalence is greater than 1% (D614G only) or if they are located within the RBD. The location of conserved N343 is also indicated.

Example 22

Competition of Antibody S309 with Antibodies Isolated from SARS-CoV-2 Patients

Human monoclonal antibodies isolated from patients who recovered from SARS-CoV-2 infection were tested for overlapping RBD binding sites with antibody S309 (VH: SEQ ID NO:105; VL: SEQ ID NO.:113). Competition assays were performed using Octet (instrument: Octet Red96, ForteBio). Anti-His sensors (BIOSENSOR ANTI-PENTA-HIS (HIS1K)1*1ST) were used to immobilize in house produced His-tagged RBD of SARS-CoV-2 (residues 331-550 of Spike protein from BetaCoV/Wuhan-Hu-1/2019, accession number MN908947) at a concentration of 3 μg/ml. Antibodies were associated for 6 min at 15 μg/ml. All proteins were diluted in kinetics buffer (KB). Competing antibodies were then associated at the same concentration for additional 6 mins. Two antibodies were shown to compete with S309 for binding to RBD but, unlike S309, they were not neutralizing for SARS-CoV-2. Data not shown.

Example 23

Resistance Selection of SARS-CoV-2 Against Monoclonal Antibody S309-12-MLNS

Figure 44A:
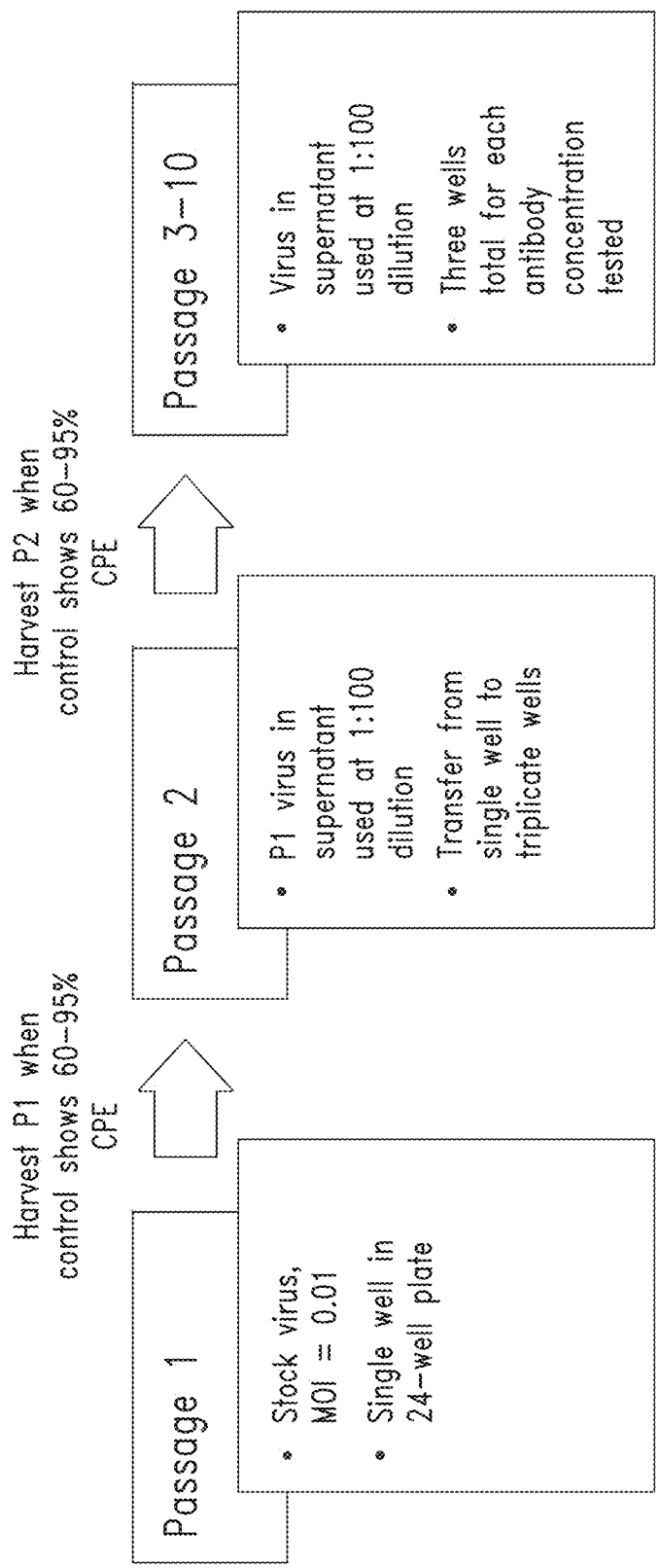
Figure 44B:
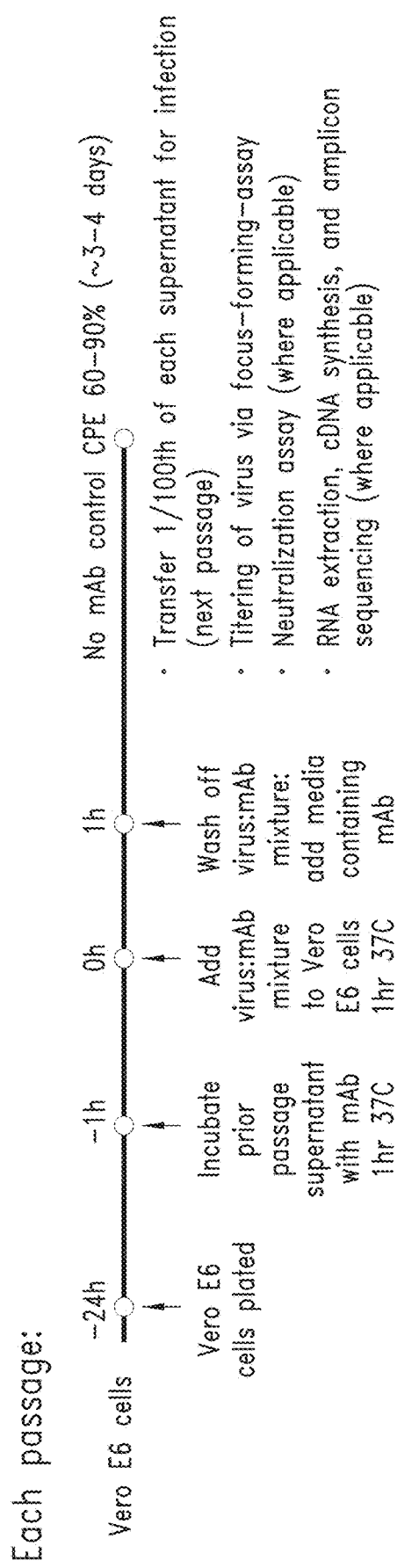

To examine resistance selection, SARS CoV-2 was passaged for over one month in the presence of Vero E6 cells and fixed concentrations of antibody S309 N55Q MLNS GAALIE (VH of SEQ ID NO.:113 and VL of SEQ ID NO.:168, with G236A, A330L, I332E, M428L, and N434S mutations in the Fc). The experimental scheme is illustrated in FIG. 44A. The details of infection and continuous viral culturing are summarized in FIG. 44B. Cytopathogenic effect (CPE) was evaluated by visual inspection of plates. Even when no CPE was observed, viral titers were evaluated by focus-forming assay with a methylcellulose overlay. Results are shown in FIG. 44C. No evidence of viral breakthrough in antibody-treated wells was observed, even at the minimum antibody concentration tested. Data are representative of wells in triplicate.

Example 24

Neutralization of SARS-CoV-2 Infection of Calu-3 Human Lung Cells by Antibody S309

Figure 46:
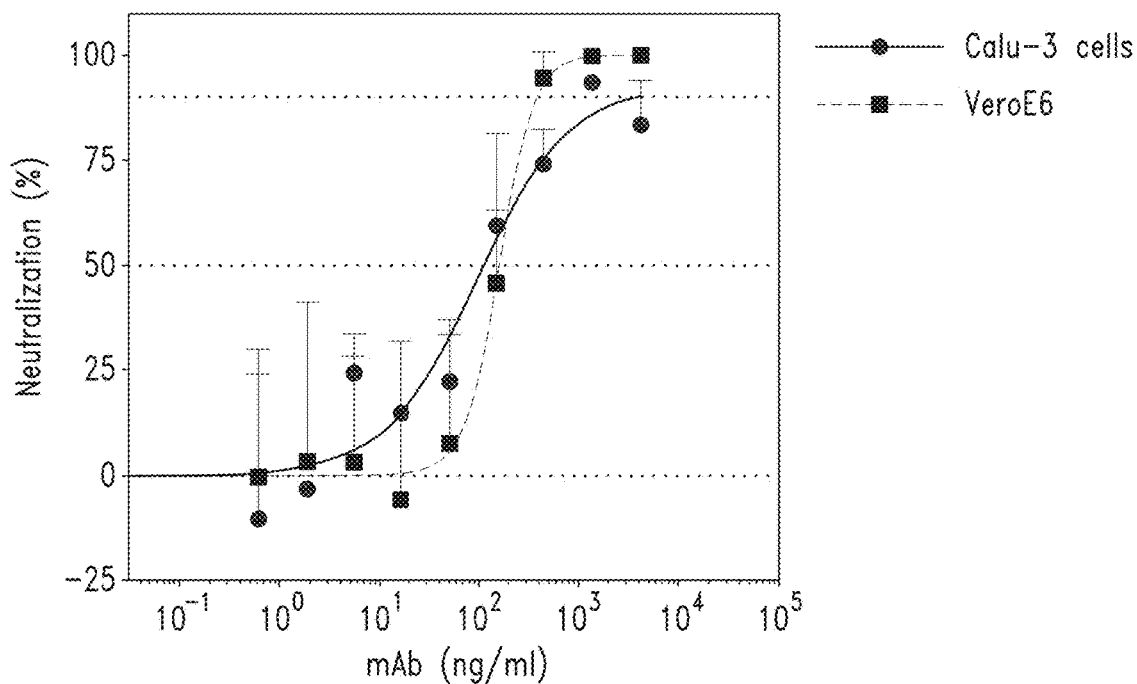
FIG. 46 shows neutralization of SARS-CoV-2 infection in Calu-3 human lung cells and VeroE6 cells by antibody S309 N55Q MLNS, as described in Example 24.

Antibody S309 N55Q MLNS (VH of SEQ ID NO.:113 and VL of SEQ ID NO.:168, with M428L and N434S mutations in the Fc) was tested for its ability to neutralize live SARS-CoV-2 infection of Calu-3 human lung cells (which are positive for the transmembrane protease TMPRSS2) and VeroE6 cells using a nano luciferase assay. Results, including calculated IC50 values, are shown in FIG. 46.

Example 25

Neutralization of SARS-CoV-2 Infection by Antibody S309

Figure 47:
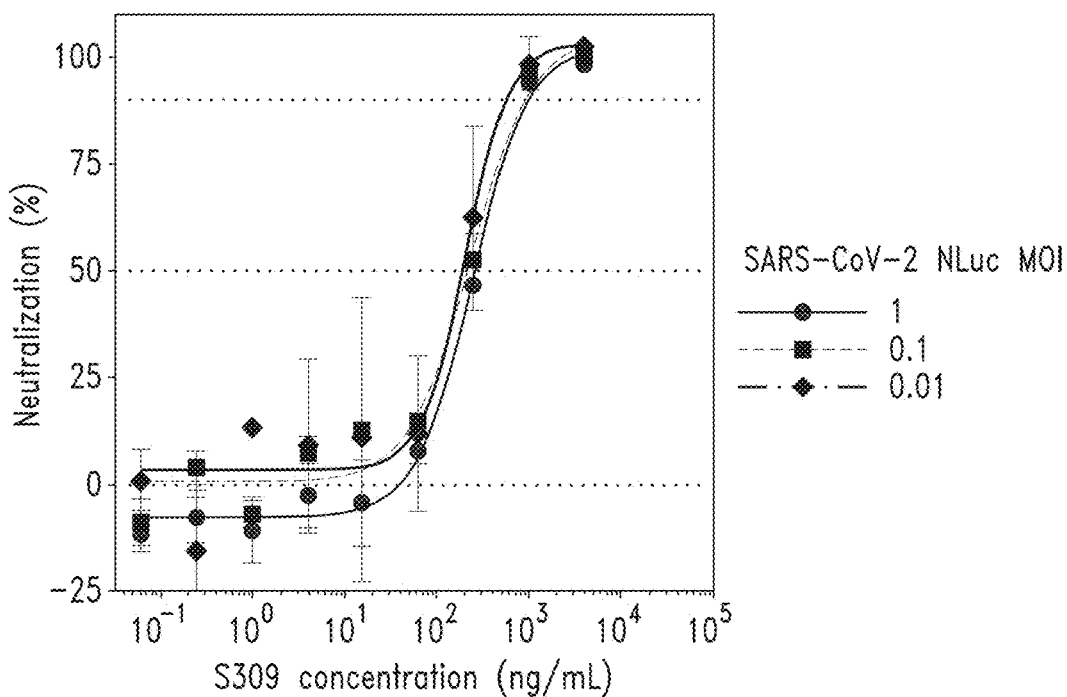
FIG. 47 shows neutralization of SARS-CoV-2 infection by antibody S309 (VH SEQ ID NO.:105; VL SEQ ID NO.:168), as detected by nano luciferase assay. See Example 25. The x-axis shows antibody concentration. The three curves represent assays using three different viral concentrations in MOI (multiplicity of infection) units, as shown in the figure key at right. Data were collected six hours after infection with SARS-CoV-2 virus. Calculated IC50 values for each MOI are shown in the boxes below the graph.
Figure 48A:
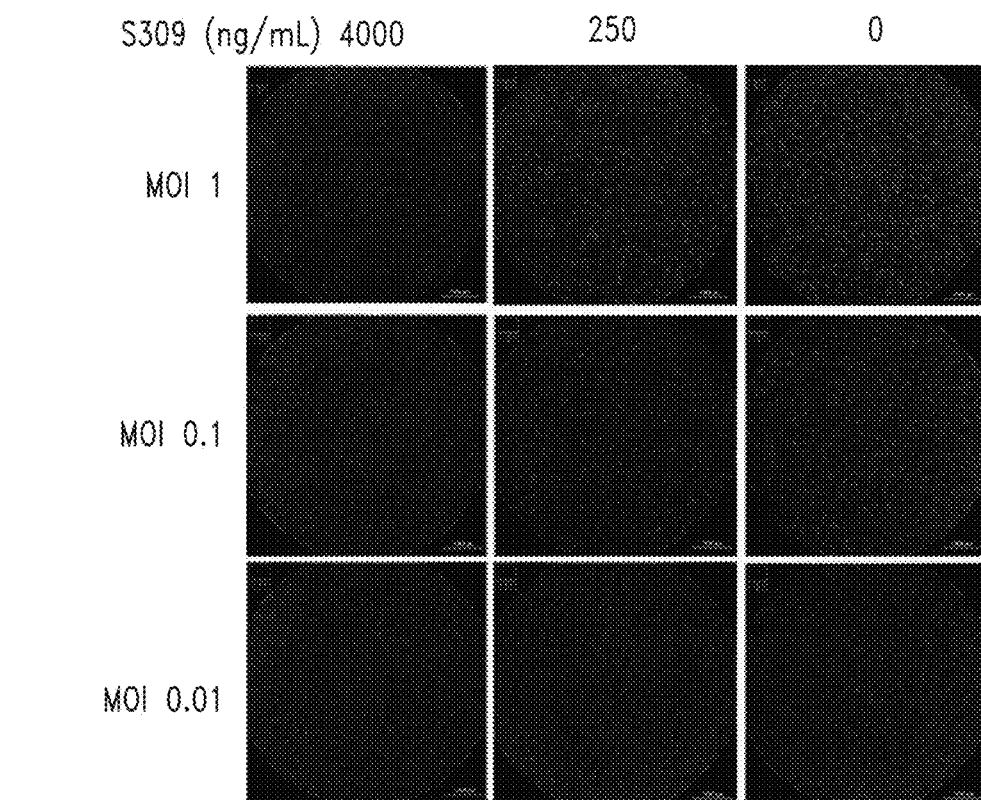
FIGS. 48A and 48B show neutralization of SARS-CoV-2 infection by antibody S309 (VH SEQ ID NO.:105; VL SEQ ID NO.:168) as assayed by IFA (immunofluorescence antibody assay). See Example 25. Data were collected six hours after infection with SARS-CoV-2 virus.
Figure 48B:
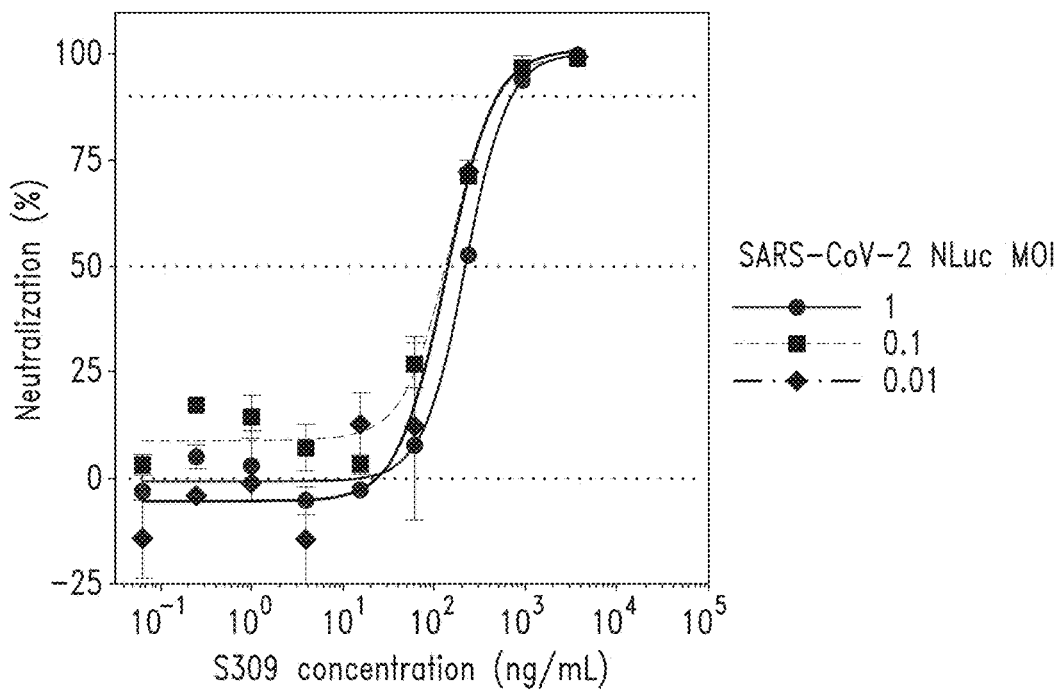

Antibody S309 was tested for its ability to neutralize live SARS-CoV-2 virus infection using a nano luciferase assay and a IFA assay. Briefly, Vero E6 cells were infected with live SARS-CoV-2 luciferase virus for six hours. Data were collected using three different antibody concentrations: 1, 0.1, and 0.01 MOI. Results from the nano luciferase assay are shown in FIG. 47. Results from the IFA assay are shown in FIGS. 48A (representative wells counted in the IFA) and 48B (quantified data using Cytation 5). Calculated IC50 values for each MOI are shown in the boxes below the graph in FIGS. 47 and 48B. Notably, no clusters of infection (or foci) were observed in this infection format.

Example 26

Figure 49:
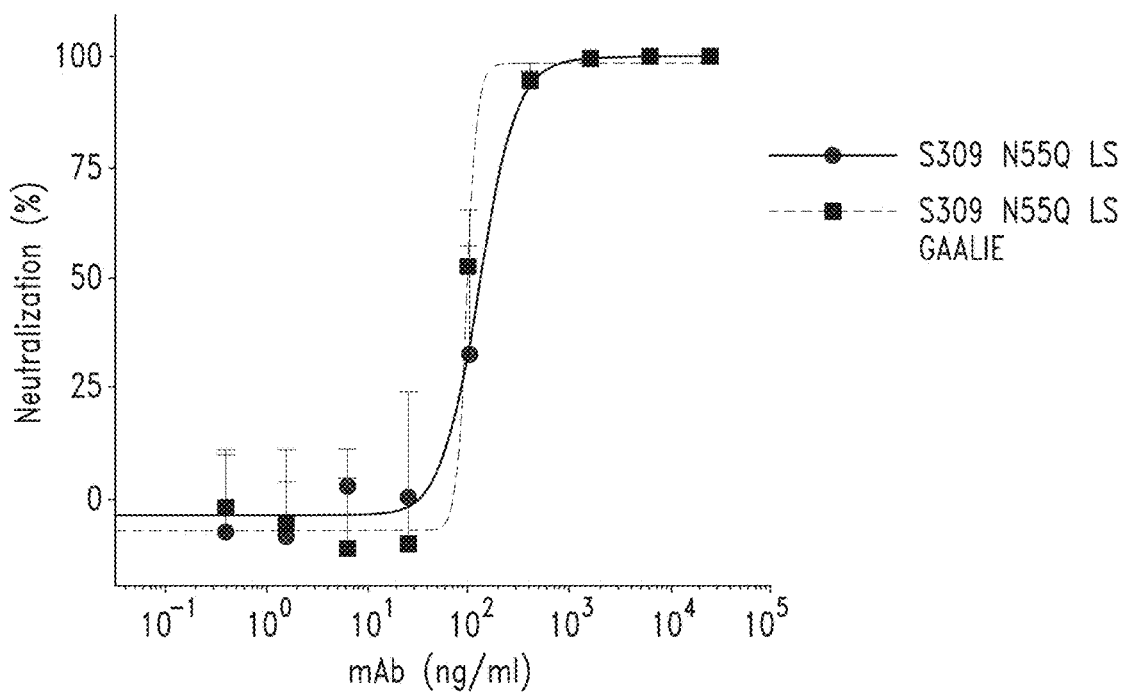
FIG. 49 shows neutralization of SARS-CoV-2 infection by antibodies S309 N55Q LS (also referred to herein as S309 N55Q MLNS, comprising M428L/N434S Fc mutations (EU numbering)) and S309 N55Q LS GAALIE (also referred to herein as S309 N55Q MLNS GAALIE, comprising G236A, A330L, I332E, M428L, and N434S Fc mutations (EU numbering)). See Example 26. Each of S309 N55Q LS and S309 N55Q LS GAALIE comprises a VH having the amino acid sequence set forth in SEQ ID NO.:113 and a VL having the amino acid sequence set forth in SEQ ID NO.:168. Data represent the means of quadruplicates, +/−standard deviation. Graph shown is representative of three independent experiments.

Neutralization of Live SARS-CoV-2 Infection by Antibodies S309 N55Q MLNS and S309 N55Q MLNS GAALIE Antibodies S309 N55Q MLNS (also referred to herein as S309 N55Q LS, comprising M428L/N434S Fc mutations) and S309 N55Q MLNS GAALIE (also referred to herein as S309 N55Q LS GAALIE, comprising G236A, A330L, I332E, M428L, and N434S Fc mutations) were assayed for the ability to neutralize live SARS-CoV-2 virus infection. Each of S309 N55Q MLNS and S309 N55Q MLNS GAALIE comprises a VH having the sequence set forth in SEQ ID NO.: 113 and a VL having the sequence set forth in SEQ ID NO.: 168. Results are shown in FIG. 49. The calculated EC50 for S309 N55Q MLNS was 100.1 ng/ml. The calculated EC50 for S309 N55Q MLNS GAALIE was 78.3 ng/ml.

Example 27

Neutralization of SARS-CoV-2 Pseudotyped Virus by Antibodies S309 N55Q MLNS and S309 N55Q MLNS GAALIE Neutralization of SARS-CoV-2 pseudotyped virus by antibodies S309 N55Q MLNS (also referred to herein as S309 N55Q LS) and S309 N55Q MLNS GAALIE (also referred to herein as S309 N55Q MLNS GAALIE) was tested. Each of S309 N55Q MLNS and S309 N55Q MLNS GAALIE comprises a VH having the sequence set forth in SEQ ID NO.: 113 and a VL having the sequence set forth in SEQ ID NO.: 168. The pseudotyped virus was VSV pseudotyped with SARS-CoV-2 Spike protein. Results are shown in FIG. 50A (S309 N55Q MLNS) and FIG. 50B (S309 N55Q MLNS GAALIE). The calculated EC50 value for S309 N55Q MLNS was 24.06 ng/ml. The calculated EC50 value for S309 N55Q MLNS GAALIE was 22.09 ng/ml.

Example 28

Binding of Antibodies S309 N55Q MLNS and S309 N55Q MLNS GAALIE to SARS-CoV-2 RBD Binding of antibodies S309 N55Q MLNS and S309 N55Q MLNS GAALIE to SARS-CoV-2 RBD was measured by surface plasmon resonance (SPR). Each of S309 N55Q MLNS and S309 N55Q MLNS GAALIE comprises a VH having the sequence set forth in SEQ ID NO.: 113 and a VL having the sequence set forth in SEQ ID NO.: 168. Results are shown in FIG. 51A (S309 N55Q MLNS) and FIG. 51B (S309 N55Q MLNS GAALIE).

Example 29

Binding of Antibodies S309 N55Q MLNS and S309 N55Q MLNS GAALIE to SARS-CoV-2 Spike Protein Binding of antibodies S309 N55Q MLNS (also referred to herein as S309 N55Q LS) and S309 N55Q MLNS GAALIE (also referred to herein as S309 N55Q LS GAALIE) to SARS-CoV-2 to SARS-CoV-2 Spike protein was measured by flow cytometry. Each of S309 N55Q MLNS and S309 N55Q MLNS GAALIE comprises a VH having the sequence set forth in SEQ ID NO.: 113 and a VL having the sequence set forth in SEQ ID NO.: 168. Results are shown in FIG. 52A (S309 N55Q MLNS) and FIG. 52B (S309 N55Q MLNS GAALIE). Data are expressed as the percentage of cells identified as positive for antibody binding.

Example 30

Binding of Antibodies S309 N55Q MLNS and S309 N55Q MLNS GAALIE to Human FcΓ Receptors Binding of antibodies S309 N55Q MLNS and S309 N55Q MLNS GAALIE to human Fcγ receptors was assayed using SPR. Binding to FcγRIIa (both low affinity R131 and high affinity H131 alleles), FcγRIIIa (both low affinity F158 and high affinity V158 alleles), and FCγRIIb was measured. Each of S309 N55Q MLNS and S309 N55Q MLNS GAALIE comprises a VH having the sequence set forth in SEQ ID NO.: 113 and a VL having the sequence set forth in SEQ ID NO.: 168.

Biotin CAPture Reagent (modified streptavidin) was injected across all flow cells of a CAP sensor chip docked in a Biacore T200 (Cytiva). Biotinylated Fc receptors at 1 µg/mL were injected across a single flow cell at 10 µL/min for 60 seconds (one receptor per flow cell), with one flow cell reserved as a reference surface. Antibody at 100 µg/mL (diluted in HBS-EP+) was injected across all flow cells for 200 seconds using a flow rate of 30 µL/min and association was monitored. Dissociation was monitored for another 200 seconds after injection. Data was collected at 10 Hz. After each binding measurement, CAP Regeneration reagent was injected to prepare the surface for a new cycle. Experiments were performed at 25° C., with the samples held at 15° C. in the instrument prior to injection. Results are shown in FIG. 53 (wherein the MLNS mutation is indicated as "LS" in the figure key).

Example 31

Binding of Antibodies S309 MLNS, S309 N55Q MLNS, and S309 N55Q MLNS GAALIE to Complement Component C1Q Binding of antibodies S309 MLNS (also referred to herein as S309 LS), S309 N55Q MLNS (also referred to herein as S309 N55Q LS), and S309 N55Q MLNS GAALIE (also referred to herein as S309 N55Q LS GAALIE) to complement component C1q was measured by biolayer interferometry (BLI) on an Octet instrument. S309 MLNS comprises a VH having the sequence set forth in SEQ ID NO.:105 and a VL having the sequence set forth in SEQ ID NO.:168. Each of S309 N55Q MLNS and S309 N55Q MLNS GAALIE comprises a VH having the sequence set forth in SEQ ID NO.: 113 and a VL having the sequence set forth in SEQ ID NO.: 168.

Anti-human Fab (CH1-specific) sensors were used to capture antibody at 10 µg/ml for 10 minutes. The IgG-loaded sensors were then exposed to kinetics buffer containing 3 µg/ml of purified human C1q for 4 minutes, followed by a dissociation step in the same buffer for additional 4 minutes. Association and dissociation profiles were measured in real time as changes in the interference pattern. Results are shown in FIG. 54.

Example 32

In Vitro Activation of Human Fc Gamma Receptors by Antibodies S309 MLNS, S309 N55Q MLNS, and S309 N55Q MLNS GAALIE The ability of antibodies S309 MLNS, S309 N55Q MLNS, and S309 N55Q MLNS GAALIE to elicit antibody-dependent activation of human Fcγ receptors was assayed in vitro. S309 MLNS comprises a VH having the sequence set forth in SEQ ID NO.:105 and a VL having the sequence set forth in SEQ ID NO.:168. Each of S309 N55Q MLNS and S309 N55Q MLNS GAALIE comprises a VH having the sequence set forth in SEQ ID NO.: 113 and a VL having the sequence set forth in SEQ ID NO.: 168.

Each of S309 MLNS (also referred to herein as S309 LS), S309 N55Q MLNS (also referred to herein as S309 N55Q LS), S309 N55Q MLNS GAALIE (also referred to herein as S309 N55Q LS GAALIE), and control antibody S309-GRLR was serially diluted 6-fold in assay buffer from 10,000 ng/ml to 0.006 ng/ml. Nine point serial dilutions of antibody were incubated with 12,500 (for FcγRIIIa and FcγRIIb) or 10,000 (for FcγRIIa) CHO-CoV-2-Spike cells per 96-plate well in a white, flat-bottom plate for 15 minutes at room temperature. Jurkat effector cells expressing the indicated FcγRs and stably transfected with an NFAT-driven luciferase gene were thawed, diluted in assay buffer, and added to the plate at an effector to target cell ratio of 6:1 for FcRγIIIa and FcγRIIb or 5:1 for FcγRIIa. Control wells were included to measure antibody-independent activation (containing target cells and effector cells but no antibody) and background luminescence of the plate (wells containing assay buffer only). Plates were incubated for 18 hours at 37° C. with 5% $CO_2$. Activation of human FcγRs in this bioassay results in the NFAT-mediated expression of the luciferase reporter gene. Luminescence was measured with a luminometer after adding the Bio-Glo™ Luciferase Assay Reagent according to the manufacturer's instructions. Results are shown in FIG. 55.

Example 33

Effector Function of Antibodies S309 MLNS, S309 N55Q MLNS, and S309 N55Q MLNS GAALIE Antibodies S309 MLNS (also referred to herein as S309 LS), S309 N55Q MLNS (also referred to herein as S309 N55Q LS), and S309 N55Q MLNS GAALIE (also referred to herein as S309 N55Q LS GAALIE) were assayed for their ability to promote NK-cell mediated antibody-dependent cell-mediated cytotoxicity (ADCC) and monocyte-mediated antibody-dependent cellular phagocytosis (ADCP) against cells expressing CoV-2-spike protein.

S309 MLNS comprises a VH having the sequence set forth in SEQ ID NO.:105 and a VL having the sequence set forth in SEQ ID NO.:168. Each of S309 N55Q MLNS and S309 N55Q MLNS GAALIE comprises a VH having the sequence set forth in SEQ ID NO.:113 and a VL having the sequence set forth in SEQ ID NO.:168.

ADCC was measured in vitro by exposing freshly isolated human NK cells from two genotyped donors expressing homozygous low-affinity (F/F158) or high-affinity (V/V158) FcγRIIIa to antibody pre-incubated with CHO-CoV-2-Spike cells and measuring LDH release as a readout according to the manufacturer's instructions (Cytotoxicity Detection Kit (LDH), Roche) after 4 hours of incubation at 37° C. In brief, plates were centrifuged for 4 minutes at 400×g, and 35 µl of supernatant was transferred to a flat 384-well plate. LDH reagent was prepared and 35 µl were added to each well. Using a kinetic protocol, the absorbance at 490 nm and 650 nm was measured once every 2 minutes for 8 minutes, and the slope of the kinetics curve was used as result. The percent specific lysis was determined by applying the following formula: (specific release−spontaneous release)/ (maximum release−spontaneous release)×100. Results are shown in FIG. 56.

The ability of antibodies S309 MLNS, S309 N55Q MLNS, S309 N55Q MLNS GAALIE, and control antibody S309-GRLR to promote ADCP by primary CD14+ monocytes was measured in vitro by exposing freshly isolated human PBMCs (labeled with cell trace violet) to CHO-CoV-2-Spike expressing cells (labeled with PKH67 Fluorescent Cell Linker Kit (Sigma Aldrich)) that were pre-incubated with antibody. Serial dilutions of mAbs (serially diluted 5-fold from 5,000 ng/ml to 0.32 ng/ml in RPMI-1640+L-glutamine supplemented with 10% Hyclone FBS+2×anti-anti (antibiotic-antimycotic)) were incubated with 10,000 CHO-CoV-2-Spike cells per well of a 96 well polypropylene plate for 10 minutes. Primary PBMCs were fluorescently labeled with Cell Trace Violet according to the manufacturer's instructions. Target cell and antibody mixtures were then incubated with labeled PBMCs at an effector-to-target ratio of 16:1. ADCP activity was measured after overnight incubation by labeling the monocyte population for CD14, and measuring the percentage of cell trace violet$^+$PKH67$^+$ cells amongst CD14$^+$ monocytes by flow cytometry. Results are shown in FIG. 57.

Example 34

Effect of Antibody S309 on SARS-CoV-2 Spike Protein-Mediated Cell Fusion

The effect of antibody S309 (VH: SEQ ID NO.:105; VL: SEQ ID NO.:168) on SARS-CoV-2 Spike protein-mediated fusion was tested using cells engineered to over-express Spike protein on the cell surface. Adding S309 to these cell cultures inhibited cell-cell fusion. Results are shown in FIGS. 58A (micrographs) and 58B (quantified data).

Example 35

Effect of Antibodies S309 N55Q MLNS and S309 N55Q MLNS GAALIE on SARS-CoV-2 Replication The effect of antibodies S309 N55Q MLNS and S309 N55Q MLNS GAALIE on SARS-CoV-2 replication was tested in VeroE6 cells, PBMCs, and dendritic cells. Each of S309 N55Q MLNS and S309 N55Q MLNS GAALIE comprises a VH having the sequence set forth in SEQ ID NO.: 113 and a VL having the sequence set forth in SEQ ID NO.: 168.

SARS-CoV-2 virus was incubated for one hour with S309 N55Q MLNS or S309 N55Q MLNS GAALIE. The virus/antibody mixture was then added to plated VeroE6, PBMC, or monocyte-derived dendritic (MoDC) cells. After incubating the cells with the virus/antibody mixture for one hour at 37° C., the cells were washed and incubated for a further 72 hours in fresh medium. The supernatant from the cultured cells was then assayed for focus-forming units (FFU). The supernatant was diluted 1:5 and added to VeroE6 cells. After one hour at 37° C., the VeroE6 cells were overlaid with methylcellulose. After 24 hours' further incubation, the VeroE6 cell cultures were stained for SARS-CoV-2 nucleoprotein. Results are shown in FIG. 59. Data for antibody S309 N55Q MLNS is shown in the top panel. Data for antibody S309 N55Q MLNS GAALIE is shown in the bottom panel. These 72-hour replication data are representative of findings at 24 and 48 hours.

Example 36

Materials and Methods

Flow-Cytometry Based Screening for Binding to CoV S Protein Expressed on Mammalian Cells ExpiCHO cells were transfected with S protein of SARS-CoV-2, SARS-CoV and MERS-CoV, or with an empty plasmid as a negative control. The monoclonal antibodies were then tested by flow-cytometry at 10 µg/ml for their ability to stain ExpiCHO cells expressing the S protein of 2019-nCoV, SARS-CoV, MERS-CoV or Mock cell transfectants.

Transient Expression of Recombinant SARS-CoV-2 Protein

The full-length S gene of SARS-CoV-2 strain (2019-nCoV-S) isolate BetaCoV/Wuhan-Hu-1/2019 (accession number MN908947) was codon optimized for human cell expression and cloned into the phCMV1 expression vector (Genlantis). Expi-CHO cells were transiently transfected with phCMV1-SARS-CoV-2-S, phCMV1-MERS-CoV-S (London1/2012), SARS-spike_pcDNA.3 (strain SARS) or the empty phCMV1 (Mock) using Expifectamine CHO Enhancer. Two days after transfection, cells were collected, fixed, or fixed and permeabilized with saponin for immunostaining with a panel of monoclonal antibodies reactive to SARS-CoV Receptor Binding Domain (RBD). An Alexa647-labelled secondary antibody anti-human IgG Fc was used for detection. Binding of antibodies to transfected cells was analyzed by flow-cytometry using a ZE5 Cell Analyzer (Biorard) and FlowJo software (TreeStar). Positive binding was defined by differential staining of CoV-S-transfectants versus mock-transfectants.

Competition Experiments Using Octet (BLI, Biolayer Interferometry)

Unless otherwise indicated herein, anti-His sensors (BIOSENSOR ANTI-PENTA-HIS (HIS1K)) were used to immobilize the S1 subunit protein of SARS-CoV (Sino Biological Europe GmbH). Sensors were hydrated for 10 min with Kinetics Buffer (KB; 0.01% endotoxin-free BSA, 0.002^Tween-20, 0.005% NaN3 in PBS). SARS-CoV 51 subunit protein was then loaded for 8 min at a concentration of 10 µg/ml in KB. Antibodies were associated for 6 min at 15 µg/ml for full length mAbs nCoV-10 and nCov-6 mAbs or 5 µg/ml for Fab nCoV-4, and in a subsequent experiment comprising nCoV-1 all at 10 µg/ml. Competing antibodies were then associated at the same concentration for additional 6 mins.

Competition Experiments Using Octet (BLI, Biolayer Interferometry)

For ACE2 competition experiments, ACE2-His (Bio-Techne AG) was loaded for 30 minutes at 5 µg/ml in KB onto anti-HIS (HIS2) biosensors (Molecular Devices-ForteBio). SARS-CoV-1 RBD-rabbitFc or SARS-CoV-2 RBD-mouseFc (Sino Biological Europe GmbH) at 1 µg/ml was associated for 15 minutes, after a preincubation with or without antibody (30 µg/ml, 30 minutes). Dissociation was monitored for 5 minutes.

Affinity Determination Using Octet (BLI, Biolayer Interferometry)

For $K_D$ determination of full-length antibodies, protein A biosensors (Pall ForteBio) were used to immobilize recombinant antibodies at 2.7 µg/ml for 1 minute, after a hydration step for 10 minutes with Kinetics Buffer. Association curves were recorded for 5 min by incubating the antibody-coated sensors with different concentration of SARS-CoV-1 RBD (Sino Biological) or SARS-CoV-2 RBD (produced in house; residues 331-550 of spike from BetaCoV/Wuhan-Hu-1/2019, accession number MN908947). Highest RBD concentration tested was 10 ug/ml, then 1:2.5 serially diluted. Dissociation was recorded for 9 min by moving the sensors to wells containing KB. $K_D$ values were calculated using a global fit model (Octet). Octet Red96 (ForteBio) equipment was used.

For $K_D$ determination of full-length antibodies compared to Fab fragments, His-tagged RBD of SARS-CoV-1 or SARS-CoV-2 were loaded at 3 µg/ml in KB for 15 minutes onto anti-HIS (HIS2) biosensors (Molecular Devices, ForteBio). Association of full-length antibody and Fab was performed in KB at 15 ug/ml and 5 ug/ml respectively for 5 minutes. Dissociation in KB was measured for 10 min.

ELISA Binding

The reactivities of mAbs with SARS-CoV Spike S1 Subunit Protein (strain WH20) protein were determined by enzyme-linked immunosorbent assays (ELISA). Briefly, 96-well plates were coated with 3 µg/ml of recombinant SARS-CoV Spike S1 Subunit Protein (Sino. Biological). Wells were washed and blocked with PBS+1% BSA for 1 h at room temperature and were then incubated with serially diluted mAbs for 1 h at room temperature. Bound mAbs were detected by incubating alkaline phosphatase-conjugated goat anti-human IgG (Southern Biotechnology: 2040-04) for 1 h at room temperature and were developed by 1 mg/ml p-nitrophenylphosphate substrate in 0.1 M glycine buffer (pH 10.4) for 30 min at room temperature. The optical density (OD) values were measured at a wavelength of 405 nm in an ELISA reader (Powerwave 340/96 spectrophotometer, BioTek).

Neutralization Assay

Unless otherwise indicated, Murine leukemia virus (MLV) pseudotyped with SARS-CoV-2 Spike protein (SARS-CoV-2pp) or SARS-CoV-1 Spike protein (SARS-CoV-1pp) were used. DBT cells stably transfected with ACE2 (DBT-ACE2) were used as target cells. SARS-CoV-2pp or SARS-CoV-1pp was activated with trypsin TPCK at 10 ug/ml. Activated SARS-CoV-2pp or SARS-CoV-1pp was added to a dilution series of antibodies (starting 50 ug/ml final concentration per antibody, 3-fold dilution). DBT-ACE2 cells were added to the antibody-virus mixtures and incubated for 48h. Luminescence was measured after aspirating cell culture supernatant and adding steady-GLO substrate (Promega).

Unless otherwise indicated, pseudoparticle neutralization assays use a VSV-based luciferase reporter pseudotyping system (Kerafast). VSV pseudoparticles and antibody are mixed in DMEM and allowed to incubate for 30 minutes at 37 C. The infection mixture is then allowed to incubate with Vero E6 cells for 1 h at 37 C, followed by the addition of DMEM with Pen-Strep and 10% FBS (infection mixture is not removed). The cells are incubated at 37 C for 18-24 hours. Luciferase is measured using an Ensight Plate Reader (Perkin Elmer) after the addition of Bio-Glo reagent (Promega).

SPR Single-Cycle Kinetics

SPR experiments were carried out with a Biacore T200 instrument using a single-cycle kinetics approach. S309 IgG was captured on the surface and increasing concentrations of purified SARS-CoV-2 RBD, either glycosylated or deglycosylated, were injected. Association and dissociation kinetics were monitored and fit to a binding model to determine affinity.

Expression of Recombinant Antibodies

Recombinant antibodies were expressed in ExpiCHO cells transiently co-transfected with plasmids expressing the heavy and light chain as previously described. (Stettler et al. (2016) Specificity, cross-reactivity, and function of antibodies elicited by Zika virus infection. Science, 353(6301), 823-826) Monoclonal antibodies S303, S304, S306, S309, S310, and S315 were expressed as rIgG-MLNS antibodies. The MLNS mutation confers a longer half-life in vivo. (Zalevsky et al. (2010) Enhanced antibody half-life improves in vivo activity. Nature Biotechnology, 28(2), 157-159)

Sequence Alignment

SARS-CoV-2 genomics sequences were downloaded from GISAID on Mar. 29, 2020, using the "complete (>29,000 bp)" and "low coverage exclusion" filters. Bat and pangolin sequences were removed to yield human-only sequences. The spike ORF was localized by performing reference protein (YP_009724390.1)-genome alignments with GeneWise2. Incomplete matches and indel-containing ORFs were rescued and included in downstream analysis. Nucleotide sequences were translated in silico using seqkit. Sequences with more than 10% undetermined aminoacids (due to N basecalls) were removed. Multiple sequence alignment was performed using MAFFT. Variants were determined by comparison of aligned sequences (n=2,229) to the reference sequence using the R/Bioconductor package Biostrings. A similar strategy was used to extract and translate spike protein sequences from SARS-CoV genomes sourced from ViPR (search criteria: SARS-related coronavirus, full-length genomes, human host, deposited before December 2019 to exclude SARS-CoV-2, n=53). Sourced SARS-CoV genome sequences comprised all the major published strains, such as Urbani, Tor2, TW1, P2, Frankfurt1, among others. Pangolin sequences as shown by Tsan-Yuk Lam et al were sourced from GISAID. Bat sequences from the three clades of Sarbecoviruses as shown by Lu et al (Lancet 2020) were sourced from Genbank. Civet and racoon dog sequences were similarly sourced from Genbank.

Example 37

ACE2-Independent Mechanism of SARS-CoV2 Neutralization by S309 Antibody

In the following experiments, S309 antibody (VH of SEQ ID NO.:105, VL of SEQ ID NO.:168) was expressed as recombinant IgG1 with M428L and N434S Fc mutations. The effect of ACE2 overexpression on S309 antibody neutralization of infection was investigated. Vero E6 or Vero E6-TMPRSS2 cells were infected with SARS-CoV-2 (isolate USA-WA1/2020) at MOI 0.01 in the presence of S309 (10 µg/ml). Cells were fixed 24 h post infection, viral nucleocapsid protein was immunostained and quantified. Nucleocapsid staining was effectively absent in antibody-treated cells. S309 had an IC50 (ng/mL) in Vero E6 cells of 65 and in Vero E6-TMPRSS2 of 91 (data not shown).

A panel of 7 cell lines (HeLa, 293T (wt), Vero E6, Huh7, 293T ACE2, MRC 5-ACE2-TMPRSS2, A549-ACE2-TMPRSS2 clone 5, A549-ACE2-TMPRSS2 clone 10) were infected with SARS-CoV-2-Nluc or VSV pseudotyped with the SARS-CoV-2 spike protein in the presence of S309. Luciferase signal was quantified 24h post infection. S309 maximum neutralization values were as shown in Table 12.

TABLE 12

Maximum Neutralization Values of S309

| Cell Type | Virus/Pseudotype | |
|---|---|---|
| | SARS-CoV-2-Nluc | VSV Pseudotype |
| Vero E6 | >99% | >99% |
| Vero E6-TMPRSS2 | >99% | 96% |
| Huh7 | 98% | 78% |
| 293T ACE2 | 26% | 34% |
| MRC5-ACE2-TMPRSS2 | 87% | 45% |

TABLE 12-continued

Maximum Neutralization Values of S309

| Cell Type | Virus/Pseudotype | |
|---|---|---|
| | SARS-CoV-2-Nluc | VSV Pseudotype |
| A549-ACE2-TMPRSS2 clone 5 | 89% | 65% |
| A549-ACE2-TMPRSS2 clone 10 | 81% | 42% |

Binding of purified, fluorescently-labeled SARS-CoV-2 spike protein binding to these cell lines was quantified by flow cytometry. HeLa and 239T WT cells had he lowest MFIs, followed by Huh7 and VeroE6 cells. 293T ACE2 cells (highest), MRC 5-ACE2-TMPRSS2 (third-highest), A549-ACE2-TMPRSS2 clone 5 (fourth-highest), and A549-ACE2-TMPRSS2 clone 10 (second-highest) had higher MFIs. Correlation analysis between spike binding maximum neutralization potential of S309 was determined; S309 Spearman correlation values were: r=−0.94 for both viral models. p=0.017.

To further characterize SARS-CoV-2-susceptible cell lines, the seven cell lines described above were incubated with purified, fluorescently-labeled SARS-CoV-2 spike protein or RBD protein and protein binding was quantified by flow cytometry. In descending order of MFI, the cell lines were: A549-ACE2-TMPRSS2 clone 10; 293T ACE2; MRC 5-ACE2-TMPRSS2; A549-ACE2-TMPRSS2 clone 5; Vero E6; Huh7; 293T (wt); and HeLa.

Selected lectins and published receptor candidates were screened using HEK293T cells infected with SARS-CoV-2 VSV pseudoviruses. ACE2, DC-SIGN, L-SIGN, and SIGLEC-1 gave the highest signals. ACE2 provided a signal of approximately $10^5$ relative luminescence units (RLUs), and DC-SIGN, SIGLEC-1, and L-SIGN had signals of approximately $10^4$ RLUs. All other lectins/candidates tested gave signals of approximately $10^2$-$10^3$ RLUs.

HEK 293T, HeLa and MRCS cells were transiently transduced to overexpress DC-SIGN, L-SIGN, SIGLEC1 or ACE2 and infected with SARS-CoV-2 VSV pseudoviruses. Uninfected cells and untransduced cells were included as controls. In HEK293T cells, ACE2, DC-SIGN, SIGLEC-1, and L-SIGN all provided substantial increases in infection. In HeLa and MRCS cells, only ACE2 increased infection.

Stable HEK293T cell lines overexpressing DC-SIGN, L-SIGN, SIGLEC-1 or ACE2 were infected with authentic SARS-CoV-2 (MOI 0.1), fixed and immunostained at 24 hours for the SARS-CoV-2 nucleoprotein. Wild-type cells (infected and uninfected) were used as controls. Increased staining was observed in cells overexpressing DC-SIGN, L-SIGN, or SIGLEC-1, and staining was significantly increased in cells overexpressing ACE2.

Stable cell lines were infected with SARS-CoV-2-Nluc and luciferase levels were quantified at 24 hours. In ascending order of RLUs: uninfected (approx. $10^2$-$10^3$ RLUs); parental 293T (approx. $10^4$ RLUs); DC-SIGN (approx. $10^5$ RLUs); L-SIGN (approx. $10^5$ RLUs); SIGLEC-1 (approx. $10^5$-$10^6$ RLUs); ACE2 (>$10^7$ RLUs).

Stable cell lines were incubated with different concentration of anti-SIGLEC1 mAb (clone 7-239) and infected with SARS-CoV-2-Nluc. Infection as a percentage of untreated cells remained near to exceeded 100% in 293T cells expressing DC-SIGN, L-SIGN, or ACE2, but dropped to below 50% (0.2 µg/mL anti-SIGLEC) to close to 0 (1 µg/mL or 5 µg/mL anti-SIGLEC) in 293T cells expressing SIGLEC-1.

Single cell expression levels of selected potential SARS-CoV-2 (co)receptor candidates were determined in different lung cell types derived from the Human Lung Cell Atlas (nature.com/articles/s41586-020-2922-4). DC-SIGN, L-SIGN and SIGLEC-1 are expressed in a variety of cell types in the lung at levels similar to or even higher than ACE2.

Binding of antibodies targeting DC-/L-SIGN, DC-SIGN, SIGLEC1 or ACE2 on HEK293T cells stably over-expressing the respective attachment receptor was analyzed by flow cytometry and immunofluorescence analysis. HEK 293T cells over-expressing the respective attachment receptors were infected with VSV pseudotyped with SARS-COV-2 wildtype spike or spike bearing mutations of the B1.1.7 lineage. Luminescence was analyzed one day post infection. Infection was increased in cells expressing the attachment receptors. Infection by VSV pseudotyped with either spike was similar for each test group. Cells expressing ACE2 gave the highest luminescence signal.

Vero E6 cells, in vitro differentiated moDCs or PBMCs were infected with SARS-CoV-2 at MOI 0.01. At 24h post infection, cells were fixed, immunostained for viral nucleocapsid protein and infected cells were quantified. Only VeroE6 cells showed infection (approximately 7% of cells). Supernatant of the infected cells was taken at 24, 48 and 72h and infectious viral titer was quantified by FFU assay on Vero E6 cells.

Major cell types with detectable SARS-CoV-2 genome in bronchoalveolar lavage fluid (BALF) and sputum of severe COVID-19 patients were assessed. A t-SNE plot was generated, and the count of each SARS-CoV-2+ cell type was determined (total n=3,085 cells from 8 subjects in Ren et al. Cell 2021). Cell types were T, NK, plasma, neutrophil, macrophage, ciliated, squamous, and secretory. Expression of ACE2, DC-SIGN, L-SIGN, SIGLEC-1, and combinations of these was assessed for each cell type.

ACE2, DC-SIGN (CD209), L-SIGN (CLEC4M), SIGLEC1 transcript counts were correlated with SARS-CoV-2 RNA counts in macrophages and in secretory cells. Correlation was based on counts (before log transformation), from Ren et al. Cell 2021.

Representative data showing expression of receptors in stable HEK293T cell lines are shown in FIG. 60. Cell lines were generated to overexpress DC-SIGN, L-SIGN or ACE2 by transducing HEK293T cells with lentivirus encoding the transgene, and immunofluorescence assays were performed to assess transgene expression.

Representative data showing the ability of VSV pseudovirus expressing SARS-CoV-2 S protein with luciferase reporter to infect the HEK293T cells (using a luminescence assay) are shown in FIG. 61; expression of DC-SIGN or L-SIGN increased pseudovirus infection levels by over 10-fold compared to infection of WT HEK293T cells, and expression of ACE2 increased pseudovirus infection levels by over 100-fold compared to infection of WT HEK293T cells.

Neutralizing activity of exemplary mAb S309 against the VSV pseudovirus was assessed in the engineered HEK293T cells. Data are shown in FIG. 62; S309 fully neutralized infection via DC-SIGN and L-SIGN, and to a lesser extent, ACE2.

The ability of live SARS-CoV-2 with luciferase reporter to infect the HEK293T cells was examined using a luminescence assay. Data are shown in FIG. 63; expression of DC-SIGN or L-SIGN increased live virus infection levels by over 3-fold compared to infection of WT HEK293T cells, and expression of ACE2 increased live virus infection levels by over 100-fold compared to infection of WT HEK293T cells.

Neutralizing activity of mAb S309 against the VSV pseudovirus was assessed in the engineered HEK293T cells. Data are shown in FIG. 64; S309 fully neutralized infection via DC-SIGN and L-SIGN, and neutralized infection via ACE2 to a lesser extent.

Experiments were performed to investigate whether S309 antibody can neutralize entry of SARS-CoV-2 via SIGLEC-1. Briefly, stable cell HEK293T lines were generated as described above to overexpress DC-SIGN/L-SIGN, DC-SIGN, SIGLEC-1, or ACE2. Expression data are shown in FIG. 65. As shown in FIG. 66, expression of DC-SIGN, L-SIGN, or SIGLEC increased live virus infection levels by over 10-fold compared to infection of WT HEK293T cells, and expression of ACE2 increased pseudovirus infection levels by over 100-fold compared to infection of WT HEK293T cells. As shown in FIG. 67, S309 fully neutralized infection via DC-SIGN, L-SIGN, and SIGLEC-1.

Expression of DC-SIGN (CD209) and other cell surface receptor proteins including SIGLEC-1 and other SIGLECs was determined on a variety of cell types. Data are summarized in FIGS. 68A and 68B.

Further experiments were performed to investigate the function(s) of DC-SIGN, L-SIGN, and SIGLEC-1 in SARS-CoV-2 infection. In one set of experiments, HEK293T cells stably expressing DC-SIGN, L-SIGN, SIGLEC-1 or ACE2 were infected with live SARS-CoV-2 Nluc at three different multiplicities of infection (MOI): 0.01, 0.1, and 1). Infection was determined using relative luminescence units and compared to infection in HEK293T cells (parental). Data are shown in FIG. 69. At the lowest MOI tested, an increase of infection in cells expressing DC-SIGN, L-SIGN, or SIGLEC was observed. At the highest MOI tested, infection was not further increased versus parental by expression of DC-SIGN, L-SIGN, or SIGLEC. These data indicate that the parental 293T cells are susceptible to infection by SARS-CoV-2 and L-SIGN, DC-SIGN, and SIGLEC-1 enhance infection levels but do not function as primary receptors for infection.

In another set of experiments, 293T cells, HeLa cells, and MRCS cells were transiently transduced with lentivirus encoding DC-SIGN, L-SIGN, SIGLEC-1 or ACE2 and infected with VSV pseudovirus three days after transduction. Data are shown in FIG. 70. While the 293T cells showed a low level of susceptibility (compare uninfected with untransduced), HeLa and MRCS cells were completely refractory to the virus. The low level of infection in 293T cells can be increased by expression of L-SIGN, DC-SIGN, or SIGLEC-1, consistent with a role for these proteins as as attachment factors. The HeLa and MRCS cells remained refractory to infection even after expression of L-SIGN, DC-SIGN, or SIGLEC-1, and only become susceptible after expression of ACE2. These data indicate that L-SIGN, DC-SIGN, and SIGLEC-1 are not primary receptors for SARS-CoV-2.

Example 38

In Vivo Efficacy of S309 Antibody

Figure 73A:
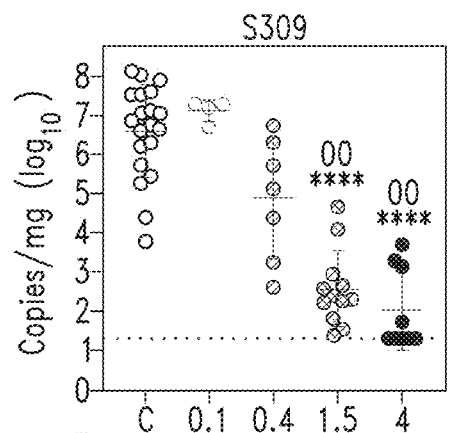
Figure 73B:
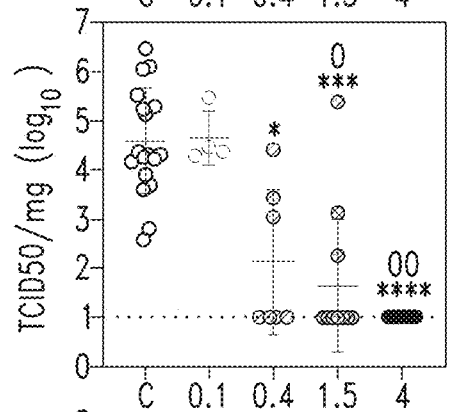
Figure 73C:
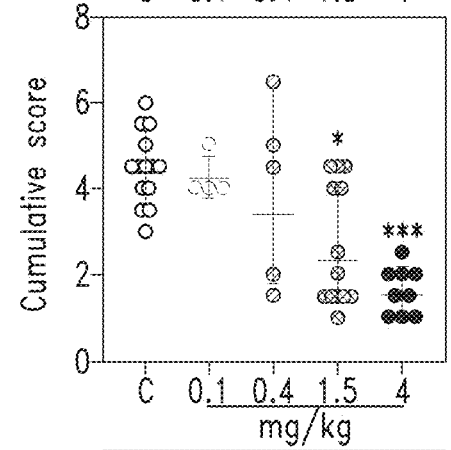
Figure 73D:
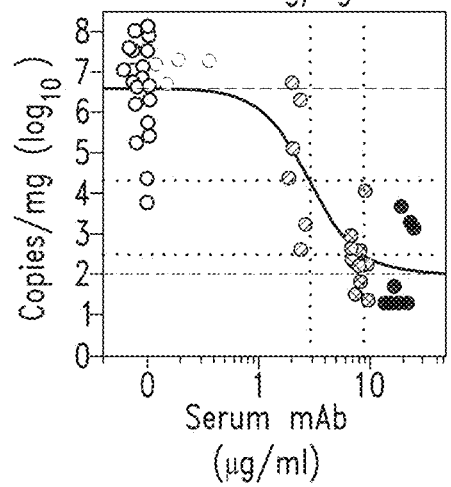

The efficacy of S309 was investigated in Syrian hamsters. This animal model represents to-date the most relevant model of SARS-CoV-2 infection that did not require in vivo over-expression of ACE2 to support productive infection and disease. Prophylactic administration of S309 induced dose-dependent protection against SARS-CoV-2 infection and tissue damage in hamsters, as demonstrated by the viral RNA levels, the viral load as well as the histopathological score in the lungs (FIGS. 73A-7C). These data indicate that poor and incomplete neutralization of entry by S309 in vitro when using ACE2 over-expressing cells did not compromise in vivo efficacy of non-RBM mAbs.

S309 carrying the N297A mutation has a reduced capacity to trigger effector functions as a consequence of diminished engagement to Fcγ receptors. This was further confirmed by the reduced binding of S309-N297A variant to hamster monocytes in the spleen. The in vivo efficacy measured with the N297A mAb is similar or just slightly inferior to the wt S309, suggesting that neutralizing capacity of the mAb is prevailing upon its effector function capacity in these conditions. The serum concentration of S309 required to reduce the viral RNA in the lung by 90% was 9 µg/ml, FIG. 73D.

Example 39

Antibody Activity Against SARS-CoV-2 Variants

A number of SARS-CoV-2 variants have emerged, with increasing numbers of infection by variants reported in late 2020. The Receptor Binding Motif (RBM) appears to be particularly variable to mutation. Notable emerging variants have been observed in Scotland, the UK, South Africa, California, Columbus, and in minks in Denmark, and some mutations have been reported to confer escape from antibodies or serum neutralization. Experiments were performed to assess the ability of S309 antibodies to neutralize variants. S309 N55Q MLNS (VH: SEQ ID NO.:113; VL: SEQ ID NO.:168; with M428L and N434S Fc mutations) was tested against SARS-CoV-2 bearing a panel of the 20 most-frequent SARS-CoV-2 RBD variant mutations, as determined by sequence reads. Antibodies REGN10933 and REGN10987 (Hansen et al., Science 369(6506):1010-1014; eabd0827-0810 (2020) and PDB 6XDG (rcsb.org/structure/6XDG)) were included for comparison. Results are summarized in Table 13.

Y=less than three-fold decrease in neutralizing of live virus or pseudovirus;
N=greater than three-fold decrease in neutralizing of live virus or pseudovirus;
P=neutralization by antibody is predicted due to variant amino acid being outside of epitope; ?=unknown.

TABLE 13

Summary of Neutralization by Antibodies Against SARS CoV-2 Variants

| Variant Mutation | S309 N55Q MLNS | REGN10933 | REGN10987 |
|---|---|---|---|
| N501Y (UK, South African, and Brazilian mutant) | Y | Y | Y |
| S477N | Y | Y | Y |
| N439K (Scottish mutant) | Y | Y | N |
| L452R (Californian mutant) | Y | P | P |
| E484K (South African and Brazilian mutant) | Y | N | Y |
| Y453F (mink mutant) | Y | N | N (4× decrease) |
| A520S | Y | Y | Y |
| K417N (South African mutant) | Y (K417N/V) | N | Y (K417N/E/V) |
| S494P | Y | N | P |
| S477R | P | ? | P |
| V367F | Y | Y | Y |
| P384L | Y | P | P |
| A522S | Y | P | P |
| A522V | Y | P | P |
| V382L | Y | P | P |
| N501T | Y | P | P |
| P330S | Y | P | P |
| T478I | Y | ? | P |
| S477I | Y | ? | P |
| P479S | Y | P | P |

Y = less than three-fold decrease in neutralizing of live virus or pseudovirus
N = greater than three-fold decrease in neutralizing of live virus or pseudovirus
P = neutralization by antibody is predicted due to variant amino acid being outside of epitope
? = unknown.

Total counts of SARS-CoV-2 sequenced mutants known to escape the antibodies (as of Jan. 29, 2021) were: S309 N55Q MLNS=29; REGN10987=10,425; REGN10933=3,621.

Binding of S309 antibodies to SARS-CoV-2 variant RBDs was assessed by BLI. S309 (VH: SEQ ID NO.:105; VL: SEQ ID NO.:168) with wild-type Fc and S309 N55Q (VH: SEQ ID NO.:113; VL: SEQ ID NO.:168) bearing MLNS or MLNS+GAALIE Fc mutations were assessed. REGN10987 and REGN10933 were included as comparators. Briefly, antibodies were diluted in kinetics buffer at 3 ug/ml and loaded on Protein-A sensors for 75 seconds. After a short equilibration step in kinetics buffer, loaded sensors were moved in wells containing the RBD variants at 5 ug/ml in kinetics buffer and association was recorded during 3 minutes. Dissociation of the complex was performed in kinetics buffer for 3 minutes. Data are shown in FIGS. 71A-71B; "WT"=Wuhan-Hu-1 with D614G; "Triple Mutant" in lower row=Wuhan-Hu-1 with D614G and added South Africa variant B.1.351 RBD mutations K417N, E484K, and N501Y. Other mutations present in the South Africa variant B.1.351 were not present in the "SA" RBD tested.

Neutralization of S309 antibodies against SARS-CoV-2 variants was assessed using MLV pseudovirus and Vero-E6 target cells expressing TMPRSS2. S309 (VH: SEQ ID NO.:105; VL: SEQ ID NO.:168) with wild-type Fc and S309 N55Q (VH: SEQ ID NO.:113; VL: SEQ ID NO.:168) bearing MLNS or MLNS+GAALIE Fc mutations were assessed. REGN10987, REGN10933, and the combination of REGN10987+REGN10933, were also assessed. Data are shown in FIG. 72. "WT"=Wuhan-Hu-1; "UK"=SARS-CoV-2 variant B.1.1.7; and "SA"=variant B.1.351.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Patent Application No. 62/981,984, filed on Feb. 26, 2020, U.S. Patent Application No. 62/982,661, filed on Feb. 27, 2020, U.S. Patent Application No. 62/987,298, filed on Mar. 9, 2020, U.S. Patent Application No. 62/989,522, filed on Mar. 13, 2020, U.S. Patent Application No. 62/990,369, filed on Mar. 16, 2020, U.S. Patent Application No. 62/992,082, filed on Mar. 19, 2020, U.S. Patent Application No. 62/994,235, filed on Mar. 24, 2020, U.S. Patent Application No. 63/001,204, filed on Mar. 27, 2020, U.S. Patent Application No. 63/003,214, filed on Mar. 31, 2020, U.S. Patent Application No. 63/005,206, filed on Apr. 3, 2020, U.S. Patent Application No. 63/010,589, filed on Apr. 15, 2020, U.S. Patent Application No. 63/011,971, filed on Apr. 17, 2020, U.S. Patent Application No. 63/014,024, filed on Apr. 22, 2020, U.S. Patent Application No. 63/023,788, filed on May 12, 2020, U.S. Patent Application No. 63/025,133, filed on May 14, 2020, U.S. Patent Application No. 63/039,813, filed on Jun. 16, 2020, U.S. Patent Application No. 63/043,653, filed on Jun. 24, 2020, U.S. Patent Application No. 63/050,331, filed on Jul. 10, 2020, and U.S. Patent Application No. 63/052,810, filed on Jul. 16, 2020, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating a SARS-CoV-2 infection in a subject, the method comprising administering to the subject an effective amount of a SARS-CoV-2 neutralizing antibody or antigen-binding fragment that comprises:
   a heavy chain variable domain (VH) that comprises: the complementarity determining region (CDR)H1 amino acid sequence set forth in SEQ ID NO.:106, the CDRH2 amino acid sequence set forth in SEQ ID NO.:121, and the CDRH3 amino acid sequence set forth in SEQ ID NO.:108; and
   (ii) a light chain variable domain (VL) that comprises: the CDRL1 amino acid sequence set forth in SEQ ID NO.:169, the CDRL2 amino acid sequence set forth in SEQ ID NO.:170, and the CDRL3 amino acid sequence set forth in SEQ ID NO.:171.

2. The method of claim 1, wherein the SARS-CoV-2 comprises:
   (i) a SARS-CoV-2 Wuhan-Hu-1;
   (ii) a SARS-CoV-2 B.1.1.7;
   (iii) a SARS-CoV-2 B.1.351;
   (iv) a SARS-CoV-2 comprising, in a surface glycoprotein (S) thereof, any one or more of the following substitution mutations relative to SEQ ID NO.:165: N501Y; S477N; N439K; L452R; E484K; Y453F; A520S; K417N; K417V; S494P; N501T; 5477R; V367F; P384L; A522S; A522V; V382L; P330S; T478I; S477I; P479S; or
   (v) any combination of (i)-(iv).

3. The method of claim 1, comprising administering the antibody or antigen-binding fragment to the subject intravenously.

4. The method of claim 1, wherein:
(i) the VH comprises or consists of an amino acid sequence having at least 85% identity to the amino acid sequence set forth in SEQ ID NO.:113; and/or
(ii) the VL comprises or consists of an amino acid sequence having at least 85% identity to the amino acid sequence set forth in SEQ ID NO.:168.

5. The method of claim 4, wherein:
the VH comprises or consists of an amino acid sequence having at least 90% identity to the amino acid sequence set forth in SEQ ID NO.:113; and/or
(ii) the VL comprises or consists of an amino acid sequence having at least 90% identity to the amino acid sequence set forth in SEQ ID NO.:168.

6. The method of claim 4, wherein:
the VH comprises or consists of an amino acid sequence having at least 95% identity to the amino acid sequence set forth in SEQ ID NO.:113; and/or
(ii) the VL comprises or consists of an amino acid sequence having at least 95% identity to the amino acid sequence set forth in SEQ ID NO.:168.

7. The method of claim 4, wherein:
the VH comprises or consists of an amino acid sequence having at least 99% identity to the amino acid sequence set forth in SEQ ID NO.:113; and/or
(ii) the VL comprises or consists of an amino acid sequence having at least 99% identity to the amino acid sequence set forth in SEQ ID NO.:168.

8. The method of claim 1, wherein the antibody or antigen-binding fragment is capable of inhibiting an interaction between:
(i) SARS-CoV-2 and a human DC-SIGN;
(ii) SARS-CoV-2 and a human L-SIGN;
(iii) SARS-CoV-2 and a human SIGLEC-1; or
(iv) any combination of (i)-(iii).

9. The method of claim 1, wherein the antibody or antigen-binding fragment comprises a human antibody, a monoclonal antibody, a purified antibody, a single chain antibody, a Fab, a Fab', a F(ab')2, a Fv, a scFv, or a scFab.

10. The method of claim 1, wherein the antibody or antigen-binding fragment is a IgG, IgA, IgM, IgE, or IgD isotype.

11. The method of claim 1, wherein the antibody or antigen-binding fragment further comprises a CH1-CH3 that comprises or consists of the amino acid sequence set forth in SEQ ID NO.:265 or 266.

12. The method of claim 1, wherein the antibody or antigen-binding fragment further comprises a Fc polypeptide or a fragment thereof.

13. The method of claim 12, wherein the Fc polypeptide or fragment thereof comprises:
a mutation that enhances binding to a FcRn as compared to a reference Fc polypeptide that does not comprise the mutation; and/or
(ii) a mutation that enhances binding to a FcγR as compared to a reference Fc polypeptide that does not comprise the mutation.

14. The method of claim 13, wherein the mutation that enhances binding to a FcRn comprises:
(i) M428L/N434S;
(ii) M252Y/S254T/T256E;
(iii) T250Q/M428L;
(iv) P257I/Q311I;
(v) P257I/N434H;
(vi) D376V/N434H;
(vii) T307A/E380A/N434A; or
(viii) any combination of (i)-(vii).

15. The method of claim 14, wherein the mutation that enhances binding to a FcRn comprises M428L/N434S.

16. The method of claim 13, wherein the mutation that enhances binding to a FcγR comprises S239D, I332E, A330L, G236A, or any combination thereof.

17. The method of claim 16, wherein the mutation that enhances binding to a FcγR comprises:
(i) S239D/I332E;
(ii) S239D/A330L/I332E;
(iii) G236A/S239D/I332E; or
(iv) G236A/A330L/I332E.

18. A method of treating a SARS-CoV-2 infection in a subject, the method comprising administering to the subject an effective amount of a SARS-CoV-2 neutralizing antibody or antigen-binding fragment that comprises a heavy chain variable domain (VH) and a light chain variable domain (VL), wherein the VH comprises or consists of the amino acid sequence set forth in SEQ ID NO.:113 and the VL comprises or consists of the amino acid sequence set forth in SEQ ID NO.:168.

19. The method of claim 18, comprising administering the antibody or antigen-binding fragment to the subject intravenously.

20. The method of claim 18, wherein the antibody or antigen-binding fragment is capable of inhibiting an interaction between:
(i) SARS-CoV-2 and a human DC-SIGN;
(ii) SARS-CoV-2 and a human L-SIGN;
(iii) SARS-CoV-2 and a human SIGLEC-1; or
(iv) any combination of (i)-(iii).

21. The method of claim 18, wherein the antibody or antigen-binding fragment further comprises a CH1-CH3 that comprises or consists of the amino acid sequence set forth in SEQ ID NO.:265 or 266.

22. The method of claim 18, wherein the antibody or antigen-binding fragment further comprises a Fc polypeptide or a fragment thereof.

23. The method of claim 22, wherein the antibody or antigen-binding fragment is a IgG, IgA, IgM, IgE, or IgD isotype.

24. The method of claim 22, wherein the Fc polypeptide or fragment thereof comprises:
a mutation that enhances binding to a FcRn as compared to a reference Fc polypeptide that does not comprise the mutation; and/or
(ii) a mutation that enhances binding to a FcγR as compared to a reference Fc polypeptide that does not comprise the mutation.

25. The method of claim 24, wherein the mutation that enhances binding to a FcRn comprises:
(i) M428L/N434S;
(ii) M252Y/S254T/T256E;
(iii) T250Q/M428L;
(iv) P257I/Q311I;
(v) P257I/N434H;
(vi) D376V/N434H;
(vii) T307A/E380A/N434A; or
(viii) any combination of (i)-(vii).

26. The method of claim 25, wherein the mutation that enhances binding to a FcRn comprises M428L/N434S.

27. The method of claim 24, wherein the mutation that enhances binding to a FcγR comprises S239D, I332E, A330L, G236A, or any combination thereof.

28. The method of claim 27, wherein the mutation that enhances binding to a FcγR comprises:
(i) S239D/I332E;
(ii) S239D/A330L/I332E;

(iii) G236A/S239D/I332E; or
(iv) G236A/A330L/I332E.

29. A method of treating a SARS-CoV-2 infection in a subject, the method comprising administering to the subject an effective amount of a SARS-CoV-2 neutralizing antibody that comprises:
- a heavy chain comprising (i)(1) a VH that comprises or consists of the amino acid sequence set forth in SEQ ID NO.:113, and (i)(2) a CH1-CH3 that comprises or consists of the amino acid sequence set forth in SEQ ID NO.:173; and
- (ii) a light chain comprising (ii)(1) a VL that comprises or consists of the amino acid sequence set forth in SEQ ID NO.: 168, and (ii)(2) a CL that comprises or consists of the amino acid sequence set forth in SEQ ID NO.:174.

30. A method of treating a SARS-CoV-2 infection in a subject, the method comprising administering to the subject an effective amount of a SARS-CoV-2 neutralizing antibody that comprises:
- a heavy chain comprising (i)(1) a VH that comprises or consists of the amino acid sequence set forth in SEQ ID NO.:113, and (i)(2) a CH1-CH3 that comprises or consists of the amino acid sequence set forth in SEQ ID NO.:175; and
- (ii) a light chain comprising (ii)(1) a VL that comprises or consists of the amino acid sequence set forth in SEQ ID NO.: 168, and (ii)(2) a CL that comprises or consists of the amino acid sequence set forth in SEQ ID NO.:174.

* * * * *

SEQUENCE LISTING

<160> NUMBER OF SEQ ID NOS: 267

<210> SEQ ID NO 1
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v1 mAb VH

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
        35                  40                  45

Gly Trp Val Asn Gly Tyr Ser Gly Ala Thr Arg Tyr Ala Gln Lys Tyr
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120

<210> SEQ ID NO 2
<211> LENGTH: 8
<212> TYPE: PRT
<213> ORGANISM: Artificial Sequence
<220> FEATURE:
<223> OTHER INFORMATION: Synthetic sequence SARS-CoV-2 S300-v1 mAb CDRH1

<400> SEQUENCE: 2

Gly Tyr Thr Phe Thr Asp Tyr Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic sequence SARS-CoV-2 S300-v1 mAb CDRH2

<400> SEQUENCE: 3

Val Asn Gly Tyr Ser Gly Ala Thr
1               5

<210> SEQ ID NO 4
<211> LENGTH: 16
<212> TYPE: PRT
<213> ORGANISM: Artificial Sequence
<220> FEATURE:
<223> OTHER INFORMATION: Synthetic sequence SARS-CoV-2 S300-v1 mAb CDRH3

<400> SEQUENCE: 4

Ala Arg Asp Arg Pro Ser His Glu Trp Ala Met Tyr Phe Phe Asp Asn
1               5                   10                  15

<210> SEQ ID NO 5
<211> LENGTH: 109
<212> TYPE: PRT

<213> ORGANISM: Artificial Sequence
<220> FEATURE:
<223> OTHER INFORMATION: Synthetic sequence SARS-CoV-2 S300-v1 mAb VL
(VK)

<400> SEQUENCE: 5

```
Gln Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Pro Ser Ser
            20                  25                  30

Cys Leu Ala Trp Tyr Gln Gln Lys Pro Gly Gln Ala Pro Arg Leu Leu
        35                  40                  45

Ile Tyr Gly Ala Ser Gly Arg Ala Thr Gly Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Phe Ala Val Tyr Tyr Cys Gln Gln Tyr Gly Ser Ser Pro
                85                  90                  95

Pro Leu Thr Phe Gly Gly Gly Thr Lys Val Glu Ile Lys
            100                 105
```

<210> SEQ ID NO 6
<211> LENGTH: 7
<212> TYPE: PRT
<213> ORGANISM: Artificial Sequence
<220> FEATURE:
<223> OTHER INFORMATION: Synthetic sequence SARS-CoV-2 S300-v1 mAb CDRL1

<400> SEQUENCE: 6

```
Gln Ser Val Pro Ser Ser Cys
1               5
```

<210> SEQ ID NO 7
<211> LENGTH: 3
<212> TYPE: PRT
<213> ORGANISM: Artificial Sequence
<220> FEATURE:
<223> OTHER INFORMATION: Synthetic sequence SARS-CoV-2 S300-v1 mAb CDRL2

<400> SEQUENCE: 7

```
Gly Ala Ser
1
```

<210> SEQ ID NO 8
<211> LENGTH: 10
<212> TYPE: PRT
<213> ORGANISM: Artificial Sequence
<220> FEATURE:
<223> OTHER INFORMATION: Synthetic sequence SARS-CoV-2 S300-v1 mAb CDRL3

<400> SEQUENCE: 8

```
Gln Gln Tyr Gly Ser Ser Pro Pro Leu Thr
1               5                   10
```

<210> SEQ ID NO 9
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v1.1 mAb VH

<400> SEQUENCE: 9

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
            35                  40                  45

Gly Trp Val Gln Gly Tyr Ser Gly Ala Thr Arg Tyr Ala Gln Lys Tyr
        50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120
```

<210> SEQ ID NO 10
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v1.2 mAb VH

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
            35                  40                  45

Gly Trp Val Asn Ala Tyr Ser Gly Ala Thr Arg Tyr Ala Gln Lys Tyr
        50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120
```

<210> SEQ ID NO 11
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v1.3 mAb VH

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
            35                  40                  45

Gly Trp Val Asn Ser Tyr Ser Gly Ala Thr Arg Tyr Ala Gln Lys Tyr
        50                  55                  60

Gln Gly Arg Val Thr Met Thr Arg Asp Thr Ser Ile Ser Thr Ala Tyr
```

```
                65                  70                  75                  80
Met Gln Leu Ser Arg Leu Arg Pro Asp Asp Thr Ala Val Tyr Tyr Cys
                    85                  90                  95

Ala Arg Asp Arg Pro Ser His Glu Trp Ala Met Tyr Phe Phe Asp Asn
                100                 105                 110

Trp Gly Gln Gly Thr Leu Val Thr Val Ser Ser
            115                 120

<210> SEQ ID NO 12
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v1.4 mAb VH

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Leu
            35                  40                  45

Gly Trp Val Asn Pro Tyr Ser Gly Ala Thr Arg Tyr Ala Gln Lys Tyr
        50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                    85                  90                  95

Ala Arg Asp Arg Pro Ser His Glu Trp Ala Met Tyr Phe Phe Asp Asn
                100                 105                 110

Trp Gly Gln Gly Thr Leu Val Thr Val Ser Ser
            115                 120

<210> SEQ ID NO 13
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v1.5 mAb VH

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Leu
            35                  40                  45

Gly Trp Val Asn Gln Tyr Ser Gly Ala Thr Arg Tyr Ala Gln Lys Tyr
        50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                    85                  90                  95

Ala Arg Asp Arg Pro Ser His Glu Trp Ala Met Tyr Phe Phe Asp Asn
                100                 105                 110

Trp Gly Gln Gly Thr Leu Val Thr Val Ser Ser
            115                 120
```

<210> SEQ ID NO 14
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v1.6 mAb VH

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
        35                  40                  45

Gly Trp Val Leu Gly Tyr Ser Gly Ala Thr Arg Tyr Ala Gln Lys Tyr
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120
```

<210> SEQ ID NO 15
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v1.7 mAb VH

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
        35                  40                  45

Gly Trp Val Thr Gly Tyr Ser Gly Ala Thr Arg Tyr Ala Gln Lys Tyr
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120
```

<210> SEQ ID NO 16
<211> LENGTH: 8
<212> TYPE: PRT
<213> ORGANISM: Artificial Sequence
<220> FEATURE:
<223> OTHER INFORMATION: Synthetic sequence SARS-CoV-2 S300-v1.1 mAb
      CDRH2

<400> SEQUENCE: 16

```
Val Gln Gly Tyr Ser Gly Ala Thr
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic sequence SARS-CoV-2 S300-v1.2 mAb
      CDRH2

<400> SEQUENCE: 17

Val Asn Ala Tyr Ser Gly Ala Thr
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic sequence SARS-CoV-2 S300-v1.3 mAb
      CDRH2

<400> SEQUENCE: 18

Val Asn Ser Tyr Ser Gly Ala Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic sequence SARS-CoV-2 S300-v1.4 mAb
      CDRH2

<400> SEQUENCE: 19

Val Asn Pro Tyr Ser Gly Ala Thr
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic sequence SARS-CoV-2 S300-v1.5 mAb
      CDRH2

<400> SEQUENCE: 20

Val Asn Gln Tyr Ser Gly Ala Thr
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic sequence SARS-CoV-2 S300-v1.6 mAb
      CDRH2

<400> SEQUENCE: 21

Val Leu Gly Tyr Ser Gly Ala Thr
1               5

<210> SEQ ID NO 22
<211> LENGTH: 8
<212> TYPE: PRT
<213> ORGANISM: Artificial Sequence
<220> FEATURE:
```

<223> OTHER INFORMATION: Synthetic sequence SARS-CoV-2 S300-v1.7 mAb
     CDRH2

<400> SEQUENCE: 22

Val Thr Gly Tyr Ser Gly Ala Thr
1               5

<210> SEQ ID NO 23
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v1.8 mAb VH

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Leu
            35                  40                  45

Gly Trp Val Asn Gly Tyr Ser Gly Ala Thr Arg Tyr Ala Gln Lys Tyr
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Phe Ala Met Tyr Phe Phe Asp Asn
            100                 105                 110

Trp Gly Gln Gly Thr Leu Val Thr Val Ser Ser
        115                 120

<210> SEQ ID NO 24
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v1.9 mAb VH

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Leu
            35                  40                  45

Gly Trp Val Asn Gly Tyr Ser Gly Ala Thr Arg Tyr Ala Gln Lys Tyr
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Tyr Ala Met Tyr Phe Phe Asp Asn
            100                 105                 110

Trp Gly Gln Gly Thr Leu Val Thr Val Ser Ser
        115                 120

<210> SEQ ID NO 25
<211> LENGTH: 16

```
<212> TYPE: PRT
<213> ORGANISM: Artificial Sequence
<220> FEATURE:
<223> OTHER INFORMATION: Synthetic sequence SARS-CoV-2 S300-v1.8 mAb
      CDRH3

<400> SEQUENCE: 25

Ala Arg Asp Arg Pro Ser His Glu Phe Ala Met Tyr Phe Phe Asp Asn
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic sequence SARS-CoV-2 S300-v1.9 mAb
      CDRH3

<400> SEQUENCE: 26

Ala Arg Asp Arg Pro Ser His Glu Tyr Ala Met Tyr Phe Phe Asp Asn
1               5                   10                  15

<210> SEQ ID NO 27
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v2 mAb VH

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Leu
            35                  40                  45

Gly Phe Val Asn Gly Tyr Ser Gly Ala Thr Arg Tyr Ala Gln Lys Tyr
        50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120

<210> SEQ ID NO 28
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v2.1 mAb VH

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Leu
            35                  40                  45

Gly Phe Val Gln Gly Tyr Ser Gly Ala Thr Arg Tyr Ala Gln Lys Tyr
```

```
                    50                  55                  60
Gln Gly Arg Val Thr Met Thr Arg Asp Thr Ser Ile Ser Thr Ala Tyr
 65                  70                  75                  80

Met Gln Leu Ser Arg Leu Arg Pro Asp Thr Ala Val Tyr Tyr Cys
                 85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120

<210> SEQ ID NO 29
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v2.2 mAb VH

<400> SEQUENCE: 29

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
                 20                  25                  30

Tyr Ile His Trp Val Arg Gln Ala Pro Gly Gln Gly Pro Glu Trp Leu
             35                  40                  45

Gly Phe Val Asn Ala Tyr Ser Gly Ala Thr Arg Tyr Ala Gln Lys Tyr
         50                  55                  60

Gln Gly Arg Val Thr Met Thr Arg Asp Thr Ser Ile Ser Thr Ala Tyr
 65                  70                  75                  80

Met Gln Leu Ser Arg Leu Arg Pro Asp Thr Ala Val Tyr Tyr Cys
                 85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120

<210> SEQ ID NO 30
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v2.3 mAb VH

<400> SEQUENCE: 30

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
                 20                  25                  30

Tyr Ile His Trp Val Arg Gln Ala Pro Gly Gln Gly Pro Glu Trp Leu
             35                  40                  45

Gly Phe Val Asn Ser Tyr Ser Gly Ala Thr Arg Tyr Ala Gln Lys Tyr
         50                  55                  60

Gln Gly Arg Val Thr Met Thr Arg Asp Thr Ser Ile Ser Thr Ala Tyr
 65                  70                  75                  80

Met Gln Leu Ser Arg Leu Arg Pro Asp Thr Ala Val Tyr Tyr Cys
                 85                  90                  95

Ala Arg Asp Arg Pro Ser His Glu Trp Ala Met Tyr Phe Phe Asp Asn
            100                 105                 110
```

Trp Gly Gln Gly Thr Leu Val Thr Val Ser Ser
        115                 120

<210> SEQ ID NO 31
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v2.4 mAb VH

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
        35                  40                  45

Gly Phe Val Asn Pro Tyr Ser Gly Ala Thr Arg Tyr Ala Gln Lys Tyr
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120

<210> SEQ ID NO 32
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v2.5 mAb VH

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
        35                  40                  45

Gly Phe Val Asn Gln Tyr Ser Gly Ala Thr Arg Tyr Ala Gln Lys Tyr
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120

<210> SEQ ID NO 33
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v2.6 mAb VH

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
        35                  40                  45

Gly Phe Val Leu Gly Tyr Ser Gly Ala Thr Arg Tyr Ala Gln Lys Tyr
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120

<210> SEQ ID NO 34
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v2.7 mAb VH

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
        35                  40                  45

Gly Phe Val Thr Gly Tyr Ser Gly Ala Thr Arg Tyr Ala Gln Lys Tyr
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120

<210> SEQ ID NO 35
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v2.8 mAb VH

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
        35                  40                  45

Gly Phe Val Asn Gly Tyr Ser Gly Ala Thr Arg Tyr Ala Gln Lys Tyr
            50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Thr Ala Val Tyr Tyr Cys
                85                  90                  95

Ala Arg Asp Arg Pro Ser His Glu Phe Ala Met Tyr Phe Phe Asp Asn
                100                 105                 110

Trp Gly Gln Gly Thr Leu Val Thr Val Ser Ser
            115                 120

<210> SEQ ID NO 36
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v2.9 mAb VH

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Leu
            35                  40                  45

Gly Phe Val Asn Gly Tyr Ser Gly Ala Thr Arg Tyr Ala Gln Lys Tyr
        50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Thr Ala Val Tyr Tyr Cys
                85                  90                  95

Ala Arg Asp Arg Pro Ser His Glu Tyr Ala Met Tyr Phe Phe Asp Asn
                100                 105                 110

Trp Gly Gln Gly Thr Leu Val Thr Val Ser Ser
            115                 120

<210> SEQ ID NO 37
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v3 mAb VH

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Leu
            35                  40                  45

Gly Tyr Val Asn Gly Tyr Ser Gly Ala Thr Arg Tyr Ala Gln Lys Tyr
        50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Thr Ala Val Tyr Tyr Cys
                85                  90                  95

Ala Arg Asp Arg Pro Ser His Glu Trp Ala Met Tyr Phe Phe Asp Asn
                100                 105                 110

Trp Gly Gln Gly Thr Leu Val Thr Val Ser Ser
        115                 120

<210> SEQ ID NO 38
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v3.1 mAb VH

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Leu
            35                  40                  45

Gly Tyr Val Gln Gly Tyr Ser Gly Ala Thr Arg Tyr Ala Gln Lys Tyr
        50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120

<210> SEQ ID NO 39
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v3.2 mAb VH

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Leu
            35                  40                  45

Gly Tyr Val Asn Ala Tyr Ser Gly Ala Thr Arg Tyr Ala Gln Lys Tyr
        50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120

<210> SEQ ID NO 40
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v3.3 mAb VH

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
        35                  40                  45

Gly Tyr Val Asn Ser Tyr Ser Gly Ala Thr Arg Tyr Ala Gln Lys Tyr
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
            115                 120

<210> SEQ ID NO 41
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v3.4 mAb VH

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
        35                  40                  45

Gly Tyr Val Asn Pro Tyr Ser Gly Ala Thr Arg Tyr Ala Gln Lys Tyr
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
            115                 120

<210> SEQ ID NO 42
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v3.5 mAb VH

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
        35                  40                  45

Gly Tyr Val Asn Gln Tyr Ser Gly Ala Thr Arg Tyr Ala Gln Lys Tyr
        50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120

<210> SEQ ID NO 43
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v3.6 mAb VH

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Leu
            35                  40                  45

Gly Tyr Val Leu Gly Tyr Ser Gly Ala Thr Arg Tyr Ala Gln Lys Tyr
        50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn
            100                 105                 110

Trp Gly Gln Gly Thr Leu Val Thr Val Ser Ser
        115                 120

<210> SEQ ID NO 44
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v3.7 mAb VH

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Leu
            35                  40                  45

Gly Tyr Val Thr Gly Tyr Ser Gly Ala Thr Arg Tyr Ala Gln Lys Tyr
        50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Asp Thr Ala Val Tyr Tyr Cys
                85                  90                  95

Ala Arg Asp Arg Pro Ser His Glu Trp Ala Met Tyr Phe Phe Asp Asn

```
                     100                 105                 110

Trp Gly Gln Gly Thr Leu Val Thr Val Ser Ser
        115                 120

<210> SEQ ID NO 45
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v3.8 mAb VH

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
        35                  40                  45

Gly Tyr Val Asn Gly Tyr Ser Gly Ala Thr Arg Tyr Ala Gln Lys Tyr
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Thr Ala Val Tyr Tyr Cys
                85                  90                  95

Ala Arg Asp Arg Pro Ser His Glu Phe Ala Met Tyr Phe Phe Asp Asn
            100                 105                 110

Trp Gly Gln Gly Thr Leu Val Thr Val Ser Ser
        115                 120

<210> SEQ ID NO 46
<211> LENGTH: 123
<212> TYPE: PRT
<213> ORGANISM: Artificial Sequence
<220> FEATURE:
<223> OTHER INFORMATION: Synthetic sequence SARS-CoV-2 S300-v3.9 mAb VH

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Leu
        35                  40                  45

Gly Tyr Val Asn Gly Tyr Ser Gly Ala Thr Arg Tyr Ala Gln Lys Tyr
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Pro Asp Thr Ala Val Tyr Tyr Cys
                85                  90                  95

Ala Arg Asp Arg Pro Ser His Glu Tyr Ala Met Tyr Phe Phe Asp Asn
            100                 105                 110

Trp Gly Gln Gly Thr Leu Val Thr Val Ser Ser
        115                 120

<210> SEQ ID NO 47
<211> LENGTH: 109
<212> TYPE: PRT
<213> ORGANISM: Artificial Sequence
<220> FEATURE:
```

<223> OTHER INFORMATION: Synthetic sequence SARS-CoV-2 S300-v10 mAb VL
(VK)

<400> SEQUENCE: 47

Gln Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Pro Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Gly Arg Ala Thr Gly Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Phe Ala Val Tyr Tyr Cys Gln Gln Tyr Gly Ser Ser Pro
                85                  90                  95

Pro Leu Thr Phe Gly Gly Gly Thr Lys Val Glu Ile Lys
            100                 105

<210> SEQ ID NO 48
<211> LENGTH: 109
<212> TYPE: PRT
<213> ORGANISM: Artificial Sequence
<220> FEATURE:
<223> OTHER INFORMATION: Synthetic sequence SARS-CoV-2 S300-v11 mAb VL
(VK)

<400> SEQUENCE: 48

Gln Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Pro Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Gly Arg Ala Thr Gly Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Phe Ala Val Tyr Tyr Cys Gln Gln Tyr Gly Ser Ser Pro
                85                  90                  95

Pro Leu Thr Phe Gly Gly Gly Thr Lys Val Glu Ile Lys
            100                 105

<210> SEQ ID NO 49
<211> LENGTH: 109
<212> TYPE: PRT
<213> ORGANISM: Artificial Sequence
<220> FEATURE:
<223> OTHER INFORMATION: Synthetic sequence SARS-CoV-2 S300-v12 mAb VL
(VK)

<400> SEQUENCE: 49

Gln Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Pro Ser Ser
            20                  25                  30

Thr Leu Ala Trp Tyr Gln Gln Lys Pro Gly Gln Ala Pro Arg Leu Leu
        35                  40                  45

Ile Tyr Gly Ala Ser Gly Arg Ala Thr Gly Ile Pro Asp Arg Phe Ser

```
                    50                  55                  60

Gly Ser Gly Ser Gly Thr Asp Phe Thr Leu Thr Ile Arg Arg Leu Glu
 65                  70                  75                  80

Pro Glu Asp Phe Ala Val Tyr Tyr Cys Gln Gln Tyr Gly Ser Ser Pro
                     85                  90                  95

Pro Leu Thr Phe Gly Gly Gly Thr Lys Val Glu Ile Lys
                100                 105

<210> SEQ ID NO 50
<211> LENGTH: 109
<212> TYPE: PRT
<213> ORGANISM: Artificial Sequence
<220> FEATURE:
<223> OTHER INFORMATION: Synthetic sequence SARS-CoV-2 S300-v13 mAb VL
      (VK)

<400> SEQUENCE: 50

Gln Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Pro Ser Ser
                 20                  25                  30

Ala Leu Ala Trp Tyr Gln Gln Lys Pro Gly Gln Ala Pro Arg Leu Leu
             35                  40                  45

Ile Tyr Gly Ala Ser Gly Arg Ala Thr Gly Ile Pro Asp Arg Phe Ser
 50                  55                  60

Gly Ser Gly Ser Gly Thr Asp Phe Thr Leu Thr Ile Arg Arg Leu Glu
 65                  70                  75                  80

Pro Glu Asp Phe Ala Val Tyr Tyr Cys Gln Gln Tyr Gly Ser Ser Pro
                     85                  90                  95

Pro Leu Thr Phe Gly Gly Gly Thr Lys Val Glu Ile Lys
                100                 105

<210> SEQ ID NO 51
<211> LENGTH: 7
<212> TYPE: PRT
<213> ORGANISM: Artificial Sequence
<220> FEATURE:
<223> OTHER INFORMATION: Synthetic sequence SARS-CoV-2 S300-v10 mAb
      CDRL1

<400> SEQUENCE: 51

Gln Ser Val Pro Ser Ser Tyr
  1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic sequence SARS-CoV-2 S300-v11 mAb
      CDRL1

<400> SEQUENCE: 52

Gln Ser Val Pro Ser Ser Ser
  1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic sequence SARS-CoV-2 S300-v12 mAb
      CDRL1
```

<400> SEQUENCE: 53

Gln Ser Val Pro Ser Ser Thr
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic sequence SARS-CoV-2 S300-v13 mAb
      CDRL1

<400> SEQUENCE: 54

Gln Ser Val Pro Ser Ser Ala
1               5

<210> SEQ ID NO 55
<211> LENGTH: 121
<212> TYPE: PRT
<213> ORGANISM: Artificial Sequence
<220> FEATURE:
<223> OTHER INFORMATION: Synthetic sequence SARS-CoV-2 S302 mAb VH

<400> SEQUENCE: 55

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Ser Ser Gly Trp Asp Arg Val Phe Asp Tyr Trp Gly
            100                 105                 110

Gln Gly Thr Leu Val Thr Val Ser Ser
        115                 120

<210> SEQ ID NO 56
<211> LENGTH: 8
<212> TYPE: PRT
<213> ORGANISM: Artificial Sequence
<220> FEATURE:
<223> OTHER INFORMATION: Synthetic sequence SARS-CoV-2 S302 mAb CDRH1

<400> SEQUENCE: 56

Gly Phe Thr Phe Ser Ser Tyr Gly
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic sequence SARS-CoV-2 S302 mAb CDRH2

<400> SEQUENCE: 57

Ile Ser Tyr Asp Gly Ser Asn Lys
1               5

<210> SEQ ID NO 58
<211> LENGTH: 14
<212> TYPE: PRT
<213> ORGANISM: Artificial Sequence
<220> FEATURE:
<223> OTHER INFORMATION: Synthetic sequence SARS-CoV-2 S302 mAb CDRH3

<400> SEQUENCE: 58

Ala Lys Asp Ile Ser Ser Gly Trp Asp Arg Val Phe Asp Tyr
1               5                   10

<210> SEQ ID NO 59
<211> LENGTH: 108
<212> TYPE: PRT
<213> ORGANISM: Artificial Sequence
<220> FEATURE:
<223> OTHER INFORMATION: Synthetic sequence SARS-CoV-2 S302 mAb VL (VK)

<400> SEQUENCE: 59

Glu Ile Leu Leu Thr Gln Ser Pro Gly Thr Leu Ser Leu Ser Pro Gly
1               5                   10                  15

Glu Arg Ala Thr Leu Ser Cys Arg Thr Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Ala Ala Ser Ser Arg Ala Ile Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 60
<211> LENGTH: 7
<212> TYPE: PRT
<213> ORGANISM: Artificial Sequence
<220> FEATURE:
<223> OTHER INFORMATION: Synthetic sequence SARS-CoV-2 S302 mAb CDRL1

<400> SEQUENCE: 60

Gln Ser Val Gly Ser Ser Tyr
1               5

<210> SEQ ID NO 61
<211> LENGTH: 3
<212> TYPE: PRT
<213> ORGANISM: Artificial Sequence
<220> FEATURE:
<223> OTHER INFORMATION: Synthetic sequence SARS-CoV-2 S302 mAb CDRL2

<400> SEQUENCE: 61

Ala Ala Ser
1

<210> SEQ ID NO 62
<211> LENGTH: 9
<212> TYPE: PRT
<213> ORGANISM: Artificial Sequence
<220> FEATURE:
<223> OTHER INFORMATION: Synthetic sequence SARS-CoV-2 S302 mAb CDRL3

<400> SEQUENCE: 62

Gln Gln Tyr Gly Ser Ser Pro Trp Thr
1               5

<210> SEQ ID NO 63
<211> LENGTH: 124
<212> TYPE: PRT
<213> ORGANISM: Artificial Sequence
<220> FEATURE:
<223> OTHER INFORMATION: Synthetic sequence SARS-CoV-2 S303-v1 mAb VH

<400> SEQUENCE: 63

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Leu Thr Tyr
            20                  25                  30

Ser Met Asn Trp Val Arg Gln Thr Pro Gly Lys Arg Leu Gln Trp Val
        35                  40                  45

Ser Ala Ile Ser Gly Ser Gly Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Val Thr Ala Asp Thr Ala Ile Tyr Phe Cys
                85                  90                  95

Ala Arg Glu Arg Asp Asp Ile Phe Pro Met Gly Leu Asn Ala Phe Asp
            100                 105                 110

Ile Trp Gly Gln Gly Ala Met Val Ile Val Ser Ser
        115                 120

<210> SEQ ID NO 64
<211> LENGTH: 8
<212> TYPE: PRT
<213> ORGANISM: Artificial Sequence
<220> FEATURE:
<223> OTHER INFORMATION: Synthetic sequence SARS-CoV-2 S303-v1 mAb CDRH1

<400> SEQUENCE: 64

Gly Phe Thr Phe Leu Thr Tyr Ser
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic sequence SARS-CoV-2 S303-v1 mAb CDRH2

<400> SEQUENCE: 65

Ile Ser Gly Ser Gly Gly Ala Thr
1               5

<210> SEQ ID NO 66
<211> LENGTH: 17
<212> TYPE: PRT
<213> ORGANISM: Artificial Sequence
<220> FEATURE:
<223> OTHER INFORMATION: Synthetic sequence SARS-CoV-2 S303-v1 mAb CDRH3

<400> SEQUENCE: 66

Ala Arg Glu Arg Asp Asp Ile Phe Pro Met Gly Leu Asn Ala Phe Asp
1               5                   10                  15

Ile

<210> SEQ ID NO 67
<211> LENGTH: 107
<212> TYPE: PRT
<213> ORGANISM: Artificial Sequence
<220> FEATURE:
<223> OTHER INFORMATION: Synthetic sequence SARS-CoV-2 S303-v1 mAb VL
(VK)

<400> SEQUENCE: 67

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Ser Ala Thr Tyr Tyr Cys Gln Gln Tyr Asp Thr Tyr Ser Trp
                85                  90                  95

Thr Phe Gly Gln Gly Thr Lys Val Glu Ile Lys
            100                 105

<210> SEQ ID NO 68
<211> LENGTH: 6
<212> TYPE: PRT
<213> ORGANISM: Artificial Sequence
<220> FEATURE:
<223> OTHER INFORMATION: Synthetic sequence SARS-CoV-2 S303-v1 mAb CDRL1

<400> SEQUENCE: 68

Gln Ser Ile Ser Asn Trp
1               5

<210> SEQ ID NO 69
<211> LENGTH: 3
<212> TYPE: PRT
<213> ORGANISM: Artificial Sequence
<220> FEATURE:
<223> OTHER INFORMATION: Synthetic sequence SARS-CoV-2 S303-v1 mAb CDRL2

<400> SEQUENCE: 69

Lys Ala Ser
1

<210> SEQ ID NO 70
<211> LENGTH: 9
<212> TYPE: PRT
<213> ORGANISM: Artificial Sequence
<220> FEATURE:
<223> OTHER INFORMATION: Synthetic sequence SARS-CoV-2 S303-v1 mAb CDRL3

<400> SEQUENCE: 70

Gln Gln Tyr Asp Thr Tyr Ser Trp Thr
1               5

<210> SEQ ID NO 71
<211> LENGTH: 107
<212> TYPE: PRT
<213> ORGANISM: Artificial Sequence
<220> FEATURE:
<223> OTHER INFORMATION: Synthetic sequence SARS-CoV-2 S303-v2 mAb VL (VK)

<400> SEQUENCE: 71

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Phe
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Ser Ala Thr Tyr Tyr Cys Gln Gln Tyr Asp Thr Tyr Ser Trp
                85                  90                  95

Thr Phe Gly Gln Gly Thr Lys Val Glu Ile Lys
            100                 105

<210> SEQ ID NO 72
<211> LENGTH: 107
<212> TYPE: PRT
<213> ORGANISM: Artificial Sequence
<220> FEATURE:
<223> OTHER INFORMATION: Synthetic sequence SARS-CoV-2 S303-v3 mAb VL
      (VK)

<400> SEQUENCE: 72

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Ser Ala Thr Tyr Tyr Cys Gln Gln Tyr Asp Thr Tyr Ser Trp
                85                  90                  95

Thr Phe Gly Gln Gly Thr Lys Val Glu Ile Lys
            100                 105

<210> SEQ ID NO 73
<211> LENGTH: 6
<212> TYPE: PRT
<213> ORGANISM: Artificial Sequence
<220> FEATURE:
<223> OTHER INFORMATION: Synthetic sequence SARS-CoV-2 S303-v2 mAb CDRL1

<400> SEQUENCE: 73

Gln Ser Ile Ser Asn Phe
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic sequence SARS-CoV-2 S303-v3 mAb CDRL1

<400> SEQUENCE: 74

```
Gln Ser Ile Ser Asn Tyr
1               5
```

```
<210> SEQ ID NO 75
<211> LENGTH: 107
<212> TYPE: PRT
<213> ORGANISM: Artificial Sequence
<220> FEATURE:
<223> OTHER INFORMATION: Synthetic sequence SARS-CoV-2 S303-v4 mAb VL
      (VK)

<400> SEQUENCE: 75
```

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Ser Ala Thr Tyr Tyr Cys Gln Gln Tyr Asp Thr Tyr Ser Phe
                85                  90                  95

Thr Phe Gly Gln Gly Thr Lys Val Glu Ile Lys
            100                 105
```

```
<210> SEQ ID NO 76
<211> LENGTH: 107
<212> TYPE: PRT
<213> ORGANISM: Artificial Sequence
<220> FEATURE:
<223> OTHER INFORMATION: Synthetic sequence SARS-CoV-2 S303-v5 mAb VL
      (VK)

<400> SEQUENCE: 76
```

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Ser Ala Thr Tyr Tyr Cys Gln Gln Tyr Asp Thr Tyr Ser Tyr
                85                  90                  95

Thr Phe Gly Gln Gly Thr Lys Val Glu Ile Lys
            100                 105
```

```
<210> SEQ ID NO 77
<211> LENGTH: 9
<212> TYPE: PRT
<213> ORGANISM: Artificial Sequence
<220> FEATURE:
<223> OTHER INFORMATION: Synthetic sequence SARS-CoV-2 S303-v4 mAb CDRL3

<400> SEQUENCE: 77

Gln Gln Tyr Asp Thr Tyr Ser Phe Thr
```

<210> SEQ ID NO 78
<211> LENGTH: 9
<212> TYPE: PRT
<213> ORGANISM: Artificial Sequence
<220> FEATURE:
<223> OTHER INFORMATION: Synthetic sequence SARS-CoV-2 S303-v5 mAb CDRL3

<400> SEQUENCE: 78

Gln Gln Tyr Asp Thr Tyr Ser Tyr Thr
1               5

<210> SEQ ID NO 79
<211> LENGTH: 120
<212> TYPE: PRT
<213> ORGANISM: Artificial Sequence
<220> FEATURE:
<223> OTHER INFORMATION: Synthetic sequence SARS-CoV-2 S304 mAb VH

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Thr Thr Gly Lys Gly Leu Glu Trp Val
        35                  40                  45

Ser Thr Ile Gly Thr Ala Gly Asp Thr Tyr Tyr Pro Asp Ser Val Lys
    50                  55                  60

Gly Arg Phe Thr Ile Ser Arg Glu Asp Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Asp Ser Ser Gly Tyr Tyr Tyr Phe Asp Tyr Trp Gly Gln
            100                 105                 110

Gly Thr Leu Leu Thr Val Ser Ser
        115                 120

<210> SEQ ID NO 80
<211> LENGTH: 8
<212> TYPE: PRT
<213> ORGANISM: Artificial Sequence
<220> FEATURE:
<223> OTHER INFORMATION: Synthetic sequence SARS-CoV-2 S304 mAb CDRH1

<400> SEQUENCE: 80

Gly Phe Thr Phe Ser Ser Tyr Asp
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic sequence SARS-CoV-2 S304 mAb CDRH2

<400> SEQUENCE: 81

Ile Gly Thr Ala Gly Asp Thr
1               5

<210> SEQ ID NO 82
<211> LENGTH: 14
<212> TYPE: PRT

```
<213> ORGANISM: Artificial Sequence
<220> FEATURE:
<223> OTHER INFORMATION: Synthetic sequence SARS-CoV-2 S304 mAb CDRH3

<400> SEQUENCE: 82

Ala Arg Gly Asp Ser Ser Gly Tyr Tyr Tyr Phe Asp Tyr
1               5                   10

<210> SEQ ID NO 83
<211> LENGTH: 108
<212> TYPE: PRT
<213> ORGANISM: Artificial Sequence
<220> FEATURE:
<223> OTHER INFORMATION: Synthetic sequence SARS-CoV-2 S304 mAb VL (VK)

<400> SEQUENCE: 83

Asp Ile Gln Met Thr Gln Ser Pro Ser Ser Leu Ser Ala Ala Val Gly
1               5                   10                  15

Asp Arg Val Thr Ile Thr Cys Arg Ala Ser Gln Ser Ile Gly Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Ser Tyr Val Ser Pro Thr
                85                  90                  95

Tyr Thr Phe Gly Pro Gly Thr Lys Val Asp Ile Lys
            100                 105

<210> SEQ ID NO 84
<211> LENGTH: 6
<212> TYPE: PRT
<213> ORGANISM: Artificial Sequence
<220> FEATURE:
<223> OTHER INFORMATION: Synthetic sequence SARS-CoV-2 S304 mAb CDRL1

<400> SEQUENCE: 84

Gln Ser Ile Gly Ser Tyr
1               5

<210> SEQ ID NO 85
<211> LENGTH: 3
<212> TYPE: PRT
<213> ORGANISM: Artificial Sequence
<220> FEATURE:
<223> OTHER INFORMATION: Synthetic sequence SARS-CoV-2 S304 mAb CDRL2

<400> SEQUENCE: 85

Ala Ala Ser
1

<210> SEQ ID NO 86
<211> LENGTH: 10
<212> TYPE: PRT
<213> ORGANISM: Artificial Sequence
<220> FEATURE:
<223> OTHER INFORMATION: Synthetic sequence SARS-CoV-2 S304 mAb CDRL3

<400> SEQUENCE: 86

Gln Gln Ser Tyr Val Ser Pro Thr Tyr Thr
1               5                   10
```

<210> SEQ ID NO 87
<211> LENGTH: 123
<212> TYPE: PRT
<213> ORGANISM: Artificial Sequence
<220> FEATURE:
<223> OTHER INFORMATION: Synthetic sequence SARS-CoV-2 S306 mAb VH

<400> SEQUENCE: 87

```
Gln Val Gln Leu Val Gln Ser Gly Ala Glu Val Lys Lys Pro Gly Ala
1               5                   10                  15

Ser Val Lys Val Ser Cys Lys Ala Ser Thr Tyr Thr Phe Thr Ser Phe
            20                  25                  30

Gly Ile Ser Trp Val Arg Gln Ala Pro Gly Gln Gly Leu Glu Trp Met
        35                  40                  45

Gly Trp Ile Thr Thr Tyr Ser Gly Asp Thr Asn Tyr Ala Gln Lys Phe
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Ser Asp Tyr Phe Asp Ser Ser Gly Tyr Tyr His Ser Phe Asp Tyr
            100                 105                 110

Trp Gly Gln Gly Thr Leu Val Thr Val Ser Ser
        115                 120
```

<210> SEQ ID NO 88
<211> LENGTH: 8
<212> TYPE: PRT
<213> ORGANISM: Artificial Sequence
<220> FEATURE:
<223> OTHER INFORMATION: Synthetic sequence SARS-CoV-2 S306 mAb CDRH1

<400> SEQUENCE: 88

```
Thr Tyr Thr Phe Thr Ser Phe Gly
1               5
```

<210> SEQ ID NO 89
<211> LENGTH: 8
<212> TYPE: PRT
<213> ORGANISM: Artificial Sequence
<220> FEATURE:
<223> OTHER INFORMATION: Synthetic sequence SARS-CoV-2 S306 mAb CDRH2

<400> SEQUENCE: 89

```
Ile Thr Thr Tyr Ser Gly Asp Thr
1               5
```

<210> SEQ ID NO 90
<211> LENGTH: 16
<212> TYPE: PRT
<213> ORGANISM: Artificial Sequence
<220> FEATURE:
<223> OTHER INFORMATION: Synthetic sequence SARS-CoV-2 S306 mAb CDRH3

<400> SEQUENCE: 90

```
Ala Ser Asp Tyr Phe Asp Ser Ser Gly Tyr Tyr His Ser Phe Asp Tyr
1               5                   10                  15
```

<210> SEQ ID NO 91
<211> LENGTH: 109
<212> TYPE: PRT
<213> ORGANISM: Artificial Sequence
<220> FEATURE:

<223> OTHER INFORMATION: Synthetic sequence SARS-CoV-2 S306 mAb VL (VK)

<400> SEQUENCE: 91

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Arg Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Gly Cys Ser Phe Gly Gln Gly Thr Lys Val Glu Ile Lys
            100                 105

<210> SEQ ID NO 92
<211> LENGTH: 6
<212> TYPE: PRT
<213> ORGANISM: Artificial Sequence
<220> FEATURE:
<223> OTHER INFORMATION: Synthetic sequence SARS-CoV-2 S306 mAb CDRL1

<400> SEQUENCE: 92

Gln Ser Val Ser Ser Tyr
1               5

<210> SEQ ID NO 93
<211> LENGTH: 3
<212> TYPE: PRT
<213> ORGANISM: Artificial Sequence
<220> FEATURE:
<223> OTHER INFORMATION: Synthetic sequence SARS-CoV-2 S306 mAb CDRL2

<400> SEQUENCE: 93

Asp Ala Ser
1

<210> SEQ ID NO 94
<211> LENGTH: 11
<212> TYPE: PRT
<213> ORGANISM: Artificial Sequence
<220> FEATURE:
<223> OTHER INFORMATION: Synthetic sequence SARS-CoV-2 S306 mAb CDRL3

<400> SEQUENCE: 94

Gln Gln Arg Ser Asn Trp Pro Pro Gly Cys Ser
1               5                   10

<210> SEQ ID NO 95
<211> LENGTH: 127
<212> TYPE: PRT
<213> ORGANISM: Artificial Sequence
<220> FEATURE:
<223> OTHER INFORMATION: Synthetic sequence SARS-CoV-2 S308-v1 mAb VH

<400> SEQUENCE: 95

Gln Val Gln Leu Val Glu Ser Gly Gly Gly Val Val Gln Pro Gly Arg
1               5                   10                  15

Ser Leu Arg Leu Ser Cys Ala Ala Ser Arg Phe Thr Phe Ser Ser Tyr
            20                  25                  30

```
Gly Met His Trp Val Arg Gln Ala Pro Gly Lys Gly Leu Glu Trp Val
            35                  40                  45

Ala Val Ile Trp His Asp Gly Asn Asn Lys His Tyr Gly Asp Ser Val
 50                  55                  60

Lys Gly Arg Val Thr Ile Ser Arg Asp Asn Ser Lys Asn Thr Leu Tyr
 65                  70                  75                  80

Leu Gln Met Thr Ser Leu Arg Ala Glu Asp Thr Ala Val Tyr Tyr Cys
                85                  90                  95

Ala Arg Ala Val Thr Thr Phe Lys Gly Ser Gly Arg Ala Arg Met Arg
                100                 105                 110

Gly Met Asp Val Trp Gly Gln Gly Thr Thr Val Thr Val Ser Ser
                115                 120                 125

<210> SEQ ID NO 96
<211> LENGTH: 8
<212> TYPE: PRT
<213> ORGANISM: Artificial Sequence
<220> FEATURE:
<223> OTHER INFORMATION: Synthetic sequence SARS-CoV-2 S308-v1 mAb CDRH1

<400> SEQUENCE: 96

Arg Phe Thr Phe Ser Ser Tyr Gly
 1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic sequence SARS-CoV-2 S308-v1 mAb CDRH2

<400> SEQUENCE: 97

Ile Trp His Asp Gly Asn Asn Lys
 1               5

<210> SEQ ID NO 98
<211> LENGTH: 20
<212> TYPE: PRT
<213> ORGANISM: Artificial Sequence
<220> FEATURE:
<223> OTHER INFORMATION: Synthetic sequence SARS-CoV-2 S308-v1 mAb CDRH3

<400> SEQUENCE: 98

Ala Arg Ala Val Thr Thr Phe Lys Gly Ser Gly Arg Ala Arg Met Arg
 1               5                   10                  15

Gly Met Asp Val
            20

<210> SEQ ID NO 99
<211> LENGTH: 107
<212> TYPE: PRT
<213> ORGANISM: Artificial Sequence
<220> FEATURE:
<223> OTHER INFORMATION: Synthetic sequence SARS-CoV-2 S308-v1 mAb VL
      (VK)

<400> SEQUENCE: 99

Asp Ile Gln Leu Thr Gln Ser Pro Ser Phe Leu Ser Ala Ser Val Gly
 1               5                   10                  15

Asp Arg Val Thr Ile Thr Cys Arg Ala Ser Gln Gly Ile Asn Thr Tyr
            20                  25                  30

Leu Ala Trp Tyr Gln Gln Lys Pro Gly Lys Ala Pro Lys Leu Leu Ile
```

```
                    35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Leu Asp Thr Tyr Pro Phe
                85                  90                  95

Thr Phe Gly Pro Gly Thr Lys Val Asp Ile Lys
            100                 105

<210> SEQ ID NO 100
<211> LENGTH: 6
<212> TYPE: PRT
<213> ORGANISM: Artificial Sequence
<220> FEATURE:
<223> OTHER INFORMATION: Synthetic sequence SARS-CoV-2 S308-v1 mAb CDRL1

<400> SEQUENCE: 100

Gln Gly Ile Asn Thr Tyr
1               5

<210> SEQ ID NO 101
<211> LENGTH: 3
<212> TYPE: PRT
<213> ORGANISM: Artificial Sequence
<220> FEATURE:
<223> OTHER INFORMATION: Synthetic sequence SARS-CoV-2 S308-v1 mAb CDRL2

<400> SEQUENCE: 101

Ala Ala Ser
1

<210> SEQ ID NO 102
<211> LENGTH: 9
<212> TYPE: PRT
<213> ORGANISM: Artificial Sequence
<220> FEATURE:
<223> OTHER INFORMATION: Synthetic sequence SARS-CoV-2 S308-v1 mAb CDRL3

<400> SEQUENCE: 102

Gln His Leu Asp Thr Tyr Pro Phe Thr
1               5

<210> SEQ ID NO 103
<211> LENGTH: 127
<212> TYPE: PRT
<213> ORGANISM: Artificial Sequence
<220> FEATURE:
<223> OTHER INFORMATION: Synthetic sequence SARS-CoV-2 S308-v2 mAb VH

<400> SEQUENCE: 103

Gln Val Gln Leu Val Glu Ser Gly Gly Gly Val Val Gln Pro Gly Arg
1               5                   10                  15

Ser Leu Arg Leu Ser Cys Ala Ala Ser Arg Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp His Asp Gly Asn Asn Lys His Tyr Gly Asp Ser Val
    50                  55                  60

Lys Gly Arg Val Thr Ile Ser Arg Asp Asn Ser Lys Asn Thr Leu Tyr
65                  70                  75                  80

Leu Gln Met Thr Ser Leu Arg Ala Glu Asp Thr Ala Val Tyr Tyr Cys
```

```
                    85                  90                  95
Ala Arg Ala Val Thr Thr Phe Lys Gly Ser Gly Arg Ala Arg Leu Arg
                100                 105                 110
Gly Met Asp Val Trp Gly Gln Gly Thr Thr Val Thr Val Ser Ser
        115                 120                 125

<210> SEQ ID NO 104
<211> LENGTH: 20
<212> TYPE: PRT
<213> ORGANISM: Artificial Sequence
<220> FEATURE:
<223> OTHER INFORMATION: Synthetic sequence SARS-CoV-2 S308-v2 mAb CDRH3

<400> SEQUENCE: 104

Ala Arg Ala Val Thr Thr Phe Lys Gly Ser Gly Arg Ala Arg Leu Arg
1               5                   10                  15

Gly Met Asp Val
            20

<210> SEQ ID NO 105
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v1 mAb VH

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Asn Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
                100                 105                 110

Gly Phe Asp Asn Trp Gly Gln Gly Thr Leu Val Thr Val Ser Ser
        115                 120                 125

<210> SEQ ID NO 106
<211> LENGTH: 8
<212> TYPE: PRT
<213> ORGANISM: Artificial Sequence
<220> FEATURE:
<223> OTHER INFORMATION: Synthetic sequence SARS-CoV-2 S309-v1 mAb CDRH1

<400> SEQUENCE: 106

Gly Tyr Pro Phe Thr Ser Tyr Gly
1               5

<210> SEQ ID NO 107
<211> LENGTH: 8
<212> TYPE: PRT
<213> ORGANISM: Artificial Sequence
<220> FEATURE:
<223> OTHER INFORMATION: Synthetic sequence SARS-CoV-2 S309-v1 mAb CDRH2
```

```
<400> SEQUENCE: 107

Ile Ser Thr Tyr Asn Gly Asn Thr
1               5

<210> SEQ ID NO 108
<211> LENGTH: 20
<212> TYPE: PRT
<213> ORGANISM: Artificial Sequence
<220> FEATURE:
<223> OTHER INFORMATION: Synthetic sequence SARS-CoV-2 S309-v1 mAb CDRH3

<400> SEQUENCE: 108

Ala Arg Asp Tyr Thr Arg Gly Ala Trp Phe Gly Glu Ser Leu Ile Gly
1               5                   10                  15

Gly Phe Asp Asn
            20

<210> SEQ ID NO 109
<211> LENGTH: 107
<212> TYPE: PRT
<213> ORGANISM: Artificial Sequence
<220> FEATURE:
<223> OTHER INFORMATION: Synthetic sequence SARS-CoV-2 S309-v1 mAb VL
      (VK)

<400> SEQUENCE: 109

Asp Ile Gln Met Thr Gln Ser Pro Ser Ser Leu Ser Thr Ser Val Gly
1               5                   10                  15

Asp Arg Val Thr Ile Thr Cys Arg Ala Ser Gln Gly Ile Asn Asn Tyr
            20                  25                  30

Val Ala Trp Tyr Gln Gln Lys Pro Gly Lys Val Pro Lys Leu Leu Ile
        35                  40                  45

Tyr Gly Ala Ser Thr Leu Gln Ser Gly Val Pro Ser Arg Phe Arg Gly
    50                  55                  60

Ser Gly Ser Gly Thr Gly Phe Thr Leu Thr Ile Ser Ser Leu Gln Pro
65                  70                  75                  80

Glu Asp Val Ala Ser Tyr Tyr Cys Arg Lys Tyr Asn Ser Ala Pro Trp
                85                  90                  95

Thr Phe Gly Gln Gly Thr Arg Val Glu Ile Lys
            100                 105

<210> SEQ ID NO 110
<211> LENGTH: 6
<212> TYPE: PRT
<213> ORGANISM: Artificial Sequence
<220> FEATURE:
<223> OTHER INFORMATION: Synthetic sequence SARS-CoV-2 S309-v1 mAb CDRL1

<400> SEQUENCE: 110

Gln Gly Ile Asn Asn Tyr
1               5

<210> SEQ ID NO 111
<211> LENGTH: 3
<212> TYPE: PRT
<213> ORGANISM: Artificial Sequence
<220> FEATURE:
<223> OTHER INFORMATION: Synthetic sequence SARS-CoV-2 S309-v1 mAb CDRL2

<400> SEQUENCE: 111

Gly Ala Ser
1
```

<210> SEQ ID NO 112
<211> LENGTH: 9
<212> TYPE: PRT
<213> ORGANISM: Artificial Sequence
<220> FEATURE:
<223> OTHER INFORMATION: Synthetic sequence SARS-CoV-2 S309-v1 mAb CDRL3

<400> SEQUENCE: 112

Arg Lys Tyr Asn Ser Ala Pro Trp Thr
1               5

<210> SEQ ID NO 113
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v1.1 mAb VH

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Gln Gly Asn Thr Asn Tyr Ala Gln Lys Phe
        50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 114
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v1.2 mAb VH

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Asn Ser Asn Thr Asn Tyr Ala Gln Lys Phe
        50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser

<210> SEQ ID NO 115
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v1.3 mAb VH

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Asn Ala Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 116
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v1.4 mAb VH

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Asn Gln Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 117
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v1.5 mAb VH

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Leu Gly Asn Thr Asn Tyr Ala Gln Lys Phe
50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 118
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v1.6 mAb VH

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Thr Gly Asn Thr Asn Tyr Ala Gln Lys Phe
50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 119
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v1.7 mAb VH

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Asn Gly Asn Thr Asn Tyr Ala Gln Lys Phe

```
                    50                  55                  60

Gln Gly Arg Val Thr Met Thr Thr Asp Thr Ser Thr Thr Thr Gly Tyr
 65                  70                  75                  80

Met Glu Leu Arg Arg Leu Arg Ser Asp Asp Thr Ala Val Tyr Tyr Cys
                     85                  90                  95

Ala Arg Asp Tyr Thr Arg Gly Ala Phe Phe Gly Glu Ser Leu Ile Gly
                100                 105                 110

Gly Phe Asp Asn Trp Gly Gln Gly Thr Leu Val Thr Val Ser Ser
            115                 120                 125

<210> SEQ ID NO 120
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v1.8 mAb VH

<400> SEQUENCE: 120

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Pro Phe Thr Ser Tyr
                20                  25                  30

Gly Ile Ser Trp Val Arg Gln Ala Pro Gly Gln Gly Leu Glu Trp Met
             35                  40                  45

Gly Trp Ile Ser Thr Tyr Asn Gly Asn Thr Asn Tyr Ala Gln Lys Phe
         50                  55                  60

Gln Gly Arg Val Thr Met Thr Thr Asp Thr Ser Thr Thr Thr Gly Tyr
 65                  70                  75                  80

Met Glu Leu Arg Arg Leu Arg Ser Asp Asp Thr Ala Val Tyr Tyr Cys
                     85                  90                  95

Ala Arg Asp Tyr Thr Arg Gly Ala Tyr Phe Gly Glu Ser Leu Ile Gly
                100                 105                 110

Gly Phe Asp Asn Trp Gly Gln Gly Thr Leu Val Thr Val Ser Ser
            115                 120                 125

<210> SEQ ID NO 121
<211> LENGTH: 8
<212> TYPE: PRT
<213> ORGANISM: Artificial Sequence
<220> FEATURE:
<223> OTHER INFORMATION: Synthetic sequence SARS-CoV-2 S309-v1.1 mAb
      CDRH2

<400> SEQUENCE: 121

Ile Ser Thr Tyr Gln Gly Asn Thr
 1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic sequence SARS-CoV-2 S309-v1.2 mAb
      CDRH2

<400> SEQUENCE: 122

Ile Ser Thr Tyr Asn Ser Asn Thr
 1               5

<210> SEQ ID NO 123
<211> LENGTH: 8
```

```
<212> TYPE: PRT
<213> ORGANISM: Artificial Sequence
<220> FEATURE:
<223> OTHER INFORMATION: Synthetic sequence SARS-CoV-2 S309-v1.3 mAb
      CDRH2

<400> SEQUENCE: 123

Ile Ser Thr Tyr Asn Ala Asn Thr
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic sequence SARS-CoV-2 S309-v1.4 mAb
      CDRH2

<400> SEQUENCE: 124

Ile Ser Thr Tyr Asn Gln Asn Thr
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic sequence SARS-CoV-2 S309-v1.5 mAb
      CDRH2

<400> SEQUENCE: 125

Ile Ser Thr Tyr Leu Gly Asn Thr
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic sequence SARS-CoV-2 S309-v1.6 mAb
      CDRH2

<400> SEQUENCE: 126

Ile Ser Thr Tyr Thr Gly Asn Thr
1               5

<210> SEQ ID NO 127
<211> LENGTH: 20
<212> TYPE: PRT
<213> ORGANISM: Artificial Sequence
<220> FEATURE:
<223> OTHER INFORMATION: Synthetic sequence SARS-CoV-2 S309-v1.7 mAb
      CDRH3

<400> SEQUENCE: 127

Ala Arg Asp Tyr Thr Arg Gly Ala Phe Phe Gly Glu Ser Leu Ile Gly
1               5                   10                  15

Gly Phe Asp Asn
            20

<210> SEQ ID NO 128
<211> LENGTH: 20
<212> TYPE: PRT
<213> ORGANISM: Artificial Sequence
<220> FEATURE:
<223> OTHER INFORMATION: Synthetic sequence SARS-CoV-2 S309-v1.8 mAb
      CDRH3
```

```
<400> SEQUENCE: 128

Ala Arg Asp Tyr Thr Arg Gly Ala Tyr Phe Gly Glu Ser Leu Ile Gly
1               5                   10                  15

Gly Phe Asp Asn
            20

<210> SEQ ID NO 129
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v2 mAb VH

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Phe Ile Ser Thr Tyr Asn Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 130
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v2.1 mAb VH

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Phe Ile Ser Thr Tyr Gln Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 131
<211> LENGTH: 127
```

```
<212> TYPE: PRT
<213> ORGANISM: Artificial Sequence
<220> FEATURE:
<223> OTHER INFORMATION: Synthetic sequence SARS-CoV-2 S309-v2.2 mAb VH

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Phe Ile Ser Thr Tyr Asn Ser Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 132
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v2.3 mAb VH

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser

```
                    20                  25                  30

Gly Ile Ser Trp Val Arg Gln Ala Pro Gly Gln Gly Leu Glu Trp Met
            35                  40                  45

Gly Phe Ile Ser Thr Tyr Asn Gln Asn Thr Asn Tyr Ala Gln Lys Phe
        50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 134
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v2.5 mAb VH

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
                20                  25                  30

Gly Ile Ser Trp Val Arg Gln Ala Pro Gly Gln Gly Leu Glu Trp Met
            35                  40                  45

Gly Phe Ile Ser Thr Tyr Leu Gly Asn Thr Asn Tyr Ala Gln Lys Phe
        50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 135
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v2.6 mAb VH

<400> SEQUENCE: 135

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
                20                  25                  30

Gly Ile Ser Trp Val Arg Gln Ala Pro Gly Gln Gly Leu Glu Trp Met
            35                  40                  45

Gly Phe Ile Ser Thr Tyr Thr Gly Asn Thr Asn Tyr Ala Gln Lys Phe
        50                  55                  60

Gln Gly Arg Val Thr Met Thr Thr Asp Thr Ser Thr Thr Thr Gly Tyr
65                  70                  75                  80
```

-continued

Met Glu Leu Arg Arg Leu Arg Ser Asp Asp Thr Ala Val Tyr Tyr Cys
            85                  90                  95

Ala Arg Asp Tyr Thr Arg Gly Ala Trp Phe Gly Glu Ser Leu Ile Gly
        100                 105                 110

Gly Phe Asp Asn Trp Gly Gln Gly Thr Leu Val Thr Val Ser Ser
        115                 120                 125

<210> SEQ ID NO 136
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v2.7 mAb VH

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Phe Ile Ser Thr Tyr Asn Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
            85                  90                  95

Ala Arg Asp Tyr Thr Arg Gly Ala Phe Phe Gly Glu Ser Leu Ile Gly
        100                 105                 110

Gly Phe Asp Asn Trp Gly Gln Gly Thr Leu Val Thr Val Ser Ser
        115                 120                 125

<210> SEQ ID NO 137
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v2.8 mAb VH

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Phe Ile Ser Thr Tyr Asn Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
            85                  90                  95

Ala Arg Asp Tyr Thr Arg Gly Ala Tyr Phe Gly Glu Ser Leu Ile Gly
        100                 105                 110

Gly Phe Asp Asn Trp Gly Gln Gly Thr Leu Val Thr Val Ser Ser
        115                 120                 125

<210> SEQ ID NO 138

```
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v3 mAb VH

<400> SEQUENCE: 138

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Tyr Ile Ser Thr Tyr Asn Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 139
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v3.1 mAb VH

<400> SEQUENCE: 139

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Tyr Ile Ser Thr Tyr Gln Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 140
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v3.2 mAb VH

<400> SEQUENCE: 140

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Tyr Ile Ser Thr Tyr Asn Ser Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 141
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v3.3 mAb VH

<400> SEQUENCE: 141

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Tyr Ile Ser Thr Tyr Asn Ala Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
        115                 120                 125

<210> SEQ ID NO 142
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v3.4 mAb VH

<400> SEQUENCE: 142

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Tyr Ile Ser Thr Tyr Asn Gln Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
            85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
            115                 120                 125

<210> SEQ ID NO 143
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v3.5 mAb VH

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Tyr Ile Ser Thr Tyr Leu Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
            85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
            115                 120                 125

<210> SEQ ID NO 144
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v3.6 mAb VH

<400> SEQUENCE: 144

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Tyr Ile Ser Thr Tyr Thr Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
            85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser
            115                 120                 125

<210> SEQ ID NO 145
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v3.7 mAb VH

<400> SEQUENCE: 145

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Tyr Ile Ser Thr Tyr Asn Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Phe Phe Gly Glu Ser Leu Ile Gly
            100                 105                 110

Gly Phe Asp Asn Trp Gly Gln Gly Thr Leu Val Thr Val Ser Ser
        115                 120                 125
```

<210> SEQ ID NO 146
<211> LENGTH: 127
<212> TYPE: PRT
<213> ORGANISM: Artificial Sequence
<220> FEATURE:
<223> OTHER INFORMATION: Synthetic sequence SARS-CoV-2 S309-v3.8 mAb VH

<400> SEQUENCE: 146

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Tyr Ile Ser Thr Tyr Asn Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Tyr Phe Gly Glu Ser Leu Ile Gly
            100                 105                 110

Gly Phe Asp Asn Trp Gly Gln Gly Thr Leu Val Thr Val Ser Ser
        115                 120                 125
```

<210> SEQ ID NO 147
<211> LENGTH: 107
<212> TYPE: PRT
<213> ORGANISM: Artificial Sequence
<220> FEATURE:
<223> OTHER INFORMATION: Synthetic sequence SARS-CoV-2 S309-v9 mAb VL
      (VK)

<400> SEQUENCE: 147

```
Asp Ile Gln Met Thr Gln Ser Pro Ser Ser Leu Ser Thr Ser Val Gly
```

```
                1               5                  10                  15
Asp Arg Val Thr Ile Thr Cys Arg Ala Ser Gln Gly Ile Asn Asn Tyr
                20                  25                  30

Val Ala Trp Tyr Gln Gln Lys Pro Gly Lys Val Pro Lys Leu Leu Ile
                35                  40                  45

Tyr Gly Ala Ser Thr Leu Gln Ser Gly Val Pro Ser Arg Phe Arg Gly
            50                  55                  60

Ser Gly Ser Gly Thr Gly Phe Thr Leu Thr Ile Ser Ser Leu Gln Pro
65                  70                  75                  80

Glu Asp Val Ala Ser Tyr Tyr Cys Arg Lys Tyr Asn Ser Ala Pro Gly
                85                  90                  95

Thr Phe Gly Gln Gly Thr Arg Val Glu Ile Lys
                100                 105

<210> SEQ ID NO 148
<211> LENGTH: 107
<212> TYPE: PRT
<213> ORGANISM: Artificial Sequence
<220> FEATURE:
<223> OTHER INFORMATION: Synthetic sequence SARS-CoV-2 S309-v10 mAb VL
      (VK)

<400> SEQUENCE: 148

Asp Ile Gln Met Thr Gln Ser Pro Ser Ser Leu Ser Thr Ser Val Gly
1               5                   10                  15

Asp Arg Val Thr Ile Thr Cys Arg Ala Ser Gln Gly Ile Asn Asn Tyr
                20                  25                  30

Val Ala Trp Tyr Gln Gln Lys Pro Gly Lys Val Pro Lys Leu Leu Ile
                35                  40                  45

Tyr Gly Ala Ser Thr Leu Gln Ser Gly Val Pro Ser Arg Phe Arg Gly
            50                  55                  60

Ser Gly Ser Gly Thr Gly Phe Thr Leu Thr Ile Ser Ser Leu Gln Pro
65                  70                  75                  80

Glu Asp Val Ala Ser Tyr Tyr Cys Arg Lys Tyr Asn Ser Ala Pro Arg
                85                  90                  95

Thr Phe Gly Gln Gly Thr Arg Val Glu Ile Lys
                100                 105

<210> SEQ ID NO 149
<211> LENGTH: 107
<212> TYPE: PRT
<213> ORGANISM: Artificial Sequence
<220> FEATURE:
<223> OTHER INFORMATION: Synthetic sequence SARS-CoV-2 S309-v11 mAb VL
      (VK)

<400> SEQUENCE: 149

Asp Ile Gln Met Thr Gln Ser Pro Ser Ser Leu Ser Thr Ser Val Gly
1               5                   10                  15

Asp Arg Val Thr Ile Thr Cys Arg Ala Ser Gln Gly Ile Asn Asn Tyr
                20                  25                  30

Val Ala Trp Tyr Gln Gln Lys Pro Gly Lys Val Pro Lys Leu Leu Ile
                35                  40                  45

Tyr Gly Ala Ser Thr Leu Gln Ser Gly Val Pro Ser Arg Phe Arg Gly
            50                  55                  60

Ser Gly Ser Gly Thr Gly Phe Thr Leu Thr Ile Ser Ser Leu Gln Pro
65                  70                  75                  80

Glu Asp Val Ala Ser Tyr Tyr Cys Arg Lys Tyr Asn Ser Ala Pro Phe
```

```
                85                  90                  95

Thr Phe Gly Gln Gly Thr Arg Val Glu Ile Lys
            100                 105

<210> SEQ ID NO 150
<211> LENGTH: 107
<212> TYPE: PRT
<213> ORGANISM: Artificial Sequence
<220> FEATURE:
<223> OTHER INFORMATION: Synthetic sequence SARS-CoV-2 S309-v12 mAb VL
      (VK)

<400> SEQUENCE: 150

Asp Ile Gln Met Thr Gln Ser Pro Ser Ser Leu Ser Thr Ser Val Gly
1               5                   10                  15

Asp Arg Val Thr Ile Thr Cys Arg Ala Ser Gln Gly Ile Asn Asn Tyr
            20                  25                  30

Val Ala Trp Tyr Gln Gln Lys Pro Gly Lys Val Pro Lys Leu Leu Ile
        35                  40                  45

Tyr Gly Ala Ser Thr Leu Gln Ser Gly Val Pro Ser Arg Phe Arg Gly
    50                  55                  60

Ser Gly Ser Gly Thr Gly Phe Thr Leu Thr Ile Ser Ser Leu Gln Pro
65                  70                  75                  80

Glu Asp Val Ala Ser Tyr Tyr Cys Arg Lys Tyr Asn Ser Ala Pro Tyr
                85                  90                  95

Thr Phe Gly Gln Gly Thr Arg Val Glu Ile Lys
            100                 105

<210> SEQ ID NO 151
<211> LENGTH: 9
<212> TYPE: PRT
<213> ORGANISM: Artificial Sequence
<220> FEATURE:
<223> OTHER INFORMATION: Synthetic sequence SARS-CoV-2 S309-v9 mAb CDRL3

<400> SEQUENCE: 151

Arg Lys Tyr Asn Ser Ala Pro Gly Thr
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic sequence SARS-CoV-2 S309-v10 mAb
      CDRL3

<400> SEQUENCE: 152

Arg Lys Tyr Asn Ser Ala Pro Arg Thr
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic sequence SARS-CoV-2 S309-v11 mAb
      CDRL3

<400> SEQUENCE: 153

Arg Lys Tyr Asn Ser Ala Pro Phe Thr
1               5
```

```
<210> SEQ ID NO 154
<211> LENGTH: 9
<212> TYPE: PRT
<213> ORGANISM: Artificial Sequence
<220> FEATURE:
<223> OTHER INFORMATION: Synthetic sequence SARS-CoV-2 S309-v12 mAb
      CDRL3

<400> SEQUENCE: 154

Arg Lys Tyr Asn Ser Ala Pro Tyr Thr
1               5

<210> SEQ ID NO 155
<211> LENGTH: 126
<212> TYPE: PRT
<213> ORGANISM: Artificial Sequence
<220> FEATURE:
<223> OTHER INFORMATION: Synthetic sequence SARS-CoV-2 S310 mAb VH

<400> SEQUENCE: 155

Gln Val Gln Leu Val Gln Ser Gly Ala Glu Leu Lys Lys Pro Gly Ser
1               5                   10                  15

Ser Val Lys Val Ser Cys Lys Ala Ser Gly Gly Thr Phe Asn Ser Tyr
            20                  25                  30

Ser Phe Asn Trp Val Arg Gln Ala Pro Gly Gln Gly Leu Glu Trp Leu
        35                  40                  45

Gly Gly Ile Ile Pro Val Leu Gly Thr Ser Asn Tyr Ala Gln Lys Phe
    50                  55                  60

Gln Gly Arg Val Ala Val Thr Ala Asp Glu Phe Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Thr Arg Thr Tyr Asp Ser Ser Gly Tyr Arg Pro Tyr Tyr Tyr Gly
            100                 105                 110

Leu Asp Val Trp Gly Gln Gly Thr Pro Val Thr Val Ser Ser
        115                 120                 125

<210> SEQ ID NO 156
<211> LENGTH: 8
<212> TYPE: PRT
<213> ORGANISM: Artificial Sequence
<220> FEATURE:
<223> OTHER INFORMATION: Synthetic sequence SARS-CoV-2 S310 mAb CDRH1

<400> SEQUENCE: 156

Gly Gly Thr Phe Asn Ser Tyr Ser
1               5

<210> SEQ ID NO 157
<211> LENGTH: 8
<212> TYPE: PRT
<213> ORGANISM: Artificial Sequence
<220> FEATURE:
<223> OTHER INFORMATION: Synthetic sequence SARS-CoV-2 S310 mAb CDRH2

<400> SEQUENCE: 157

Ile Ile Pro Val Leu Gly Thr Ser
1               5

<210> SEQ ID NO 158
<211> LENGTH: 19
<212> TYPE: PRT
<213> ORGANISM: Artificial Sequence
<220> FEATURE:
```

<223> OTHER INFORMATION: Synthetic sequence SARS-CoV-2 S310 mAb CDRH3

<400> SEQUENCE: 158

```
Ala Thr Arg Thr Tyr Asp Ser Ser Gly Tyr Arg Pro Tyr Tyr Tyr Gly
1               5                   10                  15

Leu Asp Val
```

<210> SEQ ID NO 159
<211> LENGTH: 110
<212> TYPE: PRT
<213> ORGANISM: Artificial Sequence
<220> FEATURE:
<223> OTHER INFORMATION: Synthetic sequence SARS-CoV-2 S310 mAb VL (VK)

<400> SEQUENCE: 159

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Leu Val Ser Trp Tyr Gln Gln Arg Pro Gly Lys Ala Pro Glu Leu
            35                  40                  45

Met Ile Tyr Glu Val Thr Lys Arg Pro Ser Gly Leu Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Asp Thr Val Ile Phe Gly Gly Gly Thr Lys Val Thr Val Leu
            100                 105                 110
```

<210> SEQ ID NO 160
<211> LENGTH: 9
<212> TYPE: PRT
<213> ORGANISM: Artificial Sequence
<220> FEATURE:
<223> OTHER INFORMATION: Synthetic sequence SARS-CoV-2 S310 mAb CDRL1

<400> SEQUENCE: 160

```
Ser Ser Asp Val Gly Ser Tyr Asn Leu
1               5
```

<210> SEQ ID NO 161
<211> LENGTH: 3
<212> TYPE: PRT
<213> ORGANISM: Artificial Sequence
<220> FEATURE:
<223> OTHER INFORMATION: Synthetic sequence SARS-CoV-2 S310 mAb CDRL2

<400> SEQUENCE: 161

```
Glu Val Thr
1
```

<210> SEQ ID NO 162
<211> LENGTH: 10
<212> TYPE: PRT
<213> ORGANISM: Artificial Sequence
<220> FEATURE:
<223> OTHER INFORMATION: Synthetic sequence SARS-CoV-2 S310 mAb CDRL3

<400> SEQUENCE: 162

```
Cys Ser Tyr Ala Gly Ser Asp Thr Val Ile
1               5                   10
```

<210> SEQ ID NO 163
<211> LENGTH: 29902
<212> TYPE: DNA
<213> ORGANISM: betacoronavirus SARS coronavirus 2

<400> SEQUENCE: 163

```
attaaaggtt tataccttcc caggtaacaa accaaccaac tttcgatctc ttgtagatct    60
gttctctaaa cgaactttaa atctgtgtg gctgtcactc ggctgcatgc ttagtgcact    120
cacgcagtat aattaataac taattactgt cgttgacagg acacgagtaa ctcgtctatc    180
ttctgcaggc tgcttacggt ttcgtccgtg ttgcagccga tcatcagcac atctaggttt    240
cgtccgggtg tgaccgaaag gtaagatgga gagccttgtc cctggtttca acgagaaaac    300
acacgtccaa ctcagtttgc ctgttttaca ggttcgcgac gtgctcgtac gtggctttgg    360
agactccgtg gaggaggtct tatcagaggc cgtcaacatc ttaaagatgg cacttgtggc    420
ttagtagaag ttgaaaaagg cgttttgcct caacttgaac agccctatgt gttcatcaaa    480
cgttcggatg ctcgaactgc acctcatggt catgttatgg ttgagctggt agcagaactc    540
gaaggcattc agtacggtcg tagtggtgag acacttggtg tccttgtccc tcatgtgggc    600
gaaataccag tggcttaccg caaggttctt cttcgtaaga acggtaataa aggagctggt    660
ggccatagtt acggcgccga tctaaagtca tttgacttag gcgacgagct tggcactgat    720
ccttatgaag attttcaaga aaactggaac actaaacata gcagtggtgt tacccgtgaa    780
ctcatgcgtg agcttaacgg aggggcatac actcgctatg tcgataacaa cttctgtggc    840
cctgatggct accctcttga gtgcattaaa gaccttctag cacgtgctgg taaagcttca    900
tgcactttgt ccgaacaact ggactttatt gacactaaga ggggtgtata ctgctgccgt    960
gaacatgagc atgaaattgc ttggtacacg gaacgttctg aaaagagcta tgaattgcag    1020
acacctttg aaattaaatt ggcaaagaaa tttgacacct tcaatgggga atgtccaaat    1080
tttgtatttc ccttaaattc cataatcaag actattcaac caagggttga aaagaaaaag    1140
cttgatggct ttatgggtag aattcgatct gtctatccag ttgcgtcacc aaatgaatgc    1200
aaccaaatgt gcctttcaac tctcatgaag tgtgatcatt gtggtgaaac ttcatggcag    1260
acgggcgatt ttgttaaagc cacttgcgaa ttttgtggca ctgagaattt gactaaagaa    1320
ggtgccacta cttgtggtta cttaccccaa aatgctgttg ttaaaattta ttgtccagca    1380
tgtcacaatt cagaagtagg acctgagcat agtcttgccg aataccataa tgaatctggc    1440
ttgaaaacca ttcttcgtaa gggtggtcgc actattgcct ttggaggctg tgtgttctct    1500
tatgttggtt gccataacaa gtgtgcctat tgggttccac gtgctagcgc taacataggt    1560
tgtaaccata caggtgttgt tggagaaggt tccgaaggtc ttaatgacaa ccttcttgaa    1620
atactccaaa agagaaagt caacatcaat attgttggtg actttaaact taatgaagag    1680
atcgccatta ttttggcatc ttttttctgct ccacaagtg cttttgtgga aactgtgaaa    1740
ggtttggatt ataagcatt caaacaaatt gttgaatcct gtggtaattt taaagttaca    1800
aaaggaaaag ctaaaaagg tgcctggaat attggtgaac agaaatcaat actgagtcct    1860
ctttatgcat ttgcatcaga ggctgctcgt gttgtacgat caattttctc ccgcactctt    1920
gaaactgctc aaaattctgt gcgtgtttta cagaaggccg ctataacaat actagatgga    1980
atttcacagt attcactgag actcattgat gctatgatgt tcacatctga tttggctact    2040
aacaatctag ttgtaatggc ctacattaca ggtggtgttg ttcagttgac ttcgcagtgg    2100
ctaactaaca tctttggcac tgtttatgaa aaactcaaac ccgtccttga ttggcttgaa    2160
```

```
gagaagttta aggaaggtgt agagtttctt agagacggtt gggaaattgt taaatttatc   2220
tcaacctgtg cttgtgaaat tgtcggtgga caaattgtca cctgtgcaaa ggaaattaag   2280
gagagtgttc agacattctt taagcttgta aataaatttt tggctttgtg tgctgactct   2340
atcattattg gtggagctaa acttaaagcc ttgaatttag gtgaaacatt tgtcacgcac   2400
tcaaagggat tgtacagaaa gtgtgttaaa tccagagaag aaactggcct actcatgcct   2460
ctaaaagccc caaagaaat tatcttctta gagggagaaa cacttcccac agaagtgtta    2520
acagaggaag ttgtcttgaa aactggtgat ttacaaccat tagaacaacc tactagtgaa   2580
gctgttgaag ctccattggt tggtacacca gtttgtatta acgggcttat gttgctcgaa   2640
atcaaagaca cagaaaagta ctgtgccctt gcacctaata tgatggtaac aaacaatacc   2700
ttcacactca aggcggtgc accaacaaag gttacttttg gtgatgacac tgtgatagaa    2760
gtgcaaggtt acaagagtgt gaatatcact tttgaacttg atgaaaggat tgataaagta   2820
cttaatgaga agtgctctgc ctatacagtt gaactcggta cagaagtaaa tgagttcgcc   2880
tgtgttgtgg cagatgctgt cataaaaact ttgcaaccag tatctgaatt acttacacca   2940
ctgggcattg atttagatga gtggagtatg gctacatact acttatttga tgagtctggt   3000
gagtttaaat tggcttcaca tatgtattgt tcttctctacc ctccagatga ggatgaagaa  3060
gaaggtgatt gtgaagaaga agagtttgag ccatcaactc aatatgagta tggtactgaa  3120
gatgattacc aaggtaaacc tttggaattt ggtgccactt ctgctgctct tcaacctgaa   3180
gaagagcaag aagaagattg ttagatgat gatagtcaac aaactgttgg tcaacaagac   3240
ggcagtgagg acaatcagac aactactatt caaacaattg ttgaggttca acctcaatta   3300
gagatggaac ttacaccagt tgttcagact attgaagtga atagttttag tggttattta   3360
aaacttactg acaatgtata cattaaaaat gcagacattg tggaagaagc taaaaaggta   3420
aaaccaacag tggttgttaa tgcagccaat gtttaccta aacatggagg aggtgttgca    3480
ggagccttaa ataaggctac taacaatgcc atgcaagttg aatctgatga ttacatagct   3540
actaatggac cacttaaagt gggtggtagt tgtgttttaa gcggacacaa tcttgctaaa   3600
cactgtcttc atgttgtcgg cccaaatgtt aacaaaggtg aagacattca acttcttaag   3660
agtgcttatg aaaattttaa tcagcacgaa gttctacttg caccattatt atcagctggt   3720 attttggtg ctgaccctat acattcttta agagtttgtg tagatactgt tcgcacaaat    3780
gtctacttag ctgtctttga taaaaatctc tatgacaaac ttgtttcaag cttttttggaa  3840 atgaagagtg aaaagcaagt tgaacaaaag atcgctgaga ttcctaaaga ggaagttaag   3900
ccatttataa ctgaaagtaa accttcagtt gaacagagaa acaagatga taagaaaatc    3960 aaagcttgtg ttgaagaagt tacaacaact ctggaagaaa ctaagttcct cacagaaaac  4020
ttgttacttt atattgacat taatggcaat cttcatccag attctgccac tcttgttagt   4080
gacattgaca tcactttctt aaagaaagat gctccatata tagtgggtga tgttgttcaa   4140
gagggtgttt taactgctgt ggttatacct actaaaaagg ctggtggcac tactgaaatg   4200
ctagcgaaag ctttgagaaa agtgccaaca gacaattata taaccactta cccgggtcag   4260
ggtttaaatg gttacactgt agaggaggca agacagtgc ttaaaagtg taaaagtgcc     4320 ttttacattc taccatctat tatctctaat gagaagcaag aaattcttgg aactgttttct  4380 tggaatttgc gagaaatgct tgcacatgca gaagaaacac gcaaattaat gcctgtctgt   4440
gtggaaacta aagccatagt ttcaactata cagcgtaaat ataagggtat taaaatacaa   4500
```

```
gagggtgtgg ttgattatgg tgctagattt tacttttaca ccagtaaaac aactgtagcg    4560
tcacttatca acacacttaa cgatctaaat gaaactcttg ttacaatgcc acttggctat    4620
gtaacacatg gcttaaattt ggaagaagct gctcggtata tgagatctct caaagtgcca    4680
gctacagttt ctgtttcttc acctgatgct gttacagcgt ataatggtta tcttacttct    4740
tcttctaaaa cacctgaaga acattttatt gaaaccatct cacttgctgg ttcctataaa    4800
gattggtcct attctggaca atctacacaa ctaggtatag aatttcttaa gagaggtgat    4860
aaaagtgtat attacactag taatcctacc acattccacc tagatggtga agttatcacc    4920
tttgacaatc ttaagacact tctttctttg agagaagtga ggactattaa ggtgttttaca    4980 acagtagaca acattaacct ccacacgcaa gttgtggaca tgtcaatgac atatggacaa    5040
cagtttggtc caacttattt ggatggagct gatgttacta aaataaaacc tcataattca    5100
catgaaggta aaacatttta tgttttacct aatgatgaca ctctacgtgt tgaggctttt    5160
gagtactacc acacaactga tcctagtttt ctgggtaggt acatgtcagc attaaatcac    5220
actaaaaagt ggaaataccc acaagttaat ggtttaactt ctattaaatg gcagataac     5280 aactgttatc ttgccactgc attgttaaca ctccaacaaa tagagttgaa gtttaatcca    5340
cctgctctac aagatgctta ttacagagca agggctggtg aagctgctaa cttttgtgca    5400
cttatcttag cctactgtaa taagacagta ggtgagttag gtgatgttag agaaacaatg    5460
agttacttgt ttcaacatgc caatttagat tcttgcaaaa gagtcttgaa cgtggtgtgt    5520
aaaacttgtg acaacagca gacaaccctt aagggtgtag aagctgttat gtacatgggc    5580
acactttctt atgaacaatt taagaaaggt gttcagatac cttgtacgtg tggtaaacaa    5640
gctacaaaat atctagtaca acaggagtca cctttttgtta tgatgtcagc accacctgct    5700
cagtatgaac ttaagcatgg tacatttact tgtgctagtg agtacactgg taattaccag    5760
tgtggtcact ataaacatat aacttctaaa gaaactttgt attgcataga cggtgcttta    5820
cttacaaagt cctcagaata caaaggtcct attacgGatg ttttctacaa agaaaacagt    5880
tacacaacaa ccataaaacc agttacttat aaattggatg gtgttgtttg tacagaaatt    5940
gaccctaagt tggacaatta ttataagaaa gacaattctt atttcacaga gcaaccaatt    6000
gatcttgtac caaaccaacc atatccaaac gcaagcttcg ataattttaa gtttgtatgt    6060
gataatatca aatttgctga tgatttaaac cagttaactg ttataagaa acctgcttca    6120 agagagctta aagttacatt tttccctgac ttaaatggtg atgtggtggc tattgattat    6180
aaacactaca caccctcttt taagaaagga gctaaattgt tacataaacc tattgtttgg    6240
catgttaaca atgcaactaa taagccacg tataaaccaa atacctggtg tatacgttgt    6300
ctttggagca caaaaccagt tgaaacatca aattcgtttg atgtactgaa gtcagaggac    6360
gcgcagggaa tggataatct tgcctgcgaa gatctaaaac cagtctctga agaagtagtg    6420
gaaaatccta ccatacagaa agacgttctt gagtgtaatg tgaaaactac cgaagttgta    6480
ggagacatta tacttaaacc agcaaataat agtttaaaaa ttacagaaga ggttggccac    6540
acagatctaa tggctgctta tgtagacaat tctagtctta ctattaagaa acctaatgaa    6600
ttatctagag tattaggttt gaaaaccctt gctactcatg gtttagctgc tgttaatagt    6660
gtcccttggg atactatagc taattatgct aagcctttc ttaacaaagt tgttagtaca    6720
actactaaca tagttacacg tgtgtttaaac cgtgtttgta ctaattatat gccttatttc    6780
tttactttat tgctacaatt gtgtacttt actagaagta caaattctag aattaaagca    6840
tctatgccga ctactatagc aaagaatact gttaagagtg tcggtaaatt ttgtctagag    6900
```

```
gcttcattta attatttgaa gtcacctaat ttttctaaac tgataaatat tataatttgg   6960
tttttactat taagtgtttg cctaggttct ttaatctact caaccgctgc tttaggtgtt   7020
ttaatgtcta atttaggcat gccttcttac tgtactggtt acagagaagg ctatttgaac   7080
tctactaatg tcactattgc aacctactgt actggttcta taccttgtag tgtttgtctt   7140
agtggtttag attctttaga cacctatcct tctttagaaa ctatacaaat taccatttca   7200
tcttttaaat gggattaaac tgcttttggc ttagttgcag agtggttttt ggcatatatt   7260
cttttcacta ggtttttcta tgtacttgga ttggctgcaa tcatgcaatt gttttttcagc  7320
tatttttgcag tacattttat tagtaattct tggcttatgt ggttaataat taatcttgta   7380
caaatggccc cgatttcagc tatggttaga atgtacatct tctttgcatc attttattat   7440
gtatggaaaa gttatgtgca tgttgtagac ggttgtaatt catcaacttg tatgatgtgt   7500
tacaaacgta atagagcaac aagagtcgaa tgtacaacta ttgttaatgg tgttagaagg   7560
tccttttatg tctatgctaa tggaggtaaa ggcttttgca aactacacaa ttggaattgt   7620
gttaattgtg atacattctg tgctggtagt acatttatta gtgatgaagt tgcgagagac   7680
ttgtcactac agtttaaaag accaataaat cctactgacc agtcttctta catcgttgat   7740
agtgttacag tgaagaatgg ttccatccat ctttactttg ataaagctgg tcaaaagact   7800
tatgaaagac attctctctc tcattttgtt aacttagaca acctgagagc taataacact   7860
aaaggttcat tgcctattaa tgttatagtt tttgatggta aatcaaaatg tgaagaatca   7920
tctgcaaaat cagcgtctgt ttactacagt cagcttatgt gtcaacctat actgttacta   7980
gatcaggcat tagtgtctga tgttggtgat agtgcggaag ttgcagttaa aatgtttgat   8040
gcttacgtta atacgtttc atcaactttt aacgtaccaa tggaaaaact caaaacacta   8100
gttgcaactg cagaagctga acttgcaaag aatgtgtcct tagacaatgt cttatctact   8160
tttatttcag cagctcggca agggtttgtt gattcagatg tagaaactaa agatgttgtt   8220
gaatgtctta aattgtcaca tcaatctgac atagaagtta ctggcgatag ttgtaataac   8280
tatatgctca cctataacaa agttgaaaac atgacacccc gtgaccttgg tgcttgtatt   8340
gactgtagtg cgcgtcatat taatgcgcag gtagcaaaaa gtcacaacat tgctttgata   8400
tggaacgtta aagatttcat gtcattgtct gaacaactac gaaaacaaat acgtagtgct   8460
gctaaaaga taacttacc ttttaagttg acatgtgcaa ctactagaca agttgttaat   8520
gttgtaacaa caagagatagc acttaagggt ggtaaaattg ttaataattg gttgaagcag   8580
ttaattaaag ttacacttgt gttccttttt gttgctgcta ttttctattt aataacacct   8640
gttcatgtca tgtctaaaca tactgacttt tcaagtgaaa tcataggata caaggctatt   8700
gatggtggtg tcactcgtga catagcatct acagatactg ttttgctaa caaacatgct   8760
gattttgaca catggtttag ccagcgtggt ggtagttata ctaatgacaa agcttgccca   8820
ttgattgctg cagtcataac aagagaagtg ggttttgtcg tgcctggttt gcctggcacg   8880
atattacgca caactaatgg tgacttttg catttcttac ctagagtttt tagtgcagtt   8940
ggtaacatct gttacacacc atcaaaactt atagagtaca ctgactttgc aacatcagct   9000
tgtgttttgg ctgctgaatg tacaattttt aaagatgctt ctggtaagcc agtaccatat   9060
tgttatgata ccaatgtact agaaggttct gttgcttatg aaagtttacg ccctgacaca   9120
cgttatgtgc tcatggatgg ctctattatt caatttccta acacctacct tgaaggttct   9180
gttagagtgg taacaacttt tgattctgag tactgtaggc acggcacttg tgaaagatca   9240
```

```
gaagctggtg tttgtgtatc tactagtggt agatgggtac ttaacaatga ttattacaga    9300
tctttaccag gagttttctg tggtgtagat gctgtaaatt tacttactaa tatgtttaca    9360
ccactaattc aacctattgg tgctttggac atatcagcat ctatagtagc tggtggtatt    9420
gtagctatcg tagtaacatg ccttgcctac tattttatga ggtttagaag agcttttggt    9480
gaatacagtc atgtagttgc ctttaatact ttactattcc ttatgtcatt cactgtactc    9540
tgtttaacac cagtttactc attcttacct ggtgtttatt ctgttattta cttgtacttg    9600
acattttatc ttactaatga tgtttctttt ttagcacata ttcagtggat ggttatgttc    9660
acacctttag tacctttctg gataacaatt gctatatca tttgtatttc cacaaagcat    9720
ttctattggt tctttagtaa ttacctaaag agacgtgtag tctttaatgg tgtttccttt    9780
agtacttttg aagaagctgc gctgtgcacc tttttgttaa ataaagaaat gtatctaaag    9840
ttgcgtagtg atgtgctatt acctcttacg caatataata gatacttagc tctttataat    9900
aagtacaagt attttagtgg agcaatggat acaactagct acagagaagc tgcttgttgt    9960
catctcgcaa aggctctcaa tgacttcagt aactcaggtt ctgatgttct ttaccaacca   10020
ccacaaacct ctatcacctc agctgttttg cagagtggtt ttagaaaaat ggcattccca   10080
tctggtaaag ttgagggttg tatggtacaa gtaacttgtg gtacaactac acttaacggt   10140
ctttggcttg atgacgtagt ttactgtcca agacatgtga tctgcacctc tgaagacatg   10200
cttaaccctc tattatgaaga tttactcatt cgtaagtcta atcataattt cttggtacag   10260
gctggtaatg ttcaactcag ggttattgga cattctatgc aaaattgtgt acttaagctt   10320
aaggttgata cagccaatcc taagacacct aagtataagt tgttcgcat tcaaccagga   10380
cagactttt cagtgttagc ttgttacaat ggttcaccat ctggtgttta ccaatgtgct   10440
atgaggccca atttcactat taagggttca ttccttaatg gttcatgtgg tagtgttggt   10500
tttaacatag attatgactg tgtctctttt tgttacatgc accatatgga attaccaact   10560
ggagttcatg ctggcacaga cttagaaggt aacttatatg gacctttgt tgacaggcaa   10620
acagcacaag cagctggtac ggacacaact attacagtta atgttttagc ttggttgtac   10680
gctgctgtta aaatggagga caggtggttt ctcaatcgat ttaccacaac tcttaatgac   10740
tttaaccttg tggctatgaa gtacaattat gaacctctaa cacaagacca tgttgacata   10800
ctaggacctc tttctgctca aactggaatt gccgttttag atatgtgtgc ttcattaaaa   10860
gaattactgc aaaatggtat gaatggacgt accatattgg gtagtgcttt attagaagat   10920
gaatttacac ttttgatgt tgttagacaa tgctcaggtg ttactttcca aagtgcagtg   10980
aaaagaacaa tcaagggtac acaccactgg ttgttactca caatttgac ttcactttta   11040
gttttagtcc agagtactca atggtctttg ttctttttt tgtatgaaa tgccttttta   11100
ccttttgcta tgggtattat tgctatgtct gcttttgcaa tgatgtttgt caaacataag   11160
catgcatttc tctgtttgtt tttgttacct tctcttgcca ctgtagctta ttttaatatg   11220
gtctatatgc ctgctagttg ggtgatgcgt attatgacat ggttggatat ggttgatact   11280
agtttgtctg gttttaagct aaaagactgt gttatgtatg catcagctgt agtgttacta   11340
atccttatga cagcaagaac tgtgtatgat gatggtgcta ggagagtgtg gacacttatg   11400
aatgtcttga cactcgttta taagtttat tatggtaatg cttagatca agccatttcc   11460
atgtgggctc ttataatctc tgttacttct aactactcag gtgtagttac aactgtcatg   11520
tttttggcca gaggtattgt ttttatgtgt gttgagtatt gccctatttt cttcataact   11580
ggtaatacac ttcagtgtat aatgctagtt tattgtttct taggctattt ttgtacttgt   11640
```

```
tactttggcc tcttttgttt actcaaccgc tactttagac tgactcttgg tgtttatgat   11700
tacttagttt ctacacagga gtttagatat atgaattcac agggactact cccacccaag   11760
aatagcatag atgccttcaa actcaacatt aaattgttgg gtgttggtgg caaaccttgt   11820
atcaaagtag ccactgtaca gtctaaaatg tcagatgtaa agtgcacatc agtagtctta   11880
ctctcagttt tgcaacaact cagagtagaa tcatcatcta aattgtgggc tcaatgtgtc   11940
cagttacaca atgacattct cttagctaaa gatactactg aagcctttga aaaatggtt    12000
tcactacttt ctgttttgct ttccatgcag ggtgctgtag acataaacaa gctttgtgaa   12060
gaaatgctgg acaacagggc aaccttacaa gctatagcct cagagtttag ttcccttcca   12120
tcatatgcag cttttgctac tgctcaagaa gcttatgagc aggctgttgc taatggtgat   12180
tctgaagttg ttcttaaaaa gttgaagaag tctttgaatg tggctaaatc tgaatttgac   12240
cgtgatgcag ccatgcaacg taagttggaa aagatggctg atcaagctat gacccaaatg   12300
tataaacagg ctagatctga ggacaagagg gcaaaagtta ctagtgctat gcagacaatg   12360
cttttcacta tgcttagaaa gttggataat gatgcactca acaacattat caacaatgca   12420
agagatggtt gtgttccctt gaacataata cctcttacaa cagcagccaa actaatggtt   12480
gtcataccag actataacac atataaaaat acgtgtgatg gtacaacatt tacttatgca   12540
tcagcattgt gggaaatcca acaggttgta gatgcagata gtaaaattgt tcaacttagt   12600
gaaattagta tggacaattc acctaattta gcatggcctc ttattgtaac agctttaagg   12660
gccaattctg ctgtcaaatt acagaataat gagcttagtc ctgttgcact acgacagatg   12720
tcttgtgctg ccggtactac acaaactgct tgcactgatg acaatgcgtt agcttactac   12780
aacacaacaa agggaggtag gtttgtactt gcactgttat ccgatttaca ggatttgaaa   12840
tgggctagat tccctaagag tgatggaact ggtactatct atacagaact ggaaccacct   12900
tgtaggtttg ttacagacac acctaaaggt cctaaagtga agtatttata ctttattaaa   12960
ggattaaaca acctaaatag aggtatggta cttggtagtt tagctgccac agtacgtcta   13020
caagctggta atgcaacaga agtgcctgcc aattcaactg tattatcttt ctgtgctttt   13080
gctgtagatg ctgctaaagc ttacaaagat tatctagcta gtgggggaca accaatcact   13140
aattgtgtta agatgttgtg tacacacact ggtactggtc aggcaataac agttacaccg   13200
gaagccaata tggatcaaga atcctttggt ggtgcatcgt gttgtctgta ctgccgttgc   13260
cacatagatc atccaaatcc taaaggattt tgtgacttaa aggtaagta tgtacaaata    13320
cctacaactt gtgctaatga ccctgtgggt tttacactta aaacacagt ctgtaccgtc     13380
tgcggtatgt ggaaaggtta tggctgtagt tgtgatcaac tccgcgaacc catgcttcag   13440
tcagctgatg cacaatcgtt tttaaacggg tttgcggtgt aagtgcagcc cgtcttacac   13500
cgtgcggcac aggcactagt actgatgtcg tatacagggc ttttgacatc tacaatgata   13560
aagtagctgg ttttgctaaa ttcctaaaaa ctaattgttg tcgcttccaa gaaaaggacg   13620
aagatgacaa tttaattgat tcttactttg tagttaagag acacactttc tctaactacc   13680
aacatgaaga aacaatttat aatttactta aggattgtcc agctgttgct aaacatgact   13740
tctttaagtt tagaatagac ggtgacatgg taccacatat atcacgtcaa cgtcttacta   13800
aatacacaat ggcagacctc gtctatgctt taaggcattt tgatgaaggt aattgtgaca   13860
cattaaaaga aatacttgtc acatacaatt gttgtgatga tgattattc aataaaaagg    13920
actggtatga ttttgtagaa aacccagata tattacgcgt atacgccaac ttaggtgaac   13980
```

```
gtgtacgcca agctttgtta aaaacagtac aattctgtga tgccatgcga aatgctggta  14040
ttgttggtgt actgacatta gataatcaag atctcaatgg taactggtat gatttcggtg  14100
atttcataca aaccacgcca ggtagtggag ttcctgttgt agattcttat tattcattgt  14160
taatgcctat attaaccttg accagggctt taactgcaga gtcacatgtt gacactgact  14220
taacaaagcc ttacattaag tgggatttgt taaaatatga cttcacggaa gagaggttaa  14280
aactctttga ccgttatttt aaatattggg atcagacata ccacccaaat tgtgttaact  14340
gtttggatga cagatgcatt ctgcattgtg caaactttaa tgttttattc tctacagtgt  14400
tcccacctac aagttttgga ccactagtga gaaaaatatt tgttgatggt gttccatttg  14460
tagtttcaac tggataccac ttcagagagc taggtgttgt acataatcag gatgtaaact  14520
tacatagctc tagacttagt tttaaggaat tacttgtgta tgctgctgac cctgctatgc  14580
acgctgcttc tggtaatcta ttactagata aacgcactac gtgcttttca gtagctgcac  14640
ttactaacaa tgttgctttt caaactgtca aacccggtaa ttttaacaaa gacttctatg  14700
actttgctgt gtctaagggt ttctttaagg aaggaagttc tgttgaatta aaacacttct  14760
tctttgctca ggatggtaat gctgctatca gcgattatga ctactatcgt tataatctac  14820
caacaatgtg tgatatcaga caactactat ttgtagttga agttgttgat aagtactttg  14880
attgttacga tggtggctgt attaatgcta accaagtcat cgtcaacaac ctagacaaat  14940
cagctggttt tccatttaat aaatggggta aggctagact ttattatgat tcaatgagtt  15000
atgaggatca agatgcactt ttcgcatata caaaacgtaa tgtcatccct actataactc  15060
aaatgaatct taagtatgcc attagtgcaa agaatagagc tcgcaccgta gctggtgtct  15120
ctatctgtag tactatgacc aatagacagt tcatcaaaaa attattgaaa tcaatagccg  15180
ccactagagg agctactgta gtaattggaa caagcaaatt ctatggtggt tggcacaaca  15240
tgttaaaaac tgtttatagt gatgtagaaa accctcacct tatgggttgg gattatccta  15300
aatgtgatag agccatgcct aacatgctta gaattatggc ctcacttgtt cttgctcgca  15360
aacatacaac gtgttgtagc ttgtcacacc gtttctatag attagctaat gagtgtgctc  15420
aagtattgag tgaaatggtc atgtgtggcg gttcactata tgttaaacca ggtggaacct  15480
catcaggaga tgccacaact gcttatgcta atagtgtttt taacatttgt caagctgtca  15540
cggccaatgt taatgcactt ttatctctg atggtaacaa aattgccgat aagtatgtcc  15600
gcaatttaca acacagactt tatgagtgtc tctatagaaa tagagatgtt gacacagact  15660
ttgtgaatga gttttacgca tatttgcgta aacatttctc aatgatgata ctctctgacg  15720
atgctgttgt gtgtttcaat agcacttatg catctcaagg tctagtggct agcataaaga  15780
actttaagtc agttctttat tatcaaaaca tgtttttat gtctgaagca aaatgttgga  15840
ctgagactga ccttactaaa ggacctcatg aattttgctc tcaacataca atgctagtta  15900 aacagggtg tgattatgtg taccttcctt acccagatcc atcaagaatc ctaggggccg  15960
gctgttttgt agatgatatc gtaaaaacag atggtacact tatgattgaa cggttcgtgt  16020
ctttagctat agatgcttac ccacttacta acatcctaa tcaggagtat gctgatgtct  16080
ttcatttgta cttacaatac ataagaaagc tacatgatga gttaacagga cacatgttag  16140
acatgtattc tgttatgctt actaatgata acacttcaag gtattgggaa cctgagtttt  16200
atgaggctat gtacacaccg catacagtct tacaggctgt tggggcttgt gttctttgca  16260
attcacagac ttcattaaga tgtggtgctt gcatacgtag accattctta tgttgtaaat  16320
gctgttacga ccatgtcata tcaacatcac ataaaattagt cttgtctgtt aatccgtatg  16380
```

```
tttgcaatgc tccaggttgt gatgtcacag atgtgactca actttactta ggaggtatga   16440
gctattattg taaatcacat aaaccaccca ttagttttcc attgtgtgct aatggacaag   16500
tttttggttt atataaaaat acatgtgttg gtagcgataa tgttactgac tttaatgcaa   16560
ttgcaacatg tgactggaca aatgctggtg attacatttt agctaacacc tgtactgaaa   16620
gactcaagct ttttgcagca gaaacgctca aagctactga ggagacattt aaactgtctt   16680
atggtattgc tactgtacgt gaagtgctgt ctgacagaga attacatctt tcatgggaag   16740
ttggtaaacc tagaccacca cttaaccgaa attatgtctt tactggttat cgtgtaacta   16800
aaaacagtaa agtacaaata ggagagtaca cctttgaaaa aggtgactat ggtgatgctg   16860
ttgtttaccg aggtacaaca acttacaaat aaatgttgg tgattatttt gtgctgacat   16920
cacatacagt aatgccatta agtgcaccta cactagtgcc acaagagcac tatgttagaa   16980
ttactggctt atacccaaca ctcaatatct cagatgagtt ttctagcaat gttgcaaatt   17040
atcaaaaggt tggtatgcaa aagtattcta cactccaggg accacctggt actggtaaga   17100
gtcattttgc tattggccta gctctctact acccttctgc tcgcatagtg tatacagctt   17160
gctctcatgc cgctgttgat gcactatgtg agaaggcatt aaaatatttg cctatagata   17220
aatgtagtag aattatacct gcacgtgctc gtgtagagtg ttttgataaa ttcaaagtga   17280
attcaacatt agaacagtat gtcttttgta ctgtaaatgc attgcctgag acgacagcag   17340
atatagttgt ctttgatgaa atttcaatgg ccacaaatta tgatttgagt gttgtcaatg   17400
ccagattacg tgctaagcac tatgtgtaca ttggcgaccc tgctcaatta cctgcaccac   17460
gcacattgct aactaagggc acactagaac cagaatattt caattcagtg tgtagactta   17520
tgaaaactat aggtccagac atgttcctcg gaacttgtcg gcgttgtcct gctgaaattg   17580
ttgacactgt gagtgctttg gtttatgata taagcttaa agcacataaa gacaaatcag   17640
ctcaatgctt taaaatgttt tataagggtg ttatcacgca tgatgtttca tctgcaatta   17700
acaggccaca aataggcgtg gtaagagaat tccttacacg taaccctgct tggagaaaag   17760
ctgtctttat ttcaccttat aattcacaga atgctgtagc ctcaaagatt ttgggactac   17820
caactcaaac tgttgattca tcacagggct cagaatatga ctatgtcata ttcactcaaa   17880
ccactgaaac agctcactct tgtaatgtaa acagatttaa tgttgctatt accagagcaa   17940
aagtaggcat actttgcata atgtctgata gagacctttta tgacaagttg caatttacaa   18000
gtcttgaaat tccacgtagg aatgtggcaa ctttacaagc tgaaaatgta acaggactct   18060
ttaaagattg tagtaaggta atcactgggt tacatcctac acaggcacct acacacctca   18120
gtgttgacac taaattcaaa actgaaggtt tatgtgttga catacctggc ataccaaggg   18180
acatgaccta tagaagactc atctctatga tgggtttta aatgaattat caagttaatg   18240
gttaccctaa catgtttatc acccgcgaag aagctataag acatgtacgt gcatggattg   18300
gcttcgatgt cgaggggtgt catgctacta gagaagctgt tggtaccaat ttacctttac   18360
agctaggttt ttctacaggt gttaacctag ttgctgtacc tacaggttat gttgatacac   18420
ctaataatac agattttttcc agagttagtg ctaaaccacc gcctggagat caatttaaac   18480
acctcatacc acttatgtac aaaggacttc cttggaatgt agtgcgtata aagattgtac   18540
aaatgttaag tgacacactt aaaaatctct ctgacagagt cgtatttgtc ttatgggcac   18600
atggctttga gttgacatct atgaagtatt ttgtgaaaat aggacctgag cgcacctgtt   18660
gtctatgtga tagacgtgcc acatgctttt ccactgcttc agacacttat gcctgttggc   18720
```

```
atcattctat tggatttgat tacgtctata atccgtttat gattgatgtt caacaatggg    18780
gttttacagg taacctacaa agcaaccatg atctgtattg tcaagtccat ggtaatgcac    18840
atgtagctag ttgtgatgca atcatgacta ggtgtctagc tgtccacgag tgctttgtta    18900
agcgtgttga ctggactatt gaatatccta taattggtga tgaactgaag attaatgcgg    18960
cttgtagaaa ggttcaacac atggttgtta aagctgcatt attagcagac aaattcccag    19020
ttcttcacga cattggtaac cctaaagcta ttaagtgtgt acctcaagct gatgtagaat    19080
ggaagttcta tgatgcacag ccttgtagtg acaaagctta taaaatagaa gaattattct    19140
attcttatgc cacacattct gacaaattca cagatggtgt atgcctattt tggaattgca    19200
atgtcgatag atatcctgct aattccattg tttgtagatt tgacactaga gtgctatcta    19260
accttaactt gcctggttgt gatggtggca gtttgtatgt aaataaacat gcattccaca    19320
caccagcttt tgataaaagt gctttgtta atttaaaaca attaccattt ttctattact    19380
ctgacagtcc atgtgagtct catggaaaac aagtagtgtc agatatagat tatgtaccac    19440
taaagtctgc tacgtgtata acacgttgca atttaggtgg tgctgtctgt agacatcatg    19500
ctaatgagta cagattgtat ctcgatgctt ataacatgat gatctcagct ggctttagct    19560
tgtgggttta caaacaattt gatacttata acctctggaa cacttttaca agacttcaga    19620
gtttagaaaa tgtggctttt aatgttgtaa ataagggaca ctttgatgga caacagggtg    19680
aagtaccagt ttctatcatt aataacactg tttacacaaa agttgatggt gttgatgtag    19740
aattgtttga aaataaaaca acattacctg ttaatgtagc atttgagctt tgggctaagc    19800
gcaacattaa accagtacca gaggtgaaaa tactcaataa tttgggtgtg acattgctg    19860
ctaatactgt gatctgggac tacaaaagag atgctccagc acatatatct actattggtg    19920
tttgttctat gactgacata gccaagaaac caactgaaac gatttgtgca ccactcactg    19980
tcttttttga tggtagagtt gatggtcaag tagacttatt tagaaatgcc cgtaatggtg    20040
ttcttattac agaaggtagt gttaaaggtt tacaaccatc tgtaggtccc aaacaagcta    20100
gtcttaatgg agtcacatta attggagaag ccgtaaaaac acagttcaat tattataaga    20160
aagttgatgg tgttgtccaa caattacctg aaacttactt tactcagagt agaaatttac    20220
aagaatttaa acccaggagt caaatggaaa ttgatttctt agaattagct atggatgaat    20280
tcattgaacg gtataaatta gaaggctatg ccttcgaaca tatcgtttat ggagatttta    20340
gtcatagtca gttaggtggt ttacatctac tgattggact agctaaacgt tttaaggaat    20400
cacctttga attagaagat tttattccta tggacagtac agttaaaaac tatttcataa    20460
cagatgcgca aacaggttca tctaagtgtg tgtgttctgt tattgattta ttacttgatg    20520
attttgttga ataataaaa tcccaagatt tatctgtagt ttctaaggtt gtcaaagtga    20580
ctattgacta tacagaaatt tcatttatgc tttggtgtaa agatggccat gtagaaacat    20640
tttacccaaa attacaatct agtcaagcgt ggcaaccggg tgttgctatg cctaatcttt    20700
acaaaatgca aagaatgcta ttagaaaagt gtgaccttca aaattatggt gatagtgcaa    20760
cattacctaa aggcataatg atgaatgtcg caaaatatac tcaactgtgt caatatttaa    20820
acacattaac attagctgta ccctataata tgagagttat acttttggt gctggttctg    20880
ataaaggagt tgcaccaggt acagctgttt taagacagtg gttgcctacg ggtacgctgc    20940
ttgtcgattc agatcttaat gactttgtct ctgatgcaga ttcaactttg attggtgatt    21000
gtgcaactgt acatacagct aataaatggg atctcattat tagtgatatg tacgacccta    21060
agactaaaaa tgttacaaaa gaaaatgact ctaaagaggg ttttttcact tacatttgtg    21120
```

```
ggtttataca acaaaagcta gctcttggag gttccgtggc tataaagata acagaacatt    21180
cttggaatgc tgatctttat aagctcatgg gacacttcgc atggtggaca gcctttgtta    21240
ctaatgtgaa tgcgtcatca tctgaagcat ttttaattgg atgtaattat cttggcaaac    21300
cacgcgaaca aatagatggt tatgtcatgc atgcaaatta catattttgg aggaatacaa    21360
atccaattca gttgtcttcc tattctttat ttgacatgag taaatttccc cttaaattaa    21420
ggggtactgc tgttatgtct ttaaaagaag gtcaaatcaa tgatatgatt ttatctcttc    21480
ttagtaaagg tagacttata attagagaaa acaacagagt tgttatttct agtgatgttc    21540
ttgttaacaa ctaaacgaac aatgtttgtt tttcttgttt tattgccact agtctctagt    21600
cagtgtgtta atcttacaac cagaactcaa ttaccccctg catacactaa ttctttcaca    21660
cgtggtgttt attaccctga caaagttttc agatcctcag ttttacattc aactcaggac    21720
ttgttcttac ctttcttttc caatgttact tggttccatg ctatacatgt ctctgggacc    21780
aatggtacta agaggtttga taaccctgtc ctaccattta atgatggtgt ttattttgct    21840
tccactgaga agtctaacat aataagaggc tggatttttg gtactacttt agattcgaag    21900
acccagtccc tacttattgt taataacgct actaatgttg ttattaaagt ctgtgaattt    21960
caattttgta atgatccatt tttgggtgtt tattaccaca aaaacaacaa aagttggatg    22020
gaaagtgagt tcagagttta ttctagtgcg aataattgca cttttgaata tgtctctcag    22080
ccttttctta tggaccttga aggaaaacag ggtaatttca aaaatcttag ggaatttgtg    22140
tttaagaata ttgatggtta ttttaaaata tattctaagc acacgcctat taatttagtg    22200
cgtgatctcc ctcagggttt ttcggcttta gaaccattgg tagatttgcc aataggtatt    22260
aacatcacta ggtttcaaac tttacttgct ttacatagaa gttatttgac tcctggtgat    22320
tcttcttcag gttggacagc tggtgctgca gcttattatg tgggttatct tcaacctagg    22380
acttttctat taaaatataa tgaaaatgga accattacag atgctgtaga ctgtgcactt    22440
gaccctctct cagaaacaaa gtgtacgttg aaatccttca ctgtagaaaa aggaatctat    22500
caaacttcta actttagagt ccaaccaaca gaatctattg ttagatttcc taatattaca    22560
aacttgtgcc cttttggtga gtttttaac gccaccagat ttgcatctgt ttatgcttgg    22620
aacaggaaga gaatcagcaa ctgtgttgct gattattctg tcctatataa ttccgcatca    22680
ttttccactt ttaagtgtta tggagtgtct cctactaaat taaatgatct ctgctttact    22740
aatgtctatg cagattcatt tgtaattaga ggtgatgaag tcagacaaat cgctccaggg    22800
caaactggaa agattgctga ttataattat aaattaccag atgattttac aggctgcgtt    22860
atagcttgga attctaacaa tcttgattct aaggttggtg gtaattataa ttacctgtat    22920 agattgtttta ggaagtctaa tctcaaacct tttgagagag atatttcaac tgaaatctat    22980
caggccggta gcacaccttg taatggtgtt gaaggtttta attgttactt ccctttacaa    23040
tcatatggtt tccaacccac taatggtgtt ggttaccaac atacagagt agtagtactt    23100 tcttttgaac ttctacatgc accagcaact gtttgtggac ctaaaaagtc tactaatttg    23160
gttaaaaaca atgtgtcaa tttcaacttc aatggttaa caggcacagg tgttcttact    23220
gagtctaaca aaaagtttct gcctttccaa caatttggca gagacattgc tgacactact    23280
gatgctgtcc gtgatccaca gacacttgag attcttgaca ttacaccatg ttctttggt    23340 ggtgtcagtg ttataacacc aggaacaaat acttctaacc aggttgctgt tctttatcag    23400
gatgttaact gcacagaagt ccctgttgct attcatgcag atcaacttac tcctacttgg    23460
```

```
cgtgtttatt ctacaggttc taatgttttt caaacacgtg caggctgttt aatagggct    23520 gaacatgtca acaactcata tgagtgtgac atacccattg gtgcaggtat atgcgctagt   23580
tatcagactc agactaattc tcctcggcgg gcacgtagtg tagctagtca atccatcatt   23640
gcctacacta tgtcacttgg tgcagaaaat tcagttgctt actctaataa ctctattgcc   23700
atacccacaa attttactat tagtgttacc acagaaattc taccagtgtc tatgaccaag   23760
acatcagtag attgtacaat gtacatttgt ggtgattcaa ctgaatgcag caatcttttg   23820
ttgcaatatg gcagtttttg tacacaatta aaccgtgctt taactggaat agctgttgaa   23880
caagacaaaa acacccaaga agttttttgca caagtcaaac aaatttacaa acaccacca   23940 attaaagatt ttggtggttt taattttca caaatattac cagatccatc aaaaccaagc   24000
aagaggtcat ttattgaaga tctacttttc aacaaagtga cacttgcaga tgctggcttc   24060
atcaaacaat atggtgattg ccttggtgat attgctgcta gagacctcat tgtgcacaa    24120 aagtttaacg gccttactgt tttgccacct ttgctcacag atgaaatgat tgctcaatac   24180
acttctgcac tgttagcggg tacaatcact tctggttgga ccttttggtgc aggtgctgca  24240 ttacaaatac catttgctat gcaaatggct tataggttta atggtattgg agttacacag   24300
aatgttctct atgagaacca aaaattgatt gccaaccaat ttaatagtgc tattggcaaa   24360
attcaagact cactttcttc cacagcaagt gcacttggaa aacttcaaga tgtggtcaac   24420
caaaatgcac aagcttttaaa cacgcttgtt aaacaactta gctccaattt tggtgcaatt   24480
tcaagtgttt taaatgatat cctttcacgt cttgacaaag ttgaggctga agtgcaaatt   24540
gataggttga tcacaggcag acttcaaagt ttgcagacat atgtgactca acaattaatt   24600
agagctgcag aaatcagagc ttctgctaat cttgctgcta ctaaaatgtc agagtgtgta   24660
cttggacaat caaaaagagt tgattttgt ggaagggct atcatcttat gtccttccct    24720
cagtcagcac ctcatggtgt agtcttcttg catgtgactt atgtccctgc acaagaaaag   24780
aacttcacaa ctgctcctgc catttgtcat gatggaaag cacactttcc tcgtgaaggt    24840
gtctttgttt caaatggcac acactggttt gtaacacaaa ggaattttta tgaaccacaa   24900
atcattacta cagacaacac atttgtgtct ggtaactgtg atgttgtaat aggaattgtc   24960
aacaacacag tttatgatcc tttgcaacct gaattagact cattcaagga ggagttagat   25020
aaatatttta agaatcatac atcaccagat gttgatttag gtgacatctc tggcattaat   25080
gcttcagttg taaacattca aaaagaaatt gaccgcctca atgaggttgc caagaattta   25140
aatgaatctc tcatcgatct ccaagaactt ggaaagtatg agcagtatat aaaatggcca   25200
tggtacattt ggctaggttt tatagctggc ttgattgcca tagtaatggt gacaattatg   25260
ctttgctgta tgaccagttg ctgtagttgt ctcaagggct gttgttcttg tggatcctgc   25320
tgcaaatttg atgaagacga ctctgagcca gtgctcaaag gagtcaaatt acattacaca   25380
taaacgaact tatggatttg tttatgagaa tcttcacaat tggaactgta actttgaagc   25440
aaggtgaaat caaggatgct actccttcag attttgttcg cgctactgca acgataccga   25500
tacaagcctc actccctttc ggatggctta ttgttggcgt tgcacttctt gctgtttttc   25560
agagcgcttc caaaatcata accctcaaaa agagatggca actagcactc tccaagggtg   25620
ttcactttgt ttgcaacttg ctgttgttgt ttgtaacagt ttactcacac cttttgctcg   25680
ttgctgctgg ccttgaagcc ccttttctct atctttatgc tttagtctac ttcttgcaga   25740
gtataaactt gtgtaagaata ataatgaggc tttggctttg ctggaaatgc cgttccaaaa   25800
acccattact ttatgatgcc aactattttc tttgctggca tactaattgt tacgactatt   25860
```

```
gtataccttta caatagtgta acttcttcaa ttgtcattac ttcaggtgat ggcacaacaa   25920
gtcctatttc tgaacatgac taccagattg gtggttatac tgaaaaatgg gaatctggag   25980
taaaagactg tgttgtatta cacagttact tcacttcaga ctattaccag ctgtactcaa   26040
ctcaattgag tacagacact ggtgttgaac atgttacctt cttcatctac aataaaattg   26100
ttgatgagcc tgaagaacat gtccaaattc acacaatcga cggttcatcc ggagttgtta   26160
atccagtaat ggaaccaatt tatgatgaac cgacgacgac tactagcgtg cctttgtaag   26220
cacaagctga tgagtacgaa cttatgtact cattcgtttc ggaagagaca ggtacgttaa   26280
tagttaatag cgtacttctt tttcttgctt tcgtggtatt cttgctagtt acactagcca   26340
tccttactgc gcttcgattg tgtgcgtact gctgcaatat tgttaacgtg agtcttgtaa   26400
aaccttcttt ttacgtttac tctcgtgtta aaaatctgaa ttcttctaga gttcctgatc   26460
ttctggtcta aacgaactaa atattatatt agttttctg tttggaactt taattttagc   26520
catggcagat tccaacggta ctattaccgt tgaagagctt aaaaagctcc ttgaacaatg   26580
gaacctagta ataggtttcc tattccttac atggatttgt cttctacaat tgcctatgc   26640 caacaggaat aggttttgt atataattaa gttaattttc ctctggctgt tatggccagt   26700
aactttagct tgttttgtgc ttgctgctgt ttacagaata aattggatca ccggtggaat   26760
tgctatcgca atggcttgtc ttgtaggctt gatgtggctc agctacttca ttgcttcttt   26820
cagactgttt gcgcgtacgc gttccatgtg gtcattcaat ccagaaacta acattcttct   26880
caacgtgcca ctccatggca ctattctgac cagaccgctt ctagaaagtg aactcgtaat   26940
cggagctgtg atccttcgtg gacatcttcg tattgctgga caccatctag gacgctgtga   27000
catcaaggac ctgcctaaag aaatcactgt tgctacatca cgaacgcttt cttattacaa   27060
attgggagct tcgcagcgtg tagcaggtga ctcaggtttt gctgcataca gtcgctacag   27120
gattggcaac tataaattaa acacagacca ttccagtagc agtgacaata ttgctttgct   27180
tgtacagtaa gtgacaacag atgtttcatc tcgttgactt tcaggttact atagcagaga   27240
tattactaat tattatgagg acttttaaag tttccatttg gaatcttgat tacatcataa   27300
acctcataat taaaaattta tctaagtcac taactgagaa taaatattct caattagatg   27360
aagagcaacc aatggagatt gattaaacga catgaaaat tattctttc ttggcactga   27420 taacactcgc tacttgtgag ctttatcact accaagagtg tgttagaggt acaacagtac   27480
ttttaaaaga accttgctct tctggaacat acgagggcaa ttcaccattt catcctctag   27540
ctgataacaa atttgcactg acttgcttta gcactcaatt tgcttttgct tgtcctgacg   27600
gcgtaaaaca cgtctatcag ttacgtgcca gatcagtttc acctaaactg ttcatcagac   27660
aagaggaagt tcaagaactt tactctccaa tttttcttat tgttgcggca atagtgttta   27720
taacactttg cttcacactc aaaagaaaga cagaatgatt gaactttcat taattgactt   27780
ctatttgtgc tttttagcct ttctgctatt ccttgtttta attatgctta ttatcttttg   27840
gttctcactt gaactgcaag atcataatga aacttgtcac gcctaaacga acatgaaatt   27900 tcttgtttc ttaggaatca tcacaactgt agctgcattt caccagaat gtagtttaca   27960 gtcatgtact caacatcaac catatgtagt tgatgacccg tgtcctattc acttctattc   28020
taaatggtat attagagtag gagctagaaa atcagcacct ttaattgaat tgtgcgtgga   28080
tgaggctggt tctaaatcac ccattcagta catcgtatc ggtaattata cagtttcctg   28140 tttaccttt acaattaatt gccaggaacc taaattgggt agtcttgtag tgcgttgttc   28200
```

-continued

```
gttctatgaa gacttttag agtatcatga cgttcgtgtt gttttagatt tcatctaaac   28260
gaacaaacta aaatgtctga taatggaccc caaaatcagc gaaatgcacc ccgcattacg   28320
tttggtggac cctcagattc aactggcagt aaccagaatg gagaacgcag tggggcgcga   28380
tcaaaacaac gtcggcccca aggtttaccc aataatactg cgtcttggtt caccgctctc   28440
actcaacatg gcaaggaaga ccttaaattc cctcgaggac aaggcgttcc aattaacacc   28500
aatagcagtc cagatgacca aattggctac taccgaagag ctaccagacg aattcgtggt   28560
ggtgacggta aaatgaaaga tctcagtcca agatggtatt tctactacct aggaactggg   28620
ccagaagctg gacttcccta tggtgctaac aaagacggca tcatatgggt tgcaactgag   28680
ggagccttga atacaccaaa agatcacatt ggcacccgca atcctgctaa caatgctgca   28740
atcgtgctac aacttcctca aggaacaaca ttgccaaaag gcttctacgc agaagggagc   28800
agaggcggca gtcaagcctc ttctcgttcc tcatcacgta gtcgcaacag ttcaagaaat   28860
tcaactccag gcagcagtag gggaacttct cctgctagaa tggctggcaa tggcggtgat   28920
gctgctcttg ctttgctgct gcttgacaga ttgaaccagc ttgagagcaa aatgtctggt   28980
aaaggccaac aacaacaagg ccaaactgtc actaagaaat ctgctgctga ggcttctaag   29040
aagcctcggc aaaaacgtac tgccactaaa gcatacaatg taacacaagc tttcggcaga   29100
cgtggtccag aacaaaccca aggaaatttt ggggaccagg aactaatcag acaaggaact   29160
gattacaaac attggccgca aattgcacaa tttgccccca gcgcttcagc gttcttcgga   29220
atgtcgcgca ttggcatgga agtcacacct tcgggaacgt ggttgaccta cacaggtgcc   29280
atcaaattgg atgacaaaga tccaaatttc aaagatcaag tcattttgct gaataagcat   29340
attgacgcat acaaaacatt cccaccaaca gagcctaaaa aggacaaaaa gaagaaggct   29400
gatgaaactc aagccttacc gcagagacag aagaaacagc aaactgtgac tcttcttcct   29460
gctgcagatt tggatgattt ctccaaacaa ttgcaacaat ccatgagcag tgctgactca   29520
actcaggcct aaactcatgc agaccacaca aggcagatgg gctatataaa cgttttcgct   29580
tttccgttta cgatatatag tctactcttg tgcagaatga attctcgtaa ctacatagca   29640
caagtagatg tagttaactt taatctcaca tagcaatctt taatcagtgt gtaacattag   29700
ggaggacttg aaagagccac cacatttca ccgaggccac gcggagtacg atcgagtgta   29760
cagtgaacaa tgctagggag agctgcctat atggaagagc cctaatgtgt aaaattaatt   29820
ttagtagtgc tatccccatg tgattttaat agcttcttag gagaatgaca aaaaaaaaa   29880
aaaaaaaaa aaaaaaaaaa aa                                            29902
```

<210> SEQ ID NO 164
<211> LENGTH: 7096
<212> TYPE: PRT
<213> ORGANISM: betacoronavirus SARS coronavirus 2

<400> SEQUENCE: 164

```
Met Glu Ser Leu Val Pro Gly Phe Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Val Leu Ser Glu Ala Arg Gln His Leu Lys Asp
        35                  40                  45

Gly Thr Cys Gly Leu Val Glu Val Glu Lys Gly Val Leu Pro Gln Leu
    50                  55                  60

Glu Gln Pro Tyr Val Phe Ile Lys Arg Ser Asp Ala Arg Thr Ala Pro
```

-continued

```
            65                  70                  75                  80
His Gly His Val Met Val Glu Leu Val Ala Glu Leu Glu Gly Ile Gln
                    85                  90                  95
Tyr Gly Arg Ser Gly Glu Thr Leu Gly Val Leu Val Pro His Val Gly
                    100                 105                 110
Glu Ile Pro Val Ala Tyr Arg Lys Val Leu Leu Arg Lys Asn Gly Asn
                    115                 120                 125
Lys Gly Ala Gly Gly His Ser Tyr Gly Ala Asp Leu Lys Ser Phe Asp
            130                 135                 140
Leu Gly Asp Glu Leu Gly Thr Asp Pro Tyr Glu Asp Phe Gln Glu Asn
145                 150                 155                 160
Trp Asn Thr Lys His Ser Ser Gly Val Thr Arg Glu Leu Met Arg Glu
                    165                 170                 175
Leu Asn Gly Gly Ala Tyr Thr Arg Tyr Val Asp Asn Asn Phe Cys Gly
                    180                 185                 190
Pro Asp Gly Tyr Pro Leu Glu Cys Ile Lys Asp Leu Leu Ala Arg Ala
                    195                 200                 205
Gly Lys Ala Ser Cys Thr Leu Ser Glu Gln Leu Asp Phe Ile Asp Thr
            210                 215                 220
Lys Arg Gly Val Tyr Cys Arg Glu His Glu His Glu Ile Ala Trp
225                 230                 235                 240
Tyr Thr Glu Arg Ser Glu Lys Ser Tyr Glu Leu Gln Thr Pro Phe Glu
                    245                 250                 255
Ile Lys Leu Ala Lys Lys Phe Asp Thr Phe Asn Gly Glu Cys Pro Asn
                    260                 265                 270
Phe Val Phe Pro Leu Asn Ser Ile Ile Lys Thr Ile Gln Pro Arg Val
                    275                 280                 285
Glu Lys Lys Lys Leu Asp Gly Phe Met Gly Arg Ile Arg Ser Val Tyr
                    290                 295                 300
Pro Val Ala Ser Pro Asn Glu Cys Asn Gln Met Cys Leu Ser Thr Leu
305                 310                 315                 320
Met Lys Cys Asp His Cys Gly Glu Thr Ser Trp Gln Thr Gly Asp Phe
                    325                 330                 335
Val Lys Ala Thr Cys Glu Phe Cys Gly Thr Glu Asn Leu Thr Lys Glu
                    340                 345                 350
Gly Ala Thr Thr Cys Gly Tyr Leu Pro Gln Asn Ala Val Val Lys Ile
                    355                 360                 365
Tyr Cys Pro Ala Cys His Asn Ser Glu Val Gly Pro Glu His Ser Leu
            370                 375                 380
Ala Glu Tyr His Asn Glu Ser Gly Leu Lys Thr Ile Leu Arg Lys Gly
385                 390                 395                 400
Gly Arg Thr Ile Ala Phe Gly Gly Cys Val Phe Ser Tyr Val Gly Cys
                    405                 410                 415
His Asn Lys Cys Ala Tyr Trp Val Pro Arg Ala Ser Ala Asn Ile Gly
                    420                 425                 430
Cys Asn His Thr Gly Val Val Gly Glu Gly Ser Glu Gly Leu Asn Asp
                    435                 440                 445
Asn Leu Leu Glu Ile Leu Gln Lys Glu Lys Val Asn Ile Asn Ile Val
            450                 455                 460
Gly Asp Phe Lys Leu Asn Glu Glu Ile Ala Ile Ile Leu Ala Ser Phe
465                 470                 475                 480
Ser Ala Ser Thr Ser Ala Phe Val Glu Thr Val Lys Gly Leu Asp Tyr
                    485                 490                 495
```

```
Lys Ala Phe Lys Gln Ile Val Glu Ser Cys Gly Asn Phe Lys Val Thr
                500                 505                 510

Lys Gly Lys Ala Lys Gly Ala Trp Asn Ile Gly Glu Gln Lys Ser
    515                 520                 525

Ile Leu Ser Pro Leu Tyr Ala Phe Ala Ser Glu Ala Ala Arg Val Val
530                 535                 540

Arg Ser Ile Phe Ser Arg Thr Leu Glu Thr Ala Gln Asn Ser Val Arg
545                 550                 555                 560

Val Leu Gln Lys Ala Ala Ile Thr Ile Leu Asp Gly Ile Ser Gln Tyr
                565                 570                 575

Ser Leu Arg Leu Ile Asp Ala Met Met Phe Thr Ser Asp Leu Ala Thr
                580                 585                 590

Asn Asn Leu Val Val Met Ala Tyr Ile Thr Gly Gly Val Val Gln Leu
                595                 600                 605

Thr Ser Gln Trp Leu Thr Asn Ile Phe Gly Thr Val Tyr Glu Lys Leu
        610                 615                 620

Lys Pro Val Leu Asp Trp Leu Glu Glu Lys Phe Lys Glu Gly Val Glu
625                 630                 635                 640

Phe Leu Arg Asp Gly Trp Glu Ile Val Lys Phe Ile Ser Thr Cys Ala
                645                 650                 655

Cys Glu Ile Val Gly Gly Gln Ile Val Thr Cys Ala Lys Glu Ile Lys
                660                 665                 670

Glu Ser Val Gln Thr Phe Phe Lys Leu Val Asn Lys Phe Leu Ala Leu
            675                 680                 685

Cys Ala Asp Ser Ile Ile Ile Gly Gly Ala Lys Leu Lys Ala Leu Asn
            690                 695                 700

Leu Gly Glu Thr Phe Val Thr His Ser Lys Gly Leu Tyr Arg Lys Cys
705                 710                 715                 720

Val Lys Ser Arg Glu Glu Thr Gly Leu Leu Met Pro Leu Lys Ala Pro
                725                 730                 735

Lys Glu Ile Ile Phe Leu Glu Gly Glu Thr Leu Pro Thr Glu Val Leu
                740                 745                 750

Thr Glu Glu Val Val Leu Lys Thr Gly Asp Leu Gln Pro Leu Glu Gln
            755                 760                 765

Pro Thr Ser Glu Ala Val Glu Ala Pro Leu Val Gly Thr Pro Val Cys
770                 775                 780

Ile Asn Gly Leu Met Leu Leu Glu Ile Lys Asp Thr Glu Lys Tyr Cys
785                 790                 795                 800

Ala Leu Ala Pro Asn Met Met Val Thr Asn Asn Thr Phe Thr Leu Lys
                805                 810                 815

Gly Gly Ala Pro Thr Lys Val Thr Phe Gly Asp Asp Thr Val Ile Glu
                820                 825                 830

Val Gln Gly Tyr Lys Ser Val Asn Ile Thr Phe Glu Leu Asp Glu Arg
            835                 840                 845

Ile Asp Lys Val Leu Asn Glu Lys Cys Ser Ala Tyr Thr Val Glu Leu
            850                 855                 860

Gly Thr Glu Val Asn Glu Phe Ala Cys Val Val Ala Asp Ala Val Ile
865                 870                 875                 880

Lys Thr Leu Gln Pro Val Ser Glu Leu Leu Thr Pro Leu Gly Ile Asp
                885                 890                 895

Leu Asp Glu Trp Ser Met Ala Thr Tyr Tyr Leu Phe Asp Glu Ser Gly
            900                 905                 910
```

Glu Phe Lys Leu Ala Ser His Met Tyr Cys Ser Phe Tyr Pro Pro Asp
    915                 920                 925

Glu Asp Glu Glu Glu Gly Asp Cys Glu Glu Glu Phe Glu Pro Ser
    930                 935                 940

Thr Gln Tyr Glu Tyr Gly Thr Glu Asp Asp Tyr Gln Gly Lys Pro Leu
945                 950                 955                 960

Glu Phe Gly Ala Thr Ser Ala Ala Leu Gln Pro Glu Glu Gln Glu
                965                 970                 975

Glu Asp Trp Leu Asp Asp Asp Ser Gln Gln Thr Val Gly Gln Gln Asp
            980                 985                 990

Gly Ser Glu Asp Asn Gln Thr Thr Thr Ile Gln Thr Ile Val Glu Val
            995                 1000                1005

Gln Pro Gln Leu Glu Met Glu Leu Thr Pro Val Val Gln Thr Ile
    1010                1015                1020

Glu Val Asn Ser Phe Ser Gly Tyr Leu Lys Leu Thr Asp Asn Val
    1025                1030                1035

Tyr Ile Lys Asn Ala Asp Ile Val Glu Glu Ala Lys Lys Val Lys
    1040                1045                1050

Pro Thr Val Val Asn Ala Ala Asn Val Tyr Leu Lys His Gly
    1055                1060                1065

Gly Gly Val Ala Gly Ala Leu Asn Lys Ala Thr Asn Asn Ala Met
    1070                1075                1080

Gln Val Glu Ser Asp Asp Tyr Ile Ala Thr Asn Gly Pro Leu Lys
    1085                1090                1095

Val Gly Gly Ser Cys Val Leu Ser Gly His Asn Leu Ala Lys His
    1100                1105                1110

Cys Leu His Val Val Gly Pro Asn Val Asn Lys Gly Glu Asp Ile
    1115                1120                1125

Gln Leu Leu Lys Ser Ala Tyr Glu Asn Phe Asn Gln His Glu Val
    1130                1135                1140

Leu Leu Ala Pro Leu Leu Ser Ala Gly Ile Phe Gly Ala Asp Pro
    1145                1150                1155

Ile His Ser Leu Arg Val Cys Val Asp Thr Val Arg Thr Asn Val
    1160                1165                1170

Tyr Leu Ala Val Phe Asp Lys Asn Leu Tyr Asp Lys Leu Val Ser
    1175                1180                1185

Ser Phe Leu Glu Met Lys Ser Glu Lys Gln Val Glu Gln Lys Ile
    1190                1195                1200

Ala Glu Ile Pro Lys Glu Glu Val Lys Pro Phe Ile Thr Glu Ser
    1205                1210                1215

Lys Pro Ser Val Glu Gln Arg Lys Gln Asp Asp Lys Lys Ile Lys
    1220                1225                1230

Ala Cys Val Glu Glu Val Thr Thr Thr Leu Glu Glu Thr Lys Phe
    1235                1240                1245

Leu Thr Glu Asn Leu Leu Leu Tyr Ile Asp Ile Asn Gly Asn Leu
    1250                1255                1260

His Pro Asp Ser Ala Thr Leu Val Ser Asp Ile Asp Ile Thr Phe
    1265                1270                1275

Leu Lys Lys Asp Ala Pro Tyr Ile Val Gly Asp Val Val Gln Glu
    1280                1285                1290

Gly Val Leu Thr Ala Val Val Ile Pro Thr Lys Lys Ala Gly Gly
    1295                1300                1305

Thr Thr Glu Met Leu Ala Lys Ala Leu Arg Lys Val Pro Thr Asp

|  |  |  | 1310 |  |  |  | 1315 |  |  |  | 1320 |
|---|---|---|---|---|---|---|---|---|---|---|---|

Asn Tyr Ile Thr Thr Tyr Pro Gly Gln Gly Leu Asn Gly Tyr Thr
  1325                        1330                      1335

Val Glu Glu Ala Lys Thr Val Leu Lys Lys Cys Lys Ser Ala Phe
  1340                        1345                      1350

Tyr Ile Leu Pro Ser Ile Ile Ser Asn Glu Lys Gln Glu Ile Leu
  1355                        1360                      1365

Gly Thr Val Ser Trp Asn Leu Arg Glu Met Leu Ala His Ala Glu
  1370                        1375                      1380

Glu Thr Arg Lys Leu Met Pro Val Cys Val Glu Thr Lys Ala Ile
  1385                        1390                      1395

Val Ser Thr Ile Gln Arg Lys Tyr Lys Gly Ile Lys Ile Gln Glu
  1400                        1405                      1410

Gly Val Val Asp Tyr Gly Ala Arg Phe Tyr Phe Tyr Thr Ser Lys
  1415                        1420                      1425

Thr Thr Val Ala Ser Leu Ile Asn Thr Leu Asn Asp Leu Asn Glu
  1430                        1435                      1440

Thr Leu Val Thr Met Pro Leu Gly Tyr Val Thr His Gly Leu Asn
  1445                        1450                      1455

Leu Glu Glu Ala Ala Arg Tyr Met Arg Ser Leu Lys Val Pro Ala
  1460                        1465                      1470

Thr Val Ser Val Ser Ser Pro Asp Ala Val Thr Ala Tyr Asn Gly
  1475                        1480                      1485

Tyr Leu Thr Ser Ser Ser Lys Thr Pro Glu Glu His Phe Ile Glu
  1490                        1495                      1500

Thr Ile Ser Leu Ala Gly Ser Tyr Lys Asp Trp Ser Tyr Ser Gly
  1505                        1510                      1515

Gln Ser Thr Gln Leu Gly Ile Glu Phe Leu Lys Arg Gly Asp Lys
  1520                        1525                      1530

Ser Val Tyr Tyr Thr Ser Asn Pro Thr Thr Phe His Leu Asp Gly
  1535                        1540                      1545

Glu Val Ile Thr Phe Asp Asn Leu Lys Thr Leu Leu Ser Leu Arg
  1550                        1555                      1560

Glu Val Arg Thr Ile Lys Val Phe Thr Thr Val Asp Asn Ile Asn
  1565                        1570                      1575

Leu His Thr Gln Val Val Asp Met Ser Met Thr Tyr Gly Gln Gln
  1580                        1585                      1590

Phe Gly Pro Thr Tyr Leu Asp Gly Ala Asp Val Thr Lys Ile Lys
  1595                        1600                      1605

Pro His Asn Ser His Glu Gly Lys Thr Phe Tyr Val Leu Pro Asn
  1610                        1615                      1620

Asp Asp Thr Leu Arg Val Glu Ala Phe Glu Tyr Tyr His Thr Thr
  1625                        1630                      1635

Asp Pro Ser Phe Leu Gly Arg Tyr Met Ser Ala Leu Asn His Thr
  1640                        1645                      1650

Lys Lys Trp Lys Tyr Pro Gln Val Asn Gly Leu Thr Ser Ile Lys
  1655                        1660                      1665

Trp Ala Asp Asn Asn Cys Tyr Leu Ala Thr Ala Leu Leu Thr Leu
  1670                        1675                      1680

Gln Gln Ile Glu Leu Lys Phe Asn Pro Pro Ala Leu Gln Asp Ala
  1685                        1690                      1695

Tyr Tyr Arg Ala Arg Ala Gly Glu Ala Ala Asn Phe Cys Ala Leu
  1700                        1705                      1710

Ile Leu Ala Tyr Cys Asn Lys Thr Val Gly Glu Leu Gly Asp Val
1715                1720                1725

Arg Glu Thr Met Ser Tyr Leu Phe Gln His Ala Asn Leu Asp Ser
1730                1735                1740

Cys Lys Arg Val Leu Asn Val Val Cys Lys Thr Cys Gly Gln Gln
1745                1750                1755

Gln Thr Thr Leu Lys Gly Val Glu Ala Val Met Tyr Met Gly Thr
1760                1765                1770

Leu Ser Tyr Glu Gln Phe Lys Lys Gly Val Gln Ile Pro Cys Thr
1775                1780                1785

Cys Gly Lys Gln Ala Thr Lys Tyr Leu Val Gln Gln Glu Ser Pro
1790                1795                1800

Phe Val Met Met Ser Ala Pro Pro Ala Gln Tyr Glu Leu Lys His
1805                1810                1815

Gly Thr Phe Thr Cys Ala Ser Glu Tyr Thr Gly Asn Tyr Gln Cys
1820                1825                1830

Gly His Tyr Lys His Ile Thr Ser Lys Glu Thr Leu Tyr Cys Ile
1835                1840                1845

Asp Gly Ala Leu Leu Thr Lys Ser Ser Glu Tyr Lys Gly Pro Ile
1850                1855                1860

Thr Asp Val Phe Tyr Lys Glu Asn Ser Tyr Thr Thr Thr Ile Lys
1865                1870                1875

Pro Val Thr Tyr Lys Leu Asp Gly Val Val Cys Thr Glu Ile Asp
1880                1885                1890

Pro Lys Leu Asp Asn Tyr Tyr Lys Lys Asp Asn Ser Tyr Phe Thr
1895                1900                1905

Glu Gln Pro Ile Asp Leu Val Pro Asn Gln Pro Tyr Pro Asn Ala
1910                1915                1920

Ser Phe Asp Asn Phe Lys Phe Val Cys Asp Asn Ile Lys Phe Ala
1925                1930                1935

Asp Asp Leu Asn Gln Leu Thr Gly Tyr Lys Lys Pro Ala Ser Arg
1940                1945                1950

Glu Leu Lys Val Thr Phe Phe Pro Asp Leu Asn Gly Asp Val Val
1955                1960                1965

Ala Ile Asp Tyr Lys His Tyr Thr Pro Ser Phe Lys Lys Gly Ala
1970                1975                1980

Lys Leu Leu His Lys Pro Ile Val Trp His Val Asn Asn Ala Thr
1985                1990                1995

Asn Lys Ala Thr Tyr Lys Pro Asn Thr Trp Cys Ile Arg Cys Leu
2000                2005                2010

Trp Ser Thr Lys Pro Val Glu Thr Ser Asn Ser Phe Asp Val Leu
2015                2020                2025

Lys Ser Glu Asp Ala Gln Gly Met Asp Asn Leu Ala Cys Glu Asp
2030                2035                2040

Leu Lys Pro Val Ser Glu Glu Val Val Glu Asn Pro Thr Ile Gln
2045                2050                2055

Lys Asp Val Leu Glu Cys Asn Val Lys Thr Thr Glu Val Val Gly
2060                2065                2070

Asp Ile Ile Leu Lys Pro Ala Asn Asn Ser Leu Lys Ile Thr Glu
2075                2080                2085

Glu Val Gly His Thr Asp Leu Met Ala Ala Tyr Val Asp Asn Ser
2090                2095                2100

```
Ser Leu Thr Ile Lys Lys Pro Asn Glu Leu Ser Arg Val Leu Gly
    2105            2110                2115

Leu Lys Thr Leu Ala Thr His Gly Leu Ala Ala Val Asn Ser Val
    2120            2125                2130

Pro Trp Asp Thr Ile Ala Asn Tyr Ala Lys Pro Phe Leu Asn Lys
    2135            2140                2145

Val Val Ser Thr Thr Thr Asn Ile Val Thr Arg Cys Leu Asn Arg
    2150            2155                2160

Val Cys Thr Asn Tyr Met Pro Tyr Phe Phe Thr Leu Leu Leu Gln
    2165            2170                2175

Leu Cys Thr Phe Thr Arg Ser Thr Asn Ser Arg Ile Lys Ala Ser
    2180            2185                2190

Met Pro Thr Thr Ile Ala Lys Asn Thr Val Lys Ser Val Gly Lys
    2195            2200                2205

Phe Cys Leu Glu Ala Ser Phe Asn Tyr Leu Lys Ser Pro Asn Phe
    2210            2215                2220

Ser Lys Leu Ile Asn Ile Ile Trp Phe Leu Leu Leu Ser Val
    2225            2230                2235

Cys Leu Gly Ser Leu Ile Tyr Ser Thr Ala Ala Leu Gly Val Leu
    2240            2245                2250

Met Ser Asn Leu Gly Met Pro Ser Tyr Cys Thr Gly Tyr Arg Glu
    2255            2260                2265

Gly Tyr Leu Asn Ser Thr Asn Val Thr Ile Ala Thr Tyr Cys Thr
    2270            2275                2280

Gly Ser Ile Pro Cys Ser Val Cys Leu Ser Gly Leu Asp Ser Leu
    2285            2290                2295

Asp Thr Tyr Pro Ser Leu Glu Thr Ile Gln Ile Thr Ile Ser Ser
    2300            2305                2310

Phe Lys Trp Asp Leu Thr Ala Phe Gly Leu Val Ala Glu Trp Phe
    2315            2320                2325

Leu Ala Tyr Ile Leu Phe Thr Arg Phe Phe Tyr Val Leu Gly Leu
    2330            2335                2340

Ala Ala Ile Met Gln Leu Phe Phe Ser Tyr Phe Ala Val His Phe
    2345            2350                2355

Ile Ser Asn Ser Trp Leu Met Trp Leu Ile Ile Asn Leu Val Gln
    2360            2365                2370

Met Ala Pro Ile Ser Ala Met Val Arg Met Tyr Ile Phe Phe Ala
    2375            2380                2385

Ser Phe Tyr Tyr Val Trp Lys Ser Tyr Val His Val Val Asp Gly
    2390            2395                2400

Cys Asn Ser Ser Thr Cys Met Met Cys Tyr Lys Arg Asn Arg Ala
    2405            2410                2415

Thr Arg Val Glu Cys Thr Thr Ile Val Asn Gly Val Arg Arg Ser
    2420            2425                2430

Phe Tyr Val Tyr Ala Asn Gly Gly Lys Gly Phe Cys Lys Leu His
    2435            2440                2445

Asn Trp Asn Cys Val Asn Cys Asp Thr Phe Cys Ala Gly Ser Thr
    2450            2455                2460

Phe Ile Ser Asp Glu Val Ala Arg Asp Leu Ser Leu Gln Phe Lys
    2465            2470                2475

Arg Pro Ile Asn Pro Thr Asp Gln Ser Ser Tyr Ile Val Asp Ser
    2480            2485                2490

Val Thr Val Lys Asn Gly Ser Ile His Leu Tyr Phe Asp Lys Ala
```

```
                2495                2500                2505

Gly Gln Lys Thr Tyr Glu Arg His Ser Leu Ser His Phe Val Asn
    2510                2515                2520

Leu Asp Asn Leu Arg Ala Asn Asn Thr Lys Gly Ser Leu Pro Ile
    2525                2530                2535

Asn Val Ile Val Phe Asp Gly Lys Ser Lys Cys Glu Glu Ser Ser
    2540                2545                2550

Ala Lys Ser Ala Ser Val Tyr Tyr Ser Gln Leu Met Cys Gln Pro
    2555                2560                2565

Ile Leu Leu Leu Asp Gln Ala Leu Val Ser Asp Val Gly Asp Ser
    2570                2575                2580

Ala Glu Val Ala Val Lys Met Phe Asp Ala Tyr Val Asn Thr Phe
    2585                2590                2595

Ser Ser Thr Phe Asn Val Pro Met Glu Lys Leu Lys Thr Leu Val
    2600                2605                2610

Ala Thr Ala Glu Ala Glu Leu Ala Lys Asn Val Ser Leu Asp Asn
    2615                2620                2625

Val Leu Ser Thr Phe Ile Ser Ala Ala Arg Gln Gly Phe Val Asp
    2630                2635                2640

Ser Asp Val Glu Thr Lys Asp Val Val Glu Cys Leu Lys Leu Ser
    2645                2650                2655

His Gln Ser Asp Ile Glu Val Thr Gly Asp Ser Cys Asn Asn Tyr
    2660                2665                2670

Met Leu Thr Tyr Asn Lys Val Glu Asn Met Thr Pro Arg Asp Leu
    2675                2680                2685

Gly Ala Cys Ile Asp Cys Ser Ala Arg His Ile Asn Ala Gln Val
    2690                2695                2700

Ala Lys Ser His Asn Ile Ala Leu Ile Trp Asn Val Lys Asp Phe
    2705                2710                2715

Met Ser Leu Ser Glu Gln Leu Arg Lys Gln Ile Arg Ser Ala Ala
    2720                2725                2730

Lys Lys Asn Asn Leu Pro Phe Lys Leu Thr Cys Ala Thr Thr Arg
    2735                2740                2745

Gln Val Val Asn Val Val Thr Thr Lys Ile Ala Leu Lys Gly Gly
    2750                2755                2760

Lys Ile Val Asn Asn Trp Leu Lys Gln Leu Ile Lys Val Thr Leu
    2765                2770                2775

Val Phe Leu Phe Val Ala Ala Ile Phe Tyr Leu Ile Thr Pro Val
    2780                2785                2790

His Val Met Ser Lys His Thr Asp Phe Ser Ser Glu Ile Ile Gly
    2795                2800                2805

Tyr Lys Ala Ile Asp Gly Gly Val Thr Arg Asp Ile Ala Ser Thr
    2810                2815                2820

Asp Thr Cys Phe Ala Asn Lys His Ala Asp Phe Asp Thr Trp Phe
    2825                2830                2835

Ser Gln Arg Gly Gly Ser Tyr Thr Asn Asp Lys Ala Cys Pro Leu
    2840                2845                2850

Ile Ala Ala Val Ile Thr Arg Glu Val Gly Phe Val Val Pro Gly
    2855                2860                2865

Leu Pro Gly Thr Ile Leu Arg Thr Thr Asn Gly Asp Phe Leu His
    2870                2875                2880

Phe Leu Pro Arg Val Phe Ser Ala Val Gly Asn Ile Cys Tyr Thr
    2885                2890                2895
```

```
Pro Ser Lys Leu Ile Glu Tyr Thr Asp Phe Ala Thr Ser Ala Cys
    2900            2905                2910

Val Leu Ala Ala Glu Cys Thr Ile Phe Lys Asp Ala Ser Gly Lys
    2915            2920                2925

Pro Val Pro Tyr Cys Tyr Asp Thr Asn Val Leu Glu Gly Ser Val
    2930            2935                2940

Ala Tyr Glu Ser Leu Arg Pro Asp Thr Arg Tyr Val Leu Met Asp
    2945            2950                2955

Gly Ser Ile Ile Gln Phe Pro Asn Thr Tyr Leu Glu Gly Ser Val
    2960            2965                2970

Arg Val Val Thr Thr Phe Asp Ser Glu Tyr Cys Arg His Gly Thr
    2975            2980                2985

Cys Glu Arg Ser Glu Ala Gly Val Cys Val Ser Thr Ser Gly Arg
    2990            2995                3000

Trp Val Leu Asn Asn Asp Tyr Tyr Arg Ser Leu Pro Gly Val Phe
    3005            3010                3015

Cys Gly Val Asp Ala Val Asn Leu Leu Thr Asn Met Phe Thr Pro
    3020            3025                3030

Leu Ile Gln Pro Ile Gly Ala Leu Asp Ile Ser Ala Ser Ile Val
    3035            3040                3045

Ala Gly Gly Ile Val Ala Ile Val Val Thr Cys Leu Ala Tyr Tyr
    3050            3055                3060

Phe Met Arg Phe Arg Arg Ala Phe Gly Glu Tyr Ser His Val Val
    3065            3070                3075

Ala Phe Asn Thr Leu Leu Phe Leu Met Ser Phe Thr Val Leu Cys
    3080            3085                3090

Leu Thr Pro Val Tyr Ser Phe Leu Pro Gly Val Tyr Ser Val Ile
    3095            3100                3105

Tyr Leu Tyr Leu Thr Phe Tyr Leu Thr Asn Asp Val Ser Phe Leu
    3110            3115                3120

Ala His Ile Gln Trp Met Val Met Phe Thr Pro Leu Val Pro Phe
    3125            3130                3135

Trp Ile Thr Ile Ala Tyr Ile Ile Cys Ile Ser Thr Lys His Phe
    3140            3145                3150

Tyr Trp Phe Phe Ser Asn Tyr Leu Lys Arg Arg Val Val Phe Asn
    3155            3160                3165

Gly Val Ser Phe Ser Thr Phe Glu Glu Ala Ala Leu Cys Thr Phe
    3170            3175                3180

Leu Leu Asn Lys Glu Met Tyr Leu Lys Leu Arg Ser Asp Val Leu
    3185            3190                3195

Leu Pro Leu Thr Gln Tyr Asn Arg Tyr Leu Ala Leu Tyr Asn Lys
    3200            3205                3210

Tyr Lys Tyr Phe Ser Gly Ala Met Asp Thr Thr Ser Tyr Arg Glu
    3215            3220                3225

Ala Ala Cys Cys His Leu Ala Lys Ala Leu Asn Asp Phe Ser Asn
    3230            3235                3240

Ser Gly Ser Asp Val Leu Tyr Gln Pro Pro Gln Thr Ser Ile Thr
    3245            3250                3255

Ser Ala Val Leu Gln Ser Gly Phe Arg Lys Met Ala Phe Pro Ser
    3260            3265                3270

Gly Lys Val Glu Gly Cys Met Val Gln Val Thr Cys Gly Thr Thr
    3275            3280                3285
```

-continued

```
Thr Leu Asn Gly Leu Trp Leu Asp Asp Val Val Tyr Cys Pro Arg
    3290                3295                3300

His Val Ile Cys Thr Ser Glu Asp Met Leu Asn Pro Asn Tyr Glu
    3305                3310                3315

Asp Leu Leu Ile Arg Lys Ser Asn His Asn Phe Leu Val Gln Ala
    3320                3325                3330

Gly Asn Val Gln Leu Arg Val Ile Gly His Ser Met Gln Asn Cys
    3335                3340                3345

Val Leu Lys Leu Lys Val Asp Thr Ala Asn Pro Lys Thr Pro Lys
    3350                3355                3360

Tyr Lys Phe Val Arg Ile Gln Pro Gly Gln Thr Phe Ser Val Leu
    3365                3370                3375

Ala Cys Tyr Asn Gly Ser Pro Ser Gly Val Tyr Gln Cys Ala Met
    3380                3385                3390

Arg Pro Asn Phe Thr Ile Lys Gly Ser Phe Leu Asn Gly Ser Cys
    3395                3400                3405

Gly Ser Val Gly Phe Asn Ile Asp Tyr Asp Cys Val Ser Phe Cys
    3410                3415                3420

Tyr Met His His Met Glu Leu Pro Thr Gly Val His Ala Gly Thr
    3425                3430                3435

Asp Leu Glu Gly Asn Phe Tyr Gly Pro Phe Val Asp Arg Gln Thr
    3440                3445                3450

Ala Gln Ala Ala Gly Thr Asp Thr Thr Ile Thr Val Asn Val Leu
    3455                3460                3465

Ala Trp Leu Tyr Ala Ala Val Ile Asn Gly Asp Arg Trp Phe Leu
    3470                3475                3480

Asn Arg Phe Thr Thr Thr Leu Asn Asp Phe Asn Leu Val Ala Met
    3485                3490                3495

Lys Tyr Asn Tyr Glu Pro Leu Thr Gln Asp His Val Asp Ile Leu
    3500                3505                3510

Gly Pro Leu Ser Ala Gln Thr Gly Ile Ala Val Leu Asp Met Cys
    3515                3520                3525

Ala Ser Leu Lys Glu Leu Leu Gln Asn Gly Met Asn Gly Arg Thr
    3530                3535                3540

Ile Leu Gly Ser Ala Leu Leu Glu Asp Glu Phe Thr Pro Phe Asp
    3545                3550                3555

Val Val Arg Gln Cys Ser Gly Val Thr Phe Gln Ser Ala Val Lys
    3560                3565                3570

Arg Thr Ile Lys Gly Thr His His Trp Leu Leu Leu Thr Ile Leu
    3575                3580                3585

Thr Ser Leu Leu Val Leu Val Gln Ser Thr Gln Trp Ser Leu Phe
    3590                3595                3600

Phe Phe Leu Tyr Glu Asn Ala Phe Leu Pro Phe Ala Met Gly Ile
    3605                3610                3615

Ile Ala Met Ser Ala Phe Ala Met Met Phe Val Lys His Lys His
    3620                3625                3630

Ala Phe Leu Cys Leu Phe Leu Leu Pro Ser Leu Ala Thr Val Ala
    3635                3640                3645

Tyr Phe Asn Met Val Tyr Met Pro Ala Ser Trp Val Met Arg Ile
    3650                3655                3660

Met Thr Trp Leu Asp Met Val Asp Thr Ser Leu Ser Gly Phe Lys
    3665                3670                3675

Leu Lys Asp Cys Val Met Tyr Ala Ser Ala Val Val Leu Leu Ile
```

-continued

```
            3680            3685            3690

Leu Met Thr Ala Arg Thr Val Tyr Asp Asp Gly Ala Arg Arg Val
    3695            3700            3705

Trp Thr Leu Met Asn Val Leu Thr Leu Val Tyr Lys Val Tyr Tyr
    3710            3715            3720

Gly Asn Ala Leu Asp Gln Ala Ile Ser Met Trp Ala Leu Ile Ile
    3725            3730            3735

Ser Val Thr Ser Asn Tyr Ser Gly Val Val Thr Thr Val Met Phe
    3740            3745            3750

Leu Ala Arg Gly Ile Val Phe Met Cys Val Glu Tyr Cys Pro Ile
    3755            3760            3765

Phe Phe Ile Thr Gly Asn Thr Leu Gln Cys Ile Met Leu Val Tyr
    3770            3775            3780

Cys Phe Leu Gly Tyr Phe Cys Thr Cys Tyr Phe Gly Leu Phe Cys
    3785            3790            3795

Leu Leu Asn Arg Tyr Phe Arg Leu Thr Leu Gly Val Tyr Asp Tyr
    3800            3805            3810

Leu Val Ser Thr Gln Glu Phe Arg Tyr Met Asn Ser Gln Gly Leu
    3815            3820            3825

Leu Pro Pro Lys Asn Ser Ile Asp Ala Phe Lys Leu Asn Ile Lys
    3830            3835            3840

Leu Leu Gly Val Gly Gly Lys Pro Cys Ile Lys Val Ala Thr Val
    3845            3850            3855

Gln Ser Lys Met Ser Asp Val Lys Cys Thr Ser Val Val Leu Leu
    3860            3865            3870

Ser Val Leu Gln Gln Leu Arg Val Glu Ser Ser Lys Leu Trp
    3875            3880            3885

Ala Gln Cys Val Gln Leu His Asn Asp Ile Leu Leu Ala Lys Asp
    3890            3895            3900

Thr Thr Glu Ala Phe Glu Lys Met Val Ser Leu Leu Ser Val Leu
    3905            3910            3915

Leu Ser Met Gln Gly Ala Val Asp Ile Asn Lys Leu Cys Glu Glu
    3920            3925            3930

Met Leu Asp Asn Arg Ala Thr Leu Gln Ala Ile Ala Ser Glu Phe
    3935            3940            3945

Ser Ser Leu Pro Ser Tyr Ala Ala Phe Ala Thr Ala Gln Glu Ala
    3950            3955            3960

Tyr Glu Gln Ala Val Ala Asn Gly Asp Ser Glu Val Val Leu Lys
    3965            3970            3975

Lys Leu Lys Lys Ser Leu Asn Val Ala Lys Ser Glu Phe Asp Arg
    3980            3985            3990

Asp Ala Ala Met Gln Arg Lys Leu Glu Lys Met Ala Asp Gln Ala
    3995            4000            4005

Met Thr Gln Met Tyr Lys Gln Ala Arg Ser Glu Asp Lys Arg Ala
    4010            4015            4020

Lys Val Thr Ser Ala Met Gln Thr Met Leu Phe Thr Met Leu Arg
    4025            4030            4035

Lys Leu Asp Asn Asp Ala Leu Asn Asn Ile Ile Asn Asn Ala Arg
    4040            4045            4050

Asp Gly Cys Val Pro Leu Asn Ile Ile Pro Leu Thr Thr Ala Ala
    4055            4060            4065

Lys Leu Met Val Val Ile Pro Asp Tyr Asn Thr Tyr Lys Asn Thr
    4070            4075            4080
```

-continued

```
Cys Asp Gly Thr Thr Phe Thr Tyr Ala Ser Ala Leu Trp Glu Ile
4085                4090                4095

Gln Gln Val Val Asp Ala Asp Ser Lys Ile Val Gln Leu Ser Glu
4100                4105                4110

Ile Ser Met Asp Asn Ser Pro Asn Leu Ala Trp Pro Leu Ile Val
4115                4120                4125

Thr Ala Leu Arg Ala Asn Ser Ala Val Lys Leu Gln Asn Asn Glu
4130                4135                4140

Leu Ser Pro Val Ala Leu Arg Gln Met Ser Cys Ala Ala Gly Thr
4145                4150                4155

Thr Gln Thr Ala Cys Thr Asp Asp Asn Ala Leu Ala Tyr Tyr Asn
4160                4165                4170

Thr Thr Lys Gly Gly Arg Phe Val Leu Ala Leu Leu Ser Asp Leu
4175                4180                4185

Gln Asp Leu Lys Trp Ala Arg Phe Pro Lys Ser Asp Gly Thr Gly
4190                4195                4200

Thr Ile Tyr Thr Glu Leu Glu Pro Pro Cys Arg Phe Val Thr Asp
4205                4210                4215

Thr Pro Lys Gly Pro Lys Val Lys Tyr Leu Tyr Phe Ile Lys Gly
4220                4225                4230

Leu Asn Asn Leu Asn Arg Gly Met Val Leu Gly Ser Leu Ala Ala
4235                4240                4245

Thr Val Arg Leu Gln Ala Gly Asn Ala Thr Glu Val Pro Ala Asn
4250                4255                4260

Ser Thr Val Leu Ser Phe Cys Ala Phe Ala Val Asp Ala Ala Lys
4265                4270                4275

Ala Tyr Lys Asp Tyr Leu Ala Ser Gly Gly Gln Pro Ile Thr Asn
4280                4285                4290

Cys Val Lys Met Leu Cys Thr His Thr Gly Thr Gly Gln Ala Ile
4295                4300                4305

Thr Val Thr Pro Glu Ala Asn Met Asp Gln Glu Ser Phe Gly Gly
4310                4315                4320

Ala Ser Cys Cys Leu Tyr Cys Arg Cys His Ile Asp His Pro Asn
4325                4330                4335

Pro Lys Gly Phe Cys Asp Leu Lys Gly Lys Tyr Val Gln Ile Pro
4340                4345                4350

Thr Thr Cys Ala Asn Asp Pro Val Gly Phe Thr Leu Lys Asn Thr
4355                4360                4365

Val Cys Thr Val Cys Gly Met Trp Lys Gly Tyr Gly Cys Ser Cys
4370                4375                4380

Asp Gln Leu Arg Glu Pro Met Leu Gln Ser Ala Asp Ala Gln Ser
4385                4390                4395

Phe Leu Asn Arg Val Cys Gly Val Ser Ala Ala Arg Leu Thr Pro
4400                4405                4410

Cys Gly Thr Gly Thr Ser Thr Asp Val Val Tyr Arg Ala Phe Asp
4415                4420                4425

Ile Tyr Asn Asp Lys Val Ala Gly Phe Ala Lys Phe Leu Lys Thr
4430                4435                4440

Asn Cys Cys Arg Phe Gln Glu Lys Asp Glu Asp Asp Asn Leu Ile
4445                4450                4455

Asp Ser Tyr Phe Val Val Lys Arg His Thr Phe Ser Asn Tyr Gln
4460                4465                4470
```

```
His Glu Glu Thr Ile Tyr Asn Leu Leu Lys Asp Cys Pro Ala Val
4475                4480                4485

Ala Lys His Asp Phe Phe Lys Phe Arg Ile Asp Gly Asp Met Val
4490                4495                4500

Pro His Ile Ser Arg Gln Arg Leu Thr Lys Tyr Thr Met Ala Asp
4505                4510                4515

Leu Val Tyr Ala Leu Arg His Phe Asp Glu Gly Asn Cys Asp Thr
4520                4525                4530

Leu Lys Glu Ile Leu Val Thr Tyr Asn Cys Cys Asp Asp Asp Tyr
4535                4540                4545

Phe Asn Lys Lys Asp Trp Tyr Asp Phe Val Glu Asn Pro Asp Ile
4550                4555                4560

Leu Arg Val Tyr Ala Asn Leu Gly Glu Arg Val Arg Gln Ala Leu
4565                4570                4575

Leu Lys Thr Val Gln Phe Cys Asp Ala Met Arg Asn Ala Gly Ile
4580                4585                4590

Val Gly Val Leu Thr Leu Asp Asn Gln Asp Leu Asn Gly Asn Trp
4595                4600                4605

Tyr Asp Phe Gly Asp Phe Ile Gln Thr Thr Pro Gly Ser Gly Val
4610                4615                4620

Pro Val Val Asp Ser Tyr Tyr Ser Leu Leu Met Pro Ile Leu Thr
4625                4630                4635

Leu Thr Arg Ala Leu Thr Ala Glu Ser His Val Asp Thr Asp Leu
4640                4645                4650

Thr Lys Pro Tyr Ile Lys Trp Asp Leu Leu Lys Tyr Asp Phe Thr
4655                4660                4665

Glu Glu Arg Leu Lys Leu Phe Asp Arg Tyr Phe Lys Tyr Trp Asp
4670                4675                4680

Gln Thr Tyr His Pro Asn Cys Val Asn Cys Leu Asp Asp Arg Cys
4685                4690                4695

Ile Leu His Cys Ala Asn Phe Asn Val Leu Phe Ser Thr Val Phe
4700                4705                4710

Pro Pro Thr Ser Phe Gly Pro Leu Val Arg Lys Ile Phe Val Asp
4715                4720                4725

Gly Val Pro Phe Val Val Ser Thr Gly Tyr His Phe Arg Glu Leu
4730                4735                4740

Gly Val Val His Asn Gln Asp Val Asn Leu His Ser Ser Arg Leu
4745                4750                4755

Ser Phe Lys Glu Leu Leu Val Tyr Ala Ala Asp Pro Ala Met His
4760                4765                4770

Ala Ala Ser Gly Asn Leu Leu Leu Asp Lys Arg Thr Thr Cys Phe
4775                4780                4785

Ser Val Ala Ala Leu Thr Asn Asn Val Ala Phe Gln Thr Val Lys
4790                4795                4800

Pro Gly Asn Phe Asn Lys Asp Phe Tyr Asp Phe Ala Val Ser Lys
4805                4810                4815

Gly Phe Phe Lys Glu Gly Ser Ser Val Glu Leu Lys His Phe Phe
4820                4825                4830

Phe Ala Gln Asp Gly Asn Ala Ala Ile Ser Asp Tyr Asp Tyr Tyr
4835                4840                4845

Arg Tyr Asn Leu Pro Thr Met Cys Asp Ile Arg Gln Leu Leu Phe
4850                4855                4860

Val Val Glu Val Val Asp Lys Tyr Phe Asp Cys Tyr Asp Gly Gly
```

```
              4865                4870                4875
Cys Ile Asn Ala Asn Gln Val Ile Val Asn Asn Leu Asp Lys Ser
              4880                4885                4890
Ala Gly Phe Pro Phe Asn Lys Trp Gly Lys Ala Arg Leu Tyr Tyr
              4895                4900                4905
Asp Ser Met Ser Tyr Glu Asp Gln Asp Ala Leu Phe Ala Tyr Thr
              4910                4915                4920
Lys Arg Asn Val Ile Pro Thr Ile Thr Gln Met Asn Leu Lys Tyr
              4925                4930                4935
Ala Ile Ser Ala Lys Asn Arg Ala Arg Thr Val Ala Gly Val Ser
              4940                4945                4950
Ile Cys Ser Thr Met Thr Asn Arg Gln Phe His Gln Lys Leu Leu
              4955                4960                4965
Lys Ser Ile Ala Ala Thr Arg Gly Ala Thr Val Val Ile Gly Thr
              4970                4975                4980
Ser Lys Phe Tyr Gly Gly Trp His Asn Met Leu Lys Thr Val Tyr
              4985                4990                4995
Ser Asp Val Glu Asn Pro His Leu Met Gly Trp Asp Tyr Pro Lys
              5000                5005                5010
Cys Asp Arg Ala Met Pro Asn Met Leu Arg Ile Met Ala Ser Leu
              5015                5020                5025
Val Leu Ala Arg Lys His Thr Thr Cys Cys Ser Leu Ser His Arg
              5030                5035                5040
Phe Tyr Arg Leu Ala Asn Glu Cys Ala Gln Val Leu Ser Glu Met
              5045                5050                5055
Val Met Cys Gly Gly Ser Leu Tyr Val Lys Pro Gly Gly Thr Ser
              5060                5065                5070
Ser Gly Asp Ala Thr Thr Ala Tyr Ala Asn Ser Val Phe Asn Ile
              5075                5080                5085
Cys Gln Ala Val Thr Ala Asn Val Asn Ala Leu Leu Ser Thr Asp
              5090                5095                5100
Gly Asn Lys Ile Ala Asp Lys Tyr Val Arg Asn Leu Gln His Arg
              5105                5110                5115
Leu Tyr Glu Cys Leu Tyr Arg Asn Arg Asp Val Asp Thr Asp Phe
              5120                5125                5130
Val Asn Glu Phe Tyr Ala Tyr Leu Arg Lys His Phe Ser Met Met
              5135                5140                5145
Ile Leu Ser Asp Asp Ala Val Val Cys Phe Asn Ser Thr Tyr Ala
              5150                5155                5160
Ser Gln Gly Leu Val Ala Ser Ile Lys Asn Phe Lys Ser Val Leu
              5165                5170                5175
Tyr Tyr Gln Asn Asn Val Phe Met Ser Glu Ala Lys Cys Trp Thr
              5180                5185                5190
Glu Thr Asp Leu Thr Lys Gly Pro His Glu Phe Cys Ser Gln His
              5195                5200                5205
Thr Met Leu Val Lys Gln Gly Asp Asp Tyr Val Tyr Leu Pro Tyr
              5210                5215                5220
Pro Asp Pro Ser Arg Ile Leu Gly Ala Gly Cys Phe Val Asp Asp
              5225                5230                5235
Ile Val Lys Thr Asp Gly Thr Leu Met Ile Glu Arg Phe Val Ser
              5240                5245                5250
Leu Ala Ile Asp Ala Tyr Pro Leu Thr Lys His Pro Asn Gln Glu
              5255                5260                5265
```

```
Tyr Ala Asp Val Phe His Leu Tyr Leu Gln Tyr Ile Arg Lys Leu
        5270            5275            5280

His Asp Glu Leu Thr Gly His Met Leu Asp Met Tyr Ser Val Met
5285            5290            5295

Leu Thr Asn Asp Asn Thr Ser Arg Tyr Trp Glu Pro Glu Phe Tyr
    5300            5305            5310

Glu Ala Met Tyr Thr Pro His Thr Val Leu Gln Ala Val Gly Ala
5315            5320            5325

Cys Val Leu Cys Asn Ser Gln Thr Ser Leu Arg Cys Gly Ala Cys
    5330            5335            5340

Ile Arg Arg Pro Phe Leu Cys Cys Lys Cys Cys Tyr Asp His Val
5345            5350            5355

Ile Ser Thr Ser His Lys Leu Val Leu Ser Val Asn Pro Tyr Val
    5360            5365            5370

Cys Asn Ala Pro Gly Cys Asp Val Thr Asp Val Thr Gln Leu Tyr
5375            5380            5385

Leu Gly Gly Met Ser Tyr Tyr Cys Lys Ser His Lys Pro Pro Ile
    5390            5395            5400

Ser Phe Pro Leu Cys Ala Asn Gly Gln Val Phe Gly Leu Tyr Lys
5405            5410            5415

Asn Thr Cys Val Gly Ser Asp Asn Val Thr Asp Phe Asn Ala Ile
    5420            5425            5430

Ala Thr Cys Asp Trp Thr Asn Ala Gly Asp Tyr Ile Leu Ala Asn
5435            5440            5445

Thr Cys Thr Glu Arg Leu Lys Leu Phe Ala Ala Glu Thr Leu Lys
    5450            5455            5460

Ala Thr Glu Glu Thr Phe Lys Leu Ser Tyr Gly Ile Ala Thr Val
5465            5470            5475

Arg Glu Val Leu Ser Asp Arg Glu Leu His Leu Ser Trp Glu Val
    5480            5485            5490

Gly Lys Pro Arg Pro Pro Leu Asn Arg Asn Tyr Val Phe Thr Gly
5495            5500            5505

Tyr Arg Val Thr Lys Asn Ser Lys Val Gln Ile Gly Glu Tyr Thr
    5510            5515            5520

Phe Glu Lys Gly Asp Tyr Gly Asp Ala Val Val Tyr Arg Gly Thr
5525            5530            5535

Thr Thr Tyr Lys Leu Asn Val Gly Asp Tyr Phe Val Leu Thr Ser
    5540            5545            5550

His Thr Val Met Pro Leu Ser Ala Pro Thr Leu Val Pro Gln Glu
5555            5560            5565

His Tyr Val Arg Ile Thr Gly Leu Tyr Pro Thr Leu Asn Ile Ser
    5570            5575            5580

Asp Glu Phe Ser Ser Asn Val Ala Asn Tyr Gln Lys Val Gly Met
5585            5590            5595

Gln Lys Tyr Ser Thr Leu Gln Gly Pro Pro Gly Thr Gly Lys Ser
    5600            5605            5610

His Phe Ala Ile Gly Leu Ala Leu Tyr Tyr Pro Ser Ala Arg Ile
5615            5620            5625

Val Tyr Thr Ala Cys Ser His Ala Ala Val Asp Ala Leu Cys Glu
    5630            5635            5640

Lys Ala Leu Lys Tyr Leu Pro Ile Asp Lys Cys Ser Arg Ile Ile
5645            5650            5655
```

```
Pro Ala Arg Ala Arg Val Glu Cys Phe Asp Lys Phe Lys Val Asn
5660                5665                5670

Ser Thr Leu Glu Gln Tyr Val Phe Cys Thr Val Asn Ala Leu Pro
5675                5680                5685

Glu Thr Thr Ala Asp Ile Val Val Phe Asp Glu Ile Ser Met Ala
5690                5695                5700

Thr Asn Tyr Asp Leu Ser Val Val Asn Ala Arg Leu Arg Ala Lys
5705                5710                5715

His Tyr Val Tyr Ile Gly Asp Pro Ala Gln Leu Pro Ala Pro Arg
5720                5725                5730

Thr Leu Leu Thr Lys Gly Thr Leu Glu Pro Glu Tyr Phe Asn Ser
5735                5740                5745

Val Cys Arg Leu Met Lys Thr Ile Gly Pro Asp Met Phe Leu Gly
5750                5755                5760

Thr Cys Arg Arg Cys Pro Ala Glu Ile Val Asp Thr Val Ser Ala
5765                5770                5775

Leu Val Tyr Asp Asn Lys Leu Lys Ala His Lys Asp Lys Ser Ala
5780                5785                5790

Gln Cys Phe Lys Met Phe Tyr Lys Gly Val Ile Thr His Asp Val
5795                5800                5805

Ser Ser Ala Ile Asn Arg Pro Gln Ile Gly Val Val Arg Glu Phe
5810                5815                5820

Leu Thr Arg Asn Pro Ala Trp Arg Lys Ala Val Phe Ile Ser Pro
5825                5830                5835

Tyr Asn Ser Gln Asn Ala Val Ala Ser Lys Ile Leu Gly Leu Pro
5840                5845                5850

Thr Gln Thr Val Asp Ser Ser Gln Gly Ser Glu Tyr Asp Tyr Val
5855                5860                5865

Ile Phe Thr Gln Thr Thr Glu Thr Ala His Ser Cys Asn Val Asn
5870                5875                5880

Arg Phe Asn Val Ala Ile Thr Arg Ala Lys Val Gly Ile Leu Cys
5885                5890                5895

Ile Met Ser Asp Arg Asp Leu Tyr Asp Lys Leu Gln Phe Thr Ser
5900                5905                5910

Leu Glu Ile Pro Arg Arg Asn Val Ala Thr Leu Gln Ala Glu Asn
5915                5920                5925

Val Thr Gly Leu Phe Lys Asp Cys Ser Lys Val Ile Thr Gly Leu
5930                5935                5940

His Pro Thr Gln Ala Pro Thr His Leu Ser Val Asp Thr Lys Phe
5945                5950                5955

Lys Thr Glu Gly Leu Cys Val Asp Ile Pro Gly Ile Pro Lys Asp
5960                5965                5970

Met Thr Tyr Arg Arg Leu Ile Ser Met Met Gly Phe Lys Met Asn
5975                5980                5985

Tyr Gln Val Asn Gly Tyr Pro Asn Met Phe Ile Thr Arg Glu Glu
5990                5995                6000

Ala Ile Arg His Val Arg Ala Trp Ile Gly Phe Asp Val Glu Gly
6005                6010                6015

Cys His Ala Thr Arg Glu Ala Val Gly Thr Asn Leu Pro Leu Gln
6020                6025                6030

Leu Gly Phe Ser Thr Gly Val Asn Leu Val Ala Val Pro Thr Gly
6035                6040                6045

Tyr Val Asp Thr Pro Asn Asn Thr Asp Phe Ser Arg Val Ser Ala
```

```
                6050               6055               6060
Lys Pro Pro Pro Gly Asp Gln Phe Lys His Leu Ile Pro Leu Met
    6065               6070               6075

Tyr Lys Gly Leu Pro Trp Asn Val Val Arg Ile Lys Ile Val Gln
    6080               6085               6090

Met Leu Ser Asp Thr Leu Lys Asn Leu Ser Asp Arg Val Val Phe
    6095               6100               6105

Val Leu Trp Ala His Gly Phe Glu Leu Thr Ser Met Lys Tyr Phe
    6110               6115               6120

Val Lys Ile Gly Pro Glu Arg Thr Cys Cys Leu Cys Asp Arg Arg
    6125               6130               6135

Ala Thr Cys Phe Ser Thr Ala Ser Asp Thr Tyr Ala Cys Trp His
    6140               6145               6150

His Ser Ile Gly Phe Asp Tyr Val Tyr Asn Pro Phe Met Ile Asp
    6155               6160               6165

Val Gln Gln Trp Gly Phe Thr Gly Asn Leu Gln Ser Asn His Asp
    6170               6175               6180

Leu Tyr Cys Gln Val His Gly Asn Ala His Val Ala Ser Cys Asp
    6185               6190               6195

Ala Ile Met Thr Arg Cys Leu Ala Val His Glu Cys Phe Val Lys
    6200               6205               6210

Arg Val Asp Trp Thr Ile Glu Tyr Pro Ile Ile Gly Asp Glu Leu
    6215               6220               6225

Lys Ile Asn Ala Ala Cys Arg Lys Val Gln His Met Val Val Lys
    6230               6235               6240

Ala Ala Leu Leu Ala Asp Lys Phe Pro Val Leu His Asp Ile Gly
    6245               6250               6255

Asn Pro Lys Ala Ile Lys Cys Val Pro Gln Ala Asp Val Glu Trp
    6260               6265               6270

Lys Phe Tyr Asp Ala Gln Pro Cys Ser Asp Lys Ala Tyr Lys Ile
    6275               6280               6285

Glu Glu Leu Phe Tyr Ser Tyr Ala Thr His Ser Asp Lys Phe Thr
    6290               6295               6300

Asp Gly Val Cys Leu Phe Trp Asn Cys Asn Val Asp Arg Tyr Pro
    6305               6310               6315

Ala Asn Ser Ile Val Cys Arg Phe Asp Thr Arg Val Leu Ser Asn
    6320               6325               6330

Leu Asn Leu Pro Gly Cys Asp Gly Gly Ser Leu Tyr Val Asn Lys
    6335               6340               6345

His Ala Phe His Thr Pro Ala Phe Asp Lys Ser Ala Phe Val Asn
    6350               6355               6360

Leu Lys Gln Leu Pro Phe Phe Tyr Tyr Ser Asp Ser Pro Cys Glu
    6365               6370               6375

Ser His Gly Lys Gln Val Val Ser Asp Ile Asp Tyr Val Pro Leu
    6380               6385               6390

Lys Ser Ala Thr Cys Ile Thr Arg Cys Asn Leu Gly Gly Ala Val
    6395               6400               6405

Cys Arg His His Ala Asn Glu Tyr Arg Leu Tyr Leu Asp Ala Tyr
    6410               6415               6420

Asn Met Met Ile Ser Ala Gly Phe Ser Leu Trp Val Tyr Lys Gln
    6425               6430               6435

Phe Asp Thr Tyr Asn Leu Trp Asn Thr Phe Thr Arg Leu Gln Ser
    6440               6445               6450
```

-continued

```
Leu Glu Asn Val Ala Phe Asn Val Val Asn Lys Gly His Phe Asp
6455                6460                6465

Gly Gln Gln Gly Glu Val Pro Val Ser Ile Ile Asn Asn Thr Val
6470                6475                6480

Tyr Thr Lys Val Asp Gly Val Asp Val Glu Leu Phe Glu Asn Lys
6485                6490                6495

Thr Thr Leu Pro Val Asn Val Ala Phe Glu Leu Trp Ala Lys Arg
6500                6505                6510

Asn Ile Lys Pro Val Pro Glu Val Lys Ile Leu Asn Asn Leu Gly
6515                6520                6525

Val Asp Ile Ala Ala Asn Thr Val Ile Trp Asp Tyr Lys Arg Asp
6530                6535                6540

Ala Pro Ala His Ile Ser Thr Ile Gly Val Cys Ser Met Thr Asp
6545                6550                6555

Ile Ala Lys Lys Pro Thr Glu Thr Ile Cys Ala Pro Leu Thr Val
6560                6565                6570

Phe Phe Asp Gly Arg Val Asp Gly Gln Val Asp Leu Phe Arg Asn
6575                6580                6585

Ala Arg Asn Gly Val Leu Ile Thr Glu Gly Ser Val Lys Gly Leu
6590                6595                6600

Gln Pro Ser Val Gly Pro Lys Gln Ala Ser Leu Asn Gly Val Thr
6605                6610                6615

Leu Ile Gly Glu Ala Val Lys Thr Gln Phe Asn Tyr Tyr Lys Lys
6620                6625                6630

Val Asp Gly Val Val Gln Gln Leu Pro Glu Thr Tyr Phe Thr Gln
6635                6640                6645

Ser Arg Asn Leu Gln Glu Phe Lys Pro Arg Ser Gln Met Glu Ile
6650                6655                6660

Asp Phe Leu Glu Leu Ala Met Asp Glu Phe Ile Glu Arg Tyr Lys
6665                6670                6675

Leu Glu Gly Tyr Ala Phe Glu His Ile Val Tyr Gly Asp Phe Ser
6680                6685                6690

His Ser Gln Leu Gly Gly Leu His Leu Leu Ile Gly Leu Ala Lys
6695                6700                6705

Arg Phe Lys Glu Ser Pro Phe Glu Leu Glu Asp Phe Ile Pro Met
6710                6715                6720

Asp Ser Thr Val Lys Asn Tyr Phe Ile Thr Asp Ala Gln Thr Gly
6725                6730                6735

Ser Ser Lys Cys Val Cys Ser Val Ile Asp Leu Leu Leu Asp Asp
6740                6745                6750

Phe Val Glu Ile Ile Lys Ser Gln Asp Leu Ser Val Val Ser Lys
6755                6760                6765

Val Val Lys Val Thr Ile Asp Tyr Thr Glu Ile Ser Phe Met Leu
6770                6775                6780

Trp Cys Lys Asp Gly His Val Glu Thr Phe Tyr Pro Lys Leu Gln
6785                6790                6795

Ser Ser Gln Ala Trp Gln Pro Gly Val Ala Met Pro Asn Leu Tyr
6800                6805                6810

Lys Met Gln Arg Met Leu Leu Glu Lys Cys Asp Leu Gln Asn Tyr
6815                6820                6825

Gly Asp Ser Ala Thr Leu Pro Lys Gly Ile Met Met Asn Val Ala
6830                6835                6840
```

-continued

```
Lys Tyr Thr Gln Leu Cys Gln Tyr Leu Asn Thr Leu Thr Leu Ala
    6845                6850                6855

Val Pro Tyr Asn Met Arg Val Ile His Phe Gly Ala Gly Ser Asp
    6860                6865                6870

Lys Gly Val Ala Pro Gly Thr Ala Val Leu Arg Gln Trp Leu Pro
    6875                6880                6885

Thr Gly Thr Leu Leu Val Asp Ser Asp Leu Asn Asp Phe Val Ser
    6890                6895                6900

Asp Ala Asp Ser Thr Leu Ile Gly Asp Cys Ala Thr Val His Thr
    6905                6910                6915

Ala Asn Lys Trp Asp Leu Ile Ile Ser Asp Met Tyr Asp Pro Lys
    6920                6925                6930

Thr Lys Asn Val Thr Lys Glu Asn Asp Ser Lys Glu Gly Phe Phe
    6935                6940                6945

Thr Tyr Ile Cys Gly Phe Ile Gln Gln Lys Leu Ala Leu Gly Gly
    6950                6955                6960

Ser Val Ala Ile Lys Ile Thr Glu His Ser Trp Asn Ala Asp Leu
    6965                6970                6975

Tyr Lys Leu Met Gly His Phe Ala Trp Trp Thr Ala Phe Val Thr
    6980                6985                6990

Asn Val Asn Ala Ser Ser Ser Glu Ala Phe Leu Ile Gly Cys Asn
    6995                7000                7005

Tyr Leu Gly Lys Pro Arg Glu Gln Ile Asp Gly Tyr Val Met His
    7010                7015                7020

Ala Asn Tyr Ile Phe Trp Arg Asn Thr Asn Pro Ile Gln Leu Ser
    7025                7030                7035

Ser Tyr Ser Leu Phe Asp Met Ser Lys Phe Pro Leu Lys Leu Arg
    7040                7045                7050

Gly Thr Ala Val Met Ser Leu Lys Glu Gly Gln Ile Asn Asp Met
    7055                7060                7065

Ile Leu Ser Leu Leu Ser Lys Gly Arg Leu Ile Ile Arg Glu Asn
    7070                7075                7080

Asn Arg Val Val Ile Ser Ser Asp Val Leu Val Asn Asn
    7085                7090                7095

<210> SEQ ID NO 165
<211> LENGTH: 1273
<212> TYPE: PRT
<213> ORGANISM: betacoronavirus SARS coronavirus 2

<400> SEQUENCE: 165

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110
```

```
Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
130                 135                 140

Tyr His Lys Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525
```

```
Lys Ser Thr Asn Leu Val Lys Asn Lys Cys Val Asn Phe Asn Phe Asn
        530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
        610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
        690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
        770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
        850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
```

```
                945                 950                 955                 960
Thr Leu Val Lys Gln Leu Ser Ser Asn Phe Gly Ala Ile Ser Ser Val
                    965                 970                 975
Leu Asn Asp Ile Leu Ser Arg Leu Asp Lys Val Glu Ala Glu Val Gln
                    980                 985                 990
Ile Asp Arg Leu Ile Thr Gly Arg Leu Gln Ser Leu Gln Thr Tyr Val
                    995                 1000                1005
Thr Gln Gln Leu Ile Arg Ala Ala Glu Ile Arg Ala Ser Ala Asn Leu
                    1010                1015                1020
Ala Ala Thr Lys Met Ser Glu Cys Val Leu Gly Gln Ser Lys Arg Val
1025                1030                1035                1040
Asp Phe Cys Gly Lys Gly Tyr His Leu Met Ser Phe Pro Gln Ser Ala
                    1045                1050                1055
Pro His Gly Val Val Phe Leu His Val Thr Tyr Val Pro Ala Gln Glu
                    1060                1065                1070
Lys Asn Phe Thr Thr Ala Pro Ala Ile Cys His Asp Gly Lys Ala His
                    1075                1080                1085
Phe Pro Arg Glu Gly Val Phe Val Ser Asn Gly Thr His Trp Phe Val
                    1090                1095                1100
Thr Gln Arg Asn Phe Tyr Glu Pro Gln Ile Ile Thr Thr Asp Asn Thr
1105                1110                1115                1120
Phe Val Ser Gly Asn Cys Asp Val Val Ile Gly Ile Val Asn Asn Thr
                    1125                1130                1135
Val Tyr Asp Pro Leu Gln Pro Glu Leu Asp Ser Phe Lys Glu Glu Leu
                    1140                1145                1150
Asp Lys Tyr Phe Lys Asn His Thr Ser Pro Asp Val Asp Leu Gly Asp
                    1155                1160                1165
Ile Ser Gly Ile Asn Ala Ser Val Val Asn Ile Gln Lys Glu Ile Asp
                    1170                1175                1180
Arg Leu Asn Glu Val Ala Lys Asn Leu Asn Glu Ser Leu Ile Asp Leu
1185                1190                1195                1200
Gln Glu Leu Gly Lys Tyr Glu Gln Tyr Ile Lys Trp Pro Trp Tyr Ile
                    1205                1210                1215
Trp Leu Gly Phe Ile Ala Gly Leu Ile Ala Ile Val Met Val Thr Ile
                    1220                1225                1230
Met Leu Cys Cys Met Thr Ser Cys Cys Ser Leu Lys Gly Cys Cys
                    1235                1240                1245
Ser Cys Gly Ser Cys Cys Lys Phe Asp Glu Asp Asp Ser Glu Pro Val
                    1250                1255                1260
Leu Lys Gly Val Lys Leu His Tyr Thr
1265                1270

<210> SEQ ID NO 166
<211> LENGTH: 220
<212> TYPE: PRT
<213> ORGANISM: Artificial Sequence
<220> FEATURE:
<223> OTHER INFORMATION: surface glycoprotein RBD [Wuhan seafood market
      pneumonia virus]

<400> SEQUENCE: 166

Asn Ile Thr Asn Leu Cys Pro Phe Gly Glu Val Phe Asn Ala Thr Arg
1               5                   10                  15
Phe Ala Ser Val Tyr Ala Trp Asn Arg Lys Arg Ile Ser Asn Cys Val
            20                  25                  30
```

```
Ala Asp Tyr Ser Val Leu Tyr Asn Ser Ala Ser Phe Ser Thr Phe Lys
         35                  40                  45

Cys Tyr Gly Val Ser Pro Thr Lys Leu Asn Asp Leu Cys Phe Thr Asn
 50                  55                  60

Val Tyr Ala Asp Ser Phe Val Ile Arg Gly Asp Glu Val Arg Gln Ile
 65                  70                  75                  80

Ala Pro Gly Gln Thr Gly Lys Ile Ala Asp Tyr Asn Tyr Lys Leu Pro
                 85                  90                  95

Asp Asp Phe Thr Gly Cys Val Ile Ala Trp Asn Ser Asn Asn Leu Asp
                100                 105                 110

Ser Lys Val Gly Gly Asn Tyr Asn Tyr Leu Tyr Arg Leu Phe Arg Lys
            115                 120                 125

Ser Asn Leu Lys Pro Phe Glu Arg Asp Ile Ser Thr Glu Ile Tyr Gln
        130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Thr Asn Leu Val Lys Asn Lys Cys
        195                 200                 205

Val Asn Phe Asn Phe Asn Gly Leu Thr Gly Thr Gly
    210                 215                 220

<210> SEQ ID NO 167
<211> LENGTH: 72
<212> TYPE: PRT
<213> ORGANISM: Artificial Sequence
<220> FEATURE:
<223> OTHER INFORMATION: Receptor Binding Motif (RBM) in surface
      glycoprotein RBD [Wuhan seafood market pneumonia
      virus]

<400> SEQUENCE: 167

Asn Ser Asn Asn Leu Asp Ser Lys Val Gly Gly Asn Tyr Asn Tyr Leu
1               5                   10                  15

Tyr Arg Leu Phe Arg Lys Ser Asn Leu Lys Pro Phe Glu Arg Asp Ile
            20                  25                  30

Ser Thr Glu Ile Tyr Gln Ala Gly Ser Thr Pro Cys Asn Gly Val Glu
        35                  40                  45

Gly Phe Asn Cys Tyr Phe Pro Leu Gln Ser Tyr Gly Phe Gln Pro Thr
    50                  55                  60

Asn Gly Val Gly Tyr Gln Pro Tyr
65                  70

<210> SEQ ID NO 168
<211> LENGTH: 107
<212> TYPE: PRT
<213> ORGANISM: Artificial Sequence
<220> FEATURE:
<223> OTHER INFORMATION: SARS-CoV-2 S309-v13 mAb VL (VK)

<400> SEQUENCE: 168

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Thr
            20                  25                  30
```

```
Ser Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln His Asp Thr Ser Leu
                 85                  90                  95

Thr Phe Gly Gly Gly Thr Lys Val Glu Ile Lys
            100                 105

<210> SEQ ID NO 169
<211> LENGTH: 7
<212> TYPE: PRT
<213> ORGANISM: Artificial Sequence
<220> FEATURE:
<223> OTHER INFORMATION: SARS-CoV-2 S309-v13 mAb CDRL1

<400> SEQUENCE: 169

Gln Thr Val Ser Ser Thr Ser
1               5

<210> SEQ ID NO 170
<211> LENGTH: 3
<212> TYPE: PRT
<213> ORGANISM: Artificial Sequence
<220> FEATURE:
<223> OTHER INFORMATION: SARS-CoV-2 S309-v13 mAb CDRL2

<400> SEQUENCE: 170

Gly Ala Ser
1

<210> SEQ ID NO 171
<211> LENGTH: 8
<212> TYPE: PRT
<213> ORGANISM: Artificial Sequence
<220> FEATURE:
<223> OTHER INFORMATION: SARS-CoV-2 S309-v13 mAb CDRL3

<400> SEQUENCE: 171

Gln Gln His Asp Thr Ser Leu Thr
1               5

<210> SEQ ID NO 172
<211> LENGTH: 127
<212> TYPE: PRT
<213> ORGANISM: Artificial Sequence
<220> FEATURE:
<223> OTHER INFORMATION: SARS-CoV-2 S309-v2.9 mAb VH

<400> SEQUENCE: 172

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Pro Phe Thr Ser Tyr
                 20                  25                  30

Gly Ile Ser Trp Val Arg Gln Ala Pro Gly Gln Gly Leu Glu Trp Met
             35                  40                  45

Gly Phe Ile Ser Thr Tyr Asn Ala Asn Thr Asn Tyr Ala Gln Lys Phe
 50                  55                  60

Gln Gly Arg Val Thr Met Thr Asp Thr Ser Thr Thr Thr Gly Tyr
 65                  70                  75                  80
```

Met Glu Leu Arg Arg Leu Arg Ser Asp Asp Thr Ala Val Tyr Tyr Cys
            85                  90                  95

Ala Arg Asp Tyr Thr Arg Gly Ala Phe Phe Gly Glu Ser Leu Ile Gly
            100                 105                 110

Gly Phe Asp Asn Trp Gly Gln Gly Thr Leu Val Thr Val Ser Ser
            115                 120                 125

<210> SEQ ID NO 173
<211> LENGTH: 330
<212> TYPE: PRT
<213> ORGANISM: Artificial Sequence
<220> FEATURE:
<223> OTHER INFORMATION: SARS-CoV-2 CH1-CH3 G1m17; IgG1*01 LS

<400> SEQUENCE: 173

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
            325                 330

<210> SEQ ID NO 174
<211> LENGTH: 107
<212> TYPE: PRT
<213> ORGANISM: Artificial Sequence
<220> FEATURE:
<223> OTHER INFORMATION: SARS-CoV-2 mAb CL (Ck) IgKC*01 k1m3

<400> SEQUENCE: 174

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 175
<211> LENGTH: 330
<212> TYPE: PRT
<213> ORGANISM: Artificial Sequence
<220> FEATURE:
<223> OTHER INFORMATION: SARS-CoV-2 CH1-CH3 G1m17; IgG1*01 LS GAALIE

<400> SEQUENCE: 175

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Ala Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Leu Pro Glu Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
                325                 330

<210> SEQ ID NO 176
<211> LENGTH: 123
<212> TYPE: PRT
<213> ORGANISM: Artificial Sequence
<220> FEATURE:
<223> OTHER INFORMATION: SARS-CoV-2 S300-v2.10 mAb VH

<400> SEQUENCE: 176

Gln Val Gln Leu Val Gln Ser Gly Ala Glu Val Lys Lys Pro Gly Ala
1               5                   10                  15

Ser Val Lys Val Ser Cys Lys Ala Ser Gly T

```
                35                  40                  45
Gly Phe Val Gln Gly Tyr Ser Gly Ala Thr Arg Tyr Ala Gln Lys Tyr
         50                  55                  60
Gln Gly Arg Val Thr Met Thr Arg Asp Thr Ser Ile Ser Thr Ala Tyr
 65                  70                  75                  80
Met Gln Leu Ser Arg Leu Arg Pro Asp Asp Thr Ala Val Tyr Tyr Cys
                 85                  90                  95
Ala Arg Asp Arg Pro Ser His Glu Phe Ala Met Tyr Phe Phe Asp Asn
            100                 105                 110
Trp Gly Gln Gly Thr Leu Val Thr Val Ser Ser
        115                 120

<210> SEQ ID NO 178
<211> LENGTH: 124
<212> TYPE: PRT
<213> ORGANISM: Artificial Sequence
<220> FEATURE:
<223> OTHER INFORMATION: SARS-CoV-2 S315-v1 mAb VH

<400> SEQUENCE: 178

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
             20                  25                  30
Trp Met Thr Trp Val Arg Gln Ala Pro Gly Lys Gly Leu Glu Trp Val
         35                  40                  45
Ala Asn Ile Lys Gln Asp Gly Ser Glu Lys Tyr Tyr Val Asp Ser Val
     50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Asp Leu Trp Trp Asn Asp Gln Ala His Tyr Tyr Gly Met Asp
            100                 105                 110
Val Trp Gly Gln Gly Thr Thr Val Thr Val Ser Ser
        115                 120

<210> SEQ ID NO 179
<211> LENGTH: 8
<212> TYPE: PRT
<213> ORGANISM: Artificial Sequence
<220> FEATURE:
<223> OTHER INFORMATION: SARS-CoV-2 S315-v1 mAb CDRH1

<400> SEQUENCE: 179

Gly Phe Thr Phe Ser Asn Tyr Trp
1               5

<210> SEQ ID NO 180
<211> LENGTH: 8
<212> TYPE: PRT
<213> ORGANISM: Artificial Sequence
<220> FEATURE:
<223> OTHER INFORMATION: SARS-CoV-2 S315-v1 mAb CDRH2

<400> SEQUENCE: 180

Ile Lys Gln Asp Gly Ser Glu Lys
1               5

<210> SEQ ID NO 181
```

-continued

```
<211> LENGTH: 17
<212> TYPE: PRT
<213> ORGANISM: Artificial Sequence
<220> FEATURE:
<223> OTHER INFORMATION: SARS-CoV-2 S315-v1 mAb CDRH3

<400> SEQUENCE: 181

Ala Arg Asp Leu Trp Trp Asn Asp Gln Ala His Tyr Tyr Gly Met Asp
1               5                   10                  15

Val

<210> SEQ ID NO 182
<211> LENGTH: 106
<212> TYPE: PRT
<213> ORGANISM: Artificial Sequence
<220> FEATURE:
<223> OTHER INFORMATION: SARS-CoV-2 S315-v1 mAb VL

<400> SEQUENCE: 182

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Phe Pro Asn Gln Tyr Ala
            20                  25                  30

Tyr Trp Tyr Gln Gln Lys Pro Gly Gln Ala Pro Val Met Leu Ile Tyr
        35                  40                  45

Lys Asp Ser Glu Arg Pro Ser Gly Ile Pro Glu Arg Phe Phe Gly Ser
    50                  55                  60

Ser Ser Gly Thr Thr Val Thr Leu Thr Ile Arg Gly Val Gln Ala Glu
65                  70                  75                  80

Asp Glu Ala Asp Tyr Tyr Cys Gln Ser Ala Asp Ser Ser Gly Thr Val
                85                  90                  95

Phe Gly Gly Gly Thr Lys Leu Thr Val Leu
            100                 105

<210> SEQ ID NO 183
<211> LENGTH: 6
<212> TYPE: PRT
<213> ORGANISM: Artificial Sequence
<220> FEATURE:
<223> OTHER INFORMATION: SARS-CoV-2 S315-v1 mAb CDRL1

<400> SEQUENCE: 183

Ala Phe Pro Asn Gln Tyr
1               5

<210> SEQ ID NO 184
<211> LENGTH: 3
<212> TYPE: PRT
<213> ORGANISM: Artificial Sequence
<220> FEATURE:
<223> OTHER INFORMATION: SARS-CoV-2 S315-v1 mAb CDRL2

<400> SEQUENCE: 184

Lys Asp Ser
1

<210> SEQ ID NO 185
<211> LENGTH: 9
<212> TYPE: PRT
<213> ORGANISM: Artificial Sequence
<220> FEATURE:
<223> OTHER INFORMATION: SARS-CoV-2 S315-v1 mAb CDRL3

<400> SEQUENCE: 185
```

Gln Ser Ala Asp Ser Ser Gly Thr Val
1               5

<210> SEQ ID NO 186
<211> LENGTH: 373
<212> TYPE: DNA
<213> ORGANISM: Artificial Sequence
<220> FEATURE:
<223> OTHER INFORMATION: SARS-CoV-2 S315-v1 mAb VH

<400> SEQUENCE: 186
gaggtgcagc tggtggagtc tggggaggc ttggtccagc ctgggggtc cctgagactc        60 tcctgtgcag cctctggatt cacctttagt aattattgga tgacctgggt ccgccaggct      120
ccagggaagg gctggagtg gtggccaac ataaagcaag atggaagtga aaatactat         180 gtggactctg tgaagggccg attcaccatc tccagagaca cgccaagaa ctcactgtat       240 ctgcaaatga acagcctgag agccgaggac acggctgtgt attactgtgc gagagatctt     300
tggtggaacg accaggctca ctactacggt atggacgtct ggggccaagg gaccacggtc     360
accgtctcct cag                                                        373

<210> SEQ ID NO 187
<211> LENGTH: 319
<212> TYPE: DNA
<213> ORGANISM: Artificial Sequence
<220> FEATURE:
<223> OTHER INFORMATION: SARS-CoV-2 S315-v1 mAb VL

<400> SEQUENCE: 187
tcctatgagc tgacacagcc accctcggtg tcagtgtccc caggacagac ggccaggatc       60
acctgctctg gagatgcatt cccaaaccaa tatgcttatt ggtaccagca gaagccaggc      120
caggcccctg tgatgctgat ctataaagac agtgagaggc cctcagggat ccctgagcga     180
ttctttggct ccagctcagg acaacagtc acgttgacca tcagaggagt ccaggcagaa      240
gacgaggctg actattactg tcaatcagca gacagcagtg gtaccgtgtt cggcggaggg     300
accaagctga ccgtcctag                                                  319

<210> SEQ ID NO 188
<211> LENGTH: 372
<212> TYPE: DNA
<213> ORGANISM: Artificial Sequence
<220> FEATURE:
<223> OTHER INFORMATION: SARS-CoV-2 S315-v1 mAb VH (nt - codon
      optimized)

<400> SEQUENCE: 188
gaagtgcagc ttgtcgagag cggcggaggc ctcgttcagc caggtgggag tctccgtctt        60
tcatgcgccg cttcaggatt tacgttctcc aactactgga tgacatgggt gaggcaggca      120
cctgggaagg gctggagtg gtggctaac atcaagcagg acggatctga aaatattat         180 gtagattctg tgaagggcg gtttaccatc tcaagggata atgccaaaaa ctctttgtat       240
ttacagatga actctcttcg agccgaggac accgccgttt actactgtgc ccgagatcta      300
tggtggaatg accaggctca ctattatgga atggacgtgt ggggccaggg tactaccgtt      360
accgtctcct ca                                                          372

<210> SEQ ID NO 189
<211> LENGTH: 318
<212> TYPE: DNA

<213> ORGANISM: Artificial Sequence
<220> FEATURE:
<223> OTHER INFORMATION: SARS-CoV-2 S315-v1 mAb VL (nt- codon optimized)

<400> SEQUENCE: 189

```
tcttacgagc tcacccagcc accctcagtg tcagtgagcc ctggccaaac agctcgcatc    60
acctgttcag gtgacgcctt tccaaatcag tacgcctact ggtatcagca gaaacccggc   120
caggcacccg ttatgctcat ctacaaagat tctgagcggc catccggtat ccccgaacgc   180
tttttcggaa gctccagtgg gactacagtt acacttacta tccggggagt gcaagctgaa   240
gatgaggccg actattattg ccagagcgca gactcctcag cacagtgtt tggggggcggg   300 actaaactaa ctgtgctg                                                  318
```

<210> SEQ ID NO 190
<211> LENGTH: 106
<212> TYPE: PRT
<213> ORGANISM: Artificial Sequence
<220> FEATURE:
<223> OTHER INFORMATION: SARS-CoV-2 S315-v2 mAb VL

<400> SEQUENCE: 190

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Phe Pro Asn Gln Tyr Ala
            20                  25                  30

Tyr Trp Tyr Gln Gln Lys Pro Gly Gln Ala Pro Val Met Leu Ile Tyr
        35                  40                  45

Lys Asp Ser Glu Arg Pro Ser Gly Ile Pro Glu Arg Phe Phe Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Val
                85                  90                  95

Phe Gly Gly Gly Thr Lys Leu Thr Val Leu
            100                 105
```

<210> SEQ ID NO 191
<211> LENGTH: 319
<212> TYPE: DNA
<213> ORGANISM: Artificial Sequence
<220> FEATURE:
<223> OTHER INFORMATION: SARS-CoV-2 S315-v2 mAb VL

<400> SEQUENCE: 191

```
tcctatgagc tgacacagcc accctcggtg tcagtgtccc caggacagac ggccaggatc    60
acctgctctg gagatgcatt cccaaaccaa tatgcttatt ggtaccagca gaagccaggc   120
caggcccctg tgatgctgat ctataaagac agtgagaggc cctcagggat ccctgagcga   180
ttctttggct ccagctcagg gacaacagtc acgttgacca tcagtggagt ccaggcagaa   240
gacgaggctg actattactg tcaatcagca gacagcagtg gtaccgtgtt cggcggaggg   300
accaagctga ccgtcctag                                                 319
```

<210> SEQ ID NO 192
<211> LENGTH: 318
<212> TYPE: DNA
<213> ORGANISM: Artificial Sequence
<220> FEATURE:
<223> OTHER INFORMATION: SARS-CoV-2 S315-v2 mAb VL (nt - codon optimized)

<400> SEQUENCE: 192

```
tcctacgagc tcacccagcc cccctcagtc tctgtgtctc ctggacagac agccagaatc    60
acctgctcgg agatgctttt tcccaaccaa tacgcctact ggtaccaaca gaaaccaggt   120
caggcgcctg tcatgctgat ttataaagac tcagagcggc cttcaggaat tcccgaaaga   180
ttcttcggga gttcaagcgg aactaccgtg accttaacca taagcggggt gcaggccgaa   240
gatgaagcag actattattg ccagagtgcc gatagtagtg gcacagtctt tgggggggg    300
acaaagctga cagtactc                                                 318
```

<210> SEQ ID NO 193
<211> LENGTH: 106
<212> TYPE: PRT
<213> ORGANISM: Artificial Sequence
<220> FEATURE:
<223> OTHER INFORMATION: SARS-CoV-2 mAb CL IgLC*01

<400> SEQUENCE: 193

```
Gly Gln Pro Lys Ala Ala Pro Ser Val Thr Leu Phe Pro Pro Ser Ser
1               5                   10                  15
Glu Glu Leu Gln Ala Asn L

<210> SEQ ID NO 195
<211> LENGTH: 8
<212> TYPE: PRT
<213> ORGANISM: Artificial Sequence
<220> FEATURE:
<223> OTHER INFORMATION: SARS-CoV-2 S315-v3 mAb CDRH1

<400> SEQUENCE: 195

Gly Phe Thr Phe Ser Asn Tyr Phe
1               5

<210> SEQ ID NO 196
<211> LENGTH: 124
<212> TYPE: PRT
<213> ORGANISM: Artificial Sequence
<220> FEATURE:
<223> OTHER INFORMATION: SARS-CoV-2 S315-v4 mAb VH

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Lys Gly Leu Glu Trp Val
        35                  40                  45

Ala Asn Ile Lys Gln Asp Ala Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Trp Asn Asp Gln Ala His Tyr Tyr Gly Met Asp
            100                 105                 110

Val Trp Gly Gln Gly Thr Thr Val Thr Val Ser Ser
        115                 120

<210> SEQ ID NO 197
<211> LENGTH: 8
<212> TYPE: PRT
<213> ORGANISM: Artificial Sequence
<220> FEATURE:
<223> OTHER INFORMATION: SARS-CoV-2 S315-v4 mAb CDRH2

<400> SEQUENCE: 197

Ile Lys Gln Asp Ala Ser Glu Lys
1               5

<210> SEQ ID NO 198
<211> LENGTH: 124
<212> TYPE: PRT
<213> ORGANISM: Artificial Sequence
<220> FEATURE:
<223> OTHER INFORMATION: SARS-CoV-2 S315-v5 mAb VH

<400> SEQUENCE: 198

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Lys Gly Leu Glu Trp Val
        35                  40                  45

Ala Asn Ile Lys Gln Glu Gly Ser Glu Lys Tyr Tyr Val Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Trp Trp Asn Asp Gln Ala His Tyr Tyr Gly Met Asp
            100                 105                 110

Val Trp Gly Gln Gly Thr Thr Val Thr Val Ser Ser
            115                 120

<210> SEQ ID NO 199
<211> LENGTH: 8
<212> TYPE: PRT
<213> ORGANISM: Artificial Sequence
<220> FEATURE:
<223> OTHER INFORMATION: SARS-CoV-2 S315-v5 mAb CDRH2

<400> SEQUENCE: 199

Ile Lys Gln Glu Gly Ser Glu Lys
1               5

<210> SEQ ID NO 200
<211> LENGTH: 124
<212> TYPE: PRT
<213> ORGANISM: Artificial Sequence
<220> FEATURE:
<223> OTHER INFORMATION: SARS-CoV-2 S315-v6 mAb VH

<400> SEQUENCE: 200

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Phe Trp Asn Asp Gln Ala His Tyr Tyr Gly Met Asp
            100                 105                 110

Val Trp Gly Gln Gly Thr Thr Val Thr Val Ser Ser
            115                 120

<210> SEQ ID NO 201
<211> LENGTH: 17
<212> TYPE: PRT
<213> ORGANISM: Artificial Sequence
<220> FEATURE:
<223> OTHER INFORMATION: SARS-CoV-2 S315-v6 mAb CDRH3

<400> SEQUENCE: 201

Ala Arg Asp Leu Phe Trp Asn Asp Gln Ala His Tyr Tyr Gly Met Asp
1               5                  10                  15

Val

```
<210> SEQ ID NO 202
<211> LENGTH: 124
<212> TYPE: PRT
<213> ORGANISM: Artificial Sequence
<220> FEATURE:
<223> OTHER INFORMATION: SARS-CoV-2 S315-v7 mAb VH

<400> SEQUENCE: 202

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu L

Gly Phe Asp Asn Trp Gly Gln Gly Thr Leu Val Thr Val Ser Ser Ala
            115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
210                 215                 220

Val Glu Pro Lys Ser Cys
225                 230

<210> SEQ ID NO 205
<211> LENGTH: 214
<212> TYPE: PRT
<213> ORGANISM: Artificial Sequence
<220> FEATURE:
<223> OTHER INFORMATION: SARS-CoV-2 Light Chain IgKC*01

<400> SEQUENCE: 205

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Thr
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Thr Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 206
<211> LENGTH: 18

```
<212> TYPE: PRT
<213> ORGANISM: Artificial Sequence
<220> FEATURE:
<223> OTHER INFORMATION: Linker

<400> SEQUENCE: 206

Gly Ser Thr Ser Gly Ser Gly Lys Pro Gly Ser Gly Glu Gly Ser Thr
1               5                   10                  15

Lys Gly

<210> SEQ ID NO 207
<211> LENGTH: 10
<212> TYPE: PRT
<213> ORGANISM: Artificial Sequence
<220> FEATURE:
<223> OTHER INFORMATION: Linker

<400> SEQUENCE: 207

Gly Ser Gly Lys Pro Gly Ser Gly Glu Gly
1               5                   10

<210> SEQ ID NO 208
<211> LENGTH: 8
<212> TYPE: PRT
<213> ORGANISM: Artificial Sequence
<220> FEATURE:
<223> OTHER INFORMATION: Linker

<400> SEQUENCE: 208

Gly Lys Pro Gly Ser Gly Glu Gly
1               5

<210> SEQ ID NO 209
<211> LENGTH: 8
<212> TYPE: PRT
<213> ORGANISM: Artificial Sequence
<220> FEATURE:
<223> OTHER INFORMATION: Linker

<400> SEQUENCE: 209

Ser Gly Lys Pro Gly Ser Gly Glu
1               5

<210> SEQ ID NO 210
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: VARIANT
<222> LOCATION: 1
<223> OTHER INFORMATION: Xaa = positively charged amino acid and Z is
      glycine or a negatively charged amino acid
<220> FEATURE:
<221> NAME/KEY: VARIANT
<222> LOCATION: (3)...(5)
<223> OTHER INFORMATION: Xaa = Gly or Ser

<400> SEQUENCE: 210

Xaa Pro Xaa Xaa Xaa Glx
1               5

<210> SEQ ID NO 211
<211> LENGTH: 121
<212> TYPE: PRT
<213> ORGANISM: Artificial Sequence
<220> FEATURE:
```

```
<223> OTHER INFORMATION: Linker
<220> FEATURE:
<221> NAME/KEY: VARIANT
<222> LOCATION: (2)...(10)
<223> OTHER INFORMATION: any one or all of amino acids 2-10 can either
      be present or absent
<220> FEATURE:
<221> NAME/KEY: VARIANT
<222> LOCATION: (12)...(121)
<223> OTHER INFORMATION: any one or all of amino acids 12-121 can either
      be present or absent

<400> SEQUENCE: 211

Gly Gly Gly Gly Gly Gly Gly Gly Ser Gly Gly Gly Gly
1               5                   10                  15

Gly Gly Gly Gly Gly Ser Gly Gly Gly Gly Gly Gly Gly Gly
            20                  25                  30

Ser Gly Gly Gly Gly Gly Gly Gly Gly Ser Gly Gly Gly
            35                  40                  45

Gly Gly Gly Gly Gly Ser Gly Gly Gly Gly Gly Gly Gly
        50                  55                  60

Gly Ser Gly Gly Gly Gly Gly Gly Gly Gly Ser Gly Gly
65                  70                  75                  80

Gly Gly Gly Gly Gly Gly Ser Gly Gly Gly Gly Gly Gly
            85                  90                  95

Gly Gly Ser Gly Gly Gly Gly Gly Gly Gly Ser Gly Gly
            100                 105                 110

Gly Gly Gly Gly Gly Gly Gly Ser
        115                 120

<210> SEQ ID NO 212
<211> LENGTH: 15
<212> TYPE: PRT
<213> ORGANISM: Artificial Sequence
<220> FEATURE:
<223> OTHER INFORMATION: Linker

<400> SEQUENCE: 212

Gly Gly Gly Gly Ser Gly Gly Gly Gly Ser Gly Gly Gly Gly Ser
1               5                   10                  15

<210> SEQ ID NO 213
<211> LENGTH: 50
<212> TYPE: PRT
<213> ORGANISM: Artificial Sequence
<220> FEATURE:
<223> OTHER INFORMATION: Linker

<400> SEQUENCE: 213

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 214
<211> LENGTH: 18
<212> TYPE: PRT
<213> ORGANISM: Artificial Sequence
<220> FEATURE:
```

```
<223> OTHER INFORMATION: Linker

<400> SEQUENCE: 214

Gly Ser Thr Ser Gly Gly Gly Ser Gly Gly Ser Gly Gly Gly
1               5                   10                  15

Ser Ser

<210> SEQ ID NO 215
<211> LENGTH: 14
<212> TYPE: PRT
<213> ORGANISM: Artificial Sequence
<220> FEATURE:
<223> OTHER INFORMATION: Linker

<400> SEQUENCE: 215

Glu Gly Lys Ser Ser Gly Ser Gly Ser Glu Ser Lys Val Asp
1               5                   10

<210> SEQ ID NO 216
<211> LENGTH: 18
<212> TYPE: PRT
<213> ORGANISM: Artificial Sequence
<220> FEATURE:
<223> OTHER INFORMATION: Linker

<400> SEQUENCE: 216

Lys Glu Ser Gly Ser Val Ser Ser Glu Gln Leu Ala Gln Phe Arg Ser
1               5                   10                  15

Leu Asp

<210> SEQ ID NO 217
<211> LENGTH: 5
<212> TYPE: PRT
<213> ORGANISM: Artificial Sequence
<220> FEATURE:
<223> OTHER INFORMATION: Linker

<400> SEQUENCE: 217

Gly Gly Gly Gly Ser
1               5

<210> SEQ ID NO 218
<211> LENGTH: 494
<212> TYPE: PRT
<213> ORGANISM: Artificial Sequence
<220> FEATURE:
<223> OTHER INFORMATION: SARS-CoV-2
      Synthetic sequence S309-scFab (H-L)

<400> SEQUENCE: 218

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Asn Gly Asn Thr Asn Tyr Ala Gln Lys Phe
        50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95
```

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Arg
        210                 215                 220

Val Glu Pro Lys Ser Cys Gly Gly Gly Ser Gly Gly Gly Gly Ser
225                 230                 235                 240

Gly Gly Gly Gly Ser Gly Gly Gly Ser Gly Gly Gly Gly Ser Gly
                245                 250                 255

Gly Gly Gly Ser Gly Gly Gly Ser Gly Gly Gly Gly Ser Gly Gly
            260                 265                 270

Gly Gly Ser Gly Gly Gly Ser Glu Ile Val Leu Thr Gln Ser Pro
        275                 280                 285

Gly Thr Leu Ser Leu Ser Pro Gly Glu Arg Ala Thr Leu Ser Cys Arg
290                 295                 300

Ala Ser Gln Thr Val Ser Ser Thr Ser Leu Ala Trp Tyr Gln Gln Lys
305                 310                 315                 320

Pro Gly Gln Ala Pro Arg Leu Leu Ile Tyr Gly Ala Ser Ser Arg Ala
                325                 330                 335

Thr Gly Ile Pro Asp Arg Phe Ser Gly Ser Gly Ser Gly Thr Asp Phe
                340                 345                 350

Thr Leu Thr Ile Ser Arg Leu Glu Pro Glu Asp Phe Ala Val Tyr Tyr
            355                 360                 365

Cys Gln Gln His Asp Thr Ser Leu Thr Phe Gly Gly Gly Thr Lys Val
        370                 375                 380

Glu Ile Lys Arg Thr Val Ala Ala Pro Ser Val Phe Ile Phe Pro Pro
385                 390                 395                 400

Ser Asp Glu Gln Leu Lys Ser Gly Thr Ala Ser Val Val Cys Leu Leu
                405                 410                 415

Asn Asn Phe Tyr Pro Arg Glu Ala Lys Val Gln Trp Lys Val Asp Asn
                420                 425                 430

Ala Leu Gln Ser Gly Asn Ser Gln Glu Ser Val Thr Glu Gln Asp Ser
            435                 440                 445

Lys Asp Ser Thr Tyr Ser Leu Ser Ser Thr Leu Thr Leu Ser Lys Ala
        450                 455                 460

Asp Tyr Glu Lys His Lys Val Tyr Ala Cys Glu Val Thr His Gln Gly
465                 470                 475                 480

Leu Ser Ser Pro Val Thr Lys Ser Phe Asn Arg Gly Glu Cys
                485                 490

<210> SEQ ID NO 219
<211> LENGTH: 494
<212> TYPE: PRT

<213> ORGANISM: Artificial Sequence
<220> FEATURE:
<223> OTHER INFORMATION: SARS-CoV-2 S309-scFab (L-H)

<400> SEQUENCE: 219

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Thr
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Asp Thr Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Gly Gly Gly Gly Ser Gly Gly Gly Gly Ser Gly
225                 230                 235                 240

Gly Gly Gly Ser Gly Gly Gly Gly Ser Gly Gly Gly Gly Ser Gly Gly
                245                 250                 255

Gly Gly Ser Gly Gly Gly Gly Ser Gln Val Gln Leu Val Gln Ser Gly
            260                 265                 270

Ala Glu Val Lys Lys Pro Gly Ala Ser Val Lys Val Ser Cys Lys Ala
        275                 280                 285

Ser Gly Tyr Pro Phe Thr Ser Tyr Gly Ile Ser Trp Val Arg Gln Ala
    290                 295                 300

Pro Gly Gln Gly Leu Glu Trp Met Gly Trp Ile Ser Thr Tyr Asn Gly
305                 310                 315                 320

Asn Thr Asn Tyr Ala Gln Lys Phe Gln Gly Arg Val Thr Met Thr Thr
                325                 330                 335

Asp Thr Ser Thr Thr Thr Gly Tyr Met Glu Leu Arg Arg Leu Arg Ser
            340                 345                 350

Asp Asp Thr Ala Val Tyr Tyr Cys Ala Arg Asp Tyr Thr Arg Gly Ala
        355                 360                 365

Trp Phe Gly Glu Ser Leu Ile Gly Gly Phe Asp Asn Trp Gly Gln Gly
    370                 375                 380

Thr Leu Val Thr Val Ser Ser Ala Ser Thr Lys Gly Pro Ser Val Phe
```

```
                385                 390                 395                 400
Pro Leu Ala Pro Ser Ser Lys Ser Thr Ser Gly Gly Thr Ala Ala Leu
                    405                 410                 415

Gly Cys Leu Val Lys Asp Tyr Phe Pro Glu Pro Val Thr Val Ser Trp
                420                 425                 430

Asn Ser Gly Ala Leu Thr Ser Gly Val His Thr Phe Pro Ala Val Leu
                435                 440                 445

Gln Ser Ser Gly Leu Tyr Ser Leu Ser Ser Val Val Thr Val Pro Ser
            450                 455                 460

Ser Ser Leu Gly Thr Gln Thr Tyr Ile Cys Asn Val Asn His Lys Pro
465                 470                 475                 480

Ser Asn Thr Lys Val Asp Lys Arg Val Glu Pro Lys Ser Cys
                485                 490

<210> SEQ ID NO 220
<211> LENGTH: 249
<212> TYPE: PRT
<213> ORGANISM: Artificial Sequence
<220> FEATURE:
<223> OTHER INFORMATION: SARS-CoV-2 S309-scFv (VH-VL)

<400> SEQUENCE: 220

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Asn Gly Asn Thr Asn Tyr Ala Gln Lys Phe
        50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Thr Ala Val Tyr Tyr Cys
                85                  90                  95

Ala Arg Asp Tyr Thr Arg Gly Ala Trp Phe Gly Glu Ser Leu Ile Gly
                100                 105                 110

Gly Phe Asp Asn Trp Gly Gln Gly Thr Leu Val Thr Val Ser Ser Gly
            115                 120                 125

Gly Gly Gly Ser Gly Gly Gly Gly Ser Gly Gly Gly Gly Ser Glu Ile
        130                 135                 140

Val Leu Thr Gln Ser Pro Gly Thr Leu Ser Leu Ser Pro Gly Glu Arg
145                 150                 155                 160

Ala Thr Leu Ser Cys Arg Ala Ser Gln Thr Val Ser Ser Thr Ser Leu
                165                 170                 175

Ala Trp Tyr Gln Gln Lys Pro Gly Gln Ala Pro Arg Leu Leu Ile Tyr
                180                 185                 190

Gly Ala Ser Ser Arg Ala Thr Gly Ile Pro Asp Arg Phe Ser Gly Ser
            195                 200                 205

Gly Ser Gly Thr Asp Phe Thr Leu Thr Ile Ser Arg Leu Glu Pro Glu
        210                 215                 220

Asp Phe Ala Val Tyr Tyr Cys Gln Gln His Asp Thr Ser Leu Thr Phe
225                 230                 235                 240

Gly Gly Gly Thr Lys Val Glu Ile Lys
                245
```

<210> SEQ ID NO 221
<211> LENGTH: 249
<212> TYPE: PRT
<213> ORGANISM: Artificial Sequence
<220> FEATURE:
<223> OTHER INFORMATION: SARS-CoV-2 S309-scFv (VL-VH)

<400> SEQUENCE: 221

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Thr
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Asp Thr Ser Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gln Val Gln Leu Val Gln
        115                 120                 125

Ser Gly Ala Glu Val Lys Lys Pro Gly Ala Ser Val Lys Val Ser Cys
    130                 135                 140

Lys Ala Ser Gly Tyr Pro Phe Thr Ser Tyr Gly Ile Ser Trp Val Arg
145                 150                 155                 160

Gln Ala Pro Gly Gln Gly Leu Glu Trp Met Gly Trp Ile Ser Thr Tyr
                165                 170                 175

Asn Gly Asn Thr Asn Tyr Ala Gln Lys Phe Gln Gly Arg Val Thr Met
            180                 185                 190

Thr Thr Asp Thr Ser Thr Thr Gly Tyr Met Glu Leu Arg Arg Leu
        195                 200                 205

Arg Ser Asp Asp Thr Ala Val Tyr Tyr Cys Ala Arg Asp Tyr Thr Arg
    210                 215                 220

Gly Ala Trp Phe Gly Glu Ser Leu Ile Gly Gly Phe Asp Asn Trp Gly
225                 230                 235                 240

Gln Gly Thr Leu Val Thr Val Ser Ser
                245
```

<210> SEQ ID NO 222
<211> LENGTH: 518
<212> TYPE: PRT
<213> ORGANISM: Artificial Sequence
<220> FEATURE:
<223> OTHER INFORMATION: SARS-CoV-2 S309-scFv (VH-VL)-(VH-VL)

<400> SEQUENCE: 222

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Asn Gly Asn Thr Asn Tyr Ala Gln Lys Phe
    50                  55                  60
```

```
Gln Gly Arg Val Thr Met Thr Thr Asp Thr Ser Thr Thr Thr Gly Tyr
 65                  70                  75                  80

Met Glu Leu Arg Arg Leu Arg Ser Asp Thr Ala Val Tyr Tyr Cys
                 85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser Gly
            115                 120                 125

Gly Gly Gly Ser Gly Gly Gly Ser Gly Gly Gly Ser Glu Ile
            130                 135                 140

Val Leu Thr Gln Ser Pro Gly Thr Leu Ser Leu Ser Pro Gly Glu Arg
145                 150                 155                 160

Ala Thr Leu Ser Cys Arg Ala Ser Gln Thr Val Ser Thr Ser Leu
                165                 170                 175

Ala Trp Tyr Gln Gln Lys Pro Gly Gln Ala Pro Arg Leu Leu Ile Tyr
            180                 185                 190

Gly Ala Ser Ser Arg Ala Thr Gly Ile Pro Asp Arg Phe Ser Gly Ser
            195                 200                 205

Gly Ser Gly Thr Asp Phe Thr Leu Thr Ile Ser Arg Leu Glu Pro Glu
            210                 215                 220

Asp Phe Ala Val Tyr Tyr Cys Gln Gln His Asp Thr Ser Leu Thr Phe
225                 230                 235                 240

Gly Gly Gly Thr Lys Val Glu Ile Lys Gly Gly Gly Ser Gly Gly
                245                 250                 255

Gly Gly Ser Gly Gly Gly Ser Gly Gly Gly Ser Gln Val Gln
            260                 265                 270

Leu Val Gln Ser Gly Ala Glu Val Lys Lys Pro Gly Ala Ser Val Lys
            275                 280                 285

Val Ser Cys Lys Ala Ser Gly Tyr Pro Phe Thr Ser Tyr Gly Ile Ser
            290                 295                 300

Trp Val Arg Gln Ala Pro Gly Gln Gly Leu Glu Trp Met Gly Trp Ile
305                 310                 315                 320

Ser Thr Tyr Asn Gly Asn Thr Asn Tyr Ala Gln Lys Phe Gln Gly Arg
                325                 330                 335

Val Thr Met Thr Thr Asp Thr Ser Thr Thr Thr Gly Tyr Met Glu Leu
            340                 345                 350

Arg Arg Leu Arg Ser Asp Asp Thr Ala Val Tyr Tyr Cys Ala Arg Asp
                355                 360                 365

Tyr Thr Arg Gly Ala Trp Phe Gly Glu Ser Leu Ile Gly Gly Phe Asp
            370                 375                 380

Asn Trp Gly Gln Gly Thr Leu Val Thr Val Ser Ser Gly Gly Gly
385                 390                 395                 400

Ser Gly Gly Gly Gly Ser Gly Gly Gly Ser Glu Ile Val Leu Thr
            405                 410                 415

Gln Ser Pro Gly Thr Leu Ser Leu Ser Pro Gly Glu Arg Ala Thr Leu
            420                 425                 430

Ser Cys Arg Ala Ser Gln Thr Val Ser Thr Ser Leu Ala Trp Tyr
            435                 440                 445

Gln Gln Lys Pro Gly Gln Ala Pro Arg Leu Leu Ile Tyr Gly Ala Ser
            450                 455                 460

Ser Arg Ala Thr Gly Ile Pro Asp Arg Phe Ser Gly Ser Gly Ser Gly
465                 470                 475                 480

Thr Asp Phe Thr Leu Thr Ile Ser Arg Leu Glu Pro Glu Asp Phe Ala
```

```
                    485                 490                 495
Val Tyr Tyr Cys Gln Gln His Asp Thr Ser Leu Thr Phe Gly Gly Gly
                500                 505                 510

Thr Lys Val Glu Ile Lys
        515

<210> SEQ ID NO 223
<211> LENGTH: 518
<212> TYPE: PRT
<213> ORGANISM: Artificial Sequence
<220> FEATURE:
<223> OTHER INFORMATION: SARS-CoV-2 S309-scFv-(VH-VL)-(VL-VH)

<400> SEQUENCE: 223

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Asn Gly Asn Thr Asn Tyr Ala Gln Lys Phe
        50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
                100                 105                 110

Gly Phe Asp Asn Trp Gly Gln Gly Thr Leu Val Thr Val Ser Ser Gly
            115                 120                 125

Gly Gly Gly Ser Gly Gly Gly Ser Gly Gly Gly Ser Glu Ile
        130                 135                 140

Val Leu Thr Gln Ser Pro Gly Thr Leu Ser Leu Ser Pro Gly Glu Arg
145                 150                 155                 160

Ala Thr Leu Ser Cys Arg Ala Ser Gln Thr Val Ser Ser Thr Ser Leu
                165                 170                 175

Ala Trp Tyr Gln Gln Lys Pro Gly Gln Ala Pro Arg Leu Leu Ile Tyr
            180                 185                 190

Gly Ala Ser Ser Arg Ala Thr Gly Ile Pro Asp Arg Phe Ser Gly Ser
        195                 200                 205

Gly Ser Gly Thr Asp Phe Thr Leu Thr Ile Ser Arg Leu Glu Pro Glu
    210                 215                 220

Asp Phe Ala Val Tyr Tyr Cys Gln Gln His Asp Thr Ser Leu Thr Phe
225                 230                 235                 240

Gly Gly Gly Thr Lys Val Glu Ile Lys Gly Gly Gly Ser Gly Gly
                245                 250                 255

Gly Gly Ser Gly Gly Gly Ser Gly Gly Gly Ser Glu Ile Val
            260                 265                 270

Leu Thr Gln Ser Pro Gly Thr Leu Ser Leu Ser Pro Gly Glu Arg Ala
        275                 280                 285

Thr Leu Ser Cys Arg Ala Ser Gln Thr Val Ser Ser Thr Ser Leu Ala
    290                 295                 300

Trp Tyr Gln Gln Lys Pro Gly Gln Ala Pro Arg Leu Leu Ile Tyr Gly
305                 310                 315                 320

Ala Ser Ser Arg Ala Thr Gly Ile Pro Asp Arg Phe Ser Gly Ser Gly
```

-continued

```
                    325                 330                 335
        Ser Gly Thr Asp Phe Thr Leu Thr Ile Ser Arg Leu Glu Pro Glu Asp
                340                 345                 350

Phe Ala Val Tyr Tyr Cys Gln Gln His Asp Thr Ser Leu Thr Phe Gly
                355                 360                 365

Gly Gly Thr Lys Val Glu Ile Lys Gly Gly Gly Ser Gly Gly Gly
                370                 375                 380

Gly Ser Gly Gly Gly Ser Gln Val Gln Leu Val Gln Ser Gly Ala
        385                 390                 395                 400

Glu Val Lys Lys Pro Gly Ala Ser Val Lys Val Ser Cys Lys Ala Ser
                        405                 410                 415

Gly Tyr Pro Phe Thr Ser Tyr Gly Ile Ser Trp Val Arg Gln Ala Pro
                    420                 425                 430

Gly Gln Gly Leu Glu Trp Met Gly Trp Ile Ser Thr Tyr Asn Gly Asn
                    435                 440                 445

Thr Asn Tyr Ala Gln Lys Phe Gln Gly Arg Val Thr Met Thr Thr Asp
                450                 455                 460

Thr Ser Thr Thr Thr Gly Tyr Met Glu Leu Arg Arg Leu Arg Ser Asp
        465                 470                 475                 480

Asp Thr Ala Val Tyr Tyr Cys Ala Arg Asp Tyr Arg Gly Ala Trp
                        485                 490                 495

Phe Gly Glu Ser Leu Ile Gly Gly Phe Asp Asn Trp Gly Gln Gly Thr
                    500                 505                 510

Leu Val Thr Val Ser Ser
                515

<210> SEQ ID NO 224
<211> LENGTH: 518
<212> TYPE: PRT
<213> ORGANISM: Artificial Sequence
<220> FEATURE:
<223> OTHER INFORMATION: SARS-CoV-2 S309-scFv-(VL-VH)-(VH-VL)

<400> SEQUENCE: 224

Glu Ile Val Leu Thr Gln Ser Pro Gly Thr Leu Ser Leu Ser Pro Gly
        1               5                   10                  15

Glu Arg Ala Thr Leu Ser Cys Arg Ala Ser Gln Thr Val Ser Ser Thr
                    20                  25                  30

Ser Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
        65                  70                  75                  80

Pro Glu Asp Phe Ala Val Tyr Tyr Cys Gln Gln His Asp Thr Ser Leu
                        85                  90                  95

Thr Phe Gly Gly Gly Thr Lys Val Glu Ile Lys Gly Gly Gly Gly Ser
                    100                 105                 110

Gly Gly Gly Gly Ser Gly Gly Gly Gly Ser Gln Val Gln Leu Val Gln
                115                 120                 125

Ser Gly Ala Glu Val Lys Lys Pro Gly Ala Ser Val Lys Val Ser Cys
                130                 135                 140

Lys Ala Ser Gly Tyr Pro Phe Thr Ser Tyr Gly Ile Ser Trp Val Arg
        145                 150                 155                 160

Gln Ala Pro Gly Gln Gly Leu Glu Trp Met Gly Trp Ile Ser Thr Tyr
```

```
                    165                 170                 175
Asn Gly Asn Thr Asn Tyr Ala Gln Lys Phe Gln Gly Arg Val Thr Met
                180                 185                 190

Thr Thr Asp Thr Ser Thr Thr Thr Gly Tyr Met Glu Leu Arg Arg Leu
            195                 200                 205

Arg Ser Asp Asp Thr Ala Val Tyr Tyr Cys Ala Arg Asp Tyr Thr Arg
        210                 215                 220

Gly Ala Trp Phe Gly Glu Ser Leu Ile Gly Gly Phe Asp Asn Trp Gly
225                 230                 235                 240

Gln Gly Thr Leu Val Thr Val Ser Ser Gly Gly Gly Ser Gly Gly Gly
                245                 250                 255

Gly Gly Ser Gly Gly Gly Ser Gly Gly Gly Ser Gln Val Gln
                260                 265                 270

Leu Val Gln Ser Gly Ala Glu Val Lys Lys Pro Gly Ala Ser Val Lys
                275                 280                 285

Val Ser Cys Lys Ala Ser Gly Tyr Pro Phe Thr Ser Tyr Gly Ile Ser
            290                 295                 300

Trp Val Arg Gln Ala Pro Gly Gln Gly Leu Glu Trp Met Gly Trp Ile
305                 310                 315                 320

Ser Thr Tyr Asn Gly Asn Thr Asn Tyr Ala Gln Lys Phe Gln Gly Arg
                325                 330                 335

Val Thr Met Thr Thr Asp Thr Ser Thr Thr Thr Gly Tyr Met Glu Leu
            340                 345                 350

Arg Arg Leu Arg Ser Asp Asp Thr Ala Val Tyr Tyr Cys Ala Arg Asp
        355                 360                 365

Tyr Thr Arg Gly Ala Trp Phe Gly Glu Ser Leu Ile Gly Gly Phe Asp
370                 375                 380

Asn Trp Gly Gln Gly Thr Leu Val Thr Val Ser Ser Gly Gly Gly Gly
385                 390                 395                 400

Ser Gly Gly Gly Gly Ser Gly Gly Gly Gly Ser Glu Ile Val Leu Thr
                405                 410                 415

Gln Ser Pro Gly Thr Leu Ser Leu Ser Pro Gly Glu Arg Ala Thr Leu
                420                 425                 430

Ser Cys Arg Ala Ser Gln Thr Val Ser Ser Thr Ser Leu Ala Trp Tyr
            435                 440                 445

Gln Gln Lys Pro Gly Gln Ala Pro Arg Leu Leu Ile Tyr Gly Ala Ser
                450                 455                 460

Ser Arg Ala Thr Gly Ile Pro Asp Arg Phe Ser Gly Ser Gly Ser Gly
465                 470                 475                 480

Thr Asp Phe Thr Leu Thr Ile Ser Arg Leu Glu Pro Glu Asp Phe Ala
                485                 490                 495

Val Tyr Tyr Cys Gln Gln His Asp Thr Ser Leu Thr Phe Gly Gly Gly
            500                 505                 510

Thr Lys Val Glu Ile Lys
        515

<210> SEQ ID NO 225
<211> LENGTH: 518
<212> TYPE: PRT
<213> ORGANISM: Artificial Sequence
<220> FEATURE:
<223> OTHER INFORMATION: Synthetic sequence SARS-CoV-2
      S309-scFv-(VL-VH)-(VL-VH)

<400> SEQUENCE: 225
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Thr
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Asp Thr Ser Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gln Val Gln Leu Val Gln
        115                 120                 125

Ser Gly Ala Glu Val Lys Lys Pro Gly Ala Ser Val Lys Val Ser Cys
    130                 135                 140

Lys Ala Ser Gly Tyr Pro Phe Thr Ser Tyr Gly Ile Ser Trp Val Arg
145                 150                 155                 160

Gln Ala Pro Gly Gln Gly Leu Glu Trp Met Gly Trp Ile Ser Thr Tyr
            165                 170                 175

Asn Gly Asn Thr Asn Tyr Ala Gln Lys Phe Gln Gly Arg Val Thr Met
        180                 185                 190

Thr Thr Asp Thr Ser Thr Thr Thr Gly Tyr Met Glu Leu Arg Arg Leu
    195                 200                 205

Arg Ser Asp Asp Thr Ala Val Tyr Tyr Cys Ala Arg Asp Tyr Thr Arg
210                 215                 220

Gly Ala Trp Phe Gly Glu Ser Leu Ile Gly Gly Phe Asp Asn Trp Gly
225                 230                 235                 240

Gln Gly Thr Leu Val Thr Val Ser Ser Gly Gly Gly Ser Gly Gly
            245                 250                 255

Gly Gly Ser Gly Gly Gly Gly Ser Gly Gly Gly Gly Ser Glu Ile Val
        260                 265                 270

Leu Thr Gln Ser Pro Gly Thr Leu Ser Leu Ser Pro Gly Glu Arg Ala
    275                 280                 285

Thr Leu Ser Cys Arg Ala Ser Gln Thr Val Ser Ser Thr Ser Leu Ala
        290                 295                 300

Trp Tyr Gln Gln Lys Pro Gly Gln Ala Pro Arg Leu Leu Ile Tyr Gly
305                 310                 315                 320

Ala Ser Ser Arg Ala Thr Gly Ile Pro Asp Arg Phe Ser Gly Ser Gly
            325                 330                 335

Ser Gly Thr Asp Phe Thr Leu Thr Ile Ser Arg Leu Glu Pro Glu Asp
        340                 345                 350

Phe Ala Val Tyr Tyr Cys Gln Gln His Asp Thr Ser Leu Thr Phe Gly
    355                 360                 365

Gly Gly Thr Lys Val Glu Ile Lys Gly Gly Gly Gly Ser Gly Gly Gly
    370                 375                 380

Gly Ser Gly Gly Gly Gly Ser Gln Val Gln Leu Val Gln Ser Gly Ala
385                 390                 395                 400

Glu Val Lys Lys Pro Gly Ala Ser Val Lys Val Ser Cys Lys Ala Ser
            405                 410                 415

Gly Tyr Pro Phe Thr Ser Tyr Gly Ile Ser Trp Val Arg Gln Ala Pro
```

```
                420             425             430
Gly Gln Gly Leu Glu Trp Met Gly Trp Ile Ser Thr Tyr Asn Gly Asn
            435             440             445

Thr Asn Tyr Ala Gln Lys Phe Gln Gly Arg Val Thr Met Thr Thr Asp
        450             455             460

Thr Ser Thr Thr Thr Gly Tyr Met Glu Leu Arg Arg Leu Arg Ser Asp
465             470             475             480

Asp Thr Ala Val Tyr Tyr Cys Ala Arg Asp Tyr Thr Arg Gly Ala Trp
                485             490             495

Phe Gly Glu Ser Leu Ile Gly Gly Phe Asp Asn Trp Gly Gln Gly Thr
            500             505             510

Leu Val Thr Val Ser Ser
            515

<210> SEQ ID NO 226
<211> LENGTH: 494
<212> TYPE: PRT
<213> ORGANISM: Artificial Sequence
<220> FEATURE:
<223> OTHER INFORMATION: Synthetic sequence SARS-CoV-2 S309-scFab-(H-L)
      v1.1

<400> SEQUENCE: 226

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Gln Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Gly Gly Gly Gly Ser Gly Gly Gly Gly Ser
225                 230                 235                 240

Gly Gly Gly Gly Ser Gly Gly Gly Ser Gly Gly Gly Gly Ser Gly
                245                 250                 255
```

```
Gly Gly Gly Ser Gly Gly Gly Ser Gly Gly Gly Ser Gly Gly
            260             265             270

Gly Gly Ser Gly Gly Gly Ser Glu Ile Val Leu Thr Gln Ser Pro
        275             280             285

Gly Thr Leu Ser Leu Ser Pro Gly Glu Arg Ala Thr Leu Ser Cys Arg
    290             295             300

Ala Ser Gln Thr Val Ser Ser Thr Ser Leu Ala Trp Tyr Gln Gln Lys
305             310             315             320

Pro Gly Gln Ala Pro Arg Leu Leu Ile Tyr Gly Ala Ser Ser Arg Ala
            325             330             335

Thr Gly Ile Pro Asp Arg Phe Ser Gly Ser Gly Ser Gly Thr Asp Phe
            340             345             350

Thr Leu Thr Ile Ser Arg Leu Glu Pro Glu Asp Phe Ala Val Tyr Tyr
        355             360             365

Cys Gln Gln His Asp Thr Ser Leu Thr Phe Gly Gly Gly Thr Lys Val
    370             375             380

Glu Ile Lys Arg Thr Val Ala Ala Pro Ser Val Phe Ile Phe Pro Pro
385             390             395             400

Ser Asp Glu Gln Leu Lys Ser Gly Thr Ala Ser Val Val Cys Leu Leu
            405             410             415

Asn Asn Phe Tyr Pro Arg Glu Ala Lys Val Gln Trp Lys Val Asp Asn
            420             425             430

Ala Leu Gln Ser Gly Asn Ser Gln Glu Ser Val Thr Glu Gln Asp Ser
        435             440             445

Lys Asp Ser Thr Tyr Ser Leu Ser Ser Thr Leu Thr Leu Ser Lys Ala
    450             455             460

Asp Tyr Glu Lys His Lys Val Tyr Ala Cys Glu Val Thr His Gln Gly
465             470             475             480

Leu Ser Ser Pro Val Thr Lys Ser Phe Asn Arg Gly Glu Cys
            485             490

<210> SEQ ID NO 227
<211> LENGTH: 494
<212> TYPE: PRT
<213> ORGANISM: Artificial Sequence
<220> FEATURE:
<223> OTHER INFORMATION: Synthetic sequence SARS-CoV-2 S309-scFab-(L-H)
      v1.1

<400> SEQUENCE: 227

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Thr
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Asp Thr Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Ser Gly Gly Gly Gly Ser
210                 215                 220

Gly Gly Gly Gly Ser Gly Gly Gly Ser Gly Gly Gly Ser Gly
225                 230                 235                 240

Gly Gly Ser Gly Gly Gly Ser Gly Gly Gly Ser Gly Gly
                245                 250                 255

Gly Gly Ser Gly Gly Gly Ser Gln Val Gln Leu Val Gln Ser Gly
            260                 265                 270

Ala Glu Val Lys Lys Pro Gly Ala Ser Val Lys Val Ser Cys Lys Ala
        275                 280                 285

Ser Gly Tyr Pro Phe Thr Ser Tyr Gly Ile Ser Trp Val Arg Gln Ala
        290                 295                 300

Pro Gly Gln Gly Leu Glu Trp Met Gly Trp Ile Ser Thr Tyr Gln Gly
305                 310                 315                 320

Asn Thr Asn Tyr Ala Gln Lys Phe Gln Gly Arg Val Thr Met Thr Thr
                325                 330                 335

Asp Thr Ser Thr Thr Thr Gly Tyr Met Glu Leu Arg Arg Leu Arg Ser
            340                 345                 350

Asp Asp Thr Ala Val Tyr Tyr Cys Ala Arg Asp Tyr Thr Arg Gly Ala
            355                 360                 365

Trp Phe Gly Glu Ser Leu Ile Gly Gly Phe Asp Asn Trp Gly Gln Gly
        370                 375                 380

Thr Leu Val Thr Val Ser Ser Ala Ser Thr Lys Gly Pro Ser Val Phe
385                 390                 395                 400

Pro Leu Ala Pro Ser Ser Lys Ser Thr Ser Gly Gly Thr Ala Ala Leu
                405                 410                 415

Gly Cys Leu Val Lys Asp Tyr Phe Pro Glu Pro Val Thr Val Ser Trp
            420                 425                 430

Asn Ser Gly Ala Leu Thr Ser Gly Val His Thr Phe Pro Ala Val Leu
        435                 440                 445

Gln Ser Ser Gly Leu Tyr Ser Leu Ser Ser Val Val Thr Val Pro Ser
450                 455                 460

Ser Ser Leu Gly Thr Gln Thr Tyr Ile Cys Asn Val Asn His Lys Pro
465                 470                 475                 480

Ser Asn Thr Lys Val Asp Lys Arg Val Glu Pro Lys Ser Cys
                485                 490
```

<210> SEQ ID NO 228
<211> LENGTH: 249
<212> TYPE: PRT
<213> ORGANISM: Artificial Sequence
<220> FEATURE:
<223> OTHER INFORMATION: Synthetic sequence SARS-CoV-2 S309-scFv-(VH-VL)
       v1.1

<400> SEQUENCE: 228

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Pro Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Thr Tyr Gln Gly Asn Thr Asn Tyr Ala Gln Lys Phe
    50                  55                  60
Gln Gly Arg Val Thr Met Thr Thr Asp Thr Ser Thr Thr Thr Gly Tyr
65                  70                  75                  80
Met Glu Leu Arg Arg Leu Arg Ser Asp Asp Thr Ala Val Tyr Tyr Cys
                85                  90                  95
Ala Arg Asp Tyr Thr Arg Gly Ala Trp Phe Gly Glu Ser Leu Ile Gly
            100                 105                 110
Gly Phe Asp Asn Trp Gly Gln Gly Thr Leu Val Thr Val Ser Ser Gly
        115                 120                 125
Gly Gly Gly Ser Gly Gly Gly Ser Gly Gly Gly Ser Glu Ile
    130                 135                 140
Val Leu Thr Gln Ser Pro Gly Thr Leu Ser Leu Ser Pro Gly Glu Arg
145                 150                 155                 160
Ala Thr Leu Ser Cys Arg Ala Ser Gln Thr Val Ser Ser Thr Ser Leu
                165                 170                 175
Ala Trp Tyr Gln Gln Lys Pro Gly Gln Ala Pro Arg Leu Leu Ile Tyr
            180                 185                 190
Gly Ala Ser Ser Arg Ala Thr Gly Ile Pro Asp Arg Phe Ser Gly Ser
        195                 200                 205
Gly Ser Gly Thr Asp Phe Thr Leu Thr Ile Ser Arg Leu Glu Pro Glu
    210                 215                 220
Asp Phe Ala Val Tyr Tyr Cys Gln Gln His Asp Thr Ser Leu Thr Phe
225                 230                 235                 240
Gly Gly Gly Thr Lys Val Glu Ile Lys
                245
```

<210> SEQ ID NO 229
<211> LENGTH: 249
<212> TYPE: PRT
<213> ORGANISM: Artificial Sequence
<220> FEATURE:
<223> OTHER INFORMATION: Synthetic sequence SARS-CoV-2 S309-scFv-(VL-VH) v1.1

<400> SEQUENCE: 229

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Thr Val Ser Ser Thr
            20                  25                  30
Ser Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln His Asp Thr Ser Leu
                85                  90                  95
```

Thr Phe Gly Gly Gly Thr Lys Val Glu Ile Lys Gly Gly Gly Ser
                100                 105                 110

Gly Gly Gly Gly Ser Gly Gly Gly Ser Gln Val Gln Leu Val Gln
            115                 120                 125

Ser Gly Ala Glu Val Lys Lys Pro Gly Ala Ser Val Lys Val Ser Cys
        130                 135                 140

Lys Ala Ser Gly Tyr Pro Phe Thr Ser Tyr Gly Ile Ser Trp Val Arg
145                 150                 155                 160

Gln Ala Pro Gly Gln Gly Leu Glu Trp Met Gly Trp Ile Ser Thr Tyr
                165                 170                 175

Gln Gly Asn Thr Asn Tyr Ala Gln Lys Phe Gln Gly Arg Val Thr Met
                180                 185                 190

Thr Thr Asp Thr Ser Thr Thr Thr Gly Tyr Met Glu Leu Arg Arg Leu
            195                 200                 205

Arg Ser Asp Asp Thr Ala Val Tyr Tyr Cys Ala Arg Asp Tyr Thr Arg
        210                 215                 220

Gly Ala Trp Phe Gly Glu Ser Leu Ile Gly Gly Phe Asp Asn Trp Gly
225                 230                 235                 240

Gln Gly Thr Leu Val Thr Val Ser Ser
                245

<210> SEQ ID NO 230
<211> LENGTH: 518
<212> TYPE: PRT
<213> ORGANISM: Artificial Sequence
<220> FEATURE:
<223> OTHER INFORMATION: Synthetic sequence SARS-CoV-2
    S309-scFv-(VH-VL)-(VH-VL) v1.1

<400> SEQUENCE: 230

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Gln Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser Gly
        115                 120                 125

Gly Gly Gly Ser Gly Gly Gly Gly Ser Gly Gly Gly Gly Ser Glu Ile
    130                 135                 140

Val Leu Thr Gln Ser Pro Gly Thr Leu Ser Leu Ser Pro Gly Glu Arg
145                 150                 155                 160

Ala Thr Leu Ser Cys Arg Ala Ser Gln Thr Val Ser Ser Thr Ser Leu
                165                 170                 175

Ala Trp Tyr Gln Gln Lys Pro Gly Gln Ala Pro Arg Leu Leu Ile Tyr
            180                 185                 190

Gly Ala Ser Ser Arg Ala Thr Gly Ile Pro Asp Arg Phe Ser Gly Ser
        195                 200                 205

Gly Ser Gly Thr Asp Phe Thr Leu Thr Ile Ser Arg Leu Glu Pro Glu
            210                 215                 220

Asp Phe Ala Val Tyr Tyr Cys Gln Gln His Asp Thr Ser Leu Thr Phe
225                 230                 235                 240

Gly Gly Gly Thr Lys Val Glu Ile Lys Gly Gly Gly Ser Gly Gly
            245                 250                 255

Gly Gly Ser Gly Gly Gly Ser Gly Gly Gly Ser Gln Val Gln
            260                 265                 270

Leu Val Gln Ser Gly Ala Glu Val Lys Lys Pro Gly Ala Ser Val Lys
            275                 280                 285

Val Ser Cys Lys Ala Ser Gly Tyr Pro Phe Thr Ser Tyr Gly Ile Ser
            290                 295                 300

Trp Val Arg Gln Ala Pro Gly Gln Gly Leu Glu Trp Met Gly Trp Ile
305                 310                 315                 320

Ser Thr Tyr Gln Gly Asn Thr Asn Tyr Ala Gln Lys Phe Gln Gly Arg
            325                 330                 335

Val Thr Met Thr Thr Asp Thr Ser Thr Thr Gly Tyr Met Glu Leu
            340                 345                 350

Arg Arg Leu Arg Ser Asp Asp Thr Ala Val Tyr Tyr Cys Ala Arg Asp
            355                 360                 365

Tyr Thr Arg Gly Ala Trp Phe Gly Glu Ser Leu Ile Gly Gly Phe Asp
            370                 375                 380

Asn Trp Gly Gln Gly Thr Leu Val Thr Val Ser Ser G

-continued

```
                35                  40                  45
Gly Trp Ile Ser Thr Tyr Gln Gly Asn Thr Asn Tyr Ala Gln Lys Phe
 50                  55                  60

Gln Gly Arg Val Thr Met Thr Thr Asp Thr Ser Thr Thr Thr Gly Tyr
 65                  70                  75                  80

Met Glu Leu Arg Arg Leu Arg Ser Asp Asp Thr Ala Val Tyr Tyr Cys
                 85                  90                  95

Ala Arg Asp Tyr Thr Arg Gly Ala Trp Phe Gly Glu Ser Leu Ile Gly
                100                 105                 110

Gly Phe Asp Asn Trp Gly Gln Gly Thr Leu Val Thr Val Ser Ser Gly
            115                 120                 125

Gly Gly Gly Ser Gly Gly Gly Ser Gly Gly Gly Ser Glu Ile
            130                 135                 140

Val Leu Thr Gln Ser Pro Gly Thr Leu Ser Leu Ser Pro Gly Glu Arg
145                 150                 155                 160

Ala Thr Leu Ser Cys Arg Ala Ser Gln Thr Val Ser Ser Thr Ser Leu
                165                 170                 175

Ala Trp Tyr Gln Gln Lys Pro Gly Gln Ala Pro Arg Leu Leu Ile Tyr
            180                 185                 190

Gly Ala Ser Ser Arg Ala Thr Gly Ile Pro Asp Arg Phe Ser Gly Ser
            195                 200                 205

Gly Ser Gly Thr Asp Phe Thr Leu Thr Ile Ser Arg Leu Glu Pro Glu
        210                 215                 220

Asp Phe Ala Val Tyr Tyr Cys Gln Gln His Asp Thr Ser Leu Thr Phe
225                 230                 235                 240

Gly Gly Gly Thr Lys Val Glu Ile Lys Gly Gly Gly Ser Gly Gly
                245                 250                 255

Gly Gly Ser Gly Gly Gly Ser Gly Gly Gly Ser Glu Ile Val
            260                 265                 270

Leu Thr Gln Ser Pro Gly Thr Leu Ser Leu Ser Pro Gly Glu Arg Ala
        275                 280                 285

Thr Leu Ser Cys Arg Ala Ser Gln Thr Val Ser Ser Thr Ser Leu Ala
    290                 295                 300

Trp Tyr Gln Gln Lys Pro Gly Gln Ala Pro Arg Leu Leu Ile Tyr Gly
305                 310                 315                 320

Ala Ser Ser Arg Ala Thr Gly Ile Pro Asp Arg Phe Ser Gly Ser Gly
                325                 330                 335

Ser Gly Thr Asp Phe Thr Leu Thr Ile Ser Arg Leu Glu Pro Glu Asp
            340                 345                 350

Phe Ala Val Tyr Tyr Cys Gln Gln His Asp Thr Ser Leu Thr Phe Gly
            355                 360                 365

Gly Gly Thr Lys Val Glu Ile Lys Gly Gly Gly Ser Gly Gly Gly
        370                 375                 380

Gly Ser Gly Gly Gly Ser Gln Val Gln Leu Val Gln Ser Gly Ala
385                 390                 395                 400

Glu Val Lys Lys Pro Gly Ala Ser Val Lys Val Ser Cys Lys Ala Ser
                405                 410                 415

Gly Tyr Pro Phe Thr Ser Tyr Gly Ile Ser Trp Val Arg Gln Ala Pro
            420                 425                 430

Gly Gln Gly Leu Glu Trp Met Gly Trp Ile Ser Thr Tyr Gln Gly Asn
        435                 440                 445

Thr Asn Tyr Ala Gln Lys Phe Gln Gly Arg Val Thr Met Thr Thr Asp
    450                 455                 460
```

```
Thr Ser Thr Thr Thr Gly Tyr Met Glu Leu Arg Arg Leu Arg Ser Asp
465                 470                 475                 480

Asp Thr Ala Val Tyr Tyr Cys Ala Arg Asp Tyr Thr Arg Gly Ala Trp
                485                 490                 495

Phe Gly Glu Ser Leu Ile Gly Gly Phe Asp Asn Trp Gly Gln Gly Thr
            500                 505                 510

Leu Val Thr Val Ser Ser
        515
```

<210> SEQ ID NO 232
<211> LENGTH: 518
<212> TYPE: PRT
<213> ORGANISM: Artificial Sequence
<220> FEATURE:
<223> OTHER INFORMATION: Synthetic sequence SARS-CoV-2
      S309-scFv-(VH-VL)-(VL-VH) v1.1

<400> SEQUENCE: 232

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Thr
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Asp Thr Ser Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Val Gln
        115                 120                 125

Ser Gly Ala Glu Val Lys Lys Pro Gly Ala Ser Val Lys Val Ser Cys
130                 135                 140

Lys Ala Ser Gly Tyr Pro Phe Thr Ser Tyr Gly Ile Ser Trp Val Arg
145                 150                 155                 160

Gln Ala Pro Gly Gln Gly Leu Glu Trp Met Gly Trp Ile Ser Thr Tyr
                165                 170                 175

Gln Gly Asn Thr Asn Tyr Ala Gln Lys Phe Gln Gly Arg Val Thr Met
            180                 185                 190

Thr Thr Asp Thr Ser Thr Thr Thr Gly Tyr Met Glu Leu Arg Arg Leu
        195                 200                 205

Arg Ser Asp Asp Thr Ala Val Tyr Tyr Cys Ala Arg Asp Tyr Thr Arg
    210                 215                 220

Gly Ala Trp Phe Gly Glu Ser Leu Ile Gly Gly Phe Asp Asn Trp Gly
225                 230                 235                 240

Gln Gly Thr Leu Val Thr Val Ser Ser Gly Gly Gly Gly Ser Gly Gly
                245                 250                 255

Gly Gly Ser Gly Gly Gly Ser Gly Gly Gly Gly Ser Gln Val Gln
            260                 265                 270

Leu Val Gln Ser Gly Ala Glu Val Lys Lys Pro Gly Ala Ser Val Lys
        275                 280                 285

Val Ser Cys Lys Ala Ser Gly Tyr Pro Phe Thr Ser Tyr Gly Ile Ser
```

```
                        290                 295                 300
Trp Val Arg Gln Ala Pro Gly Gln Gly Leu Glu Trp Met Gly Trp Ile
305

Ser Gly Ala Glu Val Lys Lys Pro Gly Ala Ser Val Lys Val Ser Cys
130                 135                 140

Lys Ala Ser Gly Tyr Pro Phe Thr Ser Tyr Gly Ile Ser Trp Val Arg
145                 150                 155                 160

Gln Ala Pro Gly Gln Gly Leu Glu Trp Met Gly Trp Ile Ser Thr Tyr
                165                 170                 175

Gln Gly Asn Thr Asn Tyr Ala Gln Lys Phe Gln Gly Arg Val Thr Met
            180                 185                 190

Thr Thr Asp Thr Ser Thr Thr Thr Gly Tyr Met Glu Leu Arg Arg Leu
        195                 200                 205

Arg Ser Asp Asp Thr Ala Val Tyr Tyr Cys Ala Arg Asp Tyr Thr Arg
210                 215                 220

Gly Ala Trp Phe Gly Glu Ser Leu Ile Gly Gly Phe Asp Asn Trp Gly
225                 230                 235                 240

Gln Gly Thr Leu Val Thr Val Ser Ser Gly Gly Gly Ser Gly Gly
                245                 250                 255

Gly Gly Ser Gly Gly Gly Ser Gly Gly Gly Ser Glu Ile Val
            260                 265                 270

Leu Thr Gln Ser Pro Gly Thr Leu Ser Leu Ser Pro Gly Glu Arg Ala
                275                 280                 285

Thr Leu Ser Cys Arg Ala Ser Gln Thr Val Ser Ser Thr Ser Leu Ala
290                 295                 300

Trp Tyr Gln Gln Lys Pro Gly Gln Ala Pro Arg Leu Leu Ile Tyr Gly
305                 310                 315                 320

Ala Ser Ser Arg Ala Thr Gly Ile Pro Asp Arg Phe Ser Gly Ser Gly
                325                 330                 335

Ser Gly Thr Asp Phe Thr Leu Thr Ile Ser Arg Leu Glu Pro Glu Asp
            340                 345                 350

Phe Ala Val Tyr Tyr Cys Gln Gln His Asp Thr Ser Leu Thr Phe Gly
        355                 360                 365

Gly Gly Thr Lys Val Glu Ile Lys Gly Gly Gly Ser Gly Gly Gly
370                 375                 380

Gly Ser Gly Gly Gly Ser Gln Val Gln Leu Val Gln Ser Gly Ala
385                 390                 395                 400

Glu Val Lys Lys Pro Gly Ala Ser Val Lys Val Ser Cys Lys Ala Ser
                405                 410                 415

Gly Tyr Pro Phe Thr Ser Tyr Gly Ile Ser Trp Val Arg Gln Ala Pro
            420                 425                 430

Gly Gln Gly Leu Glu Trp Met Gly Trp Ile Ser Thr Tyr Gln Gly Asn
        435                 440                 445

Thr Asn Tyr Ala Gln Lys Phe Gln Gly Arg Val Thr Met Thr Thr Asp
450                 455                 460

Thr Ser Thr Thr Thr Gly Tyr Met Glu Leu Arg Arg Leu Arg Ser Asp
465                 470                 475                 480

Asp Thr Ala Val Tyr Tyr Cys Ala Arg Asp Tyr Thr Arg Gly Ala Trp
                485                 490                 495

Phe Gly Glu Ser Leu Ile Gly Gly Phe Asp Asn Trp Gly Gln Gly Thr
            500                 505                 510

Leu Val Thr Val Ser Ser
        515

<210> SEQ ID NO 234
<211> LENGTH: 114
<212> TYPE: PRT

<213> ORGANISM: Artificial Sequence
<220> FEATURE:
<223> OTHER INFORMATION: Synthetic sequence SARS-CoV-2 S300-v14 mAb VL
      (VK)

<400> SEQUENCE: 234

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ala Pro Gly Ile Thr Phe Gly Gln Gly Thr Arg Leu Glu
            100                 105                 110

Ile Lys

<210> SEQ ID NO 235
<211> LENGTH: 12
<212> TYPE: PRT
<213> ORGANISM: Artificial Sequence
<220> FEATURE:
<223> OTHER INFORMATION: Synthetic sequence SARS-CoV-2 S300-v14 mAb
      CDRL1

<400> SEQUENCE: 235

Gln Ser Val Leu Tyr Ser Ser Asn Asn Lys Asn Tyr
1               5                   10

<210> SEQ ID NO 236
<211> LENGTH: 3
<212> TYPE: PRT
<213> ORGANISM: Artificial Sequence
<220> FEATURE:
<223> OTHER INFORMATION: Synthetic sequence SARS-CoV-2 S300-v14 mAb
      CDRL2

<400> SEQUENCE: 236

Trp Ala Ser
1

<210> SEQ ID NO 237
<211> LENGTH: 10
<212> TYPE: PRT
<213> ORGANISM: Artificial Sequence
<220> FEATURE:
<223> OTHER INFORMATION: Synthetic sequence SARS-CoV-2 S300-v14 mAb
      CDRL3

<400> SEQUENCE: 237

Gln Gln Tyr Tyr Ser Ala Pro Gly Ile Thr
1               5                   10

<210> SEQ ID NO 238
<211> LENGTH: 343
<212> TYPE: DNA
<213> ORGANISM: Artificial Sequence
<220> FEATURE:
<223> OTHER INFORMATION: Synthetic sequence SARS-CoV2 S300-v14 mAb VL (VK)

<400> SEQUENCE: 238

```
gacatcgtga tgacccagtc tccagactca ctggctgtgt ctctgggcga gagggccacc    60
atcaactgta gtccagcca gagtgtttta tacagctcca acaataagaa ctacttagct   120
tggtaccagc agaaaccagg acagcctcct aagctgctca tttcctgggc ttctacccgg   180
gaatccgggg tccctgaccg attcagtggc agcgggtctg ggacagattt cactctcacc   240
atcagcagcc tgcaggctga agatgtggca gtttattact gtcaacaata ttatagtgct   300
cccgggatca ccttcggcca ggggacacga ctggagatta aac                    343
```

<210> SEQ ID NO 239
<211> LENGTH: 129
<212> TYPE: PRT
<213> ORGANISM: Artificial Sequence
<220> FEATURE:
<223> OTHER INFORMATION: Synthetic sequence SARS-CoV2 S307 mAb VH

<400> SEQUENCE: 239

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Val Thr Ser Gly
            20                  25                  30
Ser Tyr Tyr Trp Ser Trp Ile Arg Gln Pro Pro Gly Lys Gly Leu Glu
        35                  40                  45
Trp Ile Gly Tyr Met Tyr Tyr Ser Gly Ser Thr Asn Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Ala Gly Cys Thr Gly Ile Thr Cys Leu Arg Tyr Asp Tyr
            100                 105                 110
Tyr Tyr Gly Leu Asp Val Trp Gly Gln Gly Thr Thr Val Thr Val Ser
        115                 120                 125
Ser
```

<210> SEQ ID NO 240
<211> LENGTH: 10
<212> TYPE: PRT
<213> ORGANISM: Artificial Sequence
<220> FEATURE:
<223> OTHER INFORMATION: Synthetic sequence SARS-CoV2 S307 mAb CDRH1

<400> SEQUENCE: 240

```
Gly Gly Ser Val Thr Ser Gly Ser Tyr Tyr
1               5                   10
```

<210> SEQ ID NO 241
<211> LENGTH: 7
<212> TYPE: PRT
<213> ORGANISM: Artificial Sequence
<220> FEATURE:
<223> OTHER INFORMATION: Synthetic sequence SARS-CoV2 S307 mAb CDRH2

<400> SEQUENCE: 241

```
Met Tyr Tyr Ser Gly Ser Thr
1               5
```

```
<210> SEQ ID NO 242
<211> LENGTH: 21
<212> TYPE: PRT
<213> ORGANISM: Artificial Sequence
<220> FEATURE:
<223> OTHER INFORMATION: Synthetic sequence SARS-CoV2 S307 mAb CDRH3

<400> SEQUENCE: 242

Ala Arg Ala Gly Cys Thr Gly Ile Thr Cys Leu Arg Tyr Asp Tyr Tyr
1               5                   10                  15

Tyr Gly Leu Asp Val
            20

<210> SEQ ID NO 243
<211> LENGTH: 108
<212> TYPE: PRT
<213> ORGANISM: Artificial Sequence
<220> FEATURE:
<223> OTHER INFORMATION: Synthetic sequence SARS-CoV2 S307 mAb VL(VK)

<400> SEQUENCE: 243

Glu Ile Val Leu Thr Gln Ser Pro Gly Thr Leu Ser Leu Ser Pro Gly
1               5                   10                  15

Lys Arg Ala Thr Leu Ser Cys Arg Ala Ser Gln Ser Val Ser Ser Ser
            20                  25                  30

Tyr Leu Ala Trp Tyr Gln Gln Arg Pro Gly Gln Ala Pro Arg Leu Leu
        35                  40                  45

Ile Tyr Gly Ala Ser Ser Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ser
                85                  90                  95

Trp Thr Phe Gly Gln Gly Thr Lys Val Glu Ile Lys
            100                 105

<210> SEQ ID NO 244
<211> LENGTH: 7
<212> TYPE: PRT
<213> ORGANISM: Artificial Sequence
<220> FEATURE:
<223> OTHER INFORMATION: Synthetic sequence SARS-CoV2 S307 mAb CDRL1

<400> SEQUENCE: 244

Gln Ser Val Ser Ser Ser Tyr
1               5

<210> SEQ ID NO 245
<211> LENGTH: 3
<212> TYPE: PRT
<213> ORGANISM: Artificial Sequence
<220> FEATURE:
<223> OTHER INFORMATION: Synthetic sequence SARS-CoV2 S307 mAb CDRL2

<400> SEQUENCE: 245

Gly Ala Ser
1

<210> SEQ ID NO 246
<211> LENGTH: 9
<212> TYPE: PRT
<213> ORGANISM: Artificial Sequence
<220> FEATURE:
<223> OTHER INFORMATION: Synthetic sequence SARS-CoV2 S307 mAb CDRL3
```

-continued

<400> SEQUENCE: 246

Gln Gln Tyr Gly Ser Ser Ser Trp Thr
1               5

<210> SEQ ID NO 247
<211> LENGTH: 387
<212> TYPE: DNA
<213> ORGANISM: Artificial Sequence
<220> FEATURE:
<223> OTHER INFORMATION: Synthetic sequence SARS-CoV2 S307 mAb VH

<400> SEQUENCE: 247

```
caggtgcagc tgcaggagtc gggcccagga ctggtgaagc cttcggagac cctgtccctc      60
acctgcactg tctctggtgg ctccgtcacc agtggtagtt actactggag ctggatccgg     120
cagcccccag ggaagggact ggagtggatt gggtatatgt attacagtgg gagcaccaat     180
tacaacccct ccctcaagag tcgagtcacc atatcagtag acacgtccaa gaaccagttc     240
tccctgaagc tgagctctgt gaccgctgcg gacacggccg tgtattactg tgcgagggca     300
ggttgtactg gtatcacctg cttacgttac gactactact acggtctgga cgtctggggc     360
caagggacca cggtcaccgt ctcctca                                         387
```

<210> SEQ ID NO 248
<211> LENGTH: 325
<212> TYPE: DNA
<213> ORGANISM: Artificial Sequence
<220> FEATURE:
<223> OTHER INFORMATION: Synthetic sequence SARS-CoV2 S307 mAb VL(VK)

<400> SEQUENCE: 248

```
gaaattgtgt tgacgcagtc tccaggcacc ctgtctttgt ctccagggaa aagagccacc      60
ctctcctgca gggccagtca gagtgttagc agcagctact tagcctggta ccagcagaga     120
cctggccagg ctcccaggct cctcatctat ggtgcatcca gcagggccgc tggcatccca     180
gacaggttca gtggcagtgg gtctgggaca gacttcactc tcaccatcag cagactggag     240
cctgaagatt ttgcagtgta ttactgtcag cagtatggta gctcatcgtg acgttcggc     300 caagggacca aggtggaaat caaac                                           325
```

<210> SEQ ID NO 249
<211> LENGTH: 381
<212> TYPE: DNA
<213> ORGANISM: Artificial Sequence
<220> FEATURE:
<223> OTHER INFORMATION: Synthetic sequence SARS-CoV-2 S309-v1 mAb VH

<400> SEQUENCE: 249

```
caggttcagc tggtgcagtc tggagctgag gtgaagaagc ctggggcctc agtgaaggtc      60
tcctgcaagg cttctggtta ccctttacc agttatggta tcagctgggt gcgacaggcc     120
cctggacaag gcttgagtg gatgggatgg atcagcactt acaatggtaa cacaaattat     180
gcacagaagt tccagggcag agtcaccatg accacagaca catccacgac cacaggctac     240
atggagctga ggaggctgag atctgacgac acggccgtgt attactgtgc gagagattat     300
actcgtggtg cttggttcgg ggagtcattg atagggggct tgacaactg gggccaggga     360 accctggtca ccgtctcctc a                                               381
```

<210> SEQ ID NO 250
<211> LENGTH: 322

<212> TYPE: DNA
<213> ORGANISM: Artificial Sequence
<220> FEATURE:
<223> OTHER INFORMATION: Synthetic sequence SAES-CoV-2 S309-v13 mAb VL (VK)

<400> SEQUENCE: 250
gaaattgtgt tgacgcagtc tccaggcacc ctgtctttgt ctccagggga aagagccacc 60
ctctcctgca gggccagtca gactgttagc agcacctcct tagcctggta ccagcagaaa 120
cctggccagg ctcccaggct cctcatctat ggtgcatcca gcagggccac tggcatccca 180
gacaggttca gcggcagtgg gtctgggaca gacttcactc tcaccatcag cagactggag 240
cctgaagatt ttgcagtgta ttactgtcag cagcatgata cctcactcac tttcggcgga 300
gggaccaagg tggagatcaa ac 322

<210> SEQ ID NO 251
<211> LENGTH: 767
<212> TYPE: DNA
<213> ORGANISM: Artificial Sequence
<220> FEATURE:
<223> OTHER INFORMATION: Synthetic sequence CMV promoter

<400> SEQUENCE: 251
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccatgacgt caataatgac gtatgttccc atagtaacgc caatagggac 180
tttccattga cgtcaatggg tggagtattt acggtaaact gcccacttgg cagtacatca 240
agtgtatcat atgccaagta cgccccctat tgacgtcaat gacggtaaat ggcccgcctg 300
gcattatgcc cagtacatga ccttatggga ctttcctact tggcagtaca tctacgtatt 360
agtcatcgct attaccatgg tgatgcggtt ttggcagtac atcaatgggc gtggatagcg 420
gtttgactca cggggatttc caagtctcca ccccattgac gtcaatggga gtttgttttg 480
gcaccaaaat caacgggact ttccaaaatg tcgtaacaac tccgccccat tgacgcaaat 540
gggcggtagg cgtgtacggt gggaggtcta tataagcaga gctcgtttag tgaaccgtca 600
gatcgcctgg agacgccatc cacgctgttt tgacctccat agaagacacc gggaccgatc 660
cagcctccgc ggccgggaac ggtgcattgg aacgcggatt ccccgtgcca agagtgacgt 720
aagtaccgcc tatagagtct ataggcccac ccccttggct tcgttag 767

<210> SEQ ID NO 252
<211> LENGTH: 50
<212> TYPE: DNA
<213> ORGANISM: Artificial Sequence
<220> FEATURE:
<223> OTHER INFORMATION: Signal peptide

<400> SEQUENCE: 252
atgggatggt catgtatcat cctttttcta gtagcaactg caaccggtgt 50

<210> SEQ ID NO 253
<211> LENGTH: 135
<212> TYPE: DNA
<213> ORGANISM: Artificial Sequence
<220> FEATURE:
<223> OTHER INFORMATION: Poly-adenylation signal sequence

<400> SEQUENCE: 253
aacttgttta ttgcagctta taatggttac aaataaagca atagcatcac aaatttcaca 60
aataaagcat ttttttcact gcattctagt tgtggtttgt ccaaactcat caatgtatct    120
tatcatgtct ggatc                                                     135

<210> SEQ ID NO 254
<211> LENGTH: 323
<212> TYPE: DNA
<213> ORGANISM: Artificial Sequence
<220> FEATURE:
<223> OTHER INFORMATION: Synthetic sequence SARS-CoV-2
      Light Chain IgKC*01

<400> SEQUENCE: 254
gtacggtggc tgcaccatct gtcttcatct tcccgccatc tgatgagcag ttgaaatctg     60
gaactgcctc tgttgtgtgc ctgctgaata acttctatcc cagagaggcc aaagtacagt    120
ggaaggtgga taacgccctc caatcgggta actcccagga gagtgtcaca gagcaggaca    180
gcaaggacag cacctacagc ctcagcagca ccctgacgct gagcaaagca gactacgaga    240
aacacaaagt ctacgcctgc gaagtcaccc atcagggcct gagctcgccc gtcacaaaga    300
gcttcaacag gggagagtgt tag                                            323

<210> SEQ ID NO 255
<211> LENGTH: 993
<212> TYPE: DNA
<213> ORGANISM: Artificial Sequence
<220> FEATURE:
<223> OTHER INFORMATION: Synthetic sequence SARS-CoV-2 CH1-CH3 G1m17;
      IgG1*01

<400> SEQUENCE: 255
gcgtcgacca agggcccatc ggtcttcccc ctggcaccct cctccaagag cacctctggg     60
ggcacagcgg ccctgggctg cctggtcaag gactacttcc ccgaacctgt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagag agttgagccc    300
aaatcttgtg acaaaactca cacatgccca ccgtgcccag cacctgaact cctggggga    360 ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc cccgggtaaa tga                                 993

<210> SEQ ID NO 256
<211> LENGTH: 16
<212> TYPE: PRT
<213> ORGANISM: Artificial Sequence
<220> FEATURE:

<223> OTHER INFORMATION: Signal peptide

<400> SEQUENCE: 256

Met Gly Trp Ser Cys Ile Ile Leu Phe Leu Val Ala Thr Ala Thr Gly
1               5                   10                  15

<210> SEQ ID NO 257
<211> LENGTH: 1431
<212> TYPE: DNA
<213> ORGANISM: Artificial Sequence
<220> FEATURE:
<223> OTHER INFORMATION: Synthetic sequence SARS-CoV-2 S309-v1.1 mAb
      CH1-CH3 G1m17; IgGHG1*01 LS; GAALIE; signal
      peptide (nt-CO)

<400> SEQUENCE: 257

```
atgggctggt cctgtatcat cctgttcctg gtcgccacag ccaccggagt gcacagccaa      60
gtgcagctgg tccagagcgg cgccgaggtg aagaagcccg gcgctagcgt gaaggtgtcc     120
tgtaaagcca gcggatatcc ttttaccagc tacggcatct cctgggtgcg gcaggcccct     180
ggccagggcc tggaatggat gggctggatc agcacctacc agggaaatac caactacgcc     240
cagaagttcc agggaagagt gacaatgacc acagatacat ctacaaccac ggctacatg      300
gaactgaggc ggctgagaag cgacgacacc gccgtgtact actgcgccag agattacacc     360
agaggcgctt ggttcggcga gagcctgatc ggcggcttcg acaactgggg ccagggaacc     420
ctggtgacag tgtctagcgc ttctaccaaa ggcccttctg tctttcctct ggccccttct     480
agcaagtcta caagcggagg caccgccgcc ctgggctgcc tggtgaagga ctacttcccc     540
gagcccgtga ccgtgagctg gaatagcggc gccctgacaa gcggcgtgca caccttccca     600
gctgtgctgc agagcagcgg cctgtatagc ctgagcagcg tggtcaccgt gccaagcagc     660
agcctgggaa cacagaccta catctgcaac gtgaaccaca gccttctaa taccaaggtg      720
gataagaagg tggaacctaa gagctgcgac aaaacacaca catgcccctc catgtcctgct    780
ccagagctgc tggccggccc cagcgttttt ctgttccccc caaacctaa agacaccctg      840
atgatcagca gaaccctga ggtgacctgt gtggtggtgg acgtgtccca cgaagatcct      900
gaggtgaagt tcaactggta cgtggatgga gtggaagtgc acaacgccaa gaccaaacct     960
agagaagagc agtacaacag cacatataga gtcgtgtccg tgcttacagt gctgcaccag    1020
gactggctga atggaaagga atacaagtgc aaggtgtcca acaaggccct gcctctgcct    1080
gaggagaaga caatctctaa agccaagggc caacctcggg aacctcaggt gtacacactg    1140
ccccccagcc gggacgagct gaccaagaac caggtgtccc tgacctgcct ggtcaagggc    1200
ttctaccct ctgatatcgc cgtggaatgg gagagcaacg gccaacctga gaacaactac    1260
aagaccaccc ctccagtgct ggacagcgac ggcagcttct cctgtacag caagctgacc    1320
gttgacaagt ccagatggca gcagggcaac gtgttcagct gtagcgtcct gcacgaggcc    1380
ctgcattctc actacaccca gaagagcctg tccctcagcc ctggcaagtg a             1431
```

<210> SEQ ID NO 258
<211> LENGTH: 1374
<212> TYPE: DNA
<213> ORGANISM: Artificial Sequence
<220> FEATURE:
<223> OTHER INFORMATION: Synthetic sequence SARS-CoV-2 S309-v1.1 mAb
      CH1-CH3 G1m17; IgGHG1*01 LS; GAALIE; (nt-CO)

<400> SEQUENCE: 258

```
caagtgcagc tggtccagag cggcgccgag gtgaagaagc ccggcgctag cgtgaaggtg      60
```

```
tcctgtaaag ccagcggata tccttttacc agctacggca tctcctgggt gcggcaggcc    120
cctggccagg gcctggaatg gatgggctgg atcagcacct accagggaaa taccaactac    180
gcccagaagt tccagggaag agtgacaatg accacagata catctacaac caccggctac    240
atggaactga ggcggctgag aagcgacgac accgccgtgt actactgcgc cagagattac    300
accagaggcg cttggttcgg cgagagcctg atcggcggct tcgacaactg gggccaggga    360
accctggtga cagtgtctag cgcttctacc aaaggccctt ctgtctttcc tctggcccct    420
tctagcaagt ctacaagcgg aggcaccgcc gccctgggct gcctggtgaa ggactacttc    480
cccgagcccg tgaccgtgag ctggaatagc ggcgccctga caagcggcgt gcacaccttc    540
ccagctgtgc tgcagagcag cggcctgtat agcctgagca gcgtggtcac cgtgcccagc    600
agcagcctgg gaacacagac ctacatctgc aacgtgaacc acaagccttc taataccaag    660
gtggataaga aggtggaacc taagagctgc gacaaaacac acacatgccc tccatgtcct    720
gctccagagc tgctggccgg ccccagcgtt tttctgttcc cccccaaacc taaagacacc    780
ctgatgatca gcagaacccc tgaggtgacc tgtgtggtgg tggacgtgtc ccacgaagat    840
cctgaggtga agttcaactg gtacgtggat ggagtggaag tgcacaacgc caagaccaaa    900
cctagagaag agcagtacaa cagcacatat agagtcgtgt ccgtgcttac agtgctgcac    960
caggactggc tgaatggaaa ggaatacaag tgcaaggtgt ccaacaaggc cctgcctctg   1020
cctgaggaga agacaatctc taaagccaag ggccaacctc gggaacctca ggtgtacaca   1080
ctgcccccca gccgggacga gctgaccaag aaccaggtgt ccctgacctg cctggtcaag   1140
ggcttctacc cctctgatat cgccgtggaa tgggagagca acggccaacc tgagaacaac   1200
tacaagacca cccctccagt gctggacagc gacggcagct tcttcctgta cagcaagctg   1260
accgttgaca agtccagatg gcagcagggc aacgtgttca gctgtagcgt cctgcacgag   1320
gccctgcatt ctcactacac ccagaagagc ctgtccctca gccctggcaa gtga         1374
```

```

<210> SEQ ID NO 259
<211> LENGTH: 1431
<212> TYPE: DNA
<213> ORGANISM: Artificial Sequence
<220> FEATURE:
<223> OTHER INFORMATION: Synthetic sequence SARS-CoV-2 S309-v1.1 mAb
      CH1-CH3 G1m17; IgGHG1*01 LS; signal peptide
      (nt-CO)

<400> SEQUENCE: 259

```

```
atgggctggt cctgtatcat cctgttcctg gtcgccacag ccaccggagt gcacagccaa     60
gtgcagctgg tccagagcgg cgccgaggtg aagaagcccg gcgctagcgt gaaggtgtcc    120
tgtaaagcca gcggatatcc ttttaccagc tacggcatct cctgggtgcg gcaggcccct    180
ggccagggcc tggaatggat gggctggatc agcacctacc agggaaatac caactacgcc    240
cagaagttcc agggaagagt gacaatgacc acagatacat ctacaaccac cggctacatg    300
gaactgaggc ggctgagaag cgacgacacc gccgtgtact actgcgccag agattacacc    360
agaggcgctt ggttcggcga gagcctgatc ggcggcttcg acaactgggg ccagggaacc    420
ctggtgacag tgtctagcgc ttctaccaaa ggcccttctg tctttcctct ggccccttct    480
agcaagtcta caagcggagg caccgccgcc ctgggctgcc tggtgaagga ctacttcccc    540
gagcccgtga ccgtgagctg gaatagcggc gccctgacaa gcggcgtgca caccttccca    600
gctgtgctgc agagcagcgg cctgtatagc ctgagcagcg tggtcaccgt gcccagcagc    660
```

```
agcctgggaa cacagaccta catctgcaac gtgaaccaca agccttctaa taccaaggtg    720
gataagaagg tggaacctaa gagctgcgac aaaacacaca catgcccctcc atgtcctgct    780
ccagagctgc tgggcggccc cagcgttttt ctgttccccc ccaaacctaa agacaccctg    840
atgatcagca gaacccctga ggtgacctgt gtggtggtgg acgtgtccca cgaagatcct    900
gaggtgaagt tcaactggta cgtggatgga gtggaagtgc acaacgccaa gaccaaacct    960
agagaagagc agtacaacag cacatataga gtcgtgtccg tgcttacagt gctgcaccag   1020
gactggctga atggaaagga atacaagtgc aaggtgtcca caaggccct gcctgcccct    1080
atcgagaaga caatctctaa agccaagggc caacctcggg aacctcaggt gtacacactg   1140
cccccagcc gggacgagct gaccaagaac caggtgtccc tgacctgcct ggtcaagggc    1200
ttctacccct ctgatatcgc cgtggaatgg gagagcaacg gccaacctga gaacaactac   1260
aagaccaccc ctccagtgct ggacagcgac ggcagcttct tcctgtacag caagctgacc   1320
gttgacaagt ccagatggca gcagggcaac gtgttcagct gtagcgtcct gcacgaggcc   1380
ctgcattctc actacaccca gaagagcctg tccctcagcc ctggcaagtg a            1431
```

<210> SEQ ID NO 260
<211> LENGTH: 1374
<212> TYPE: DNA
<213> ORGANISM: Artificial Sequence
<220> FEATURE:
<223> OTHER INFORMATION: Synthetic sequence SARS-CoV-2 S309-v1.1 mAb CH1-CH3 G1m17; IgGHG1*01 LS (nt-CO)

<400> SEQUENCE: 260

```
caagtgcagc tggtccagag cggcgccgag gtgaagaagc ccggcgctag cgtgaaggtg     60
tcctgtaaag ccagcggata ccttttacc agctacggca ctctggggt gcggcaggcc    120
cctggccagg gcctggaatg gatgggctgg atcagcacct accagggaaa taccaactac    180
gcccagaagt tccagggaag agtgacaatg accacagata catctacaac caccggctac    240
atggaactga ggcggctgag aagcgacgac accgccgtgt actactgcgc cagagattac    300
accagaggcg cttggttcgg cgagagcctg atcggcggct cgacaactg ggccagggga    360
accctggtga cagtgtctag cgcttctacc aaaggcccctt ctgtcttccc ctgggcccct    420
tctagcaagt ctacaagcgg aggcaccgcc gccctgggct gcctggtgaa ggactacttc    480
cccgagcccg tgaccgtgag ctggaatagc ggcgccctga agcggcgt gcacaccttc    540
ccagctgtgc tgcagagcag cggcctgtat agcctgagca gcgtggtcac cgtgcccagc    600
agcagcctgg gaacacagac ctacatctgc aacgtgaacc acaagccttc taataccaag    660
gtggataaga aggtggaacc taagagctgc gacaaaacac acacatgccc tccatgtcct    720
gctccagagc tgctgggcgg ccccagcgtt tttctgttcc cccccaaacc taaagacacc    780
ctgatgatca gcagaacccc tgaggtgacc tgtgtggtgg tggacgtgtc ccacgaagat    840
cctgaggtga agttcaactg gtacgtggat ggagtggaag tgcacaacgc caagaccaaa    900
cctagagaag agcagtacaa cagcacatat agagtcgtgt ccgtgcttac agtgctgcac    960
caggactggc tgaatggaaa ggaatacaag tgcaaggtgt ccaacaaggc cctgcctgcc   1020
cctatcgaga agacaatctc taagccaag ggccaacctc gggaacctca ggtgtacaca    1080
ctgcccccca gcgggacga gctgaccaag aaccaggtgt ccctgacctg cctggtcaag    1140
ggcttctacc cctctgatat cgccgtggaa tgggagagca acggccaacc tgagaacaac   1200
tacaagacca cccctccagt gctggacagc gacggcagct tcttcctgta cagcaagctg   1260
```

```
accgttgaca agtccagatg gcagcagggc aacgtgttca gctgtagcgt cctgcacgag    1320
gccctgcatt ctcactacac ccagaagagc ctgtccctca gccctggcaa gtga          1374
```

<210> SEQ ID NO 261
<211> LENGTH: 701
<212> TYPE: DNA
<213> ORGANISM: Artificial Sequence
<220> FEATURE:
<223> OTHER INFORMATION: Synthetic sequence S309-v13 Light chain k1m3;
      IgKC*01; signal peptide (nt-CO)

<400> SEQUENCE: 261

```
tgggctggtc ctgcatcatc ctgttcctgg tggccacagc caccggcgtg cacagcgaga     60
tcgtcctgac acagagcccc ggcacactga gcctctcccc aggcgagcgg ctacactgt     120 cttgtagagc ttctcagacc gtgtccagca ccagcctggc ctggtatcag cagaaacctg    180
gccaggcccc tagactgctg atctacggcg ccagcagcag agccaccggc atccctgata    240
gattcagcgg cagcggatct ggaaccgact tcaccctgac catcagccgg ctggaacccg    300
aggactttgc cgtgtactac tgccagcaac acgacaccag cctgaccttc ggcggcggaa    360
caaaggtgga aatcaagaga accgtggccg cccctagcgt gttcatcttc cccccagcg    420 acgagcagct gaagagcggt acagcttctg tggtgtgcct gctgaacaac ttctacccgc    480
gggaagccaa ggtgcagtgg aaggtggaca acgccctgca gagcggcaac agccaggaga    540
gcgtgacaga gcaggacagc aaggacagca cctacagcct gagcagcacc ctgaccctga    600
gcaaggccga ctacgagaag cacaaggtgt acgcctgtga agtgacccac cagggcctgt    660
ctagccctgt gaccaagtct tttaacagag gcgagtgctg a                        701
```

<210> SEQ ID NO 262
<211> LENGTH: 645
<212> TYPE: DNA
<213> ORGANISM: Artificial Sequence
<220> FEATURE:
<223> OTHER INFORMATION: Synthetic sequence S309-v13 Light chain k1m3;
      IgKC*01; (nt-CO)

<400> SEQUENCE: 262

```
gagatcgtcc tgacacagag ccccggcaca ctgagcctct ccccaggcga gcgggctaca    60
ctgtcttgta gagcttctca gaccgtgtcc agcaccagcc tggcctggta tcagcagaaa    120
cctggccagg cccctagact gctgatctac ggcgccagca gcagagccac cggcatccct    180
gatagattca gcggcagcgg atctggaacc gacttcaccc tgaccatcag ccggctggaa    240
cccgaggact ttgccgtgta ctactgccag caacacgaca ccagcctgac cttcggcggc    300
ggaacaaagg tggaaatcaa gagaaccgtg gccgccccta gcgtgttcat cttccccccc    360
agcgacgagc agctgaagag cggtacagct tctgtggtgt gcctgctgaa caacttctac    420
ccgcgggaag ccaaggtgca gtggaaggtg gacaacgccc tgcagagcgg caacagccag    480
gagagcgtga cagagcagga cagcaaggac agcacctaca gcctgagcag caccctgacc    540
ctgagcaagg ccgactacga gaagcacaag gtgtacgcct gtgaagtgac ccaccagggc    600
ctgtctagcc ctgtgaccaa gtcttttaac agaggcgagt gctga                    645
```

<210> SEQ ID NO 263
<211> LENGTH: 57
<212> TYPE: DNA
<213> ORGANISM: Artificial Sequence
<220> FEATURE:
<223> OTHER INFORMATION: Signal peptide

<400> SEQUENCE: 263
atgggctggt cctgcatcat cctgttcctg gtggccacag ccaccggcgt gcacagc    57

<210> SEQ ID NO 264
<211> LENGTH: 19
<212> TYPE: PRT
<213> ORGANISM: Artificial Sequence
<220> FEATURE:
<223> OTHER INFORMATION: Signal peptide

<400> SEQUENCE: 264

Met Gly Trp Ser Cys Ile Ile Leu Phe Leu Val Ala Thr Ala Thr Gly
1               5                   10                  15

Val His Ser

<210> SEQ ID NO 265
<211> LENGTH: 329
<212> TYPE: PRT
<213> ORGANISM: Artificial Sequence
<220> FEATURE:
<223> OTHER INFORMATION: Synthetic sequence SARS-CoV-2 CH1-CH3 G1m17; IgG1*01 LS no C-term Lys

<400> SEQUENCE: 265

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ser His Tyr Thr
305                 310                 315                 320

Gln Lys Ser Leu Ser Leu Ser Pro Gly
                325

<210> SEQ ID NO 266
<211> LENGTH: 329
<212> TYPE: PRT
<213> ORGANISM: Artificial Sequence
<220> FEATURE:
<223> OTHER INFORMATION: Synthetic sequence SARS-CoV-2 CH1-CH3 G1m17;
      IgG1*01 LS GAALIE no C-term Lys

<400> SEQUENCE: 266

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Ala Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

```
Leu Tyr Ser Lys Leu Thr Val Asp Lys Ser Arg Trp Gln Gln Gly Asn
        290                 295                 300

Val Phe Ser Cys Ser Val Leu His Glu Ala Leu His Ser His Tyr Thr
305                 310                 315                 320

Gln Lys Ser Leu Ser Leu Ser Pro Gly
                325

<210> SEQ ID NO 267
<211> LENGTH: 127
<212> TYPE: PRT
<213> ORGANISM: Artificial Sequence
<220> FEATURE:
<223> OTHER INFORMATION: SARS-CoV-2 S309 VH consensus sequence
<220> FEATURE:
<221> NAME/KEY: VARIANT
<222> LOCATION: 50
<223> OTHER INFORMATION: Xaa = W, F, or Y
<220> FEATURE:
<221> NAME/KEY: VARIANT
<222> LOCATION: 55
<223> OTHER INFORMATION: Xaa = N, Q, L, or T
<220> FEATURE:
<221> NAME/KEY: VARIANT
<222> LOCATION: 56
<223> OTHER INFORMATION: Xaa = G, S, A, or Q
<220> FEATURE:
<221> NAME/KEY: VARIANT
<222> LOCATION: 105
<223> OTHER INFORMATION: Xaa = W, F, or Y

<400> SEQUENCE: 267

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Xaa Ile Ser Thr Tyr Xaa Xaa Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Thr Ala Val Tyr Tyr Cys
                85                  90                  95

Ala Arg Asp Tyr Thr Arg Gly Ala Xaa Phe Gly Glu Ser Leu Ile Gly
                100                 105                 110

Gly Phe Asp Asn Trp Gly Gln Gly Thr Leu Val Thr Val Ser Ser
            115                 120                 125
```